US010160726B2

(12) United States Patent
Fidalgo et al.

(10) Patent No.: US 10,160,726 B2
(45) Date of Patent: Dec. 25, 2018

(54) QUINOLONE DERIVATIVES AS ANTIBACTERIALS

(71) Applicant: NOVARTIS AG, Basel (CH)

(72) Inventors: Javier de Vicente Fidalgo, Foster City, CA (US); Haiying He, Shanghai (CN); Cheng Hu, San Mateo, CA (US); Zhigan Jiang, Shanghai (CN); Xiaolin Li, Alameda, CA (US); Peichao Lu, Pleasant Hill, CA (US); Wosenu Mergo, Oakland, CA (US); Daniel Mutnick, Concord, CA (US); Folkert Reck, Walnut Creek, CA (US); Alexey Rivkin, Emeryville, CA (US); Colin Keith Skepper, Alameda, CA (US); Xiaojing Michael Wang, Livermore, CA (US); Jianhua Xia, Shanghai (CN); Yongjin Xu, Castro Valley, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/500,870

(22) PCT Filed: Aug. 3, 2015

(86) PCT No.: PCT/IB2015/055899
§ 371 (c)(1),
(2) Date: Jan. 31, 2017

(87) PCT Pub. No.: WO2016/020836
PCT Pub. Date: Feb. 11, 2016

(65) Prior Publication Data
US 2017/0217897 A1 Aug. 3, 2017

(30) Foreign Application Priority Data
Aug. 6, 2014 (CN) ................. PCT/CN2014/083811

(51) Int. Cl.
| | |
|---|---|
| *C07D 215/38* | (2006.01) |
| *C07D 215/22* | (2006.01) |
| *A61K 31/4709* | (2006.01) |
| *A61K 31/496* | (2006.01) |
| *A61K 31/5377* | (2006.01) |
| *A61K 31/5386* | (2006.01) |
| *A61K 45/06* | (2006.01) |
| *C07D 401/04* | (2006.01) |
| *C07D 401/14* | (2006.01) |
| *C07D 405/14* | (2006.01) |
| *C07D 413/14* | (2006.01) |

(Continued)

(52) U.S. Cl.
CPC ........ *C07D 215/38* (2013.01); *A61K 31/4709* (2013.01); *A61K 31/496* (2013.01); *A61K 31/5377* (2013.01); *A61K 31/5386* (2013.01); *A61K 45/06* (2013.01); *C07D 215/22* (2013.01); *C07D 401/04* (2013.01); *C07D 401/14* (2013.01); *C07D 405/14* (2013.01); *C07D 413/14* (2013.01); *C07D 419/14* (2013.01); *C07D 471/04* (2013.01); *C07D 471/10* (2013.01); *C07D 487/10* (2013.01); *C07D 498/10* (2013.01)

(58) Field of Classification Search
CPC .. C07D 215/38; C07D 401/04; C07D 401/14; C07D 405/14; C07D 413/14; C07D 419/14; C07D 498/10; A61K 45/06; A61K 31/4709; A61K 31/496
See application file for complete search history.

(56) References Cited

U.S. PATENT DOCUMENTS

| | | | | | |
|---|---|---|---|---|---|
| 5,861,413 | A | * | 1/1999 | Habich ................ | C07D 215/38 514/312 |
| 6,015,791 | A | | 1/2000 | Gyorkos | |

(Continued)

FOREIGN PATENT DOCUMENTS

| | | |
|---|---|---|
| EP | 1 632 477 A1 | 3/2006 |
| EP | 1 900 732 A1 | 3/2008 |

(Continued)

OTHER PUBLICATIONS

Hariskumar, Synthetic COmmunications, vol. 40, 3281-3289, 2010. (Year: 2010).*

(Continued)

*Primary Examiner* — D Margaret M Seaman
(74) *Attorney, Agent, or Firm* — Mark H. Hopkins

(57) ABSTRACT

This invention is in the field of medicinal chemistry and relates to compounds, and pharmaceutical compositions thereof, that inhibit bacterial gyrase. The compounds are useful as inhibitors of bacterial gyrase activity and bacterial infections, and have the structure of Formula (I)

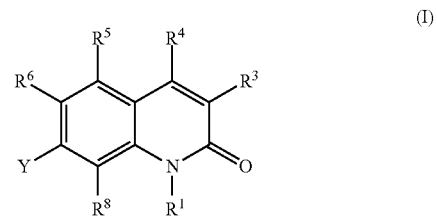

as further described herein. The invention further provides pharmaceutical compositions comprising a compound of Formula (I) and methods of using the compounds and compositions to treat bacterial infections.

22 Claims, No Drawings

(51) Int. Cl.
*C07D 419/14* (2006.01)
*C07D 471/04* (2006.01)
*C07D 471/10* (2006.01)
*C07D 487/10* (2006.01)
*C07D 498/10* (2006.01)

(56) References Cited

U.S. PATENT DOCUMENTS

| | | | |
|---|---|---|---|
| 2007/0249605 A1* | 10/2007 | Allen | C07D 215/22 514/235.2 |
| 2016/0257651 A1* | 9/2016 | Hiramatsu | A61K 45/06 |
| 2017/0158708 A1* | 6/2017 | Ratcliffe | C07D 498/02 |

FOREIGN PATENT DOCUMENTS

| | | | |
|---|---|---|---|
| EP | 1900732 | * | 3/2008 |
| WO | 9900020 | * | 1/1999 |
| WO | 2008/069242 A1 | | 6/2008 |
| WO | 2014/171527 A1 | | 10/2014 |

OTHER PUBLICATIONS

Theodoridis, ACS Symposium Series, 1998, 686 (Synthesis and Chemistry of Agrochemicals V), 55-66. (Year: 1998).*
Tessler and Nicolau, "In Vitro Activity of Novel Gyrase Inhibitors Against a High Resistant Population of Pseudomanas Aeruginosa" Antimicrobial Agents and Chemotherapy 57(6):2887-2889, 2013.
Yamada et al., "Fluorescent retinoid X receptor ligands for fluorescence polarization assay" Bioorganic & Medicinal Chemistry Letters 20(17):5143-5146, 2010.
A. Huxley et al., "Novel Tricyclic Topoisomerase Inhibitors (NTTIs) with Potent Activity against Drug-Resistant Bacteria"—Poster—F-1192—Redx Anti-Infectives Ltd, ICAAC, San Diego Sep. 17-21, 2015.
Charrier et al., "Biological Profiling of Novel Broad-Spectrum Inhibitors of Bacterial Topoisomerases"—Poster—F-1193—Redx Anti-Infectives Ltd, ICAAC, San Diego Sep. 17-21, 2015.

* cited by examiner

QUINOLONE DERIVATIVES AS ANTIBACTERIALS

This application is a U.S. National Phase filing of International Application Serial No. PCT/IB2015/055899 filed 3 Aug. 2015 and claims priority to International Application Serial No. PCT/CN2014/083811 filed 6 Aug. 2014, the contents of which are incorporated herein by reference in their entirety.

FIELD OF THE INVENTION

This invention is in the field of medicinal chemistry and relates to compounds, and pharmaceutical compositions thereof, that exhibit antibacterial activity. The compounds are inhibitors of bacterial DNA gyrase activity, as data herein demonstrates. The invention also relates to methods for treating bacterial infections in mammals and to methods for decreasing bacterial quantity in a biological sample using these compounds.

BACKGROUND OF THE INVENTION

Some known antimicrobial agents inhibit bacterial DNA synthesis by acting on DNA gyrase and topoisomerase. DNA gyrase and topoisomerase IV are both type II topoisomerases, consisting of two protein subunits that act as $A_2B_2$ heterotetramers. The ATPase domain resides on one polypeptide of the dimer (GyrB in DNA gyrase, ParE in topoisomerase IV), while the DNA cleavage core lies on a second polypeptide (GyrA in DNA gyrase, ParC in topoisomerase IV).

Some antibacterial inhibitors of gyrase including aminocoumarins such as novobiocin, function as competitive inhibitors of energy transduction of DNA gyrase by binding to the ATPase active site in GyrB. In contrast, the quinolone antibiotics such as nalidixic acid, ciprofloxacin and moxifloxacin, preferentially bind these enzymes at the cleavage core (GyrA and ParC) and prevent DNA replication and thus halt cell division in both Gram positive and Gram negative bacteria. Although first site resistance mutations generally occur in gyrA, mutations in gyrB also have been shown to reduce susceptibility to these known quinolones.

Bacterial DNA synthesis inhibitors (e.g. fluoroquinolones) have been used to treat primarily Gram-negative infections and have historically achieved good clinical outcomes. A wealth of knowledge exists for the quinolone class of compounds, including bioavailability, tissue distribution, PK/PD relationships and photoxicity. Structurally, quinolone antibiotics possess a bicyclic (ciprofloxacin and moxifloxacin) or tricyclic ring structure (levofloxacin) with an aryl side chain containing an acyclic ring incorporating an amine functionality. Most of the known fluoroquinolones possess a keto-acid functionality, either a carboxylic acid (ciprofloxacin and moxifloxacin, levofloxacin, the monocyclic and bicyclic 2-pyridone and 4-pyridones), hydroxylamine (quinazolinediones and tricyclic isoquinolones), or a hydrazine (quinazolinediones) group, which relate to DNA gyrase and topoisomerase activity and presumably bind to a divalent cation in the activated complex. Most inhibitors also possess an amine functional group attached to the core heterocycle, making these compounds zwitterionic in nature. Monocyclic 2-pyridone and 4-pyridone (e.g., Ro-13-5478) inhibitors possess this amine functionality attached to a phenyl group. The zwitterionic nature of these inhibitors relate to the permeation of these compounds into the Gram-negative cell using porin channels.

Quinolone antibiotics have been highly effective, but wide-scale deployment of the current drugs, including usage of the effective second generation quinolones that have become generic drugs (e.g., ciprofloxacin), threatens their future long-term utility. Quinolone resistance is already rising in both hospitals and the community at large. See Tessier and Nicolau, *Antimicrob. Agents Chemother.* 54(6), 2887-89 (2013). To combat such resistant strains, new gyrase inhibitors that are active against bacteria resistant to current quinolones, especially antibiotics targeting multi-drug resistant (MDR) Gram-negative pathogens that retain efficacy against bacteria that are resistant to known quinolones, would address an important unmet medical need.

The present invention relates to antibacterial compounds having activity against both wild-type and quinolone-resistant bacteria. It relates particularly to compounds having activity against quinolone-resistant Gram-negative bacteria, including multi-drug resistant (MDR) strains of e.g. *Pseudomonas aeruginosa*, as well as antibacterial activity against wild-type and quinolone-resistant Gram-positive pathogens, including methicillin-resistant *Staphylococcus aureus* (MRSA). The present invention also relates to compounds with selectivity between bacterial topoisomerase IV and DNA gyrase enzyme inhibition compared to human topoisomerase II enzyme inhibition, providing a therapeutic index consistent with in vivo use to treat bacterial infections in humans.

SUMMARY OF THE INVENTION

The compounds of this invention and pharmaceutical compositions thereof are useful as antibacterials; without being bound by theory, it is believed they act as gyrase inhibitors. The compounds of the invention are useful for the treatment of bacterial infection in subjects in need thereof, especially in humans and other mammals. These compounds are generally represented by formula (I):

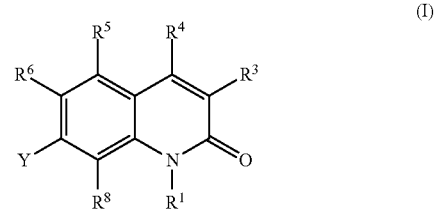

as described herein, including compounds of Formula (I) wherein:

$R^1$ is selected from the group consisting of $C_1$-$C_6$ alkyl, $C_2$-$C_6$ alkenyl, $C_2$-$C_6$ alkynyl, and $C_3$-$C_7$ cycloalkyl, each of which is optionally substituted with up to three groups selected from halogen, $C_1$-$C_3$ alkyl, -$L^1$-$OR^2$, -$L^1$-CN, -$L^1$-$N(R^2)_2$, and oxo;

$R^3$ is selected from the group consisting of H, halo, $C_1$-$C_4$ haloalkyl, -$L^1$-$OR^2$, $C_1$-$C_6$ alkyl, $C_2$-$C_6$ alkenyl, $C_2$-$C_6$ alkynyl, $C_3$-$C_7$ cycloalkyl, -$L^1$-CN, -$L^1$-$N(R^2)_2$, -$L^1$-$COOR^2$, -$L^1$-$CON(R^2)_2$, -$L^1$-$N(R^2)C(O)R^2$, -$L^1$-$N(R^2)C(O)OR$, -$L^1$-$SO_2R$, -$L^1$-$N(R^2)$—$SO_2$—R, and -$L^1$-$SO_2$—$N(R^2)_2$;

each $L^1$ is independently a bond or a $C_1$-$C_4$ straight or branched chain alkylene linker;

each R is independently $C_1$-$C_4$ alkyl optionally substituted with one to three groups selected from halogen, —OH, $C_1$-$C_4$ alkoxy, CN, —$NH_2$, —$NH(C_1$-$C_4$ alkyl), —$N(C_1$-$C_4$ alkyl)$_2$, —$SO_2(C_1$-$C_4$ alkyl), and oxo;

each $R^2$ is independently H or $C_1$-$C_4$ alkyl optionally substituted with up to three groups selected from halogen, —OH, $C_1$-$C_4$ alkoxy, CN, —$NR^{12}R^{13}$, —$SO_2R$ and oxo;
  or two $R^2$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —$NR^{12}R^{13}$, and oxo;

$R^4$ is selected from the group consisting of H, halo, $C_1$-$C_4$ haloalkyl, —$NH_2$, —CN, $C_1$-$C_6$ alkyl, $C_2$-$C_6$ alkenyl, $C_2$-$C_6$ alkynyl, $C_1$-$C_6$ alkoxy, -$L^2$-$C_3$-$C_7$ cycloalkyl, -$L^2$-CN, -$L^2$-$N(R^2)_2$, -$L^2$-$NR^2C(O)$—$R^2$, -$L^2$-$NR^2C(O)$—$OR^2$, -$L^2$-$NR^2C(O)$—$N(R^2)_2$, -$L^2$-$NR^2C(=NR^2)$—$N(R^2)_2$, -$L^2$-C(O)—$NR^2$—$OR^2$, -$L^2$-$COOR^2$, -$L^2$-$CON(R^2)_2$, -$L^2$-C(=$NR^2$)—$N(R^2)_2$, -$L^2$-C(=$NR^2$)—$NR^2$—$OR^2$, -$L^2$-$SO_2R$, -$L^2$-$SO_2$—$N(R^2)_2$, -$L^2$-Q, and -$L^2$-O—($C_1$-$C_4$ alkyl), -$L^2$-$OR^2$, wherein the $C_1$-$C_4$ alkyl is optionally substituted with one or two groups selected from —$OR^2$, —CN, oxo, =N—$OR^2$, —$N(R^2)_2$, —$COOR^2$, —C(=X)—$NR^2$—$OR^2$, —C(=X)—$N(R^2)_2$, —$NR^2C(=X)R^2$, —$NR^2C(=X)OR$, —$NR^2C(=X)N(R^2)_2$, —$NR^2C(O)$—O-$L^2$-Q, —$CON(R^2)_2$, —$SO_2R$, —$SO_2$—$N(R^2)_2$, —$NR^2$—$SO_2R$, and Q;
  wherein each Q is an optionally substituted ring selected from phenyl and a 5-6 membered heteroaryl or heterocyclyl ring containing up to four heteroatoms selected from N, O and S as ring members, wherein the optional substituents for the optionally substituted ring are up to three groups selected from $C_1$-$C_4$ alkyl, $C_1$-$C_4$ alkoxy, halo, oxo, =N—$OR^2$, —$COOR^2$, —$CON(R^2)^2$, —$NR^2C(O)R^2$, —$NR^2C(O)OR$, —C(O)$NR^2$—$OR^2$, —$SO_2R$, and —$SO_2$—$N(R^2)_2$, and
  each $L^2$ is independently selected from a bond and a divalent straight chain or branched $C_1$-$C_6$ alkyl, $C_2$-$C_6$ alkenyl, or $C_2$-$C_6$ alkynyl linking group, and is optionally substituted with one or two groups selected from halo, amino, hydroxy, and CN;
  and each X is independently O or =$NR^{11}$;

$R^5$ is selected from the group consisting of H, halo, -$L^2$-$OR^1$, -$L^2$-$N(R^2)_2$, -$L^2$-CN, $C_1$-$C_4$ alkyl, $C_{2-4}$ alkenyl, $C_{2-4}$ alkynyl, 5-6 membered heteroaryl containing 1-3 heteroatoms selected from N, O and S, $C_1$-$C_4$ alkoxy, and $C_1$-$C_4$ haloalkyl;

$R^6$ is selected from the group consisting of H, halo, CN, $C_1$-$C_4$ alkyl, $C_1$-$C_4$ alkoxy, and $C_1$-$C_4$ haloalkyl;

Y is pyridinyl optionally substituted with one to three groups selected from halo, CN, amino, hydroxy, $C_1$-$C_4$ alkyl, $C_1$-$C_4$ alkoxy, $C_1$-$C_4$ haloalkyl, and —$(CH_2)_{1-4}$—X, where X is selected from —OH, —CN, —$N(R^2)_2$, —$COOR^2$, —C(O)$N(R^2)_2$, —$NR^2C(O)R^2$, —$NR^2C(O)OR$, —$SO_2R$, and —$SO_2N(R^2)_2$;
  or Y is a group of the formula —$NR^{7A}R^{7B}$,
    wherein $R^{7A}$ is selected from the group consisting of H, —C(O)$R^2$, —C(O)$OR^2$, and $C_1$-$C_6$ alkyl optionally substituted with up to two groups independently selected from halogen, —OH, $C_1$-$C_4$ haloalkyl, $C_1$-$C_4$ alkoxy, oxo, =N—$OR^2$, —$N(R^2)_2$, $C_3$-$C_7$ cycloalkyl, —$COOR^2$, —C(O)$N(R^2)_2$, —$NR^2C(O)R^2$, —$NR^2C(O)OR$, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy;
    $R^{7B}$ is -$L^3$-$Q^3$ or $C_1$-$C_6$ alkyl optionally substituted with up to two groups independently selected from halogen, —OH, $C_1$-$C_4$ haloalkyl, $C_1$-$C_4$ alkoxy, oxo, —$N(R^2)_2$, $C_3$-$C_7$ cycloalkyl, —$COOR^2$, —C(O)$N(R^2)_2$, —$NR^2C(O)R^2$, —$NR^2C(O)OR$, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy
      wherein $L^3$ is a bond or a straight or branched chain $C_1$-$C_6$ alkyl linker, and $Q^3$ is selected from pyridinyl and a 4-7 membered heterocyclyl containing one or two heteroatoms selected from N, O and S as ring members, and wherein $Q^3$ is optionally substituted with up to three groups selected from halogen, CN, —OH, $C_1$-$C_4$ alkyl, $C_1$-$C_4$ haloalkyl, $C_1$-$C_4$ alkoxy, oxo, =N—$OR^2$, —$N(R^2)_2$, —$COOR^2$, —C(O)$N(R^2)_2$, —$NR^2C(O)R^2$, —$NR^2C(O)OR$;
    or $R^{7A}$ and $R^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by $R^{7A}$ and $R^{7B}$ together with the nitrogen atom to which they are attached is optionally substituted by up to four groups selected from halogen, —CN, hydroxy, phenyl, oxo, —$OR^9$, —$N(R^9)_2$, —$COOR^9$, —C(O)$N(R^9)_2$, $C_1$-$C_4$ alkyl, $C_1$-$C_4$ haloalkyl, $C_1$-$C_4$ alkoxy, oxo, $C_3$-$C_6$ cycloalkyl, and a 4-6 membered heteroaryl or heterocyclyl group that contains up to two heteroatoms selected from N, O and S as ring members,
    wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —$OR^{10}$, =N—$OR^{10}$, —$N(R^{10})_2$, —$COOR^{10}$, —$N(R^{10})$—C(O)—O—($C_1$-$C_4$ alkyl), —C(O)$N(R^{10})_2$, $C_1$-$C_4$ alkyl, $C_1$-$C_4$ haloalkyl, and $C_1$-$C_4$ alkoxy;

$R^8$ is selected from the group consisting of H, halo, CN, -$L^2$-$OR^1$, -$L^2$-$N(R^2)_2$, $C_{2-4}$ alkenyl, $C_1$-$C_4$ alkoxy, $C_1$-$C_4$ haloalkyl and $C_1$-$C_4$ haloalkoxy;

$R^9$ and $R^{10}$ are each independently selected from H and $C_1$-$C_4$ alkyl optionally substituted with up to three groups selected from halogen, —OH, $C_1$-$C_4$ alkoxy, CN, —$NR^{12}R^{13}$, —$SO_2R$ and oxo;
  or two $R^9$ or two $R^{10}$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —$NR^{12}R^{13}$, and oxo;

each $R^{11}$ is independently hydrogen or $C_1$-$C_4$ alkyl optionally substituted with one or two groups selected from halogen, —OH, $C_1$-$C_4$ alkoxy, CN, —$NH_2$, —NH($C_1$-$C_4$ alkyl), —N($C_1$-$C_4$ alkyl)$_2$, —$SO_2$($C_1$-$C_4$ alkyl), and oxo;

each $R^{12}$ and $R^{13}$ is independently hydrogen or $C_1$-$C_4$ alkyl optionally substituted with one or two groups selected from halogen, —OH, $C_1$-$C_4$ alkoxy, CN, —$NH_2$, —NH($C_1$-$C_4$ alkyl), —N($C_1$-$C_4$ alkyl)$_2$, —$SO_2$($C_1$-$C_4$ alkyl), and oxo;
  or $R^{12}$ and $R^{13}$ together with the nitrogen atom to which they are attached form a 4- to 6-membered heterocyclyl optionally including an additional heteroatom selected from N, O and S as a ring member and optionally substituted by one to three substituents selected from OH, halogen, oxo, =N—$OR^{11}$, $C_1$-$C_6$ alkyl optionally substituted by one to three halogen atoms or $NH_2$, $C_1$-$C_6$ alkoxy optionally substituted by one or more OH groups or $C_1$-$C_6$ alkoxy; and —C(O)O$C_1$-$C_6$ alkyl;

and include pharmaceutically acceptable salts of such compounds. Various additional embodiments of the compounds of the invention are described below.

These compounds, and pharmaceutical compositions containing them, are useful for treating or lessening the severity of bacterial infections. In particular, the compounds of the present invention are useful in treating or lessening the severity of upper respiratory infections, lower respiratory infections, ear infections, pleuropulmonary and bronchial infections, urinary tract infections, intra-abdominal infections, cardiovascular infections, a blood stream infection, sepsis, CNS infections, skin and soft tissue infections, GI infections, bone and joint infections, genital infections, eye infections, or granulomatous infections. The compounds are effective against a range of bacteria, including both Gram positive and Gram negative bacteria.

DETAILED DESCRIPTION OF THE INVENTION

For purposes of interpreting this specification, the following definitions will apply unless specified otherwise and whenever appropriate, terms used in the singular will also include the plural and vice versa.

Definitions

The term "a," "an," "the" and similar terms used in the context of the present invention (especially in the context of the claims) are to be construed to cover both the singular and plural unless otherwise indicated herein or clearly contradicted by the context.

As used herein, the term "halogen "(or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, unless otherwise specified, the term "heteroatom" refers to nitrogen (N), oxygen (O) or sulfur (S).

As used herein, the term "alkyl" refers to a fully saturated branched or unbranched hydrocarbon moiety having up to 10 carbon atoms. Unless otherwise provided, alkyl refers to hydrocarbon moieties having 1 to 6 carbon atoms (which may be written as $C_1$-$C_6$, or $C_{1-6}$ alkyl), or alternatively 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more substituents in place of a hydrogen atom of the corresponding unsubstituted alkyl group, such as one, two or three substituents, up to the number of Hydrogens on the unsubstituted alkyl group. Suitable substituents for alkyl groups, if not otherwise specified, may be selected from halogen, CN, oxo, hydroxy, amino, and $C_1$-$C_4$alkoxy groups.

As used herein, the term "alkylene" refers to a divalent alkyl group having 1 to 10 carbon atoms, and two open valences to attach to other components. Unless otherwise provided, alkylene refers to moieties having typically 1 to 6 carbon atoms, or alternatively 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable substituents are selected from the substituents listed above for alkyl groups.

As used herein, the term "haloalkyl" refers to an alkyl as defined herein, which is substituted by one or more halogen atoms as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g., trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-6 carbons, more commonly 1-4 carbon atoms.

A substituted alkoxy is an alkoxy group containing one or more, such as one, two or three substituents on the alkyl portion of the alkoxy. Unless otherwise specified, suitable substituents are selected from the substituents listed above for alkyl groups.

Similarly, each alkyl part of other groups like "alkoxyalkyl", "alkoxycarbonyl", "alkoxy-carbonylalkyl", "alkylsulfonyl", "alkylsulfoxyl", "alkylamino", or "haloalkyl" shall have the same meaning as described in the above-mentioned definition of "alkyl". When used in this way, unless otherwise indicated, the alkyl group is often a 1-4 carbon alkyl and is not further substituted by groups other than the components named. When such alkyl groups are substituted, suitable substituents are those named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3, 3-hexafluoro-2-propoxy, and the like.

As used herein, the term "cycloalkyl" refers to saturated or unsaturated non-aromatic monocyclic, bicyclic, tricyclic or spirocyclic hydrocarbon groups having 3-12 carbon atoms: the cycloalkyl group may be unsaturated, and may be fused to another ring that can be saturated, unsaturated or aromatic, provided the ring atom of the cycloalkyl group that is connected to the molecular formula of interest is in a non-aromatic ring. Unless otherwise provided, cycloalkyl refers to cyclic hydrocarbon groups having between 3 and 12 ring carbon atoms or between 3 and 8 ring carbon atoms. Frequently, cycloalkyl groups are saturated monocyclic rings having 3-7 ring atoms unless otherwise specified.

A substituted cycloalkyl is a cycloalkyl group substituted by one, or two, or three or more substituents, up to the number of hydrogens on the unsubstituted group. Typically, a substituted cycloalkyl will have 1-4 or 1-2 substituents. Suitable substituents, unless otherwise specified, are independently selected from the group consisting of halogen, hydroxyl, thiol, cyano, nitro, oxo, $C_1$-$C_4$-alkylimino, $C_1$-$C_4$-alkoximino, hydroxyimino, $C_1$-$C_4$-alkyl, $C_2$-$C_4$-alkenyl, $C_2$-$C_4$-alkynyl, $C_1$-$C_4$-alkoxy, $C_2$-$C_4$-alkenyloxy, $C_2$-$C_4$-alkynyloxy, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, $C_1$-$C_4$-alkylsulfonyl, $C_1$-$C_4$-alkylsulfamoyl, and $C_1$-$C_4$-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups provided above. Preferred substituents for cycloalkyl groups include $C_1$-$C_4$alkyl and the substituent groups listed above for alkyl groups.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkylalkyl", or "halocycloalkyl" shall have the same meaning as described in the above-mentioned definition of "cycloalkyl". When used in these terms, the cycloalkyl is typically a monocyclic 3-7 carbon ring, that is unsubstituted or substituted with 1-2 groups. When optionally substituted, the substituents are typically selected from $C_1$-$C_4$ alkyl and those set forth above as suitable for alkyl groups.

As used herein, the term "aryl" refers to an aromatic hydrocarbon group having 6-10 carbon atoms in the ring portion. Typically, aryl is monocyclic, bicyclic or tricyclic aryl having 6-10 carbon atoms, e.g., phenyl or naphthyl. Furthermore, the term "aryl" as used herein, refers to an aromatic substituent which can be a single aromatic ring, or multiple aromatic rings that are fused together. Non-limiting examples include phenyl, naphthyl and tetrahydronaphthyl, provided the tetrahydronaphthyl is connected to the formula of interest through a carbon of the aromatic ring of the tetrahydronaphthyl group.

A substituted aryl is an aryl group substituted by 1-5 (such as one, or two, or three) substituents independently selected from the group consisting of hydroxyl, thiol, cyano, nitro, $C_2$-$C_4$-alkenyl, $C_2$-$C_4$-alkynyl, $C_1$-$C_4$-alkoxy, $C_2$-$C_4$-alkenyloxy, $C_2$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, $C_1$-$C_4$-alkylsulfonyl, sulfamoyl, $C_1$-$C_4$-alkylsulfamoyl, and $C_1$-$C_4$-alkylaminosulfonyl where each of the aforementioned hydrocarbon groups (e.g., alkyl, alkenyl, alkynyl, alkoxy residues) may be further substituted by one or more groups independently selected at each occurrence from the groups listed above as suitable substituents for alkyl groups.

Similarly, the term aryl when used as part of other groups like "aryloxy" or "arylalkyl" shall have the same meaning as described in the above-mentioned definition of "aryl".

As used herein, the term "heterocyclyl" or "heterocyclic" or "heterocycle" refers to a heterocyclic group that is saturated or partially saturated but not aromatic, and is preferably a monocyclic or a polycyclic ring (in case of a polycyclic ring particularly a bicyclic, tricyclic or spirocyclic ring); and has 3 to 12, more typically 3 to 8 and most often 5 or 6 ring atoms; wherein one or more, preferably one to four, especially one or two ring atoms are heteroatoms independently selected from O, S and N (the remaining ring atoms therefore being carbon). Preferably, a heterocyclyl group has one or two such heteroatoms as ring atoms, and commonly the heteroatoms are not directly connected to each other. The bonding ring (i.e. the ring connecting to the Formula of interest) preferably has 4 to 12, especially 5 to 7 ring atoms. The heterocyclic group can be fused to an aromatic ring, provided it is attached to the Formula of interest at an atom of the heterocyclic group that is not aromatic. The heterocyclic group can be attached to the Formula of interest via a heteroatom (typically nitrogen) or a carbon atom of the heterocyclic group. The heterocyclyl can include fused or bridged rings as well as spirocyclic rings, and only one ring of a polycyclic heterocyclic group needs to contain a heteroatom as a ring. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-5 (such as one, or two, or three) substituents selected from the substituents described above for a cycloalkyl group.

Similarly, the term heterocyclyl used as part of other groups like "heterocyclylalkyl" shall have the same meaning as described in the above definition of "heterocyclyl".

As used herein, the term "heteroaryl" refers to a 5-14 membered monocyclic- or bicyclic- or tricyclic-aromatic ring system, having 1 to 8 heteroatoms as ring members; the heteroatoms are selected from N, O and S unless otherwise specified. Typically, the heteroaryl in a compound of the invention is a 5-10 membered ring system or a 5-7 membered ring system (e.g., 5-7 membered monocyclic or an 8-10 membered bicyclic group). Typical heteroaryl groups include 2- or 3-thienyl, 2- or 3-furyl, 1-, 2- or 3-pyrrolyl, 1-, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4)-triazolyl, 4- or 5-(1,2,3)-triazolyl, 1- or 2-tetrazolyl, 2-, 3-, or 4-pyridyl, 3- or 4-pyridazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings, where the radical or point of attachment to the Formula of interest is on a heteroaromatic ring. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents selected from the substituents described above as suitable for an aryl group, unless otherwise specified.

The term "hydroxy" or "hydroxyl" refers to the group —OH.

The term "spiro" as used herein includes 3- to 6-cycloalkyl or 4- to 6-atom heterocyclic rings having one or two heteroatoms selected from N, O and S as ring members, which can optionally be substituted as defined, wherein the spiro ring is fused onto a single carbon atom of a non-aromatic ring, making the carbon atom shared by both rings a spirocyclic center. Q is a suitable substituent for attachment to the spirocyclic ring, e.g. H or $C_1$-$C_4$ alkyl. Illustrative examples of spiro groups are:

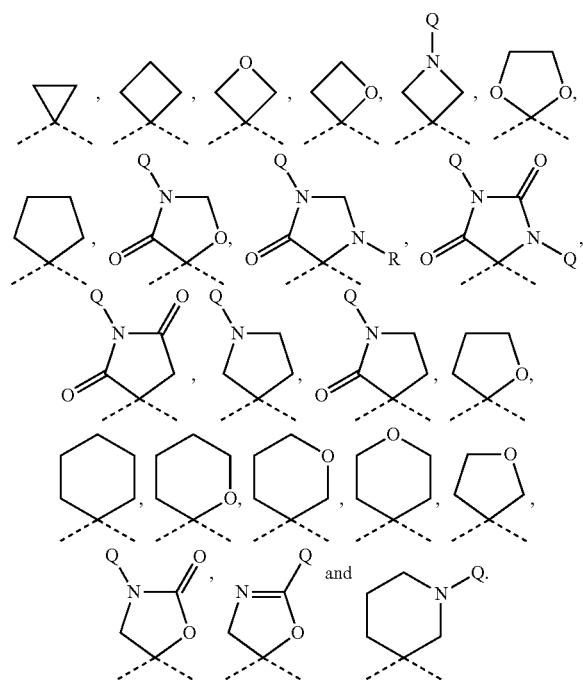

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, suitable for use in a pharmaceutical composition, as would be known to those skilled in the art (see, for example, Remington's Pharmaceutical Sciences, 18th Ed., Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease by reducing or inhibiting the activity of gyrase; or reduce or inhibit the expression of gyrase. In another non-limiting embodiment, the term "a therapeutically effective amount" refers to the amount of the compound of the present invention that, when administered to a subject treats or ameliorates a bacterial infection in said subject.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In some embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Various embodiments of the invention are described herein. It will be recognized that features specified in each embodiment may be combined with other specified features to provide further embodiments. The following enumerated embodiments are representative:

Embodiment 1 includes compounds of general structure 1A or 1B or IC and their pharmaceutically acceptable salts.

1A. A compound of formula (I):

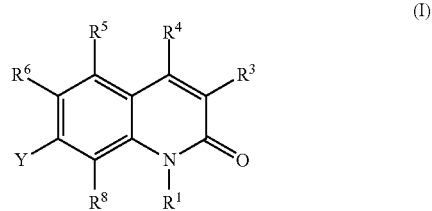

wherein:

$R^1$ is selected from the group consisting of $C_1$-$C_6$ alkyl, $C_2$-$C_6$ alkenyl, $C_2$-$C_6$ alkynyl, and $C_3$-$C_7$ cycloalkyl, each of which is optionally substituted with up to three groups selected from halogen, $C_1$-$C_3$ alkyl, -$L^1$-$OR^2$, -$L^1$-$N(R^2)_2$, and oxo;

$R^3$ is selected from the group consisting of H, halo, $C_1$-$C_4$ haloalkyl, -$L^1$-$OR^2$, $C_1$-$C_6$ alkyl, $C_2$-$C_6$ alkenyl, $C_2$-$C_6$ alkynyl, $C_3$-$C_7$ cycloalkyl, -$L^1$-CN, -$L^1$-N($R^2$)$_2$, -$L^1$-COO$R^2$, -$L^1$-CON($R^2$)$_2$, -$L^1$-N($R^2$)C(O)$R^2$, -$L^1$-N($R^2$)C(O)OR, -$L^1$-SO$_2$R, -$L^1$-N($R^2$)—SO$_2$—R, and -$L^1$-SO$_2$—N($R^2$)$_2$;

each $L^1$ is independently a bond or a $C_1$-$C_4$ straight or branched chain alkylene linker;

each R is independently $C_1$-$C_4$ alkyl optionally substituted with one to three groups selected from halogen, —OH, $C_1$-$C_4$ alkoxy, CN, —NH$_2$, —NH($C_1$-$C_4$ alkyl), —N($C_1$-$C_4$ alkyl)$_2$, —SO$_2$($C_1$-$C_4$ alkyl), and oxo;

each $R^2$ is independently H or $C_1$-$C_4$ alkyl optionally substituted with up to three groups selected from halogen, —OH, $C_1$-$C_4$ alkoxy, CN, —N$R^{12}R^{13}$, —SO$_2$R and oxo;

or two $R^2$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —N$R^{12}R^{13}$, and oxo;

$R^4$ is selected from the group consisting of H, halo, $C_1$-$C_4$ haloalkyl, —NH$_2$, —CN, $C_1$-$C_6$ alkyl, $C_2$-$C_6$ alkenyl, $C_2$-$C_6$ alkynyl, $C_1$-$C_6$ alkoxy, -$L^2$-$C_3$-$C_7$ cycloalkyl, -$L^2$-CN, -$L^2$-N($R^2$)$_2$, -$L^2$-N$R^2$C(O)—$R^2$, -$L^2$-N$R^2$C(O)—O$R^2$, -$L^2$-N$R^2$C(O)—N($R^2$)$_2$, -$L^2$-N$R^2$C(=N$R^2$)—N($R^2$)$_2$, -$L^2$-C(O)—N$R^2$—O$R^2$, -$L^2$-COO$R^2$, -$L^2$-CON($R^2$)$_2$, -$L^2$-C(=N$R^2$)—N($R^2$)$_2$, -$L^2$-C(=N$R^2$)—N$R^2$—O$R^2$, -$L^2$-SO$_2$R, -$L^2$-SO$_2$—N($R^2$)$_2$, -$L^2$-Q, and -$L^2$-O—($C_1$-$C_4$ alkyl), -$L^2$-O$R^2$, wherein the $C_1$-$C_4$ alkyl is optionally substituted with one or two groups selected from —O$R^2$, —CN, oxo, =N—O$R^2$, —N($R^2$)$_2$, —COO$R^2$, —C(=X)—N$R^2$—O$R^2$, —C(=X)—N($R^2$)$_2$, —N$R^2$C(=X)$R^2$, —N$R^2$C(=X)OR, —N$R^2$C(=X)N($R^2$)$_2$, —N$R^2$C(O)—O-$L^2$-Q, —CON($R^2$)$_2$, —SO$_2$R, —SO$_2$—N($R^2$)$_2$, —N$R^2$—SO$_2$R, and Q;

wherein each Q is an optionally substituted ring selected from phenyl and a 5-6 membered heteroaryl or heterocyclyl ring containing up to four heteroatoms selected from N, O and S as ring members, wherein the optional substituents for the optionally substituted ring are up to three groups selected from $C_1$-$C_4$ alkyl, $C_1$-$C_4$ alkoxy, halo, oxo, =N—O$R^2$, —COO$R^2$, —CON($R^2$)$_2$, —N$R^2$C(O)$R^2$, —N$R^2$C(O)OR, —C(O)N$R^2$—O$R^2$, —SO$_2$R, and —SO$_2$—N($R^2$)$_2$, and each $L^2$ is independently selected from a bond and a divalent straight chain or branched $C_1$-$C_6$ alkyl, $C_2$-$C_6$ alkenyl, or $C_2$-$C_6$ alkynyl linking group, and is optionally substituted with one or two groups selected from halo, amino, hydroxy, and CN;

and each X is independently O or =N$R^{11}$;

$R^5$ is selected from the group consisting of H, halo, -$L^2$-O$R^1$, -$L^2$-N($R^2$)$_2$, -$L^2$-CN, $C_1$-$C_4$ alkyl, $C_{2-4}$ alkenyl, $C_{2-4}$ alkynyl, 5-6 membered heteroaryl containing 1-3 heteroatoms selected from N, O and S, $C_1$-$C_4$ alkoxy, and $C_1$-$C_4$ haloalkyl;

$R^6$ is selected from the group consisting of H, halo, CN, $C_1$-$C_4$ alkyl, $C_1$-$C_4$ alkoxy, and $C_1$-$C_4$ haloalkyl;

Y is pyridinyl optionally substituted with one to three groups selected from halo, CN, amino, hydroxy, $C_1$-$C_4$ alkyl, $C_1$-$C_4$ alkoxy, $C_1$-$C_4$ haloalkyl, and —(CH$_2$)$_{1-4}$—X, where X is selected from —OH, —CN, —N($R^2$)$_2$, —COO$R^2$, —C(O)N($R^2$)$_2$, —N$R^2$C(O)$R^2$, —N$R^2$C(O)OR, —SO$_2$R, and —SO$_2$N($R^2$)$_2$;

or Y is a group of the formula —N$R^{7A}R^{7B}$, wherein $R^{7A}$ is selected from the group consisting of H, —C(O)$R^2$, —C(O)O$R^2$, and $C_1$-$C_6$ alkyl optionally substituted with up to two groups independently selected from halogen, —OH, $C_1$-$C_4$ haloalkyl, $C_1$-$C_4$ alkoxy, oxo, =N—O$R^2$, —N($R^2$)$_2$, $C_3$-$C_7$ cycloalkyl, —COO$R^2$, —C(O)N($R^2$)$_2$, —N$R^2$C(O)$R^2$, —N$R^2$C(O)OR, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy;

$R^{7B}$ is -$L^3$-$Q^3$ or $C_1$-$C_6$ alkyl optionally substituted with up to two groups independently selected from halogen, —OH, $C_1$-$C_4$ haloalkyl, $C_1$-$C_4$ alkoxy, oxo, —N($R^2$)$_2$, $C_3$-$C_7$ cycloalkyl, —COO$R^2$, —C(O)N($R^2$)$_2$, —N$R^2$C(O)$R^2$, —N$R^2$C(O)OR, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy wherein $L^3$ is a bond or a straight or branched chain $C_1$-$C_6$ alkyl linker, and $Q^3$ is selected from pyridinyl and a 4-7 membered heterocyclyl containing one or two heteroatoms selected from N, O and S as ring members, and wherein $Q^3$ is optionally substituted with up to three groups selected from halogen, CN, —OH, $C_1$-$C_4$ alkyl, $C_1$-$C_4$ haloalkyl, $C_1$-$C_4$ alkoxy, oxo, =N—O$R^2$, —N($R^2$)$_2$, —COO$R^2$, —C(O)N($R^2$)$_2$, —N$R^2$C(O)$R^2$, —N$R^2$C(O)OR;

or $R^{7A}$ and $R^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by $R^{7A}$ and $R^{7B}$ together with the nitrogen atom to which they are attached is optionally substituted by up to four groups selected from halogen, —CN, hydroxy, phenyl, oxo, —O$R^9$, —N($R^9$)$_2$, —COO$R^9$, —C(O)N($R^9$)$_2$, $C_1$-$C_4$ alkyl, $C_1$-$C_4$ haloalkyl, $C_1$-$C_4$ alkoxy, oxo, $C_3$-$C_6$ cycloalkyl, and a 4-6 membered heteroaryl or heterocyclyl group that contains up to two heteroatoms selected from N, O and S as ring members, wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —O$R^{10}$, =N—O$R^{10}$, —N($R^{10}$)$_2$, —COO$R^{10}$, —N($R^{10}$)—C(O)—O—($C_1$-$C_4$ alkyl), —C(O)N($R^{10}$)$_2$, $C_1$-$C_4$ alkyl, $C_1$-$C_4$ haloalkyl, and $C_1$-$C_4$ alkoxy;

$R^8$ is selected from the group consisting of H, halo, CN, -$L^2$-O$R^1$, -$L^2$-N($R^2$)$_2$, $C_{2-4}$ alkenyl, $C_1$-$C_4$ alkoxy, $C_1$-$C_4$ haloalkyl and $C_1$-$C_4$ haloalkoxy;

$R^9$ and $R^{10}$ are each independently selected from H and $C_1$-$C_4$ alkyl optionally substituted with up to three groups selected from halogen, —OH, $C_1$-$C_4$ alkoxy, CN, —N$R^{12}R^{13}$, —SO$_2$R and oxo;

or two $R^9$ or two $R^{10}$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —N$R^{12}R^{13}$, and oxo;

each $R^{11}$ is independently hydrogen or $C_1$-$C_4$ alkyl optionally substituted with one or two groups selected from halogen, —OH, $C_1$-$C_4$ alkoxy, CN, —NH$_2$, —NH($C_1$-$C_4$ alkyl), —N($C_1$-$C_4$ alkyl)$_2$, —SO$_2$($C_1$-$C_4$ alkyl), and oxo;

each $R^{12}$ and $R^{13}$ is independently hydrogen or $C_1$-$C_4$ alkyl optionally substituted with one or two groups selected from halogen, —OH, $C_1$-$C_4$ alkoxy, CN, —NH$_2$, —NH($C_1$-$C_4$ alkyl), —N($C_1$-$C_4$ alkyl)$_2$, —SO$_2$($C_1$-$C_4$ alkyl), and oxo;
  or R$^{12}$ and R$^{13}$ together with the nitrogen atom to which they are attached form a 4- to 6-membered heterocyclyl optionally including an additional heteroatom selected from N, O and S as a ring member and optionally substituted by one to three substituents selected from OH, halogen, oxo, =N—OR$^{11}$, $C_1$-$C_6$ alkyl optionally substituted by one to three halogen atoms or NH$_2$, $C_1$-$C_6$ alkoxy optionally substituted by one or more OH groups or $C_1$-$C_6$ alkoxy; and —C(O)O$C_1$-$C_6$ alkyl;
or a pharmaceutically acceptable salt thereof.

1B. Compounds of Formula (I) wherein:
  R$^1$ is selected from the group consisting of $C_1$-$C_6$ alkyl, $C_2$-$C_6$ alkenyl, $C_2$-$C_6$ alkynyl, and $C_3$-$C_7$ cycloalkyl, each of which is optionally substituted with up to three groups selected from halogen, —OR$^2$, CN, —N(R$^2$)$_2$, and oxo;
  R$^3$ is selected from the group consisting of H, -L$^1$-OR$^2$, $C_1$-$C_6$ alkyl, $C_2$-$C_6$ alkenyl, $C_2$-$C_6$ alkynyl, $C_3$-$C_7$ cycloalkyl, -L$^1$-N(R$^2$)$_2$, -L$^1$-COOR$^2$, -L$^1$-CON(R$^2$)$_2$, -L$^1$-N(R$^2$)C(O)R$^2$, -L$^1$-N(R$^2$)C(O)OR, -L$^1$-SO$_2$R, -L$^1$-N(R$^2$)—SO$_2$—R, and -L$^1$-SO$_2$—N(R$^2$)$_2$;
  L$^1$ is a bond or a $C_1$-$C_4$ straight or branched chain alkylene linker;
  each R is independently $C_1$-$C_4$ alkyl optionally substituted with one to three groups selected from halogen, —OH, $C_1$-$C_4$ alkoxy, CN, —NH$_2$, —NH($C_1$-$C_4$ alkyl), —N($C_1$-$C_4$ alkyl)$_2$, —SO$_2$($C_1$-$C_4$ alkyl), and oxo;
  each R$^2$ is independently H or $C_1$-$C_4$ alkyl optionally substituted with up to three groups selected from halogen, —OH, $C_1$-$C_4$ alkoxy, CN, —NR$^{12}$R$^{13}$, —SO$_2$R and oxo;
    or two R$^2$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —NR$^{12}$R$^{13}$, and oxo;
  R$^4$ is selected from the group consisting of H, halo, $C_1$-$C_4$ haloalkyl, —NH$_2$, —CN, $C_1$-$C_6$ alkyl, $C_2$-$C_6$ alkenyl, $C_2$-$C_6$ alkynyl, $C_1$-$C_6$ alkoxy, -L$^2$-$C_3$-$C_7$ cycloalkyl, -L$^2$-CN, -L$^2$-N(R$^2$)$_2$, -L$^2$-NR$^2$C(O)—R$^2$, -L$^2$-NR$^2$C(O)—OR$^2$, -L$^2$-NR$^2$C(O)—N(R$^2$)$_2$, -L$^2$-NR$^2$C(=NR$^2$)—N(R$^2$)$_2$, -L$^2$-C(O)—NR$^2$—OR$^2$, -L$^2$-COOR$^2$, -L$^2$-CON(R$^2$)$_2$, -L$^2$-C(=NR$^2$)—N(R$^2$)$_2$, -L$^2$-C(=NR$^2$)—NR$^2$—OR$^2$, -L$^2$-SO$_2$R, -L$^2$-SO$_2$—N(R$^2$)$_2$, -L$^2$-Q, and -L$^2$-O—($C_1$-$C_4$ alkyl), -L$^2$-OR$^2$, wherein the $C_1$-$C_4$ alkyl is optionally substituted with one or two groups selected from —OR$^2$, —CN, oxo, =N—OR$^2$, —N(R$^2$)$_2$, —COOR$^2$, —C(=X)—NR$^2$—OR$^2$, —C(=X)—N(R$^2$)$_2$, —NR$^2$C(=X)R$^2$, —NR$^2$C(=X)OR, —NR$^2$C(=X)N(R$^2$)$_2$, —NR$^2$C(O)—O-L$^2$-Q, —CON(R$^2$)$_2$, —SO$_2$R, —SO$_2$—N(R$^2$)$_2$, —NR$^2$—SO$_2$R, and Q;
    wherein each Q is an optionally substituted ring selected from phenyl and a 5-6 membered heteroaryl or heterocyclyl ring containing up to four heteroatoms selected from N, O and S as ring members, wherein the optional substituents for the optionally substituted ring are up to three groups selected from $C_1$-$C_4$ alkyl, $C_1$-$C_4$ alkoxy, halo, oxo, =N—OR$^2$, —COOR$^2$, —CON(R$^2$)$^2$, —NR$^2$C(O)R$^2$, —NR$^2$C(O)OR, —C(O)NR$^2$—OR$^2$, —SO$_2$R, and —SO$_2$—N(R$^2$)$_2$, and
    each L$^2$ is independently selected from a bond and a divalent straight chain or branched $C_1$-$C_6$ alkyl, $C_2$-$C_6$ alkenyl, or $C_2$-$C_6$ alkynyl linking group;
    and each X is independently O or =NR$^{11}$;
  R$^5$ is selected from the group consisting of H, halo, amino, CN, $C_1$-$C_4$ alkyl, $C_{2-4}$ alkenyl, $C_{2-4}$ alkynyl, 5-6 membered heteroaryl containing 1-3 heteroatoms selected from N, O and S, $C_1$-$C_4$ alkoxy, and $C_1$-$C_4$ haloalkyl;
  R$^6$ is selected from the group consisting of H, halo, CN, $C_1$-$C_4$ alkyl, $C_1$-$C_4$ alkoxy, and $C_1$-$C_4$ haloalkyl;
  Y is pyridinyl optionally substituted with one to three groups selected from halo, CN, amino, hydroxy, $C_1$-$C_4$ alkyl, $C_1$-$C_4$ alkoxy, $C_1$-$C_4$ haloalkyl, and —(CH$_2$)$_{1-4}$—X, where X is selected from —OH, —CN, —N(R$^2$)$_2$, —COOR$^2$, —C(O)N(R$^2$)$_2$, —NR$^2$C(O)R$^2$, —NR$^2$C(O)OR, —SO$_2$R, and —SO$_2$N(R$^2$)$_2$;
    or Y is a group of the formula —NR$^{7A}$R$^{7B}$,
      wherein R$^{7A}$ is selected from the group consisting of H, —C(O)R$^2$, —C(O)OR$^2$, and $C_1$-$C_6$ alkyl optionally substituted with up to two groups independently selected from halogen, —OH, $C_1$-$C_4$ haloalkyl, $C_1$-$C_4$ alkoxy, oxo, =N—OR$^2$, —N(R$^2$)$_2$, $C_3$-$C_7$ cycloalkyl, —COOR$^2$, —C(O)N(R$^2$)$_2$, —NR$^2$C(O)R$^2$, —NR$^2$C(O)OR, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy;
      R$^{7B}$ is -L$^3$-Q$^3$ or $C_1$-$C_6$ alkyl optionally substituted with up to two groups independently selected from halogen, —OH, $C_1$-$C_4$ haloalkyl, $C_1$-$C_4$ alkoxy, oxo, —N(R$^2$)$_2$, $C_3$-$C_7$ cycloalkyl, —COOR$^2$, —C(O)N(R$^2$)$_2$, —NR$^2$C(O)R$^2$, —NR$^2$C(O)OR, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy
        wherein L$^3$ is a bond or a straight or branched chain $C_1$-$C_6$ alkyl linker, and Q$^3$ is selected from pyridinyl and a 4-7 membered heterocyclyl containing one or two heteroatoms selected from N, O and S as ring members, and wherein Q$^3$ is optionally substituted with up to three groups selected from halogen, CN, —OH, $C_1$-$C_4$ alkyl, $C_1$-$C_4$ haloalkyl, $C_1$-$C_4$ alkoxy, oxo, =N—OR$^2$, —N(R$^2$)$_2$, —COOR$^2$, —C(O)N(R$^2$)$_2$, —NR$^2$C(O)R$^2$, —NR$^2$C(O)OR;
      or R$^{7A}$ and R$^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by R$^{7A}$ and R$^{7B}$ together with the nitrogen atom to which they are attached is optionally substituted by up to four groups selected from halogen, —CN, hydroxy, phenyl, oxo, —OR$^9$, —N(R$^9$)$_2$, —COOR$^9$, —C(O)N(R$^9$)$_2$, $C_1$-$C_4$ alkyl, $C_1$-$C_4$ haloalkyl, $C_1$-$C_4$ alkoxy, oxo, $C_3$-$C_6$ cycloalkyl, and a 4-6 membered heteroaryl or heterocyclyl group that contains up to two heteroatoms selected from N, O and S as ring members,
        wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —OR$^{10}$, =N—OR$^{10}$, —N(R$^{10}$)$_2$, —COOR$^{10}$, —N(R$^{10}$)—C(O)—O—($C_1$-$C_4$ alkyl), —C(O)N(R$^{10}$)$_2$, $C_1$-$C_4$ alkyl, $C_1$-$C_4$ haloalkyl, and $C_1$-$C_4$ alkoxy;
  R$^8$ is selected from the group consisting of H, halo, CN, $C_1$-$C_4$ alkyl optionally substituted with hydroxy or amino, $C_{2-4}$ alkenyl, $C_1$-$C_4$ alkoxy, and $C_1$-$C_4$ haloalkyl;

$R^9$ and $R^{10}$ are each independently selected from H and $C_1$-$C_4$ alkyl optionally substituted with up to three groups selected from halogen, —OH, $C_1$-$C_4$ alkoxy, CN, —$NR^{12}R^{13}$, —$SO_2R$ and oxo;
  or two $R^9$ or two $R^{10}$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —$NR^{12}R^{13}$, and oxo;
each $R^{11}$ is independently hydrogen or $C_1$-$C_4$ alkyl optionally substituted with one or two groups selected from halogen, —OH, $C_1$-$C_4$ alkoxy, CN, —$NH_2$, —$NH(C_1$-$C_4$ alkyl), —$N(C_1$-$C_4$ alkyl)$_2$, —$SO_2(C_1$-$C_4$ alkyl), and oxo;
each $R^{12}$ and $R^{13}$ is independently hydrogen or $C_1$-$C_4$ alkyl optionally substituted with one or two groups selected from halogen, —OH, $C_1$-$C_4$ alkoxy, CN, —$NH_2$, —$NH(C_1$-$C_4$ alkyl), —$N(C_1$-$C_4$ alkyl)$_2$, —$SO_2(C_1$-$C_4$ alkyl), and oxo;
  or $R^{12}$ and $R^{13}$ together with the nitrogen atom to which they are attached form a 4- to 6-membered heterocyclyl optionally including an additional heteroatom selected from N, O and S as a ring member and optionally substituted by one to three substituents selected from OH, halogen, oxo, =N—$OR^{11}$, $C_1$-$C_6$ alkyl optionally substituted by one to three halogen atoms or $NH_2$, $C_1$-$C_6$ alkoxy optionally substituted by one or more OH groups or $C_1$-$C_6$ alkoxy; and —$C(O)OC_1$-$C_6$ alkyl;
or a pharmaceutically acceptable salt thereof.

1C. In a certain aspect of embodiment 1, compounds of Formula (I) wherein $R^1$ is selected from the group consisting of $C_1$-$C_6$ alkyl, $C_2$-$C_6$ alkenyl, $C_2$-$C_6$ alkynyl, and $C_3$-$C_7$ cycloalkyl, each of which is optionally substituted with up to three groups selected from halogen, —$OR^2$, CN, —$N(R^2)_2$, and oxo;
$R^3$ is selected from the group consisting of H, —$OR^2$, $C_1$-$C_6$ alkyl, $C_2$-$C_6$ alkenyl, $C_2$-$C_6$ alkynyl, $C_3$-$C_7$ cycloalkyl, -$L^1$-$N(R^2)_2$, -$L^1$-$COOR^2$, -$L^1$-$CON(R^2)_2$, -$L^1$-$N(R^2)C(O)R^2$, -$L^1$-$N(R^2)C(O)OR$, -$L^1$—$SO_2R$, -$L^1$-$N(R^2)$—$SO_2$—R, and -$L^1$-$SO_2$—$N(R^2)_2$;
$L^1$ is a bond or a $C_1$-$C_4$ straight or branched chain alkylene linker;
each R is independently $C_1$-$C_4$ alkyl optionally substituted with one to three groups selected from halogen, —OH, $C_1$-$C_4$ alkoxy, CN, —$NH_2$, —$NH(C_1$-$C_4$ alkyl), —$N(C_1$-$C_4$ alkyl)$_2$, —$SO_2(C_1$-$C_4$ alkyl), and oxo;
each $R^2$ is independently H or $C_1$-$C_4$ alkyl optionally substituted with up to three groups selected from halogen, —OH, $C_1$-$C_4$ alkoxy, CN, —$NR^{12}R^{13}$, —$SO_2R$ and oxo;
  or two $R^2$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —$NR^{12}R^{13}$, and oxo;
$R^4$ is selected from the group consisting of H, halo, $C_1$-$C_4$ haloalkyl, —$NH_2$, —CN, $C_1$-$C_6$ alkyl, $C_2$-$C_6$ alkenyl, $C_2$-$C_6$ alkynyl, $C_1$-$C_6$ alkoxy, -$L^2$-$C_3$-$C_7$ cycloalkyl, -$L^2$-CN, -$L^2$-$N(R^2)_2$, -$L^2$-$NR^2C(O)$—$R^2$, -$L^2$-$NR^2C(O)$—$OR^2$, -$L^2$-$NR^2C(O)$—$N(R^2)_2$, -$L^2$-$NR^2C(=NR^2)$—$N(R^2)_2$, -$L^2$-$C(O)$—$NR^2$—$OR^2$, -$L^2$-$COOR^2$, -$L^2$-$CON(R^2)_2$, -$L^2$-$C(=NR^2)$—$N(R^2)_2$, -$L^2$-$C(=NR^2)$—$NR^2$—$OR^2$, -$L^2$-$SO_2R$, -$L^2$-$SO_2$—$N(R^2)_2$, -$L^2$-Q, and -$L^2$-O—($C_1$-$C_4$ alkyl) wherein the $C_1$-$C_4$ alkyl is optionally substituted with one or two groups selected from —$OR^2$, —CN, oxo, =N—$OR^2$, —$N(R^2)_2$, —$COOR^2$, —$C(=X)$—$NR^2$—$OR^2$, —$C(=X)$—$N(R^2)_2$, —$NR^2C(=X)R^2$, —$NR^2C(=X)OR$, —$NR^2C(=X)N(R^2)_2$, —$NR^2C(O)$—O-$L^2$-Q, —$CON(R^2)_2$, —$SO_2R$, —$SO_2$—$N(R^2)_2$, —$NR^2$—$SO_2R$, and Q;
  wherein each Q is an optionally substituted ring selected from phenyl and a 5-6 membered heteroaryl or heterocyclyl ring containing up to four heteroatoms selected from N, O and S as ring members, wherein the optional substituents for the optionally substituted ring are up to three groups selected from $C_1$-$C_4$ alkyl, $C_1$-$C_4$ alkoxy, halo, oxo, =N—$OR^2$, —$COOR^2$, —$CON(R^2)^2$, —$NR^2C(O)R^2$, —$NR^2C(O)OR$, —$C(O)NR^2$—$OR^2$, —$SO_2R$, and —$SO_2$—$N(R^2)_2$, and
  each $L^2$ is independently selected from a bond and a divalent straight chain or branched $C_1$-$C_6$ alkyl, $C_2$-$C_6$ alkenyl, or $C_2$-$C_6$ alkynyl linking group;
and each X is independently O or =$NR^{11}$;
$R^5$ is selected from the group consisting of H, halo, CN, $C_1$-$C_4$ alkyl, $C_1$-$C_4$ alkoxy, and $C_1$-$C_4$ haloalkyl;
$R^6$ is selected from the group consisting of H, halo, CN, $C_1$-$C_4$ alkyl, $C_1$-$C_4$ alkoxy, and $C_1$-$C_4$ haloalkyl;
Y is pyridinyl optionally substituted with one to three groups selected from halo, CN, amino, hydroxy, $C_1$-$C_4$ alkyl, $C_1$-$C_4$ alkoxy, $C_1$-$C_4$ haloalkyl, and —$(CH_2)_{1-4}$—X, where X is selected from —OH, —CN, —$N(R^2)_2$, —$COOR^2$, —$C(O)N(R^2)_2$, —$NR^2C(O)R^2$, —$NR^2C(O)OR$, —$SO_2R$, and —$SO_2N(R^2)_2$;
  or Y is a group of the formula —$NR^{7A}R^{7B}$,
  wherein $R^{7A}$ is selected from the group consisting of H, —$C(O)R^2$, —$C(O)OR^2$, and $C_1$-$C_6$ alkyl optionally substituted with up to two groups independently selected from halogen, —OH, $C_1$-$C_4$ haloalkyl, $C_1$-$C_4$ alkoxy, oxo, =N—$OR^2$, —$N(R^2)_2$, $C_3$-$C_7$ cycloalkyl, —$COOR^2$, —$C(O)N(R^2)_2$, —$NR^2C(O)R^2$, —$NR^2C(O)OR$, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy;
$R^{7B}$ is -$L^3$-$Q^3$ or $C_1$-$C_6$ alkyl optionally substituted with up to two groups independently selected from halogen, —OH, $C_1$-$C_4$ haloalkyl, $C_1$-$C_4$ alkoxy, oxo, —$N(R^2)_2$, $C_3$-$C_7$ cycloalkyl, —$COOR^2$, —$C(O)N(R^2)_2$, —$NR^2C(O)R^2$, —$NR^2C(O)OR$, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy
  wherein $L^3$ is a bond or a straight or branched chain $C_1$-$C_6$ alkyl linker, and $Q^3$ is selected from pyridinyl and a 4-7 membered heterocyclyl containing one or two heteroatoms selected from N, O and S as ring members, and wherein $Q^3$ is optionally substituted with up to three groups selected from halogen, CN, —OH, $C_1$-$C_4$ alkyl, $C_1$-$C_4$ haloalkyl, $C_1$-$C_4$ alkoxy, oxo, =N—$OR^2$, —$N(R^2)_2$, —$COOR^2$, —$C(O)N(R^2)_2$, —$NR^2C(O)R^2$, —$NR^2C(O)OR$;

or
$R^{7A}$ and $R^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by $R^{7A}$ and $R^{7B}$ together with the nitrogen atom to which they are attached is optionally substituted by up to four groups selected from halogen, —CN, hydroxy, phenyl, oxo, —OR$^9$, —N(R$^9$)$_2$, —COOR$^9$, —C(O)N(R$^9$)$_2$, C$_1$-C$_4$ alkyl, C$_1$-C$_4$ haloalkyl, C$_1$-C$_4$ alkoxy, oxo, C$_3$-C$_6$ cycloalkyl, and a 4-6 membered heteroaryl or heterocyclyl group that contains up to two heteroatoms selected from N, O and S as ring members, wherein the C$_1$-C$_4$ alkyl, C$_3$-C$_6$ cycloalkyl, phenyl, and 4-6 membered heteroaryl or heterocyclyl are each optionally substituted by up to three groups independently selected from halogen, —CN, hydroxy, oxo, —OR$^{10}$, =N—OR$^{10}$, —N(R$^{10}$)$_2$, —COOR$^{10}$, —N(R$^{10}$)—C(O)—O—(C$_1$-C$_4$ alkyl), —C(O)N(R$^{10}$)$_2$, C$_1$-C$_4$ alkyl, C$_1$-C$_4$ haloalkyl, and C$_1$-C$_4$ alkoxy;

R$^8$ is selected from the group consisting of H, halo, CN, C$_1$-C$_4$ alkyl, C$_1$-C$_4$ alkoxy, and C$_1$-C$_4$ haloalkyl;

R$^9$ and R$^{10}$ are each independently selected from H and C$_1$-C$_4$ alkyl optionally substituted with up to three groups selected from halogen, —OH, C$_1$-C$_4$ alkoxy, CN, —NR$^{12}$R$^{13}$, —SO$_2$R and oxo;

or two R$^9$ or two R$^{10}$ on the same nitrogen can be taken together to form a 4-6 membered heterocyclic ring optionally containing an additional heteroatom selected from N, O and S as a ring member and optionally substituted with up to three groups selected from halogen, —OH, C$_1$-C$_4$ alkyl, C$_1$-C$_4$ alkoxy, CN, —NR$^{12}$R$^{13}$, and oxo;

each R$^{11}$ is independently hydrogen or C$_1$-C$_4$ alkyl optionally substituted with one or two groups selected from halogen, —OH, C$_1$-C$_4$ alkoxy, CN, —NH$_2$, —NH(C$_1$-C$_4$ alkyl), —N(C$_1$-C$_4$ alkyl)$_2$, —SO$_2$(C$_1$-C$_4$ alkyl), and oxo;

each R$^{12}$ and R$^{13}$ is independently hydrogen or C$_1$-C$_4$ alkyl optionally substituted with one or two groups selected from halogen, —OH, C$_1$-C$_4$ alkoxy, CN, —NH$_2$, —NH(C$_1$-C$_4$ alkyl), —N(C$_1$-C$_4$ alkyl)$_2$, —SO$_2$(C$_1$-C$_4$ alkyl), and oxo;

or R$^{12}$ and R$^{13}$ together with the nitrogen atom to which they are attached form a 4- to 6-membered heterocyclyl optionally including an additional heteroatom selected from N, O and S as a ring member and optionally substituted by one to three substituents selected from OH, halogen, oxo, =N—OR$^{11}$, C$_1$-C$_6$ alkyl optionally substituted by one to three halogen atoms or NH$_2$, C$_1$-C$_6$ alkoxy optionally substituted by one or more OH groups or C$_1$-C$_6$ alkoxy; and —C(O)OC$_1$-C$_6$ alkyl;

or a pharmaceutically acceptable salt thereof.

2. The compound or pharmaceutically acceptable salt according to embodiment 1, wherein R$^1$ is C$_3$-C$_6$ cycloalkyl or C$_2$-C$_4$ alkyl. In certain of these embodiments, R$^1$ is cyclopropyl.

3. The compound or pharmaceutically acceptable salt according to embodiment 1 or 2 or a pharmaceutically acceptable salt thereof, wherein R$^5$ is H or halogen. In certain of these embodiments, R$^5$ is H or F.

4. The compound or pharmaceutically acceptable salt of any of embodiments 1-3, wherein R$^6$ is H or F. Compounds wherein R$^6$ is F are sometimes preferred.

5. The compound or pharmaceutically acceptable salt of any of embodiments 1-4, wherein R$^8$ is methyl, ethyl or methoxy; in certain of these embodiments, R$^8$ is methyl or methoxy.

6. The compound or pharmaceutically acceptable salt of any of embodiments 1-5, wherein R$^3$ is H, C$_{1-2}$ alkyl, or C$_{1-2}$ haloalkyl. In specific examples of these embodiments, R$^3$ is H, Me or Cl.

7. The compound or pharmaceutically acceptable salt of any of embodiments 1-5, wherein R$^3$ is —COOR$^2$ or —SO$_2$R. In particular, embodiments wherein R$^3$ is COOH, COOMe, or COOEt. In an alternative version of embodiment 7, the compound of any of embodiments 1-5 wherein R$^3$ is halo, particularly F or Cl.

8. The compound or pharmaceutically acceptable salt of any of embodiments 1-7, wherein R$^4$ is H.

9. The compound or pharmaceutically acceptable salt of any of embodiments 1-7, wherein R$^4$ is H, Me or CN. An alternative version of embodiment 9 is a compound of any of embodiments 1-7, wherein R$^4$ is —CH$_2$NH$_2$.

10. The compound or pharmaceutically acceptable salt of embodiment 1 (1A, 1B or 1C), which is of the formula (II):

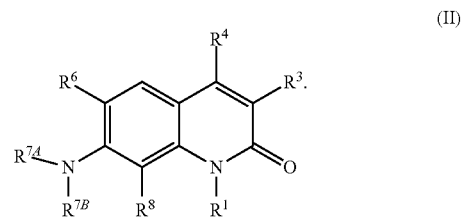

(II)

11. The compound or pharmaceutically acceptable salt according to embodiment 10, wherein R$^{7A}$ is H.

12. The compound or pharmaceutically acceptable salt according to embodiment 10, wherein R$^{7A}$ and R$^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by R$^{7A}$ and R$^{7B}$ together with the nitrogen atom to which they are attached is optionally substituted by up to three groups selected from halogen, —CN, hydroxy, phenyl, oxo, —OR$^9$, —N(R$^9$)$_2$, —COOR$^9$, —C(O)N(R$^9$)$_2$, C$_1$-C$_4$ alkyl, C$_1$-C$_4$ haloalkyl, C$_1$-C$_4$ alkoxy, oxo, C$_3$-C$_6$ cycloalkyl, and a 4-6 membered heteroaryl or heterocyclyl group that contains up to two heteroatoms selected from N, O and S as ring members, wherein the C$_1$-C$_4$ alkyl, C$_3$-C$_6$ cycloalkyl, phenyl, and 4-6 membered heteroaryl or heterocyclyl are each optionally substituted by up to three groups independently selected from halogen, —CN, hydroxy, oxo, —OR$^{10}$, =N—OR$^{10}$, —N(R$^{10}$)$_2$, —COOR$^{10}$, —C(O)N(R$^{10}$)$_2$, C$_1$-C$_4$ alkyl, C$_1$-C$_4$ haloalkyl, and C$_1$-C$_4$ alkoxy.

In certain of these embodiments, R$^{7A}$ and R$^{7B}$ together with the nitrogen atom to which they are attached form a pyrrolidine ring that may be substituted as described. In other of these embodiments, R$^{7A}$ and R$^{7B}$ together with the nitrogen atom to which they are attached form a 3-azabicyclo[3.1.0]hexan-3-yl group that may be substituted as described, e.g. with 0, 1 or 2 groups selected from halogen, —CN, hydroxy, phenyl, oxo, —OR$^9$, —N(R$^9$)$_2$, —COOR$^9$, —C(O)N(R$^9$)$_2$, C$_1$-C$_4$ alkyl, C$_1$-C$_4$ haloalkyl, C$_1$-C$_4$ alkoxy.

13. The compound according to any of the proceeding embodiments, or a pharmaceutically acceptable salt thereof, wherein the compound is represented by formula (III),

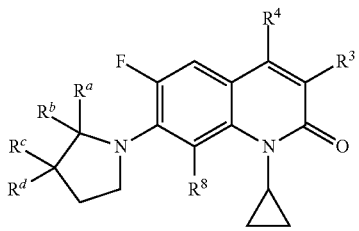

(III)

Wherein R³ is hydrogen, $C_{1-2}$ alkyl, $C_{1-2}$ haloalkyl, halo, or —C(O)OR²;

R⁴ is H or CN or —CH₂NH₂;

R⁸ is hydrogen, CN, methoxy, or methyl;

$R^a$, $R^b$, $R^c$, and $R^d$ are independently selected from the group consisting of hydrogen, OH, $C_1$-$C_4$ alkyl, $C_3$-$C_5$ cycloalkyl, —NH($C_1$-$C_4$ alkyl), and —N($C_1$-$C_4$ alkyl)₂, wherein each $C_1$-$C_4$ alkyl and each $C_3$-$C_5$ cycloalkyl is optionally substituted by OH, $C_1$-$C_4$ alkyl, $C_1$-$C_4$ alkoxy, or —NR⁹₂; or $R^a$ and $R^b$ taken together, or $R^c$ and $R^d$ taken together, may form oxo or a 3-6 membered spirocyclic ring that may contain N, O or S as a ring member;

R⁹ is independently at each occurrence selected from H, —C(O)—($C_1$-$C_4$ alkyl), —C(O)—O—($C_1$-$C_4$ alkyl), and $C_1$-$C_4$ alkyl, where each $C_1$-$C_4$ alkyl is optionally substituted with up to three groups selected from halogen, —OH, $C_1$-$C_4$ alkoxy, CN, —NR¹²R¹³, —SO₂R and oxo;

and two R⁹ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —NR¹²R¹³, and oxo; and each R¹² and R¹³ is independently hydrogen or $C_1$-$C_4$ alkyl optionally substituted with one or two groups selected from halogen, —OH, $C_1$-$C_4$ alkoxy, CN, —NH₂, —NH($C_1$-$C_4$ alkyl), —NH—C(O)($C_1$-$C_4$ alkyl), NH—C(O)—O—($C_1$-$C_4$ alkyl), —N($C_1$-$C_4$ alkyl)₂, —SO₂($C_1$-$C_4$ alkyl), and oxo.

In some of these embodiments,
R³ is hydrogen or —C(O)OR²;
R⁴ is H or CN; and
R⁸ is hydrogen or methyl.

In certain embodiments of these compounds, $R^a$ and $R^b$ are both hydrogen.

14. The compound according to embodiment 13 or embodiment 1, or a pharmaceutically acceptable salt thereof, wherein the compound has formula (IV):

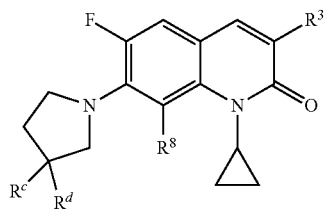

(IV)

wherein,
R³ is hydrogen, $C_{1-2}$ alkyl, $C_{1-2}$ haloalkyl, COOH or COO—$C_1$-$C_4$ alkyl;

$R^c$ is hydrogen;
$R^d$ is selected from the group consisting of —NH₂, —CH₂NH₂, —CH₂NHCH₃,

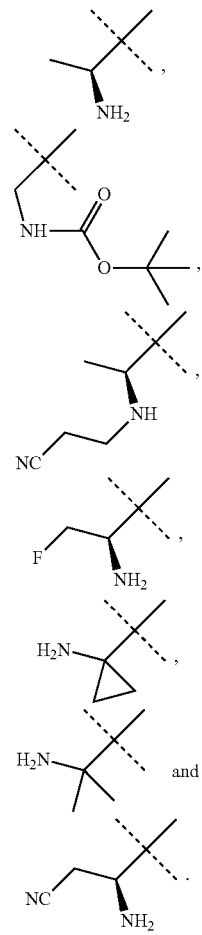

An alternative version of embodiment 14 is a compound according to embodiment 13 or embodiment 1, or a pharmaceutically acceptable salt thereof, wherein the compound has formula (IVb):

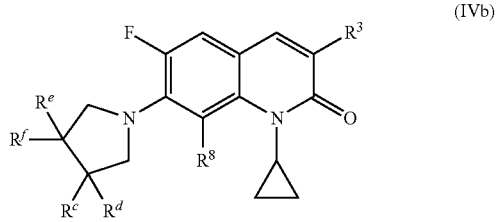

(IVb)

wherein,
R³ is hydrogen or halo;
R⁴ is H or —CH₂NH₂;
R⁵ is H, Me or halo;
$R^c$ and $R^f$ are both hydrogen, or $R^c$ and $R^f$ taken together with the atoms to which they are attached form a cyclopropyl ring;
$R^d$ and $R^e$ are each selected from the group consisting of H, —NH₂, —CH₂NH₂, —OH, —CH₂OH, —CH₂NHCH₃,

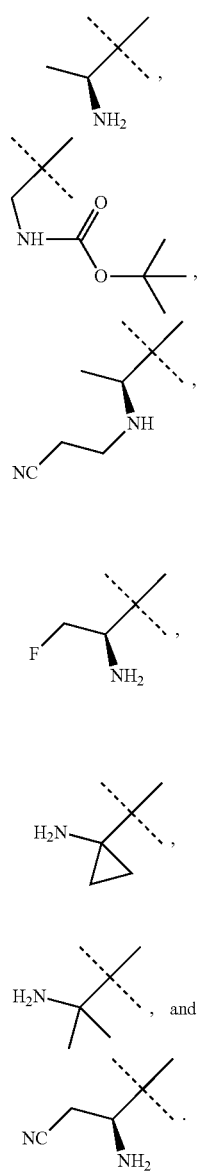
15. The compound according to embodiment 1 or 2, or a pharmaceutically acceptable salt thereof, represented by formula (V):
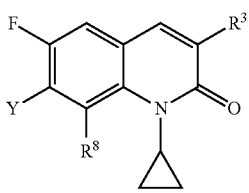
wherein,
R³ is hydrogen, $C_{1-2}$ alkyl, $C_{1-2}$ haloalkyl, —C(O)OH, C(O)—O—($C_1$-$C_4$ alkyl) or —S(O)$_2$—($C_1$-$C_4$ alkyl);
R⁸ is hydrogen, $C_1$-$C_4$ alkyl, $C_1$-$C_4$ alkoxy, or $C_1$-$C_4$ haloalkyl;
Y is selected from the group consisting of
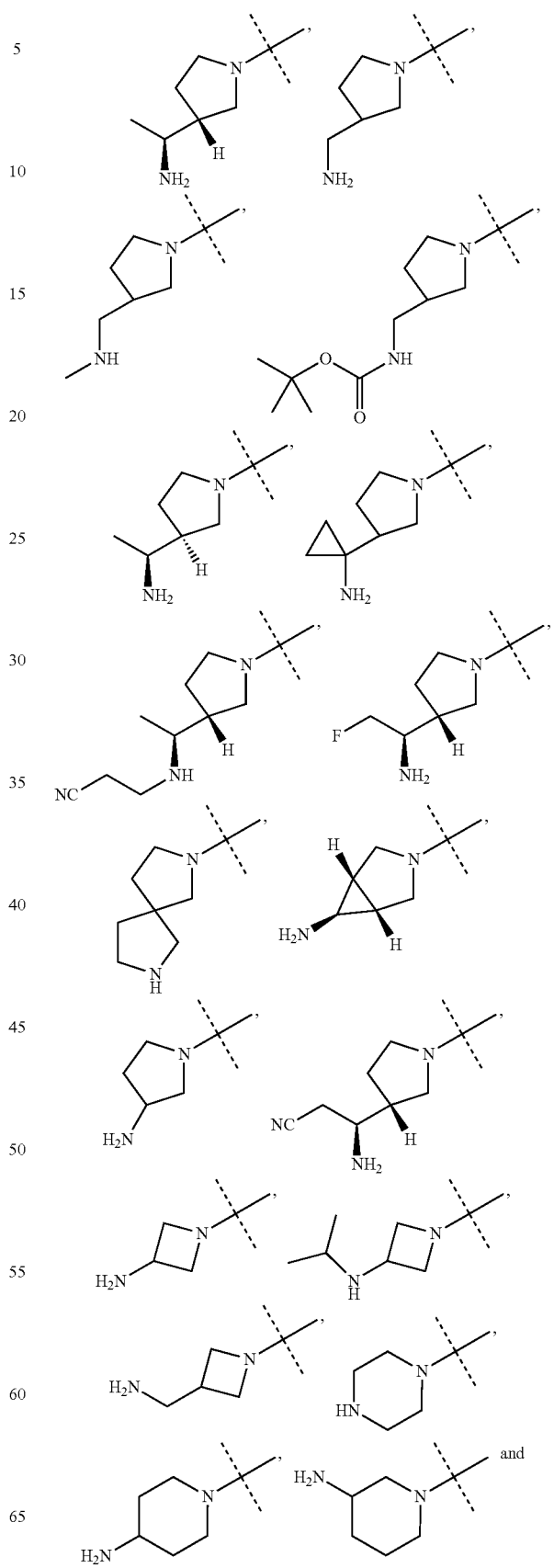

-continued

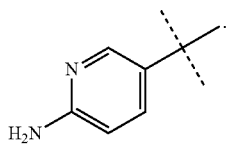

In another version of this embodiment, Y is selected from

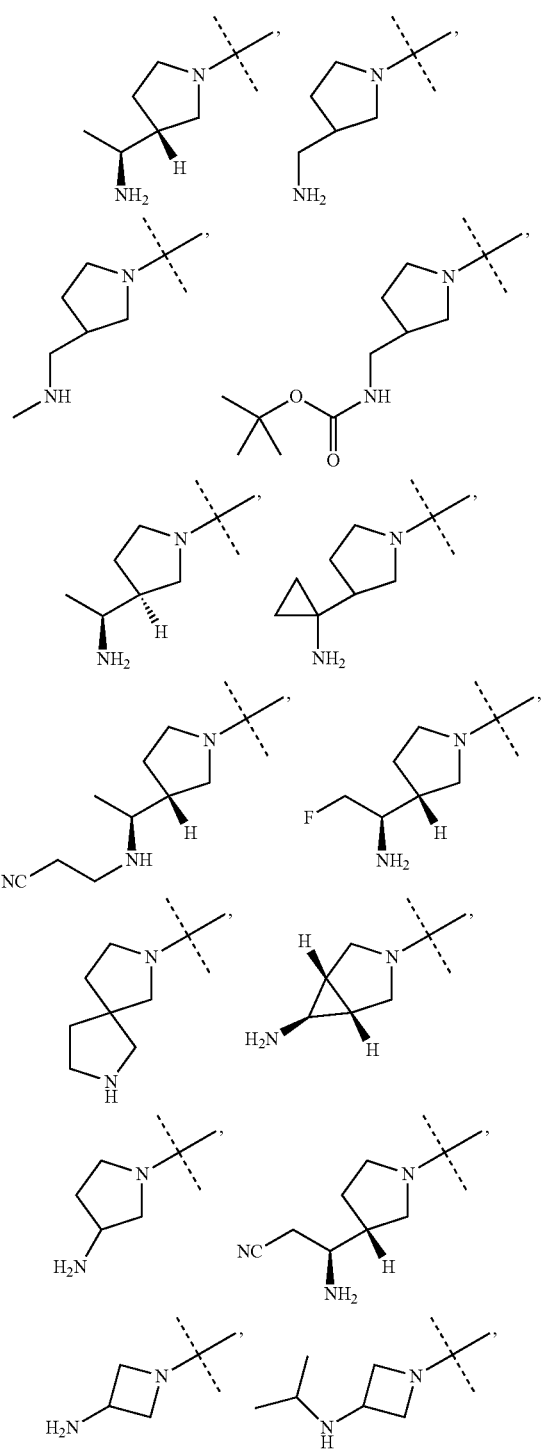

-continued

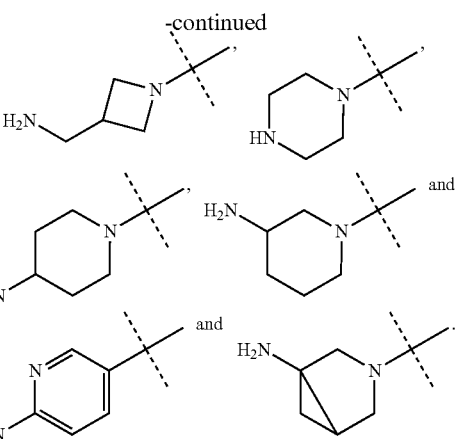

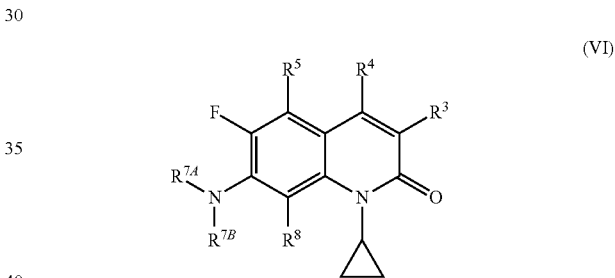

15b. Each of the compounds in the Examples and pharmaceutically acceptable salts thereof is a specific embodiment of the compounds of the invention. In particular, each of the compounds and pharmaceutically acceptable salts thereof of the Examples listed in Table 1 or in Table 2 (or both) is a specific embodiment of the compounds of the invention.

16. The compound of embodiment 1, which is a compound of formula (VI) or a pharmaceutically acceptable salt thereof, (VI)

wherein,
$R^3$ is hydrogen, $C_{1-2}$ alkyl, $C_{1-2}$ haloalkyl, or halo;
$R^4$ is hydrogen or —$CH_2NH_2$;
$R^5$ is hydrogen, Me or halo;
$R^8$ is hydrogen, $C_1$-$C_4$alkyl, $C_1$-$C_4$ alkoxy, $C_1$-$C_4$ haloalkyl, or CN; and
$R^{7A}$ and $R^{7B}$ together with the nitrogen atom to which they are attached form a 5- to 6-membered monocyclic heterocyclic group optionally including one additional heteroatom selected from N, O and S as a ring member, or a 6-7 membered bicyclic heterocyclic group optionally including one additional heteroatom selected from N, O and S as ring members,
wherein the monocyclic or bicyclic heterocyclic group formed by $R^{7A}$ and $R^{7B}$ together with the nitrogen atom to which they are attached is optionally substituted by up to four groups selected from halogen, —CN, hydroxy, phenyl, oxo, —$OR^9$, —$N(R^9)_2$, —$COOR^9$, —$C(O)N(R^9)_2$, $C_1$-$C_4$ alkyl, $C_1$-$C_4$ haloalkyl, $C_3$-$C_6$ cycloalkyl, and a 4-6 membered heteroaryl or heterocyclyl group that contains up to two heteroatoms selected from N, O and S as ring members,
wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —OR$^{10}$, =N—OR$^{10}$, —N(R$^{10}$)$_2$, —COOR$^{10}$, —N(R$^{10}$)—C(O)—O—(C$_1$-C$_4$ alkyl), —C(O)N(R$^{10}$)$_2$, C$_1$-C$_4$ alkyl, C$_1$-C$_4$ haloalkyl, and C$_1$-C$_4$ alkoxy.

17. The compound or pharmaceutically acceptable salt of embodiment 16, wherein the group represented by —NR$^{7A}$R$^{7B}$ is selected from:

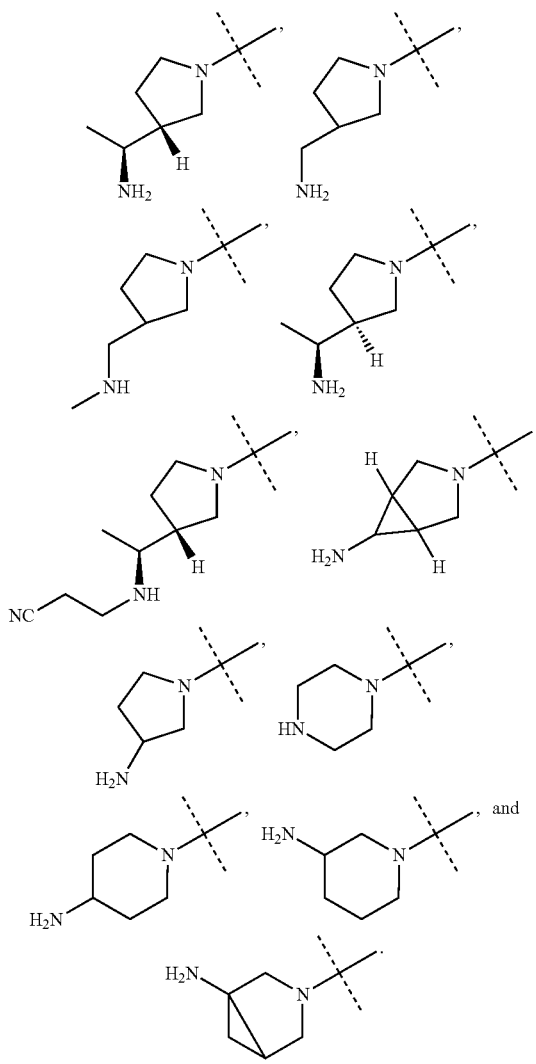

18. A pharmaceutical composition, comprising:
the compound or pharmaceutically acceptable salt according to any one of embodiments 1 to 17, and a
pharmaceutically acceptable carrier, adjuvant or vehicle.

19. The pharmaceutical composition according to embodiment 18, further comprising an additional therapeutic agent with antibacterial activity.

20. A method of inhibiting bacterial gyrase activity, comprising:
contacting bacteria with a compound or pharmaceutically acceptable salt according to any of embodiments 1 to 17. This method can be conducted in cell culture or in a live host comprising said bacteria.

21. A method for treating a subject having a bacterial infection, comprising:
administering to the subject in need thereof an antibacterially effective amount of the compound or pharmaceutically acceptable salt according to any one of embodiments 1 to 17.

22. The method of embodiment 21, wherein the bacterial infection is an infection comprising at least one bacterium selected from the group consisting of *Pseudomonas aeruginosa* and other *Pseudomonas* species, *Stenotrophomonas maltophilia*, *Burkholderia cepacia* and other *Burkholderia* species, *Acinetobacter baumannii* and other *Acinetobacter* species, *Achromobacter xylosoxidans*, *Alcaligenes denitrificans* and other Achromobacteraceae, *Citrobacter freundii* and other *Citrobacter* species, *Campylobacter jejuni*, *Klebsiella pneumoniae*, *Klebsiella oxytoca* and other *Klebsiella* species, *Enterobacter cloacae*, *Enterobacter aerogenes* and other *Enterobacter* species, *Escherichia coli*, *Salmonella enterica* and other *Salmonella* species, *Yersinia pestis*, *Proteus vulgaris* and other *Proteus* species, *Serratia marscens* and other *Serratia* species, *Morganella morganii* and other members of the Enterobacteriaceae family, *Neisseria meningitidis*, *Haemophilus influenzae*, *Moraxella cattharallis*, *Bacteroides fragilis*, *Bacteroides thetaiotaomicron* and other *Bacteroides* species, *Pasteurella multicoda* and other *Pasteurella* species, *Fransicella tularensis*, *Shigella dysenteriae* and other *Shigella* species, *Vibrio cholera* and other *Vibrio* species, *Bordetella pertussis* and other *Bordetella* species, *Helicobactor pylori* and other *Helicobacter* species, *Legionella pneumophila*, *Campylobactor jejuni*, *Staphylococcus aureus*, *Staphylococcus epidermidis* and other *Staphylococcus* species, *Enterococcus faecalis*, *Enterococcus faecium* and other *Enterococcus* species, *Streptococcus pneumoniae*, *Streptococcus pyogenes*, *Streptococcus agalactiae* and other *Streptococcus* species, *Bacillus anthracis* and other *Bacillus* species, *Peptostreptococcus magnus* and other *Peptostreptococcus* species, *Clostridium difficile* and other *Clostridium* species, *Listeria monocytogenes* and other *Listeria* species, and *Corynebacterium diptheriae* and other *Corynebacterium* species.

23. A compound according to any of embodiments 1 to 17, or a pharmaceutically acceptable salt thereof, for use in treatment of a bacterial infection.

24. Use of the compound according to any of embodiments 1 to 17, or a pharmaceutically acceptable salt thereof, in the manufacture of a medicament for the treatment of a bacterial infection.

25. The use according to embodiment 24, wherein the bacterial infection is an infection comprising at least one bacterium selected from *Pseudomonas aeruginosa* and other *Pseudomonas* species, *Stenotrophomonas maltophilia*, *Burkholderia cepacia* and other *Burkholderia* species, *Acinetobacter baumannii* and other *Acinetobacter* species, *Achromobacter xylosoxidans*, *Alcaligenes denitrificans* and other Achromobacteraceae, *Citrobacter freundii* and other *Citrobacter* species, *Campylobacter jejuni*, *Klebsiella pneumoniae*, *Klebsiella oxytoca* and other *Klebsiella* species, *Enterobacter cloacae*, *Enterobacter aerogenes* and other *Enterobacter* species, *Escherichia coli*, *Salmonella enterica* and other *Salmonella* species, *Yersinia pestis*, *Proteus vulgaris* and other *Proteus* species, *Serratia marscens* and other *Serratia* species, *Morganella morganii* and other members of the Enterobacteriaceae family, *Neisseria meningitidis*, *Haemophilus influenzae*, *Moraxella cattharallis*, *Bacteroides fragilis*, *Bacteroides thetaiotaomicron* and other Bacteriodes species, *Pasteurella multicoda* and other *Pasteurella* species, *Fransicella tularensis*, *Shigella dysenteriae* and other *Shigella* species, *Vibrio cholera* and other *Vibrio* species, *Bordetella pertussis* and other *Bordetella* species, Helicobactor pylori and other Helicobacter species, Legionella pneumophila, Campylobactor jejuni, Staphylococcus aureus, Staphylococcus epidermidis and other Staphylococcus species, Enterococcus faecalis, Enterococcus faecium and other Enterococcus species, Streptococcus pneumoniae, Streptococcus pyogenes, Streptococcus agalactiae and other Streptococcus species, Bacillus anthracis and other Bacillus species, Peptostreptococcus magnus and other Peptostreptococcus species, Clostridium difficile and other Clostridium species, Listeria monocytogenes and other Listeria species, and Corynebacterium diptheriae and other Corynebacterium species.

26. In another embodiment of the invention, the compound is selected from the compounds of the Examples, especially compounds of the Examples listed in Table 2, and pharmaceutically acceptable salts of these compound. Compounds and pharmaceutically acceptable salts of this embodiment, and pharmaceutical compositions containing them admixed with a pharmaceutically acceptable excipient or carrier, are useful in accordance with the methods described in embodiments 19-25.

The compounds as defined in the embodiments may be synthesized by the general synthetic routes below, specific examples of which are described in more detail in the Examples section. Reaction schemes in the Examples illustrate methods used to make selected compounds of the invention, and can be adapted for synthesis of additional compounds of the invention using standard methods and available starting materials. The following general methods can be used.

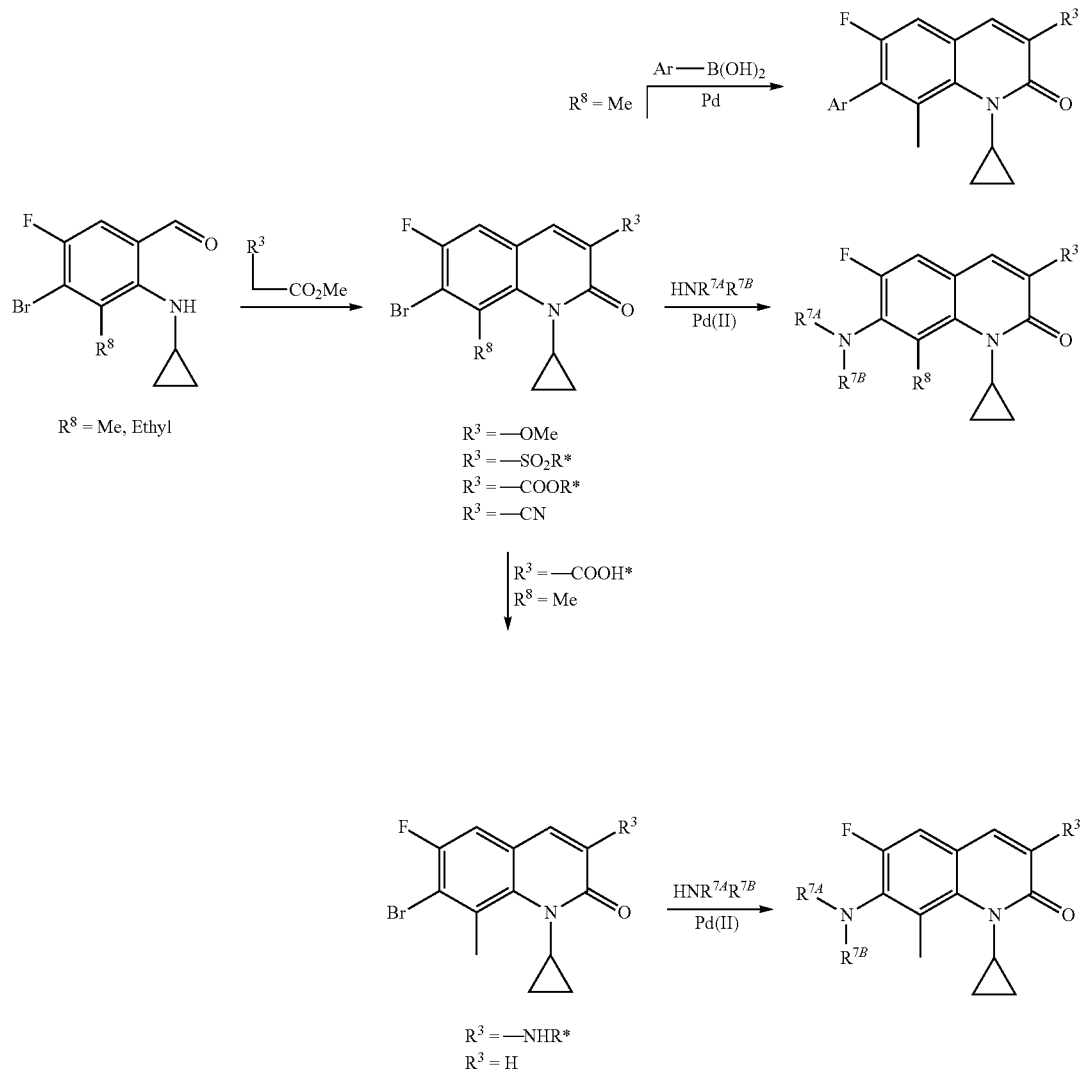

A variety of functional groups can be introduced at the $R^3$ via the route shown in Scheme 1. In addition, the ester group at the $R^3$ position can also be modified by conventional methods to introduce a variety of substituents at that position. It can also be hydrolyzed and removed by decarboxylation. The bromide at $R^3$ can be replaced by various groups by methods illustrated in the examples above. Illustrative examples are described herein.

Scheme 2. General methods to vary $R^4$.

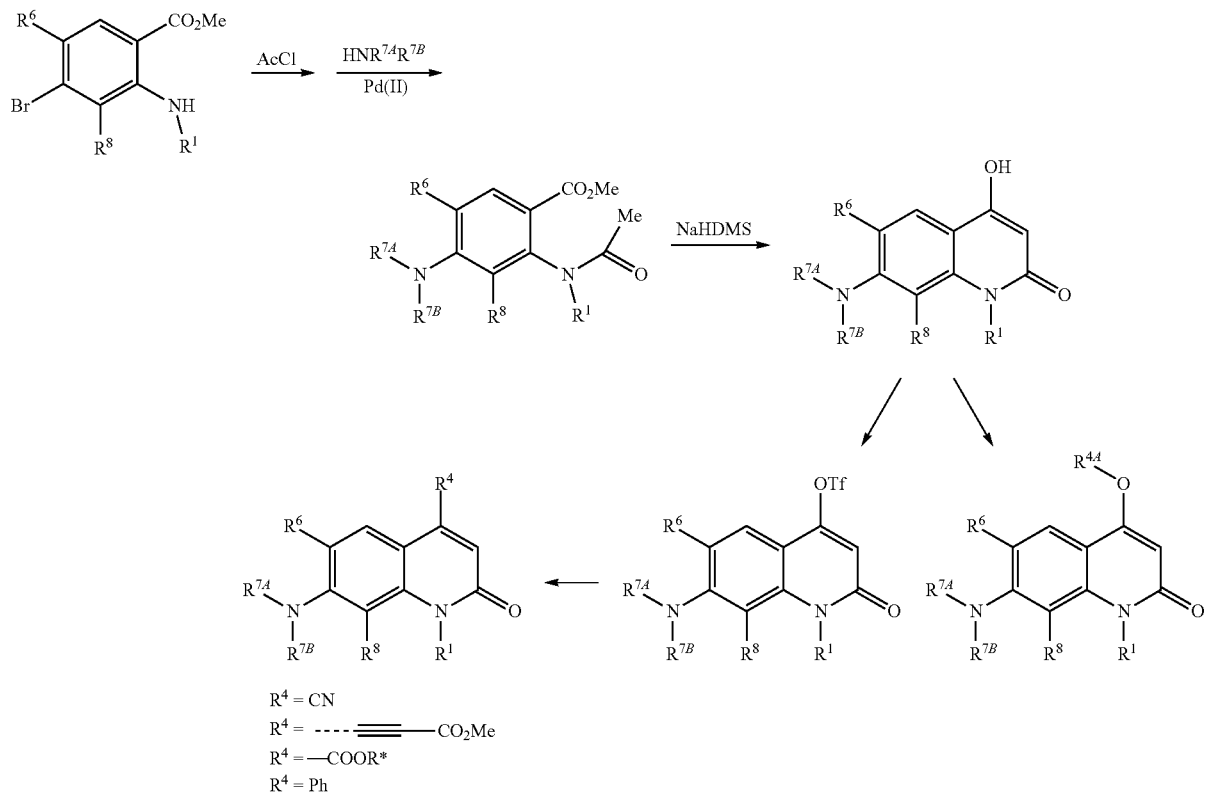

Using this method, a triflate can be introduced at the 4-position as shown, and the triflate can then be replaced by various groups by methods illustrated in the examples below. The functional groups introduced at the $R^4$ position can then be further modified by known methods—examples of such modifications are included in the examples below.

Scheme 3. Methods to vary $R^3$ and $R^8$.

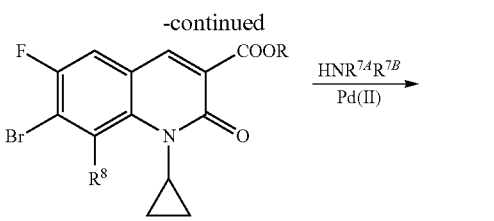

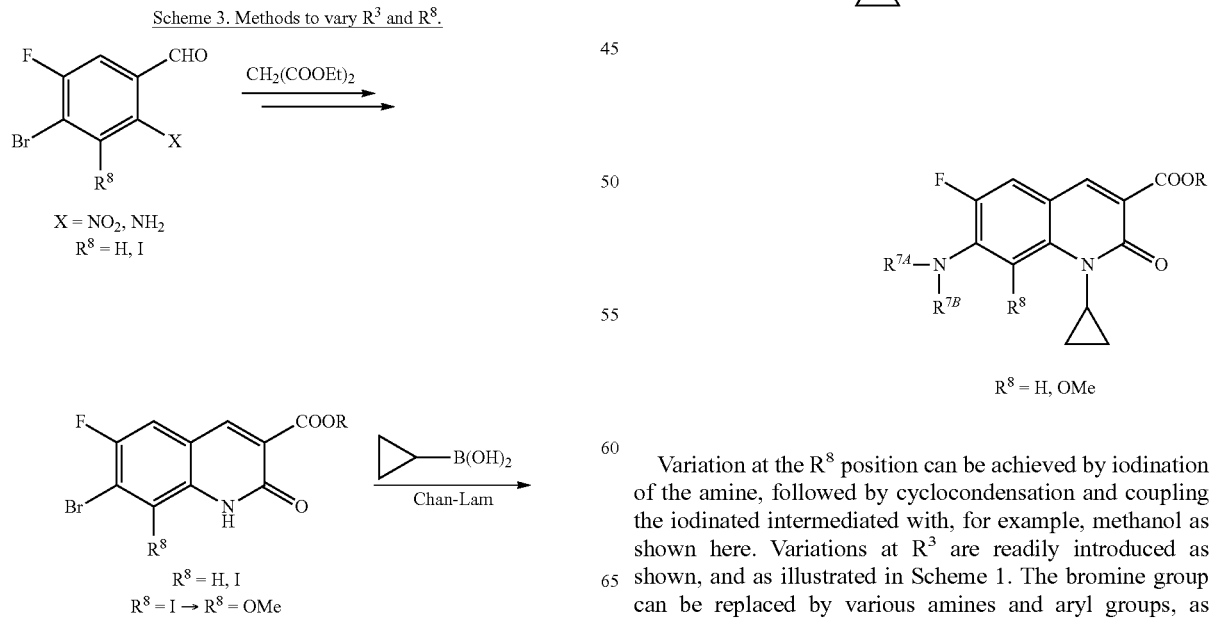

Variation at the $R^8$ position can be achieved by iodination of the amine, followed by cyclocondensation and coupling the iodinated intermediated with, for example, methanol as shown here. Variations at $R^3$ are readily introduced as shown, and as illustrated in Scheme 1. The bromine group can be replaced by various amines and aryl groups, as illustrated in Schemes 1 and 2.

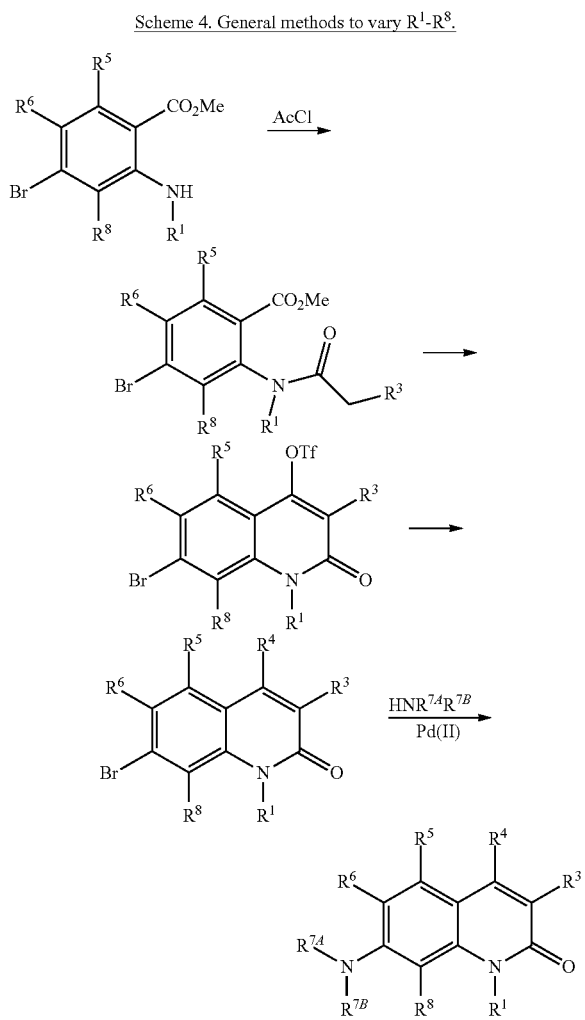

Scheme 4. General methods to vary $R^1$-$R^8$.

Variation at the various positions can be achieved by synthesis of phenyl ester intermediates, followed by cyclocondensation and coupling of the triflate intermediate. Variations at —$NR^{7A}R^{7B}$ are readily introduced by coupling different amines as shown, and as illustrated in Scheme 2.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Within the scope of this text, a readily removable group that is not a constituent of the particular desired end product of the compounds of the present invention is designated a "protecting group", a term that is well understood by those of skill in the art. A characteristic of protecting groups is that they can be removed readily (i.e. without the occurrence of undesired secondary reactions) for example by solvolysis, reduction, photolysis or alternatively under physiological conditions (e.g. by enzymatic cleavage). The protection of functional groups by such protecting groups, the protecting groups themselves, and their cleavage reactions are well known in the art and are described in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der Organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974.

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein wherein one or more atoms of the structure is enriched in or represents an isotope having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules where the active ingredient is mixed with water or an oil medium, such as peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound according to anyone of Formulae (I) to (VI), or a pharmaceutically acceptable salt thereof, and at least one other therapeutic agent as a combined preparation for simultaneous, separate or sequential use in therapy. In one embodiment, the therapy is the prevention or treatment of a disease or condition mediated by gyrase activity. Products provided as a combined preparation include a composition comprising the compound according to anyone of Formulae (I) to (VI), or a pharmaceutically acceptable salt thereof and the other therapeutic agent(s) together in the same pharmaceutical composition, or the compound according to any one of Formulae (I) to (VI), or a pharmaceutically acceptable salt thereof and the other therapeutic agent(s) in separate form, e.g. in the form of a kit.

In one embodiment, the invention provides a pharmaceutical composition comprising a compound according to anyone of Formulae (I) to (VI), or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of Formulae (I) to (VI), or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formulae (I) to (VI) for preventing and/or treating a disease or condition mediated by gyrase activity, wherein the medicament is prepared for administration with another therapeutic agent. The invention also provides the use of another therapeutic agent for preventing and/or treating a disease or condition mediated by gyrase activity, wherein the medicament is administered with a compound according to anyone of Formulae (I) to (VI), or a pharmaceutically acceptable salt thereof.

The invention also provides a compound of formulae ((I) to (VI)) for use in a method of prevention and/or treating a disease or condition mediated by gyrase activity, wherein the compound according to anyone of Formulae (I) to (VI), or a pharmaceutically acceptable salt thereof, is prepared for administration with another therapeutic agent. The invention also provides another therapeutic agent for use in a method of preventing and/or treating a disease or condition mediated by gyrase activity wherein the other therapeutic agent is prepared for administration with a compound according to anyone of Formulae (I) to (VI), or a pharmaceutically acceptable salt thereof. The invention also provides a compound according to anyone of Formulae (I) to (VI), or a pharmaceutically acceptable salt thereof, for use in a method of preventing and/or treating a disease or condition mediated by gyrase activity wherein the compound according to anyone of Formulae (I) to (VI), or a pharmaceutically acceptable salt thereof, is administered with another therapeutic agent. The invention also provides another therapeutic agent for use in a method of preventing and/or treating a disease or condition mediated by gyrase activity wherein the other therapeutic agent is administered with a compound according to anyone of Formulae (I) to (VI), or a pharmaceutically acceptable salt thereof.

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) *Curr Opin Immunol* 14: 391779-82; Bennett et al. (2003) *J. Immunol.* 170:711-8). PD-1 is expressed on activated B cells, T cells, and monocytes. PD-1 is an immune-inhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antibacterial compounds, these immunomodulators can enhance the antimicrobial response, and thus enhance efficacy relative to treatment with the antibacterial compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antibacterial compounds described herein, e.g., compounds of Formulas (I)-(VI) as described herein including those of embodiments 1-17, are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509, WO2009/114335, and WO2013/079174.

In some embodiments, the immunomodulator is Pidilizumab (CT-011; Cure Tech), a humanized IgG1 k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents useful as immunomodulators for methods of the invention include YW243.55.570 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No. 09050561, U.S. Pat. No. 8,586,023, PCT Publication Nos.: WO 2010/003118 and 2011/090754, or an anti-GITR antibody described, e.g., in U.S. Pat. No. 7,025,962, European Patent No. 194718361, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antibacterial compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antibacterial compounds of the invention in combination with an immunomodulator include these:

i. A method to treat a bacterial infection in a subject, comprising administering to the subject a compound of Formula (I) including any of embodiments 1-17 as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.570, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016.

xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg, e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

EXAMPLES

General Conditions:

If not indicated otherwise, the analytical HPLC conditions are as follows: The compounds and/or intermediates were characterized by high performance liquid chromatography (HPLC) using a UPLC Waters instrument (Milford, Mass.). HPLC solvent A was 100% Water with 0.1% trifluoroacetic acid (TFA) and solvent B was 100% acetonitrile with 0.1% TFA from EMD Chemicals Inc. The instrument was a Waters ACQUITY UPLC system with 1.2 mL/min flow rate; column Kinetex-C18, 2.6 um, 2.1×50 mm from Phenomenex, column temperature: 50° C.; gradient: 2-88% solvent B over 1.29 min or 9.79 min period; Compounds were detected by ultraviolet light (UV) absorption at either 220 or 254 nm.

HPLC/Mass spectrometric analysis (LC/MS) was performed on Waters ACQUITY UPLC system and equipped with a ZQ 2000 or SQD MS system; Column: Kinetex by Phenomenex, 2.6 um, 2.1×50 mm, column temperature: 50° C.; gradient: 2-88% (or 00-45%, or 65-95%) solvent B over a 1.29 min period; flow rate 1.2 mL/min. Compounds were detected by a Waters Photodiode Array Detector. All masses were reported as those of the protonated parent ions, molecular weight range 150-850; cone Voltage 20 V.

NMR spectra were run on open access Varian 400 NMR spectrometers. Spectra were measured at 298K and were referenced using the solvent peak.

Preparative separations are carried out using a Combiflash Rf system (Teledyne Isco, Lincoln, Nebr.) with RediSep silica gel cartridges (Teledyne Isco, Lincoln, Nebr.) or SiliaSep silica gel cartridges (Silicycle Inc., Quebec City, Canada) or by flash column chromatography using silica gel (230-400 mesh) packing material, or by HPLC using a Waters 2767 Sample Manager, C-18 reversed phase Sunfire column, 30×50 mm, flow 75 mL/min. Typical solvents employed for the Combiflash Rf system and flash column chromatography are dichloromethane, methanol, ethyl acetate, hexane, heptane, acetone, aqueous ammonia (or ammonium hydroxide), and triethyl amine. Typical solvents employed for the reverse phase HPLC are varying concentrations of acetonitrile and water with 0.1% trifluoroacetic acid.

The following examples are intended to illustrate the invention and are not to be construed as being limitations thereon. Temperatures are given in degrees centigrade. If not mentioned otherwise, all evaporations are performed under reduced pressure. The structure of final products, intermediates and starting materials is confirmed by standard analytical methods, e.g., MS, and NMR. Abbreviations used are those conventional in the art. If not defined, the terms have their generally accepted meanings.

Abbreviations:
BiPy 2,2'-bipyridine
br broad
d doublet
DCM dichloromethane
DCE Dichloroethane
DMF N,N-dimethylformamide
DMAP 4-Dimethylaminopyridine
DMSO dimethylsulfoxide
EDCI 1-ethyl-3-(3'-dimethylaminopropyl) carbodiimide
EtOAc ethyl acetate
HPLC high pressure liquid chromatography
LC-MS liquid chromatography and mass spectrometry
MeOH methanol
MS mass spectrometry
m multiplet
min minutes
ml milliliter(s)
NMR nuclear magnetic resonance
ppm parts per million
Rt retention time
RT or rt room temperature
s singlet
t triplet
THF tetrahydrofuran
UPLC Ultra Performance Liquid Chromatography Referring to the examples that follow, compounds of the invention were synthesized using the methods described herein, and other methods that are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Example 1.1: 7-((R)-3-((S)-1-aminoethyl)pyrrolidin-1-yl)-1-cyclopropyl-6-fluoro-8-methyl-2-oxo-1,2-dihydroquinoline-3-carboxylic acid hydrochloride salt

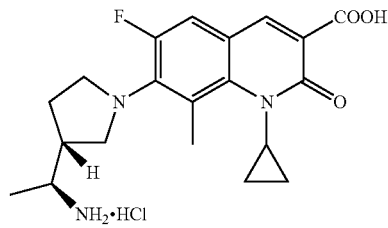

The title compound was prepared in accordance with the following scheme:

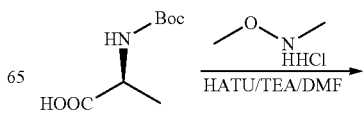

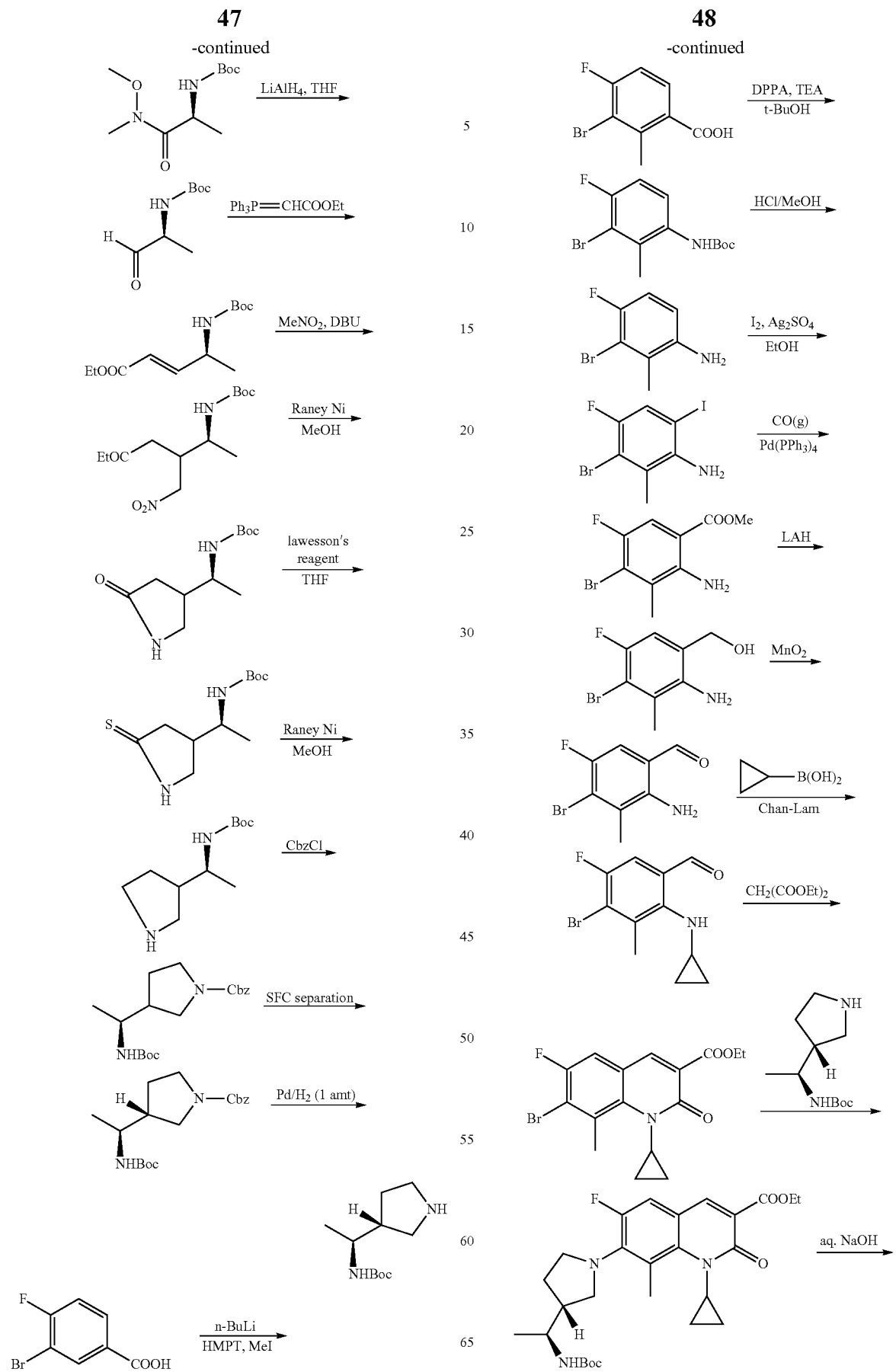

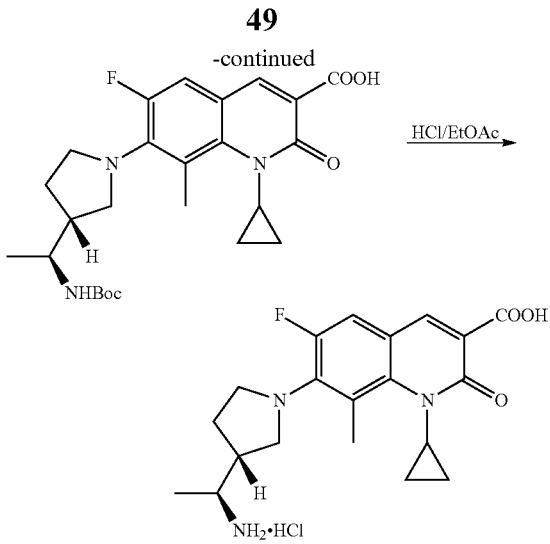

(i) (S)-tert-butyl (1-(methoxy(methyl)amino)-1-oxo-propan-2-yl)carbamate

To a solution of (S)-2-((tert-butoxycarbonyl)amino)propanoic acid (10.0 g, 52.9 mmol), N,O-dimethylhydroxylamine hydrochloride (7.7 g, 78.9 mmol) and TEA (22.0 g, 217.4 mmol) in DMF (100 mL) was added HATU (30.0 g, 78.9 mmol). The reaction mixture was then stirred at 20° C. for 10 h. After the reaction was complete, the reaction mixture was concentrated under reduced pressure. The residue was dissolved in EtOAc (50 mL), washed with sat. aq. $Na_2CO_3$ (150 mL) and brine (100 mL). The water phase was extracted with EtOAc (2×200 mL). The combined organic extracts were dried over $Na_2SO_4$, filtered and concentrated under reduced pressure to give a crude product. The crude product was recrystallized form EtOAc to get the product (8.5 g, yield: 69.2%).

$^1$H NMR (400 MHz, DMSO-$d_6$): δ 7.06 (d, J=7.6 Hz, 1H), δ 4.43-4.38 (m, 1H), 3.72 (s, 3H), 3.10 (s, 3H), 1.37 (s, 9H), 1.14 (d, J=7.2 Hz, 3H)

(ii) (S)-tert-butyl (1-oxopropan-2-yl)carbamate

To a solution of (S)-tert-butyl (1-(methoxy(methyl)amino)-1-oxopropan-2-yl)carbamate (8.5 g, 36.6 mmol) in THF (20 mL) was added LiAlH$_4$ (2.5 g, 65.9 mmol) at 0° C. The reaction was followed by TLC until reaction completion. A solution of KHSO$_4$ (50.0 g, 367.2 mmol) was added and the reaction mixture was extracted with EtOAc (2×200 mL). The combined organic extracts were washed with aq. HCl (1 M, 20 mL), sat. aq. NaHCO$_3$ (100 mL), brine (100 mL) respectively and then dried over anhydrous Na$_2$SO$_4$, filtered and concentrated under reduced pressure to give the product (4.8 g, yield: 75.7%).

$^1$H NMR (400 MHz, DMSO-$d_6$): δ 9.41 (d, J=11.6 Hz, 1H), δ 7.35 (d, J=6.4 Hz, 1H), δ 3.89-3.82 (m, 1H), 1.39 (s, 9H), 1.13 (d, J=7.2 Hz, 3H)

(iii) (S,E)-ethyl 4-((tert-butoxycarbonyl)amino)pent-2-enoate

To a solution of (S)-tert-butyl (1-oxopropan-2-yl)carbamate (4.8 g, 27.7 mmol) in DCM (20 mL) was added a solution of ethyl 2-(triphenylphosphoranylidene)acetate (18.1 g, 51.9 mmol) in DCM (10 mL) dropwise at 0° C. After addition, the solution was stirred at 20° C. for 6.0 h. The solvent was concentrated in vacuo to obtain a crude product. The crude product was purified by column chromatograph on silica gel (Eluent: PE:EtOAc=10:1) to get the product (3.6 g, yield: 53.4%).

$^1$H NMR (400 MHz, DMSO-$d_6$): δ 7.14 (d, J=8.0 Hz, 1H), 6.82 (dd, J=5.2 Hz, J=16.0 Hz, 1H), 5.81 (dd, J=1.2 Hz, J=16.0 Hz, 1H), 4.23-4.19 (m, 1H), 4.13 (q, J=7.2 Hz, 2H), 1.38 (s, 9H), 1.21 (t, J=7.2 Hz, 3H), 1.15 (d, J=7.2 Hz, 3H)

(iv) tert-butyl ((2S)-3-(nitromethyl)-5-oxoheptan-2-yl)carbamate

To a solution of (S,E)-ethyl 4-((tert-butoxycarbonyl)amino)pent-2-enoate (3.6 g, 14.8 mmol) in MeNO$_2$ (9.0 g, 0.15 mol) was slowly added DBU (2.7 g, 17.7 mmol). After addition, the reaction was stirred at 40° C. for overnight. After the reaction was complete, the reaction mixture was concentrated in vacuo to obtain a crude product. The crude product was purified by column chromatograph on silica gel (Eluent: PE:EtOAc=3:1) to get the product (2.4 g, yield: 53.3%).

$^1$H NMR (400 MHz, DMSO-$d_6$): δ 6.90 (d, J=8.4 Hz, 1H), 4.63-6.52 (m, 1H), 4.51-4.47 (m, 1H), 4.08-4.03 (m, 2H), 3.68-3.63 (m, 1H), 2.72-2.67 (m, 1H), 2.49-2.45 (m, 1H), 2.34-2.28 (m, 1H), 1.38 (s, 9H), 1.18 (t, J=7.2 Hz, 3H), 1.00 (d, J=6.8 Hz, 3H)

(v) tert-butyl ((1S)-1-(5-oxopyrrolidin-3-yl)ethyl)carbamate

To a solution of tert-butyl ((2S)-3-(nitromethyl)-5-oxoheptan-2-yl)carbamate (2.4 g, 7.9 mmol) in MeOH (50 mL) was added Raney nickel (wet, 240 mg, 10% w/w). The reaction mixture was stirred under H$_2$ atmosphere (50 psi) for 8 h. Raney nickel was then filtered. The filtrate was concentrated to dryness. The crude product was used for next step without further purification. (1.2 g, yield: 66.7%)

$^1$H NMR (400 MHz, DMSO-$d_6$): δ 7.45 (s, 1H), 6.81 (d, J=8.8 Hz, 1H), 3.51-3.45 (m, 1H), 3.22 (t, J=8.8 Hz, 1H), 2.98 (dd, J=7.2 Hz, J=9.6 Hz, 1H), 2.41-2.31 (m, 1H), 2.14-1.90 (m, 2H), 1.38 (s, 9H), 1.00 (d, J=8.0 Hz, 3H)

(vi) tert-butyl ((1S)-1-(5-thioxopyrrolidin-3-yl)ethyl)carbamate

A solution of tert-butyl ((1S)-1-(5-oxopyrrolidin-3-yl)ethyl)carbamate (800 mg, 3.5 mmol) in THF (40 mL) under nitrogen atmosphere was treated with Lawesson's Reagent (688 mg, 1.7 mmol). The reaction was stirred at 25° C. for 4 h. The reaction mixture was concentrated in vacuo to obtain a crude solid. The crude product was purified by column chromatograph on silica gel (Eluent: DCM:MeOH=100:1) to get the product (500 mg, yield: 58.4%).

$^1$H NMR (400 MHz, DMSO-$d_6$): δ 10.05 (brs, 1H), 6.89 (brd, J=7.2 Hz, 1H), 3.52-3.42 (m, 2H), 3.30-3.24 (m, 1H), 2.78-2.71 (m, 1H), 2.55-2.51 (m, 1H), 2.50-2.43 (m, 1H), 1.38 (s, 9H), 0.98 (d, J=6.8 Hz, 3H)

(vii) tert-butyl ((1S)-1-(pyrrolidin-3-yl)ethyl)carbamate

To a solution of tert-butyl ((1S)-1-(5-thioxopyrrolidin-3-yl)ethyl)carbamate (2.0 g, 8.2 mmol) in MeOH (50 mL) was added Raney nickel (wet, 400 mg, 20% w/w). The reaction mixture was stirred under H$_2$ atmosphere (50 psi) for 24 h. Raney nickel was then filtered from the reaction mixture.

The filtrate was concentrated to dryness. The crude product was purified by column chromatograph on silica gel (Eluent: DCM:MeOH:NH$_3$H$_2$O=50:1:1) to get the product (800 mg, yield: 45.6%).

$^1$H NMR (400 MHz, CDCl$_3$-d$_1$): δ 4.79 (d, J=8.0 Hz, 1H), 4.78-3.69 (m, 1H), 3.67-3.44 (m, 2H), 3.35-3.28 (m, 1H), 3.09 (t, J=9.2 Hz, 1H), 2.44-2.33 (m, 1H), 2.14-2.06 (m, 1H), 1.82-1.72 (m, 1H), 1.38 (s, 9H), 1.15 (d, J=8.0 Hz, 3H)

(viii) benzyl 3-((S)-1-((tert-butoxycarbonyl)amino) ethyl)pyrrolidine-1-carboxylate To a mixture of tert-butyl ((1S)-1-(pyrrolidin-3-yl)ethyl) carbamate (680 mg, 3.17 mmol) in sat. aq. NaHCO$_3$ (8 mL) and THF (8 mL) was added CbzCl (647 mg, 3.80 mmol). The mixture was stirred for 2 h at 25° C. Water (50 mL) was then added to the reaction mixture. The resulting solution was extracted with EtOAc (60 mL×8). The combined organic layer was dried over anhydrous Na$_2$SO$_4$ and concentrated to give the product (850 mg, yield: 76.9%).

$^1$H NMR (400 MHz, DMSO-d$_6$): δ 7.40-7.30 (m, 5H), 5.03 (s, 2H), 3.46-3.39 (m, 3H), 3.23-3.18 (m, 1H), 3.01-2.95 (m, 1H), 2.13-2.11 (m, 1H), 1.87-1.83 (m, 1H), 1.51-1.48 (m, 1H), 1.37 (d, J=7.6 Hz, 9H), 1.02 (d, J=6.4 Hz, 3H)

(ix) (R)-benzyl 3-((S)-1-((tert-butoxycarbonyl) amino)ethyl)pyrrolidine-1-carboxylate Benzyl 3-((S)-1-((tert-butoxycarbonyl)amino)ethyl)pyrrolidine-1-carboxylate (850 mg, 2.44 mmol) was separated by SFC and then concentrated to give the desired product (565 mg, yield: 66.5%).

SFC Method
Column: Chiralpak AD 250×30 mm I.D., 5 um;
Column temperature: 38° C.;
Mobile Phase: Supercritical CO$_2$/MeOH (0.1%) NH$_3$.H$_2$O=70/30 at 60 mL/min;

$^1$H NMR (400 MHz, CDCl$_3$-d$_1$): δ 7.36-7.30 (m, 5H), 5.13 (s, 2H), 4.40 (brs, 1H), 3.66-3.3.57 (m, 3H), 3.35-3.32 (m, 1H), 3.12 (t, J=10.4 Hz, 1H), 2.17-2.15 (m, 1H), 1.95-1.94 (m, 1H), 1.62-1.54 (m, 1H), 1.43 (s, 9H), 1.16 (d, J=6.4 Hz, 3H)

(x) tert-butyl ((S)-1-((R)-pyrrolidin-3-yl)ethyl)carbamate

To a solution of (R)-benzyl 3-((S)-1-((tert-butoxycarbonyl)amino)ethyl)pyrrolidine-1-carboxylate (565 mg, 1.62 mmol) in EtOAc (10 mL) was added 10% dry Pd/C (100 mg, 17.7% w/w). The resulting solution was stirred under H$_2$ atmosphere (1 atm) at 50° C. for 2 h. The mixture was filtered. The filtrate was evaporated to give the desired product. (300 mg, yield: 86.3%)

$^1$H NMR (400 MHz, DMSO-d$_6$) δ 6.72 (d, J=8.8 Hz, 1H), 3.54-3.45 (m, 1H), 2.78-2.76 (m, 2H), 2.75-2.70 (m, 1H), 2.68-2.60 (m, 1H), 1.93-1.90 (m, 1H), 1.75-1.60 (m, 1H), 1.38 (s, 9H), 1.26-1.23 (m, 1H), 1.02 (d, J=6.4 Hz, 3H)

(xi) 3-bromo-4-fluoro-2-methylbenzoic acid

To a stirred solution of n-butyllithium 2.5 M in hexanes (123.3 mL, 308.3 mmol) was added 2,2,6,6-tetramethylpiperidine (51.6 mL, 308.3 mmol) in anhydrous THF (400 mL) at −20° C. under N$_2$. After the mixture was cooled to −50° C., a solution of 3-bromo-4-fluorobenzoic acid (30 g, 137 mmol) in anhydrous THF (100 mL) was added dropwise and the mixture was stirred at this temperature for 1 h. The mixture was then treated with MeI (34.1 mL, 548 mmol). The resulting solution was allowed to warm to 15° C. within 30 mins. Water was added to quench the reaction. The resulting solution was washed with TBME (100 mL) and then acidified with 4 M HCl (20 mL). The resulting mixture was extracted with TBME (100 mL×3). The organic layer was dried over anhydrous Na$_2$SO$_4$, filtered and then concentrated in vacuo to give the crude benzoic acids, which was re-crystallized from EtOAc/PE to give pure title compound (6.5 g, yield: 20.4%).

$^1$H NMR (400 MHz, DMSO-d$_6$): δ 7.81 (dd, J=5.6, 8.8 Hz, 1H), 7.28 (t, J=8.4 Hz, 1H), 2.60 (s, 3H)

(xii) tert-butyl (3-bromo-4-fluoro-2-methylphenyl)carbamate

To a solution of 3-bromo-4-fluoro-2-methylbenzoic acid (6.0 g, 25.8 mmol) in t-BuOH (49 mL, 516 mmol) was added TEA (7.2 mL, 51.6 mmol) and DPPA (6.3 mL, 28.4 mmol) at 15° C. under N$_2$ atmosphere. The mixture was then allowed to reflux for 1.0 h. After the reaction was complete, the reaction mixture was concentrated in vacuo to give the crude product, which was purified by chromatograph on silica gel (Eluent: EtOAc/PE=1/30) to get the title compound (6.2 g, yield: 79.2%).

$^1$H NMR (400 MHz, DMSO-d$_6$): δ 8.82 (brs, 1H), 7.27 (dd, J=5.6, 9.2 Hz, 1H), 7.16 (t, J=8.4 Hz, 1H), 2.26 (s, 3H), 1.43 (s, 9H)

(xiii) 3-bromo-4-fluoro-2-methylaniline

To a mixture of tert-butyl (3-bromo-4-fluoro-2-methylphenyl)carbamate (6.2 g, 20.4 mmol) in MeOH (5 mL) was added HCl/MeOH (25.5 mL, 102 mmol) at 0° C. The reaction mixture was stirred at 20° C. for 30 min. The reaction was monitored by TLC, the result showed that the reaction was completed. The reaction was quenched by saturated NaHCO$_3$ (20 mL). The aqueous layer was extracted with EtOAc (50 mL×2). The organic layer was dried with Na$_2$SO$_4$, filtered and concentrated to give the title compound (3.8 g, yield: 91.4%).

$^1$H NMR (400 MHz, DMSO-d$_6$): δ 6.91 (t, J=8.4 Hz, 1H), 6.63 (dd, J=5.2, 8.8 Hz, 1H), 5.04 (brs, 2H), 2.18 (s, 3H)

(xiv) 3-bromo-4-fluoro-6-iodo-2-methylaniline

A solution of 3-bromo-4-fluoro-2-methylaniline (2.3 g, 11.3 mmol) in EtOH (15 mL) was added to a mixture of I$_2$ (2.9 g, 11.3 mmol) and Ag$_2$SO$_4$ (3.5 g, 11.3 mmol) in EtOH (35 mL) dropwise at 20° C. Then the resulting solution was stirred at 20° C. for 2 h. After the reaction was complete, the reaction mixture was filtered. The filtrate was concentrated in vacuum. The residue was re-dissolved in DCM (150 mL). The organic phase was washed with 5% aq. NaOH (2×50 mL) and water (60 mL), dried over Na$_2$SO$_4$, filtered and concentrated in vacuum to give a residue. The residue was purified by column chromatography on silica gel (Eluents: PE:EtOAc from 30:1 to 10:1) to give the title compound (2.1 g, 56.5% yield) as a black solid.

$^1$H NMR (400 MHz, CDCl$_3$-d$_1$) δ 7.34 (d, J=7.6 Hz, 1H), 4.02 (brs, 2H), 2.36 (s, 3H)

(xv) methyl 2-amino-4-bromo-5-fluoro-3-methylbenzoate

To a solution of 3-bromo-4-fluoro-6-iodo-2-methylaniline (2.0 g, 6.1 mmol) in MeOH (20 mL) was added Pd(PPh$_3$)$_4$ (36 mg, 0.031 mmol) and TEA (1.7 mL, 12.2 mmol). The mixture was stirred at CO (40 psi) atmosphere for 30 mins. The reaction was monitored by LCMS, the result show that the reaction was completed. The reaction mixture was concentrated in vacuo to give a crude product. The crude product was purified by chromatograph on silica gel (Eluent: EtOAc/PE=1/30) to get the title compound (1.4 g, yield: 84.4%).

$^1$H NMR (400 MHz, CDCl$_3$-d$_1$): δ 7.53 (d, J=9.6 Hz, 1H), 5.83 (brs, 2H), 3.87 (s, 3H), 2.32 (s, 3H)

(xvi) (2-amino-4-bromo-5-fluoro-3-methylphenyl)methanol

To a solution of methyl 2-amino-4-bromo-5-fluoro-3-methylbenzoate (1.47 g, 5.61 mmol) in THF (10 mL) was added LAH (234 mg, 6.17 mmol) at 0° C. After stirred at 0° C. for 20 mins, another batch LAH (117.4 mg, 3.09 mmol) was added at 0° C. The reaction mixture was then allowed to stir at 0° C. for 30 mins. After the reaction was complete, water (4 mL) was added to quench the reaction mixture. The resulting suspension was dried over anhydrous Na$_2$SO$_4$ and filtered. The filtrate was concentrated to give the desired product. (weight: 1.32 g, yield: 100%).

$^1$H NMR (400 MHz, DMSO-d$_6$): δ 6.99 (d, J=9.6 Hz, 1H), 5.29 (brt, J=5.6 Hz, 1H), 4.83 (brs, 2H), 4.38 (d, J=9.6 Hz, 1H), 2.23 (s, 3H)

(xvii) 2-amino-4-bromo-5-fluoro-3-methylbenzaldehyde

To a solution of (2-amino-4-bromo-5-fluoro-3-methylphenyl)methanol (1.32 g, 5.64 mmol) in DCM (60 mL) was added MnO$_2$ (3.68 g, 42.3 mmol) at 0° C. After stirred at 10° C. for 30 mins, another batch MnO$_2$ (1.84 g, 21.2 mmol) was added at 0° C. The reaction mixture was then allowed to stir at 0° C. for 30 mins. The reaction suspension was filtered. The filtrate was concentrated to give the desired product. (weight: 1.17 g, yield: 89.4%).

$^1$H NMR (400 MHz, DMSO-d$_6$): δ 9.80 (s, 1H), 7.52 (d, J=8.8 Hz, 1H), 7.15 (brs, 2H), 2.23 (s, 3H)

(xviii) 4-bromo-2-(cyclopropylamino)-5-fluoro-3-methylbenzaldehyde

To a solution of 2-amino-4-bromo-5-fluoro-3-methylbenzaldehyde (1.70 g, 7.3 mmol) in DCE (30 mL) was added cyclopropylboronic acid (1.25 g, 14.6 mmol), Cu(OAc)$_2$ (1.33 g, 7.3 mmol), bipyridine (1.14 g, 7.3 mmol) and Na$_2$CO$_3$ (1.55 g, 14.6 mmol). The mixture was stirred at 80° C. for 40 mins. The reaction mixture was filtered and the filtrate was concentrated to give the crude product. The crude product was purified by flash chromatography (Eluent: PE:EtOAc=20:1) to give the title compound as a yellow oil (yield: 400 mg, 20.1%).

$^1$H NMR (400 MHz, DMSO-d$_6$) δ 10.02 (s, 1H), 7.49 (d, J=8.8 Hz, 1H), 7.31 (brs, 1H), 2.95-2.85 (m, 1H), 2.50 (s, 3H), 0.75-0.70 (m, 2H), 0.50-0.45 (m, 2H)

(xix) ethyl 7-bromo-1-cyclopropyl-6-fluoro-8-methyl-2-oxo-1,2-dihydroquinoline-3-carboxylate To a solution of 4-bromo-2-(cyclopropylamino)-5-fluoro-3-methylbenzaldehyde (1.40 g, 5.2 mmol) in 30 mL of EtOH was added diethyl malonate (1.67 g, 10.4 mmol) and piperidine (1.77 g, 20.8 mmol). The mixture was refluxed at 100° C. for 16 h. The mixture was concentrated to give the crude product, which was purified by flash chromatography (Eluent: PE:EtOAc=5:1) to give 840 mg title compound as a yellow solid (yield: 44.4%).

$^1$H NMR (400 MHz, CDCl$_3$-d$_1$) δ 8.13 (s, 1H), 7.17 (d, J=7.2 Hz, 1H), 4.40 (q, J=7.2 Hz, 2H), 3.52-3.45 (m., 1H), 2.78 (s, 3H), 1.41 (t, J=7.2 Hz, 3H), 1.28-1.20 (m, 2H), 0.60-0.50 (m, 2H)

(xx) ethyl 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-3-carboxylate To a solution of ethyl 7-bromo-1-cyclopropyl-6-fluoro-8-methyl-2-oxo-1,2-dihydroquinoline-3-carboxylate (250.0 mg, 0.68 mmol) in toluene (50 mL) was added tert-butyl ((S)-1-((R)-pyrrolidin-3-yl)ethyl)carbamate (291.0 mg, 1.36 mmol), CS$_2$CO$_3$ (665.6 mg, 2.04 mmol), Xant-phos (59.0 mg, 0.10 mmol) and Pd$_2$(dba)$_3$ (31.1 mg, 0.03 mmol) at 20° C. The reaction mixture was stirred at 110° C. for 12 h. After the reaction was complete, the mixture was dissolved in water (20 mL) and extracted with EtOAc (30 mL×3). The organic layer was dried over Na$_2$SO$_4$ and evaporated to give a crude product. The crude product was purified by column chromatography on silica gel (Eluents: EtOAc:PE from 1:8 to 1:2) to get the desired product (280.0 mg, yield: 82.2%).

$^1$H NMR (400 MHz, CDCl$_3$-d$_1$) δ 8.16 (s, 1H), 7.05 (d, J=12.4 Hz, 1H), 4.51 (brs., 1H), 4.41 (q, J=7.2 Hz, 2H), 3.80-3.70 (m, 1H), 3.68-3.60 (m, 1H), 3.54-3.45 (m, 4H), 2.45 (s, 3H), 2.12-2.10 (m, 1H), 2.11-2.07 (m, 1H), 1.80-1.70 (m, 1H), 1.47-1.40 (m, 12H), 1.30-1.26 (m, 5H), 0.60-0.56 (m, 2H)

(xxi) 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-3-carboxylic acid To a solution of ethyl 7-((R)-3-((S)-1-((tert-butoxycarbonyl)amino)ethyl) pyrrolidin-1-yl)-1-cyclopropyl-6-fluoro-8-methyl-2-oxo-1,2-dihydroquinoline-3-carboxylate (200.0 mg, 0.40 mmol) in THF/H$_2$O (8 mL, 1:1) was added NaOH (32.0 mg, 0.80 mmol) 25° C. The reaction mixture was stirred to 45° C. for 4 h. After the reaction was complete, the reaction mixture was acidified to pH=5-6 and then extracted with EtOAc. The organic phase was dried over Na$_2$SO$_4$ and evaporated to get the desired product (175.0 mg, yield: 93.0%).

$^1$H NMR (400 MHz, DMSO-d$_6$) δ 8.64 (s, 1H), 7.64 (d, J=13.6 Hz, 1H), 7.20-7.17 (m, 1H), 4.48-4.40 (m, 2H), 4.20-4.10 (m, 2H), 3.69-3.60 (m, 1H), 3.35-3.25 (m, 2H), 2.89-2.75 (m, 1H), 2.60-2.50 (m, 1H), 2.38 (s, 3H), 1.50-1.40 (s, 11H), 1.30-1.24 (m, 3H), 0.70-0.62 (m, 2H)

(xxii) 7-((R)-3-((S)-1-aminoethyl)pyrrolidin-1-yl)-1-cyclopropyl-6-fluoro-8-methyl-2-oxo-1,2-dihydroquinoline-3-carboxylic acid hydrochloride To a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-3-carboxylic acid (180.0 mg, 0.38 mmol) in EtOAc (10 mL) was added HCl/EtOAc (10 mL) at 0° C. The reaction mixture was stirred to 25° C. for 3 h. After the reaction was complete, the organic layer was evaporated to give a crude product. The crude product was purified by pre-HPLC to get the product (140.0 mg, yield: 99.0%).

$^1$H NMR (400 MHz, DMSO-d$_6$) δ 8.67 (s, 1H), 8.25 (brs. 3H), 7.66 (d, J=13.6 Hz, 1H), 3.78-3.70 (m, 1H), 3.60-3.40 (m, 4H), 3.30-3.20 (m, 1H), 2.45-2.35 (m, 4H), 2.20-2.10 (m, 1H), 1.80-1.70 (m, 1H), 1.30-1.20 (m, 5H), 0.62-050 (m, 2H)

LCMS (0-60 AB_7 min), [MH]$^+$=374.0, RT=2.880 mins
LCMS Method 0-60 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 0%-60% (solvent B) over 6 minutes and holding at 60% for 0.5 minutes.

Example 1.2: 7-((S)-3-((S)-1-aminoethyl)pyrrolidin-1-yl)-1-cyclopropyl-6-fluoro-8-methyl-2-oxo-1,2-dihydroquinoline-3-carboxylic acid hydrochloride salt

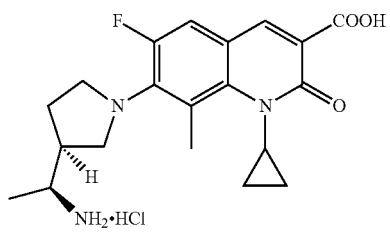

The title compound was prepared in accordance with the following scheme:

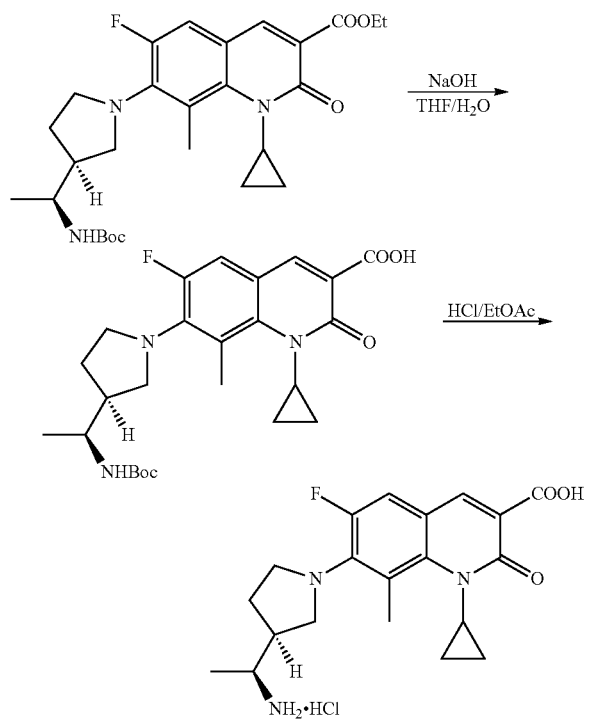

(i) 7-((S)-3-((S)-1-((tert-butoxycarbonyl)amino)ethyl)pyrrolidin-1-yl)-1-cyclopropyl-6-fluoro-8-methyl-2-oxo-1,2-dihydroquinoline-3-carboxylic acid To a solution of ethyl 7-((S)-3-((S)-1-((tert-butoxycarbonyl)amino)ethyl)pyrrolidin-1-yl)-1-cyclopropyl-6-fluoro-8-methyl-2-oxo-1,2-dihydroquinoline-3-carboxylate (7 mg, 0.014 mmol) in THF (0.5 mL) and H$_2$O (0.5 mL) was added NaOH (1 mg, 0.028 mmol). The reaction mixture was stirred at 30° C. for 4 h. After the reaction was complete, the reaction mixture was diluted with water (5 mL) and acidified with aq. HCl (0.1 mol/L) to pH=4-5. The resulting mixture was extracted with EtOAc (5 mL×3). The combined organic phases were dried over anhydrous Na$_2$SO$_4$ and concentrated to give the crude product (6 mg), which was used in the next step without further purification.

(ii) 7-((S)-3-((S)-1-aminoethyl)pyrrolidin-1-yl)-1-cyclopropyl-6-fluoro-8-methyl-2-oxo-1,2-dihydroquinoline-3-carboxylic acid hydrochloride salt To a solution of 7-((S)-3-((S)-1-((tert-butoxycarbonyl)amino)ethyl)pyrrolidin-1-yl)-1-cyclopropyl-6-fluoro-8-methyl-2-oxo-1,2-dihydroquinoline-3-carboxylic acid (6 mg, 0.013 mmol) in EtOAc (0.5 mL) was added HCl/EtOAc (0.5 mL, 2.0 mmol, 4 mol/L). The reaction mixture was stirred at 25° C. for 4 h. After the reaction was complete, the solvent was removed under reduced pressure to afford the product (1.9 mg, yield: 36.6%).

LCMS (10-80AB_7 min), RT=1.847 mins, [MH]$^+$=374.2.
$^1$H NMR (400 MHz, D$_2$O-d$_2$) δ 8.04 (s, 1H), 6.91-6.90 (m, 1H), 3.68-3.67 (m, 1H), 3.46-3.43 (m, 5H), 2.48-2.32 (m, 5H), 1.79-1.78 (m, 1H), 1.35-1.18 (m, 5H), 0.51 (m, 2H)
LCMS Method 10-80 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 10%-80% (solvent B) over 6 minutes and holding at 80% for 0.5 minutes.

Example 1.3: 7-(3-aminopyrrolidin-1-yl)-1-cyclopropyl-6-fluoro-8-methyl-2-oxo-1,2-dihydroquinoline-3-carboxylic acid hydrochloride salt

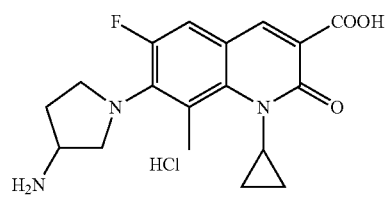

The title compound was prepared in accordance with the following scheme:

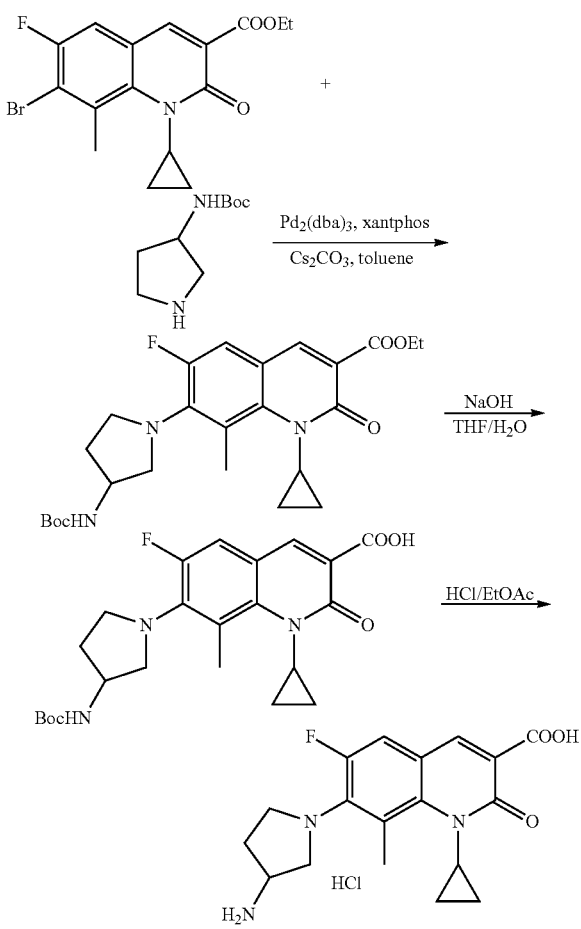

(i) Ethyl 7-(3-((tert-butoxycarbonyl)amino)pyrrolidin-1-yl)-1-cyclopropyl-6-fluoro-8-methyl-2-oxo-1,2-dihydroquinoline-3-carboxylate To a solution of ethyl 7-bromo-1-cyclopropyl-6-fluoro-8-methyl-2-oxo-1,2-dihydroquinoline-3-carboxylate (80 mg, 0.22 mmol) in toluene (8 mL) was tert-butyl pyrrolidin-3-ylcarbamate (52 mg, 0.28 mmol), $Cs_2CO_3$ (212 mg, 0.65 mmol), $Pd_2(dba)_3$ (30 mg, 0.033 mmol) and Xantphos (6.4 mg, 0.011 mmol). Then the reaction mixture was stirred at 120° C. for 18 hours. After the reaction was complete, the reaction mixture was diluted with EtOAc (20 mL) and filtered. The filtrate was concentrated in vacuum. The residue was purified by prep. TLC (Developer: PE:EtOAc=1:1) to give the product (20 mg, yield: 19.4%) as a yellow solid.

$^1$H NMR (400 MHz, $CDCl_3$-$d_1$) δ 8.16 (s, 1H), 7.07 (d, J=12 Hz, 1H), 4.79 (brs., 1H), 4.43-4.38 (m, 3H), 3.82-3.78 (m, 1H), 3.67-3.62 (m, 1H), 3.52-3.47 (m, 2H), 3.33 (dd, $J_1$=3.6 Hz, $J_2$=10.4 Hz, 1H), 2.47 (s, 3H), 2.36-2.32 (m, 1H), 1.98-1.90 (m, 1H), 1.49 (s, 9H), 1.42 (t, J=14 Hz, 3H), 1.28-1.26 (m, 2H), 0.59-0.58 (m, 2H)

(ii) 7-(3-((tert-butoxycarbonyl)amino)pyrrolidin-1-yl)-1-cyclopropyl-6-fluoro-8-methyl-2-oxo-1,2-dihydroquinoline-3-carboxylic acid To a solution of ethyl 7-(3-((tert-butoxycarbonyl)amino) pyrrolidin-1-yl)-1-cyclopropyl-6-fluoro-8-methyl-2-oxo-1,2-dihydroquinoline-3-carboxylate (20 mg, 0.042 mmol) in THF/$H_2O$ (3 mL/0.5 mL) was added a solution of NaOH (17 mg, 0.42 mmol) in $H_2O$ (0.5 mL). The reaction solution was stirred at 35° C. for 5 hours. The resulting mixture was washed with t-BuOMe (3 mL). The aqueous phase was adjusted to pH=5 by aq. HCl (0.5 N) and then extracted with EtOAc (30 mL). The organic phase was dried over $Na_2SO_4$, filtered and concentrated in vacuum to give the product (10 mg, yield: 53.1%).

$^1$H NMR (400 MHz, $CDCl_3$-$d_1$) δ 14.43 (brs., 1H), 8.61 (s, 1H), 7.20 (d, J=12.4 Hz, 1H), 4.80 (brs., 1H), 4.38 (brs, 1H), 3.89-3.74 (m, 1H), 3.72-3.70 (m, 1H), 3.61-3.58 (m, 2H), 3.42-3.39 (m, 1H), 2.50 (s, 3H), 2.39-2.33 (m, 1H), 2.01-1.93 (m, 1H), 1.49 (s, 9H), 1.28-1.26 (m, 2H), 0.59-0.58 (m, 2H)

(iii) 7-(3-aminopyrrolidin-1-yl)-1-cyclopropyl-6-fluoro-8-methyl-2-oxo-1,2-dihydroquinoline-3-carboxylic acid hydrochloride salt To a solution of 7-(3-((tert-butoxycarbonyl)amino)pyrrolidin-1-yl)-1-cyclopropyl-6-fluoro-8-methyl-2-oxo-1,2-dihydroquinoline-3-carboxylic acid (10 mg, 0.022 mmol) in EtOAc (2 mL) was added HCl/EtOAc (2 mL) at 0° C. Then the reaction solution was stirred at 15° C. for 1 hour. After the reaction was complete, the reaction mixture was concentrated. The residue was purified by prep-HPLC (HCl system) to give the product (6 mg, 70.0%) as a yellow solid.

LCMS (0-60 AB_7 min), RT=2.526 mins, [MH]$^+$=346.1.

$^1$H NMR (400 MHz, $D_2O$-$d_2$) δ 8.16 (s, 1H), 7.11 (d, J=12.8 Hz, 1H), 4.03-4.02 (m, 1H), 3.91-3.90 (m, 1H), 3.70-3.64 (m, 2H), 3.58-3.57 (m, 1H), 3.47-3.46 (m, 1H), 2.45-2.40 (m, 4H), 2.10-2.08 (m, 1H), 1.19 (d, J=6 Hz, 2H), 0.48 (d, J=2.8 Hz, 2H)

LCMS Method 0-60 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 0%-60% (solvent B) over 6 minutes and holding at 60% for 0.5 minutes.

Example 1.4: 7-(3-(aminomethyl)pyrrolidin-1-yl)-1-cyclopropyl-6-fluoro-8-methyl-2-oxo-1,2-dihydroquinoline-3-carboxylic acid hydrochloride salt The title compound was prepared in accordance with the following scheme:

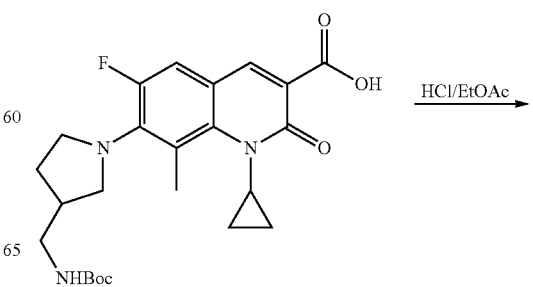

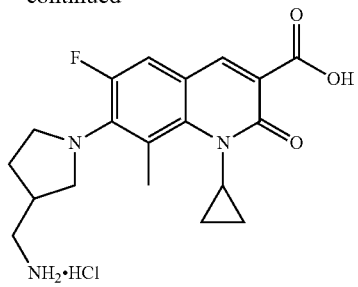

(i) 7-(3-(aminomethyl)pyrrolidin-1-yl)-1-cyclopropyl-6-fluoro-8-methyl-2-oxo-1,2-dihydroquinoline-3-carboxylic acid hydrochloride salt A mixture of 7-(3-(((tert-butoxycarbonyl)amino)methyl)pyrrolidin-1-yl)-1-cyclopropyl-6-fluoro-8-methyl-2-oxo-1,2-dihydroquinoline-3-carboxylic acid (20 mg, 0.044 mmol) in HCl/EtOAc (3 mL, 4 M) and EA (3 mL) was stirred at 25° C. for 2 h. Water (10 mL) was added to the reaction mixture. The resulting solution was washed with EtOAc (40 mL×3). The aqueous solution was lyophilized to give the product. (17 mg, 98.7% yield).

LCMS (10-80 AB_7 min), RT=1.755 mins, [MH]$^+$ =359.9.

$^1$H NMR (400 MHz, Methanol-d$_4$) δ 8.69 (s, 1H), 7.46 (d, J=13.2 Hz, 1H), 3.78-3.77 (m, 2H), 3.68-3.67 (m, 2H), 3.56-3.55 (m, 1H), 3.16 (d, J=6 Hz, 2H), 2.72-2.69 (m, 1H), 2.57 (s, 3H), 2.32-2.31 (m, 1H), 1.88-1.87 (m, 1H), 1.34-1.33 (m, 2H), 0.66-0.65 (m, 2H)

LCMS Method 10-80 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 10%-80% (solvent B) over 6 minutes and holding at 80% for 0.5 minutes.

Example 1.5: 1-cyclopropyl-6-fluoro-8-methyl-7-(3-((methylamino)methyl)pyrrolidin-1-yl)-2-oxo-1,2-dihydroquinoline-3-carboxylic acid hydrochloride salt

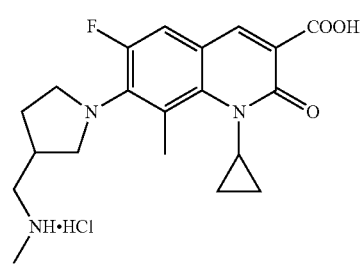

The title compound was prepared in accordance with the following scheme:

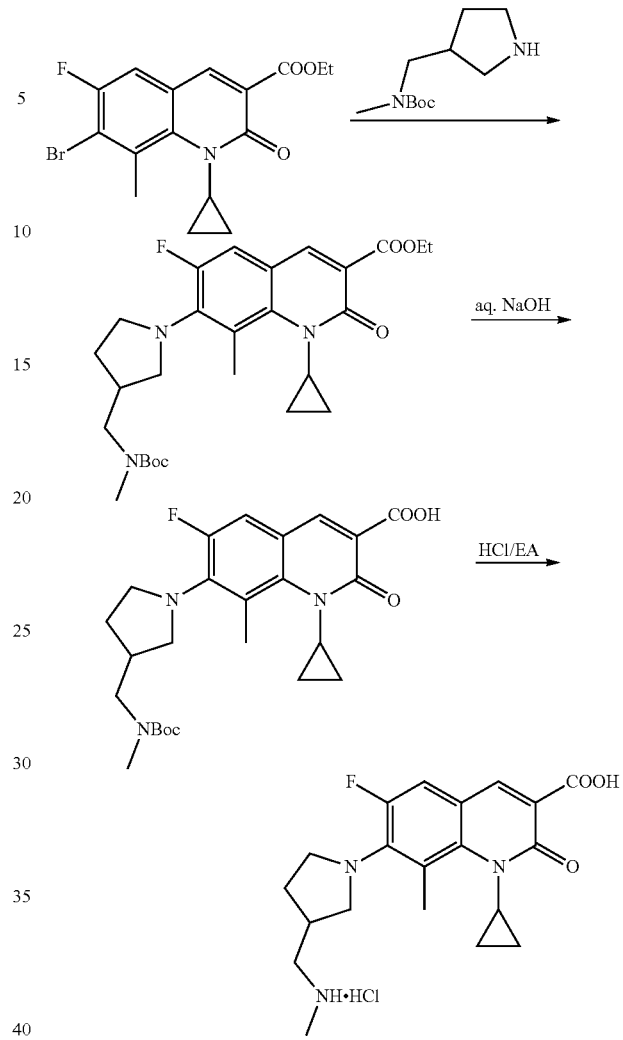

(i) ethyl 7-(3-(((tert-butoxycarbonyl)(methyl)amino)methyl)pyrrolidin-1-yl)-1-cyclopropyl-6-fluoro-8-methyl-2-oxo-1,2-dihydroquinoline-3-carboxylate To a mixture of ethyl 7-bromo-1-cyclopropyl-6-fluoro-8-methyl-2-oxo-1,2-dihydro quinoline-3-carboxylate (100 mg, 0.27 mmol), tert-butyl methyl(pyrrolidin-3-ylmethyl)carbamate (116 mg, 0.54 mmol), Cs$_2$CO$_3$ (264 mg, 0.81 mmol) and xantpohos (24 mg, 0.041 mmol) in 30 mL of PhMe was added Pd$_2$(dba)$_3$ (15 mg, 0.016 mmol). Then the reaction mixture was stirred at 120° C. for 14 h under N$_2$ atmosphere. The mixture was evaporated to give the crude product. The crude product was purified by chromatography on silica gel (Eluent: EtOAc:PE=2:1) to give the desired product. (60 mg, 44.0% yield)

LCMS (5-95 AB_1.5 min), RT=0.947, [MH]$^+$=502.1.

LCMS Method 5-95AB_1.5 MIN

Column: MERCK, RP-18e 25-2 mm, ESI source, Positive ion mode; Wavelength: 220 nm;

Column temperature: 40° C.;

Mobile Phase: A: 1.5 mL/4 L TFA in water, B: 0.75 mL/4 L TFA in acetonitrile;

Flow rate & gradient: at a flow rate of 1.0 ml/min from 0-0.08 min, using the elution gradient 5%-95% (solvent B) from 0-0.7 min and holding at 95% for 0.4 minutes, at a flow rate of 1.5 ml/min.

(ii) 7-(3-(((tert-butoxycarbonyl)(methyl)amino) methyl)pyrrolidin-1-yl)-1-cyclopropyl-6-fluoro-8-methyl-2-oxo-1,2-dihydroquinoline-3-carboxylic acid To a mixture of ethyl 7-(3-(((tert-butoxycarbonyl) (methyl)amino) methyl)pyrrolidin-1-yl)-1-cyclopropyl-6-fluoro-8-methyl-2-oxo-1,2-dihydroquinoline-3-carboxylate (60 mg, 0.12 mmol) in THF/H$_2$O (8 mL, 1:1) was added NaOH (10 mg, 0.24 mmol). Then the reaction mixture was stirred at 30° C. for 17 h. The reaction mixture was acidified to pH~6 with aq. HCl (0.5 M). The resulting solution was extracted with EtOAc (40 mL×8). The combined organic layer was dried over anhydrous Na$_2$SO$_4$ and concentrated to give the desired product. (50 mg, 88.3% yield).

LCMS (5-95 AB_1.5 min), RT=0.930, [MH]$^+$=474.1.

LCMS Method 5-95AB_1.5 MIN

Column: MERCK, RP-18e 25-2 mm, ESI source, Positive ion mode; Wavelength: 220 nm;

Column temperature: 40° C.;

Mobile Phase: A: 1.5 mL/4 L TFA in water, B: 0.75 mL/4 L TFA in acetonitrile;

Flow rate & gradient: at a flow rate of 1.0 ml/min from 0-0.08 min, using the elution gradient 5%-95% (solvent B) from 0-0.7 min and holding at 95% for 0.4 minutes, at a flow rate of 1.5 ml/min.

(iii) 1-cyclopropyl-6-fluoro-8-methyl-7-(3-((methyl-amino)methyl)pyrrolidin-1-yl)-2-oxo-1,2-dihydro-quinoline-3-carboxylic acid hydrochloride A mixture of 7-(3-(((tert-butoxycarbonyl)(methyl)amino) methyl)pyrrolidin-1-yl)-1-cyclopropyl-6-fluoro-8-methyl-2-oxo-1,2-dihydroquinoline-3-carboxylic acid (25 mg, 0.053 mmol) in HCl/EtOAc (5 mL, 4 M) and EA (5 mL) was stirred at 25° C. for 2 h. Water (10 mL) was added to the reaction mixture. The resulting solution was washed with EtOAc (40 mL×6). The aqueous phase was lyophilized to give the product. (20 mg, 92.4% yield).

LCMS (10-80 AB_7 min), RT=1.813, [MH]$^+$=374.0.

$^1$H NMR (400 MHz, Methanol-d$_4$) δ 8.70 (s, 1H), 7.45 (d, J=13.2 Hz, 1H), 3.79-3.78 (m, 2H), 3.68-3.67 (m, 2H), 3.60-3.59 (m, 1H), 3.24 (d, J=6.4 Hz, 2H), 2.80-2.77 (m, 4H), 2.57 (s, 3H), 2.35-2.33 (m, 1H), 1.92-1.88 (m, 1H), 1.36-1.35 (m, 2H), 0.66-0.65 (m, 2H)

LCMS Method 10-80 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 10%-80% (solvent B) over 6 minutes and holding at 80% for 0.5 minutes.

Example 1.6: 7-(3-aminopiperidin-1-yl)-1-cyclopropyl-6-fluoro-8-methyl-2-oxo-1,2-dihydroquinoline-3-carboxylic acid hydrochloride salt

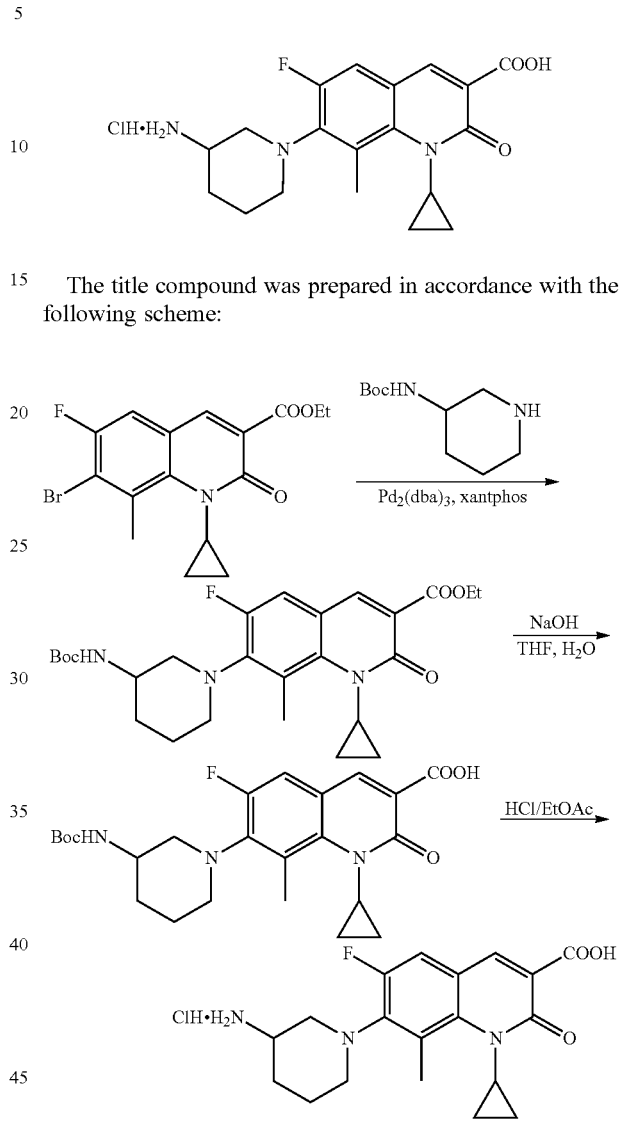

The title compound was prepared in accordance with the following scheme:

(i) Ethyl 7-(3-((tert-butoxycarbonyl)amino)piperidin-1-yl)-1-cyclopropyl-6-fluoro-8-methyl-2-oxo-1,2-dihydroquinoline-3-carboxylate To a solution of ethyl 7-bromo-1-cyclopropyl-6-fluoro-8-methyl-2-oxo-1,2-dihydroquinoline-3-carboxylate (100 mg, 0.27 mmol) in toluene (15 mL) was added tert-butyl piperidin-3-ylcarbamate (82 mg, 0.41 mmol), Pd$_2$(dba)$_3$ (13 mg, 0.014 mmol), Xantphos (24 mg, 0.041 mmol) and Cs$_2$CO$_3$ (264 mg, 0.81 mmol). Then the resulting solution was stirred at 120° C. for 12 h. After the reaction was complete, the reaction mixture was diluted with EtOAc (50 mL) and then filtered. The filtrate was concentrated in vacuum. The residue was purified by prep-TLC (developer: PE:EtOAc=1:1) to give the product (65 mg, crude) as a yellow solid, which was used for the next reaction without further purification.

LCMS (10-80 AB_2 min), RT=1.313 mins, [MH]$^+$=488.1.

LCMS Method 10-80AB_2 MIN
Column: Xtimate C18 2.1*30 mm, 3 um; ESI source, positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 1.2 mL/min;
Gradient: 10%-80% (solvent B) over 0.9 minutes and holding at 80% for 0.6 minutes.

(ii) 7-(3-((tert-butoxycarbonyl)amino)piperidin-1-yl)-1-cyclopropyl-6-fluoro-8-methyl-2-oxo-1,2-dihydroquinoline-3-carboxylic acid To a solution of ethyl 7-(3-((tert-butoxycarbonyl)amino) piperidin-1-yl)-1-cyclopropyl-6-fluoro-8-methyl-2-oxo-1,2-dihydroquinoline-3-carboxylate (65 mg, crude) in THF/H$_2$O (3 mL/3 mL) was added NaOH (10 mg, 0.25 mmol). Then the resulting solution was stirred at 20° C. for 2 h. After the reaction was complete, the reaction mixture was diluted with H$_2$O (10 mL). The resulting solution was washed with EtOAc (2×10 mL). The aqueous layer was adjusted to pH 5-7 with 2 M HCl. The resulting solution was extracted with DCM/MeOH (10 mL/1 mL) 3 times. The combined organics were dried over Na$_2$SO$_4$, filtered and concentrated in vacuum to give the product (40 mg, crude) as a yellow solid, which was used for next reaction without further purification.
LCMS (0-60 AB_2 min), RT=1.431 mins, [MH]$^+$=460.1.
LCMS Method 0-60AB_2 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 1.2 mL/min;
Gradient: 0%-60% (solvent B) over 0.9 minutes and holding at 60% for 0.6 minutes.

(iii) 7-(3-aminopiperidin-1-yl)-1-cyclopropyl-6-fluoro-8-methyl-2-oxo-1,2-dihydroquinoline-3-carboxylic acid hydrochloride To a solution of 7-(3-((tert-butoxycarbonyl)amino)piperidin-1-yl)-1-cyclopropyl-6-fluoro-8-methyl-2-oxo-1,2-dihydroquinoline-3-carboxylic acid (50 mg, crude) in EtOAc (3 mL) was added HCl/EtOAc (5 mL). Then the resulting solution was stirred at 20° C. for 30 min. After the reaction was complete, the reaction mixture was concentrated in vacuum and the residue was dissolved in H$_2$O (10 mL). The resulting solution was washed with EtOAc (10 mL×2) and then lyophilized to give the product (17 mg, 15.8% yield in 3 steps) as a yellow solid.
LCMS (0-60 AB_7 min), RT=2.751 mins, [MH]$^+$=360.1.
$^1$H NMR (400 MHz, D$_2$O-d$_2$) δ 8.27 (s, 1H), 7.19 (7.19, 1H), 3.59-3.49 (m, 3H), 3.23-3.17 (m, 2H), 2.47 (s, 3H), 2.08-2.07 (m, 1H), 1.82-1.68 (m, 3H), 1.21-1.15 (m, 2H), 0.46-0.45 (m, 2H)
LCMS Method 0-60 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 0%-60% (solvent B) over 6 minutes and holding at 60% for 0.5 minutes.

Example 1.7: 7-(3-aminoazetidin-1-yl)-1-cyclopropyl-6-fluoro-8-methyl-2-oxo-1,2-dihydroquinoline-3-carboxylic acid The title compound was prepared in accordance with the following scheme:

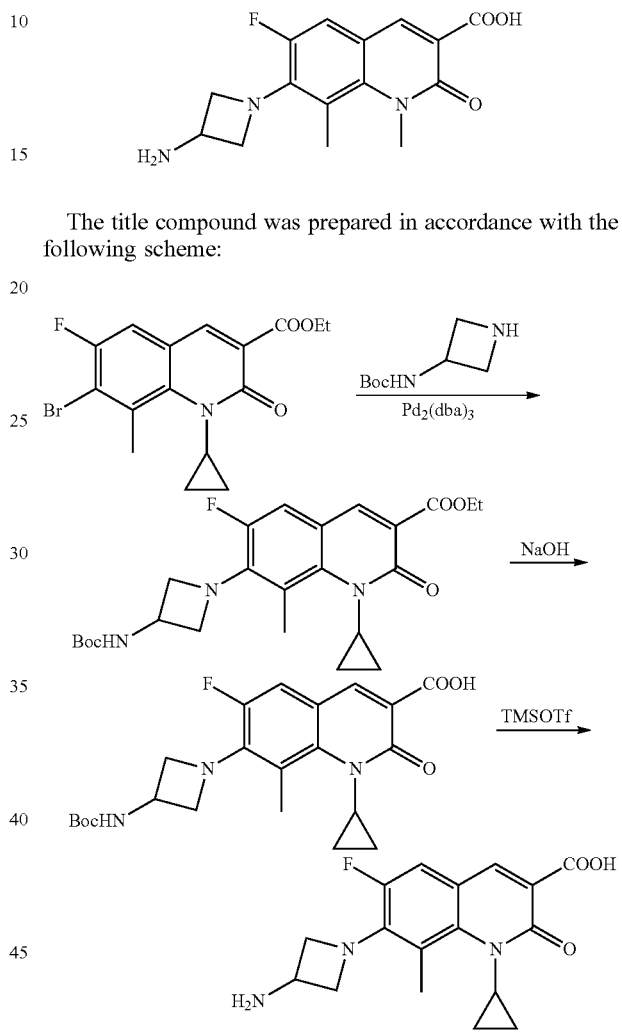

(i) ethyl 7-(3-((tert-butoxycarbonyl)amino)azetidin-1-yl)-1-cyclopropyl-6-fluoro-8-methyl-2-oxo-1,2-dihydroquinoline-3-carboxylate To a solution of ethyl 7-bromo-1-cyclopropyl-6-fluoro-8-methyl-2-oxo-1,2-dihydroquinoline-3-carboxylate (100.0 mg, 0.27 mmol) in toluene (20 mL) was added tert-butyl azetidin-3-ylcarbamate (93.5 mg, 0.54 mmol), C$_{S2}$CO$_3$ (264.3 mg, 0.81 mmol) Xantphos (23.4 mg, 0.04 mmol) and Pd$_2$(dba)$_3$ (12.4 mg, 0.01 mmol) at 20° C. The reaction mixture was stirred to 110° C. for 12 h. After the reaction was complete, the reaction mixture was dissolved in water (20 mL) and extracted with EtOAc (30 mL×3). The organic layer was dried over Na$_2$SO$_4$ and evaporated to give the crude product. The crude product was purified by column chromatography on silica gel (Eluents: EtOAc:PE from 1:8 to 1:2) to get the product (90.0 mg, yield: 72.1%).

¹H NMR (400 MHz, DMSO-d₆) δ ppm 8.19 (s, 1H), 7.58 (d, J=6.4 Hz, 1H), 7.40 (d, J=13.6 Hz, 1H), 4.53-4.52 (m, 2H), 4.38-4.36 (m, 1H), 4.25 (q, J=7.2 Hz, 2H), 4.07-4.06 (m, 2H), 2.26 (s, 3H), 1.40 (s, 9H), 1.30 (t, J=7.2 Hz, 3H), 1.17 (d, J=6.0 Hz, 2H), 0.43-0.42 (m, 2H).

(ii) 7-(3-((tert-butoxycarbonyl)amino)azetidin-1-yl)-1-cyclopropyl-6-fluoro-8-methyl-2-oxo-1,2-dihydroquinoline-3-carboxylic acid To a solution of ethyl 7-(3-((tert-butoxycarbonyl)amino)azetidin-1-yl)-1-cyclopropyl-6-fluoro-8-methyl-2-oxo-1,2-dihydroquinoline-3-carboxylate (90.0 mg, 0.20 mmol) in THF/H₂O (6 mL, 1:2) was added NaOH (15.7 mg, 0.39 mmol) at 25° C. The reaction mixture was stirred at 45° C. for 4 h. After the reaction was complete, the reaction mixture was extracted with EtOAc. The organic phase was dried over Na₂SO₄ and evaporated to get the product. (70.0 mg, yield: 83.0%).

¹H NMR (400 MHz, DMSO-d₆) δ 8.47 (s, 1H), 7.61 (d, J=6.8 Hz, 1H), 7.55 (d, J=12.8 Hz, 1H), 4.58-4.57 (m, 2H), 4.37-4.36 (m, 1H), 4.12-4.11 (m, 2H), 3.54-3.53 (m, 1H), 2.30 (s, 3H), 1.40 (s, 9H), 1.24-1.16 (m, 2H), 0.55-0.54 (m, 2H)

(iii) 7-(3-aminoazetidin-1-yl)-1-cyclopropyl-6-fluoro-8-methyl-2-oxo-1,2-dihydroquino line-3-carboxylic acid To a solution of 7-(3-((tert-butoxycarbonyl)amino)azetidin-1-yl)-1-cyclopropyl-6-fluoro-8-methyl-2-oxo-1,2-dihydroquinoline-3-carboxylic acid (50.0 mg, 0.12 mmol) in DCM (10 mL) was added 2,6-dimethylpyridine (24.8 mg, 0.23 mmol) and TMSOTf (80.1 mg, 0.36 mmol) at 0° C. The reaction mixture was stirred at 30° C. for 3 h. After the reaction was complete, the reaction mixture was quenched by water (10 mL) and then extracted with EtOAc (20 mL×3). The organic layer was dried over Na₂SO₄ and evaporated to give the crude product. The crude product was purified by pre-HPLC to get the product (10.0 mg, yield: 26.0%).

LCMS (0-60 AB_7 min), RT=2.293 mins, [MH]⁺=332.1.

¹H NMR (400 MHz, DMSO-d₆) δ 8.43 (s, 1H), 7.52 (d, J=13.6 Hz, 1H), 4.53-4.52 (m, 2H), 3.91-3.90 (m, 2H), 3.78-3.75 (m, 1H), 3.55-3.54 (m, 1H), 2.31 (s, 3H), 1.23 (d, J=6.8 Hz, 2H), 0.55-0.54 (m, 2H)

LCMS Method 0-60 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 0%-60% (solvent B) over 6 minutes and holding at 60% for 0.5 minutes.

Example 1.8: 7-(3-(1-aminocyclopropyl)pyrrolidin-1-yl)-1-cyclopropyl-6-fluoro-8-methyl-2-oxo-1,2-dihydroquinoline-3-carboxylic acid hydrochloride salt

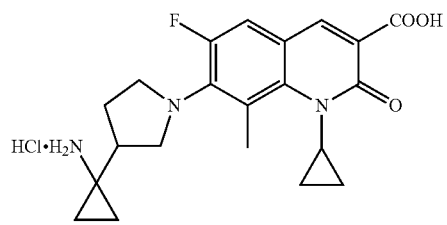

The title compound was prepared in accordance with the following scheme:

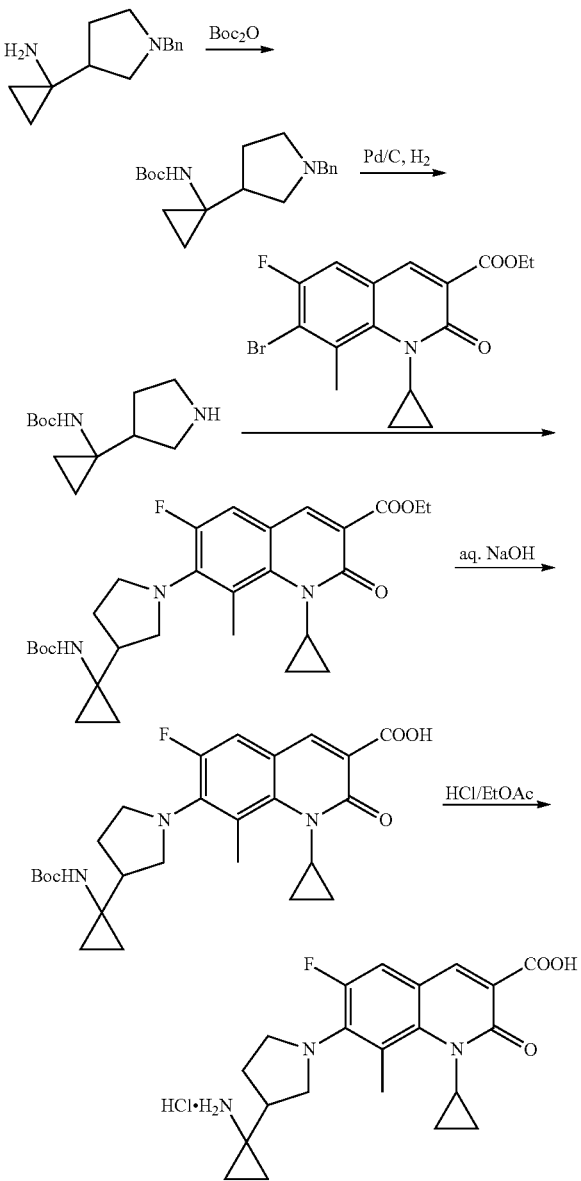

(i) tert-butyl (1-(1-benzylpyrrolidin-3-yl)cyclopropyl)carbamate

To a mixture of 1-(1-benzylpyrrolidin-3-yl)cyclopropanamine (500 mg, 2.31 mmol) in sat. aq. NaHCO$_3$/THF (45 mL, 1:2) was added Boc$_2$O (1.513 g, 6.93 mmol). The reaction mixture was stirred at 25° C. for 2 h. Water (50 mL) was added to the mixture. The resulting solution was extracted with EtOAc (40 mL×8). The combined organic layer was dried over anhydrous Na$_2$SO$_4$ and concentrated to give a crude product. The crude product was purified by chromatography on silica gel (Eluent: EtOAc:PE=10:1) to give the title compound (500 mg, 68.4% yield).

$^1$H NMR (400 MHz, CDCl$_3$-d$_1$) δ d 7.25-7.20 (m, 4H), 7.19-7.12 (m, 1H), 4.99 (brs., 1H), 3.51 (s, 2H), 2.68-2.59 (m, 1H), 2.55-2.49 (m, 1H), 2.45-2.35 (m, 1H), 2.25-2.17 (m, 2H), 1.90-1.77 (m, 1H), 1.55-1.36 (m, 1H), 1.36 (s, 9H), 0.78-0.72 (m, 2H), 0.70-0.58 (m, 2H)

(ii) tert-butyl (1-(pyrrolidin-3-yl)cyclopropyl)carbamate

To a solution of tert-butyl (1-(1-benzylpyrrolidin-3-yl)cyclopropyl)carbamate (200 mg, 0.63 mmol) in MeOH (10 mL) was added 10% dry Pd/C (40 mg, 20% w/w). The resulting solution was stirred under H$_2$ atmosphere (50 Psi) at 50° C. for 2 h. The mixture was filtered. The filtrate was evaporated to give the title compound (140 mg, 97.9% yield).

$^1$H NMR (400 MHz, CDCl$_3$-d$_1$) δ 4.98 (brs., 1H), 3.13-2.98 (m, 3H), 2.75-2.65 (m, 1H), 2.25-2.15 (m, 1H), 1.95-1.85 (m, 1H), 1.48-1.40 (m, 10H), 0.85-0.77 (m, 2H), 0.75-0.65 (m, 2H)

(iii) ethyl 7-(3-(1-((tert-butoxycarbonyl)amino)cyclopropyl)pyrrolidin-1-yl)-1-cyclopropyl-6-fluoro-8-methyl-2-oxo-1,2-dihydroquinoline-3-carboxylate To a mixture of tert-butyl (1-(pyrrolidin-3-yl)cyclopropyl)carbamate (140 mg, 0.62 mmol), ethyl 7-bromo-1-cyclopropyl-6-fluoro-8-methyl-2-oxo-1,2-dihydroquinoline-3-carboxylate (150 mg, 0.41 mmol), Cs$_2$CO$_3$ (401 mg, 1.23 mmol) and Xantphos (36 mg, 0.062 mmol) in toluene (30 mL) was added Pd$_2$(dba)$_3$ (19 mg, 0.021 mmol). Then the reaction mixture was stirred at 110° C. for 14 h under N$_2$ atmosphere. The reaction mixture was evaporated to give a crude product. The crude product was purified by chromatography on silica gel (Eluent: EtOAc:PE=2:1) to give the title compound (80 mg, 38.2% yield).

$^1$H NMR (400 MHz, CDCl$_3$-d$_1$) δ d 8.16 (s, 1H), 7.02 (d, J=12.8 Hz, 1H), 4.97 (brs., 1H), 4.40 (q, J=6.8 Hz, 2H), 3.75-3.68 (m, 1H), 3.60-3.56 (m, 1H), 3.50-3.44 (m, 3H), 2.45-2.35 (m, 4H), 1.85-1.75 (m, 1H), 1.48-0.40 (m, 10H), 1.42 (t, J=7.2 Hz, 3H), 0.88-0.80 (m, 6H), 0.60-0.50 (m, 2H)

(iv) 7-(3-(1-((tert-butoxycarbonyl)amino)cyclopropyl)pyrrolidin-1-yl)-1-cyclopropyl-6-fluoro-8-methyl-2-oxo-1,2-dihydroquinoline-3-carboxylic acid To a mixture of ethyl 7-(3-(1-((tert-butoxycarbonyl)amino)cyclopropyl)pyrrolidin-1-yl)-1-cyclopropyl-6-fluoro-8-methyl-2-oxo-1,2-dihydroquinoline-3-carboxylate (40 mg, 0.078 mmol) in THF/H$_2$O (8 mL, 1:1) was added NaOH (6 mg, 0.15 mmol). Then the reaction mixture was stirred at 30° C. for 17 h. The reaction mixture was acidified to pH~6 with aq. HCl (0.5 M). The resulting solution was extracted with EtOAc (40 mL×8). The combined organic layer was dried over anhydrous Na$_2$SO$_4$ and concentrated to give the title compound (35 mg, 92.5% yield).

$^1$H NMR (400 MHz, CDCl$_3$-d$_1$) δ 8.58 (s, 1H), 7.14 (d, J=12.8 Hz, 1H), 5.00 (brs, 1H), 3.85-3.75 (m, 1H), 3.72-3.65 (m, 1H), 3.62-3.58 (m, 1H), 3.55-3.46 (m, 2H), 2.46 (s, 3H), 1.85-1.78 (m, 1H), 1.68-1.60 (m, 1H), 1.8-1.40 (s, 10H), 0.95-0.85 (m, 6H), 0.68-0.60 (m, 2H)

(v) 7-(3-(1-aminocyclopropyl)pyrrolidin-1-yl)-1-cyclopropyl-6-fluoro-8-methyl-2-oxo-1,2-dihydroquinoline-3-carboxylic acid hydrochloride salt A mixture of 7-(3-(1-((tert-butoxycarbonyl)amino)cyclopropyl)pyrrolidin-1-yl)-1-cyclopropyl-6-fluoro-8-methyl-2-oxo-1,2-dihydroquinoline-3-carboxylic acid (35 mg, 0.072 mmol) in HCl/EtOAc (5 mL, 4 M) and EtOAc (5 mL) was stirred at 25° C. for 2 h. Water (10 mL) was added to the mixture. The resulting solution was washed with EtOAc (40 mL×6). The aqueous solution was lyophilized to give the title compound (12 mg, 39.5% yield).

$^1$H NMR (400 MHz, DMSO-d$_6$) δ 8.65 (s., 1H), 7.63 (d, J=13.6 Hz, 1H), 3.76-3.67 (m, 2H), 3.66-3.62 (m, 3H), 2.70-2.65 (m, 1H), 2.44 (s, 3H), 2.05-1.95 (m, 1H), 1.72-1.65 (m, 1H), 1.30-1.20 (m, 2H), 1.02-0.80 (m, 4H), 0.62-0.52 (m, 2H)

LCMS (0-60 AB_7 min), [MH]$^+$=386.1, RT=2.978 mins

LCMS Method 0-60 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 0%-60% (solvent B) over 6 minutes and holding at 60% for 0.5 minutes.

Example 2: 7-((R)-3-((S)-1-((2-cyanoethyl)amino)ethyl)pyrrolidin-1-yl)-1-cyclopropyl-6-fluoro-8-methyl-2-oxo-1,2-dihydroquinoline-3-carboxylic acid hydrochloride salt

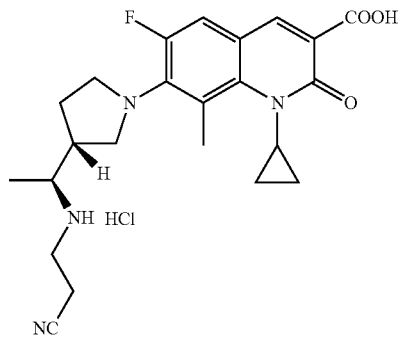 [SMILES: Cc1c(N2CC[C@@H]([C@H](C)NCCC#N)C2)c(F)cc2cc(C(=O)O)c(=O)n(C3CC3)c12 ; Cl]

The title compound was prepared in accordance with the following scheme:

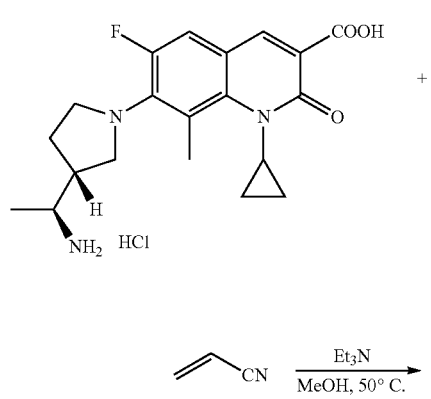

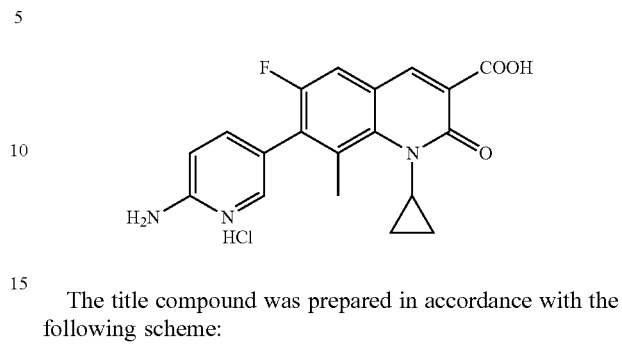

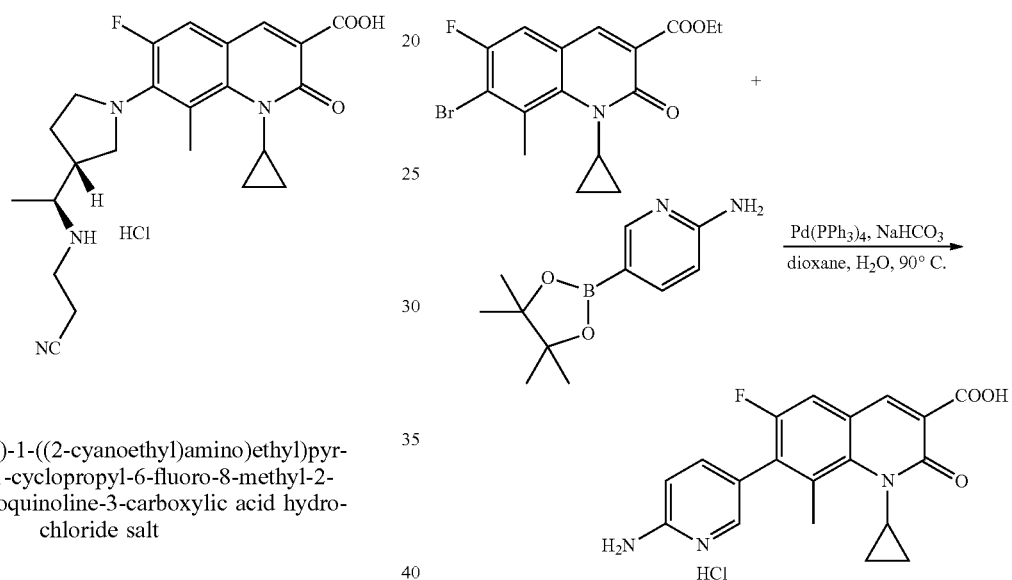

(i) 7-((R)-3-((S)-1-((2-cyanoethyl)amino)ethyl)pyrrolidin-1-yl)-1-cyclopropyl-6-fluoro-8-methyl-2-oxo-1,2-dihydroquinoline-3-carboxylic acid hydrochloride salt To a solution of 7-((R)-3-((S)-1-aminoethyl)pyrrolidin-1-yl)-1-cyclopropyl-6-fluoro-8-methyl-2-oxo-1,2-dihydroquinoline-3-carboxylic acid hydrochloride (30 mg, 0.073 mmol) and acrylonitrile (0.01 mL, 0.22 mmol) in MeOH (8 mL) was added Et$_3$N (0.05 mL, 0.37 mmol) at 15° C. Then the solution was stirred at 50° C. for 3 hours. After the reaction was complete, the mixture was concentrated in vacuum to give a residue. The residue was purified by prep-HPLC to give the title compound (8.0 mg, 25.6%) as a yellow solid.

$^1$H NMR (400 MHz, CD$_3$OD-d$_4$) δ d 8.67 (s, 1H), 7.45 (d, J=12.8 Hz, 1H), 3.90-3.60 (m, 4H), 3.58-3.40 (m, 4H), 3.10-3.00 (m, 1H), 2.70-2.63 (m, 1H), 2.59 (s, 3H), 2.30-2.20 (m, 1H), 2.00-1.90 (m, 1H), 1.49 (d, J=6.4 Hz, 3H), 1.40-1.30 (m, 2H), 0.70-0.60 (m, 2H)

LCMS (0-60 AB_7 min), [MH]$^+$=427.0, RT=2.935 mins.

LCMS Method 0-60 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 0%-60% (solvent B) over 6 minutes and holding at 60% for 0.5 minutes.

Example 3: 7-(6-aminopyridin-3-yl)-1-cyclopropyl-6-fluoro-8-methyl-2-oxo-1,2-dihydroquinoline-3-carboxylic acid hydrochloride salt The title compound was prepared in accordance with the following scheme:

(i) 7-(6-aminopyridin-3-yl)-1-cyclopropyl-6-fluoro-8-methyl-2-oxo-1,2-dihydroquinoline-3-carboxylic acid hydrochloride salt A mixture of ethyl 7-bromo-1-cyclopropyl-6-fluoro-8-methyl-2-oxo-1,2-dihydroquinoline-3-carboxylate (100 mg, 0.27 mmol), 5-(4,4,5,5-tetramethyl-1,3,2-dioxaborolan-2-yl)pyridin-2-amine (66 mg, 0.33 mmol), Pd(PPh$_3$)$_4$ (16 mg, 0.014 mmol) and NaHCO$_3$ (69 mg, 0.82 mmol) in 1,4-dioxane (2 mL) and H$_2$O (2 mL) was degassed under vacuum and then purged with N$_2$ three times. The resulting mixture was stirred at 90° C. for 3 h. The reaction mixture was concentrated to give the crude product, which was purified by pre-HPLC (HCl-system) to give the product. (30 mg, 28.3% yield).

LCMS (0-30 AB_7 min), RT=3.584 mins, [MH]$^+$=353.9.

$^1$H NMR (400 MHz, DMSO-d$_6$) δ 8.82 (s, 1H), 8.32 (brs, 2H), 8.18 (s, 1H), 7.99 (d, J=8.8 Hz, 1H), 7.94 (d, J=8.8 Hz, 1H), 7.15 (d, J=8.8 Hz, 1H), 3.70-3.65 (m, 1H), 2.51 (s, 3H), 1.25-1.19 (m, 2H), 0.75-0.62 (m, 2H)

LCMS Method 0-30 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;
Flow rate: 0.8 mL/min;
Gradient: 0%-30% (solvent B) over 6 minutes and holding at 30% for 0.5 minutes.

Example 4.1: 7-((R)-3-((S)-1-aminoethyl)pyrrolidin-1-yl)-1-cyclopropyl-6-fluoro-8-methyl-3-(methylsulfonyl)quinolin-2(1H)-one hydrochloride salt

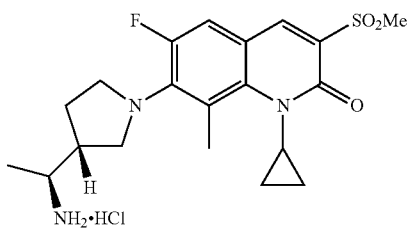

The title compound was prepared in accordance with the following scheme:

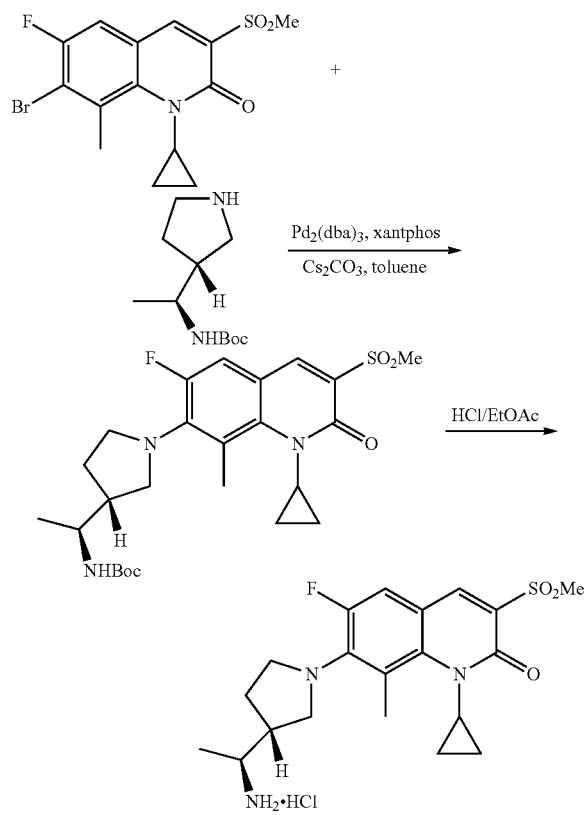

(i) Tert-butyl((S)-1-((R)-1-(1-cyclopropyl-6-fluoro-8-methyl-3-(methylsulfonyl)-2-oxo-1,2-dihydroquinolin-7-yl)pyrrolidin-3-yl)ethyl)carbamate To a solution of 7-bromo-1-cyclopropyl-6-fluoro-8-methyl-3-(methylsulfonyl)quinolin-2(1H)-one (100 mg, 0.27 mmol) in toluene (20 mL) was added tert-butyl ((S)-1-((R)-pyrrolidin-3-yl)ethyl)carbamate (75 mg, 0.35 mmol), Cs$_2$CO$_3$ (261 mg, 0.80 mmol), Pd$_2$(dba)$_3$ (37 mg, 0.040 mmol) and Xantphos (7.5 mg, 0.013 mmol). Then the reaction mixture was stirred at 120° C. for 18 hours. After the reaction was complete, the reaction mixture was diluted with EtOAc (20 mL) and then filtered. The filtrate was concentrated in vacuum. The residue was purified by prep. TLC (Developer: PE:EtOAc=1:1.5) to give the crude product (30 mg, yield: 22.1%), which was used in the next step directly.

(ii) 7-((R)-3-((S)-1-aminoethyl)pyrrolidin-1-yl)-1-cyclopropyl-6-fluoro-8-methyl-3-(methylsulfonyl)quinolin-2(1H)-one hydrochloride salt To a solution of tert-butyl ((S)-1-((R)-1-(1-cyclopropyl-6-fluoro-8-methyl-3-(methylsulfonyl)-2-oxo-1,2-dihydroquinolin-7-yl)pyrrolidin-3-yl)ethyl)carbamate (30 mg, 0.059 mmol) in EtOAc (2 mL) was added HCl/EtOAc (2 mL) at 0° C. The reaction solution was stirred at 15° C. for 2 hours. After the reaction was complete, the reaction mixture was concentrated. The residue was dissolved in water (15 mL) and washed with EtOAc (20 mL). The aqueous phase was lyophilized to give the product (15 mg, 57.2%) as a yellow solid.

LCMS (0-60 AB_7 min), RT=2.751 mins, [MH]$^+$=408.1.
$^1$H NMR (400 MHz, D$_2$O-d$_2$) δ 8.21-8.195 (m, 1H), 7.051 (s, 1H), 3.70-3.60 (m, 1H), 3.55-3.50 (m, 2H), 3.42-3.34 (m, 3H), 3.25 (s, 3H), 2.45-2.40 (m, 1H), 2.25 (s, 3H), 2.15-2.10 (m, 1H), 1.70-1.60 (m, 1H), 1.30 (d, J=6.8 Hz, 3H), 1.21-1.11 (m, 2H), 0.50-0.40 (m, 2H)

LCMS Method 0-60 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 0%-60% (solvent B) over 6 minutes and holding at 60% for 0.5 minutes.

Example 4.2: 7-(3-(aminomethyl)pyrrolidin-1-yl)-1-cyclopropyl-6-fluoro-8-methyl-3-(methylsulfonyl)quinolin-2(1H)-one hydrochloride salt

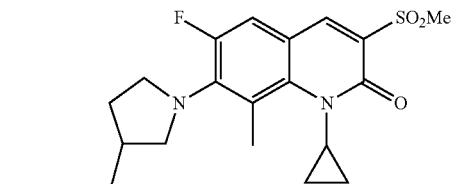

The title compound was prepared in accordance with the following scheme:

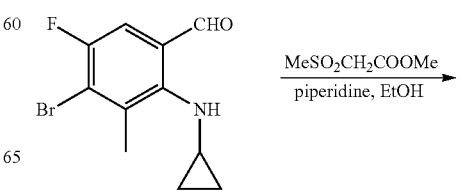

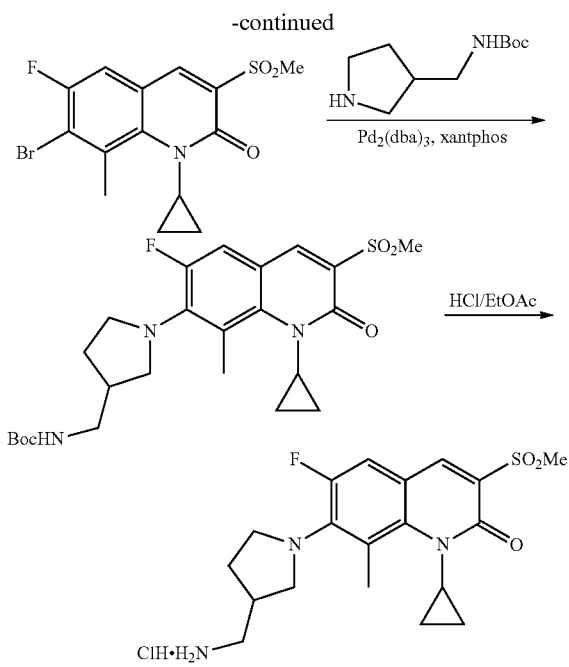

(i) 7-bromo-1-cyclopropyl-6-fluoro-8-methyl-3-(methylsulfonyl)quinolin-2(1H)-one To a solution of 4-bromo-2-(cyclopropylamino)-5-fluoro-3-methylbenzaldehyde (170 mg, 0.62 mmol) and MeSO$_2$CH$_2$COOMe (167 mg, 1.1 mmol) in EtOH (8 mL) was added piperidine (162 mg, 1.9 mmol). Then the reaction mixture was stirred at 80° C. for 18 hours. After the reaction was complete, the resulting mixture was concentrated in vacuum. The residue was purified by TLC (Developer: PE:EtOAc=1:1) to give the product (180 mg, yield: 77.0%) as a yellow solid.

$^1$H NMR (400 MHz, CD$_3$OD-d$_4$) δ 8.55 (s, 1H), 7.64 (d, J=8 Hz, 1H), 3.68-3.63 (m, 1H), 3.35 (s, 3H), 2.89 (s, 3H), 1.32-1.27 (m, 2H), 0.63-0.59 (m, 2H)

(ii) tert-butyl((1-(1-cyclopropyl-6-fluoro-8-methyl-3-(methylsulfonyl)-2-oxo-1,2-dihydroquinolin-7-yl)pyrrolidin-3-yl)methyl)carbamate To a solution of 7-bromo-1-cyclopropyl-6-fluoro-8-methyl-3-(methylsulfonyl)quinolin-2(1H)-one (70 mg, 0.19 mmol) in toluene (8 mL) was added tert-butyl (pyrrolidin-3-ylmethyl)carbamate (112 mg, 0.56 mmol), Cs$_2$CO$_3$ (182 mg, 0.56 mmol), Pd$_2$(dba)$_3$ (26 mg, 0.028 mmol) and Xantphos (5.4 mg, 0.0094 mmol). Then the reaction mixture was stirred at 120° C. for 18 hours. After the reaction was complete, the resulting mixture was diluted with EtOAc (10 mL) and then filtered. The filtrate was concentrated in vacuum. The residue was purified by prep. TLC (Developer: PE:EtOAc=1:1.5) to give the product (18 mg, yield: 19.5%) as a yellow solid.

LCMS (5-95 AB_1.5 min), RT=0.863 min, [MH]$^+$=494.1.
LCMS Method 5-95AB_1.5 MIN
Column: MERCK, RP-18e 25-2 mm, ESI source, Positive ion mode; Wavelength: 220 nm;
Column temperature: 40° C.;
Mobile Phase: A: 1.5 mL/4 L TFA in water, B: 0.75 mL/4 L TFA in acetonitrile;
Flow rate & gradient: at a flow rate of 1.0 ml/min from 0-0.08 min, using the elution gradient 5%-95% (solvent B) from 0-0.7 min and holding at 95% for 0.4 minutes, at a flow rate of 1.5 ml/min

(iii) 7-(3-(aminomethyl)pyrrolidin-1-yl)-1-cyclopropyl-6-fluoro-8-methyl-3-(methylsulfonyl)quinolin-2(1H)-one hydrochloride salt To a solution of tert-butyl ((1-(1-cyclopropyl-6-fluoro-8-methyl-3-(methylsulfonyl)-2-oxo-1,2-dihydroquinolin-7-yl)pyrrolidin-3-yl)methyl)carbamate (20 mg, 0.041 mmol) in EtOAc (2 mL) was added HCl/EtOAc (2 mL) at 0° C. And then the reaction mixture was stirred at 15° C. for 2 hours. After the reaction was complete, the resulting mixture was concentrated in vacuum. The residue was dissolved with H$_2$O (8 mL) and then washed with EtOAc (10 mL). The water phase was lyophilized to give the product (9.0 mg, 56.4%) as a yellow solid.

LCMS (0-60 AB_7 min), RT=2.568 mins, [MH]$^+$=393.9.
$^1$H NMR (400 MHz, D$_2$O-d$_2$) δ 8.11 (s, 1H), 6.94 (d, J=13.2 Hz, 1H), 3.59-3.58 (m, 2H), 3.40-3.35 (m, 3H), 3.24 (s, 3H), 3.09-3.05 (m, 2H), 2.58-2.56 (m, 1H), 2.20-2.15 (m, 4H), 1.70-1.69 (m, 1H), 1.14-1.07 (m, 2H), 0.39-0.37 (m, 2H)

LCMS Method 0-60 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 0%-60% (solvent B) over 6 minutes and holding at 60% for 0.5 minutes.

Example 5: 7-((R)-3-((S)-1-aminoethyl)pyrrolidin-1-yl)-1-cyclopropyl-6-fluoro-N,N,8-trimethyl-2-oxo-1,2-dihydroquinoline-3-sulfonamide hydrochloride salt

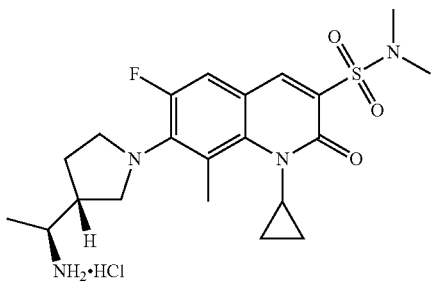

The title compound was prepared in accordance with the following scheme:

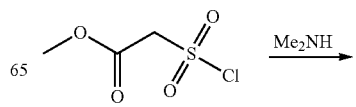

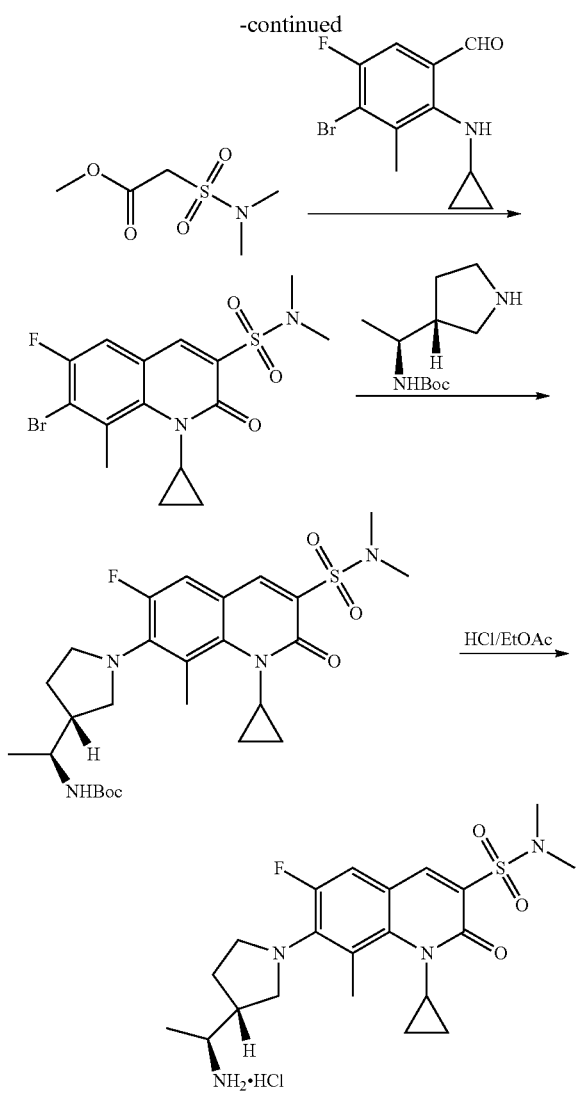

(i) methyl 2-(N,N-dimethylsulfamoyl)acetate

To a mixture of dimethylamine (2.18 mL, 4.36 mmol, 2 M in THF) in DCM (15 mL) was added a solution of methyl 2-(chlorosulfonyl)acetate (500 mg, 2.90 mmol) in DCM (10 mL) was added at −20° C. The solution was then stirred at 0° C. for 2 h. After the reaction was complete, water (50 mL) was added to the reaction mixture. The resulting solution was extracted with DCM (40 mL×4). The organic phase was dried over anhydrous $Na_2SO_4$ and evaporated to give a crude product. The crude product was purified by chromatography on silica gel (Eluents: EtOAc:PE from 1:15 to 1:7) to give the title compound (173 mg, 33.0% yield).

$^1$H NMR (400 MHz, DMSO-$d_6$) δ ppm 4.28 (s, 2H), 3.71 (s, 3H), 2.81 (s, 6H)

(ii) 7-bromo-1-cyclopropyl-6-fluoro-N,N,8-trimethyl-2-oxo-1,2-dihydroquinoline-3-sulfonamide To a mixture of 4-bromo-2-(cyclopropylamino)-5-fluoro-3-methylbenzaldehyde (100 mg, 0.37 mmol) and methyl 2-(N,N-dimethylsulfamoyl)acetate (101 mg, 0.56 mmol) in EtOH (5 mL) was added piperidine (95 mg, 1.12 mmol). The sealed vial was irradiated in the microwave on a Biotage Smith Synthesis at 120° C. for 6 h under $N_2$ atmosphere. The mixture was evaporated to give the crude product, which was recrystallized from co-solvent (PE:EtOAc=15:1) to give the title compound (140 mg, 94.5% yield).

$^1$H NMR (400 MHz, CDCl$_3$-$d_1$) δ 8.23 (s, 1H), 7.14 (d, J=7.2 Hz, 1H), 3.49-3.42 (m, 1H), 2.92 (s, 6H), 2.74 (s, 3H), 1.25-0.95 (m, 2H), 0.58-0.45 (m, 2H)

(iii) tert-butyl ((S)-1-((R)-1-(1-cyclopropyl-3-(N,N-dimethylsulfamoyl)-6-fluoro-8-methyl-2-oxo-1,2-dihydroquinolin-7-yl)pyrrolidin-3-yl)ethyl)carbamate To a mixture of 7-bromo-1-cyclopropyl-6-fluoro-N,N,8-trimethyl-2-oxo-1,2-dihydroquinoline-3-sulfonamide (140 mg, 0.35 mmol), tert-butyl ((S)-1-((R)-pyrrolidin-3-yl)ethyl) carbamate (99 mg, 0.46 mmol), $Cs_2CO_3$ (342 mg, 1.05 mmol) and Xantphos (31 mg, 0.053 mmol) in toluene (30 mL) was added $Pd_2(dba)_3$ (16 mg, 0.018 mmol). Then the reaction mixture was stirred at 110° C. for 14 h under $N_2$ atmosphere. After the reaction was complete, the reaction mixture was evaporated to give a crude product. The crude product was purified by chromatography on silica gel (Eluent: EtOAc:PE=2:1) to give the title compound (25 mg, 13.4% yield).

$^1$H NMR (400 MHz, CDCl$_3$-$d_1$) δ 8.16 (s, 1H), 6.97 (d, J=12.8 Hz, 1H), 4.41 (d, J=8.8 Hz, 1H), 3.70-3.55 (m, 2H), 3.52-3.45 (m, 1H), 3.44-3.35 (m, 3H), 2.90 (s, 6H), 2.37 (s, 3H), 2.25-2.18 (m, 1H), 2.05-1.95 (m, 1H), 1.67-1.73 (m, 1H), 1.20-1.15 (m, 12H), 1.18-1.10 (m, 2H), 0.60-0.48 (m, 2H)

(iv) 7-((R)-3-((S)-1-aminoethyl)pyrrolidin-1-yl)-1-cyclopropyl-6-fluoro-N,N,8-trimethyl-2-oxo-1,2-dihydroquinoline-3-sulfonamide hydrochloride salt A mixture of tert-butyl ((S)-1-((R)-1-(1-cyclopropyl-3-(N,N-dimethylsulfamoyl)-6-fluoro-8-methyl-2-oxo-1,2-dihydroquinolin-7-yl)pyrrolidin-3-yl)ethyl)carbamate (25 mg, 0.047 mmol) in HCl/EtOAc (5 mL, 4 M) and EtOAc (5 mL) was stirred at 25° C. for 2 h. Water (10 mL) was added to the reaction mixture. The resulting solution was washed with EtOAc (40 mL×2). The aqueous solution was lyophilized to give the title compound (20 mg, 90.8% yield).

$^1$H NMR (400 MHz, $D_2O$-$d_2$) δ 8.06 (s, 1H), 6.86 (d, J=13.6 Hz, 1H), 3.65-3.55 (m, 1H), 3.42-3.53 (m, 2H), 3.35-3.28 (m, 2H), 3.27-3.18 (m, 1H), 2.67 (s, 6H), 2.41-2.36 (m, 1H), 2.15 (s, 3H), 2.08-2.00 (m, 1H), 1.68-1.61 (m, 1H), 1.25 (d, J=6.8 Hz, 3H), 1.12-1.00 (m, 2H), 0.35-0.25 (m, 2H)

LCMS (0-60 AB_7 min), [MH]$^+$=437.2, RT=2.938 mins.
LCMS Method 0-60 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 0%-60% (solvent B) over 6 minutes and holding at 60% for 0.5 minutes.

Example 6: 7-((R)-3-((S)-1-aminoethyl)pyrrolidin-1-yl)-1-cyclopropyl-6-fluoro-3-methoxy-8-methylquinolin-2(1H)-one The title compound was prepared in accordance with the following scheme:

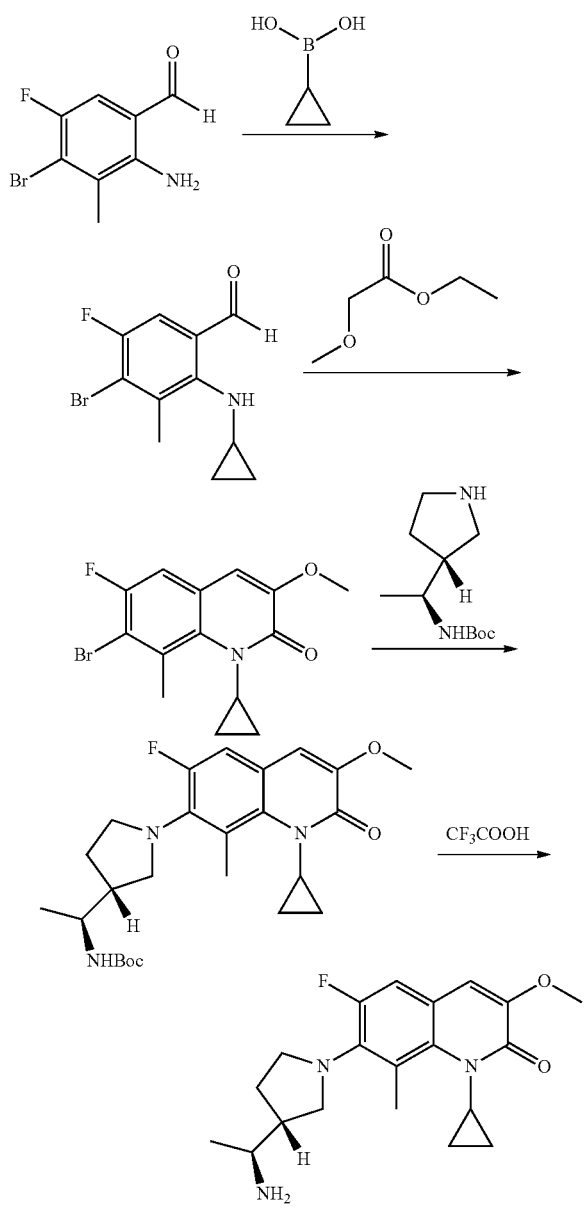

(i) 4-Bromo-2-(cyclopropylamino)-5-fluoro-3-methylbenzaldehyde

To a solution of 2-amino-4-bromo-5-fluoro-3-methylbenzaldehyde (0.5 g, 2.1 mmol) in DCE (25 mL) at ambient temperature was added cesium carbonate (4.21 g, 12.9 mmol), copper (II) acetate (0.78 g, 4.3 mmol), 2,2'-bipyridine (0.67 g, 4.3 mmol), and followed by the addition of cyclopropylboronic acid (0.37 g, 4.3 mmol). The reaction solution was stirred for 3 min, and then was heated to 80° C. in an oil bath for 20 min. The reaction mixture was removed from heating source, and was stirred at ambient temperature for 1 h. The additional cyclopropylboronic acid (4.3 mmol), copper (II) acetate (2.1 mmol) were added. The reaction was continued for another 2 h and then to the mixture was added third portion of cyclopropyl boronic acid (4.3 mmol), copper (II) acetate (2.1 mmol). The resulting reaction mixture was stirred at ambient temperature for 18 h. The reaction suspension was diluted with ethyl acetate (80 mL), washed with water (2×50 mL), brine (50 mL), dried over sodium sulfate, filtered and the filtrate was concentrated. The resulting residue was purified by ISCO eluting with 0-30-50-100% ethyl acetate in heptane to give 4-bromo-2-(cyclopropylamino)-5-fluoro-3-methylbenzaldehyde (380 mg, 55.1% yield). LCMS (m/z): 272/274, RT 1.09 min.

(ii) 7-Bromo-1-cyclopropyl-6-fluoro-3-methoxy-8-methylquinolin-2(1H)-one

To a solution of LiHMDS (6.61 mL, 6.61 mmol) in THF (5 mL) at −78° C. was added ethyl 2-methoxyacetate (0.78 mL, 6.61 mmol). The reaction solution was stirred for 20 min, then a solution of 4-bromo-2-(cyclopropylamino)-5-fluoro-3-methylbenzaldehyde (180 mg, 0.66 mmol) in THF (5 mL) was added to above reaction mixture. The resulting solution was allowed to come slowly to ambient temperature as the cooling bath warmed up. The reaction mixture was stirred at ambient temperature for 16 h. The reaction was quenched with 2 mL 6N HCl (the pH was 4 at this point), and the resulting mixture was refluxed at 110° C. in an oil bath for 2 h. The solution was diluted with ethyl acetate, washed with water, brine, dried over sodium sulfate, and concentrated. The residue was purified by ISCO eluting with 0-20-50-100% ethyl acetate in heptane to give 7-bromo-1-cyclopropyl-6-fluoro-3-methoxy-8-methylquinolin-2(1H)-one (95 mg, 28.6% yield) as light yellow color oil. LCMS (m/z): 326/328, RT 0.88 min.

(iii) tert-Butyl ((S)-1-((R)-1-(1-cyclopropyl-6-fluoro-3-methoxy-8-methyl-2-oxo-1,2-dihydroquinolin-7-yl)pyrrolidin-3-yl)ethyl)carbamate To a solution of 7-bromo-1-cyclopropyl-6-fluoro-3-methoxy-8-methylquinolin-2(1H)-one (95 mg, 0.29 mmol) in dioxane (3 mL) was added tert-butyl ((S)-1-((R)-pyrrolidin-3-yl)ethyl)carbamate (112 mg, 0.52 mmol), $Cs_2CO_3$ (285 mg, 0.87 mmol), xantphos (33.7 mg, 0.058 mmol) and $Pd_2(dba)_3$ (26.7 mg, 0.029 mmol) at ambient temperature. The resulting mixture was heated to 110° C. in an oil bath for 18 h. The reaction mixture was diluted with water (20 mL) and the solution was extracted with ethyl acetate (3×10 mL). The combined organic phase was dried over sodium sulfate and was concentrated. The resulting residue was purified by ISCO eluting with 0-20-50-100% ethyl acetate in heptane to give tert-butyl ((S)-1-((R)-1-(1-cyclopropyl-6-fluoro-3-methoxy-8-methyl-2-oxo-1,2-dihydroquinolin-7-yl)pyrrolidin-3-yl)ethyl)carbamate (40 mg, 29.9% yield). LCMS (m/z): 460, RT 0.97 min.

(iv) 7-((R)-3-((S)-1-Aminoethyl)pyrrolidin-1-yl)-1-cyclopropyl-6-fluoro-3-methoxy-8-methylquinolin-2(1H)-one To a solution of tert-butyl ((S)-1-((R)-1-(1-cyclopropyl-6-fluoro-3-methoxy-8-methyl-2-oxo-1,2-dihydroquinolin-7-yl)pyrrolidin-3-yl)ethyl)carbamate (20 mg, 0.044 mmol) in DCM (2 mL) was added TFA (2 mL, 26.0 mmol) in 2 ml DCM at ambient temperature. The resulting mixture was stirred for 1 h. The mixture was concentrated to remove solvent. The residue was purified by HPLC to give 7-((R)-3-((S)-1-aminoethyl)pyrrolidin-1-yl)-1-cyclopropyl-6-fluoro-3-methoxy-8-methylquinolin-2(1H)-one (2 mg, 9.22% yield). LCMS (m/z): 360, RT 0.62 min.

1H NMR (400 MHz, $CD_3OD$) δ 7.04 (d, J=12.52 Hz, 1H), 6.90 (s, 1H), 3.76 (s, 3H), 3.34-3.51 (m, 3H), 3.27 (dd,

J=2.54, 9.20 Hz, 3H), 2.52 (s, 3H), 2.32-2.47 (m, 1H), 2.03-2.21 (m, 1H), 1.63-1.84 (m, 1H), 1.31 (d, J=6.65 Hz, 3H), 1.04-1.19 (m, 2H), 0.32-0.50 (m, 2H)

$^{19}$F NMR (376 MHz, CD$_3$OD) δ −77.13 (br. s., 3F), −128.38 (d, J=12.47 Hz, 1F)

Example 7: 7-(6-aminopyridin-3-yl)-1-cyclopropyl-6-fluoro-3-methoxy-8-methylquinolin-2(1H)-one The title compound was prepared in accordance with the following scheme:

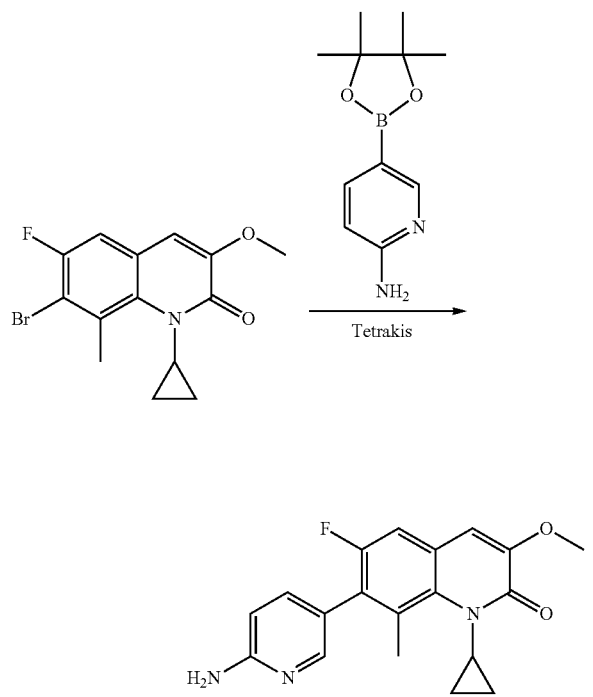

(i) 7-(6-Aminopyridin-3-yl)-1-cyclopropyl-6-fluoro-3-methoxy-8-methylquinolin-2(1H)-one A suspension of 7-bromo-1-cyclopropyl-6-fluoro-3-methoxy-8-methylquinolin-2(1H)-one (20 mg, 0.06 mmol), 2-aminopyridine-5-boronicester (27.0 mg, 0.12 mmol), Tetrakis (3.54 mg, 3.07 μmol), NaHCO$_3$ (20.6 mg, 0.24 mmol) in dioxane (2 mL) and water (2 mL) was purged with nitrogen for 5 min. The resulting mixture was stirred at 100° C. in an oil bath for 4 h. The suspension was diluted with water, and was extracted with ethyl acetate (2×10 mL). The organic phase was dried over sodium sulfate, and concentrated. The resulting residue was purified by ISCO eluting with 0-30-60-100% ethyl acetate in heptane to give 30 mg product with 90% purity. The collected compound was re-purified by HPLC to give 7-(6-aminopyridin-3-yl)-1-cyclopropyl-6-fluoro-3-methoxy-8-methylquinolin-2(1H)-one (2 mg, 6.83% yield).

LCMS (m/z): 340, RT 0.54 min.

$^1$H NMR (400 MHz, CDCl$_3$) δ 7.79 (s, 1H), 7.75 (d, J=9.00 Hz, 1H), 7.09 (d, J=9.00 Hz, 1H), 6.90 (d, J=9.00 Hz, 1H), 6.65 (s, 1H), 3.92 (s, 3H), 2.49 (s, 3H), 1.93-2.10 (m, 1H), 0.88 (t, J=6.65 Hz, 4H)

Example 8: 3-amino-7-((R)-3-((S)-1-aminoethyl)pyrrolidin-1-yl)-1-cyclopropyl-6-fluoro-8-methylquinolin-2(1H)-one hydrochloride salt

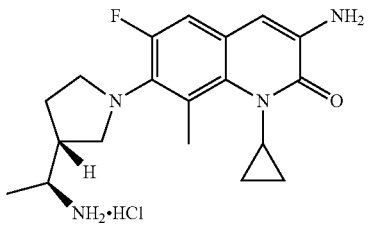

The title compound was prepared in accordance with the following scheme:

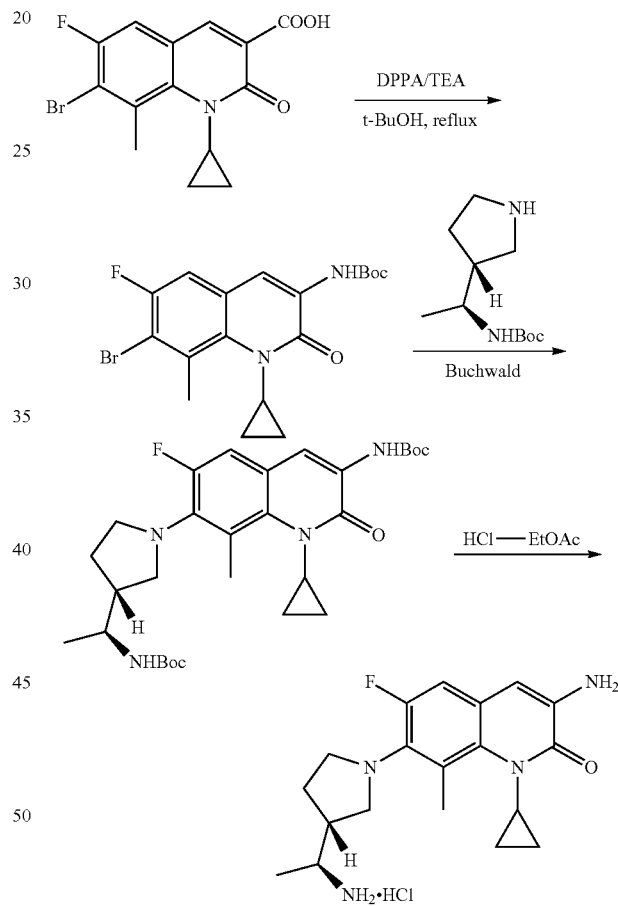

(i) tert-butyl(7-bromo-1-cyclopropyl-6-fluoro-8-methyl-2-oxo-1,2-dihydroquinolin-3-yl)carbamate To a solution of 7-bromo-1-cyclopropyl-6-fluoro-8-methyl-2-oxo-1,2-dihydroquinoline-3-carboxylic acid (350 mg, 1.0 mmol) and TEA (0.3 mL, 2.0 mmol) in t-BuOH (5.0 mL, 50 mmol) was added DPPA (0.3 mL, 1.1 mmol) at 25° C. under argon. The mixture was heated to reflux for 1.0 h. When the reaction was complete, the reaction mixture was concentrated to get a crude product. The crude product was purified by chromatograph on silica gel (Eluent: EtOAc/PE=1/10) to get the title compound (230 mg, yield: 54.3%).

¹H NMR (400 MHz, CDCl₃-d₁) δ 8.05 (brs, 1H), 7.77 (s, 1H), 7.08 (d, J=8.0 Hz, 1H), 3.60-3.55 (m, 1H), 1.15 (s, 9H), 1.30-1.25 (m, 2H), 0.60-0.55 (m, 2H)

(ii) tert-butyl((S)-1-((R)-1-(3-tert-butylcarbamatyl-amino-1-cyclopropyl-6-fluoro-8-methyl-2-oxo-1,2-dihydroquinolin-7-yl)pyrrolidin-3-yl)ethyl)carbamate A mixture of tert-butyl (7-bromo-1-cyclopropyl-6-fluoro-8-methyl-2-oxo-1,2-dihydroquinolin-3-yl)carbamate (220 mg, 0.53 mmol), tert-butyl ((S)-1-((R)-pyrrolidin-3-yl)ethyl)carbamate (229 mg, 1.07 mmol), Pd₂(dba)₃ (24 mg, 0.027 mmol), Xantphos (31 mg, 0.053 mmol) and Cs₂CO₃ (518 mg, 1.59 mmol) in dry toluene (60 mL) was stirred at 120° C. under N₂ for 20 h. The reaction mixture was concentrated. The residue was purified by flash chromatography (Eluent: PE:EtOAc=3:1) to give 120 mg crude product (85% purity), which was then re-purified by prep. TLC to give the title compound (80 mg, yield: 27.5%) as a light yellow solid.

¹H NMR (400 MHz, DMSO-d₆): δ 7.99 (brs, 1H), 7.69 (s, 1H), 6.93 (d, J=12.4 Hz, 1H), 4.70-4.60 (m, 1H), 3.75-3.65 (m, 1H), 3.60-3.23 (m, 5H), 2.53 (s, 3H), 2.29-2.19 (m, 1H), 2.11-2.01 (m, 1H), 1.79-1.69 (m, 1H), 1.51 (s, 9H), 1.42 (s, 9H), 1.27-1.07 (m, 5H), 0.60-0.40 (m, 2H)

(iii) 3-amino-7-((R)-3-((S)-1-aminoethyl)pyrrolidin-1-yl)-1-cyclopropyl-6-fluoro-8-methylquinolin-2(1H)-one hydrochloride A mixture of tert-butyl ((S)-1-((R)-1-(3-tert-butyl carbamatyl-amino-1-cyclopropyl-6-fluoro-8-methyl-2-oxo-1,2-dihydroquinolin-7-yl)pyrrolidin-3-yl)ethyl)carbamate (80 mg, 0.15 mmol) in HCl-EtOAc (10 mL, 20 mmol, 2 M) was stirred at 15° C. for 6 h. The mixture was concentrated to give a residue. The residue was dissolved in water and then lyophilized to give the title compound (30 mg, yield: 53.6%).

¹H NMR (400 MHz, D₂O-d₂): δ 7.33 (s, 1H), 7.30 (d, J=12.4 Hz, 1H), 4.10-3.95 (m, 1H), 3.95-3.77 (m, 2H), 3.75-3.60 (m, 1H), 3.58-3.40 (m, 2H), 2.95-2.78 (m, 1H), 2.65 (s, 3H), 2.43-2.29 (m, 1H), 2.15-2.05 (m, 1H), 1.35 (d, J=6.8 Hz, 3H), 1.25-1.05 (m, 2H), 0.60-0.40 (m, 2H).

LCMS (0-60 AB_7 min), [MH]⁺=345.1, RT=2.705 mins.
LCMS Method 0-60 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 0%-60% (solvent B) over 6 minutes and holding at 60% for 0.5 minutes.

Example 9.1: 7-((R)-3-((S)-1-aminoethyl)pyrrolidin-1-yl)-1-cyclopropyl-6-fluoro-8-methylquinolin-2(1H)-one hydrochloride salt

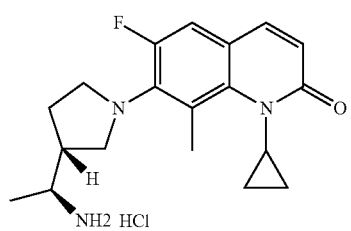 [SMILES: Cc1c(N2CC[C@@H]([C@H](C)N)C2)c(F)cc2ccc(=O)n(C3CC3)c12 ; Cl]

The title compound was prepared in accordance with the following scheme:

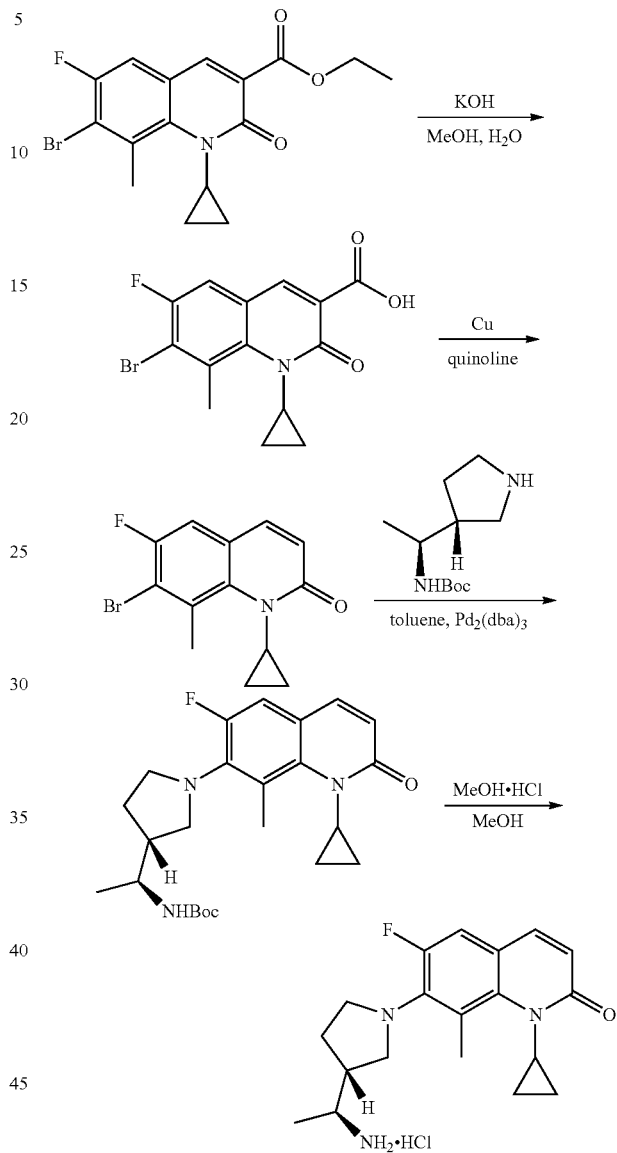

(i) 7-bromo-1-cyclopropyl-6-fluoro-8-methyl-2-oxo-1,2-dihydroquinoline-3-carboxylic acid To a solution of ethyl 7-bromo-1-cyclopropyl-6-fluoro-8-methyl-2-oxo-1,2-dihydroquinoline-3-carboxylate (300 mg, 0.81 mmol) in mixture of MeOH (12 mL) and H₂O (3 mL) was added KOH (91.4 mg, 1.63 mmol) at 10° C. The resulting mixture was stirred at 40° C. for 2 h. After the reaction was complete, the reaction mixture was acidified to pH=~4 by aq. HCl (2 N). The resulting solution was extracted with DCM (15 mL×2). The organic layer was washed with brine, dried over anhydrous Na₂SO₄, filtered and concentrated in vacuum to give the title compound (230 mg, yield: 83.0%).

¹H NMR (400 MHz, CDCl₃-d₁) δ 14.16 (brs, 1H), 8.68 (s, 1H), 7.33 (d, J=6.4 Hz, 1H), 3.65-3.60 (m, 1H), 2.86 (s, 3H), 1.40-1.30 (m, 2H), 0.70-0.60 (m, 2H)

(ii) 7-bromo-1-cyclopropyl-6-fluoro-8-methylquinolin-2(1H)-one

To a solution of 7-bromo-1-cyclopropyl-6-fluoro-8-methyl-2-oxo-1,2-dihydroquinoline-3-carboxylic acid (230 mg, 0.68 mmol) in quinoline (2 mL) was added Cu (42.9 mg, 0.68 mmol) at 10° C. The resulting mixture was stirred at 240° C. for 30 mins. The reaction mixture was cooled to 10° C. and water was added. The resulting suspension was extracted with EtOAc (50 mL×2). The organic layer was washed with brine, dried over Na$_2$SO$_4$, filtered and concentrated in vacuum. The crude product was purified by column chromatography on silica gel (Eluent: PE:EtOAc=2:1) to give the title compound as a yellow solid (120 mg, yield: 60.0%).

$^1$H NMR (400 MHz, CDCl$_3$-d$_1$) δ 7.44 (d, J=9.6 Hz, 1H), 7.08 (d, J=7.6 Hz, 1H), 6.61 (d, J=9.6 Hz, 1H), 3.53-3.48 (m, 1H), 2.78 (s, 3H), 1.30-1.20 (m, 2H), 0.58-0.54 (m, 2H)

(iii) tert-butyl ((S)-1-((R)-1-(1-cyclopropyl-6-fluoro-8-methyl-2-oxo-1,2-dihydroquinolin-7-yl)pyrrolidin-3-yl)ethyl)carbamate To a solution of 7-bromo-1-cyclopropyl-6-fluoro-8-methylquinolin-2(1H)-one (50 mg, 0.17 mmol) in toluene (3 mL) was added tert-butyl ((S)-1-((R)-pyrrolidin-3-yl) ethyl)carbamate (45.4 mg, 0.21 mmol) and Cs$_2$CO$_3$ (138.0 mg, 0.42 mmol) at 25° C., followed by Xantphos (12.3 mg, 0.021 mmol) and Pd$_2$(dba)$_3$ (6.5 mg, 0.007 mmol). The resulting mixture was stirred at 110° C. under nitrogen for 16 h. The reaction mixture was concentrated in vacuum. The residue was dissolved in water. The resulting solution was extracted with DCM (10 mL×2). The organic layer was dried over anhydrous Na$_2$SO$_4$, filtered and concentrated to afford the crude product. The crude product was purification purified by prep. TLC to give the title compound (35 mg, yield: 48.3%).

$^1$H NMR (400 MHz, CDCl$_3$-d$_1$) δ 7.38 (d, J=9.2 Hz, 1H), 6.94 (d, J=12.4 Hz, 1H), 6.45 (d, J=9.6 Hz, 1H), 4.63 (brd, J=8.0 Hz, 1H), 3.80-3.73 (m, 1H), 3.60-3.35 (m, 5H), 2.76-2.68 (m, 1H), 2.49 (s, 3H), 2.32-2.27 (m, 1H), 2.10-2.00 (m, 1H), 1.43 (s, 9H), 1.22 (d, J=6.8 Hz, 3H), 1.25-1.15 (s, 2H), 0.60-0.50 (m, 2H)

(iv) 7-((R)-3-((S)-1-aminoethyl)pyrrolidin-1-yl)-1-cyclopropyl-6-fluoro-8-methylquinolin-2(1H)-one hydrochloride To a solution of tert-butyl ((S)-1-((R)-1-(1-cyclopropyl-6-fluoro-8-methyl-2-oxo-1,2-dihydroquinolin-7-yl)pyrrolidin-3-yl)ethyl)carbamate (35 mg, 0.08 mmol) in MeOH (2 mL) was added HCl/MeOH (2 mL, 4M) at 10° C. The resulting mixture was stirred at 20° C. under argon for 1 h. The reaction mixture was concentrated in vacuum. The residue was purified by prep-HPLC (acid) to give the title compound (10.9 mg, yield: 36.6%).

$^1$H NMR (400 MHz, D$_2$O-d$_2$) δ 7.63 (d, J=9.2 Hz, 1H), 7.25 (d, J=12.0 Hz, 1H), 6.49 (d, J=9.2 Hz, 1H), 3.90-3.83 (m, 1H), 3.82-3.75 (m, 2H), 3.70-3.60 (m, 1H), 3.55-3.40 (m, 2H), 2.90-2.80 (m, 1H), 2.56 (s, 3H), 2.40-2.30 (m, 1H), 2.07-1.96 (m, 1H), 1.40 (d, J=6.4 Hz, 3H), 1.20-1.15 (m, 2H), 0.50-0.40 (m, 2H)

LCMS (10-80 AB_7 min), [MH]$^+$=330.2, RT=1.877 mins.

LCMS Method 10-80 AB_7 MIN
Column: Xtimate C18 2.1*30 mm, 3 um; ESI source, Positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 0.8 mL/min;
Gradient: 10%-80% (solvent B) over 6 minutes and holding at 80% for 0.5 minutes.

Example 9.2: 7-(3-(1-Aminocyclopropyl)pyrrolidin-1-yl)-1-cyclopropyl-6-fluoro-8-methylquinolin-2(1H)-one

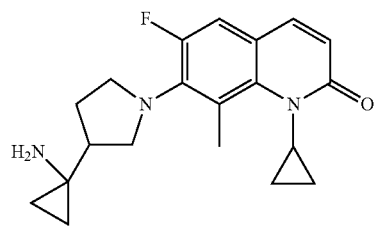 [SMILES: Cc1c(N2CCC(C3(N)CC3)C2)c(F)cc2ccc(=O)n(C3CC3)c12]

The title compound was prepared in accordance with the following scheme:

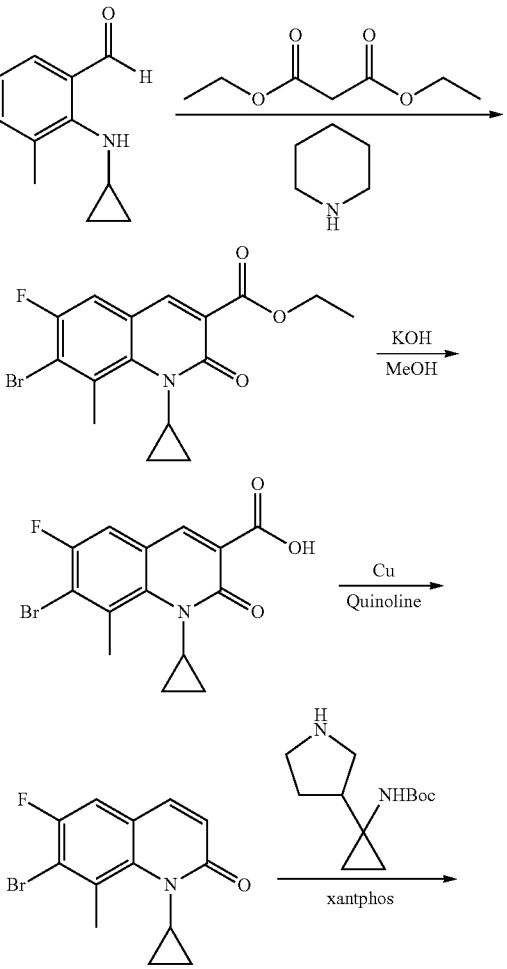

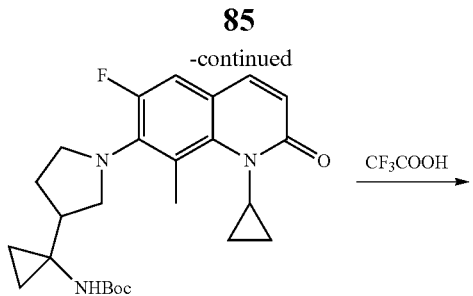

CF₃COOH

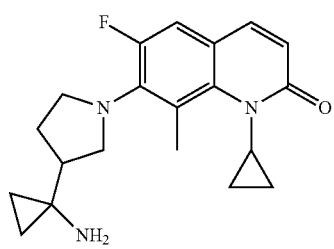

(i) Ethyl 7-bromo-1-cyclopropyl-6-fluoro-8-methyl-2-oxo-1,2-dihydroquinoline-3-carboxylate To a solution of 4-bromo-2-(cyclopropylamino)-5-fluoro-3-methylbenzaldehyde (530 mg, 1.94 mmol) in EtOH (12 mL) was added diethyl malonate (0.59 mL, 3.90 mmol) and piperidine (0.77 mL, 7.79 mmol). The mixture was stirred at 100° C. in an oil bath for 16 h. The reaction mixture was concentrated and the residue was purified by ISCO eluting with 0-20-50% ethyl acetate in heptane to give ethyl 7-bromo-1-cyclopropyl-6-fluoro-8-methyl-2-oxo-1,2-dihydroquinoline-3-carboxylate (280 mg, 39.0% yield). LCMS (m/z): 368/370, RT 0.91 min.

(ii) 7-Bromo-1-cyclopropyl-6-fluoro-8-methyl-2-oxo-1,2-dihydroquinoline-3-carboxylic acid To a solution of ethyl 7-bromo-1-cyclopropyl-6-fluoro-8-methyl-2-oxo-1,2-dihydroquinoline-3-carboxylate (280 mg, 0.76 mmol) in MeOH (10 mL), water (2.5 mL) was added KOH (85 mg, 1.52 mmol). The mixture was stirred at ambient temperature for 40 min. The solution was acidified to pH=4 by adding 2N HCl. The resulting solution was extracted with DCM (3×20 mL). And the organic phase was washed with brine, dried over sodium sulfate, filtered and concentrated to give 7-bromo-1-cyclopropyl-6-fluoro-8-methyl-2-oxo-1,2-dihydroquinoline-3-carboxylic acid (240 mg, 93% yield). LCMS (m/z): 340/342, RT 0.84 min.

(iii) 7-Bromo-1-cyclopropyl-6-fluoro-8-methylquinolin-2(1H)-one

To an cold dioxane in ice bath solution of 7-bromo-1-cyclopropyl-6-fluoro-8-methyl-2-oxo-1,2-dihydroquinoline-3-carboxylic acid (230 mg, 0.67 mmol) in quinoline (2 mL) was added Cu (25.8 mg, 0.4 mmol). The resulting mixture was stirred at 210° C. in an oil bath for 30 min. The solution was recooled to 10° C. in dry-ice-dioxane bath, and water was added to. The suspension was extracted with ethyl acetate (2×30 mL). The organic phase was dried over sodium sulfate, and concentrated. The resulting residue was purified by ISCO eluting with 0-20-50% ethyl acetate in heptane to give 7-bromo-1-cyclopropyl-6-fluoro-8-methylquinolin-2(1H)-one (140 mg, 69.9% yield). LCMS (m/z): 296/298, RT 0.84 min.

(iv) tert-Butyl (1-(1-(1-cyclopropyl-6-fluoro-8-methyl-2-oxo-1,2-dihydroquinolin-7-yl)pyrrolidin-3-yl)cyclopropyl)carbamate To a suspension of 7-bromo-1-cyclopropyl-6-fluoro-8-methylquinolin-2(1H)-one (30 mg, 0.10 mmol) in Dioxane (1.5 mL) was added tert-butyl (1-(pyrrolidin-3-yl)cyclopropyl)carbamate (41.3 mg, 0.18 mmol), Cs₂CO₃ (49.5 mg, 0.15 mmol), xantphos (35.2 mg, 0.061 mmol) and followed by the addition of Pd₂(dba)₃ (21.3 mg, 0.023 mmol) at ambient temperature. The resulting mixture was purged with nitrogen for 5 min and was heated to 110° C. in an oil bath for 14 h. The reaction mixture was diluted with ethyl acetate, and was washed with water, dried over sodium sulfate, and concentrated. The residue was purified by ISCO eluting with 0-10-30-60% ethyl acetate in heptane to give tert-butyl (1-(1-(1-cyclopropyl-6-fluoro-8-methyl-2-oxo-1,2-dihydroquinolin-7-yl)pyrrolidin-3-yl)cyclopropyl)carbamate (15 mg, 33.5% yield). LCMS (m/z): 442 (MH⁺), RT 1.01 min.

(v) 7-(3-(1-aminocyclopropyl)pyrrolidin-1-yl)-1-cyclopropyl-6-fluoro-8-methylquinolin-2(1H)-one To a solution of tert-butyl (1-(1-(1-cyclopropyl-6-fluoro-8-methyl-2-oxo-1,2-dihydroquinolin-7-yl)pyrrolidin-3-yl)cyclopropyl)carbamate (15 mg, 0.034 mmol) in DCM (5 mL) was added TFA (3 mL, 38.9 mmol) at ambient temperature. The resulting mixture was stirred for 1 h. The mixture was concentrated. The resulting residue was purified by HPLC give 7-(3-(1-aminocyclopropyl)pyrrolidin-1-yl)-1-cyclopropyl-6-fluoro-8-methylquinolin-2(1H)-one (4.3 mg, 26.4% yield). LCMS (m/z): 342, RT 0.62 min.

¹H NMR (400 MHz, CDCl₃) δ 7.39 (d, J=9.39 Hz, 1H), 6.91-7.03 (m, 1H), 6.51 (d, J=9.39 Hz, 1H), 3.24-3.63 (m, 4H), 2.52-2.60 (m, 1H), 2.51 (s, 3H), 2.17-2.29 (m, 1H), 2.01 (d, J=5.87 Hz, 1H), 1.91 (dd, J=7.83, 12.52 Hz, 1H), 1.23-1.40 (m, 4H), 1.10-1.23 (m, 3H), 0.80-0.94 (m, 2H), 0.53 (d, J=3.91 Hz, 2H)

Example 9.3: 1-Cyclopropyl-6-fluoro-8-methyl-7-(piperazin-1-yl)quinolin-2(1H)-one

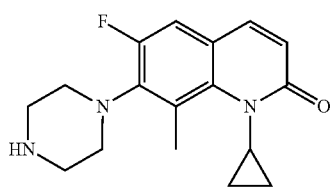 [SMILES: Cc1c(N2CCNCC2)c(F)cc2ccc(=O)n(C3CC3)c12]

The title compound was prepared in accordance with the following scheme:

<sup>19</sup>F NMR (376 MHz, d6-DMSO) δ −73.91 (s, 3F), −129.24 (d, J=12.47 Hz, 1F)

Example 10: 7-(6-Aminopyridin-3-yl)-1-cyclopropyl-6-fluoro-8-methylquinolin-2(1H)-one The title compound was prepared in accordance with the following scheme:

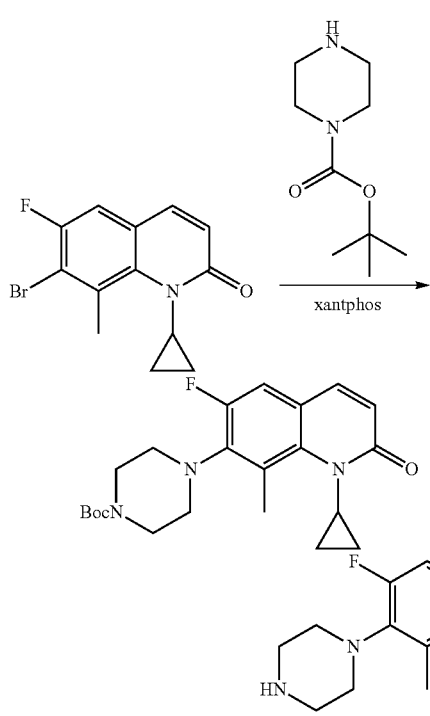

(i) tert-butyl 4-(1-cyclopropyl-6-fluoro-8-methyl-2-oxo-1,2-dihydroquinolin-7-yl)piperazine-1-carboxylate To a suspension of 7-bromo-1-cyclopropyl-6-fluoro-8-methylquinolin-2(1H)-one (30 mg, 0.1 mmol) in dioxane (1.5 mL) was added tert-butyl piperazine-1-carboxylate (56.6 mg, 0.30 mmol), Cs$_2$CO$_3$ (99 mg, 0.30 mmol), xantphos (35.2 mg, 0.06 mmol) and followed by the addition of Pd$_2$(dba)$_3$ (21.3 mg, 0.023 mmol) at ambient temperature. The resulting mixture was purged with nitrogen for 5 min and was heated to 110° C. in an oil bath for 15 h. The reaction mixture was diluted with ethyl acetate, and the resulting mixture was washed with water, dried over sodium sulfate, concentrated. The resulting residue was purified by ISCO eluting with 0-10-30-60% ethyl acetate in heptane to give tert-butyl 4-(1-cyclopropyl-6-fluoro-8-methyl-2-oxo-1,2-dihydroquinolin-7-yl)piperazine-1-carboxylate (15 mg, 36.9% yield).

LCMS (m/z): 402, RT 1.00 min.

(ii) 1-cyclopropyl-6-fluoro-8-methyl-7-(piperazin-1-yl)quinolin-2(1H)-one

To a solution of tert-butyl 4-(1-cyclopropyl-6-fluoro-8-methyl-2-oxo-1,2-dihydroquinolin-7-yl)piperazine-1-carboxylate (15 mg, 0.037 mmol) in Dichloromethane (5 mL) was added TFA (3 mL, 38.9 mmol) at ambient temperature. The resulting mixture was stirred for 1 h. The reaction solution was concentrated. The resulting residue was purified by HPLC to give 1-cyclopropyl-6-fluoro-8-methyl-7-(piperazin-1-yl)quinolin-2(1H)-one (9.6 mg, 58.8% yield).

LCMS (m/z): 302, RT 0.48 min.

<sup>1</sup>H NMR (400 MHz, d6-DMSO) δ 8.69 (br. s., 1H), 7.59 (d, J=9.39 Hz, 1H), 7.30 (d, J=12.13 Hz, 1H), 6.36 (d, J=9.39 Hz, 1H), 3.3 (1H), 3.10-3.32 (m, 8H), 2.54 (s, 3H), 1.05 (d, J=6.26 Hz, 2H), 0.30 (br. s., 2H).

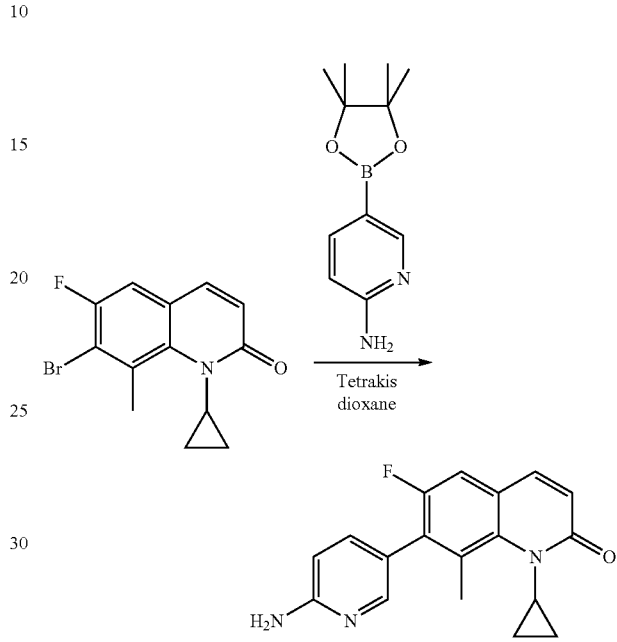

(i) 7-(6-aminopyridin-3-yl)-1-cyclopropyl-6-fluoro-8-methylquinolin-2(1H)-one

A suspension of 7-bromo-1-cyclopropyl-6-fluoro-8-methylquinolin-2(1H)-one (10 mg, 0.034 mmol), 2-aminopyridine-5-boronicester (8.9 mg, 0.041 mmol), Tetrakis (1.95 mg, 1.68 μmol), NaHCO$_3$ (8.5 mg, 0.10 mmol) in dioxane (1 mL) and water (1 mL) was purged with nitrogen for 5 min. The resulting mixture was stirred at 100° C. in an oil bath for 1 h. The suspension was diluted with water, and was extracted with ethyl acetate (2×10 mL). The organic phase was dried over sodium sulfate, concentrated. The resulting residue was purified by HPLC to give 7-(6-aminopyridin-3-yl)-1-cyclopropyl-6-fluoro-8-methylquinolin-2(1H)-one (5.1 mg, 33.9% yield). LCMS (m/z): 310 (MH+), RT 0.51 min.

<sup>1</sup>H NMR (400 MHz, CDCl$_3$) δ 7.81 (s, 1H), 7.75 (d, J=9.39 Hz, 1H), 7.51 (d, J=9.39 Hz, 1H), 7.16 (d, J=8.61 Hz, 1H), 6.95 (d, J=9.00 Hz, 1H), 6.68 (d, J=9.39 Hz, 1H), 3.51 (td, J=3.23, 6.85 Hz, 1H), 2.51 (s, 3H), 1.29 (q, J=6.39 Hz, 2H), 0.64 (d, J=3.13 Hz, 2H)

Example 11.1: 7-((R)-3-((S)-1-aminoethyl)pyrrolidin-1-yl)-1-cyclopropyl-6-fluoro-3-hydroxy-8-methylquinolin-2(1H)-one The title compound was prepared in accordance with the following scheme:

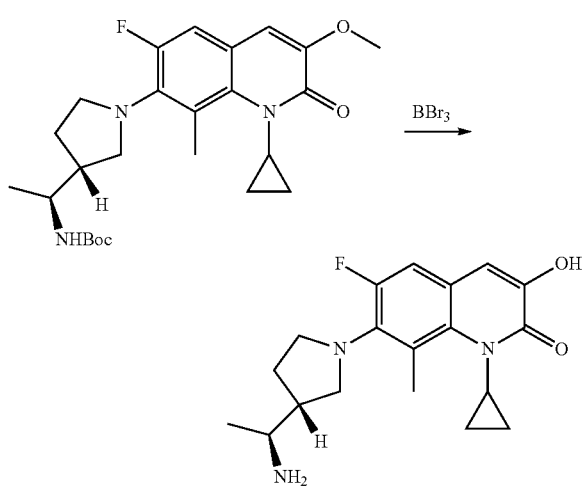

(i) 7-((R)-3-((S)-1-Aminoethyl)pyrrolidin-1-yl)-1-cyclopropyl-6-fluoro-3-hydroxy-8-methylquinolin-2(1H)-one To an ice cold solution of tert-butyl ((S)-1-((R)-1-(1-cyclopropyl-6-fluoro-3-methoxy-8-methyl-2-oxo-1,2-dihydroquinolin-7-yl)pyrrolidin-3-yl)ethyl)carbamate (20 mg, 0.044 mmol) in DCM (2 mL) was added 1.0 M/DCM boron tribromide (0.22 mL, 0.22 mmol). The resulting mixture was stirred at ambient temperature for 2 hr. The reaction mixture was quenched with ice water (20 mL). The aqueous solution was extracted with ethyl acetate (2×10 mL). The combined organic phase was washed with brine, dried over sodium sulfate and concentrated to remove solvent. The resulting residue was purified by HPLC to give 7-((R)-3-((S)-1-aminoethyl)pyrrolidin-1-yl)-1-cyclopropyl-6-fluoro-3-hydroxy-8-methylquinolin-2(1H)-one (4.2 mg, 19.9% yield). LCMS (m/z): 346, RT 0.57 min.

$^1$H NMR (400 MHz, CD$_3$OD) δ 6.94 (d, J=12.52 Hz, 1H), 6.78 (s, 1H), 3.47 (qd, J=3.49, 7.14 Hz, 1H), 3.32-3.43 (m, 2H), 3.24-3.31 (m, 3H), 2.53 (s, 3H), 2.32-2.47 (m, 1H), 2.12 (tdd, J=3.62, 7.68, 11.69 Hz, 1H), 1.63-1.83 (m, 1H), 1.30 (d, J=6.65 Hz, 3H), 1.03-1.18 (m, 2H), 0.42 (q, J=3.91 Hz, 2H)

$^{19}$F NMR (376 MHz, CD$_3$OD) δ −77.01 (s, 3F), −128.47 (d, J=12.47 Hz, 1F)

Example 11.2: 7-(6-aminopyridin-3-yl)-1-cyclopropyl-6-fluoro-3-hydroxy-8-methylquinolin-2(1H)-one The title compound was prepared in accordance with the following scheme:

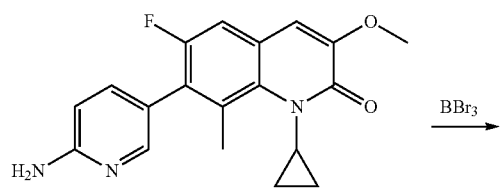

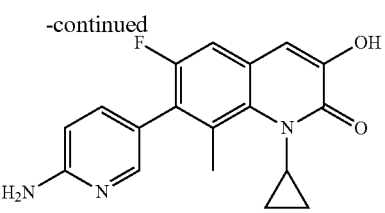

(i) 7-(6-Aminopyridin-3-yl)-1-cyclopropyl-6-fluoro-3-hydroxy-8-methylquinolin-2(1H)-one To an ice cold solution of 7-(6-aminopyridin-3-yl)-1-cyclopropyl-6-fluoro-3-methoxy-8-methylquinolin-2(1H)-one (70 mg, 0.16 mmol) in DCM (5 ml) was added 1.0M DCM solution of boron tribromide (0.82 mL, 0.82 mmol). The resulting mixture was stirred for 4 h at ambient temperature. The mixture was quenched with ice water (30 mL), the aqueous solution was extracted with ethyl acetate (2×15 mL). The combined organic phase was washed with brine, dried over sodium sulfate and concentrated to remove solvent. The resulting residue was purified by HPLC to give 7-(6-aminopyridin-3-yl)-1-cyclopropyl-6-fluoro-3-hydroxy-8-methylquinolin-2(1H)-one (21.3 mg, 27.9% yield). LCMS (m/z): 326, RT 0.54 min.

$^1$H NMR (400 MHz, CD$_3$OD) δ 7.75-7.92 (m, 2H), 6.99-7.17 (m, 2H), 6.86 (s, 1H), 3.50 (td, J=3.28, 7.14 Hz, 1H), 2.45 (s, 3H), 1.17 (q, J=6.78 Hz, 2H), 0.47-0.60 (m, 2H)

$^{19}$F NMR (376 MHz, CD$_3$OD) δ −77.05 (s, 3F), −123.15 (d, J=9.54 Hz, 1F)

Example 12: 7-((R)-3-((S)-1-aminoethyl)pyrrolidin-1-yl)-1-cyclopropyl-6-fluoro-8-methoxy-2-oxo-1,2-dihydroquinoline-3-carboxylic acid hydrochloride

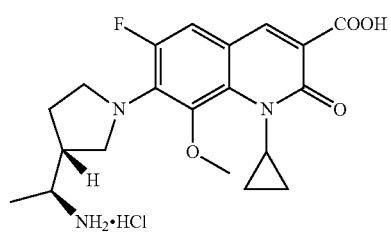

The title compound was prepared in accordance with the following scheme:

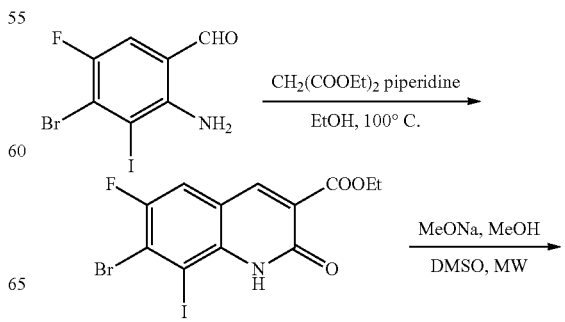

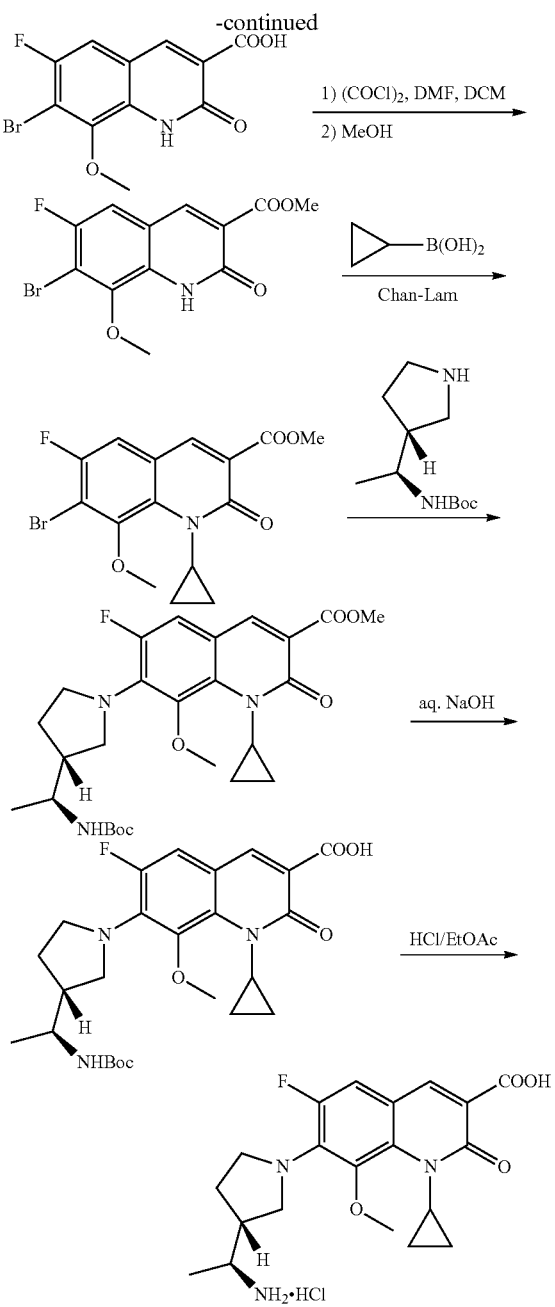

(i) ethyl 7-bromo-6-fluoro-8-iodo-2-oxo-1,2-dihydroquinoline-3-carboxylate

To a solution of 2-amino-4-bromo-5-fluoro-3-iodobenzaldehyde (20.00 g, 58.2 mmol) in 500 mL of EtOH was added diethyl malonate (18.65 g, 116.4 mmol) and piperidine (19.83 g, 232.7 mmol). The mixture was stirred at 100° C. for 12 h. The mixture was filtered to give the crude product. The crude product was purified by flash chromatography (Eluents: DCM:EtOAc=0 to 10:1) to give the title compound (16.5 g, yield: 64.5%).

$^1$H NMR (400 MHz, DMSO-d$_6$) δ 9.07 (brs, 1H), 8.32 (d, J=5.6 Hz, 1H), 7.44 (d, J=7.6 Hz, 1H), 4.41 (t, J=7.0 Hz, 2H), 1.40 (q, J=6.9 Hz, 3H)

(ii) 7-bromo-6-fluoro-8-methoxy-2-oxo-1,2-dihydroquinoline-3-carboxylic acid

To a solution of ethyl 7-bromo-6-fluoro-8-iodo-2-oxo-1,2-dihydroquinoline-3-carboxylate (500 mg, 1.1 mmol) in 1 mL of MeOH and 1 mL of DMSO was added CuI (42 mg, 0.22 mmol) and MeONa (594 mg, 11.0 mmol). The reaction mixture was stirred at 100° C. for 2.5 h under microwave condition. The reaction mixture was acidified to pH~2 with aq. HCl (2 M). The resulting suspension was filtered to give the crude title compound (400 mg), which was used in the next step without further purification.

(iii) methyl 7-bromo-6-fluoro-8-methoxy-2-oxo-1,2-dihydroquinoline-3-carboxylate To a solution of 7-bromo-6-fluoro-8-methoxy-2-oxo-1,2-dihydroquinoline-3-carboxylic acid (3.0 g, 9.5 mmol) and DMF (1 mL) in dry DCM (100 mL) was added a solution of (COCl)$_2$ (1.3 g, 10.4 mmol) in dry DCM (10 mL). The reaction mixture was stirred at 20° C. for 30 min. After the reaction was complete, the mixture was quenched with MeOH (2 mL). The resulting suspension was filtered. The residue was washed with DCM (2×30 mL) and then dried to give the title compound (2.8 g, yield: 89.4%).

$^1$H NMR (400 MHz, DMSO-d$_6$) δ 8.37 (s., 1H), 7.59 (d, J=8.4 Hz, 1H), 3.86 (s, 3H), 3.78 (s, 3H)

(iv) methyl 7-bromo-1-cyclopropyl-6-fluoro-8-methoxy-2-oxo-1,2-dihydroquinoline-3-carboxylate To a solution of methyl 7-bromo-6-fluoro-8-methoxy-2-oxo-1,2-dihydroquinoline-3-carboxylate (1.60 g, 4.9 mmol) in DCE (70 mL) was added cyclopropylboronic acid (2.08 g, 24.2 mmol), Cu(OAc)$_2$ (881 mg, 4.9 mmol), bipyridine (765 mg, 4.9 mmol) and Cs$_2$CO$_3$ (3.16 g, 9.7 mmol). The mixture was stirred at 100° C. under O$_2$ atmosphere for 16 h. The reaction mixture was then filtered. The filtrate was concentrated to give the crude product, which was purified by flash chromatography (Eluent: PE:EtOAC=2:1) to give the title compound (680 mg, yield: 37.9%).

$^1$H NMR (400 MHz, CDCl$_3$-d$_1$) δ 8.18 (s, 1H), 7.14 (d, J=7.2 Hz, 1H), 3.94 (s, 3H), 3.77 (s, 3H), 3.42-3.38 (m, 1H), 1.27-1.18 (m, 3H), 0.63-0.59 (m, 2H)

(v) methyl 7-((R)-3-((S)-1-((tert-butoxycarbonyl)amino)ethyl)pyrrolidin-1-yl)-1-cyclopropyl-6-fluoro-8-methoxy-2-oxo-1,2-dihydroquinoline-3-carboxylate To a solution of methyl 7-bromo-1-cyclopropyl-6-fluoro-8-methoxy-2-oxo-1,2-dihydroquinoline-3-carboxylate (100.0 mg, 0.27 mmol) in toluene (40 mL) was added tert-butyl ((S)-1-((R)-pyrrolidin-3-yl)ethyl)carbamate (115.8 mg, 0.54 mmol), Cs$_2$CO$_3$ (264.3 mg, 0.81 mmol), X-phos (23.4 mg, 0.04 mmol) and Pd$_2$(dba)$_3$ (12.4 mg, 0.01 mmol) at 20° C. The reaction mixture was stirred at 110° C. for 12 h. After the reaction was complete, the mixture was dissolved in water (20 mL) and then extracted with EtOAc (30 mL×3). The organic layer was dried over Na$_2$SO$_4$ and evaporated to give a crude product. The crude product was purified by chromatography on silica gel (Eluents: EtOAc:PE from 1:8 to 1:2) to get the title compound (50.0 mg, yield: 36.8%).

$^1$H NMR (400 MHz, DMSO-d$_6$) δ 8.22 (s, 1H), 7.36 (d, J=13.6 Hz, 1H), 6.95-6.85 (m, 1H), 3.84-3.70 (m, 4H), 3.60-3.30 (m, 8H), 2.20-2.10 (m, 1H), 1.60-1.50 (m, 2H), 1.53 (s, 9H), 1.15-1.05 (m, 4H), 1.00-0.90 (m, 1H), 0.45-0.35 (m, 2H)

(vi) 7-((R)-3-((S)-1-((tert-butoxycarbonyl)amino) ethyl)pyrrolidin-1-yl)-1-cyclopropyl-6-fluoro-8-methoxy-2-oxo-1,2-dihydroquinoline-3-carboxylic acid To a solution of methyl 7-((R)-3-((S)-1-((tert-butoxycarbonyl)amino)ethyl)pyrrolidin-1-yl)-1-cyclopropyl-6-fluoro-8-methoxy-2-oxo-1,2-dihydroquinoline-3-carboxylate (50.0 mg, 0.10 mmol) in THF/H$_2$O (6 mL, 1:1) was added NaOH (7.9 mg, 0.20 mmol) at 25° C. The reaction mixture was stirred at 45° C. for 4 h. After the reaction was complete, the reaction mixture was acidified to pH=5-6 by aq. HCl (0.5 N). The resulting solution was extracted with EtOAc. The organic phase was dried over Na$_2$SO$_4$, filtered and evaporated to get the title compound (40.0 mg, yield: 82.3%).

$^1$H NMR (400 MHz, DMSO-d$_6$) δ 8.63 (s, 1H), 7.59 (d, J=14.0 Hz, 1H), 6.92 (d, J=8.4 Hz, 1H), 3.84-3.70 (m, 1H), 3.60-3.55 (m, 4H), 3.45-3.35 (m, 4H), 2.25-2.15 (m, 1H), 1.65-1.50 (m, 2H), 1.53 (s, 9H), 1.15-1.05 (m, 5H), 0.45-0.35 (m, 2H)

(vii) 7-((R)-3-((S)-1-aminoethyl)pyrrolidin-1-yl)-1-cyclopropyl-6-fluoro-8-methoxy-2-oxo-1,2-dihydroquinoline-3-carboxylic acid hydrochloride To a solution of 7-((R)-3-((S)-1-((tert-butoxycarbonyl)amino)ethyl)pyrrolidin-1-yl)-1-cyclopropyl-6-fluoro-8-methoxy-2-oxo-1,2-dihydroquinoline-3-carboxylic acid (40.0 mg, 0.08 mmol) in EtOAc (10 mL) was added HCl/EtOAc (10 mL) at 0° C. The reaction mixture was stirred at 25° C. for 3 h. After the reaction was complete, the reaction mixture was concentrated to give a crude product. The crude product was purified by pre-HPLC to get the title compound (15.0 mg, yield: 43.1%).

$^1$H NMR (400 MHz, DMSO-d$_6$) δ 8.65 (s, 1H), 8.32 (brs, 3H), 7.62 (d, J=13.6 Hz, 1H), 3.80-3.60 (m, 5H), 3.46 (s, 3H), 3.30-3.20 (m, 1H), 2.50-2.40 (m, 1H), 2.25-2.15 (m, 1H), 1.65-1.50 (m, 1H), 1.31 (d, J=6.4 Hz, 3H), 1.25-1.00 (m, 2H), 0.65-0.55 (m, 2H)

LCMS (10-80 AB_7 min), [MH]$^+$=390.2, RT=2.010 mins

LCMS Method 10-80 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 10%-80% (solvent B) over 6 minutes and holding at 80% for 0.5 minutes.

Example 13: 7-((R)-3-((S)-1-aminoethyl)pyrrolidin-1-yl)-1-cyclopropyl-8-ethyl-6-fluoro-2-oxo-1,2-dihydroquinoline-3-carboxylic acid hydrochloride

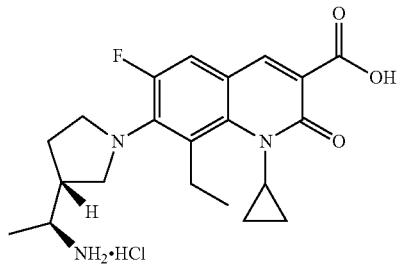

The title compound was prepared in accordance with the following scheme:

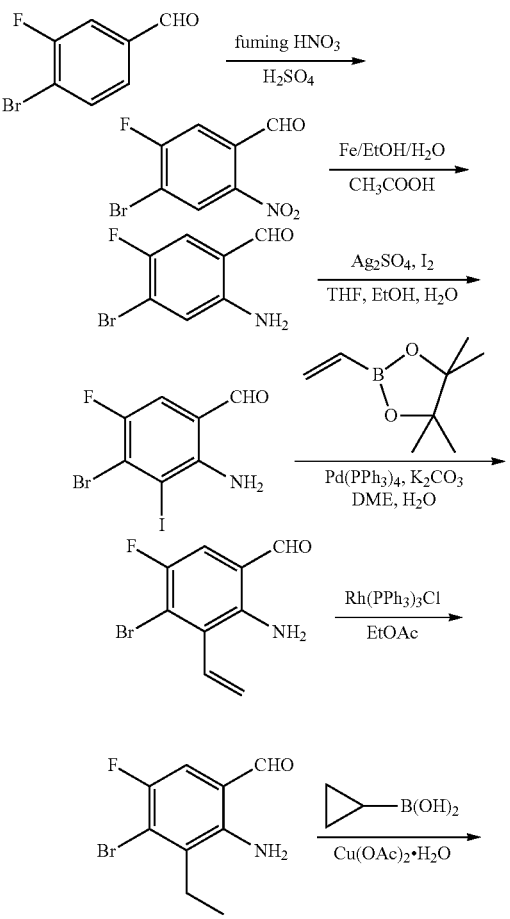

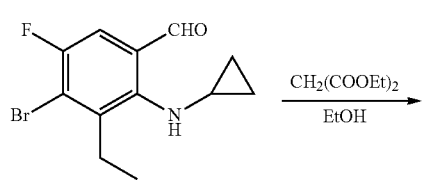

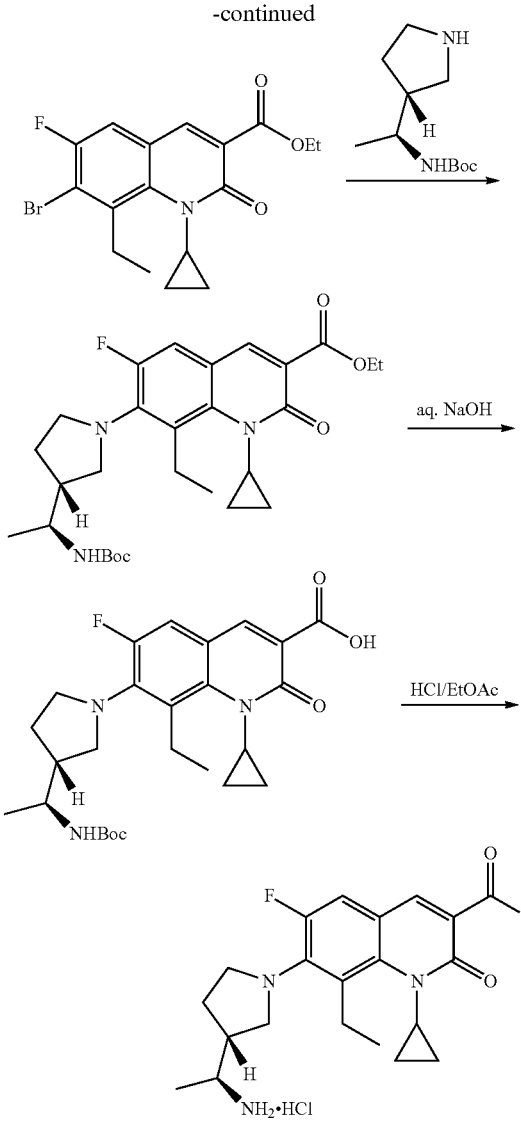

(i) 4-bromo-5-fluoro-2-nitrobenzaldehyde

To a mixture of 4-bromo-3-fluorobenzaldehyde (50 g, 246.3 mmol) in conc. H$_2$SO$_4$ (250 mL, 4595.3 mmol) was added fuming HNO$_3$ (25 mL, 595.0 mmol) in portions at 0° C. The reaction mixture was stirred at 0° C. for 30 min. After the reaction was completed detected by 1HNMR, the reaction mixture was poured into 1 L ice-water. The aqueous layer was extracted with DCM (3×500 mL). The organic phase was dried over anhydrous Na$_2$SO$_4$ and concentrated to give the title compound (50 g, yield: 81.9%).

$^1$H NMR (400 MHz, DMSO-d$_6$) δ 10.18 (s, 1H), 8.62 (d, J=5.6 Hz, 1H), 7.87 (d, J=8.0 Hz, 1H)

(ii) 2-amino-4-bromo-5-fluorobenzaldehyde

Iron powder (99 g, 1774.2 mmol) was added in portion to a solution of 4-bromo-5-fluoro-2-nitrobenzaldehyde (100 g, 403.2 mmol) in EtOH (750 mL), water (500 mL) and AcOH (150 mL) at 10° C. The reaction mixture was stirred at 90° C. for 30 min. After the reaction was complete, the volatile was concentrated in vacuo. The resulting suspension was extracted with EtOAc (3×500 mL). The organic phase was dried over anhydrous Na$_2$SO$_4$ and concentrated to give a crude product. The crude product was purified by column chromatograph on silica gel (Eluent: EtOAc/PE=1/15) to give the title compound (15.0 g, yield: 17.1%).

$^1$H NMR (400 MHz, DMSO-d$_6$) δ 9.74 (s, 1H), 7.55 (d, J=8.8 Hz, 1H), 7.10-7.05 (m, 3H)

(iii) 2-amino-4-bromo-5-fluoro-3-iodobenzaldehyde

To a mixture of 2-amino-4-bromo-5-fluorobenzaldehyde (35 g, 161 mmol) and Ag$_2$SO$_4$ (55.2 g, 177 mmol) in H$_2$O (300 mL) and EtOH (350 mL) was added a solution of I$_2$ (44.9 g, 177 mmol) in THF (200 mL). The reaction mixture was stirred at 20° C. for 3 h. After the reaction was complete, aq. Na$_2$S$_2$O$_3$ (100 mL, 1 M) and aq. Na$_2$CO$_3$ (100 mL, 1 M) was added to the reaction mixture. The resulting suspension was filtered. The residue was washed with DCM (800 mL). The aqueous phase was extracted with DCM (3×300 mL). The combined organic phase was dried over anhydrous Na$_2$SO$_4$, filtered and concentrated to give a crude product. The crude product was purified by flash chromatography (Eluent: PE:EtOAc=20:1) to give the title compound (18 g, yield: 32.6%).

$^1$H NMR (400 MHz, DMSO-d$_6$) δ 9.74 (s, 1H), 7.74 (d, J=8.4 Hz, 1H), 7.18 (brs, 2H)

(iv) 2-amino-4-bromo-5-fluoro-3-vinylbenzaldehyde

To a solution of 2-amino-4-bromo-5-fluoro-3-iodobenzaldehyde (8 g, 23.3 mmol) in DME and H$_2$O (70 mL, DME:H$_2$O=6:1) was treated with 4,4,5,5-tetramethyl-2-vinyl-1,3,2-dioxaborolane (17.9 g, 116.2 mmol), K$_2$CO$_3$ (6.4 g, 46.3 mmol) and Pd (PPh$_3$)$_4$ (2.7 g, 2.3 mmol) at 25° C. The reaction mixture was stirred at 110° C. for 48 h. After the reaction was complete monitored by $^1$HNMR, the reaction mixture was diluted with EtOAc (12 mL) and water (2 mL). The resulting solution was extracted with EtOAc (2×100 mL). The organic phase was combined, dried over anhydrous Na$_2$SO$_4$ and concentrated to give a crude product. The crude product was purified by chromatograph on silica gel (Eluent: EtOAc/PE=1/30) to give the title compound (2.8 g, yield: 49.3%).

$^1$H NMR (400 MHz, CDCl$_3$-d$_1$) δ 9.78 (s, 1H), 7.17 (d, J=8.0 Hz, 1H), 6.53 (dd, J=7.6 Hz, 18.0 Hz, 1H), 5.81 (dd, J=0.4 Hz, 7.6 Hz, 1H), 5.66 (dd, J=0.4 Hz, 7.6 Hz, 1H)

(v) 2-amino-4-bromo-3-ethyl-5-fluorobenzaldehyde

To a solution of 2-amino-4-bromo-5-fluoro-3-vinylbenzaldehyde (2.8 g, 11.5 mmol) in EtOAc (30 mL) was added Rh(PPh$_3$)$_3$Cl (1.0 g, 1.1 mmol). The mixture was stirred under H$_2$ atmosphere for 24 h. After the reaction was complete monitored by $^1$H NMR, the reaction mixture was filtered. The filtrate was concentrated and then purified by chromatography on silica gel (Eluent: EtOAc/PE=1/30) to give the title compound (2.0 g, yield: 70.8%).

$^1$H NMR (400 MHz, CDCl$_3$-d$_1$) δ 9.78 (s, 1H), 7.12 (d, J=8.0 Hz, 1H), 6.29 (brs, 2H), 2.80 (q, J=7.6 Hz, 2H), 1.17 (t, J=7.6 Hz, 3H)

(vi) 4-bromo-2-(cyclopropylamino)-3-ethyl-5-fluorobenzaldehyde

To a mixture of 2-amino-4-bromo-3-ethyl-5-fluorobenzaldehyde (1.4 g, 5.69 mmol), cyclopropylboronic acid (978 mg, 11.38 mmol), bipyridine (888 mg, 5.69 mmol) and Na₂CO₃ (1.206 g, 11.38 mmol) in DCE (50 mL) was added Cu(OAc)₂ (1.033 g, 5.69 mmol). Then the reaction mixture was stirred at 80° C. for 18 min. After the reaction was complete, the reaction mixture was filtered. The filtrate was evaporated to give the crude product, which was purified by column chromatography on silica gel (Eluents: EtOAc:PE from 3:100 to 1:10) to give the title compound (279 mg, 17.1% yield).

¹H NMR (400 MHz, CDCl₃-d₁) δ 9.78 (s, 1H), 7.72 (brs, 1H), 7.12 (d, J=8.0 Hz, 1H), 2.80 (q, J=7.6 Hz, 2H), 2.90-2.80 (m, 1H), 1.17 (t, J=7.6 Hz, 3H), 0.85-0.75 (m, 2H), 0.70-0.60 (m, 2H)

(vii) ethyl 7-bromo-1-cyclopropyl-8-ethyl-6-fluoro-2-oxo-1,2-dihydroquinoline-3-carboxylate To a mixture of 4-bromo-2-(cyclopropylamino)-3-ethyl-5-fluorobenzaldehyde (380 mg, 1.33 mmol) and diethyl malonate (426 mg, 2.66 mmol) in 15 mL of EtOH was added piperidine (453 mg, 5.32 mmol). Then the reaction mixture was stirred at 110° C. for 17 h. After the reaction was complete, the reaction mixture was evaporated to give a crude product. The crude product was purified by chromatography on silica gel (Eluents: EtOAc:PE from 3:100 to 1:10) to give the title compound (100 mg, 19.7% yield).

¹H NMR (400 MHz, CDCl₃-d₁) δ 8.15 (s, 1H), 7.19 (d, J=7.2 Hz, 1H), 4.42 (q, J=6.8 Hz, 2H), 3.63 (q, J=7.6 Hz, 2H), 3.55-3.45 (m, 1H), 1.43 (t, J=7.2 Hz, 3H), 1.30-1.20 (m, 2H), 1.05 (t, J=7.6 Hz, 3H), 0.65-0.55 (m, 2H)

(viii) ethyl 7-((R)-3-((S)-1-((tert-butoxycarbonyl)amino)ethyl)pyrrolidin-1-yl)-1-cyclopropyl-8-ethyl-6-fluoro-2-oxo-1,2-dihydroquinoline-3-carboxylate To a mixture of ethyl 7-bromo-1-cyclopropyl-8-ethyl-6-fluoro-2-oxo-1,2-dihydroquinoline-3-carboxylate (100 mg, 0.26 mmol), tert-butyl ((S)-1-((R)-pyrrolidin-3-yl)ethyl)carbamate (84 mg, 0.39 mmol), Cs₂CO₃ (254 mg, 0.78 mmol) and Xantphos (23 mg, 0.039 mmol) in PhMe (30 mL) was added Pd₂(dba)₃ (12 mg, 0.013 mmol). Then the reaction mixture was stirred at 110° C. for 14 h under N₂ atmosphere. After the reaction was complete, the reaction mixture was evaporated to give a crude product. The crude product was purified by chromatography on silica gel (Eluent: EtOAc:PE=1:1) to give the crude title compound (40 mg), which was used in the next step directly.

(ix) 7-((R)-3-((S)-1-((tert-butoxycarbonyl)amino)ethyl)pyrrolidin-1-yl)-1-cyclopropyl-8-ethyl-6-fluoro-2-oxo-1,2-dihydroquinoline-3-carboxylic acid To a mixture of ethyl 7-((R)-3-((S)-1-((tert-butoxycarbonyl)amino)ethyl)pyrrolidin-1-yl)-1-cyclopropyl-8-ethyl-6-fluoro-2-oxo-1,2-dihydroquinoline-3-carboxylate (40 mg, 0.078 mmol) in THF/H₂O (8 mL, 1:1) was added NaOH (6 mg, 0.15 mmol). Then the reaction mixture was stirred at 30° C. for 17 h. The reaction mixture was acidified to pH~6 with aq. HCl (0.5 M). The resulting solution was extracted with EtOAc (40 mL×8). The combined organic layer was dried over anhydrous Na₂SO₄, filtered and concentrated to give the crude title compound (32 mg), which was used in the next step directly.

(x) 7-((R)-3-((S)-1-aminoethyl)pyrrolidin-1-yl)-1-cyclopropyl-8-ethyl-6-fluoro-2-oxo-1,2-dihydroquinoline-3-carboxylic acid hydrochloride A mixture of 7-((R)-3-((S)-1-((tert-butoxycarbonyl)amino)ethyl)pyrrolidin-1-yl)-1-cyclopropyl-8-ethyl-6-fluoro-2-oxo-1,2-dihydroquinoline-3-carboxylic acid (22 mg, 0.045 mmol) in HCl/EtOAc (5 mL, 4 M) and EtOAc (5 mL) was stirred at 25° C. for 2 h. After the reaction was complete, water (10 mL) was added to the reaction mixture. The resulting solution was washed with EtOAc (40 mL×6). The aqueous solution was lyophilized to give the title compound (8 mg, 41.8% yield).

¹H NMR (400 MHz, CD₃OD-d₁) δ 8.73 (s, 1H), 7.44 (d, J=12.4 Hz, 1H), 3.80-3.75 (m, 1H), 3.70-3.40 (m, 6H), 3.25-3.10 (m, 1H), 2.60-2.50 (m, 1H), 2.35-2.25 (m, 1H), 1.90-1.80 (m, 1H), 1.46 (d, J=6.4 Hz, 3H), 1.45-1.30 (m, 2H), 0.94 (t, J=6.8 Hz, 3H), 0.70-0.55 (m, 2H)

LCMS (0-60 AB_7 min), [MH]⁺=388.2, RT=3.049 mins

LCMS Method 0-60 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 0%-60% (solvent B) over 6 minutes and holding at 60% for 0.5 minutes.

Example 14: 7-((R)-3-((S)-1-aminoethyl)pyrrolidin-1-yl)-1-cyclopropyl-6-fluoro-2-oxo-1,2-dihydroquinoline-3-carboxylic acid hydrochloride salt

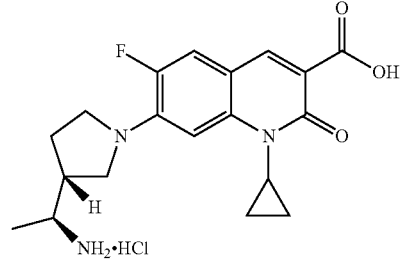

The title compound was prepared in accordance with the following scheme:

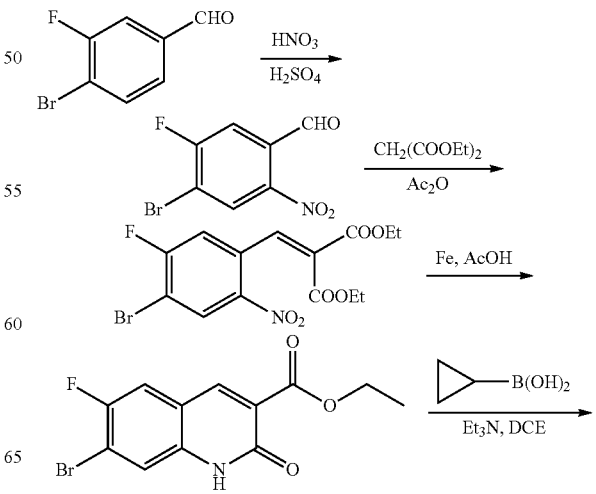

-continued

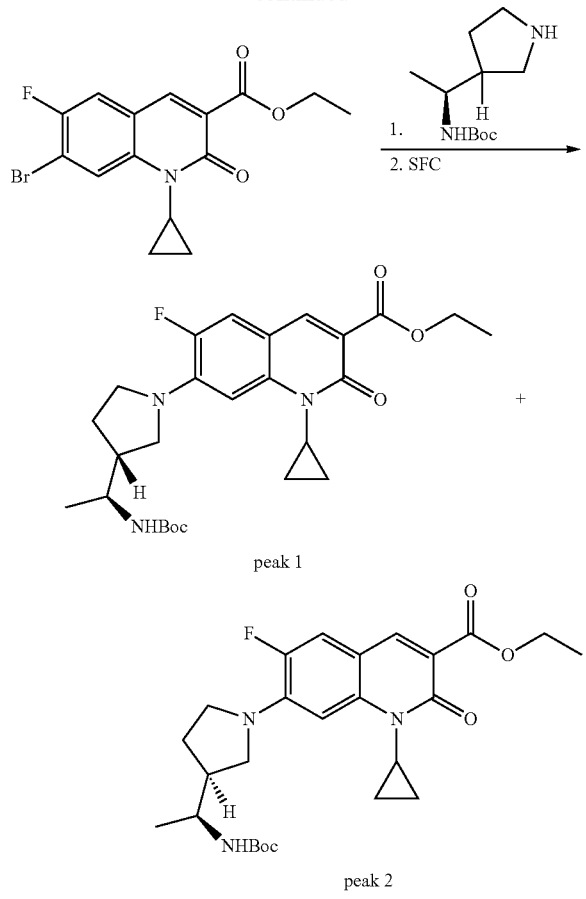

peak 1 peak 2

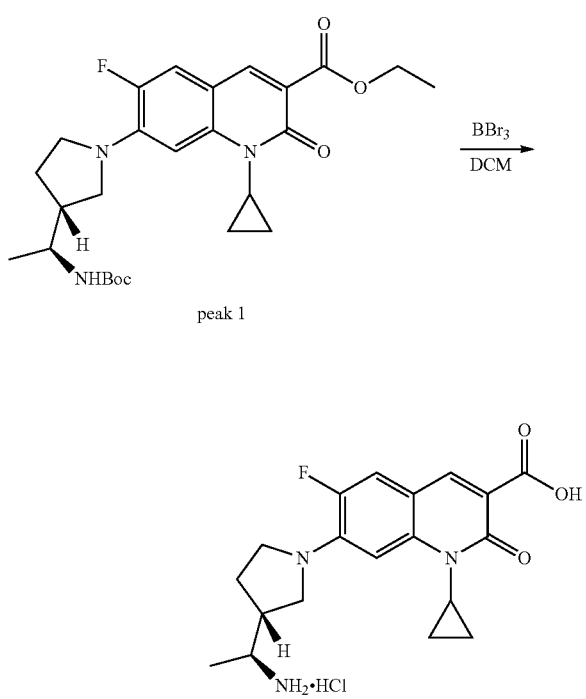

peak 1

(i) 4-bromo-5-fluoro-2-nitrobenzaldehyde

To a mixture of 4-bromo-3-fluorobenzaldehyde (40 g, 0.2 mol) in conc. $H_2SO_4$ (160 mL) was added conc. $HNO_3$ (320 mL) at 0° C. The reaction was then stirred at 25° C. for 2 h. After the reaction was complete, the reaction mixture was then poured into cold water (600 mL). The resulting solution was extracted with EtOAc (2×500 mL). The organic layer was washed with water, dried over anhydrous $Na_2SO_4$ and concentrated in vacuum to give the desired product (weight: 34 g, yield: 69.6%).

$^1$H NMR (400 MHz, $CDCl_3$-$d_1$) δ 10.42 (d, J=2.0 Hz, 1H), 8.45 (d, J=5.6 Hz, 1H), 7.72 (d, J=7.6 Hz, 1H)

(ii) Diethyl 2-(4-bromo-5-fluoro-2-nitrobenzylidene)malonate

To a mixture of 4-bromo-5-fluoro-2-nitrobenzaldehyde (34 g, 0.14 mmol) in acetic anhydride (400 mL) was added diethyl malonate (28.8 g, 0.18 mol) and $NaHCO_3$ (18.5 g, 0.22 mol). The reaction mixture was stirred at 100° C. for 6 h. After the reaction was complete, the reaction mixture was partitioned with EtOAc and water. The organic layer was washed with water, 5% aq. $Na_2CO_3$ and brine, dried over anhydrous $Na_2SO_4$ and concentrated in vacuum to give the desired product (weight: 52 g, yield: 97.2%).

$^1$H NMR (400 MHz, $CDCl_3$-$d_1$) δ 8.48 (d, J=6.0 Hz, 1H), 8.02 (s, 1H), 7.23 (d, J=8.0 Hz, 1H), 4.36-4.31 (m, 2H), 4.25-4.19 (m, 2H), 1.36-1.32 (m, 3H), 1.30-1.25 (m, 3H)

(iii) Ethyl 7-bromo-6-fluoro-2-oxo-1,2-dihydroquinoline-3-carboxylate

To a solution of diethyl 2-(4-bromo-5-fluoro-2-nitrobenzylidene)malonate (52 g, 0.13) in acetic acid (450 mL) was added Fe (48.5 g, 0.87 mol) at 25° C. The resulting mixture was stirred at 80° C. for 3 h. After the reaction was complete, the volatile was evaporated. The residue was washed with water, DCM/MeOH (2:1, 400 mL) and then EtOAc (4×80 mL) to give the desired product (weight: 33 g, yield: 78.8%).

$^1$H NMR (400 MHz, DMSO-$d_6$) δ 12.11 (brs, 1H), 8.43 (s, 1H), 7.85 (s, 1H), 7.56 (s, 1H), 4.28 (s, 2H), 1.30 (s, 3H)

(iv) Ethyl 7-bromo-1-cyclopropyl-6-fluoro-2-oxo-1,2-dihydroquinoline-3-carboxylate To a mixture of ethyl 7-bromo-6-fluoro-2-oxo-1,2-dihydroquinoline-3-carboxylate (10 g, 31.8 mmol), cyclopropylboronic acid (5.46 g, 63.6 mmol) and $Et_3N$ (6.44 g, 63.6 mmol) in DCE (150 mL) was added BiPy (4.97 g, 31.8 mmol) and $Cu(OAc)_2$ (5.78 g, 31.8 mmol). The reaction mixture was stirred at 50° C. for 10 h under oxygen. After the reaction was complete, the reaction mixture was filtered. The filtrate was concentrated to give the crude product, which was purified by column chromatography on silica gel (Eluent: PE:EtOAc=2:1) to give the desired product as a yellow solid (weight: 3.3 g, yield: 29.3%).

$^1$H NMR (400 MHz, DMSO-$d_6$) δ 8.19 (s, 1H), 8.04 (d, J=6.0, 1H), 7.33 (d, J=7.6 Hz, 1H), 4.40 (q, J=7.2 Hz, 2H), 2.95-2.90 (m, 1H), 1.45-1.35 (m, 5H), 0.94-0.90 (m, 2H)

(v) ethyl 7-((R)-3-((S)-1-((tert-butoxycarbonyl)amino)ethyl)pyrrolidin-1-yl)-1-cyclopropyl-6-fluoro-2-oxo-1,2-dihydroquinoline-3-carboxylate & ethyl 7-((S)-3-((S)-1-((tert-butoxy carbonyl)amino)ethyl)pyrrolidin-1-yl)-1-cyclopropyl-6-fluoro-2-oxo-1,2-dihydroquinoline-3-carboxylate

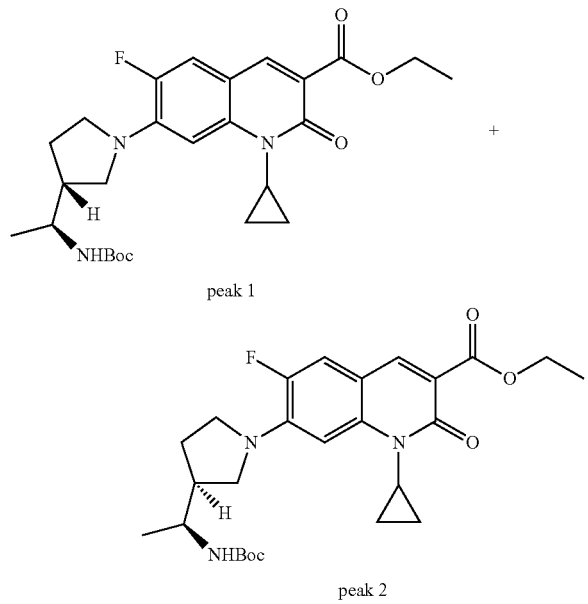

peak 1 peak 2

To a solution of ethyl 7-bromo-1-cyclopropyl-6-fluoro-2-oxo-1,2-dihydroquinoline-3-carboxylate (1.5 g, 4.2 mmol) in DMSO (30 mL) was added tert-butyl ((1S)-1-(pyrrolidin-3-yl)ethyl)carbamate (0.3 g, 1.4 mmol) and $K_3PO_4$ (2.7 g, 12.7 mmol) at 25° C., followed by Xantphos (0.36 g, 0.62 mmol) and $Pd(OAc)_2$ (0.1 g, 0.42 mmol). The resulting mixture was stirred at 60° C. under argon for 4 h. The reaction mixture was concentrated in vacuum. The residue was extracted with DCM (20 mL×2). The organic layer was dried over $Na_2SO_4$, filtered and concentrated and purified by column chromatography on silica gel (Eluent: PE:EtOAC=2:1) to give the desired product, which was separated by SFC to give ethyl 7-((R)-3-((S)-1-((tert-butoxycarbonyl)amino)ethyl)pyrrolidin-1-yl)-1-cyclopropyl-6-fluoro-2-oxo-1,2-dihydroquinoline-3-carboxylate (PEAK1: weight: 460 mg, yield: 22.3%) and ethyl 7-((S)-3-((S)-1-((tert-butoxycarbonyl)amino)ethyl)pyrrolidin-1-yl)-1-cyclopropyl-6-fluoro-2-oxo-1,2-dihydroquinoline-3-carboxylate (PEAK2: weight: 230 mg, yield: 11.1%).

peak 1: $^1$H NMR (400 MHz, CDCl$_3$-d$_1$) δ 8.21 (s, 1H), 7.11 (d, J=13.6 Hz, 1H), 6.76 (d, J=7.6 Hz, 1H), 4.55-4.45 (m, 1H), 4.37 (q, J=6.8 Hz, 2H), 3.80-3.60 (m, 4H), 3.50-3.45 (m, 1H), 2.85-2.80 (m, 1H), 2.33-2.27 (m, 1H), 2.14-2.08 (m, 1H), 1.82-1.72 (m, 1H), 1.45 (m, 9H), 1.40 (t, J=7.2 Hz, 3H), 1.34 (t, J=5.4 Hz, 2H), 1.24 (d, J=6.4 Hz, 3H), 0.95-0.85 (m, 2H)

peak 2: $^1$H NMR (400 MHz, CDCl$_3$-d$_1$) δ 8.21 (s, 1H), 7.14 (d, J=13.6 Hz, 1H), 6.77 (d, J=8.0 Hz, 1H), 4.55-4.45 (m, 1H), 4.39-4.34 (q, J=7.2 Hz, 2H), 3.80-3.61 (m, 4H), 3.37 (d, J=8.4 Hz, 1H), 2.87-2.81 (m, 1H), 2.33-2.27 (m, 1H), 2.17-2.13 (m, 1H), 1.91-1.83 (m, 1H), 1.45 (s, 9H), 1.40 (t, J=7 Hz, 3H), 1.34 (t, J=6.8 Hz, 2H), 1.23 (d, J=6.4 Hz, 3H), 0.89 (d, J=7.2 Hz, 2H)

(vi) 7-((R)-3-((S)-1-aminoethyl)pyrrolidin-1-yl)-1-cyclopropyl-6-fluoro-2-oxo-1,2-dihydroquinoline-3-carboxylic acid hydrochloride salt To a solution of ethyl 7-((R)-3-((S)-1-((tert-butoxycarbonyl)amino)ethyl)pyrrolidin-1-yl)-1-cyclopropyl-6-fluoro-2-oxo-1,2-dihydroquinoline-3-carboxylate (260 mg, 0.53 mmol) in DCM (10 mL) was added 1311'$_3$ (534 mg, 2.13 mmol) at 15° C. The resulting mixture was stirred at 15° C. for 16 h. The reaction mixture was quenched with water at 0° C. The resulting suspension was extracted with DCM. The organic phase was dried over anhydrous $Na_2SO_4$ and concentrated to give the crude product, which was purified by prep-HPLC (basic) to give the desired product (weight: 15 mg, yield: 7.1%).

LCMS (10-80 AB_7 min), RT=1.818 mins, [MH]$^+$=360.0

$^1$H NMR (400 MHz, CD$_3$OD-d$_4$) δ 8.68 (s, 1H), 7.47 (d, J=13.6 Hz, 1H), 7.10 (d, J=6.8 Hz, 1H), 3.98-3.92 (m, 1H), 3.81-3.74 (m, 2H), 3.59 (t, J=9.6 Hz, 1H), 3.45-3.40 (m, 1H), 3.18-3.10 (m, 1H), 2.60-2.50 (m, 1H), 2.35-2.25 (m, 1H), 1.96-1.86 (m, 1H), 1.55-1.50 (m, 2H), 1.44 (d, J=6.8 Hz, 3H), 1.00-0.90 (m, 2H)

LCMS Method 10-80 AB_7 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 0.8 mL/min;

Gradient: 10%-80% (solvent B) over 6 minutes and holding at 80% for 0.5 minutes.

Intermediate 15: 7-bromo-1-cyclopropyl-6-fluoro-8-methylquinolin-2(1H)-one

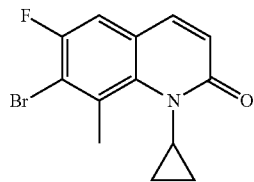 [SMILES: Cc1c(Br)c(F)cc2ccc(=O)n(C3CC3)c12]

The title compounds were prepared in accordance with the following scheme:

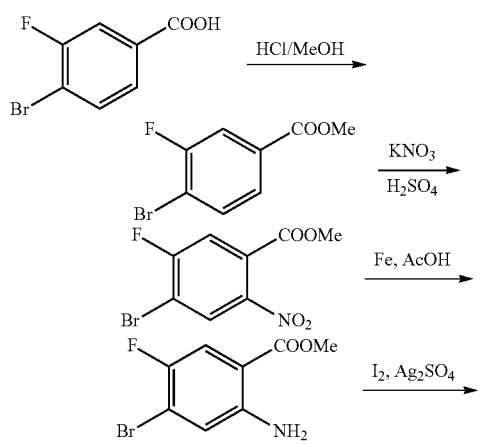

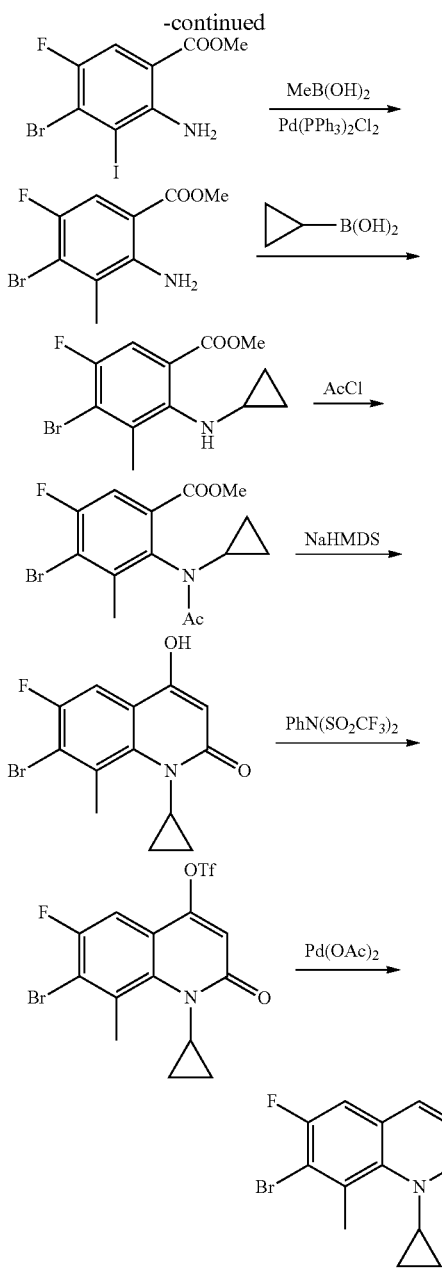

(i) Methyl 4-bromo-3-fluorobenzoate

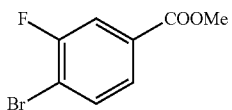 [SMILES: COC(=O)c1ccc(Br)c(F)c1]

A solution of 4-bromo-3-fluorobenzoic acid (350 g, 1.6 mol, 1.0 eq.) in HCl/MeOH (2 L) was stirred at 50 ⌊ for 3 h. The reaction mixture was concentrated to give crude title compound (372.3 g) as a gray solid.

$^1$H NMR (400 MHz, CDCl$_3$-d$_1$) δ 7.78-7.64 (m, 3H), 3.93 (s, 3H)

(ii) Methyl 4-bromo-5-fluoro-2-nitrobenzoate

To a solution of methyl 4-bromo-3-fluorobenzoate (372 g, 1.6 mol, 1.0 eq.) in H$_2$SO$_4$ (1000 mL) was added KNO$_3$ (169.5 g, 1.678 mol, 1.05 eq.) at 0 ⌊. The mixture was then stirred at r.t. for 2 h. After the reaction was complete, the reaction mixture was quenched with ice water and then extracted with EtOAc. The organic layer was dried over anhydrous Na$_2$SO$_4$ and concentrated to give the crude product, which was purified by column chromatography on silica gel (Eluents: PE:EtOAc=20:1) to get the title compound (380 g, yield: 85.8%) as a yellow solid.

$^1$H NMR (400 MHz, CDCl$_3$-d$_1$) δ 8.21 (d, J=5.6 Hz, 1H), 7.45 (d, J=7.6 Hz, 1H), 3.94 (s, 3H)

(iii) Methyl 2-amino-4-bromo-5-fluorobenzoate

To a solution of methyl 4-bromo-5-fluoro-2-nitrobenzoate (95 g, 0.34 mol, 1.0 eq.) in MeOH (1000 mL) was added AcOH (102 g, 1.7 mol, 5.0 eq.). Then Fe power (95.4 g, 1.7 mol, 5.0 eq.) was added slowly at 0 ⌊. After stirred at r.t. for 1 h, the reaction mixture was filtered. The filtrate was concentrated. The residue was purified by column chromatography on silica gel (Eluents: PE:EtOAc=20:1) to get the title compound (62.5 g, yield: 73.7%) as a white solid.

$^1$H NMR (400 MHz, CDCl$_3$-d$_1$) δ 7.59 (d, J=9.6 Hz, 1H), 6.88 (d, J=5.6 Hz, 1H), 5.62 (brs, 2H), 3.88 (s, 3H).

(iv) Methyl 2-amino-4-bromo-5-fluoro-3-iodobenzoate

To a solution of methyl 2-amino-4-bromo-5-fluorobenzoate (50 g, 0.2 mol, 1.0 eq.) in MeOH (480 mL) was added water (400 mL) and Ag$_2$SO$_4$ (100 g, 0.32 mol, 1.6 eq.). Then a solution of I$_2$ (81.2 g, 0.32 mol, 1.6 eq.) in THF (480 mL) was added at r.t. After stirred at r.t. for 30 min, the volitale was evaporated, the resulting suspension was filtered. The filtrate was extracted with EtOAc. The organic phase was dried over anhydrous Na$_2$SO$_4$ and concentrated to give the crude product, which was purified by column chromatography on silica gel (Eluents: PE:EtOAc=15:1) to get the title compound (68 g, yield: 90.2%) as a yellow solid.

$^1$H NMR (400 MHz, CDCl$_3$-d$_1$) δ 7.75 (d, J=9.6 Hz, 1H), 6.55 (brs, 2H), 3.90 (s, 3H)

(v) Methyl 2-amino-4-bromo-5-fluoro-3-methylbenzoate

To a solution of methyl 2-amino-4-bromo-5-fluoro-3-iodobenzoate (80 g, 0.214 mol, 1.0 eq.) in DME (1170 mL) was added water (200 mL), CH$_3$B(OH)$_2$ (77 g, 1.28 mol, 6.0 eq.), K$_2$CO$_3$ (59 g, 0.428 mol, 2.0 eq.) and Pd(PPh$_3$)$_2$Cl$_2$ (15 g, 0.0214 mol, 0.1 eq.) at r.t. The reaction mixture was stirred at 60 ⌊ for 18 h and then the mixture stirred at 90 ⌊ for 6 h under N$_2$ atmosphere. After the reaction was complete, the reaction mixture was quenched with water and extracted with EtOAc. The organic phase was dried over anhydrous Na$_2$SO$_4$ and concentrated and then purified by column chromatography on silica gel (Eluents: PE:EA=50:1) to get crude compound, which was then recrystallized from PE/EtOAc to give the title compound (29 g, yield: 51.78%) as a yellow solid.

$^1$H NMR (400 MHz, CDCl$_3$-d$_1$) δ 7.52 (d, J=9.6 Hz, 1H), 5.83 (brs, 2H), 3.87 (s, 3H), 2.32 (s, 3H)
LCMS (10-80 AB_2 min), RT=1.153 mins, [MH]$^+$=262.0
LCMS Method 10-80AB_2 MIN Column: Xtimate C18 2.1*30 mm, 3 um; ESI source, positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 1.2 mL/min;
Gradient: 10%-80% (solvent B) over 0.9 minutes and holding at 80% for 0.6 minutes.
HPLC (10-80 AB_8 min), RT=2.91 mins.
HPLC Method 10-80AB_8 MIN
Column: Xtimate C18 2.1*30 mm, 3 um; Wavelength UV 220 nm, 215 nm, 254 nm;
Column temperature: 50° C.;
Mobie Phase: A: 2.75 mL/4 L TFA in water, B: 2.50 mL/4 L TFA in acetonitrile;
Flow rate: 1.2 mL/min;
Gradient: 10%-80% (solvent B) over 6 minutes and holding at 80% for 2 minutes.

(vi) Methyl 4-bromo-2-(cyclopropylamino)-5-fluoro-3-methylbenzoate

To a solution of methyl 2-amino-4-bromo-5-fluoro-3-methylbenzoate (5 g, 19.2 mmol) in DCE (50 mL) was added $Na_2CO_3$ (4.07 g, 38.4 mmol), 2,2'-bipyridine (2.9 g, 19.2 mmol), $Cu(OAc)_2$ (3.5 g, 19.2 mmol) and cyclopropylboronic acid (3.5 g, 19.2 mmol) at 10 ⌊. The reaction mixture was stirred at 10 ⌊ for 20 min and then at 70 ⌊ for 5 h. After the reaction was complete, the reaction mixture was filtered. The filtrate was concentrated in vacuo. The residue was purified by column chromatography on silica gel (Eluent: PE:EtOAc=50:1) to give the title compound (2.4 g, yield: 41.5%) as a yellow oil.
$^1$H NMR (400 MHz, $CDCl_3$-$d_1$) δ 7.52 (d, J=9.03 Hz, 1H), 7.22 (brs, 1H), 3.85 (s, 3H), 2.71 (tt, J=3.51, 6.78 Hz, 1H), 2.57 (s, 3H), 0.68-0.62 (m, 2H), 0.49-0.45 (m, 2H)
LCMS (10-80 AB_2 min), RT=1.311 mins, [MH]$^+$=302.2
LCMS Method 10-80AB_2 MIN
Column: Xtimate C18 2.1*30 mm, 3 um; ESI source, positive ion mode; Wavelength 220 nm;
Column temperature: 40° C.;
Mobile Phase: A: 1.5 mL/4 L TFA in water, B: 0.75 mL/4 L TFA in acetonitrile;
Flow rate: 1.2 mL/min;
Gradient: 10%-80% (solvent B) over 0.9 minutes and holding at 80% for 0.6 minutes.
HPLC (10-80 AB_8 min), RT=3.87 mins.
HPLC Method 10-80AB_8 MIN
Column: Xtimate C18 2.1*30 mm, 3 um; Wavelength UV 220 nm, 215 nm, 254 nm;
Column temperature: 50° C.;
Mobile Phase: A: 2.75 mL/4 L TFA in water, B: 2.50 mL/4 L TFA in acetonitrile;
Flow rate: 1.2 mL/min;
Gradient: 10%-80% (solvent B) over 6 minutes and holding at 80% for 2 minutes.

(vii) Methyl 4-bromo-2-(N-cyclopropylacetamido)-5-fluoro-3-methylbenzoate

To a solution of methyl 4-bromo-2-(cyclopropylamino)-5-fluoro-3-methylbenzoate (13 g, 43.0 mmol) in DCM (260 mL) was added DIEA (27.8 g, 215 mmol) and acetyl chloride (33.8 g, 430 mmol) at 20 ⌊. The reaction mixture was stirred at 20 ⌊ for 20 min. After the reaction was complete, the reaction mixture was poured into ice water. The two phases were separated. The organic layer was washed with brine, dried over $Na_2SO_4$, filtered and concentrated in vacuo. The residue was purified by column chromatography on silica gel (Eluent: PE:EtOAc=2:1) to give the title compound (10.5 g, yield: 70.9%) as a brown oil.
$^1$H NMR (400 MHz, $CDCl_3$-$d_1$) δ 7.63-7.53 (m, 1H), 3.90-3.80 (m, 3H), 3.15-3.01 (m, 1H), 2.41 (s, 2H), 2.34 (s, 1H), 2.27 (s, 2H), 1.76 (s, 1H), 0.93-0.83 (m, 1H), 0.79-0.60 (m, 3H), 0.47-0.27 (m, 1H)
LCMS (5-95 AB_1.5 min), RT=1.311 mins, [MH]$^+$=302.2
LCMS Method 5-95AB_1.5 MIN
Column: MERCK, RP-18e 25-2 mm, ESI source, Positive ion mode; Wavelength: 220 nm;
Column temperature: 40° C.;
Mobile Phase: A: 1.5 mL/4 L TFA in water, B: 0.75 mL/4 L TFA in acetonitrile;
Flow rate & gradient: at a flow rate of 1.0 ml/min from 0-0.08 min, using the elution gradient 5%-95% (solvent B) from 0-0.7 min and holding at 95% for 0.4 minutes, at a flow rate of 1.5 ml/min;
HPLC (10-80 AB_8 min), RT=2.50 mins.
HPLC Method 10-80AB_8 MIN
Column: Xtimate C18 2.1*30 mm, 3 um; Wavelength UV 220 nm, 215 nm, 254 nm;
Column temperature: 50° C.;
Mobile Phase: A: 2.75 mL/4 L TFA in water, B: 2.50 mL/4 L TFA in acetonitrile;
Flow rate: 1.2 mL/min;
Gradient: 10%-80% (solvent B) over 6 minutes and holding at 80% for 2 minutes.

(viii) 7-bromo-1-cyclopropyl-6-fluoro-4-hydroxy-8-methylquinolin-2(1H)-one

To a solution of methyl 4-bromo-2-(N-cyclopropylacetamido)-5-fluoro-3-methylbenzoate (14.4 g, 0.042 mol, 1.0 eq.) in THF (140 mL) was added 1M NaHMDS (125.6 mL, 0.126 mol, 3.0 eq.) under $N_2$ at 0 ⌊. After stirred at r.t. for 30 min, the reaction mixture was quenched with water. The resulting solution was washed with EtOAc, adjusted to PH<5 with 4M aq. HCl and then filtered. The residue was washed with PE and then dried to get the title compound (10.3 g, yield: 75.7%) as a yellow solid.
$^1$H NMR (400 MHz, DMSO-$d_6$) δ 7.50 (d, J=8.4 Hz, 1H), 5.30 (s, 1H), 3.45-3.35 (m, 1H), 2.71 (s, 3H), 1.10-1.00 (m, 2H), 0.40-0.30 (m, 2H)

(ix) 7-bromo-1-cyclopropyl-6-fluoro-8-methyl-2-oxo-1,2-dihydroquinolin-4-yl trifluoromethanesulfonate To a solution of 7-bromo-1-cyclopropyl-6-fluoro-4-hydroxy-8-methylquinolin-2(1H)-one (10.3 g, 0.033 mol, 1.0 eq.) in DMF (100 mL) was added TEA (13.8 mL, 0.099 mol, 3.0 eq.). Then a solution of $PhN(SO_2CF_3)_2$ (14.14 g, 0.0396 mol, 1.2 eq.) in DMF was added dropwise at OH The reaction mixture was then stirred at r.t. for 1 h. After the reaction was complete, the mixture was quenched with water and then extracted with EtOAc. The organic phase was washed with brine for three times, dried with anhydrous $Na_2SO_4$ and then concentrated to give the crude product, which was purified by column chromatography on silica gel (Eluents: E:EtOAc=10:1) to get the title compound (9 g, yield: 61.4%) as a yellow solid.
$^1$H NMR (400 MHz, $CDCl_3$-$d_1$) δ 7.34 (d, J=7.6 Hz, 1H), 6.71 (s, 1H), 3.55-3.45 (m, 1H), 2.84 (s, 3H), 1.30-1.20 (m, 2H), 0.65-0.60 (m, 2H)

(x) 7-bromo-1-cyclopropyl-6-fluoro-8-methylquinolin-2(1H)-one

To a solution of 7-bromo-1-cyclopropyl-6-fluoro-8-methyl-2-oxo-1,2-dihydroquinolin-4-yl trifluoromethanesulfonate (5.1 g, 11.5 mmol, 1.0 eq.) in DMF (100 mL) was added 1, 3-DPPP (1.42 g, 3.4 mmol, 0.3 eq.), Et$_3$SiH (1.6 g, 13.8 mmol, 1.2 eq.) and Pd(OAc)$_2$ (0.38 g, 1.7 mmol, 0.15 eq.) under N$_2$. The reaction mixture was stirred at 100 ⌊ for 18 h. After the reaction was complete, the reaction mixture was quenched with water and extracted with DCM. The organic phase was washed with brine for three times, dried with anhydrous Na$_2$SO$_4$ and concentrated to give the crude product, which was purified by column chromatography on silica gel (Eluents: PE:EtOAc=5:1) to get the title compound (2 g, yield: 58.8%) as a yellow solid.

$^1$H NMR (400 MHz, CDCl$_3$-d$_1$) δ 7.44 (d, J=9.2 Hz, 1H), 7.09 (d, J=7.6 Hz, 1H), 6.61 (d, J=9.2 Hz, 1H), 3.55-3.45 (m, 1H), 2.80 (s, 3H), 1.30-1.20 (m, 2H), 0.60-0.50 (m, 2H)

LCMS (0-60 AB_2 min), RT=1.561 mins, [MH]$^+$=295.9

LCMS Method 0-60AB_2 MIN

Column: Xtimate C18 2.1*30 mm, 3 um; ESI source, Positive ion mode; Wavelength 220 nm;

Column temperature: 40° C.;

Mobile Phase: A: 1.5 mL/4 L TFA in water, B: 0.75 mL/4 L TFA in acetonitrile;

Flow rate: 1.2 mL/min;

Gradient: 0%-60% (solvent B) over 0.9 minutes and holding at 60% for 0.6 minutes.

HPLC (0-60 AB_8 min), RT=3.69 mins.

HPLC Method 0-60AB_8 MIN

Column: Xtimate C18 2.1*30 mm, 3 um; Wavelength UV 220 nm, 215 nm, 254 nm;

Column temperature: 50° C.;

Mobile Phase: A: 2.75 mL/4 L TFA in water, B: 2.50 mL/4 L TFA in acetonitrile;

Flow rate: 1.2 mL/min;

Gradient: 0%-60% (solvent B) over 6 minutes and holding at 60% for 2 minutes.

Example 16: tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate

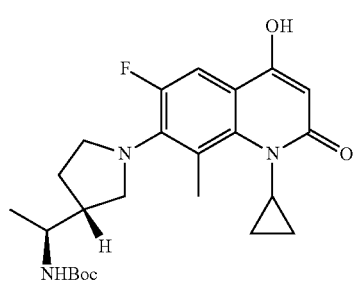 [SMILES: Cc1c(N2CC[C@@H]([C@H](C)NC(=O)OC(C)(C)C)C2)c(F)cc2c(O)cc(=O)n(C3CC3)c12]

The title compound was prepared in accordance with the following scheme:

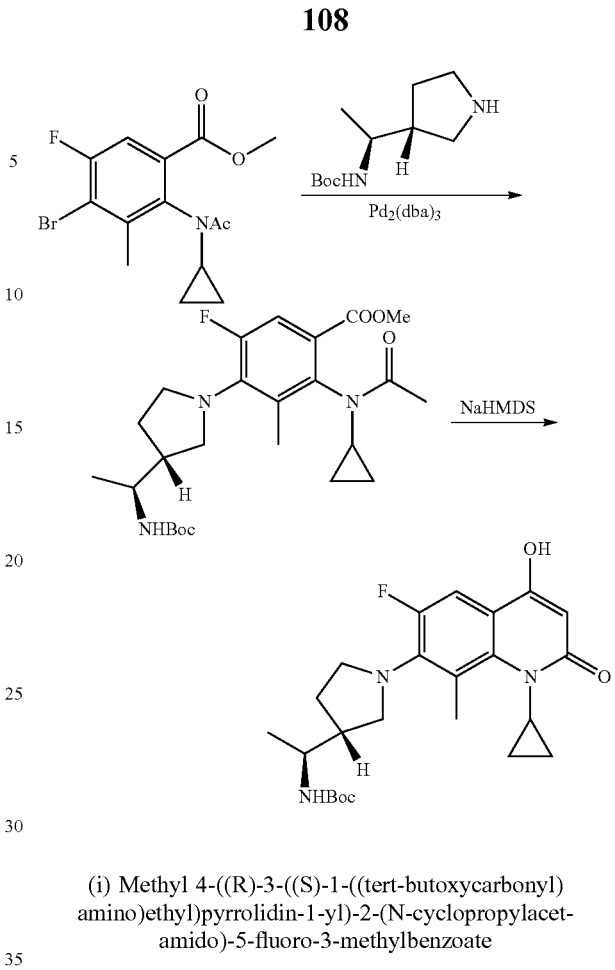

(i) Methyl 4-((R)-3-((S)-1-((tert-butoxycarbonyl)amino)ethyl)pyrrolidin-1-yl)-2-(N-cyclopropylacetamido)-5-fluoro-3-methylbenzoate To a suspension of methyl 4-bromo-2-(N-cyclopropylacetamido)-5-fluoro-3-methylbenzoate (6 g, 17.49 mmol) in toluene (180 mL) was added tert-butyl ((S)-1-((R)-pyrrolidin-3-yl)ethyl) carbamate (6.72 g, 31.48 mol), Cs$_2$CO$_3$ (11.4 g, 34.98 mmol), Xantphos (3 g, 5.25 mmol) and Pd$_2$(dba)$_3$ (1.6 g, 1.75 mmol) at 10° C. The resulting mixture was purged with nitrogen for 5 min and heated to 110 ⌊ for 24 h. The reaction mixture was filtered and the filtrate was concentrated in vacuo. The residue was purified by column chromatography on silica gel (Eluent: PE:EtOAc=1:1) to give crude title compound (5 g, yield: 59.9%) as a brown oil.

$^1$H NMR (400 MHz, CDCl$_3$-d$_1$) δ 7.54-7.45 (m, 1H), 4.61 (brs, 1H), 3.85-3.80 (m, 3H), 3.75-3.65 (m, 1H), 3.40-3.26 (m, 3H), 3.12-3.05 (m, 1H), 2.44-2.37 (m, 2H), 2.29-2.23 (m, 1H), 2.13 (s, 2H), 2.08-2.02 (m, 3H), 1.79-1.72 (m, 2H), 1.66 (s, 1H), 1.43 (s, 9H), 1.22-1.16 (m, 3H), 0.89-0.79 (m, 1H), 0.75-0.61 (m, 3H), 0.45-0.30 (m, 1H)

(ii) tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate To a solution of methyl 4-((R)-3-((S)-1-((tert-butoxycarbonyl)amino)ethyl)pyrrolidin-1-yl)-2-(N-cyclopropylacetamido)-5-fluoro-3-methylbenzoate (5 g, 10.48 mmol) in THF (150 mL) was added NaHMDS (52 mL, 52.4 mmol, 1 M in THF) at 10 ⌊. The resulting mixture was stirred at 10 ⌊ for 20 min. After the reaction was complete, the reaction mixture was quenched with water and then acidified to pH=4 with 1 M aq. HCl. The resulting suspension was extracted with EtOAc (100 mL×2). The organic layer was washed with brine, dried over Na$_2$SO$_4$, filtered and concentrated in vacuo. The residue was purified by prep-HPLC to give the title compound (2.3 g, yield: 49.3%) as a yellow solid.

$^1$H NMR (400 MHz, CD$_3$OD-d$_4$) δ 7.40 (d, J=13.55 Hz, 1H), 6.71 (d, J=8.78 Hz, 1H), 5.79 (s, 1H), 3.62 (d, J=6.53 Hz, 2H), 3.48-3.38 (m, 4H), 2.54 (s, 3H), 2.40-2.29 (m, 1H), 2.11 (ddd, J=3.89, 7.28, 11.42 Hz, 1H), 1.80-1.68 (m, 1H), 1.45 (s, 9H), 1.25-1.10 (m, 5H), 0.55-0.44 (m, 2H)

LCMS (5-95 AB_1.5 min), RT=0.881 mins, [MH]$^+$ =447.2

LCMS Method 5-95AB_1.5 MIN

Column: MERCK, RP-18e 25-2 mm, ESI source, Positive ion mode; Wavelength: 220 nm;

Column temperature: 40° C.;

Mobile Phase: A: 1.5 mL/4 L TFA in water, B: 0.75 mL/4 L TFA in acetonitrile;

Flow rate & gradient: at a flow rate of 1.0 ml/min from 0-0.08 min, using the elution gradient 5%-95% (solvent B) from 0-0.7 min and holding at 95% for 0.4 minutes, at a flow rate of 1.5 ml/min;

HPLC (0-60 AB_8.0 min), RT=5.53 mins.

HPLC Method 0-60AB_8 MIN

Column: Xtimate C18 2.1*30 mm, 3 um; Wavelength UV 220 nm, 215 nm, 254 nm;

Column temperature: 50° C.;

Mobile Phase: A: 2.75 mL/4 L TFA in water, B: 2.50 mL/4 L TFA in acetonitrile;

Flow rate: 1.2 mL/min;

Gradient: 0%-60% (solvent B) over 6 minutes and holding at 60% for 2 minutes.

de % Analysis Method, RT=6.377 mins.

de % Analysis Method

Column: Chiralpak AD-H 250*4.6 mm I.D., 5 um.

Mobile Phase: ethanol (0.05% DEA) in CO2 from 5% to 40%;

Flow rate: 2.35 mL/min;

Wavelength: 220 nm

Example 17: 7-((R)-3-((S)-1-(((tert-butoxycarbonyl) amino)ethyl)pyrrolidin-1-yl)-1-cyclopropyl-6-fluoro-8-methyl-2-oxo-1,2-dihydroquinolin-4-yl trifluoromethanesulfonate

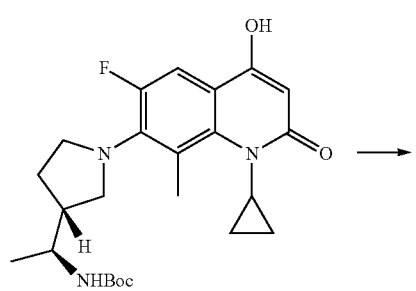

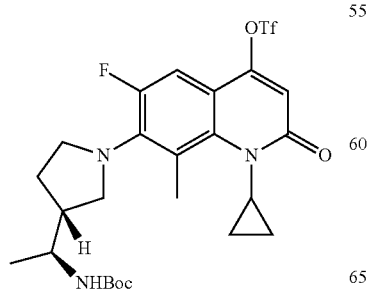

To a cold (0° C.) solution of tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (170.1 mg, 0.382 mmol) and triethylamine (160 µL, 1.145 mmol) in DMF (1273 µl) was added the dropwise addition of 1,1,1-trifluoro-N-phenyl-N-((trifluoromethyl)sulfonyl)methanesulfonamide (164 mg, 0.458 mmol) in DMF (1 mL). The reaction stirred for 1 hour and was then was poured into water, extracted with ethyl acetate and washed with brine. The organic phase was collected, dried (MgSO$_4$), filtered, and concentrated. The crude material was purified by silica gel column chromatography eluting using a linear gradient of 0-100% ethyl acetate in heptane to afford the desired material (92% yield).

1H NMR (400 MHz, Chloroform-d) δ 7.16 (d, J=12.9 Hz, 1H), 6.49 (s, 1H), 3.75 (m, 1H), 3.65 (m, 1H), 3.55-3.39 (m, 4H), 2.47 (s, 3H), 2.29 (m, 1H), 2.09 (dtd, J=14.0, 6.8, 2.8 Hz, 1H), 1.80-1.69 (m, 1H), 1.44 (s, 9H), 1.30-1.24 (m, 2H), 1.23 (d, J=6.7 Hz, 3H), 1.14 (m, 1H), 0.66-0.52 (m, 2H)

LC/MS calc'd for C$_{25}$H$_{32}$F$_4$N$_3$O$_6$S [M+H]$^+$ 578.6, found 578.2.

Example 18: 7-((R)-3-((S)-1-aminoethyl)pyrrolidin-1-yl)-1-cyclopropyl-6-fluoro-8-methyl-4-(1H-pyrazol-4-yl)quinolin-2(1H)-one

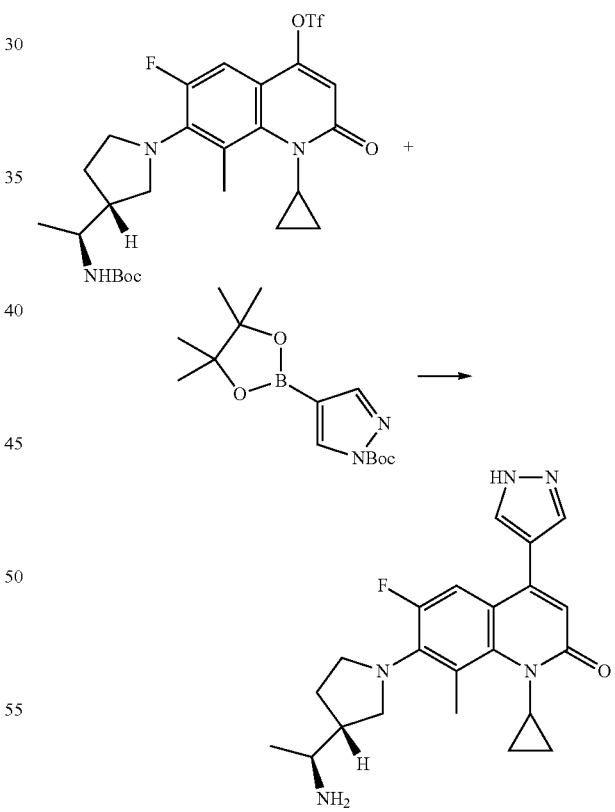

A vial charged with a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (50 mg, 0.087 mmol), tert-butyl 4-(4,4,5,5-tetramethyl-1,3,2-dioxaborolan-2-yl)-1H-pyrazole-1-carboxylate (25.5 mg, 0.087 mmol), sodium carbonate (27.5 mg, 0.260 mmol) and tetrakis(triphenylphosphine)

palladium (5.00 mg, 4.33 µmol) in Dioxane (750 µl) and Water (577 µl) was heated at 80° C. for 2 hours. The reaction cooled to room temperature and partitioned between water and ethyl acetate. The organic phase was collected, dried (MgSO$_4$), filtered, concentrated, and chromatographed on silica gel using a linear gradient of 0-100% ethyl acetate in heptane to afford tert-butyl ((S)-1-((R)-1-(1-cyclopropyl-6-fluoro-8-methyl-2-oxo-4-(1H-pyrazol-4-yl)-1,2-dihydroquinolin-7-yl)pyrrolidin-3-yl)ethyl)carbamate (LC/MS calc'd for C$_{27}$H$_{35}$FN$_5$O$_3$ [M+H] 496.6, found 496.1) which was subsequently diluted with dichloromethane (500 µL) and treated with trifluoroacetic acid (1 mL) and aged for 1 hour. The reaction was concentrated under reduced pressure and purified by prep HPLC to afford the title compound (32% yield).

1H NMR (400 MHz, DMSO-d6) δ 7.99 (m, 2H), 7.24 (d, J=14.3 Hz, 1H), 6.34 (s, 1H), 3.62-3.49 (m, 1H), 3.46-3.34 (m, 4H), 2.85-2.73 (m, 1H), 2.45 (s, 3H), 2.14-2.04 (m, 1H), 1.98 (m, 1H), 1.72-1.59 (m, 1H), 1.21-1.09 (m, 3H), 1.07 (d, J=6.3 Hz, 3H), 0.39 (s, 2H)

LC/MS calc'd for C$_{22}$H$_{27}$FN$_5$O [M+H]$^+$ 396.5, found 396.1.

Example 19: 7-((R)-3-((S)-1-aminoethyl)pyrrolidin-1-yl)-1-cyclopropyl-6-fluoro-8-methyl-4-phenylquinolin-2(1H)-one

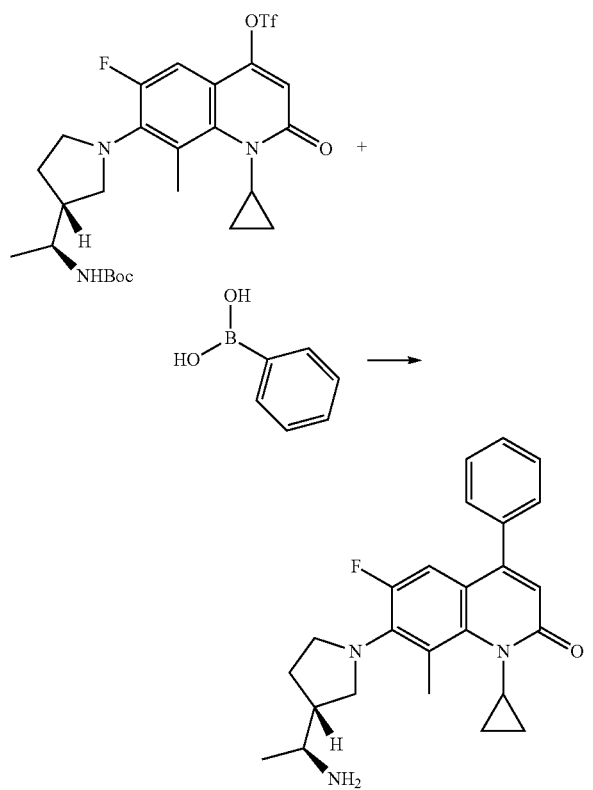

Using a similar procedure as Example 18, but substituting phenyl boronic acid for tert-butyl 4-(4,4,5,5-tetramethyl-1,3,2-dioxaborolan-2-yl)-1H-pyrazole-1-carboxylate, the title compound was obtained in 65% yield.

1H NMR (400 MHz, DMSO-d6) δ 7.56-7.48 (m, 3H), 7.43-7.39 (m, 2H), 6.76 (d, J=14.2 Hz, 1H), 6.24 (s, 1H), 3.60-3.51 (m, 1H), 3.48 (m, 1H), 3.39 (m, 2H), 3.34 (m, 2H), 2.76 (m, 1H), 2.47 (s, 3H), 2.07 (m, 1H), 1.97 (m, 1H), 1.69-1.57 (m, 1H), 1.16 (m, 3H), 1.06 (d, J=6.3 Hz, 3H), 0.52-0.39 (m, 2H)

LC/MS calc'd for C$_{25}$H$_{29}$FN$_3$O [M+H]$^+$ 406.5, found 406.1.

Example 20: 7-((R)-3-((S)-1-aminoethyl)pyrrolidin-1-yl)-1-cyclopropyl-4-(3,5-difluoro-4-hydroxyphenyl)-6-fluoro-8-methylquinolin-2(1H)-one

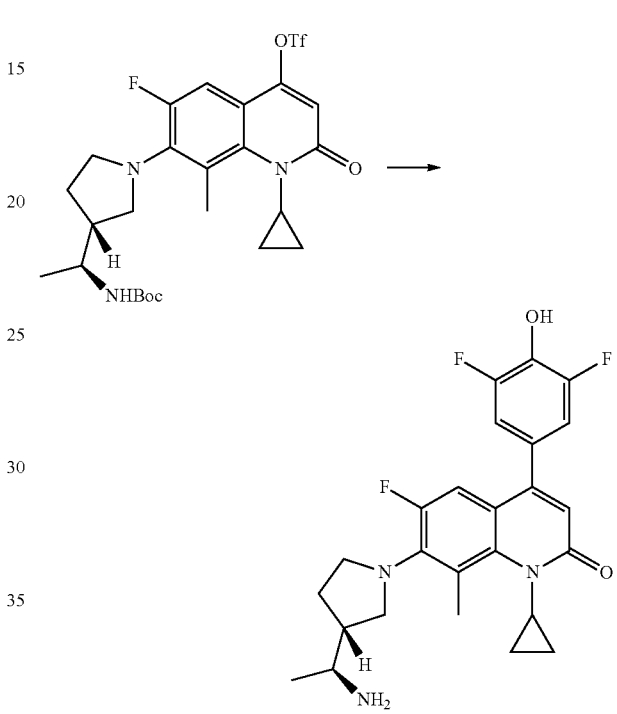

A vial charged with 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (from example 32, 25 mg, 0.043 mmol), 2,6-difluoro-4-(4,4,5,5-tetramethyl-1,3,2-dioxaborolan-2-yl) phenol (11.08 mg, 0.043 mmol), sodium carbonate (13.76 mg, 0.130 mmol) and PdCl$_2$(PPh$_3$)$_2$ (0.608 mg, 0.866 µmol) in dioxane (131 µl) and water (13.12 µl) was heated at 80° C. overnight. The reaction was poured into brine and extracted with ethyl acetate. The organic phase was collected, dried (MgSO$_4$), filtered and concentrated. The crude residue was taken up in dichloromethane (1 mL) and treated with trifluoroacetic acid (1 mL) and aged for 30 minutes. Volatiles were removed under reduced pressure and the residue purified by prep HPLC to give the desired material (37.2% yield).

1H NMR (400 MHz, DMSO-d6) δ 10.58 (s, 1H), 7.81 (bs, 2H), 7.15 (d, J=7.5 Hz, 2H), 6.90 (d, J=14.0 Hz, 1H), 6.29 (s, 1H), 3.49 (m, 3H), 3.40-3.25 (m, 3H), 2.47 (s, 3H), 2.38 (m, 1H), 2.09 (m, 1H), 1.75 (m, 1H), 1.26 (d, J=6.5 Hz, 3H), 1.15 (m, 2H), 0.42 (m, 2H)

LC/MS calc'd for C$_{25}$H$_{27}$F$_3$N$_3$O$_2$[M+H]$^+$ 458.5, found 458.2.

Example 21: (E)-ethyl 3-(7-((R)-3-((S)-1-amino-ethyl)pyrrolidin-1-yl)-1-cyclopropyl-6-fluoro-8-methyl-2-oxo-1,2-dihydroquinolin-4-yl)acrylate Example 22: (E)-3-(7-((R)-3-((S)-1-aminoethyl)pyrrolidin-1-yl)-1-cyclopropyl-6-fluoro-8-methyl-2-oxo-1,2-dihydroquinolin-4-yl)acrylic acid

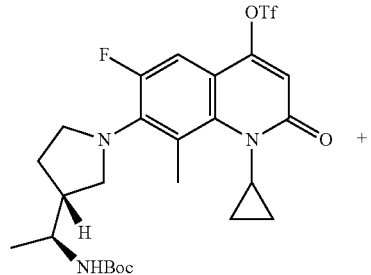

+

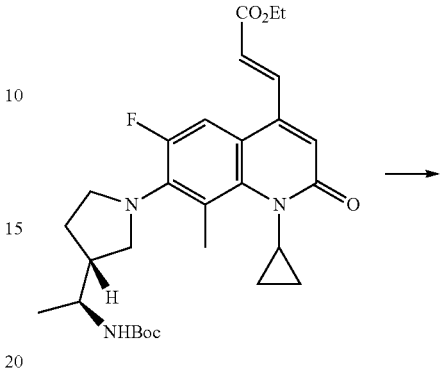

→

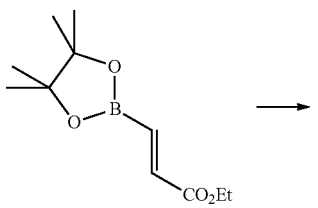

→

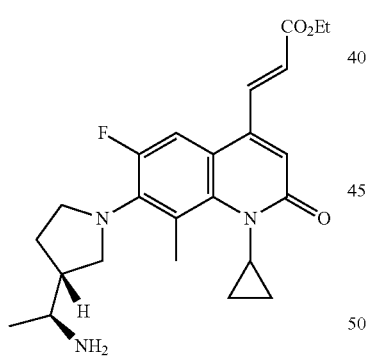

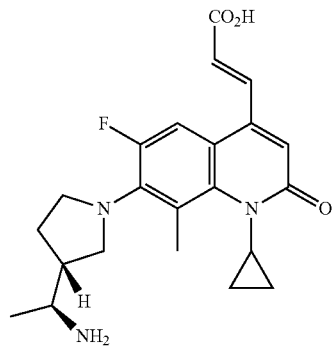

Using a similar procedure as example 18, but substituting (E)-ethyl 3-(4,4,5,5-tetramethyl-1,3,2-dioxaborolan-2-yl)acrylate for tert-butyl 4-(4,4,5,5-tetramethyl-1,3,2-dioxaborolan-2-yl)-1H-pyrazole-1-carboxylate, the title compound was obtained in 28% yield.

1H NMR (400 MHz, DMSO-d6) δ 7.89 (d, J=15.7 Hz, 1H), 7.83 (bs, 2H), 7.37 (d, J=14.0 Hz, 1H), 6.67 (s, 1H), 6.63 (d, J=15.7 Hz, 1H), 4.22 (q, J=7.1 Hz, 2H), 3.54 (m, 1H), 3.50-3.43 (m, 2H), 3.43-3.31 (m, 2H), 3.28 (m, 1H), 2.45 (s, 3H), 2.38 (m, 1H), 2.09 (m, 1H), 1.81-1.67 (m, 1H), 1.28 (m, 5H), 1.19-1.05 (m, 2H), 0.38 (m, 2H)

LC/MS calc'd for $C_{24}H_{31}FN_3O_3$ [M+H]$^+$ 428.5, found 428.1.

A solution of (E)-ethyl 3-(7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)acrylate (13 mg, 0.025 mmol) in ethanol (2 mL) and water (100 μL) was treated with sodium hydroxide (4.93 mg, 0.123 mmol) and stirred at 60° C. for 1 hour. The reaction was concentrated under reduced pressure, taken up in dichloromethane (1 mL) and treated with trifluoroacetic acid (1 mL). After 30 minutes, the reaction was concentrated and the title compound isolated by prep HPLC (31.2% yield).

1H NMR (400 MHz, DMSO-d6) δ 7.82 (d, J=15.8 Hz, 1H), 7.82 (bs, 2H), 7.35 (d, J=14.0 Hz, 1H), 6.64 (s, 1H), 6.53 (d, J=15.6 Hz, 1H), 3.54 (m, 1H), 3.47 (m, 2H), 3.42-3.32 (m, 2H), 3.28 (m, 1H), 2.45 (s, 3H), 2.38 (m, 1H), 2.15-2.05 (m, 1H), 1.75 (m, 1H), 1.27 (d, J=6.5 Hz, 3H), 1.13 (m, 2H), 0.44-0.32 (m, 2H)

LC/MS calc'd for $C_{22}H_{27}FN_3O_3$ [M+H]$^+$ 400.5, found 400.0.

Example 23: tert-butyl ((S)-1-((R)-1-(1-cyclopropyl-6-fluoro-8-methyl-2-oxo-4-vinyl-1,2-dihydroquinolin-7-yl)pyrrolidin-3-yl)ethyl)carbamate

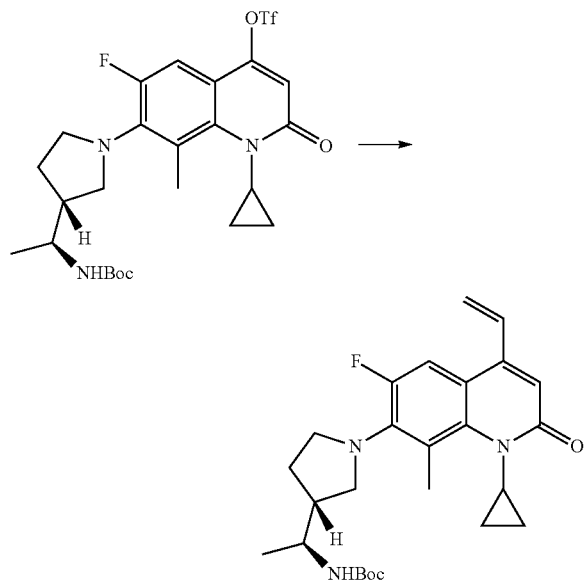

A vial charged with 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (50 mg, 0.087 mmol), 4,4,5,5-tetramethyl-2-vinyl-1,3,2-dioxaborolane (14.67 mg, 0.095 mmol), sodium carbonate (27.5 mg, 0.260 mmol) and PdCl$_2$(PPh$_3$)$_2$ (1.215 mg, 1.731 µmol) in dioxane (1385 µl) and water (346 µl) was heated at 80° C. overnight. The reaction was poured into brine and extracted with ethyl acetate. The organic phase was collected, dried (MgSO$_4$), filtered and concentrated. The crude residue was purified by silica gel column chromatography eluting with a linear gradient of 0-100% ethyl acetate in heptane to afford the desired material (49.7% yield).

LC/MS calc'd for C$_{26}$H$_{35}$FN$_3$O$_3$[M+H]$^+$ 456.6, found 456.1.

Example 24: 7-((R)-3-((S)-1-aminoethyl)pyrrolidin-1-yl)-1-cyclopropyl-4-ethyl-6-fluoro-8-methylquinolin-2(1H)-one

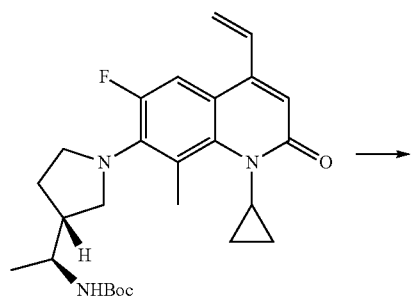

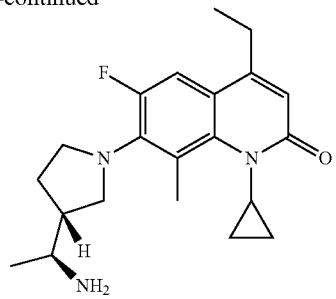

A mixture of tert-butyl ((S)-1-((R)-1-(1-cyclopropyl-6-fluoro-8-methyl-2-oxo-4-vinyl-1,2-dihydroquinolin-7-yl)pyrrolidin-3-yl)ethyl)carbamate (19.6 mg, 0.043 mmol) and 10% Pd/C (10 mg) in methanol was sparged with H$_2$ (g) for 1 hour. The reaction was filtered over Celite and concentrated under reduced pressure. The residue was dissolved in dichloromethane (1 mL) and treated with TFA (1 mL). The reaction aged for 30 minutes and was then concentrated and purified by prep HPLC to afford the title compound (60.2% yield).

1H NMR (400 MHz, DMSO-d6) δ 7.81 (bs, 2H), 7.33 (d, J=14.1 Hz, 1H), 6.24 (s, 1H), 3.48-3.38 (m, 3H), 3.39-3.30 (m, 2H), 3.27 (m, 1H), 2.69 (q, J=7.3 Hz, 2H), 2.45 (s, 3H), 2.39 (m, 1H), 2.09 (m, 1H), 1.80-1.68 (m, 1H), 1.27 (d, J=6.5 Hz, 3H), 1.18 (t, J=7.4 Hz, 3H), 1.14-1.04 (m, 2H), 0.34 (m, 2H)

LC/MS calc'd for C$_{21}$H$_{29}$FN$_3$O [M+H]$^+$ 358.5, found 358.3.

Example 25: 7-((R)-3-((S)-1-aminoethyl)pyrrolidin-1-yl)-1-cyclopropyl-4-ethynyl-6-fluoro-8-methylquinolin-2(1H)-one

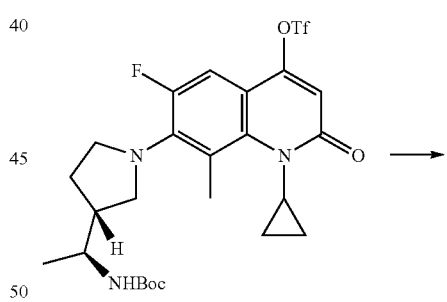

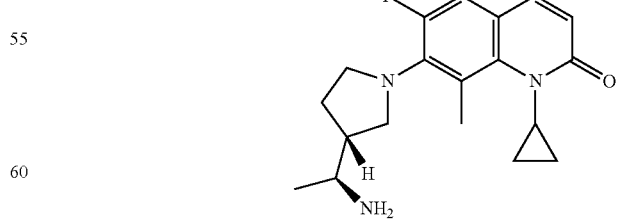

A sealed vial charged with a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (50 mg, 0.087 mmol), tributyl (ethynyl)stannane (25.05 μL, 0.087 mmol), lithium chloride (46.8 mg, 1.104 mmol), tetrakis(triphenylphosphine)palladium (10.00 mg, 8.66 μmol), and THF (866 μl) was heated at 80° C. overnight. The reaction cooled to room temperature and was poured into brine and extracted with ethyl acetate. The organic phase was collected, dried, filtered, concentrated, and purified by column chromatographed on silica gel eluting with a linear gradient of 0-100% ethyl acetate in heptane to afford tert-butyl ((S)-1-((R)-1-(1-cyclopropyl-4-ethynyl-6-fluoro-8-methyl-2-oxo-1,2-dihydroquinolin-7-yl)pyrrolidin-3-yl)ethyl)carbamate which was dissolved in dichloromethane (1 mL) and treated with trifluoroacetic acid (1 mL). The solution was aged for 30 minutes, concentrated under reduced pressure, and then purified prep HPLC to afford the title compound (15.5% yield).

1H NMR (400 MHz, DMSO-d6) δ 7.81 (bs, 2H), 7.34 (d, J=13.3 Hz, 1H), 6.59 (s, 1H), 4.95 (s, 1H), 3.54 (m, 1H), 3.46 (m, 2H), 3.38 (m, 2H), 3.27 (m, 1H), 2.44 (s, 3H), 2.38 (m, 1H), 2.09 (m, 1H), 1.81-1.67 (m, 1H), 1.27 (d, J=6.4 Hz, 3H), 1.12 (m, 2H), 0.40 (m, 2H)

LC/MS calc'd for $C_{21}H_{25}FN_3O$ [M+H]$^+$ 354.4, found 354.0.

Example 26: Methyl 3-(7-((R)-3-((S)-1-aminoethyl)pyrrolidin-1-yl)-1-cyclopropyl-6-fluoro-8-methyl-2-oxo-1,2-dihydroquinolin-4-yl)propiolate μL of THF. The reaction warmed to room temperature and stirred overnight. The reaction was treated with sat'd NH$_4$Cl (aq) and extracted with ethyl acetate. The organic phase was collected, dried (MgSO$_4$), filtered, concentrated, and purified by column chromatography on silica gel eluting with a linear gradient of 0-100% ethyl acetate in heptane to afford methyl 3-(7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)propiolate which was dissolved in dichloromethane (1 mL) and treated with trifluoroacetic acid (1 mL). The solution aged for 30 minutes and was then concentrated under reduced pressure and purified by prep HPLC to afford the title compound (29.0% yield).

1H NMR (400 MHz, DMSO-d6) δ 7.83 (bs, 2H), 7.27 (d, J=13.1 Hz, 1H), 6.80 (s, 1H), 3.82 (s, 3H), 3.56 (m, 1H), 3.49-3.41 (m, 2H), 3.41-3.32 (m, 2H), 3.27 (m, 1H), 2.42 (s, 3H), 2.35 (m, 1H), 2.08 (m, 1H), 1.78-1.67 (m, 1H), 1.25 (d, J=6.4 Hz, 3H), 1.18-1.07 (m, 2H), 0.40 (m, 2H)

LC/MS calc'd for $C_{23}H_{27}FN_3O_3$[M+H]$^+$ 412.5, found 412.1.

Example 27: 7-((R)-3-((S)-1-aminoethyl)pyrrolidin-1-yl)-1-cyclopropyl-6-fluoro-8-methyl-2-oxo-1,2-dihydroquinoline-4-carbonitrile

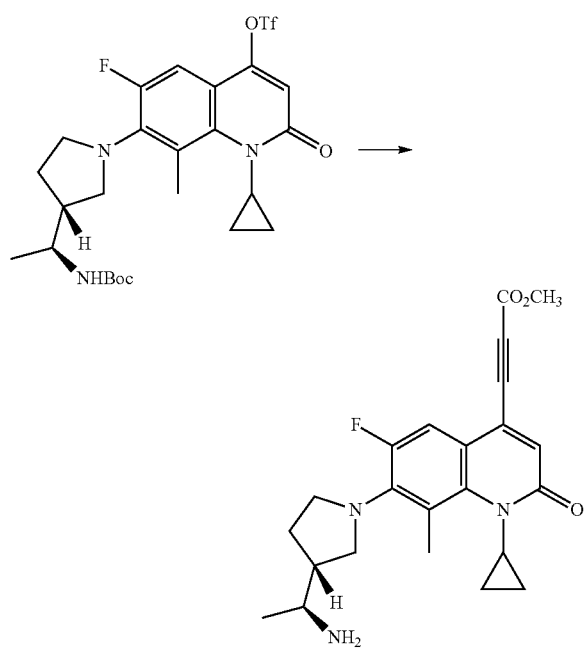

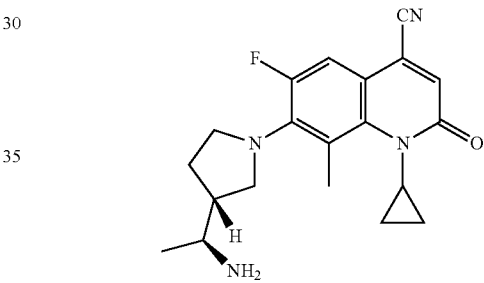

The title compound was prepared in accordance with the following scheme:

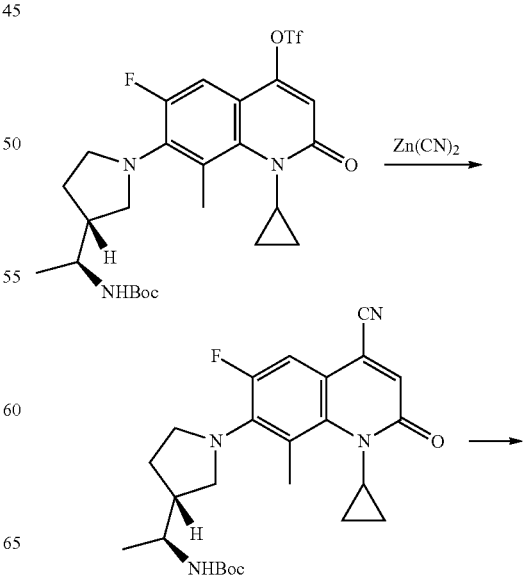

A cold (0° C.) solution of diisopropylamine (0.012 mL, 0.094 mmol) in THF (1 mL) was treated with n-butyllithium (0.038 mL, 0.094 mmol) and stirred for 30 minutes. The reaction was then cooled to −78° C. and treated with methyl propiolate (7.68 μl, 0.094 mmol). After 20 minutes, zinc(II) bromide (21.13 mg, 0.094 mmol) in 500 μL of THF was added dropwise. The reaction warmed to 0° C. and was treated with a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (example 41, 54.2 mg, 0.094 mmol) and tetrakis(triphenylphosphine)palladium (4.34 mg, 3.75 μmol) in 500

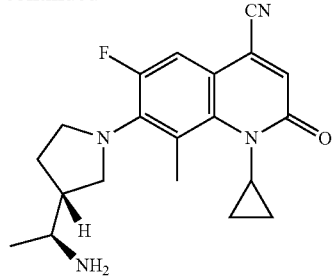 [SMILES: Cc1c(N2CC[C@@H]([C@H](C)N)C2)c(F)cc2c(C#N)cc(=O)n(C3CC3)c12]

(i) tert-butyl ((S)-1-((R)-1-(4-cyano-1-cyclopropyl-6-fluoro-8-methyl-2-oxo-1,2-dihydroquinolin-7-yl)pyrrolidin-3-yl)ethyl)carbamate A sealed vial charged with a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (112.6 mg, 0.195 mmol), tetrakis(triphenylphosphine)palladium (2.253 mg, 1.949 µmol), and dicyanozinc (13.73 mg, 0.117 mmol) in DMF (650 µl) was heated at 80° C. for two days. The reaction cooled to room temperature and was partitioned between brine and ethyl acetate. The organic phase was collected, dried (MgSO$_4$), filtered, concentrated, and chromatographed on silica gel using a linear gradient of 0-100% ethyl acetate in heptane to afford the desired material (60% yield).

1H NMR (400 MHz, Chloroform-d) δ 7.31 (d, J=12.7 Hz, 1H), 6.85 (s, 1H), 4.48 (m, 1H), 3.73 (m, 1H), 3.70-3.60 (m, 1H), 3.47 (m, 4H), 2.46 (s, 3H), 2.29 (m, 1H), 2.10 (m, 1H), 1.75 (dq, J=12.0, 8.9 Hz, 1H), 1.44 (s, 9H), 1.32-1.24 (m, 2H), 1.23 (d, J=6.6 Hz, 3H), 0.62-0.48 (m, 2H)

LC/MS calc'd for C$_{25}$H$_{32}$FN$_4$O$_3$ [M+H]$^+$ 455.5, found 455.1.

(ii) 7-((R)-3-((S)-1-aminoethyl)pyrrolidin-1-yl)-1-cyclopropyl-6-fluoro-8-methyl-2-oxo-1,2-dihydroquinoline-4-carbonitrile A solution of tert-butyl ((S)-1-((R)-1-(4-cyano-1-cyclopropyl-6-fluoro-8-methyl-2-oxo-1,2-dihydroquinolin-7-yl)pyrrolidin-3-yl)ethyl)carbamate (26.4 mg, 0.058 mmol) in dichloromethane (1 mL) was treated with trifluoroacetic acid (1 mL) and aged for 30 minutes at room temperature. The reaction was concentrated and purified by prep HPLC to afford the title compound (60.2% yield).

1H NMR (400 MHz, DMSO-d6) δ 7.84 (bs, 2H), 7.24 (d, J=12.9 Hz, 1H), 7.12 (s, 1H), 3.61 (m, 1H), 3.54-3.44 (m, 3H), 3.40 (m, 1H), 3.29 (m, 1H), 2.43 (s, 3H), 2.43-2.31 (m, 2H), 2.10 (m, 1H), 1.81-1.68 (m, 1H), 1.27 (d, J=6.5 Hz, 3H), 1.21-1.10 (m, 1H), 0.44 (ddd, J=10.5, 6.2, 4.5 Hz, 2H)

LC/MS calc'd for C$_{20}$H$_{24}$FN$_4$O [M+H]$^+$ 355.4, found 355.2.

Example 28: 7-((R)-3-((S)-1-aminoethyl)pyrrolidin-1-yl)-1-cyclopropyl-6-fluoro-3,8-dimethyl-2-oxo-1,2-dihydroquinoline-4-carbonitrile

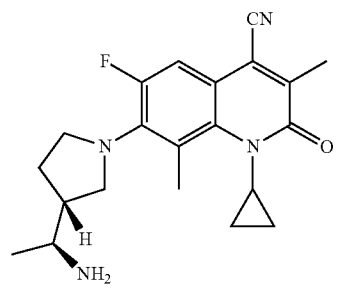 [SMILES: Cc1c(C#N)c2cc(F)c(N3CC[C@@H]([C@H](C)N)C3)c(C)c2n(C2CC2)c1=O]

The title compound was prepared in accordance with the following scheme:

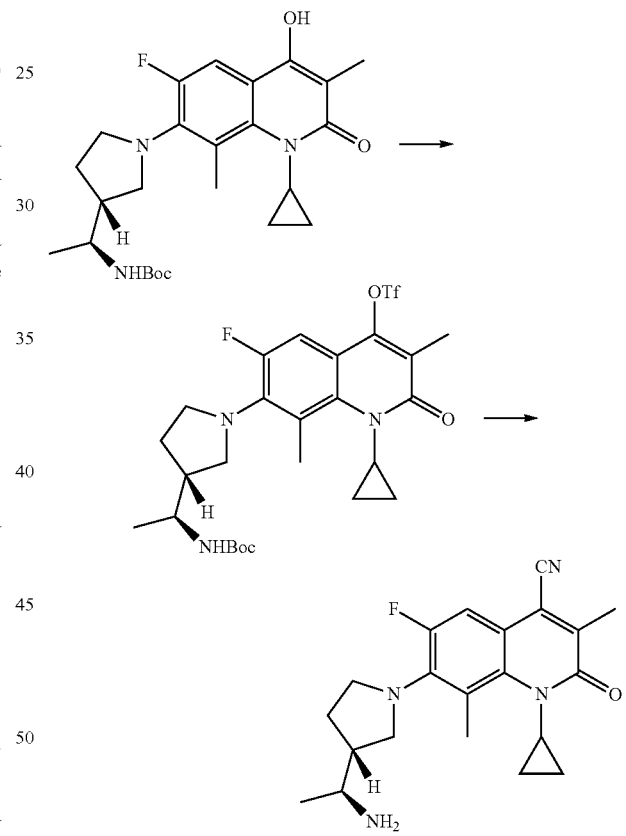

(i) 7-((R)-3-((S)-1-((tert-butoxycarbonyl)amino)ethyl)pyrrolidin-1-yl)-1-cyclopropyl-6-fluoro-3,8-dimethyl-2-oxo-1,2-dihydroquinolin-4-yl trifluoromethanesulfonate A cold (0° C.) solution of tert-butyl ((S)-1-((R)-1-(1-cyclopropyl-6-fluoro-4-hydroxy-3,8-dimethyl-2-oxo-1,2-dihydroquinolin-7-yl)pyrrolidin-3-yl)ethyl)carbamate (128 mg, 0.223 mmol) and triethylamine (93 µl, 0.668 mmol) in DMF (2.5 mL) was treated with the dropwise addition of 1,1,1-trifluoro-N-phenyl-N-((trifluoromethyl)sulfonyl)

methanesulfonamide (96 mg, 0.267 mmol) in DMF (1 mL) and stirred for 1 hour. The reaction was poured into water, extracted with ethyl acetate and washed with brine. The organic phase was collected, dried (MgSO$_4$), filtered, and concentrated. The crude material was purified by column chromatography on silica gel eluting with a linear gradient of 0-100% ethyl acetate in heptane to afford the desired material (51.1% yield).

1H NMR (400 MHz, Chloroform-d) δ 7.16 (d, J=13.1 Hz, 1H), 4.49 (m, 1H), 3.75 (m, 1H), 3.58 (m, 1H), 3.50 (m, 1H), 3.47-3.36 (m, 3H), 2.49 (s, 3H), 2.31 (m, 1H), 2.23 (s, 3H), 2.08 (m, 1H), 1.74 (m, 1H), 1.44 (s, 9H), 1.26 (m, 1H), 1.22 (d, J=6.7 Hz, 3H), 1.20-1.10 (m, 1H), 0.63-0.48 (m, 2H)

LC/MS calc'd for $C_{26}H_{34}F_4N_3O_6S$ [M+H]$^+$ 592.6, found 592.2.

(ii) 7-((R)-3-((S)-1-aminoethyl)pyrrolidin-1-yl)-1-cyclopropyl-6-fluoro-3,8-dimethyl-2-oxo-1,2-dihydroquinoline-4-carbonitrile Using a procedure similar to Example 27(i), but substituting 7-((R)-3-((S)-1-((tert-butoxycarbonyl)amino)ethyl)pyrrolidin-1-yl)-1-cyclopropyl-6-fluoro-3,8-dimethyl-2-oxo-1,2-dihydroquinolin-4-yl trifluoromethanesulfonate for 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate, the title compound was obtained (42.8% yield).

1H NMR (400 MHz, DMSO-d6) δ 7.83 (bs, 2H), 7.21 (d, J=12.8 Hz, 1H), 3.54 (m, 2H), 3.49-3.42 (m, 1H), 3.42-3.33 (m, 2H), 3.27 (m, 1H), 2.45 (s, 3H), 2.38 (m, 1H), 2.30 (s, 3H), 2.15-2.06 (m, 1), 1.74 (m, 1H), 1.27 (d, J=6.5 Hz, 3H), 1.14 (m, 2H), 0.42 (m, 2H)

LC/MS calc'd for $C_{21}H_{26}FN_4O$ [M+H]$^+$ 369.5, found 369.1.

Example 29: (R)-7-(3-(aminomethyl)pyrrolidin-1-yl)-1-cyclopropyl-6-fluoro-8-methyl-2-oxo-1,2-dihydroquinoline-4-carbonitrile

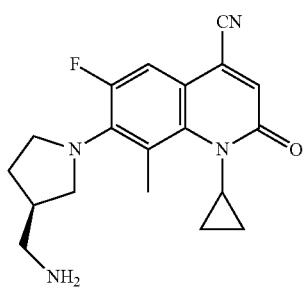 [SMILES: Cc1c(N2CC[C@H](CN)C2)c(F)cc2c(C#N)cc(=O)n(C3CC3)c12]

The title compound was prepared in accordance with the following scheme:

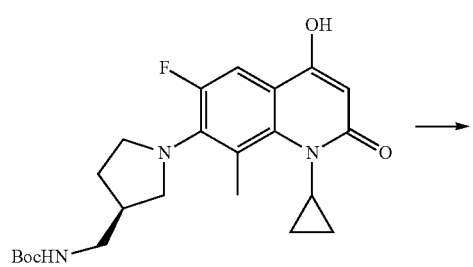

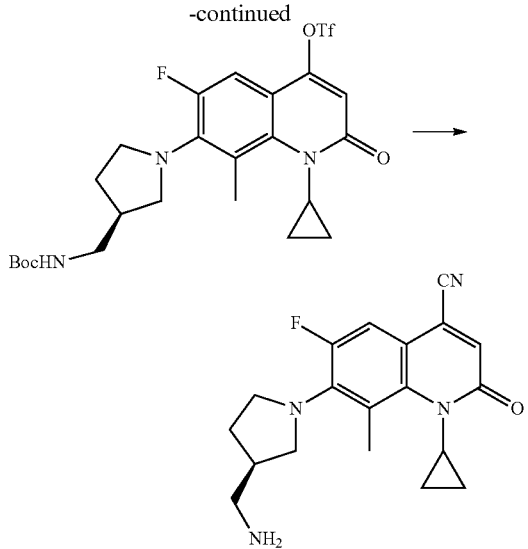

(i) (R)-7-(3-(((tert-butoxycarbonyl)amino)methyl)pyrrolidin-1-yl)-1-cyclopropyl-6-fluoro-8-methyl-2-oxo-1,2-dihydroquinolin-4-yl trifluoromethanesulfonate Using a procedure similar to Example 17 but substituting (R)-tert-butyl ((1-(1-cyclopropyl-6-fluoro-4-hydroxy-8-methyl-2-oxo-1,2-dihydroquinolin-7-yl)pyrrolidin-3-yl)methyl)carbamate for tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate, the title compound was obtained (22% yield).

LC/MS calc'd for $C_{24}H_{30}F_4N_3O_6S$ [M+H]$^+$ 564.6, found 564.1.

(ii) (R)-7-(3-(aminomethyl)pyrrolidin-1-yl)-1-cyclopropyl-6-fluoro-8-methyl-2-oxo-1,2-dihydroquinoline-4-carbonitrile A sealed vial charged with a solution of (R)-7-(3-(((tert-butoxycarbonyl)amino)methyl)pyrrolidin-1-yl)-1-cyclopropyl-6-fluoro-8-methyl-2-oxo-1,2-dihydroquinolin-4-yl trifluoromethanesulfonate (28.9 mg, 0.051 mmol), tetrakis(triphenylphosphine)palladium (2.96 mg, 2.56 μmol), and dicyanozinc (6.02 mg, 0.051 mmol) in DMF (1 mL) was heated at 70° C. and maintained for 24 hours. The reaction cooled to room temperature and was poured into water and extracted with ethyl acetate. The organic phase was washed with brine, dried (MgSO$_4$), filtered, and concentrated. The crude residue was taken up in dichloromethane (1 mL) and treated with trifluoroacetic acid (1 mL). The reaction aged for 30 minutes and was then concentrated under reduced pressure and purified by prep HPLC to afford the title compound (43.1% yield).

1H NMR (400 MHz, DMSO-d6) δ 7.81 (bs, 2H), 7.24 (d, J=12.9 Hz, 1H), 7.12 (s, 1H), 3.56 (m, 1H), 3.49 (m, 3H), 3.33 (ddd, J=9.4, 6.8, 2.3 Hz, 1H), 2.97 (m, 2H), 2.58-2.51 (m, 1H), 2.43 (s, 3H), 2.21-2.10 (m, 1H), 1.81-1.70 (m, 1H), 1.15 (m, 2H), 0.45 (m, 2H)

LC/MS calc'd for $C_{19}H_{22}FN_4O$ [M+H]$^+$ 341.4, found 341.0.

Example 30: (S)-7-(3-aminopyrrolidin-1-yl)-1-cyclopropyl-6-fluoro-8-methyl-2-oxo-1,2-dihydroquinoline-4-carbonitrile

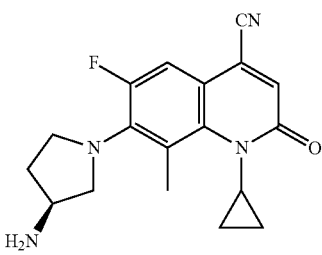 [SMILES: Cc1c(N2CC[C@H](N)C2)c(F)cc2c(C#N)cc(=O)n(C3CC3)c12]

The title compound was prepared in accordance with the following scheme:

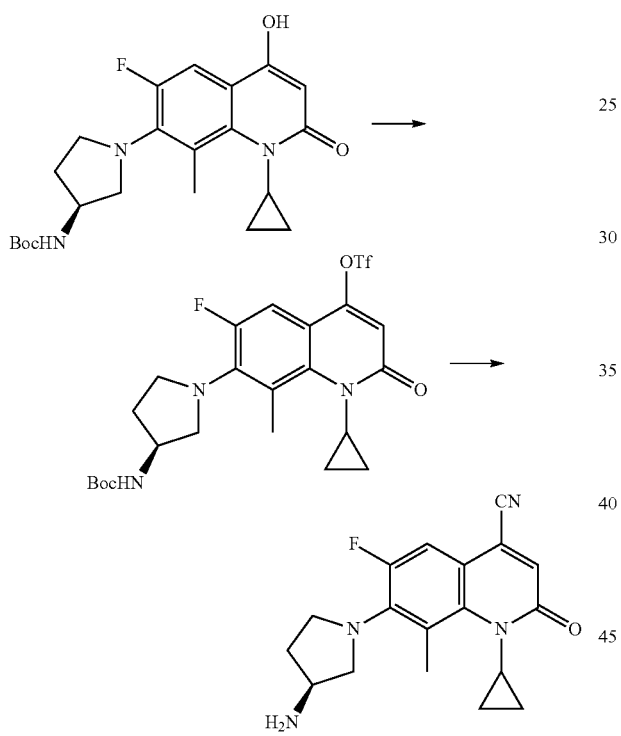

(i) (S)-7-(3-((tert-butoxycarbonyl)amino)pyrrolidin-1-yl)-1-cyclopropyl-6-fluoro-8-methyl-2-oxo-1,2-dihydroquinolin-4-yl trifluoromethanesulfonate A cold (0° C.) mixture of (S)-tert-butyl (1-(1-cyclopropyl-6-fluoro-4-hydroxy-8-methyl-2-oxo-1,2-dihydroquinolin-7-yl)pyrrolidin-3-yl)carbamate (232 mg, 0.278 mmol) and triethylamine (116 μL, 0.834 mmol) in DMF (2.5 mL) was treated with the dropwise addition of 1,1,1-trifluoro-N-phenyl-N-(((trifluoromethyl)sulfonyl)methanesulfonamide (119 mg, 0.333 mmol) in DMF (1 mL) and stirred for 1 hour. The reaction was poured into water and extracted with ethyl acetate and washed with brine. The organic phase was collected, dried (MgSO$_4$), filtered, and concentrated. The crude material was purified by silica gel column chromatography eluting with a linear gradient of 0-100% ethyl acetate in heptane to afford the desired material (22.3% yield).

1H NMR (400 MHz, Chloroform-d) δ 7.18 (d, J=12.7 Hz, 1H), 6.51 (s, 1H), 3.76 (m, 1H), 3.65-3.56 (m, 1H), 3.46 (m, 3H), 3.29 (dd, J=10.1, 4.4 Hz, 1H), 2.48 (s, 3H), 2.33 (m, 1H), 1.91 (m, 2H), 1.46 (s, 9H), 1.33-1.17 (m, 2H), 0.58 (m, 2H)

LC/MS calc'd for $C_{23}H_{28}F_4N_3O_6S$ [M+H]$^+$ 550.5, found 550.1.

(ii) (S)-7-(3-aminopyrrolidin-1-yl)-1-cyclopropyl-6-fluoro-8-methyl-2-oxo-1,2-dihydroquinoline-4-carbonitrile A sealed vial charged with a solution of (S)-7-(3-((tert-butoxycarbonyl)amino)pyrrolidin-1-yl)-1-cyclopropyl-6-fluoro-8-methyl-2-oxo-1,2-dihydroquinolin-4-yl trifluoromethanesulfonate (34 mg, 0.062 mmol), tetrakis(triphenylphosphine)palladium (3.57 mg, 3.09 μmol), and dicyanozinc (7.26 mg, 0.062 mmol) in DMF (1 mL) was heated at 70° C. for 24 hours. The reaction cooled to room temperature and was poured into water and extracted with ethyl acetate. The organic phase was washed with brine, dried (MgSO$_4$), filtered, and concentrated. The crude residue was taken up in dichloromethane (1 mL) and treated with trifluoroacetic acid (1 mL). The reaction aged for 30 minutes and was then concentrated under reduced pressure and purified by prep HPLC (60.7% yield). 1H NMR (400 MHz, DMSO-d6) δ 8.10 (bs, 2H), 7.26 (d, J=12.8 Hz, 1H), 7.16 (s, 1H), 3.92 (m, 1H), 3.74 (m, 1H), 3.61 (m, 1H), 3.54-3.42 (m, 3H), 2.48 (s, 3H), 2.38-2.27 (m, 1H), 2.00 (m, 1H), 1.15 (m, 2H), 0.44 (m, 2H)

LC/MS calc'd for $C_{18}H_{20}FN_4O$ [M+H]$^+$ 327.4, found 327.0.

Example 31: (S)-7-(3-(aminomethyl)pyrrolidin-1-yl)-1-cyclopropyl-6-fluoro-8-methyl-2-oxo-1,2-dihydroquinoline-4-carbonitrile The title compound was prepared in accordance with the following scheme:

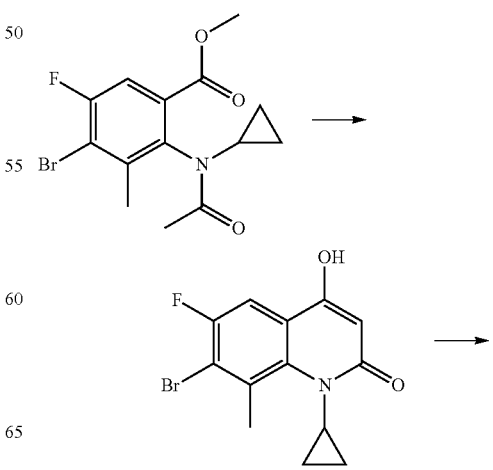

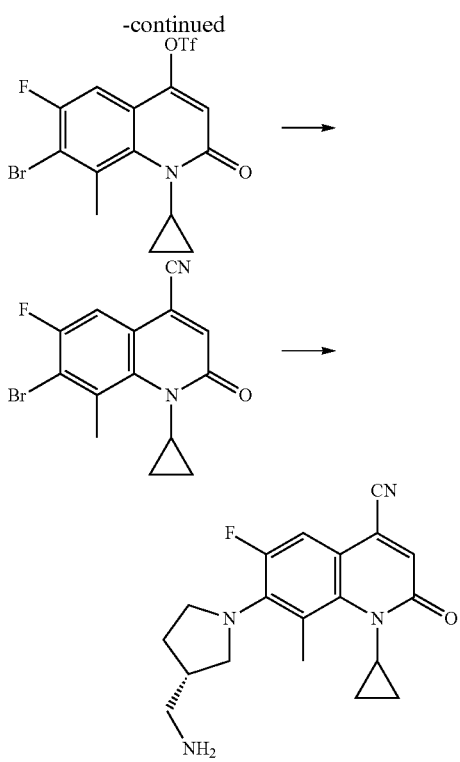

(i) 7-bromo-1-cyclopropyl-6-fluoro-4-hydroxy-8-methylquinolin-2(1H)-one

A cold (0° C.) solution of methyl 4-bromo-2-(N-cyclopropylacetamido)-5-fluoro-3-methylbenzoate (595 mg, 1.729 mmol) in THF (12 mL) was treated with the dropwise addition of NaHMDS (1.0 M in THF, 8.64 mL, 8.64 mmol). After thirty minutes of stirring, 1N HCl (aq) was added dropwise until the pH was <2. A solid precipitated and was collected by filtration and washed with water. The aqueous phase was extracted with ethyl acetate and the organic phase collected, dried (MgSO$_4$), filtered, and concentrated under reduced product. The extracted material was combined with the solid filtrate to give the title compound (85% yield).

1H NMR (400 MHz, DMSO-d6) δ 11.60 (bs, 1H), 7.50 (d, J=8.6 Hz, 1H), 5.78 (s, 2H), 3.39 (tt, J=6.8, 4.0 Hz, 1H), 2.71 (s, 3H), 1.11-1.03 (m, 2H), 0.38-0.32 (m, 2H)

LC/MS calc'd for $C_{13}H_{12}BrFNO_2$ [M+H]$^+$ 313.1, found 313.9.

(ii) 7-bromo-1-cyclopropyl-6-fluoro-8-methyl-2-oxo-1,2-dihydroquinolin-4-yl trifluoromethanesulfonate A cold (0° C.) mixture of 7-bromo-1-cyclopropyl-6-fluoro-4-hydroxy-8-methylquinolin-2(1H)-one (286.8 mg, 0.919 mmol) and triethylamine (384 µl, 2.76 mmol) in DMF (2.5 mL) was treated with the dropwise addition of 1,1,1-trifluoro-N-phenyl-N-((trifluoromethyl)sulfonyl)methanesulfonamide (394 mg, 1.103 mmol) in DMF (1 mL) and stirred for 1 hour. The reaction was poured into water and extracted with ethyl acetate and washed with brine. The organic phase was collected, dried (MgSO$_4$), filtered, and concentrated. The crude material purified by silica gel column chromatography eluting with a linear gradient of 0-100% ethyl acetate in heptane to afford the desired material (90% yield).

1H NMR (400 MHz, Chloroform-d) δ 7.32 (d, J=7.8 Hz, 1H), 6.68 (s, 1H), 3.51 (tt, J=6.8, 4.0 Hz, 1H), 2.81 (s, 3H), 1.30-1.22 (m, 2H), 0.63-0.56 (m, 2H)

LC/MS calc'd for $C_{14}H_{11}BrF_4NO_4S$ [M+H]$^+$ 445.2, found 446.0.

(iii) 7-bromo-1-cyclopropyl-6-fluoro-8-methyl-2-oxo-1,2-dihydroquinoline-4-carbonitrile A sealed vial charged with a solution of 7-bromo-1-cyclopropyl-6-fluoro-8-methyl-2-oxo-1,2-dihydroquinolin-4-yl trifluoromethanesulfonate (237.8 mg, 0.535 mmol), tetrakis(triphenylphosphine)palladium (30.9 mg, 0.027 mmol), and dicyanozinc (32.7 mg, 0.278 mmol) in DMF (1784 µl) was heated at 85° C. for 18 hours. The reaction was treated with water and extracted with ethyl acetate. The organic phase was collected, washed with brine, dried (MgSO$_4$), filtered, concentrated, and purified by silica gel column chromatography eluting with a linear gradient of 0-100% ethyl acetate in heptane to afford the desired material (72.2% yield).

LC/MS calc'd for $C_{14}H_{11}BrFN_2O$ [M+H]$^+$ 322.2, found 322.9.

(iv) (S)-7-(3-(aminomethyl)pyrrolidin-1-yl)-1-cyclopropyl-6-fluoro-8-methyl-2-oxo-1,2-dihydroquinoline-4-carbonitrile A sealed vial charged with a mixture of 7-bromo-1-cyclopropyl-6-fluoro-8-methyl-2-oxo-1,2-dihydroquinoline-4-carbonitrile (51.9 mg, 0.162 mmol), XANTPHOS (9.35 mg, 0.016 mmol), (R)-tert-butyl (pyrrolidin-3-ylmethyl)carbamate (32.4 mg, 0.162 mmol), tris(dibenzylideneacetone)dipalladium(0), 4.44 mg, 4.85 µmol), and cesium carbonate (73.7 mg, 0.226 mmol) in dioxane (539 µl) was heated at 160° C. via microwave and maintained for 30 minutes. The reaction was poured into water and extracted with ethyl acetate. The organic phase was washed with brine, dried (MgSO$_4$), filtered, concentrated, and diluted with dichloromethane (1 mL) and treated with trifluoroacetic acid (1 mL). The reaction was aged for 30 minutes, concentrated under reduced pressure and purified by prep HPLC to afford the title compound.

1H NMR (400 MHz, Methanol-d4) δ 7.34 (d, J=12.7 Hz, 1H), 6.95 (s, 1H), 5.48 (s, 2H), 3.72-3.65 (m, 1H), 3.63 (m, 1H), 3.55 (m, 2H), 3.40 (ddd, J=9.5, 6.9, 2.1 Hz, 1H), 3.10 (d, J=7.5 Hz, 2H), 2.69-2.59 (m, 1H), 2.55 (s, 3H), 2.29 (m, 1H), 1.83 (m, 1H), 1.23 (m, 2H), 0.57-0.51 (mM, 2H)

LC/S calc'd for $C_{19}H_{22}FN_4O$ [M+H]$^+$ 341.4, found 341.0.

Example 32: 1-cyclopropyl-6-fluoro-8-methyl-2-oxo-7-(piperazin-1-yl)-1,2-dihydroquinoline-4-carbonitrile The title compound was prepared in accordance with the following scheme:

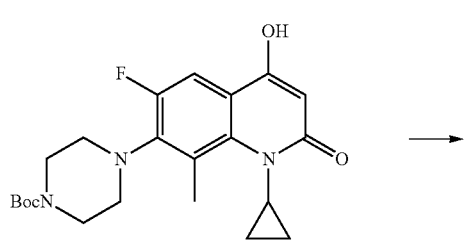

-continued

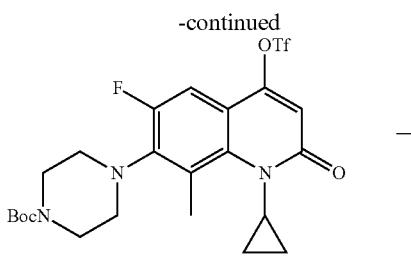

(i) tert-butyl 4-(1-cyclopropyl-6-fluoro-8-methyl-2-oxo-4-(((trifluoromethyl)sulfonyl)oxy)-1,2-dihydroquinolin-7-yl)piperazine-1-carboxylate A cold (0° C.) mixture of tert-butyl 4-(1-cyclopropyl-6-fluoro-4-hydroxy-8-methyl-2-oxo-1,2-dihydroquinolin-7-yl)piperazine-1-carboxylate (139 mg, 0.334 mmol) and triethylamine (140 µL, 1.002 mmol) in DMF (3.2 mL) was treated with the dropwise addition of 1,1,1-trifluoro-N-phenyl-N-((trifluoromethyl)sulfonyl)methanesulfonamide (143 mg, 0.401 mmol) in DMF (1 mL) and stirred for 1 hour. The reaction was poured into water and extracted with ethyl acetate and washed with brine. The organic phase was collected, dried (MgSO$_4$), filtered, and concentrated. The crude material was purified by silica gel column chromatographed eluting with a linear gradient of 0-100% ethyl acetate in heptane to afford the desired material (99% yield).

LC/MS calc'd for $C_{23}H_{28}F_4N_3O_6S$ [M+H]$^+$ 550.5, found 550.0.

(ii) 1-cyclopropyl-6-fluoro-8-methyl-2-oxo-7-(piperazin-1-yl)-1,2-dihydroquinoline-4-carbonitrile A sealed vial charged with a solution of tert-butyl 4-(1-cyclopropyl-6-fluoro-8-methyl-2-oxo-4-(((trifluoromethyl)sulfonyl)oxy)-1,2-dihydroquinolin-7-yl)piperazine-1-carboxylate (45 mg, 0.082 mmol), tetrakis(triphenylphosphine)palladium (4.73 mg, 4.09 µmol), and dicyanozinc (9.61 mg, 0.082 mmol) in DMF (1 mL) was heated at 85° C. for 72 hours. The reaction was treated with water and extracted with ethyl acetate. The organic phase was collected, washed with brine, dried (MgSO$_4$), filtered, concentrated under reduced pressure and then diluted with dichloromethane (1 mL) and treated with trifluoroacetic acid (1 mL). After 30 minutes, volatiles were removed under reduced pressure and purified by prep HPLC to afford the title compound (31.7% yield).

1H NMR (400 MHz, DMSO-d6) δ 8.75 (bs, 1H), 7.34 (d, J=11.7 Hz, 1H), 7.26 (s, 1H), 3.53 (m, 2H), 3.27 (m, 6H), 2.60 (s, 3H), 1.13 (dd, J=7.5, 5.8 Hz, 2H), 0.47-0.38 (m, 2H)

LC/MS calc'd for $C_{18}H_{20}FN_4O$ [M+H]$^+$ 327.4, found 327.0.

Examples 33 and 34: 7-((R)-3-((S)-1-aminoethyl)pyrrolidin-1-yl)-1-cyclopropyl-6-fluoro-8-methyl-2-oxo-1,2-dihydroquinoline-4-carboxylic acid (33) and 7-((R)-3-((S)-1-aminoethyl)pyrrolidin-1-yl)-1-cyclopropyl-6-fluoro-8-methyl-2-oxo-1,2-dihydroquinoline-4-carboxamide (34)

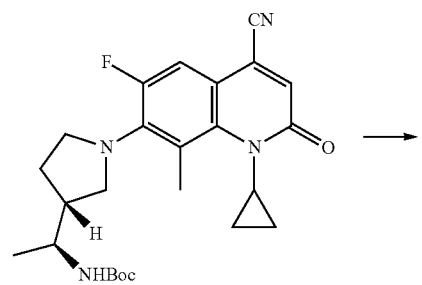

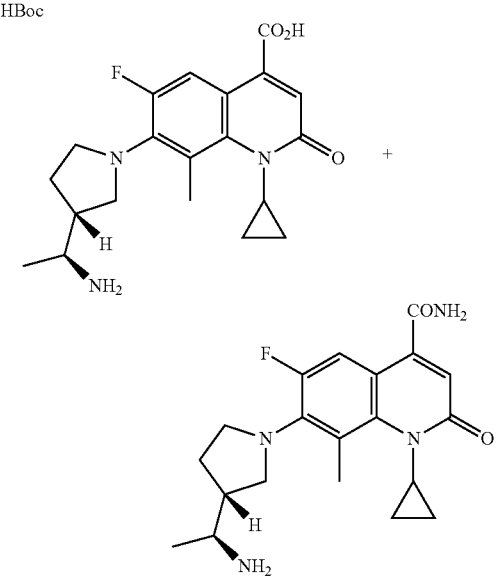

A solution of tert-butyl ((S)-1-((R)-1-(4-cyano-1-cyclopropyl-6-fluoro-8-methyl-2-oxo-1,2-dihydroquinolin-7-yl)pyrrolidin-3-yl)ethyl)carbamate (27.7 mg, 0.061 mmol) in 10% aqueous ethanol (2 mL) was treated with sodium hydroxide (12.19 mg, 0.305 mmol) and stirred at 120° C. for 30 minutes. The reaction was concentrated under reduced pressure, dissolved in dichloromethane (1 mL) and treated with trifluoroacetic acid (1 mL). After 30 minutes, the reaction was concentrated and the desired products isolated by prep HPLC (33, 19.2% yield; 34, 38.3% yield).

33: 1H NMR (400 MHz, DMSO-d6) δ 7.83 (bs, 2H), 7.73 (d, J=14.7 Hz, 1H), 6.74 (s, 1H), 3.56 (m, 1H), 3.52-3.44 (m, 2H), 3.40 (m, 2H), 3.28 (m, 1H), 2.44 (s, 3H), 2.42-2.34 (m, 2H), 2.14-2.04 (m, 1H), 1.80-1.68 (m, 1H), 1.27 (d, J=6.5 Hz, 3H), 1.14 (m, 2H), 0.40 (m, 2H)

LC/MS calc'd for $C_{20}H_{25}FN_3O_3$ [M+H]$^+$ 374.4, found 374.0.

34: 1H NMR (400 MHz, DMSO-d6) δ 8.12 (d, J=1.9 Hz, 1H), 7.84 (bs, 2H), 7.76 (s, 1H), 7.34 (d, J=14.2 Hz, 1H), 6.42 (s, 1H), 3.59-3.50 (m, 1H), 3.50-3.42 (m, 2H), 3.42-3.32 (m, 2H), 3.28 (m, 1H), 2.44 (s, 3H), 2.38 (m, 1H), 2.14-2.04 (m, 1H), 1.79-1.66 (m, 1H), 1.27 (d, J=6.5 Hz, 3H), 1.13 (dq, J=11.3, 5.9, 5.4 Hz, 2H), 0.38 (ddd, J=11.9, 7.0, 4.7 Hz, 2H)

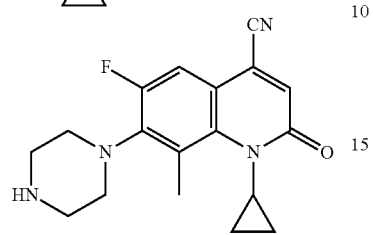

LC/MS calc'd for $C_{20}H_{26}FN_4O_2$ [M+H]$^+$ 373.4, found 373.0.

Example 35: ethyl 7-((R)-3-((S)-1-aminoethyl)pyrrolidin-1-yl)-1-cyclopropyl-6-fluoro-8-methyl-2-oxo-1,2-dihydroquinoline-4-carboxylate

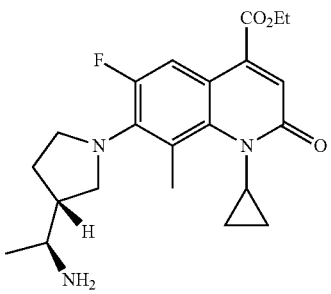 [SMILES: CCOC(=O)c1cc(=O)n(C2CC2)c2c(C)c(N3CC[C@@H]([C@H](C)N)C3)c(F)cc12]

The title compound was prepared in accordance with the following scheme:

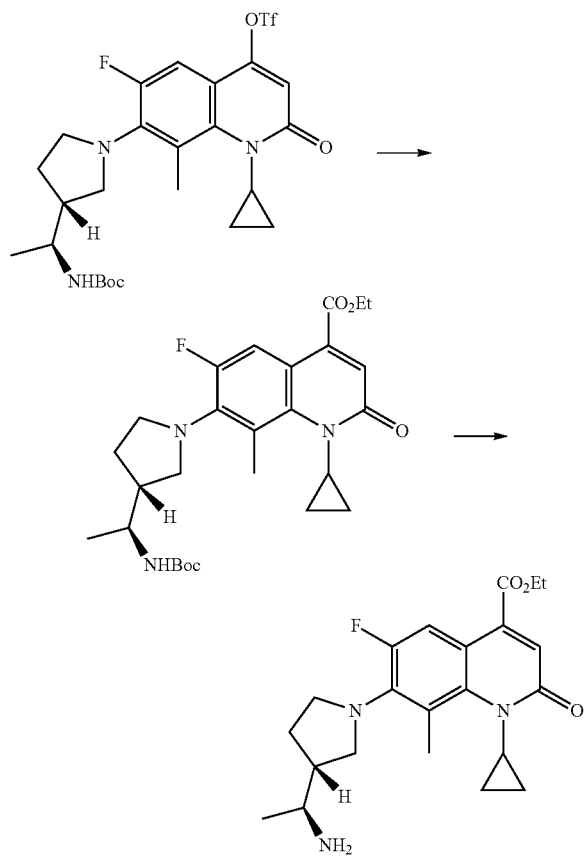

(i) ethyl 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-4-carboxylate A sealed vial charged with a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (79.9 mg, 0.138 mmol), palladium acetate (3.11 mg, 0.014 mmol), DPPF (7.67 mg, 0.014 mmol), molybdenum hexacarbonyl (18.26 mg, 0.069 mmol), ethanol (1 mL) and pyridine (0.250 mL) was heated at 150° C. via microwave for 20 minutes. The reaction was concentrated under reduced pressure, diluted with ethyl acetate and washed with water. The organic phase was collected, dried (MgSO$_4$), filtered, concentrated, and purified by silica gel column chromatography eluting with a linear gradient of 0-100% ethyl acetate in heptane to afford the desired material (51% yield).

1H NMR (500 MHz, Chloroform-d) δ 7.77 (d, J=14.4 Hz, 1H), 6.96 (s, 1H), 4.53 (d, J=9.2 Hz, 1H), 4.40 (q, J=7.1 Hz, 2H), 3.75 (m, 1H), 3.59 (m, 1H), 3.50 (m, 1H), 3.42 (m, 3H), 2.46 (s, 3H), 2.30 (m, 1H), 2.08 (m, 1H), 1.74 (m, 1H), 1.44 (s, 9H), 1.39 (t, J=7.2 Hz, 3H), 1.27 (m, 1H), 1.22 (d, J=6.6 Hz, 3H), 1.12 (m, 1H), 0.57-0.47 (m, 2H)

LC/MS calc'd for $C_{27}H_{37}FN_3O_5$ [M+H]$^+$ 502.6, found 502.3.

(ii) ethyl 7-((R)-3-((S)-1-aminoethyl)pyrrolidin-1-yl)-1-cyclopropyl-6-fluoro-8-methyl-2-oxo-1,2-dihydroquinoline-4-carboxylate A solution of ethyl 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-4-carboxylate (69.7 mg, 0.139 mmol) in dichloromethane (1 mL) was treated with trifluoroacetic acid (1 mL) and aged for 30 minutes. The reaction was concentrated under reduced pressure and purified directly by prep HPLC to afford the title compound (40% yield).

1H NMR (400 MHz, DMSO-d6) δ 7.86 (bs, 2H), 7.62 (d, J=14.6 Hz, 1H), 6.75 (s, 1H), 4.35 (q, J=7.1 Hz, 2H), 3.57 (dd, J=8.1, 8.1 Hz, 1H), 3.52-3.44 (m, 2H), 3.44-3.34 (m, 2H), 3.28 (m, 1H), 2.43 (s, 3H), 2.37 (m, 1H), 2.09 (m, 1H), 1.80-1.68 (m, 1H), 1.32 (t, J=8.1 Hz, 3H), 1.27 (d, J=6.5 Hz, 3H), 1.19-1.09 (m, 2H), 0.40 (m, 2H)

LC/MS calc'd for $C_{22}H_{29}FN_3O_3$[M+H]$^+$ 402.5, found 402.1.

Example 36: 4-amino-7-((R)-3-((S)-1-aminoethyl)pyrrolidin-1-yl)-1-cyclopropyl-6-fluoro-8-methylquinolin-2(1H)-one

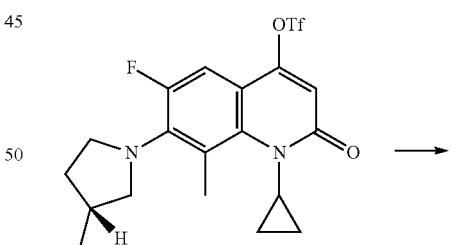

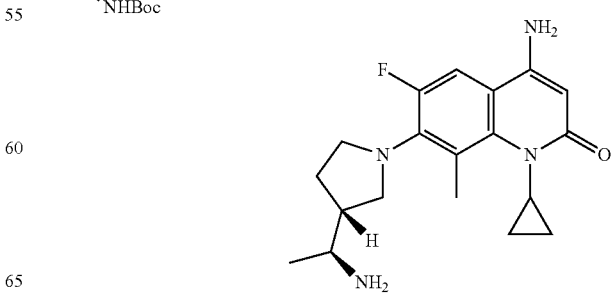

A sealed vial containing a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (45 mg, 0.078 mmol), (4-methoxyphenyl)methanamine (10.18 µl, 0.078 mmol), XANTPHOS (5.41 mg, 9.35 µmol), tris(dibenzylideneacetone)dipalladium(0) (2.85 mg, 3.12 µmol), and cesium carbonate (44.4 mg, 0.136 mmol) was heated to 120° C. via microwave and maintained for 45 minutes. The reaction cooled to room temperature, was filtered over Celite, diluted with ethyl acetate and washed with water and brine. The organic phase was collected, dried (MgSO₄), filtered, and concentrated. The residue was diluted with dichloromethane (1 mL) and treated with trifluoroacetic acid (1 mL). The reaction was heated to 60° C. and maintained for one hour. The reaction was concentrated under reduced pressure and purified by prep HPLC to afford the title compound (11.4% yield).

1H NMR (400 MHz, DMSO-d6): δ 7.82 (bs, 2H), 7.57 (d, J=14.3 Hz, 1H), 6.60 (bs, 2H), 5.43 (s, 1H), 3.48 (m, 1H), 3.43-3.39 (m, 1H), 3.38-3.22 (m, 4H), 2.41 (s, 3H), 2.40 (m, 1H), 2.08 (m, 1H), 1.79-1.67 (m, 1H), 1.26 (d, J=6.5 Hz, 3H), 1.10-0.94 (m, 2H), 0.34-0.26 (m, 2H)

LC/MS calc'd for $C_{19}H_{26}FN_4O$ [M+H]⁺ 345.4, found 345.0.

Example 37: N-(7-((R)-3-((S)-1-aminoethyl)pyrrolidin-1-yl)-1-cyclopropyl-6-fluoro-8-methyl-2-oxo-1,2-dihydroquinolin-4-yl)methanesulfonamide

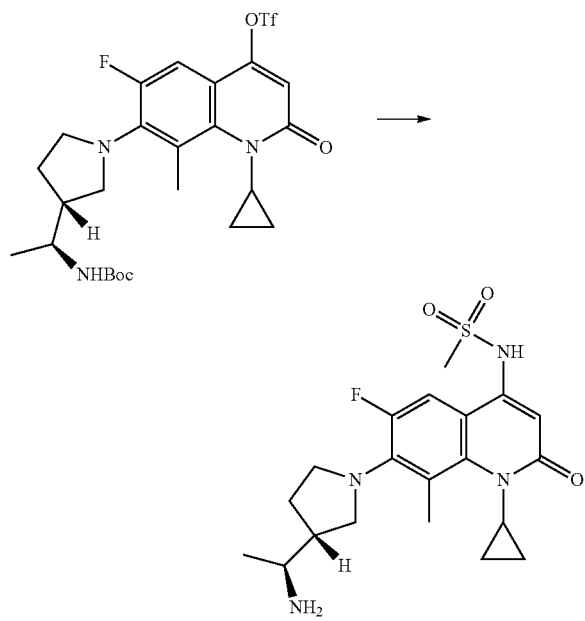

A sealed vial charged with a solution of 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate (51.2 mg, 0.089 mmol), tris(dibenzylideneacetone)dipalladium(0) (3.25 mg, 3.55 µmol), methanesulfonamide (10.12 mg, 0.106 mmol), and cesium carbonate (40.4 mg, 0.124 mmol) in dioxane (3 mL) was heated at 120° C. for 10 minutes via microwave. The reaction was treated with water and extracted with ethyl acetate. The organic phase was collected, washed with brine, dried (MgSO₄), filtered, concentrated under reduced pressure and then diluted with dichloromethane (1 mL) and treated with trifluoroacetic acid (1 mL). This solution aged for 30 minutes and was then concentrated under reduced pressure and purified by prep HPLC to afford the title compound.

1H NMR (400 MHz, DMSO-d6): δ 9.94 (s, 1H), 7.80 (bs, 2H), 7.64 (d, J=14.7 Hz, 1H), 6.31 (s, 1H), 3.54-3.28 (m, 6H), 3.20 (s, 3H), 2.42 (s, 3H), 2.38 (m, 1H), 2.15-2.04 (m, 1H), 1.80-1.67 (m, 1H), 1.26 (d, J=6.5 Hz, 3H), 1.09 (m, 2H), 0.38 (m, 2H)

LC/MS calc'd for $C_{20}H_{28}FN_4O_3S$ [M+H]⁺ 423.5, found 423.1.

Example 38: 3-(7-((R)-3-((S)-1-aminoethyl)pyrrolidin-1-yl)-1-cyclopropyl-6-fluoro-8-methyl-2-oxo-1,2-dihydroquinolin-4-yl)-1,2,4-oxadiazol-5(4H)-one

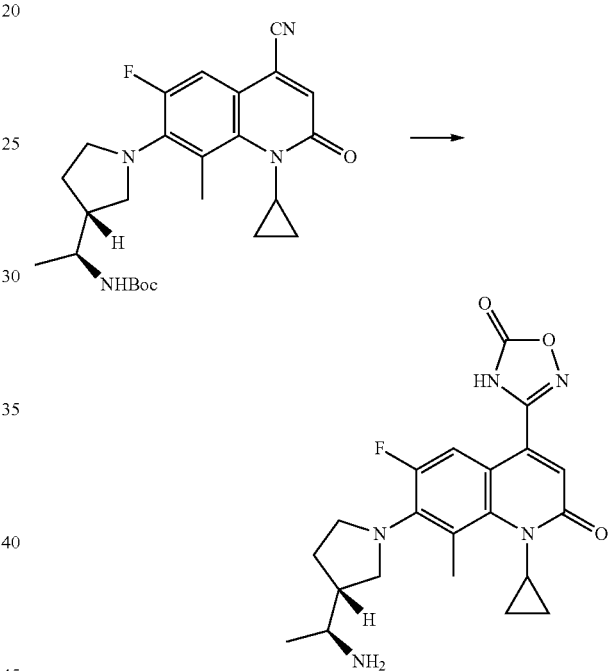

A warm (60° C.) solution of tert-butyl ((S)-1-((R)-1-(4-cyano-1-cyclopropyl-6-fluoro-8-methyl-2-oxo-1,2-dihydroquinolin-7-yl)pyrrolidin-3-yl)ethyl)carbamate (69.4 mg, 0.153 mmol) and sodium carbonate (10.52 mg, 0.099 mmol) in ethanol (1 mL) and Water (0.200 mL) was treated with hydroxylamine hydrochloride (11.67 mg, 0.168 mmol) in water (0.5 mL) and stirred for 12 hours at 60° C. The reaction cooled to room temperature and was concentrated under reduced pressure. The residue was diluted with ethyl acetate and washed with water. The organic phase was collected, dried (MgSO₄), filtered, and concentrated.

The residue was diluted with dioxane (2 mL) and treated with carbonyldiimidazole (24.76 mg, 0.153 mmol) and heated at 90° C. for 1 hour. The reaction was again concentrated and then diluted with dichloromethane (1 mL) and treated with trifluoroacetic acid (1 mL) and aged for 30 minutes. The reaction was concentrated and the residue purified by prep HPLC to afford the title compound (18.8% yield).

1H NMR (400 MHz, DMSO-d6): δ 12.99 (bs, 1H), 7.85 (bs, 2H), 7.77 (d, J=14.6 Hz, 1H), 6.77 (s, 1H), 3.59 (m, 1H), 3.56-3.43 (m, 3H), 3.43-3.35 (m, 1H), 3.33-3.24 (m, 1H), 2.45 (s, 3H), 2.38 (m, 1H), 2.11 (m, 1H), 1.80-1.68 (m, 1H), 1.27 (d, J=6.5 Hz, 3H), 1.16 (m, 2H), 0.48-0.36 (m, 2H)

LC/MS calc'd for $C_{21}H_{25}FN_5O_3$ [M+H]$^+$ 414.5, found 414.0.

Example 39: 7-((R)-3-((S)-1-aminoethyl)pyrrolidin-1-yl)-1-cyclopropyl-6-fluoro-8-methyl-4-(1H-tetrazol-5-yl)quinolin-2(1H)-one

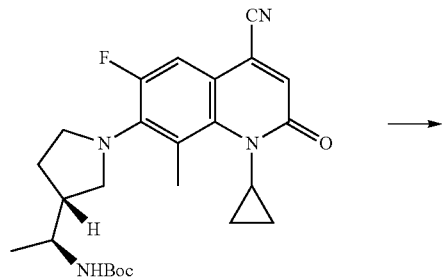

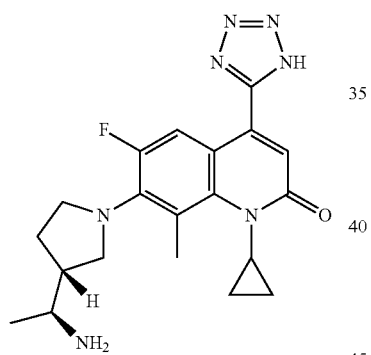

A sealed vial charged with a solution of tert-butyl ((S)-1-((R)-1-(4-cyano-1-cyclopropyl-6-fluoro-8-methyl-2-oxo-1,2-dihydroquinolin-7-yl)pyrrolidin-3-yl)ethyl)carbamate (35 mg, 0.077 mmol), sodium azide (30.0 mg, 0.462 mmol), and zinc(II) bromide (52.0 mg, 0.231 mmol) in 2-propanol (128 μl) and Water (128 μl) was heated at 100° C. for 2 hours. The reaction was concentrated in vacuo, diluted with ethyl acetate and washed with water and brine. The organic phase was collected, dried (MgSO$_4$), filtered, concentrated, and then diluted with dichloromethane (1 mL) and treated with trifluoroacetic acid (1 mL) and aged for 30 minutes. The reaction was concentrated and the residue purified by prep HPLC to afford the title compound (30.6% yield).

1H NMR (400 MHz, DMSO-d6) δ 7.94 (d, J=14.7 Hz, 1H), 7.84 (bs, 2H), 6.91 (s, 1H), 3.60 (m, 1H), 3.54 (m, 1H), 3.51-3.42 (m, 2H), 3.42-3.35 (m, 1H), 3.35-3.23 (m, 1H), 2.48 (s, 3H), 2.40 (m, 1H), 2.10 (m, 1H), 1.81-1.69 (m, 2H), 1.27 (d, J=6.5 Hz, 3H), 1.18 (m, 2H), 0.45 (m, 2H)

LC/MS calc'd for $C_{20}H_{25}FN_7O$ [M+H]$^+$ 398.5, found 398.1.

Example 40: 7-((R)-3-((S)-1-aminoethyl)pyrrolidin-1-yl)-1-cyclopropyl-6-fluoro-N-hydroxy-8-methyl-2-oxo-1,2-dihydroquinoline-4-carboximidamide

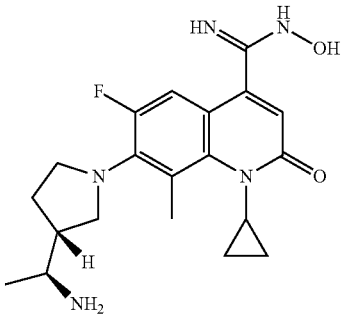

The title compound was prepared in accordance with the following scheme:

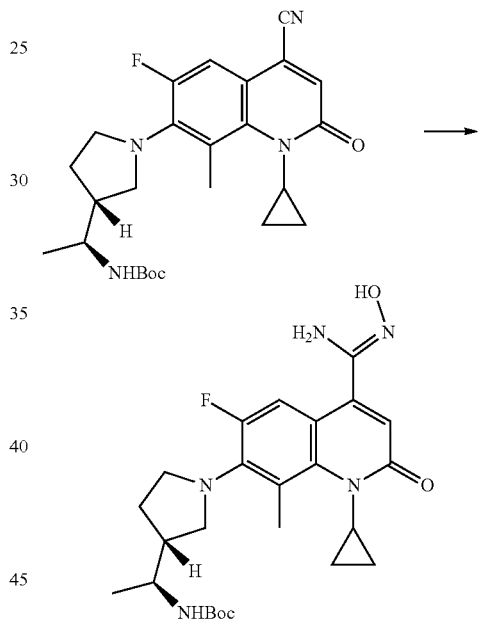

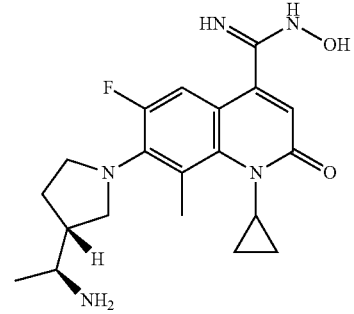 [SMILES: Cc1c(N2CC[C@@H]([C@H](C)N)C2)c(F)cc2c(C(=N)NO)cc(=O)n(C3CC3)c12]

(i) tert-butyl ((S)-1-((R)-1-(1-cyclopropyl-6-fluoro-4-(N'-hydroxycarbamimidoyl)-8-methyl-2-oxo-1,2-dihydroquinolin-7-yl)pyrrolidin-3-yl)ethyl)carbamate A solution of tert-butyl ((S)-1-((R)-1-(4-cyano-1-cyclopropyl-6-fluoro-8-methyl-2-oxo-1,2-dihydroquinolin-7-yl)

pyrrolidin-3-yl)ethyl)carbamate (70.9 mg, 0.156 mmol) and 50% hydroxylamine in water (100 μl) in Ethanol (1 mL) was stirred for 12 hours at 50° C. The reaction cooled to room temperature and was concentrated under reduced pressure to afford the desired title compound (quantitative yield).

LC/MS calc'd for $C_{25}H_{35}FN_5O_4$ [M+H]$^+$ 488.6, found 488.1.

(ii) 7-((R)-3-((S)-1-aminoethyl)pyrrolidin-1-yl)-1-cyclopropyl-6-fluoro-N-hydroxy-8-methyl-2-oxo-1,2-dihydroquinoline-4-carboximidamide A solution of tert-butyl ((S)-1-((R)-1-(1-cyclopropyl-6-fluoro-4-(N'-hydroxycarbamimidoyl)-8-methyl-2-oxo-1,2-dihydroquinolin-7-yl)pyrrolidin-3-yl)ethyl)carbamate in dichloromethane (1 mL) was treated with trifluoroacetic acid (1 mL) and stirred at room temperature for 30 minutes. The reaction was concentrated under reduced pressure and purified by mass-directed HPLC to afford the title compound (24% yield).

1H NMR (400 MHz, DMSO-d6) δ 8.25 (bs, 1H), 7.89 (bs, 2H), 7.22 (d, J=13.8 Hz, 1H), 6.64 (s, 1H), 3.59 (m, 1H), 3.51 (m, 1H), 3.48-3.41 (m, 2H), 3.41-3.33 (m, 1H), 3.28 (m, 1H), 2.44 (s, 3H), 2.39 (m, 1H), 2.14-2.05 (m, 1H), 1.81-1.68 (m, 1H), 1.27 (d, J=6.5 Hz, 3H), 1.18 (m, 2H), 0.44-0.31 (m, 2H)

LC/MS calc'd for $C_{20}H_{27}FN_5O_2$[M+H]$^+$ 388.5, found 388.1.

Example 41: 7-((R)-3-((S)-1-aminoethyl)pyrrolidin-1-yl)-1-cyclopropyl-6-fluoro-8-methyl-4-(2-oxido-3H-1,2,3,5-oxathiadiazol-4-yl)quinolin-2(1H)-one

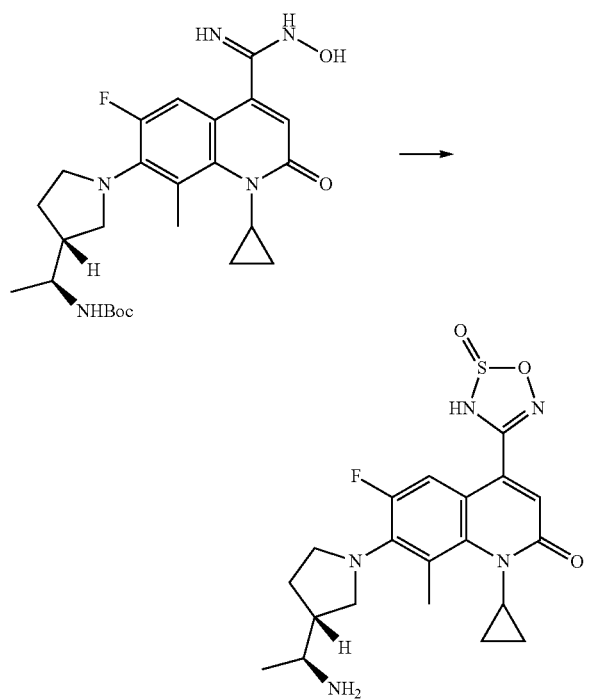

A solution of tert-butyl ((S)-1-((R)-1-(1-cyclopropyl-6-fluoro-4-(N-hydroxycarbamimidoyl)-8-methyl-2-oxo-1,2-dihydroquinolin-7-yl)pyrrolidin-3-yl)ethyl)carbamate (41.3 mg, 0.085 mmol) in dioxane (1 mL) was treated with pyridine (0.015 mL, 0.186 mmol) followed by thionyl chloride (6.45 μl, 0.089 mmol) and stirred at room temperature for 1 hour. The reaction was then concentrated under reduced pressure, diluted with dichloromethane (1 mL) and treated with TFA (1 mL) and aged for 30 minutes. The reaction was concentrated and then purified by prep HPLC to afford the title compound (11.5% yield).

1H NMR (400 MHz, DMSO-d6) δ 7.84 (bs, 2H), 7.45 (d, J=14.3 Hz, 1H), 6.73 (s, 1H), 3.58 (m, 1H), 3.53 (m, 1H), 3.46 (m, 2H), 3.39 (m, 1H), 3.29 (m, 1H), 2.46 (s, 3H), 2.38 (m, 1H), 2.15-2.07 (m, 1H), 1.75 (m, 1H), 1.27 (d, J=6.5 Hz, 3H), 1.23-1.12 (m, 2H), 0.43 (m, 2H)

LC/MS calc'd for $C_{20}H_{25}FN_5O_3S$ [M+H]$^+$ 434.5, found 434.0.

Example 42: 5-(7-((R)-3-((S)-1-aminoethyl)pyrrolidin-1-yl)-1-cyclopropyl-6-fluoro-8-methyl-2-oxo-1,2-dihydroquinolin-4-yl)-1,3,4-oxadiazol-2(3H)-one

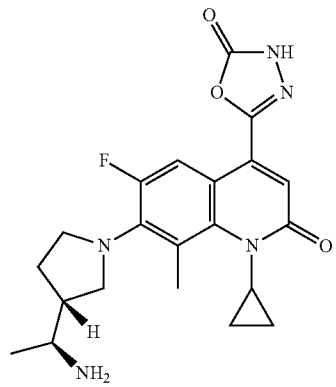 [SMILES: Cc1c(N2CC[C@@H]([C@H](C)N)C2)c(F)cc2c(-c3n[nH]c(=O)o3)cc(=O)n(C3CC3)c12]

The title compound was prepared in accordance with the following scheme:

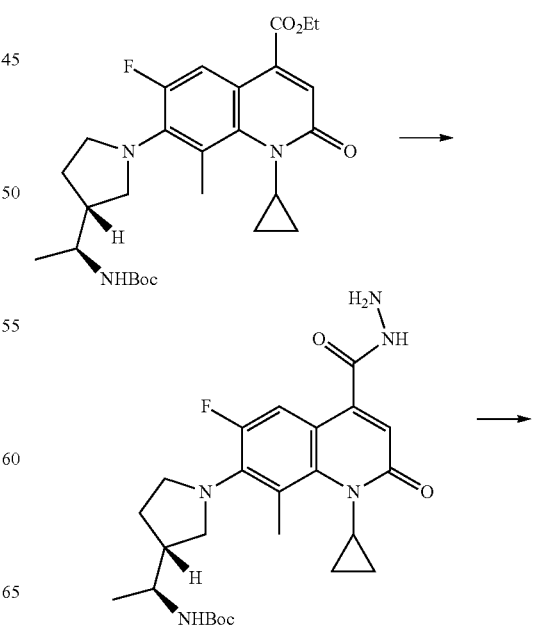

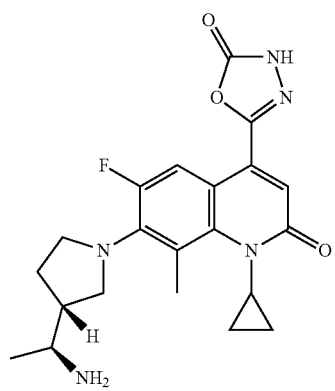

(i) tert-butyl ((S)-1-((R)-1-(1-cyclopropyl-6-fluoro-4-(hydrazinecarbonyl)-8-methyl-2-oxo-1,2-dihydroquinolin-7-yl)pyrrolidin-3-yl)ethyl)carbamate A solution of ethyl 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-4-carboxylate (48.1 mg, 0.096 mmol) and hydrazine (0.015 mL, 0.479 mmol) in ethanol (2 mL) was stirred for 12 hours at 60° C. The reaction cooled to room temperature and was concentrated under reduced pressure to afford the desired material (quantitative yield).

LC/MS calc'd for $C_{25}H_{35}FN_5O_4$ [M+H]$^+$ 488.6, found 488.1.

(ii) 5-(7-((R)-3-((S)-1-aminoethyl)pyrrolidin-1-yl)-1-cyclopropyl-6-fluoro-8-methyl-2-oxo-1,2-dihydroquinolin-4-yl)-1,3,4-oxadiazol-2(3H)-one A solution of tert-butyl ((S)-1-((R)-1-(1-cyclopropyl-6-fluoro-4-(hydrazinecarbonyl)-8-methyl-2-oxo-1,2-dihydroquinolin-7-yl)pyrrolidin-3-yl)ethyl)carbamate (51.6 mg, 0.106 mmol) and carbonyldiimidazole (34.32 mg, 0.212 mmol) in Dioxane (1 mL) was stirred for 2 days at 90° C. The reaction was concentrated and then diluted with dichloromethane (1 mL) and treated with trifluoroacetic acid (1 mL) and aged for 30 minutes. The reaction was concentrated under reduced pressure and then purified by prep HPLC to afford the title compound (5.7% yield).

1H NMR (400 MHz, DMSO-d6) δ 13.03 (s, 1H), 8.08 (d, J=15.0 Hz, 1H), 7.80 (bs, 2H), 6.72 (s, 1H), 3.68-3.16 (m, 6H), 2.45 (s, 3H), 2.42-2.34 (m, 1H), 2.10 (m, 1H), 1.75 (m, 1H), 1.27 (d, J=6.5 Hz, 3H), 1.15 (m, 2H), 0.42 (m, 2H)

LC/MS calc'd for $C_{21}H_{25}FN_5O_3$[M+H]$^+$ 414.5, found 414.1.

Example 43: 7-((R)-3-((S)-1-aminoethyl)pyrrolidin-1-yl)-1-cyclopropyl-6-fluoro-N-hydroxy-8-methyl-2-oxo-1,2-dihydroquinoline-4-carboxamide

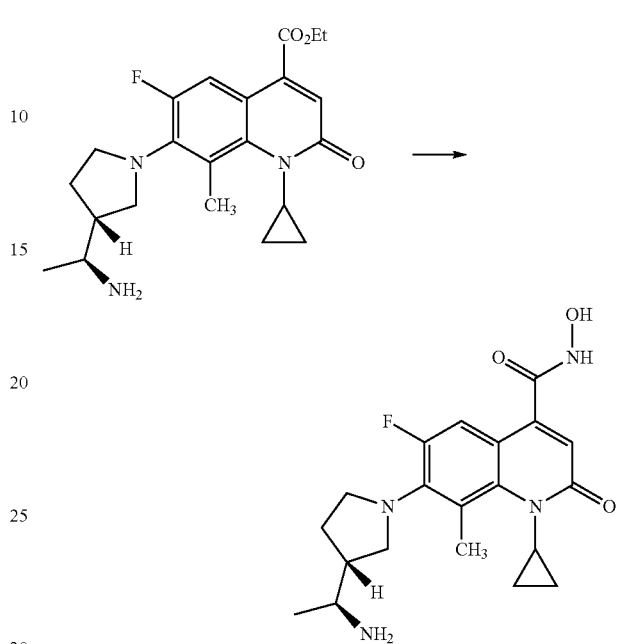

A solution of ethyl 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-4-carboxylate (28 mg, 0.044 mmol) in methanol (1 mL) was treated with hydroxylamine hydrochloride (12.36 mg, 0.178 mmol) followed by potassium hydroxide (17.47 mg, 0.311 mmol) and aged for 36 hours. The reaction was concentrated in vacuo and purified directly by prep HPLC to afford the title compound (44.4% yield).

1H NMR (400 MHz, DMSO-d6) δ 11.27 (s, 1H), 7.85 (bs, 2H), 7.25 (d, J=14.1 Hz, 1H), 6.34 (s, 1H), 3.55 (m, 1H), 3.51-3.43 (m, 2H), 3.43-3.31 (m, 2H), 3.28 (m, 1H), 2.44 (s, 3H), 2.42-2.31 (m, 1H), 2.14-2.04 (m, 1H), 1.80-1.68 (m, 1H), 1.27 (d, J=6.5 Hz, 3H), 1.15 (m, 2H), 0.39 (m, 2H)

LC/MS calc'd for $C_{20}H_{26}FN_4O_3$[M+H]$^+$ 389.4, found 389.1.

Example 44: 7-((R)-3-((S)-1-aminoethyl)pyrrolidin-1-yl)-4-chloro-1-cyclopropyl-6-fluoro-8-methylquinolin-2(1H)-one

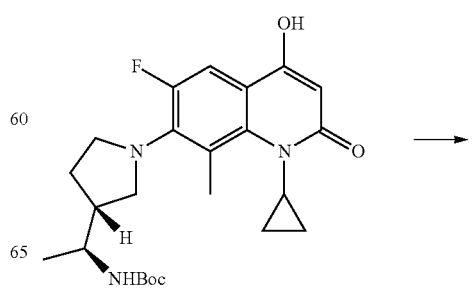

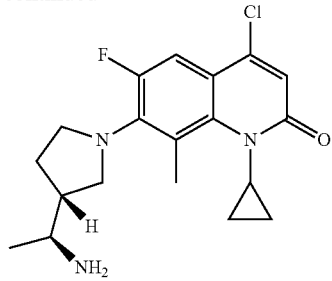

A solution of tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (65 mg, 0.146 mmol) and phosphoryl trichloride (0.027 mL, 0.146 mmol) in dioxane (2 mL) was stirred at room temperature for 2 minutes and then heated to 120° C. via microwave and maintained for 20 minutes. The reaction was cooled to room temperature and treated with ice and 6N NaOH. The reaction was extracted with ethyl acetate. The organic phase was collected, dried (MgSO4), filtered, concentrated, and purified by prep HPLC to afford the title compound (18.4% yield).

1H NMR (400 MHz, DMSO-d6) δ 7.83 (bs, 2H), 7.39 (d, J=13.6 Hz, 1H), 6.67 (s, 1H), 3.58 (m, 1H), 3.51-3.35 (m, 4H), 3.28 (m, 1H), 2.44 (s, 3H), 2.38 (dd, J=8.6, 8.6 Hz, 1H), 2.15-2.05 (m, 1H), 1.80-1.68 (m, 1H), 1.27 (d, J=6.4 Hz, 3H), 1.13 (m, 2H), 0.42 (m, 2H)

LC/MS calc'd for $C_{19}H_{24}ClFN_3O$ [M+H]$^+$ 364.9, found 364.2.

Example 45: 7-((R)-3-((S)-1-aminoethyl)pyrrolidin-1-yl)-4-(aminomethyl)-1-cyclopropyl-6-fluoro-8-methylquinolin-2(1H)-one

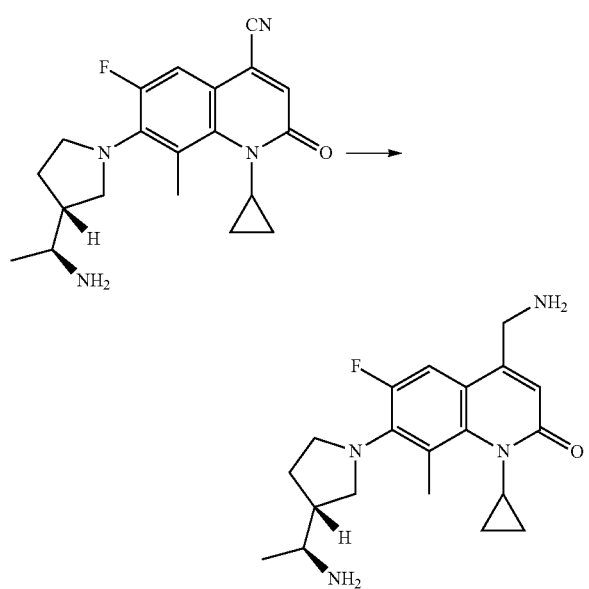

A mixture of 7-((R)-3-((S)-1-aminoethyl)pyrrolidin-1-yl)-1-cyclopropyl-6-fluoro-8-methyl-2-oxo-1,2-dihydroquinoline-4-carbonitrile (13.7 mg, 0.024 mmol), 10% Pd/C (10 mg), and acetic acid (100 μL) in Methanol (2 mL) was sparged with H$_2$ (g) for 5 minutes and then left under an atmosphere of H$_2$ (g) for 4 hours and then filtered over Celite, concentrated, and purified by prep HPLC to give the title compound (31.6% yield).

1H NMR (400 MHz, DMSO-d6) δ 8.33 (bs, 2H), 7.86 (bs, 2H), 7.38 (d, J=14.1 Hz, 1H), 6.44 (s, 1H), 4.23 (m, 2H), 3.54 (m, 1H), 3.47 (m, 1H), 3.43-3.39 (m, 1H), 3.39-3.23 (m, 3H), 2.45 (s, 3H), 2.43-2.35 (m, 1H), 2.14-2.05 (m, 1H), 1.79-1.68 (m, 1H), 1.27 (d, J=6.5 Hz, 3H), 1.14 (m, 2H), 0.38-0.26 (m, 2H)

LC/MS calc'd for $C_{20}H_{28}FN_4O$ [M+H]$^+$ 359.5, found 359.0.

Example 46: N-((7-((R)-3-((S)-1-aminoethyl)pyrrolidin-1-yl)-1-cyclopropyl-6-fluoro-8-methyl-2-oxo-1,2-dihydroquinolin-4-yl)methyl)acetamide The title compound was prepared in accordance with the following scheme:

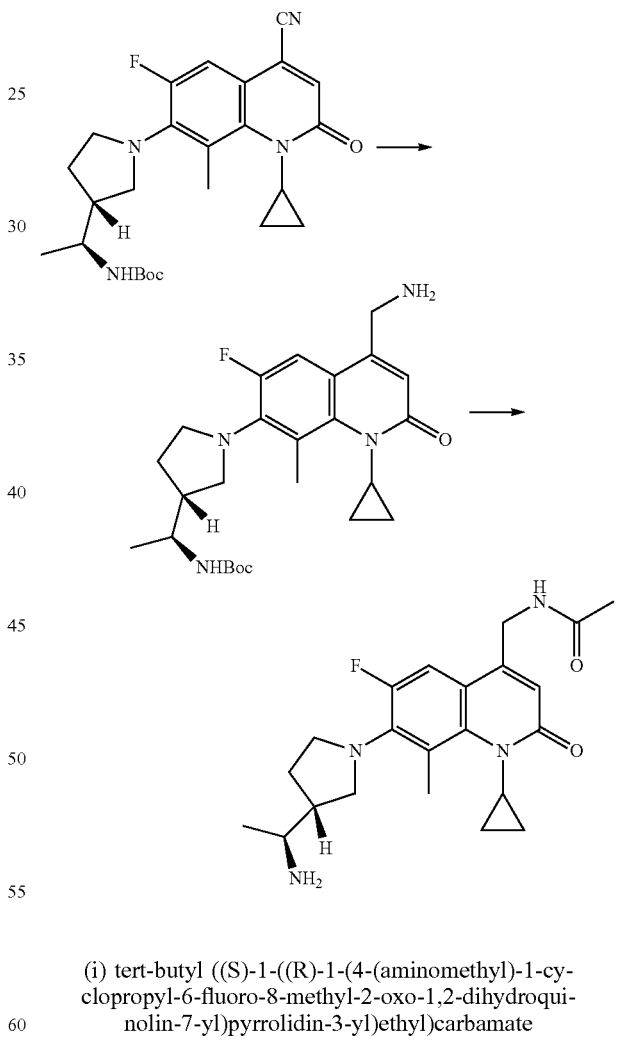

(i) tert-butyl ((S)-1-((R)-1-(4-(aminomethyl)-1-cyclopropyl-6-fluoro-8-methyl-2-oxo-1,2-dihydroquinolin-7-yl)pyrrolidin-3-yl)ethyl)carbamate A solution of tert-butyl ((S)-1-((R)-1-(4-cyano-1-cyclopropyl-6-fluoro-8-methyl-2-oxo-1,2-dihydroquinolin-7-yl)pyrrolidin-3-yl)ethyl)carbamate (103.4 mg, 0.227 mmol), 10% Pd/C (10 mg), and acetic acid (100 μL) in methanol (2 mL) was sparged with H$_2$ (g) for 5 minutes and then left under an atmosphere of H$_2$ (g) for 2 hours. The reaction was then filtered over Celite and concentrated under reduced pressure to give the title compound (99% yield).

LC/MS calc'd for $C_{25}H_{36}FN_4O_3$ [M+H]$^+$ 459.6, found 459.2.

(ii) N-((7-((R)-3-((S)-1-aminoethyl)pyrrolidin-1-yl)-1-cyclopropyl-6-fluoro-8-methyl-2-oxo-1,2-dihydroquinolin-4-yl)methyl)acetamide A solution of tert-butyl ((S)-1-((R)-1-(4-(aminomethyl)-1-cyclopropyl-6-fluoro-8-methyl-2-oxo-1,2-dihydroquinolin-7-yl)pyrrolidin-3-yl)ethyl)carbamate (15 mg, 0.033 mmol) and acetyl chloride (2.334 µl, 0.033 mmol) in dichloromethane (2 mL) was treated with triethylamine (0.018 mL, 0.131 mmol) and stirred at room temperature overnight. The reaction was then treated with trifluoroacetic acid (1 mL) and aged for 30 minutes before being concentrated under reduced pressure. The residue was purified by prep HPLC to give the desired material (27.1% yield).

1H NMR (400 MHz, DMSO-d6) δ 8.32 (t, J=5.9 Hz, 1H), 7.78 (bs, 2H), 7.35 (d, J=14.1 Hz, 1H), 6.20 (s, 1H), 4.31 (d, J=5.8 Hz, 2H), 3.62-3.21 (m, 6H), 2.43 (s, 3H), 2.42-2.32 (m, 1H), 2.09 (m, 1H), 1.90 (s, 3H), 1.78-1.66 (m, 1H), 1.25 (d, J=6.5 Hz, 3H), 1.09 (m, 2H), 0.31 (m, 2H)

LC/MS calc'd for $C_{22}H_{30}FN_4O_2$ [M+H]$^+$ 401.5, found 401.1.

Example 47: 7-((R)-3-((S)-1-aminoethyl)pyrrolidin-1-yl)-1-cyclopropyl-6-fluoro-4-(hydroxymethyl)-8-methylquinolin-2(1H)-one

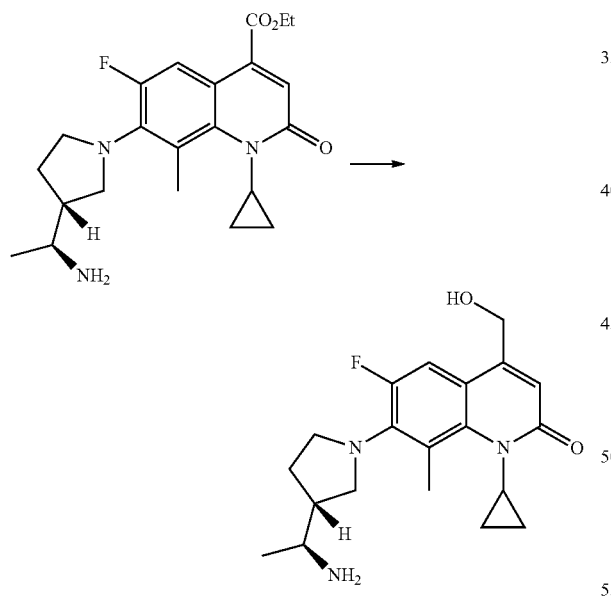

A solution of ethyl 7-((R)-3-((S)-1-aminoethyl)pyrrolidin-1-yl)-1-cyclopropyl-6-fluoro-8-methyl-2-oxo-1,2-dihydroquinoline-4-carboxylate (34.2 mg 0.085 mmol) in 2-propanol (702 µl) and water (149 µl was treated with sodium borohydride (11.28 mg, 0.298 mmol) and stirred at room temperature for 4 hours. The reaction was quenched with acetic acid, concentrated under reduced pressure and purified by reverse phase prep HPLC to afford the title compound (8.1% yield).

1H NMR (400 MHz, DMSO-d6) δ 7.79 (bs, 2H), 7.24 (d, J=13.9 Hz, 1H), 6.42 (s, 1H), 4.59 (s, 2H), 3.53-3.22 (m, 6H), 3.17 (s, 1H), 2.45 (s, 3H), 2.43-2.33 (m, 1H), 2.10 (m, 1H), 1.78-1.68 (m, 1H), 1.26 (d, J=6.5 Hz, 3H), 1.10 (m, 2H), 0.34 (m, 2H)

LC/MS calc'd for $C_{20}H_{27}FN_3O_2$ [M+H]$^+$ 360.4, found 360.1.

Example 48: 7-((R)-3-((S)-1-aminoethyl)pyrrolidin-1-yl)-1-cyclopropyl-6-fluoro-4-(methoxymethyl)-8-methylquinolin-2(1H)-one The title compound was prepared in accordance with the following scheme:

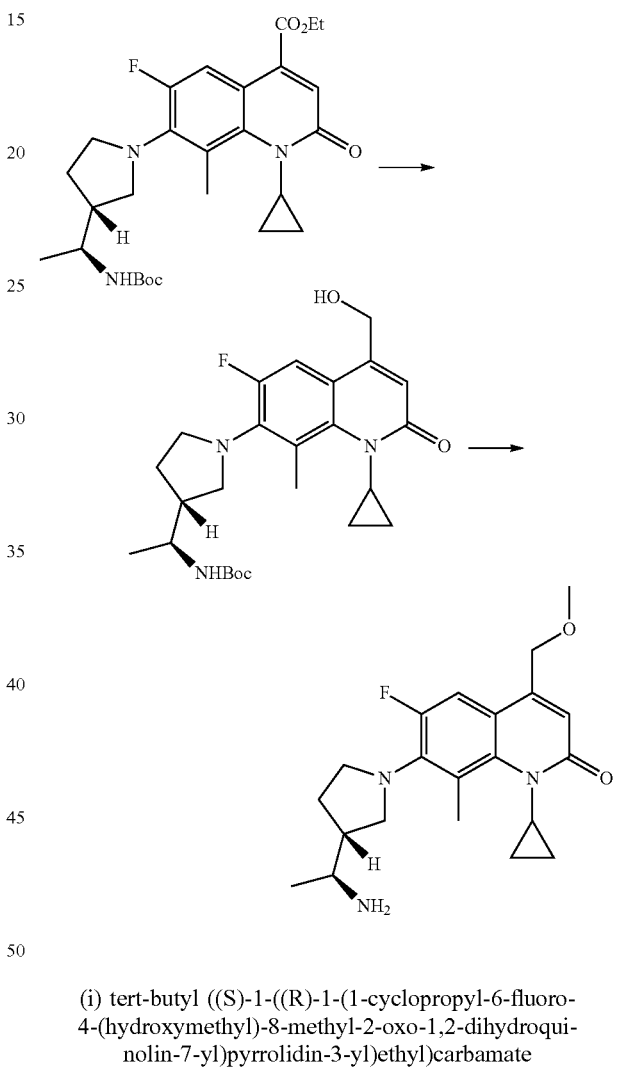

(i) tert-butyl ((S)-1-((R)-1-(1-cyclopropyl-6-fluoro-4-(hydroxymethyl)-8-methyl-2-oxo-1,2-dihydroquinolin-7-yl)pyrrolidin-3-yl)ethyl)carbamate A solution of ethyl 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinoline-4-carboxylate (63.9 mg 0.127 mmol) in 2-propanol (1050 µl) and water (223 µl) was treated with sodium borohydride (16.87 mg, 0.446 mmol). The reaction stirred for 4 hours. The reaction was treated with acetic acid and poured in sat'd NaHCO$_3$ (aq) and extracted with EtOAc. The organic phase was collected, dried (MgSO$_4$), filtered, concentrated and purified by silica gel column chromatography using a linear gradient of 0-10% methanol in dichloromethane to afford the desired product (23.6% yield).

LC/MS calc'd for $C_{25}H_{35}FN_3O_4$ [M+H]+ 460.6, found 460.1.

(ii) 7-((R)-3-((S)-1-aminoethyl)pyrrolidin-1-yl)-1-cyclopropyl-6-fluoro-4-(methoxymethyl)-8-methylquinolin-2(1H)-one A cold (0° C.) solution of tert-butyl ((S)-1-((R)-1-(1-cyclopropyl-6-fluoro-4-(hydroxymethyl)-8-methyl-2-oxo-1,2-dihydroquinolin-7-yl)pyrrolidin-3-yl)ethyl)carbamate (13.8 mg, 0.030 mmol) in THF (100 µl) was treated with sodium hydride (1.081 mg, 0.045 mmol) and stirred for 5 minutes followed by the addition of iodomethane (2.80 µl, 0.045 mmol). The reaction warmed to room temperature and stirred overnight. The reaction was then treated with trifluoroacetic acid (1 mL) and aged for 30 minutes. The reaction was then concentrated under reduced pressure and purified by prep HPLC to give the desired material (45.5% yield).

1H NMR (400 MHz, DMSO-d6) δ 7.80 (bs, 2H), 7.24 (d, J=13.9 Hz, 1H), 6.38 (s, 1H), 4.53 (s, 2H), 3.41 (m, 6H), 3.35 (s, 3H), 2.45 (s, 3H), 2.38 (m, 1H), 2.09 (m, 1H), 1.79-1.67 (m, 1H), 1.26 (d, J=6.5 Hz, 3H), 1.11 (m, 2H), 0.35 (m, 2H)

LC/MS calc'd for $C_{21}H_{29}FN_3O_2$ [M+H]+ 374.5, found 374.1.

Example 49: 7-((R)-3-((S)-1-aminoethyl)pyrrolidin-1-yl)-1-cyclopropyl-4-(2-(dimethylamino)ethoxy)-6-fluoro-8-methylquinolin-2(1H)-one

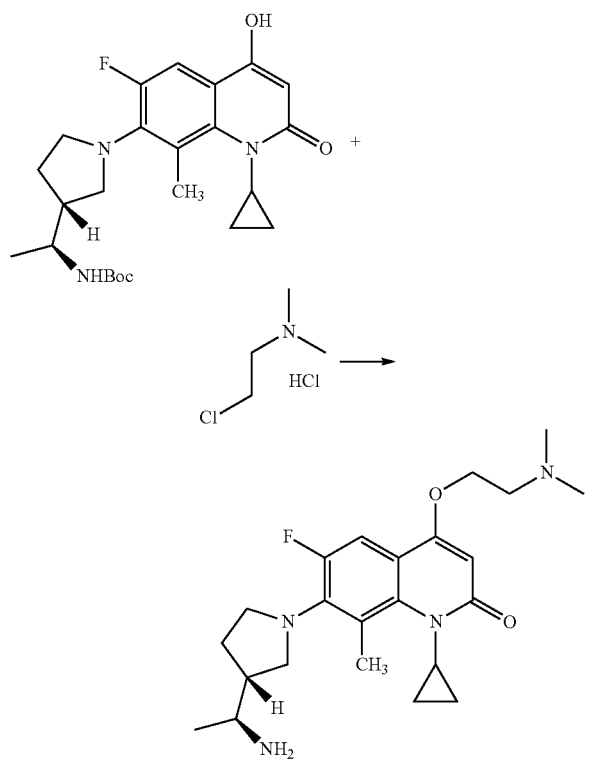

A vial charged with tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (59.4 mg, 0.133 mmol), 2-chloro-N,N-dimethylethanamine-hydrochloride (19.21 mg, 0.133 mmol), potassium carbonate (55.3 mg, 0.400 mmol) and 18-crown-6 (211 mg, 0.800 mmol) in DMA (444 µl) was heated at 85° C. and stirred overnight. The reaction was poured into brine and extracted with ethyl acetate. The organic phase was collected, dried (MgSO4), filtered, and concentrated. The crude residue was dissolved in dichloromethane (500 µL) and treated with trifluoroacetic acid (1 mL). The reaction was aged for 1 hour and then concentrated under reduced pressure. The residue was then purified by prep HPLC to afford the title compound (81% yield).

1H NMR (400 MHz, Methanol-d4) δ 7.61 (d, J=13.3 Hz, 1H), 5.95 (s, 1H), 4.47 (dd, J=5.6, 4.0 Hz, 2H), 3.74-3.68 (m, 2H), 3.65-3.54 (m, 2H), 3.50-3.40 (m, 3H), 3.40-3.33 (m, 1H), 3.01 (s, 6H), 2.56 (s, 3H), 2.49 (q, J=8.5 Hz, 1H), 2.22 (m, 1H), 1.83 (m, 1H), 1.40 (d, J=6.6 Hz, 3H), 1.19 (m, 2H), 0.47 (m, 2H);

LC/MS calc'd for $C_{23}H_{34}FN_4O_2$ [M+H]+ 417.5, found 417.1.

Example 50: N—((S)-1-((R)-1-(1-cyclopropyl-4-(2-(dimethylamino)ethoxy)-6-fluoro-8-methyl-2-oxo-1,2-dihydroquinolin-7-yl)pyrrolidin-3-yl)ethyl)acetamide

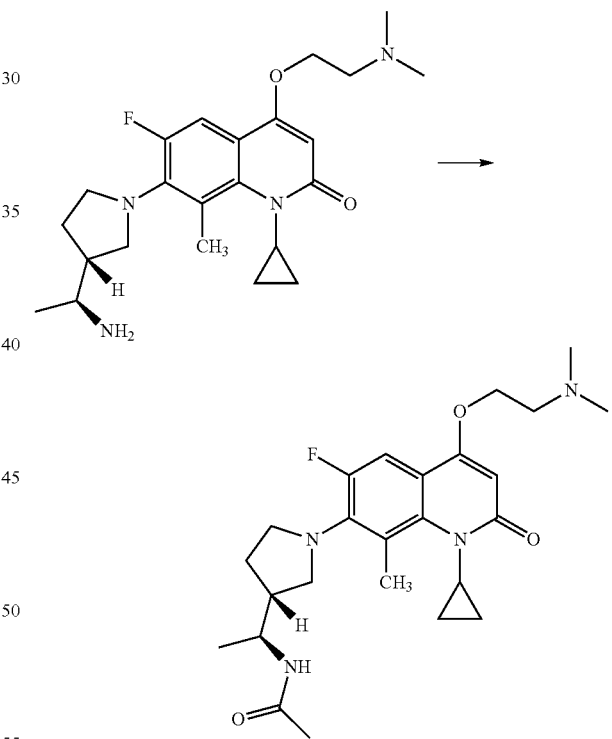

A solution of 7-((R)-3-((S)-1-aminoethyl)pyrrolidin-1-yl)-1-cyclopropyl-4-(2-(dimethylamino)ethoxy)-6-fluoro-8-methylquinolin-2(1H)-one (22.8 mg, 0.030 mmol) in dichloromethane (2 mL) was treated with Hunig's Base (0.021 mL, 0.120 mmol) and acetyl chloride (2.135 µl, 0.030 mmol). After 30 minutes, the reaction was concentrated under reduced pressure and purified by prep HPLC to afford the title compound (13.2% yield).

1H NMR (400 MHz, Methanol-d4) δ 8.02 (d, J=8.8 Hz, 1H), 7.57 (d, J=13.5 Hz, 1H), 5.93 (s, 1H), 4.48-4.44 (m, 2H), 3.99-3.91 (m, 1H), 3.74-3.68 (m, 2H), 3.59 (m, 1H), 3.46-3.35 (m, 4H), 3.01 (s, 6H), 2.52 (s, 3H), 2.35 (m, 1H), 2.11 (m, 1H), 1.92 (d, J=2.3 Hz, 3H), 1.75 (m, 1H), 1.20 (d, J=6.7 Hz, 3H), 1.19 (m, 2H), 0.46 (m, 2H)

LC/MS calc'd for $C_{25}H_{36}FN_4O_3$ [M+H]$^+$ 459.6, found 459.1.

Example 51: 4-(2-aminoethoxy)-7-((R)-3-((S)-1-aminoethyl)pyrrolidin-1-yl)-1-cyclopropyl-6-fluoro-8-methylquinolin-2(1H)-one

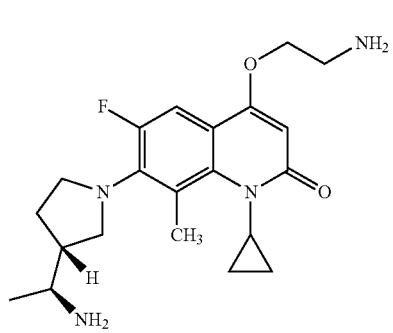 [SMILES: Cc1c(N2CC[C@@H]([C@H](C)N)C2)c(F)cc2c(OCCN)cc(=O)n(C3CC3)c12]

The title compound was prepared in accordance with the following scheme:

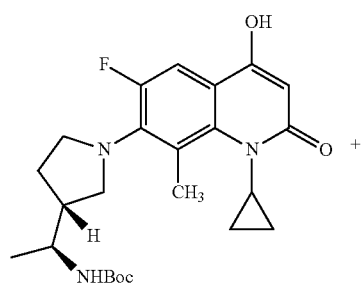

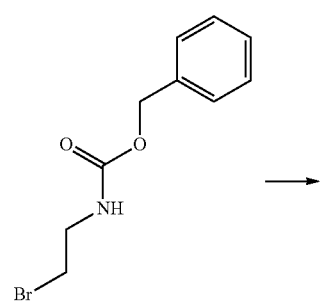

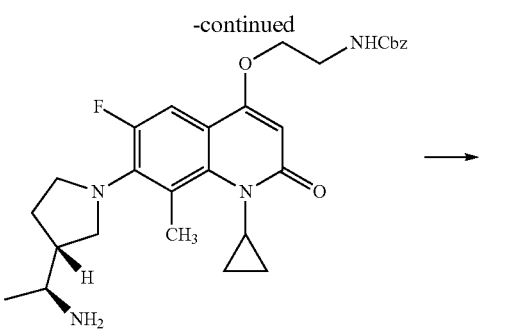

(i) benzyl (2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)carbamate Using a similar procedure to Example 49, but substituting benzyl (2-bromoethyl)carbamate for 2-chloro-N,N-dimethylethanamine-hydrochloride, the title compound was obtained in 34% yield.

1H NMR (400 MHz, DMSO-d6) δ 7.82 (bs, 2H), 7.63 (dd, J=6.0 Hz, 1H), 7.51 (d, J=13.5 Hz, 1H), 7.30 (m, 5H), 5.80 (s, 1H), 5.04 (s, 2H), 4.02 (t, J=5.1 Hz, 2H), 3.53-3.39 (m, 4H), 3.39-3.29 (m, 3H), 3.27 (m, 1H), 2.44 (s, 3H), 2.42-2.34 (m, 1H), 2.08 (m, 1H), 1.79-1.67 (m, 1H), 1.26 (d, J=6.5 Hz, 3H), 1.07 (m, 2H), 0.35 (m, 2H).

LC/MS calc'd for $C_{29}H_{36}FN_4O_4$ [M+H]$^+$ 523.6, found 523.2.

(ii) 4-(2-aminoethoxy)-7-((R)-3-((S)-1-aminoethyl)pyrrolidin-1-yl)-1-cyclopropyl-6-fluoro-8-methylquinolin-2(1H)-one A mixture of benzyl (2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)carbamate (28.0 mg, 0.037 mmol) and 10% Pd/C (10 mg) in methanol (1 mL) was purged with H$_2$ (g) for 10 minutes and left to stir under an atmosphere of H$_2$ (g) for 1 hour. The reaction was then filtered over Celite, concentrated, and purified by prep HPLC (63.4% yield).

1H NMR (400 MHz, DMSO-d6) δ 8.06 (bs, 2H), 7.89 (bs, 2H), 7.74 (d, J=13.8 Hz, 1H), 5.86 (s, 1H), 4.22 (t, J=4.8 Hz, 2H), 3.51 (m, 1H), 3.43 (m, 1H), 3.39-3.34 (m, 2H), 3.34-3.27 (m, 3H), 2.44 (s, 3H), 2.42-2.35 (m, 1H), 2.13-2.04 (m, 2H), 1.79-1.67 (m, 1H), 1.27 (d, J=6.5 Hz, 3H), 1.10 (m, 2H), 0.33 (m, 2H)

LC/MS calc'd for $C_{21}H_{30}FN_4O_2$ [M+H]$^+$ 389.5, found 389.1.

Example 52: N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)-2-hydroxyacetamide

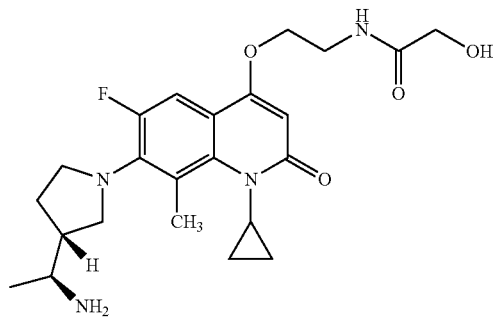 [SMILES: Cc1c(N2CC[C@@H]([C@H](C)N)C2)c(F)cc2c(OCCNC(=O)CO)cc(=O)n(C3CC3)c12]

The title compound was prepared in accordance with the following scheme:

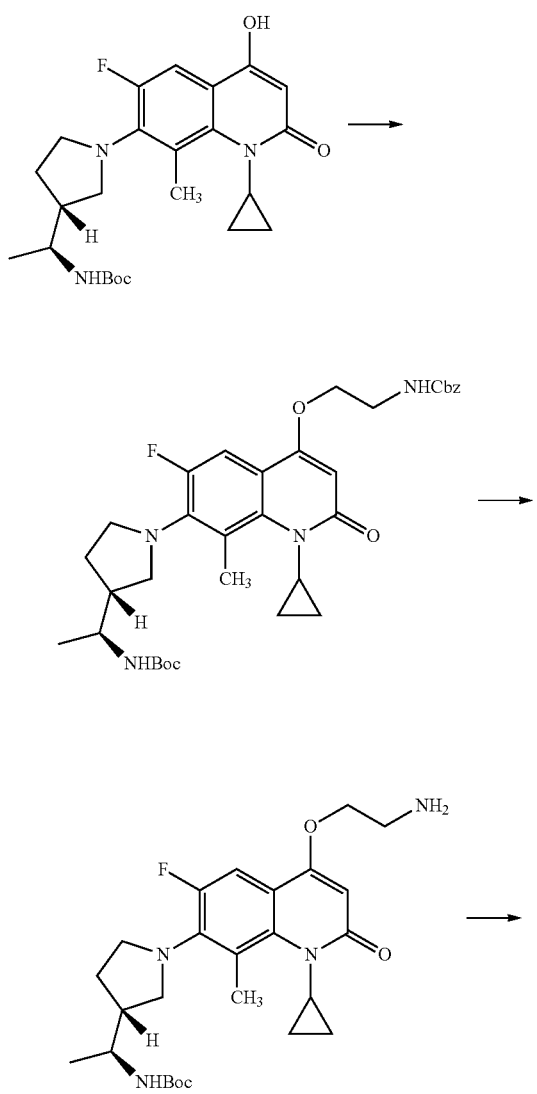

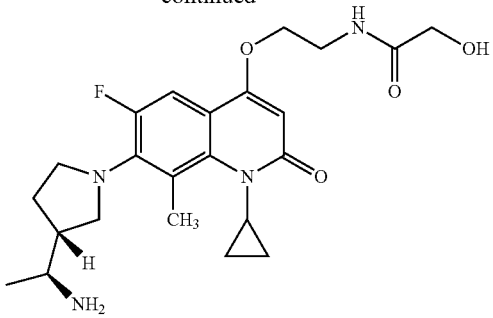

(i) tert-butyl ((S)-1-((R)-1-(4-(2-N-benzylcarbamoyl ethoxy)-1-cyclopropyl-6-fluoro-8-methyl-2-oxo-1,2-dihydroquinolin-7-yl)pyrrolidin-3-yl)ethyl)carbamate A vial charged with tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (73.4 mg, 0.140 mmol), benzyl (2-bromoethyl)carbamate (36.1 mg, 0.140 mmol), potassium carbonate (58.1 mg, 0.420 mmol) and 18-crown-6 (222 mg, 0.840 mmol) in DMA (1 mL) was heated at 80° C. overnight. The reaction was poured into brine and extracted with ethyl acetate. The organic phase was collected, dried (MgSO$_4$), filtered and concentrated. The crude material was purified by silica gel chromatography eluting with a linear gradient of 0-10% methanol in dichloromethane to afford the desired material (99% yield).
LC/MS calc'd for $C_{34}H_{44}FN_4O_6$ [M+H]$^+$ 623.7, found 623.3.

(ii) tert-butyl ((S)-1-((R)-1-(4-(2-aminoethoxy)-1-cyclopropyl-6-fluoro-8-methyl-2-oxo-1,2-dihydroquinolin-7-yl)pyrrolidin-3-yl)ethyl)carbamate A mixture of 10% Pd/C (10 mg) and tert-butyl ((S)-1-((R)-1-(4-(2-N-benzylcarbamoyl ethoxy)-1-cyclopropyl-6-fluoro-8-methyl-2-oxo-1,2-dihydroquinolin-7-yl)pyrrolidin-3-yl)ethyl)carbamate (87 mg, 0.14 mmol) in methanol (2 mL) was sparged with H$_2$ (g) for 30 minutes and then left under an atmosphere of H$_2$ (g) for 1 hour. The reaction was filtered over Celite and concentrated to give the title compound (quantitative yield).
LC/MS calc'd for $C_{26}H_{38}FN_4O_4$ [M+H]$^+$ 489.6, found 489.2.

(iii) N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)-2-hydroxyacetamide A solution of 2-(3H-[1,2,3]triazolo[4,5-b]pyridin-3-yl)-1,1,3,3-tetramethylisouronium hexafluorophosphate(V) (HATU, 58.6 mg, 0.154 mmol), tert-butyl ((S)-1-((R)-1-(4-(2-aminoethoxy)-1-cyclopropyl-6-fluoro-8-methyl-2-oxo-1,2-dihydroquinolin-7-yl)pyrrolidin-3-yl)ethyl)carbamate (68.4 mg, 0.14 mmol), and glycolic acid (10.65 mg, 0.140 mmol) in dichloromethane (1.5 mL) was treated with Hunig's Base (0.098 mL, 0.154 mmol) and stirred at room temperature for 2 hours. Trifluoroacetic acid (1 mL) was then added to the reaction. The reaction stirred at room temperature for 30 min and was then concentrated under reduced pressure and purified by prep HPLC to give the title compound (18.4% yield).

1H NMR (400 MHz, DMSO-d6) δ 8.08 (t, J=6.1 Hz, 1H), 7.80 (bs, 2H), 7.45 (d, J=13.6 Hz, 1H), 5.80 (s, 1H), 4.05 (t, J=5.3 Hz, 2H), 3.90 (s, 1H), 3.82 (s, 2H), 3.59-3.21 (m, 8H), 2.44 (s, 3H), 2.38 (m, 1H), 2.14-2.03 (m, 1H), 1.81-1.67 (m, 1H), 1.26 (d, J=6.5 Hz, 3H), 1.08 (m, 2H), 0.35 (m, 2H)

LC/MS calc'd for $C_{23}H_{32}FN_4O_4$ [M+H]$^+$ 447.5, found 447.2.

Example 53: 1-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)guanidine

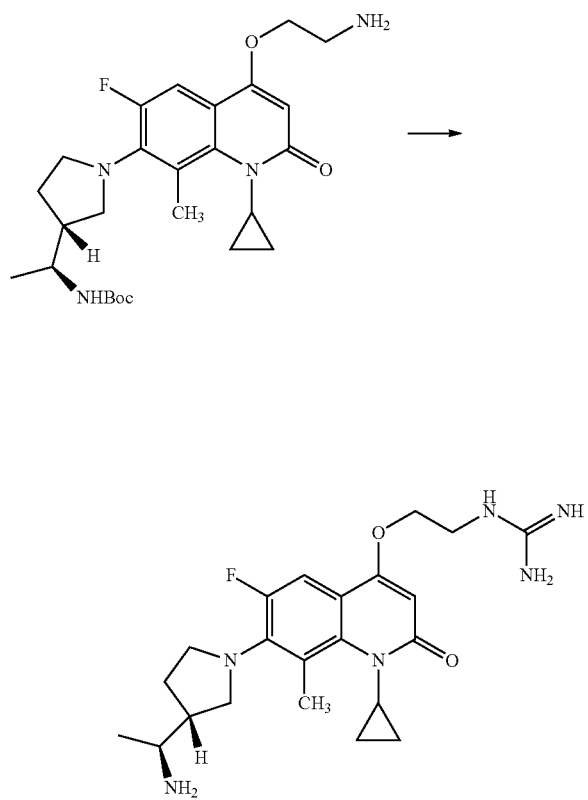

A solution of tert-butyl ((S)-1-((R)-1-(4-(2-aminoethoxy)-1-cyclopropyl-6-fluoro-8-methyl-2-oxo-1,2-dihydroquinolin-7-yl)pyrrolidin-3-yl)ethyl)carbamate (46 mg, 0.094 mmol) and Hunig's base (0.066 mL, 0.377 mmol) in DMF (1 mL) was treated with 1H-pyrazole-1-carboximidamide hydrochloride (27.6 mg, 0.188 mmol) and stirred at room temperature for 45 minutes. The reaction was immediately purified by prep HPLC. The residue was then treated with TFA (1 mL) and aged for 1 hour. The reaction was again concentrated and the residue purified by prep HPLC to afford the desired material (24.3% yield).

1H NMR (400 MHz, DMSO-d6) δ 7.86 (bs, 2H), 7.41 (d, J=13.5 Hz, 1H), 5.80 (s, 1H), 4.09 (t, J=4.9 Hz, 2H), 3.60 (m, 2H), 3.49 (m, 1H), 3.43-3.37 (m, 1H), 3.37-3.28 (m, 2H), 3.25 (m, 1H), 3.08 (m, 1H), 2.87 (s, 1H), 2.71 (s, 1H), 2.42 (s, 3H), 2.37 (m, 1H), 2.05 (m, 1H), 1.78-1.65 (m, 1H), 1.25 (d, J=6.5 Hz, 3H), 1.16 (d, J=14.5 Hz, 2H), 1.13-1.02 (m, 2H), 0.39-0.28 (m, 2H)

LC/MS calc'd for $C_{22}H_{32}FN_6O_2$[M+H]$^+$ 431.5, found 431.1.

Example 54: N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)acetamide

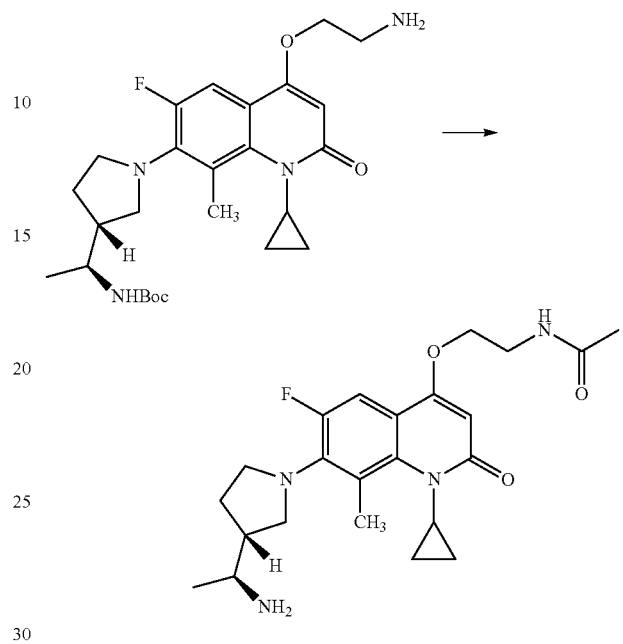

A cold (0° C.) solution of tert-butyl ((S)-1-((R)-1-(4-(2-aminoethoxy)-1-cyclopropyl-6-fluoro-8-methyl-2-oxo-1,2-dihydroquinolin-7-yl)pyrrolidin-3-yl)ethyl)carbamate (28 mg, 0.057 mmol) and triethylamine (9.58 µl, 0.069 mmol) in dichloromethane (2 mL) was treated with acetyl chloride (4.07 µl, 0.057 mmol) and stirred for 1 hour, warming to room temperature. The reaction was then treated with trifluoroacetic acid (1 mL) and aged for 30 minutes. The reaction was concentrated under reduced pressure and purified by prep HPLC to afford the desired compound (45.1% yield).

1H NMR (400 MHz, DMSO-d6) δ 8.14 (t, J=5.8 Hz, 1H), 7.79 (bs, 2H), 7.44 (d, J=13.5 Hz, 1H), 5.78 (s, 1H), 3.99 (t, J=5.2 Hz, 2H), 3.53-3.38 (m, 5H), 3.38-3.21 (m, 3H), 2.42 (s, 3H), 2.41-2.32 (m, 1H), 2.08 (m, 1H), 1.81 (s, 3H), 1.77-1.68 (m, 1H), 1.25 (d, J=6.5 Hz, 3H), 1.06 (m, 2H), 0.33 (m, 2H)

LC/MS calc'd for $C_{23}H_{32}FN_4O_3$[M+H]$^+$ 431.5, found 431.3.

Example 55: (S)-1-cyclopropyl-4-(2-(dimethylamino)ethoxy)-6-fluoro-7-(3-hydroxypyrrolidin-1-yl)-8-methylquinolin-2(1H)-one

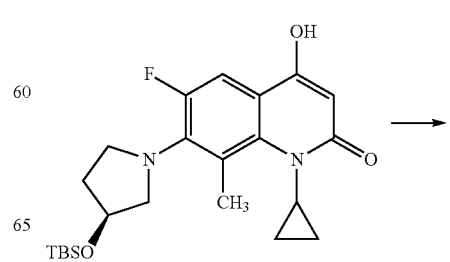

-continued

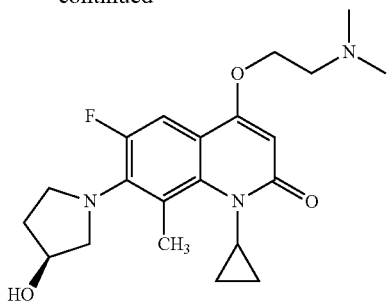

A vial charged with (S)-7-(3-((tert-butyldimethylsilyl)oxy)pyrrolidin-1-yl)-1-cyclopropyl-6-fluoro-4-hydroxy-8-methylquinolin-2(1H)-one (20.5 mg, 0.047 mmol), 2-chloro-N,N-dimethylethanamine-hydrochloride (6.83 mg, 0.047 mmol), potassium carbonate (19.65 mg, 0.142 mmol) and 18-crown-6 (75 mg, 0.284 mmol) in DMA (158 µl) was heated at 85° C. overnight. The reaction was poured into brine and extracted with ethyl acetate. The organic phase was collected, dried (MgSO$_4$), filtered and concentrated. The crude residue was dissolved in THF and treated with TBAF (1 mL, 1.0 M in THF). After 30 minutes, the reaction was concentrated and purified by prep HPLC to afford the title compound (10.1% yield).

1H NMR (400 MHz, Methanol-d4) δ 7.57 (d, J=13.6 Hz, 1H), 5.93 (s, 1H), 4.52 (m, 1H), 4.48-4.44 (m, 2H), 3.78 (m, 2H), 3.74-3.67 (m, 2H), 3.50-3.43 (m, 1H), 3.43-3.34 (m, 1H), 3.29-3.20 (m, 2H), 3.02 (s, 6H), 2.52 (s, 3H), 2.21-2.11 (m, 1H), 1.97 (m, 1H), 1.26-1.12 (m, 2H), 0.48 (m, 2H)

LC/MS calc'd for $C_{21}H_{29}FN_3O_3$ [M+H]$^+$ 390.5, found 390.1.

Example 56: 2-((7-((R)-3-((S)-1-aminoethyl)pyrrolidin-1-yl)-1-cyclopropyl-6-fluoro-8-methyl-2-oxo-1, 2-dihydroquinolin-4-yl)oxy)acetamide

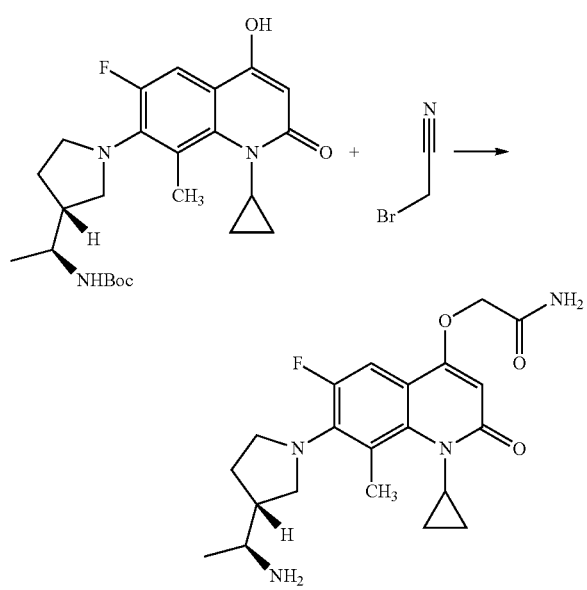

A vial charged with tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (289.3 mg, 0.649 mmol), 2-bromoacetonitrile (78 mg, 0.649 mmol), potassium carbonate (197 mg, 1.429 mmol) and 18-crown-6 (755 mg, 2.86 mmol) and DMA (2164 µl) was heated at 85° C. overnight. The reaction was poured into brine and extracted with ethyl acetate. The organic phase was collected, dried (MgSO$_4$), filtered and concentrated. The crude residue was dissolved in dichloromethane (1 mL) and treated with trifluoroacetic acid (1 mL). After aging for 30 minutes, the reaction was concentrated under reduced pressure and purified by prep HPLC to afford the title compound (56.4% yield).

1H NMR (400 MHz, DMSO-d6) δ 7.86 (bs, J=5.3 Hz, 2H), 7.67 (bs, 1H), 7.61 (d, J=13.6 Hz, 1H), 7.49 (bs, 1H), 5.73 (s, 1H), 4.53 (s, 2H), 3.51 (m, 1H), 3.44 (m, 1H), 3.36 (m, 2H), 3.28 (m, 2H), 2.44 (s, 3H), 2.39 (m, 1H), 2.09 (m, 1H), 1.80-1.67 (m, 1H), 1.27 (d, J=6.4 Hz, 3H), 1.09 (m, 2H), 0.35 (m, 2H)

LC/MS calc'd for $C_{21}H_{28}FN_4O_3$ [M+H]$^+$ 403.7, found 403.1.

Example 57: 4-((7-((R)-3-((S)-1-aminoethyl)pyrrolidin-1-yl)-1-cyclopropyl-6-fluoro-8-methyl-2-oxo-1, 2-dihydroquinolin-4-yl)oxy)butanenitrile

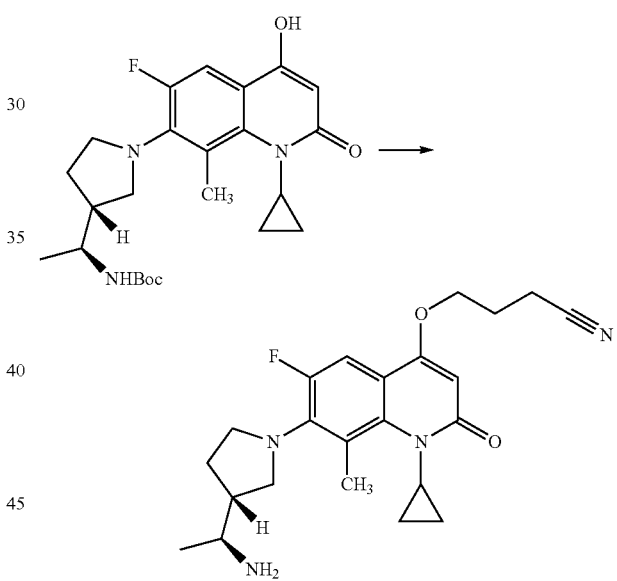

A vial charged with tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (57.4 mg, 0.129 mmol), 4-bromobutanenitrile (28.6 mg, 0.193 mmol), potassium carbonate (26.7 mg, 0.193 mmol) and 18-crown-6 (102 mg, 0.387 mmol) in DMA (429 µl) was heated at 60° C. for 1 hour. The reaction was poured into brine and extracted with ethyl acetate. The organic phase was collected, dried (MgSO$_4$), filtered, concentrated, and purified by flash chromatography on silica gel using a linear gradient of 0-100% ethyl acetate in heptane to give tert-butyl ((S)-1-((R)-1-(4-(3-cyanopropoxy)-1-cyclopropyl-6-fluoro-8-methyl-2-oxo-1,2-dihydroquinolin-7-yl)pyrrolidin-3-yl)ethyl)carbamate which was dissolved in dichloromethane (1 mL) and treated with trifluoroacetic acid (1 mL) and aged for 30 minutes. The reaction was concentrated under reduced pressure and purified by prep HPLC to give the title compound (13.4% yield).

1H NMR (400 MHz, DMSO-d6) δ 7.79 (bs, 2H), 7.48 (d, J=13.5 Hz, 1H), 5.83 (s, 1H), 4.11 (t, J=5.6 Hz, 2H), 3.49 (m, 1H), 3.43 (m, 1H), 3.39-3.24 (m, 4H), 2.72 (t, J=6.9 Hz, 2H), 2.44 (s, 3H), 2.43-2.34 (m, 1H), 2.13-2.05 (m, 3H), 1.79-1.67 (m, 1H), 1.26 (d, J=6.4 Hz, 3H), 1.08 (m, 2H), 0.36 (m, 2H)

LC/MS calc'd for $C_{23}H_{30}FN_4O_2$ $[M+H]^+$ 413.5, found 413.1.

Example 58: 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)-N'-hydroxybutanimidamide

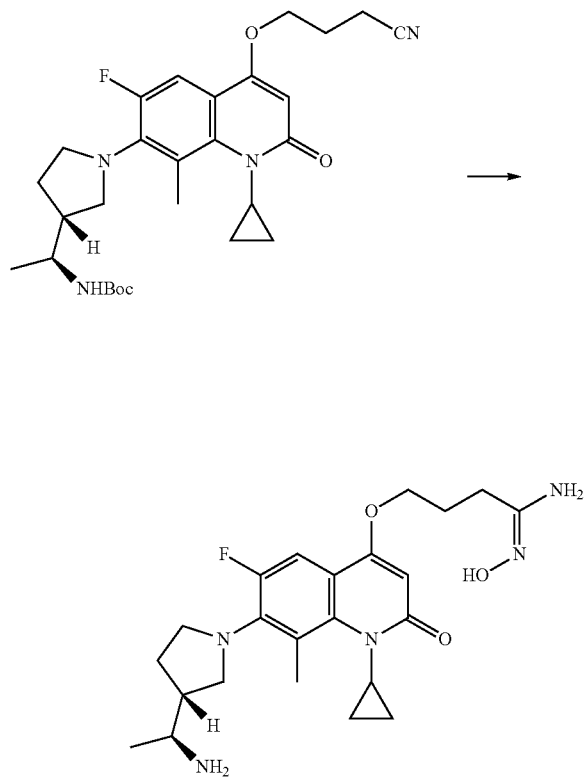

A solution of tert-butyl ((S)-1-((R)-1-(4-(3-cyanopropoxy)-1-cyclopropyl-6-fluoro-8-methyl-2-oxo-1,2-dihydroquinolin-7-yl)pyrrolidin-3-yl)ethyl)carbamate (41.2 mg, 0.080 mmol) and 50% hydroxylamine in water (100 μL) in ethanol (1 mL) was stirred at 50° C. overnight. The reaction cooled to room temperature and was concentrated under reduced pressure. The residue was diluted with dichloromethane (1 mL) and treated with trifluoroacetic acid (1 mL). The reaction aged for 30 minutes and was then concentrated and purified by prep HPLC (18.2% yield).

1H NMR (400 MHz, DMSO-d6) δ 12.34 (s, 1H), 10.85 (s, 1H), 8.65 (s, 1H), 7.83 (bs, 2H), 7.36 (d, J=13.3 Hz, 1H), 5.82 (s, 1H), 4.05 (t, J=5.8 Hz, 2H), 3.49 (m, 1H), 3.43-3.37 (m, 1H), 3.37-3.20 (m, 4H), 2.42 (s, 3H), 2.41-2.33 (m, 1H), 2.14-2.02 (m, 3H), 1.79-1.64 (m, 2H), 1.25 (d, J=6.5 Hz, 3H), 1.14-1.01 (m, 2H), 0.32 (m, 2H)

LC/MS calc'd for $C_{23}H_{33}FN_5O_3$ $[M+H]^+$ 446.5, found 446.1.

Example 59: ethyl 4-((7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)oxy)butanoate

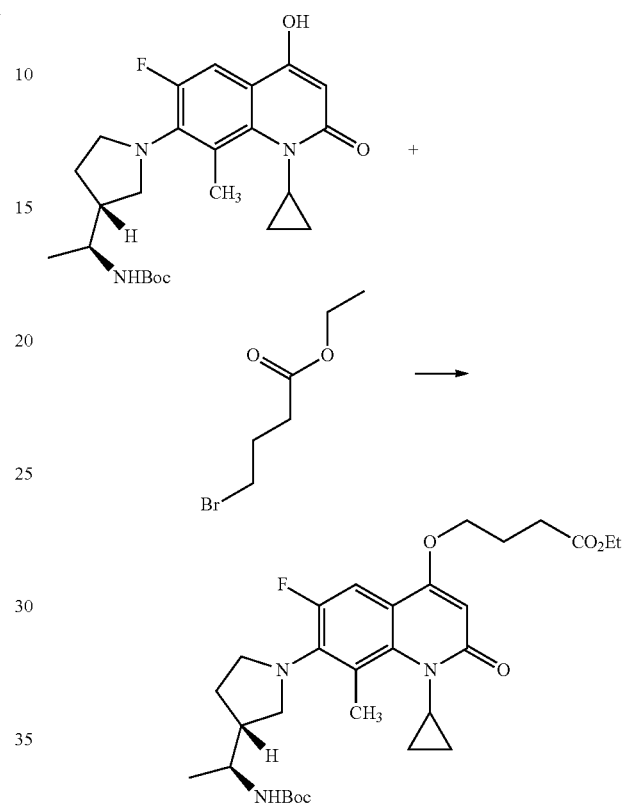

Using a procedure similar to Example 57 but substituting ethyl 4-bromobutanoate for bromobutanenitrile, the title compound was obtained (89% yield).

LC/MS calc'd for $C_{30}H_{43}FN_3O_6[M+H]^+$ 560.7, found 560.2.

Examples 60 and 61: 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)-N-hydroxybutanamide (60) and 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)butanoic acid (61)

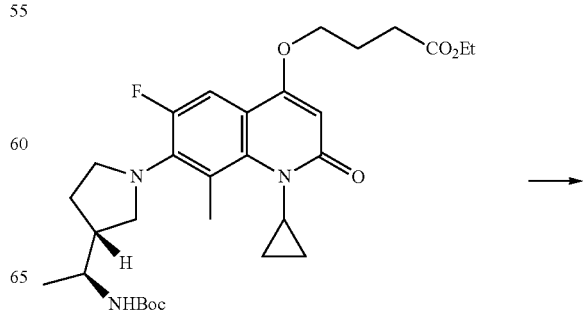

-continued

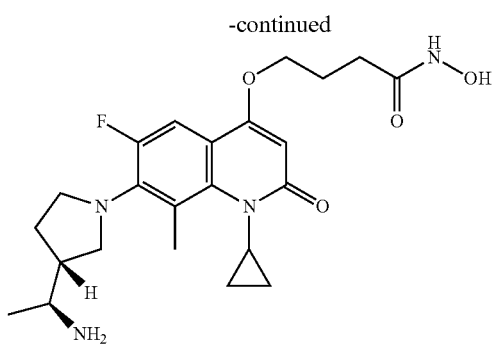

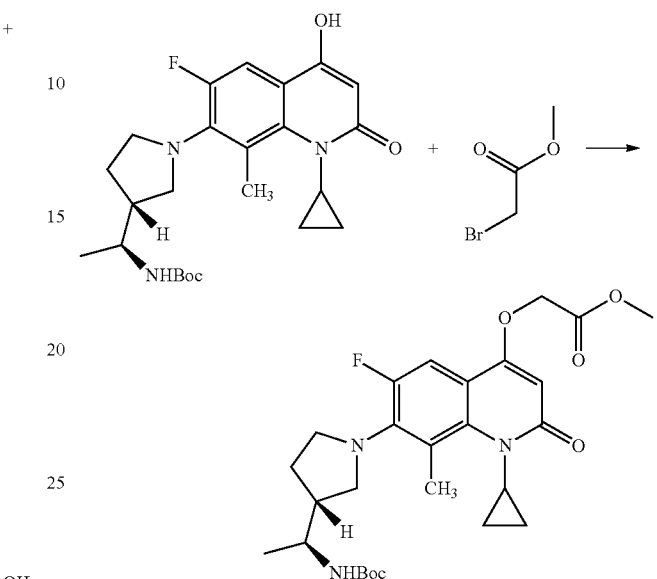

A solution of ethyl 4-((7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)oxy)butanoate (15 mg, 0.027 mmol) and aqueous hydroxyl amine (250 μL, 0.027 mmol) in Ethanol was stirred for 36 hours at 60° C. The reaction was concentrated under reduced pressure and diluted with dichloromethane (1 mL) and treated with TFA (1 mL). The reaction aged for 30 minutes and was then concentrated and purified by prep HPLC to give both titled compounds (60, 25.9% yield and 61, 21.7% yield).

60: 1H NMR (400 MHz, DMSO-d6) δ 10.42 (s, 1H), 7.79 (bs, 2H), 7.34 (d, J=13.3 Hz, 1H), 5.79 (s, 1H), 4.03 (t, J=6.0 Hz, 2H), 3.47 (m, J=17.2 Hz, 2H), 3.35 (m, 4H), 3.25 (m, 1H), 2.44 (s, 3H), 2.38 (m, 1H), 2.16 (t, J=7.3 Hz, 2H), 2.14-2.04 (m, 1H), 1.99 (m, 2H), 1.79-1.67 (m, 1H), 1.26 (d, J=6.5 Hz, 3H), 1.08 (m, 2H), 0.35 (m, 2H);

LC/MS calc'd for $C_{23}H_{32}FN_4O_4$ $[M+H]^+$ 447.5, found 447.1.

61: 1H NMR (400 MHz, DMSO-d6) δ 7.76 (bs, 2H), 7.30 (d, J=13.4 Hz, 1H), 5.78 (s, 1H), 4.04 (t, J=6.1 Hz, 2H), 3.49-3.18 (m, 6H), 2.42 (s, 3H), 2.39-2.32 (m, 3H), 2.07 (m, 1H), 1.99 (t, J=6.7 Hz, 2H), 1.79-1.66 (m, 1H), 1.24 (d, J=6.5 Hz, 3H), 1.06 (m, 2H), 0.34 (m, 2H)

LC/MS calc'd for $C_{23}H_{31}FN_3O_4$ $[M+H]^+$ 432.5, found 432.1.

Example 62: Methyl 2-((7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)oxy)acetate Using a procedure similar to Example 57 but substituting methyl 2-bromoacetate for bromobutanenitrile, the title compound was obtained (67.5% yield).

LC/MS calc'd for $C_{27}H_{37}FN_3O_6[M+H]^+$ 518.6, found 518.1.

Example 63: tert-butyl ((S)-1-((R)-1-(1-cyclopropyl-6-fluoro-4-(2-hydrazinyl-2-oxoethoxy)-8-methyl-2-oxo-1,2-dihydroquinolin-7-yl)pyrrolidin-3-yl)ethyl)carbamate

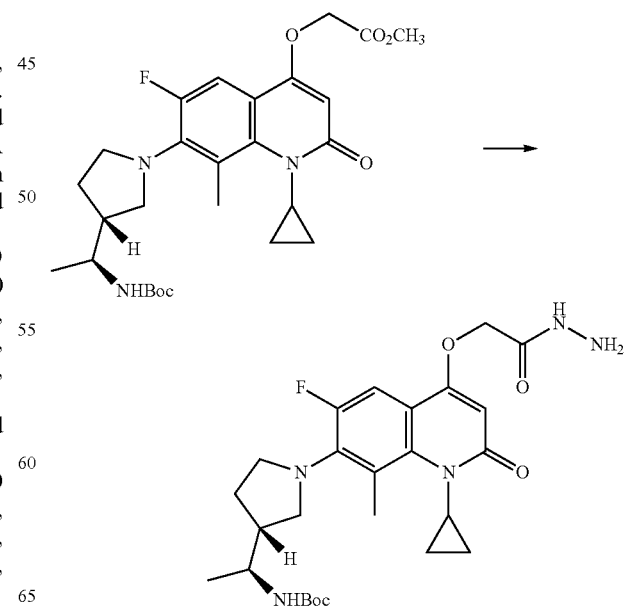

A solution of ethyl 2-((7-((R)-3-((S)-1-((tert-butoxycarbonyl)amino)methyl)pyrrolidin-1-yl)-1-cyclopropyl-6-fluoro-8-methyl-2-oxo-1,2-dihydroquinolin-4-yl)oxy)acetate (26.2 mg, 0.051 mmol) and hydrazine (7.74 μl, 0.246 mmol) in Ethanol was stirred for 12 hours at 60° C. The reaction cooled to room temperature and was concentrated under reduced pressure to give the title compound (quantitative yield).

LC/MS calc'd for $C_{26}H_{37}FN_5O_5$[M+H]$^+$ 518.6, found 518.1.

Example 64: 5-(((7-((R)-3-((S)-1-aminoethyl)pyrrolidin-1-yl)-1-cyclopropyl-6-fluoro-8-methyl-2-oxo-1,2-dihydroquinolin-4-yl)oxy)methyl)-1,3,4-oxadiazol-2(3H)-one

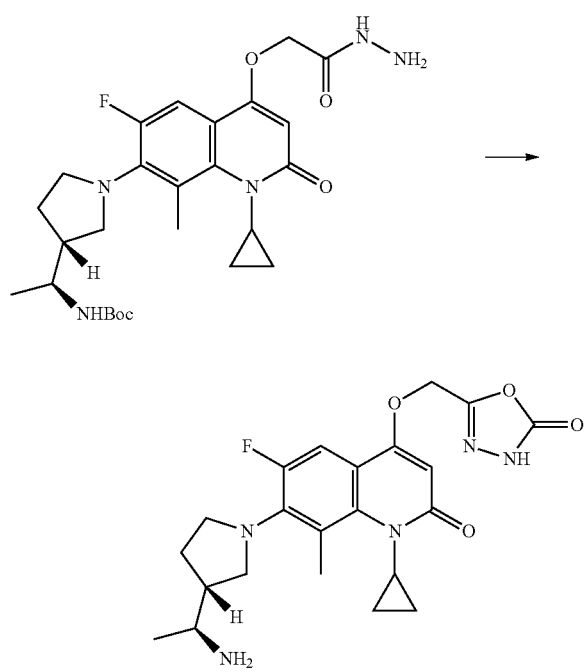

A cold (0° C.) solution of tert-butyl ((S)-1-((R)-1-(1-cyclopropyl-6-fluoro-4-(2-hydrazinyl-2-oxoethoxy)-8-methyl-2-oxo-1,2-dihydroquinolin-7-yl)pyrrolidin-3-yl)ethyl)carbamate (0.025 g, 0.049 mmol) in dichloromethane (1 mL) and a 1M solution of triphosgene (0.049 mL, 0.049 mmol) in Dichloromethane was stirred for 30 minutes and then warmed to room temperature. After 1 hour the reaction was concentrated and then dissolved with dichloromethane (1 mL) and treated with trifluoroacetic acid (1 mL). After aging for 30 minutes at room temperature, volatiles were removed under reduced pressure and the crude residue purified by prep HPLC to afford the title compound (24.6% yield).

1H NMR (400 MHz, DMSO-d6) δ 12.58 (s, 1H), 7.76 (bs, 2H), 7.28 (d, J=13.4 Hz, 1H), 5.99 (s, 1H), 5.15 (s, 2H), 3.31 (m, 6H), 2.42 (s, 3H), 2.41-2.32 (m, 1H), 2.07 (m, 1H), 1.80-1.65 (m, 1H), 1.24 (d, J=6.4 Hz, 3H), 1.09 (m, 2H), 0.35 (m, 2H)

LC/MS calc'd for $C_{22}H_{27}FN_5O_4$ [M+H]$^+$ 444.5, found 444.1.

Example 65: 5-(3-((7-((R)-3-((S)-1-aminoethyl)pyrrolidin-1-yl)-1-cyclopropyl-6-fluoro-8-methyl-2-oxo-1,2-dihydroquinolin-4-yl)oxy)propyl)-1,3,4-oxadiazol-2(3H)-one

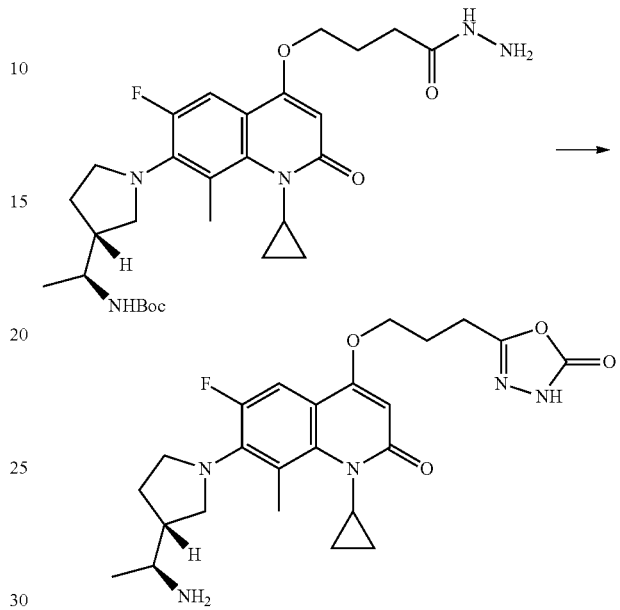

Using procedures similar to the formation of Example 64 but substituting ethyl 4-((7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)oxy)butanoate as the starting material, the title compound was obtained (45.1% yield).

1H NMR (400 MHz, DMSO-d6) δ 12.05 (s, 1H), 7.80 (bs, 2H), 7.29 (d, J=13.4 Hz, 1H), 5.81 (s, 1H), 4.12 (t, J=5.9 Hz, 2H), 3.54-3.40 (m, 2H), 3.40-3.22 (m, 4H), 2.75 (t, J=7.2 Hz, 2H), 2.44 (s, 3H), 2.38 (m, 1H), 2.15-2.04 (m, 3H), 1.79-1.67 (m, 1H), 1.26 (d, J=6.5 Hz, 3H), 1.09 (m, 2H), 0.35 (m, 2H)

LC/MS calc'd for $C_{24}H_{31}FN_5O_4$ [M+H]$^+$ 472.5, found 472.1.

Example 66: N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)methanesulfonamide

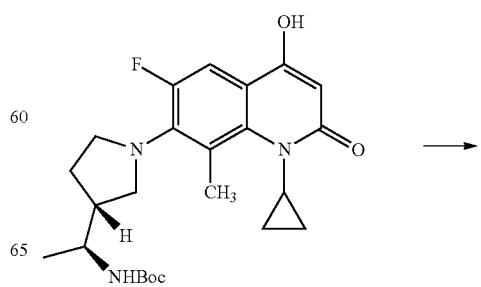

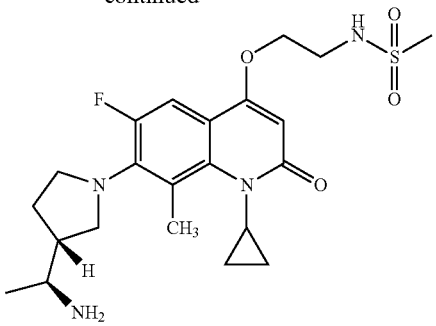

A sealed vial charged with tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (25.4 mg, 0.057 mmol), N-(2-chloroethyl)methanesulfonamide (9.44 mg, 0.060 mmol), potassium carbonate (15.76 mg, 0.114 mmol) and 18-crown-6 (60.3 mg, 0.228 mmol) in DMA (190 μl) was heated at 40° C. overnight. The reaction was poured into brine and extracted with ethyl acetate. The organic phase was collected, dried (MgSO$_4$), filtered and concentrated. The crude material was diluted with dichloromethane (1 mL), treated with trifluoroacetic acid (1 mL) and aged for 30 minutes. The reaction was concentrated under reduced pressure and purified by prep HPLC (46.6% yield).

1H NMR (400 MHz, DMSO-d6) δ 7.79 (bs, 2H), 7.57 (d, J=13.6 Hz, 1H), 7.45 (t, J=6.2 Hz, 1H), 5.81 (s, 1H), 4.08 (t, J=5.0 Hz, 2H), 3.54-3.22 (m, 8H), 2.95 (s, 3H), 2.44 (s, 3H), 2.38 (m, 1H), 2.09 (m, 1H), 1.80-1.67 (m, 1H), 1.26 (d, J=6.5 Hz, 3H), 1.08 (m, 2H), 0.35 (m, 2H)

LC/MS calc'd for $C_{22}H_{32}FN_4O_4S$ [M+H]$^+$ 467.6, found 467.2.

Example 67: 7-((R)-3-((S)-1-aminoethyl)pyrrolidin-1-yl)-1-cyclopropyl-6-fluoro-4-methoxy-8-methylquinolin-2(1H)-one A vial charged with tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate (17.1 mg, 0.038 mmol), iodomethane (10.90 mg, 0.077 mmol), potassium carbonate (10.61 mg, 0.077 mmol) and 18-crown-6 (40.6 mg, 0.154 mmol) in DMA (1 mL) was stirred at room temperature overnight. The reaction was poured into brine and extracted with ethyl acetate. The organic phase was collected, dried (MgSO$_4$), filtered and concentrated. The crude material was diluted with dichloromethane (1 mL) and treated with trifluoroacetic acid (1 mL) and aged for 30 minutes. The reaction was then concentrated under reduced pressure and purified by prep HPLC to afford the desired material (33.8% yield).

1H NMR (400 MHz, DMSO-d6) δ 7.79 (bs, 2H), 7.29 (d, J=13.5 Hz, 1H), 5.83 (s, 1H), 3.86 (s, 3H), 3.53-3.45 (m, 2H), 3.44-3.23 (m, 4H), 2.44 (s, 3H), 2.39 (m, 1H), 2.09 (m, 1H), 1.73 (m, 1H), 1.26 (d, J=6.5 Hz, 3H), 1.08 (m, 2H), 0.36 (m, 2H)

LC/MS calc'd for $C_{20}H_{27}FN_3O_2$[M+H]$^+$ 360.4, found 360.0.

Example 68: 7-((R)-3-((S)-1-aminoethyl)pyrrolidin-1-yl)-1-cyclopropyl-4-methoxy-8-methylquinolin-2(1H)-one

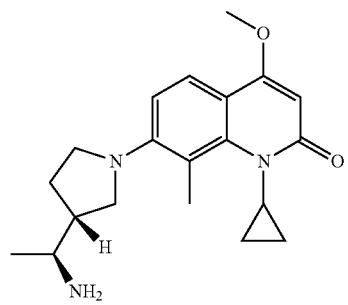 [SMILES: COc1cc(=O)n(C2CC2)c2c(C)c(N3CC[C@@H]([C@H](C)N)C3)ccc12]

The title compound was prepared in accordance with the following scheme:

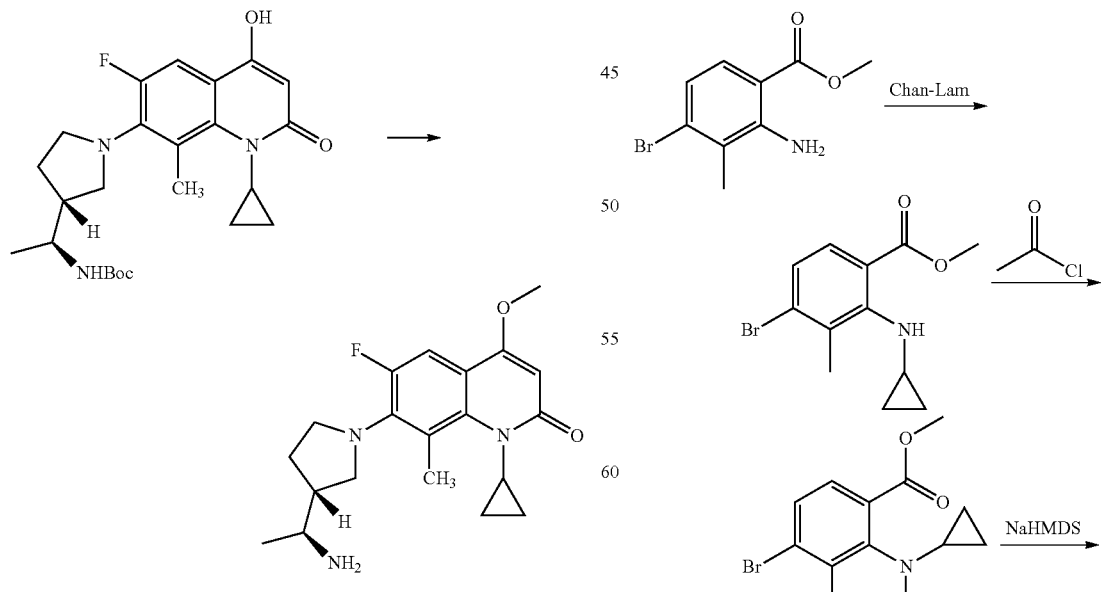

-continued

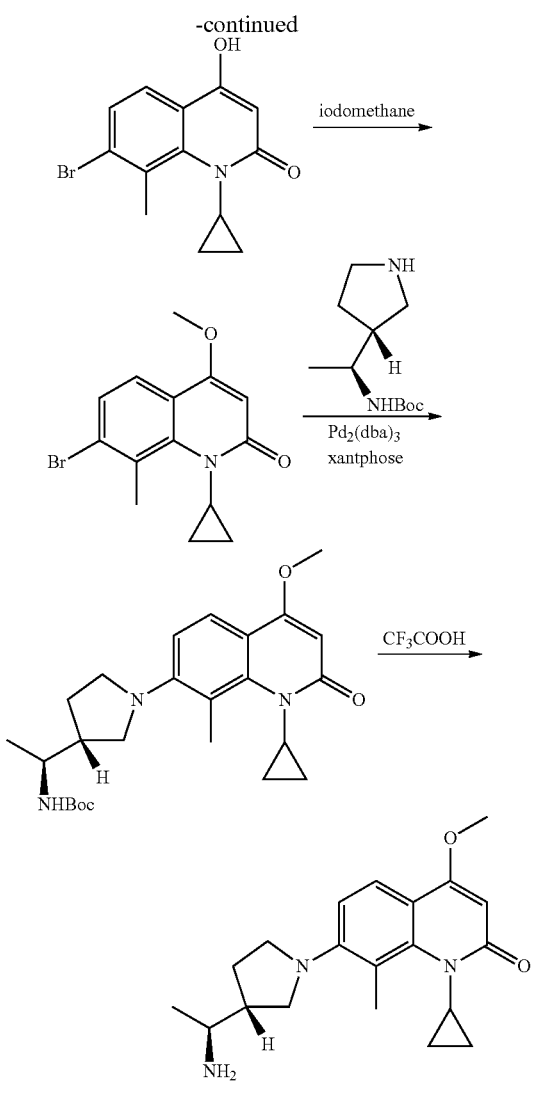

(i) Methyl 4-bromo-2-(cyclopropylamino)-3-methylbenzoate

Methyl 2-amino-4-bromo-3-methylbenzoate (0.666 g, 2.73 mmol), sodium carbonate (3.47 g, 32.7 mmol) and bipyridine (2.13 g, 13.6 mmol) were suspended in DCE and stirred at rt in open air. The dark blue mix became heterogeneous. Brief heating at 60 degree on heating block for 30 min allowed more efficient stirring. The dark blue heterogeneous rxn was cooled to rt in 60 min. Boronic acid (1.4 g, 16.4 mmol) and Cu(OAc)$_2$ (2.23 g, 12.3 mmol) were divided into 4 batches and added in 2 hrs at rt. Resume heating at 80 degree on heating block. Reaction mixture quickly turned dark brown. Gas released! After 30 min of heating, about 30-40% conversion. The dark brown mix was cooled back to rt and stirred for 24 hrs in open air. About 50-60% conversion. Additional boronic acid (1.4 g, 16.4 mmol) and Cu(OAc)$_2$ (2.23 g, 12.3 mmol) were divided into 4 batches and added in 4 batches at rt over 4 hours. The thick dark greenish blue mix was stirred at rt under slew of air for another 24 hrs (>90% conversion). Some N,N-dicyclopropyl adduct was observed. By product no more than 10% by averaging UV/LC/MS/NMR assessment. The mixture was diluted with DCM and filtered. Solid was washed with DCM and EtOH. Combined DCM was washed with water. Aqueous phase was back extracted with DCM. After drying over MgSO$_4$ and filtration, the crude was concentrated to give a dark greenish oil. The crude was purified on ISCO with silica gel column, 20-40% EtOAc/heptane, oily product was eluded out at 20% EtOAc (550 mg, 64%), followed closely by recovered starting material. LCMS (m/z): 283.9/285.9, RT 1.12 min.

$^1$H NMR (400 MHz, CDCl$_3$) δ 7.58 (d, J=8.6 Hz, 2H), 7.56 (s, 1H), 7.03 (d, J=8.6 Hz, 2H), 3.83 (s, 3H), 2.77 (t, J=3.6 Hz, 1H), 2.55 (s, 3H), 0.68 (dd, J=5.1, 3.5 Hz, 2H), 0.5 (dd, J=5.1, 3.5 Hz, 2H); $^{13}$C NMR (400 MHz, CDCl$_3$) δ 168.8, 153.3, 132.9, 129.2, 127.9, 122.7, 114.7, 51.8, 30.1, 20.8, 9.1.

(ii) Methyl 4-bromo-2-(N-cyclopropylacetamido)-3-methylbenzoate

To a solution of methyl 4-bromo-2-(cyclopropylamino)-3-methylbenzoate (180 mg, 0.63 mmol) in DCM (2 mL)) at ambient temperature was added DIEA (0.55 mL, 3.17 mmol), followed by the addition of acetyl chloride (0.22 mL, 3.17 mmol). The resulting solution was stirred at ambient temperature for 1 hr. The reaction mixture was diluted with EtOAc (50 mL), washed with brine twice and after drying over sodium sulfate, removal of solvent under vacuum to give methyl 4-bromo-2-(N-cyclopropylacetamido)-3-methylbenzoate (270 mg, 98% yield) as a brown color oil, the crude compound was used for next step without further purification.

LCMS (m/z): 326/328, RT 0.85 min.

(iii) 7-Bromo-1-cyclopropyl-4-hydroxy-8-methylquinolin-2(1H)-one

To a solution of methyl 4-bromo-2-(N-cyclopropylacetamido)-3-methylbenzoate (250 mg, 0.57 mmol) in THF (4 mL)) at ambient temperature was added NaHMDS (1.43 mL, 1.43 mmol). The resulting solution was stirred for 1 hr. The reaction mixture was diluted with EtOAc and water (1:1 v/v). The aqueous phase was acidified by adding 6N HCl (0.24 mL, 1.44 mmol) to make aqueous pH=3, then was extracted with ethyl acetate (3×25 mL). The combined organic phase was dried over sodium sulfate, and concentrated. The crude product was dried under high vacuum to give 7-bromo-1-cyclopropyl-4-hydroxy-8-methylquinolin-2 (1H)-one (180 mg, 95% yield).

$^1$H NMR (400 MHz, CD$_3$OD) δ 7.70 (d, J=8.61 Hz, 1H), 7.50 (d, J=8.22 Hz, 1H), 5.85 (s, 1H), 3.47 (td, J=3.28, 7.14 Hz, 1H), 2.76 (s, 3H), 1.05-1.24 (m, 2H), 0.39-0.55 (m, 2H)

LCMS (m/z): 294/296, RT 0.80 min (iv) 7-Bromo-1-cyclopropyl-4-methoxy-8-methylquinolin-2(1H)-one To a solution of 7-bromo-1-cyclopropyl-4-hydroxy-8-methylquinolin-2(1H)-one (160 mg, 0.54 mmol) in DMF (5 mL) and Acetone (3 mL) at ambient temperature was added sodium carbonate (231 mg, 2.17 mmol) and iodomethane (0.1 mL, 1.63 mmol). The resulting solution was stirred for 18 hr. The reaction mixture was diluted with EtOAc and water (1:1, v/v). The organic phase was dried over sodium sulfate, and concentrated to give crude 7-bromo-1-cyclopropyl-4-methoxy-8-methylquinolin-2(1H)-one (140 mg, 50.1% yield).

LCMS (m/z): 308/310, RT 0.95 min

(v) tert-Butyl ((S)-1-((R)-1-(1-cyclopropyl-4-methoxy-8-methyl-2-oxo-1,2-dihydroquinolin-7-yl)pyrrolidin-3-yl)ethyl)carbamate To a solution of 7-bromo-1-cyclopropyl-4-methoxy-8-methylquinolin-2(1H)-one (50 mg, 0.16 mmol) in dioxane (3 mL) was added tert-butyl ((S)-1-((R)-pyrrolidin-3-yl)ethyl)carbamate (69.5 mg, 0.32 mmol), Cesium carbonate (159 mg, 0.48 mmol), xantphos (18.7 mg, 0.032 mmol) and Pd₂(dba)₃ (14.86 mg, 0.016 mmol) at ambient temperature. The resulting mixture was heated to 110° C. in an oil bath for 3 h. The mixture was diluted with water (30 mL) and the solution was extracted with ethyl acetate (3×15 mL), the combined organic phase was dried over sodium sulfate, and concentrated. The residue was purified by ISCO eluting with 0-20-50-100% ethyl acetate in heptane to give tert-butyl ((S)-1-((R)-1-(1-cyclopropyl-4-methoxy-8-methyl-2-oxo-1,2-dihydroquinolin-7-yl)pyrrolidin-3-yl)ethyl)carbamate (20 mg, 27.9% yield). LCMS (m/z): 442, RT 0.99 min

(vi) 7-((R)-3-((S)-1-Aminoethyl)pyrrolidin-1-yl)-1-cyclopropyl-4-methoxy-8-methylquinolin-2(1H)-one To a solution of tert-butyl ((S)-1-((R)-1-(1-cyclopropyl-4-methoxy-8-methyl-2-oxo-1,2-dihydroquinolin-7-yl)pyrrolidin-3-yl)ethyl)carbamate (20 mg, 0.045 mmol) in DCM (2 ml) was added TFA (2 mL, 26.0 mmol) at ambient temperature. The resulting mixture was stirred for 15 min and was concentrated to remove solvent. The resulting residue was purified by HPLC to give 7-((R)-3-((S)-1-aminoethyl)pyrrolidin-1-yl)-1-cyclopropyl-4-methoxy-8-methylquinolin-2(1H)-one (4.3 mg, 19.80% yield).

¹H NMR (400 MHz, CD₃OD) δ 7.58 (d, J=9.00 Hz, 1H), 6.79 (d, J=9.00 Hz, 1H), 5.71 (s, 1H), 3.84 (s, 3H), 3.46-3.57 (m, 1H), 3.25-3.40 (m, 4H), 2.38 (br. s., 1H), 2.36 (s, 4H), 2.08-2.20 (m, 1H), 1.67-1.80 (m, 1H), 1.32 (d, J=6.65 Hz, 3H), 0.99-1.21 (m, 2H), 0.33-0.52 (m, 2H)

LCMS (m/z): 342, RT 0.59 min

Example 69: 7-(6-aminopyridin-3-yl)-1-cyclopropyl-4-methoxy-8-methylquinolin-2(1H)-one The title compound was prepared in accordance with the following scheme:

(i) 7-(6-Aminopyridin-3-yl)-1-cyclopropyl-4-methoxy-8-methylquinolin-2(1H)-one A suspension of 7-bromo-1-cyclopropyl-4-methoxy-8-methylquinolin-2(1H)-one (40 mg, 0.13 mmol), 2-aminopyridine-5-boronicester (57.1 mg, 0.26 mmol), Tetrakis (12.00 mg, 10.38 µmol), NaHCO₃ (43.6 mg, 0.52 mmol) in dioxane (2 mL) and Water (2 mL) was purged with nitrogen for 5 min. The resulting mixture was stirred at 100° C. in an oil bath for 4 h. The suspension was diluted with water, and was extracted with ethyl acetate (2×10 mL). The combined organic phase was dried over sodium sulfate, and concentrated. The resulting residue was purified by HPLC to give 7-(6-aminopyridin-3-yl)-1-cyclopropyl-4-methoxy-8-methylquinolin-2(1H)-one (6.8 mg, 11.43% yield).

¹H NMR (400 MHz, CD₃OD) δ 8.06 (dd, J=2.15, 9.20 Hz, 1H), 7.83-7.97 (m, 2H), 7.07-7.28 (m, 2H), 5.99 (s, 1H), 3.99 (s, 3H), 3.49 (qd, J=3.49, 7.14 Hz, 1H), 2.57 (s, 3H), 1.16-1.33 (m, 2H), 0.51-0.67 (m, 2H)

LCMS (m/z): 322, RT 0.58 min

Example 70: 7-(6-aminopyridin-3-yl)-1-cyclopropyl-4-methoxy-3,8-dimethylquinolin-2(1H)-one The title compound was prepared in accordance with the following scheme:

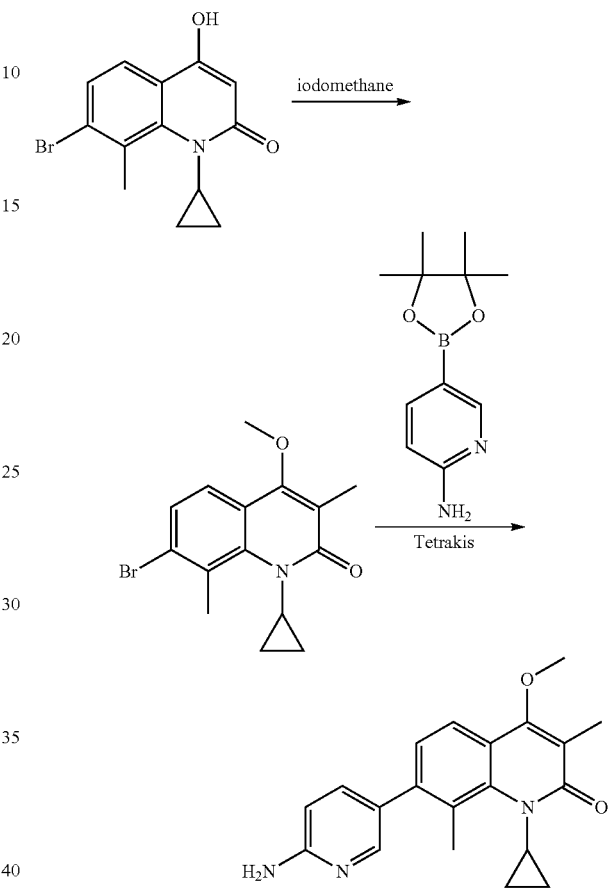

(i) 7-Bromo-1-cyclopropyl-4-methoxy-3,8-dimethylquinolin-2(1H)-one

To a solution of 7-bromo-1-cyclopropyl-4-hydroxy-8-methylquinolin-2(1H)-one (160 mg, 0.544 mmol) in DMF (5 mL) and acetone (3 mL) at ambient temperature was added sodium carbonate (231 mg, 2.176 mmol) and iodomethane (0.102 mL, 1.632 mmol). The resulting solution was stirred for 18 hr. The reaction mixture was diluted with EtOAc and water (1:1, v/v). The organic phase was dried over sodium sulfate, and concentrated to give crude 7-bromo-1-cyclopropyl-4-methoxy-3,8-dimethylquinolin-2(1H)-one (40 mg, 0.124 mmol, 22.8% yield).

LCMS (m/z): 322/324.

(ii) 7-(6-Aminopyridin-3-yl)-1-cyclopropyl-4-methoxy-3,8-dimethylquinolin-2(1H)-one A suspension of 7-bromo-1-cyclopropyl-4-methoxy-3,8-dimethylquinolin-2(1H)-one (40 mg, 0.130 mmol), 2-aminopyridine-5-boronicester (57.1 mg, 0.260 mmol), tetrakis (12 mg, 10.38 µmol), NaHCO₃ (43.6 mg, 0.519 mmol) in dioxane (2 mL) and water (2 mL) was purged with nitrogen for 5 min. The resulting mixture was stirred at 100° C. in an oil bath for 4 h. The suspension was diluted with water, and was extracted with ethyl acetate (10 mL×2). The organic phase was dried over sodium sulfate, and concentrated. The resulting residue was purified by HPLC to give 7-(6-aminopyridin-3-yl)-1-cyclopropyl-4-methoxy-3,8-dimethylquinolin-2(1H)-one (2 mg, 3.92 µmol, 3.02% yield).

$^1$H NMR (400 MHz, CD$_3$OD) 1H NMR (400 MHz, CD$_3$OD) δ 7.97 (dd, J=2.15, 9.19 Hz, 1H), 7.83 (s, 1H), 7.68 (d, J=8.22 Hz, 1H), 7.14 (d, J=8.22 Hz, 1H), 7.04 (d, J=9.39 Hz, 1H), 3.83 (s, 3H), 3.46 (qd, J=3.49, 7.14 Hz, 1H), 2.48 (s, 3H), 2.04 (s, 3H), 1.10-1.23 (m, 2H), 0.44-0.58 (m, 2H)

LCMS (m/z): 336, RT 0.66 min

Example 71: 7-((R)-3-((S)-1-aminoethyl)pyrrolidin-1-yl)-4-(benzyloxy)-1-cyclopropyl-8-methylquinolin-2(1H)-one TFA salt

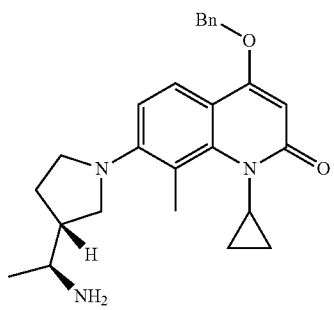 [SMILES: Cc1c(N2CC[C@@H]([C@H](C)N)C2)ccc2c(OCc3ccccc3)cc(=O)n(C3CC3)c12]

The title compound was prepared in accordance with the following scheme:

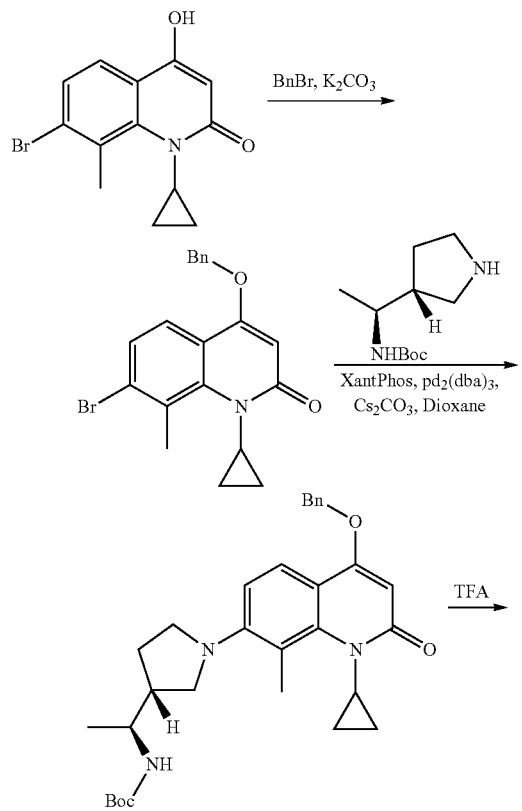

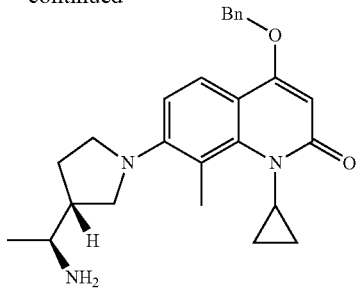

(i) 4-(benzyloxy)-7-bromo-1-cyclopropyl-8-methylquinolin-2(1H)-on 7-bromo-1-cyclopropyl-4hydroxyl-8-methylquinolin-2(1H)-one (186 mg, 0.633 mmol) was dissolved in acetone (16 mL), and to the resulting solution was added K$_2$CO$_3$ (656 mg, 4.75 mmol) and benzyl bromide (0.07 mL, 0.589 mmol). The mixture was stirred under reflux for 3 hr. After filtration to remove solid, the solvent was removed under vacuum and the residue was purified by FCC (0-60% EtOAc/heptane) to give title compound (60 mg, 23.43% yield).

$^1$H NMR (400 MHz, CD$_3$OD) δ ppm 7.70 (d, J=8.61 Hz, 1H), 7.46-7.53 (m, 3H), 7.34-7.45 (m, 3H), 6.07 (s, 1H), 5.22 (s, 2H), 3.45-3.56 (m, 1H), 2.77 (s, 3H), 1.12-1.24 (m, 2H), 0.42-0.54 (m, 2H)

LCMS (m/z): 384.1, 386.3, RT=1.16 min (ii) tert-butyl ((S)-1-((R)-1-(4-(benzyloxy)-1-cyclopropyl-8-methyl-2-oxo-1,2-dihydroquinolin-7-yl)pyrrolidin-3-yl)ethyl)carbamate To a suspension of i (30 mg, 0.078 mmol)) in dioxane (781 µL) was added tert-butyl ((S)-1-((R)-pyrrolidin-3-yl)ethyl)carbamate (30 mg, 0.078 mmol)), Cs$_2$CO$_3$ (50.9 mg, 0.156 mmol), xantphos (11.75 mg, 0.020 mmol) and Pd$_2$(dba)$_3$ (7.15 mg, 7.81 µmol) at ambient temperature. The resulting mixture was purged with nitrogen for 5 min and was heated at 110° C. for 2 h in an oil bath. The mixture was diluted with ethyl acetate, washed with water, dried and concentrated. The residue was purified by ISCO FCC (0-100% EtOAc/heptane) to give title compound (23 mg, 56.9% yield). LCMS (m/z): 518.4, RT=1.15 min (iii) 7-((R)-3-((S)-1-aminoethyl)pyrrolidin-1-yl)-4-(benzyloxy)-1-cyclopropyl-8-methylquinolin-2(1H)-one TFA salt II (22 mg, 0.042 mmol) was dissolved in dioxane (1 mL), and treated with HCl (0.404 mL, 4 M, 1.615 mmol). The reaction was complete in 1.5 hr. Solvent was removed under vacuum and the residue was purified by HPLC to give title compound (5 mg, 21.91% yield).

$^1$H NMR (500 MHz, DMSO-d$_6$) δ ppm 7.72 (d, J=8.83 Hz, 1H), 7.46-7.50 (m, 2H), 7.42 (t, J=7.41 Hz, 2H), 7.37 (d, J=7.57 Hz, 1H), 6.90 (d, J=8.83 Hz, 1H), 5.92 (s, 1H), 5.20 (s, 2H), 3.63 (d, J=7.25 Hz, 1H), 3.37-3.48 (m, 4H), 2.47 (s, 4H), 2.19-2.29 (m, 1H), 1.78-1.89 (m, 1H), 1.42 (d, J=6.62 Hz, 3H), 1.10-1.30 (m, 2H), 0.45-0.62 (m, 2H).

UPLC_10 min_Acidic RT=3.003 min.

LCMS-(m/z): 418.4, RT=0.74 min.

Example 72: 7-((R)-3-((S)-1-aminoethyl)pyrrolidin-1-yl)-1-cyclopropyl-4-hydroxy-8-methylquinolin-2(1H)-one TFA salt

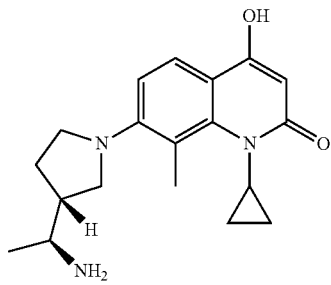 [SMILES: Cc1c(N2CC[C@@H]([C@H](C)N)C2)ccc2c(O)cc(=O)n(C3CC3)c12]

The title compound was prepared in accordance with the following scheme:

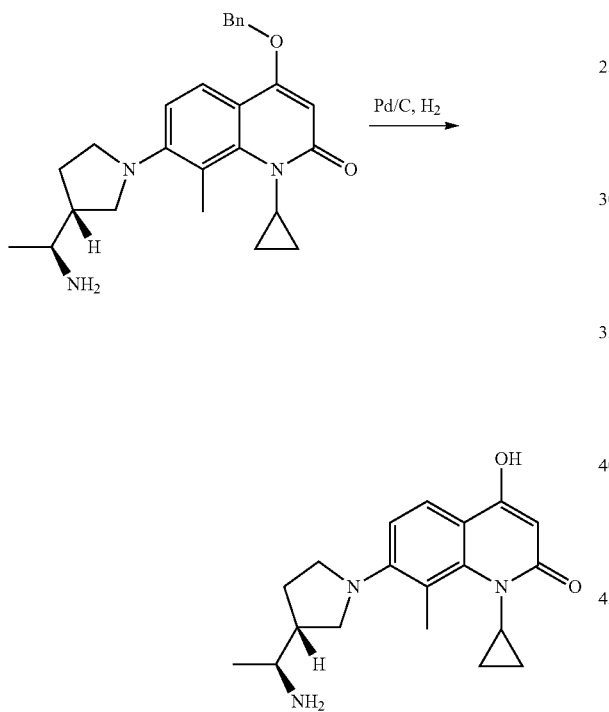

Crude 7-((R)-3-((S)-1-aminoethyl)pyrrolidin-1-yl)-4-(benzyloxy)-1-cyclopropyl-8-methylquinolin-2(1H)-one (15 mg, 0.03 mmol) was dissolved in MeOH (1.5 mL) and added Pd/C (13.57 mg, 0.013 mmol). After purged air with $H_2$, the solution stirred under $H_2$ for 20 mins. After filtration to remove solid, the solvent was removed under vacuum and the residue was purified by HPLC to give title compound (8 mg, 41.8% yield).

$^1$H NMR (500 MHz, DMSO-$d_6$) δ ppm 7.71 (d, J=8.83 Hz, 1H), 6.90 (d, J=8.83 Hz, 1H), 5.72 (s, 1H), 3.63 (d, J=7.88 Hz, 1H), 3.37-3.47 (m, 6H), 2.46 (s, 5H), 2.19-2.30 (m, 1H), 1.80-1.90 (m, 1H), 1.42 (d, J=6.62 Hz, 4H), 1.09-1.27 (m, 2H), 0.45-0.62 (m, 2H).

UPLC_10 min_Acidic RT=1.594 min

LCMS (m/z): 328.3, RT=0.49 min

Example 73: 7-((R)-3-((S)-1-aminoethyl)pyrrolidin-1-yl)-1-cyclopropyl-8-methyl-4-((tetrahydro-2H-pyran-4-yl)methoxy)quinolin-2(1H)-one TFA salt

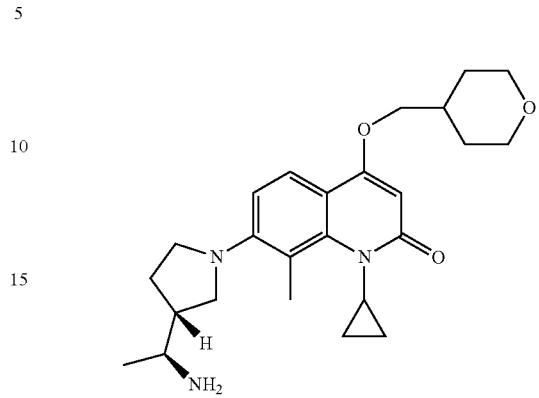

The title compound was prepared in accordance with the following scheme:

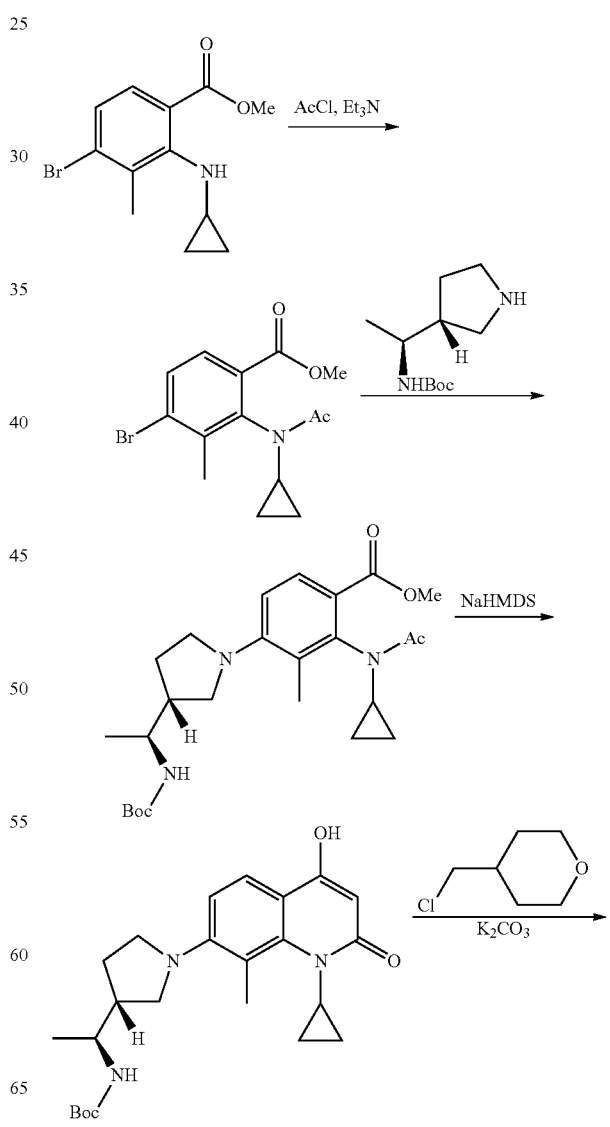

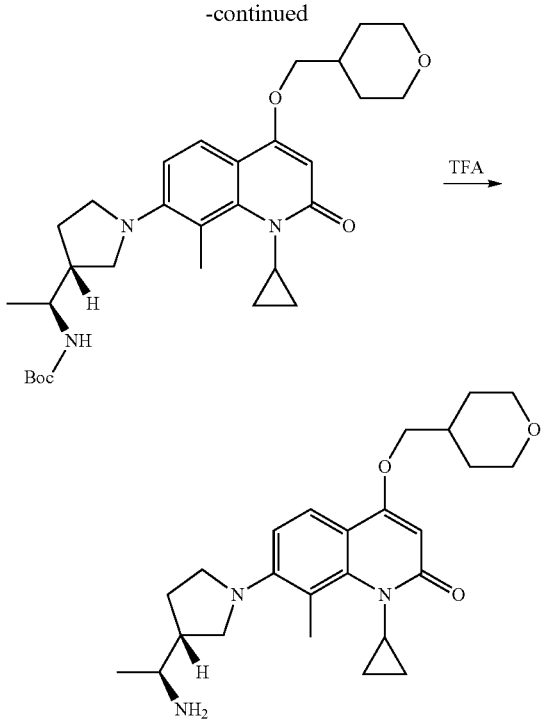

(i) methyl 4-((R)-3-((S)-1-((tert-butoxycarbonyl)amino)ethyl)pyrrolidin-1-yl)-2-(N-cyclopropylacetamido)-3-methylbenzoate To a suspension of methyl 4-bromo-2-(N-cyclopropylacetamido)-3-methylbenzoate (170 mg, 0.521 mmol) in dioxane (5.2 mL) was added tert-butyl ((S)-1-((R)-pyrrolidin-3-yl)ethyl)carbamate (190 mg, 0.886 mmol), $Cs_2CO_3$ (340 mg, 1.042 mmol), xantphos (90 mg, 0.156 mmol) and $Pd_2(dba)_3$ (47.7 mg, 0.052 mmol) at ambient temperature. The resulting mixture was purged with nitrogen for 5 min and was heated at 110° C. for 5 h in an oil bath. The mixture was diluted with ethyl acetate, filtered to remove any solid and concentrated to dryness. The residue was purified by FCC (0-100% EtOAc/heptane) to give title compound (190 mg, 71.4% yield).

LCMS (m/z): 460.3, RT=0.94 min (ii) tert-butyl ((S)-1-((R)-1-(1-cyclopropyl-4-hydroxy-8-methyl-2-oxo-1,2-dihydroquinolin-7-yl)pyrrolidin-3-yl)ethyl)carbamate I (171 mg, 0.372 mmol) was dissolved in THF (6.6 mL). To the solution was added NaHMDS (1860 μL, 1.860 mmol). The mixture was stirred at room temperature for 30 mins. The reaction mixture was concentrated to dryness under vacuum and was added EtOAc (40 mL), and water (1 mL). The mixture was cooled to 0° C. and was added HCl/Dioxane (0.5 mL, 4M, 2 mmol). The precipitate was collected and washed with EtOAc (20 mL) to give crude title compound (100 mg, 59.7% yield). LCMS (m/z): 428.3, RT=0.88 min (iii) tert-butyl ((S)-1-((R)-1-(1-cyclopropyl-8-methyl-2-oxo-4-((tetrahydro-2H-pyran-4-yl)methoxy)-1,2-dihydroquinolin-7-yl)pyrrolidin-3-yl)ethyl)carbamate A mixture of 11 (10 mg, 0.023 mmol), 4-(bromomethyl)tetrahydro-2H-pyran (12.56 mg, 0.070 mmol) and $K_2CO_3$ (6.47 mg, 0.047 mmol) in DMA (0.5 mL), stirred for 7 hr at 56° C. The reaction mixture was diluted with EtOAc (10 mL). Solid was removed by filtration, and after solvent was removed under vacuum, the residue was used in the subsequent step without further purification.

LCMS (m/z): 526.4, RT=1.06 min (iv) 7-((R)-3-((S)-1-aminoethyl)pyrrolidin-1-yl)-1-cyclopropyl-8-methyl-4-((tetrahydro-2H-pyran-4-yl)methoxy)quinolin-2(1H)-one TFA salt III (10 mg, 0.019 mmol) in DCM (2 mL) was treated with TFA (0.5 mL, 6.49 mmol) at rt for 10 mins. Solvent was removed under vacuum and the residue was purified by HPLC to give title compound (3.2 mg, 30.6% yield).

$^1$H NMR (400 MHz, $CD_3OD$) δ ppm 0.43-0.62 (m, 2H), 1.07-1.34 (m, 3H), 1.42 (d, J=6.65 Hz, 3H), 1.54 (qd, J=12.39, 4.30 Hz, 2H), 1.74-1.90 (m, 3H), 2.11-2.30 (m, 2H), 2.42-2.53 (m, 4H), 3.38-3.56 (m, 7H), 3.57-3.68 (m, 1H), 3.94-4.07 (m, 4H), 5.80 (s, 1H), 6.90 (d, J=9.00 Hz, 1H), 7.70 (d, J=8.61 Hz, 1H) UPLC_10 min_Acidic RT=2.511 min LCMS (m/z): 426.3, RT=0.69 min Example 74: 7-((R)-3-((S)-1-aminoethyl)pyrrolidin-1-yl)-1-cyclopropyl-4-(2-(dimethylamino)ethoxy)-8-methylquinolin-2(1H)-one TFA salt

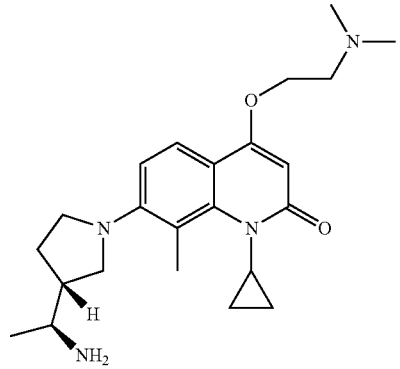 [SMILES: Cc1c(N2CC[C@@H]([C@H](C)N)C2)ccc2c(OCCN(C)C)cc(=O)n(C3CC3)c12]

The title compound was prepared in accordance with the following scheme:

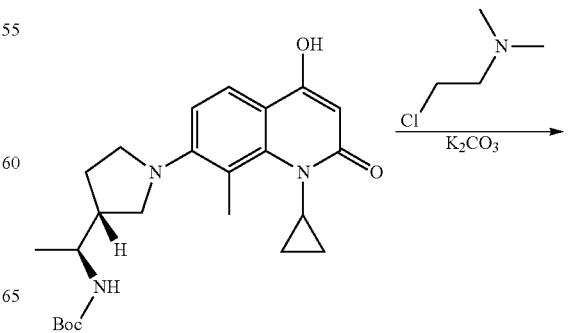

-continued

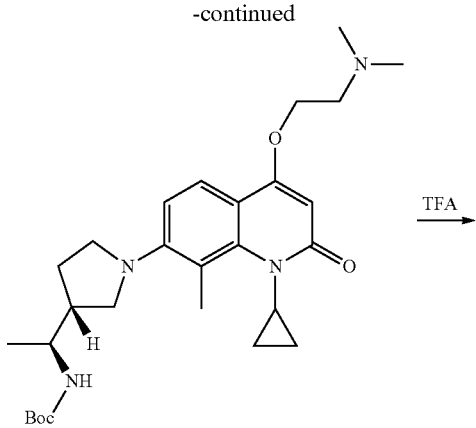

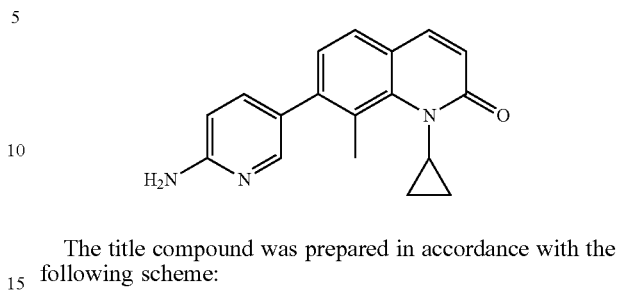

Example 75: 7-(6-aminopyridin-3-yl)-1-cyclopropyl-8-methylquinolin-2(1H)-one

The title compound was prepared in accordance with the following scheme:

(i) tert-butyl ((S)-1-((R)-1-(1-cyclopropyl-4-(2-(dimethylamino)ethoxy)-8-methyl-2-oxo-1,2-dihydroquinolin-7-yl)pyrrolidin-3-yl)ethyl)carbamate tert-Butyl ((S)-1-((R)-1-(1-cyclopropyl-4-hydroxy-8-methyl-2-oxo-1,2-dihydroquinolin-7-yl)pyrrolidin-3-yl)ethyl)carbamate (10 mg, 0.023 mmol), 2-chloro-N,N-dimethylethanamine (10.11 mg, 0.070 mmol) and K$_2$CO$_3$ (6.47 mg, 0.047 mmol) in DMA (0.5 mL) were stirred at 56° C. for 7 hr. The reaction mixture was diluted with 10 mL EtOAc. Solid was removed by filtration, and after solvent was removed under vacuum, the residue was used in the subsequent step without further purification LCMS (m/z): 499.4, RT=0.76 min (ii) 7-((R)-3-((S)-1-aminoethyl)pyrrolidin-1-yl)-1-cyclopropyl-4-(2-(dimethylamino)ethoxy)-8-methylquinolin-2(1H)-one TFA salt I (10 mg, 0.020 mmol) in CH$_2$Cl$_2$ (2 mL) was treated with TFA (0.5 mL, 6.49 mmol) at rt for 10 mins. Solvent was removed under vacuum and the residue was purified by HPLC to give title compound (2.8 mg, 27% yield).

$^1$H NMR (400 MHz, CD$_3$OD) δ ppm 0.42-0.61 (m, 2H), 1.12-1.34 (m, 3H), 1.42 (d, J=6.65 Hz, 3H), 1.77-1.91 (m, 1H), 2.24 (ddd, J=11.74, 7.04, 4.70 Hz, 1H), 2.46 (s, 3H), 2.49-2.55 (m, 1H), 3.03 (s, 6H), 3.35-3.51 (m, 5H), 3.59-3.68 (m, 1H), 3.69-3.76 (m, 2H), 4.46-4.51 (m, 2H), 5.87 (s, 1H), 6.90 (d, J=8.61 Hz, 1H), 7.79 (d, J=9.00 Hz, 1H)

LCMS (m/z): 399.4, RT=0.49 min

UPLC_10 min_Acidic RT=1.289 min

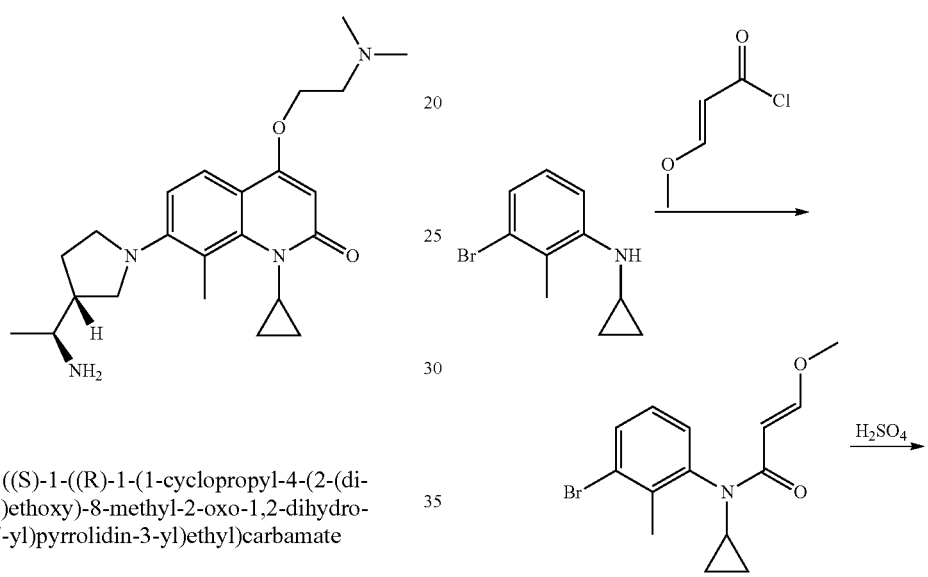

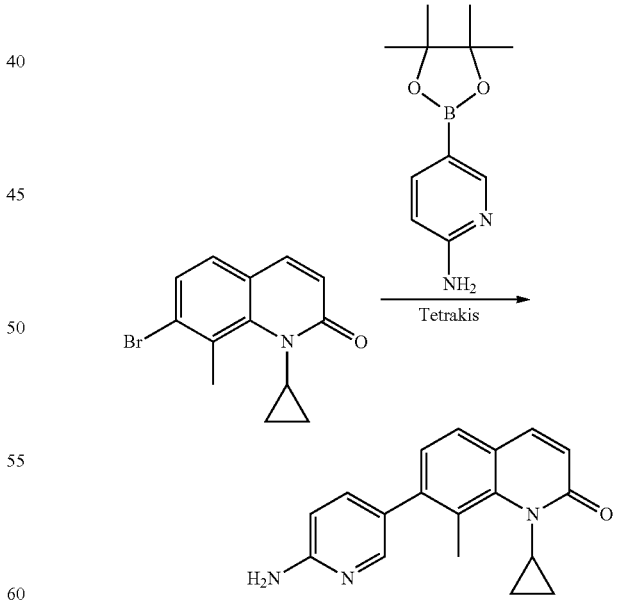

(i) (E)-N-(3-bromo-2-methylphenyl)-N-cyclopropyl-3-methoxyacrylamide

To an ice cold solution of 3-bromo-N-cyclopropyl-2-methylaniline (130 mg, 0.57 mmol) in pyridine (3 mL) was added (E)-3-ethoxyacryloyl chloride (348 mg, 2.59 mmol). The mixture was stirred at 0° C. for 1 h and ambient temperature for 16 h. The suspension was diluted with water, and was extracted with ethyl acetate (2×40 mL). The organic phase was dried over sodium sulfate, and concentrated. The resulting residue was used for next step without purification. LCMS (m/z): 324/326, RT 1.01 min.

(ii) 7-Bromo-1-cyclopropyl-8-methylquinolin-2 (1H)-one

The solution of (E)-N-(3-bromo-2-methylphenyl)-N-cyclopropyl-3-methoxyacrylamide (120 mg, 0.37 mmol) in Pyridine (0.3 mL) was added to a flask charged with $H_2SO_4$ (0.6 mL, 11.26 mmol) at ambient temperature. The mixture was stirred at same temperature for 80 min. The reaction mixture was diluted with ethyl acetate, the resulting solution was washed with water, brine, dried over sodium sulfate, concentrated. The resulting residue was purified by ISCO eluting with 0-30-50-100% ethyl acetate in heptane to give 7-bromo-1-cyclopropyl-8-methylquinolin-2(1H)-one (28 mg, 16.3% yield)

LCMS (m/z): 278/280, RT 0.86 min (iii) 7-(6-Aminopyridin-3-yl)-1-cyclopropyl-8-methylquinolin-2(1H)-one A suspension of 7-bromo-1-cyclopropyl-8-methylquinolin-2(1H)-one (28 mg, 0.10 mmol), 2-aminopyridine-5-boronicester (44.3 mg, 0.20 mmol), Tetrakis (5.82 mg, 5.03 μmol), $NaHCO_3$ (33.8 mg, 0.40 mmol) in dioxane (2 mL) and Water (2 mL) was purged with nitrogen for 5 min. The resulting mixture was stirred at 100° C. in an oil bath for 3 h. The suspension was diluted with water, and was extracted with ethyl acetate (2×10 mL). The organic phase was dried over sodium sulfate, concentrated. The resulting residue was purified by HPLC to give 7-(6-aminopyridin-3-yl)-1-cyclopropyl-8-methylquinolin-2(1H)-one (11 mg, 25.6% yield).

$^1$H NMR (400 MHz, $CD_3OD$) 8.07 (dd, J=2.15, 9.19 Hz, 1H), 7.93 (d, J=1.56 Hz, 1H), 7.81 (d, J=9.39 Hz, 1H), 7.56 (d, J=7.83 Hz, 1H), 7.22 (d, J=7.83 Hz, 1H), 7.14 (d, J=9.39 Hz, 1H), 6.58 (d, J=9.39 Hz, 1H), 3.50-3.64 (m, 1H), 2.59 (s, 3H), 1.23-1.36 (m, 2H), 0.55-0.70 (m, 2H)

LCMS (m/z): 292, RT 0.51 min

Example 76: 7-((R)-3-((S)-1-aminoethyl)pyrrolidin-1-yl)-1-cyclopropyl-8-methylquinolin-2(1H)-one trifluoroacetic acid salt

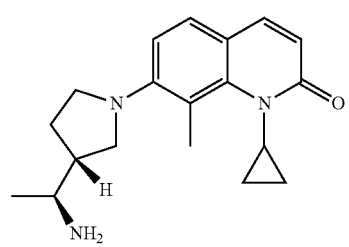 [SMILES: Cc1c(N2CC[C@@H]([C@H](C)N)C2)ccc2ccc(=O)n(C3CC3)c12]

The title compound was prepared in accordance with the following scheme:

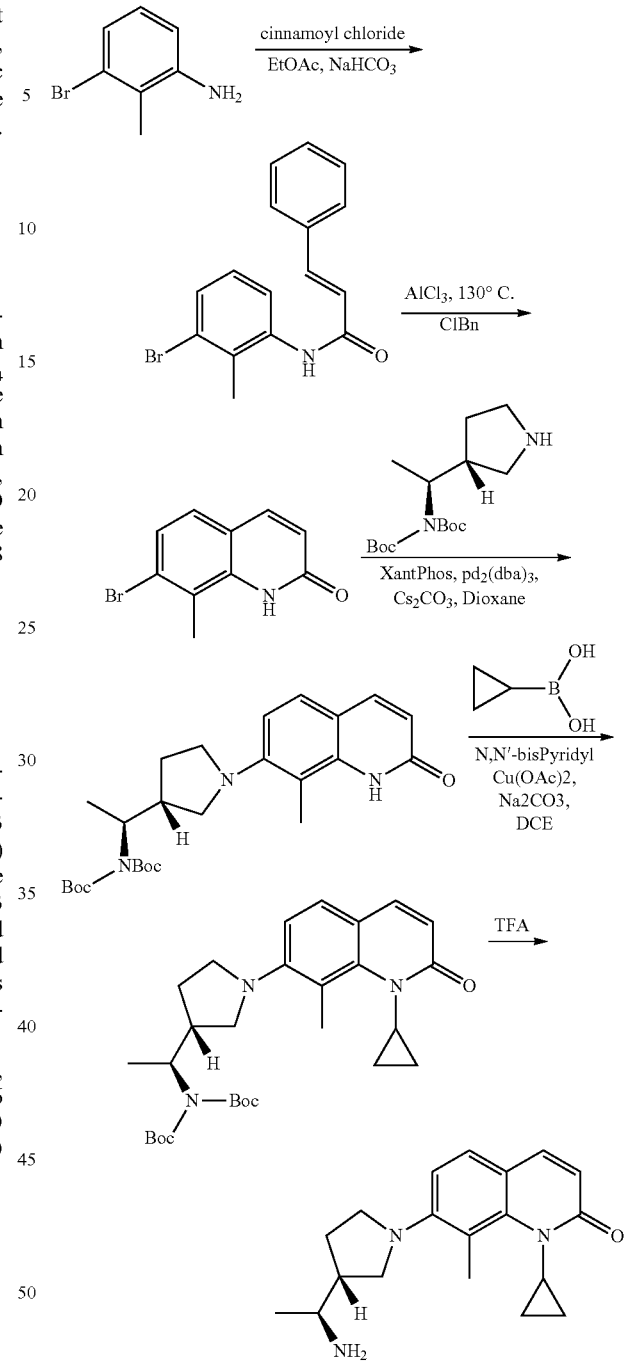

(i) N-(3-bromo-2-methylphenyl)cinnamamide

3-Bromo-2-methylaniline (7.55 g, 40.6 mmol) was dissolved in EtOAc (30 mL) at rt. $NaHCO_3$ (34.1 g, 406 mmol) was added with water (60 mL). Upon vigorous stirring, cinnamoyl chloride (7.12 g, 40.6 mmol) in EtOAc (30 mL) was added slowly. The reaction was complete in 1 hr. Most solvent was remove by vacuum. Filter to get solid which was suspended in 5% MeOH in water (40 mL). Filter and collect white solid product which was washed with MeOH in water and dried under vacuum for 16 hrs (20 g, 156% yield). The crude product was used in the next reaction without further purification. LCMS (m/z): 316.1, 318.2, RT 0.99 min ¹H NMR (400 MHz, d₆-DMSO) δ ppm 7.78 (d, J=15.7 Hz, 1H), 7.55 (d, J=3.1 Hz, 2H), 7.4 (m, 4H), 7.11 (m, 2H), 6.57 (d, J=15.6 Hz, 1H), 2.42 (s, 3H)

(ii) 7-Bromo-8-methylquinolin-2(1H)-one

I (10 g, 31.6 mmol) was suspended in chlorobenzene (40 mL) at rt. AlCl₃ (16.87 g, 127 mmol) was added. Upon vigorous stirring, temp was raised to 130 degree on hot plate. Dark brown solution in 30 min. After additional 30 min heating, SM was consumed and target product was observed. The mixture was added slowly to ice water 300 g. Filter to get solid which was washed with water, mix of ACN/water and dried o/n to get pure white solid product (3 g, 40% yield).

¹H NMR (400 MHz, d₆-DMSO) δ ppm 11.0 (s, 1H) 7.88 (d, J=8.6 Hz, 1H), 7.42 (m, 2H), 6.53 (d, J=7.8 Hz, 1H), 3.3 (s, 3H). ¹³C (376 MHz, d₆-DMSO) ppm 162.8, 141, 138.5, 127.6, 126.0, 122.3, 119, 17.3

LCMS (m/z):], 238.0, 240.1 RT 0.71 min (iii) 7-((R)-3-((S)-1-(bis(tert-butoxycarbonyl)amino)ethyl)pyrrolidin-1-yl)-8-methyl-2-oxo-1,2-dihydroquinoline To a suspension of ii (150 mg, 0.630 mmol)) in dioxane (6300 µl) was added ii (150 mg, 0.630 mmol)), Cs₂CO₃ (308 mg, 0.945 mmol)), xantphos (219 mg, 0.378 mmol) and Pd₂(dba)₃ (133 mg, 0.145 mmol)) at ambient temperature. The resulting mixture was purged with nitrogen for 5 min and was heated at 110° C. for 2 h in an oil bath. The mixture was diluted with ethyl acetate, washed with water, dried, and concentrated. The residue was purified by silica gel chromatography, eluting with 0-100% ethyl acetate in heptane to give v as a mixture of v and mono-Boc protected form of product (230 mg, 31% yield).

LCMS (m/z): 472.2, RT 1.13 min (iv) 7-((R)-3-((S)-1-(bis(tert-butoxycarbonyl)amino)ethyl)pyrrolidin-1-yl)-1-cyclopropyl-8-methyl-2-oxo-1,2-dihydroquinoline To a solution of iii (270 mg, 0.727 mmol) in DCE (14 mL) was added cyclopropylboronic acid (250 mg, 2.9 mmol), Cu(OAc)₂ (528 mg, 2.9 mmol), 2,2'-bipyridine (454 mg, 2.91 mmol) and Cs₂CO₃ (947 mg, 2.91 mmol). The mix was stirred for 10 mins and heated at 80-90° C. for 2 hr. Another batch of cyclopropylboronic acid (250 mg, 2.9 mmol) was added. The reaction was cooled to room temperature and stirred overnight. The reaction mixture was dilute with EtOAc followed by aqueous work up. Purification by FCC gave title compound (140 mg, 23.4% yield) as a mixture of starting material product.

LCMS (m/z): 412.3, RT 0.98 min (v) 7-((R)-3-((S)-1-aminoethyl)pyrrolidin-1-yl)-1-cyclopropyl-8-methylquinolin-2(1H)-one TFA salt To iv was added DCM (1 mL) and followed by TFA (1 mL). After 5 mins, solvent was removed and the residue was purified by HPLC to give title compound.

¹H NMR (400 MHz, CD₃OD) δ ppm 7.68 (d, J=9.39 Hz, 1H), 7.34 (d, J=8.22 Hz, 1H), 6.91 (d, J=8.61 Hz, 1H), 6.34 (d, J=9.00 Hz, 1H,), 3.58-3.68 (m, 1H), 3.51 (tt, J=7.04, 3.72 Hz, 1H), 3.39-3.45 (m, 3H), 3.34 (br. s., 2H), 2.50-2.53 (m, 1H), 2.48 (s, 3H), 2.19-2.30 (m, 1H), 1.77-1.92 (m, 1H), 1.42 (d, J=6.65 Hz, 3H), 1.14-1.35 (m, 3H), 0.43-0.67 (m, 2H)

LCMS (m/z): 312.3, RT=0.53
UPLC_10 min_Acidic RT=1.78 min

Example 77. 7-(6-Aminopyridin-3-yl)-1-cyclopropyl-3-hydroxy-8-methylquinolin-2(1H)-one TFA salt

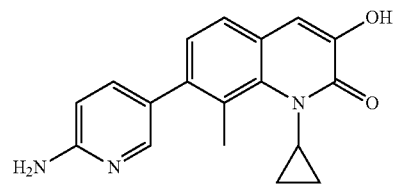 [SMILES: Cc1c(-c2ccc(N)nc2)ccc2cc(O)c(=O)n(C3CC3)c12]

The title compound was prepared in accordance with the following scheme:

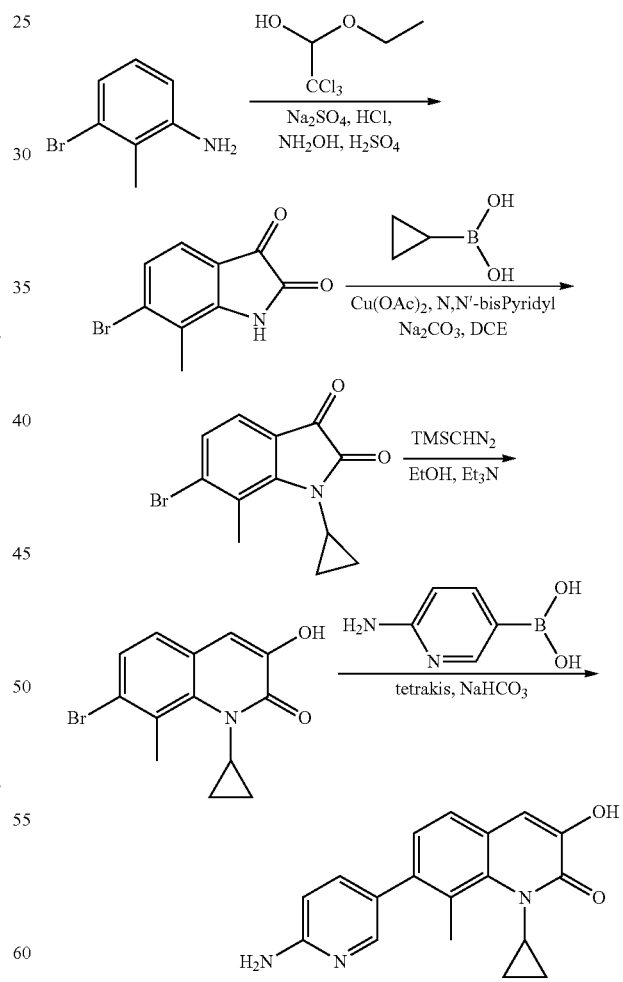

(i) 6-Bromo-7-methylindoline-2,3-dione

Chloral alcoholate (3.85 g, 16.93 mmol) and Na₂SO₄ (25.2 g, 177 mmol) were dissolved in water (91 mL).

3-bromo-2-methylaniline (3 g, 16.12 mmol) was added to the solution followed by conc HCl (1.47 mL, 48.4 mmol) aqueous solution and NH₂OH.HCl (3.36 g, 48.4 mmol). The mixture was refluxed for 15 mins and stirring was continued for additional 1 hr at rt. The precipitate was collected by filtration, washed with water and dried under vacuum.

LCMS (m/z): 257.0, 259.0, RT=0.70 min. This precipitate was dissolved in conc H₂SO₄ (9.45 mL, 177 mmol) and the solution was heated at 80° C. for 15 mins. After cooling down to rt, the mixture was poured into ice-water mixture and the precipitate was collected, washed with water and dried under vacuum to give title compound (3.25 g, 81% yield). LCMS (m/z): 240.2, 242.0, RT=0.71 min.

¹H NMR (400 MHz, CD₃OD) δ ppm 7.33-7.38 (m, 1H), 7.28-7.31 (m, 1H), 2.31 (s, 1H).

(ii) 6-Bromo-1-cyclopropyl-7-methylindoline-2,3-dione

To a solution of i (2 g, 8.33 mmol) in DCE (83 mL) was added cyclopropylboronic acid (0.72 g, 8.33 mmol), Cu(OAc)₂ (1.513 g, 8.33 mmol), 2,2'-bipyridine (1.301 g, 8.33 mmol) and Cs₂CO₃ (5.43 g, 16.66 mmol). The mix was stirred for 10 mins and heated at 80-90° C. for for 2 hr. Additional cyclopropylboronic acid (0.72 g, 8.33 mmol) was added. The reaction was cooled to room temperature and stirred overnight. The reaction mixture was dilute with EtOAc followed by aqueous workup. Purification by FCC gave ii (600 mg, 1.178 mmol, 14.14% yield) as a mixture of product and ligand (mol ratio=1:1.6).

¹H NMR (400 MHz, CD₃OD) δ ppm 8.65 (d, J=4.30 Hz, 3H), 8.30 (d, J=7.83 Hz, 3H), 7.94 (td, J=7.73, 1.76 Hz, 3H), 7.41-7.48 (m, 3H), 7.37 (d, J=8.22 Hz, 1H), 7.29 (d, J=7.83 Hz, 1H), 7.11 (d, J=7.83 Hz, 1H), 3.05 (tt, J=6.95, 3.62 Hz, 1H), 2.98 (dt, J=6.95, 3.37 Hz, 1H), 2.77 (s, 3H), 2.74 (s, 1H), 1.07-1.19 (m, 3H), 0.95-1.03 (m, 2H), 0.87 (d, J=3.91 Hz, 1H)

LCMS (m/z): 280.0, 282.0, RT=0.88 min (iii) 7-Bromo-1-cyclopropyl-3-hydroxy-8-methylquinolin-2(1H)-one II (243 mg, 0.477 mmol), TMSCHN₂/Hexane (0.21 mL, 0.42 mmol) and TEA (0.067 mL, 0.477 mmol) were dissolved in ethanol (3 mL) and placed under N₂. The reaction was stirred for 15 hr. Solvent was removed. The residue was dissolved in EtOAc (20 mL), washed with 1 N HCl (3×2 mL), followed by brine and dried over Na₂SO₄. The organic phase was concentrated to give crude title compound.

LCMS (m/z): 294.0, 296.0, RT=0.89 min (iv) 7-(6-Aminopyridin-3-yl)-1-cyclopropyl-3-hydroxy-8-methylquinolin-2(1H)-one TFA salt A suspension of iii (68 mg, 0.231 mmol), 2-aminopyridine-5-boronic ester (102 mg, 0.462 mmol), tetrakis (26.7 mg, 0.023 mmol)), and NaHCO₃ (58.3 mg, 0.694 mmol)) in dioxane (1 mL) and water (1 mL) was purged with nitrogen for 5 min. The resulting mixture was stirred at 110° C. in an oil bath for 1 h. The suspension was added saturated aq. NH₄Cl (5 mL) and was extracted with ethyl acetate (20 mL×2). The organic phase was dried and concentrated. The resulting residue was purified by HPLC to give the title compound (19 mg, 18.14% yield).

¹H NMR (500 MHz, CD₃OD) δ ppm 8.07 (dd, J=9.14, 1.89 Hz, 1H), 7.92 (d, J=1.89 Hz, 1H), 7.43 (d, J=7.88 Hz, 1H), 7.16 (dd, J=16.71, 8.51 Hz, 2H), 7.01 (s, 1H), 3.60-3.68 (m, 1H), 2.61 (s, 3H), 1.28-1.36 (m, 2H), 0.62-0.69 (m, 2H)

LCMS (m/z): 308.2, RT=0.51 min
UPLC_10 min_Acidic RT=1.489 min

Example 78. 7-(6-Aminopyridin-3-yl)-1-cyclopropyl-3-methoxy-8-methylquinolin-2(1H)-one TFA salt

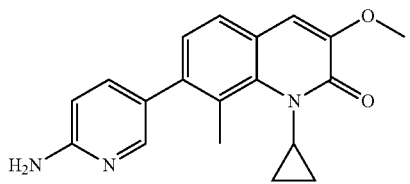 [SMILES: COc1cc2ccc(-c3ccc(N)nc3)c(C)c2n(C2CC2)c1=O]

The title compound was prepared in accordance with the following scheme:

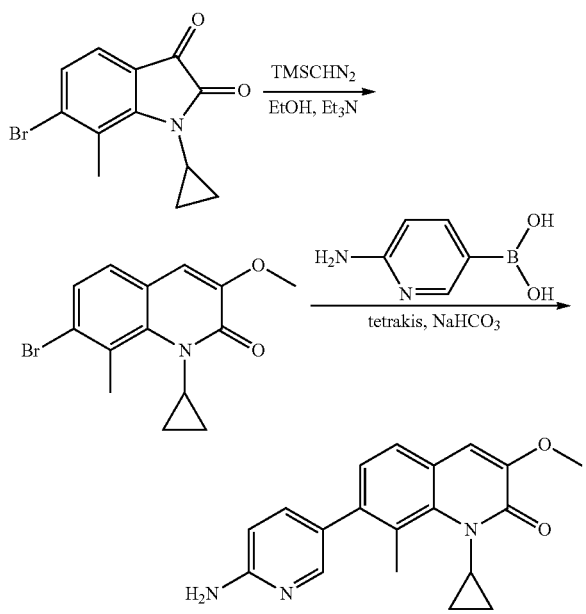

(i) 7-Bromo-1-cyclopropyl-3-methoxy-8-methylquinolin-2(1H)-one

6-Bromo-1-cyclopropyl-7-methylindoline-2,3-dione (100 mg, 0.357 mmol), TMSCHN₂/Hexane (178 μl, 0.357 mmol), and TEA (100 μl, 0.714 mmol) were dissolved in ethanol (3570 μl) and placed under N₂. Stirred for 6 hr. The solvent was removed under vacuum, and the residue was diluted with DCM (30 mL), washed with saturated NH₄Cl, brine, dried over MgSO₄, and concentrated to give the residue i which was used for the subsequent step without further purification.

LCMS (m/z): 308.0, 310.0, RT=0.88 min (ii) 7-(6-Aminopyridin-3-yl)-1-cyclopropyl-3-methoxy-8-methylquinolin-2(1H)-one TFA salt A suspension of i (80 mg, 0.260 mmol), 2-aminopyridine-5-boronic ester (86 mg, 0.389 mmol), tetrakis (15.00 mg, 0.013 mmol)), NaHCO₃ (65.4 mg, 0.779 mmol)) in dioxane (1.5 mL) and water (1.5 mL) was purged with nitrogen for 5 min. The resulting mixture was stirred at 110° C. in an oil bath for 1 h. The suspension was diluted with water, and extracted with ethyl acetate (20 mL×2). The organic phase was dried and concentrated. The resulting residue was purified by HPLC to give title compound (32 mg, 27.7% yield).

¹H NMR (500 MHz, CD₃OD) δ ppm 8.08 (dd, J=9.14, 2.21 Hz, 1H), 7.93 (d, J=1.89 Hz, 1H), 7.53 (d, J=8.20 Hz, 1H), 7.22 (d, J=7.88 Hz, 1H), 7.13-7.17 (m, 2H), 3.93 (s, 3H), 3.60-3.67 (m, 1H), 2.61 (s, 3H), 1.28-1.35 (m, 2H), 0.64 (dd, J=2.52, 1.26 Hz, 2H)

LCMS (m/z): 322.3, RT=0.49 min

UPLC_10 min_Acidic RT=1.569 min

Example 79. 7-((R)-3-((S)-1-aminoethyl)pyrrolidin-1-yl)-1-cyclopropyl-3-hydroxy-8-methylquinolin-2(1H)-one TFA salt

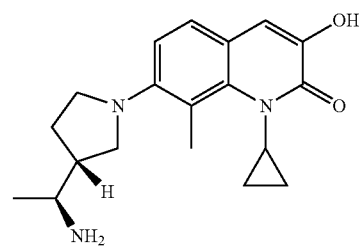 [SMILES: Cc1c(N2CC[C@@H]([C@H](C)N)C2)ccc2cc(O)c(=O)n(C3CC3)c12]

The title compound was prepared in accordance with the following scheme:

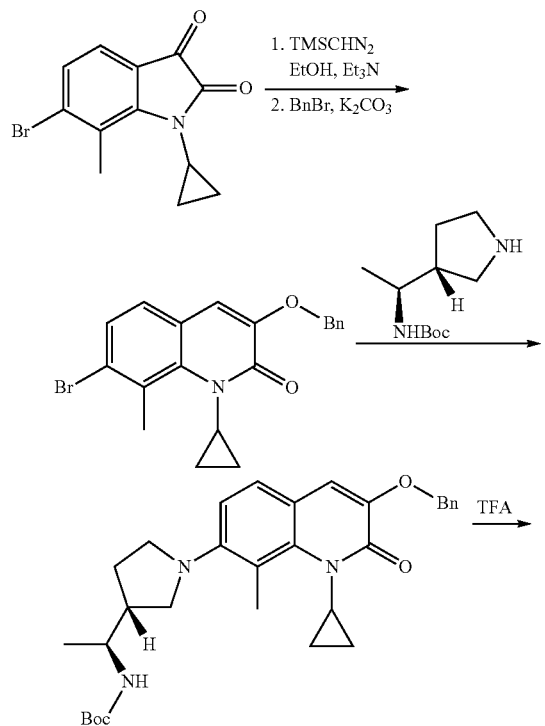

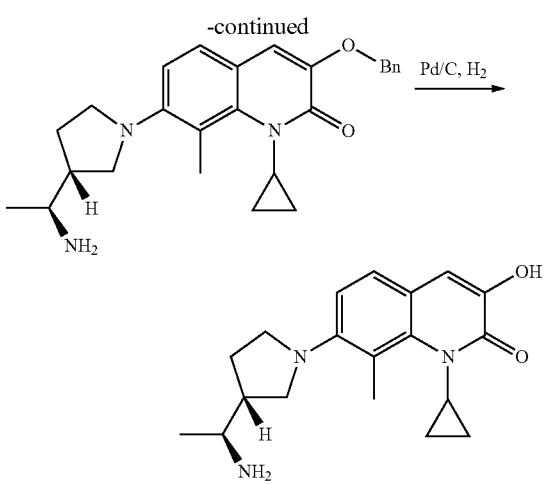

(i) 3-(Benzyloxy)-7-bromo-1-cyclopropyl-8-methylquinolin-2(1H)-one

6-Bromo-1-cyclopropyl-7-methylindoline-2,3-dione (300 mg, 0.589 mmol), TMSCHN₂/hexane (0.295 mL, 0.589 mmol), and TEA (0.164 mL, 1.178 mmol) were dissolved in ethanol (2 mL) and placed under N₂. The reaction was stirred for 15 hr. The reaction mixture was concentrated and dried under vacuum for 2 hr. The residue was dissolved in acetone (3 mL), and to the resulting solution was added K₂CO₃ (407 mg, 2.95 mmol) and benzyl bromide (0.07 mL, 0.589 mmol). The resulting mixture was stirred under reflux for 30 min. After filtration to remove solid, the solvent was removed under vacuum to dryness. The residue was dissolved in 30 mL EtOAc, washed with 1N HCl (3 mL×3), brine, dried over Na₂SO₄ and concentrated. The residue was purified by FCC (0-30% EtOAc/Heptane) to give title compound (90 mg, 39.8% yield).

LCMS (m/z): 384.2, 386.1, RT=1.10 min (ii) tert-butyl ((S)-1-((R)-1-(3-(benzyloxy)-1-cyclopropyl-8-methyl-2-oxo-1,2-dihydroquinolin-7-yl)pyrrolidin-3-yl)ethyl)carbamate To a suspension of i (90 mg, 0.234 mmol) in dioxane (3444 µL) was added tert-butyl ((S)-1-((R)-pyrrolidin-3-yl)ethyl)carbamate (90 mg, 0.234 mmol)), Cs₂CO₃ (114 mg, 0.351 mmol)), xantphos (81 mg, 0.141 mmol)) and Pd₂(dba)₃ (49.3 mg, 0.054 mmol)) at ambient temperature. The resulting mixture was purged with nitrogen for 5 min and was heated at 110° C. for 2 h in an oil bath. The mixture was diluted with ethyl acetate, washed with water, dried and concentrated. The residue was purified by FCC (0-40% EtOAc/Heptane) to give title compound (85 mg, 59.6% yield).

LCMS (m/z): 518.4, RT=1.01 min (iii) 7-((R)-3-((S)-1-aminoethyl)pyrrolidin-1-yl)-1-cyclopropyl-3-hydroxy-8-methylquinolin-2(1H)-one TFA salt II was dissolved in ethanol (4 mL), and added Pd/C (34.9 mg, 0.033 mmol). After purged with N₂ the mixture was stirred under H₂ for 90 min. After filtration to remove solid, solvent was removed under vacuum and the residue was added DCM (1 mL) and followed by TFA (1 mL). After 10 mins, the solvent was removed under vacuum and the residue was purified by HPLC to give title compound.

¹H NMR (500 MHz, METHANOL-d₄) δ ppm 7.23 (d, J=8.20 Hz, 1H), 6.89-6.98 (m, 2H), 3.56-3.62 (m, 1H), 3.50-3.55 (m, 1H), 3.35-3.44 (m, 3H), 3.29 (dd, J=3.31, 1.73 Hz, 2H), 2.53 (s, 3H), 2.50 (d, J=8.20 Hz, 1H), 2.20-2.30 (m, 1H), 1.85 (dd, J=12.14, 8.99 Hz, 1H), 1.43 (d, J=6.62 Hz, 3H), 1.18-1.34 (m, 2H), 0.47-0.65 (m, 2H)

LCMS (m/z): 328.2, RT=0.50 min

UPLC_10 min_Acidic RT=1.474 min

Example 80: 7-((R)-3-((S)-1-aminoethyl)pyrrolidin-1-yl)-1-cyclopropyl-3-methoxy-8-methylquinolin-2(1H)-one TFA salt

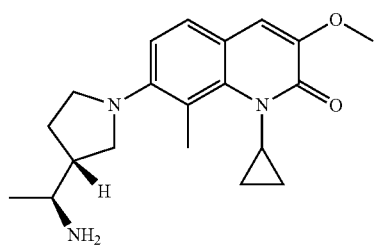 [SMILES: COc1cc2ccc(N3CC[C@@H]([C@H](C)N)C3)c(C)c2n(C2CC2)c1=O]

The title compound was prepared in accordance with the following scheme:

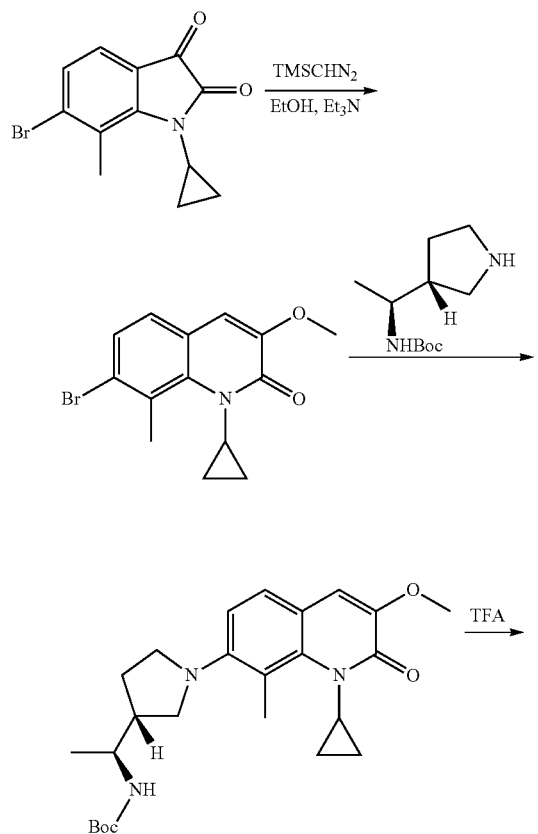

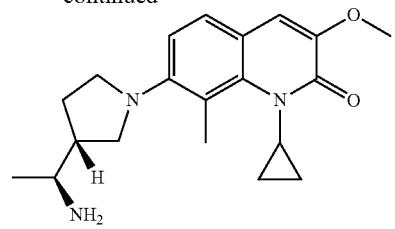

(i) 7-Bromo-1-cyclopropyl-3-methoxy-8-methylquinolin-2(1H)-one

6-Bromo-1-cyclopropyl-7-methylindoline-2,3-dione (300 mg, 0.589 mmol), TMSCHN₂/hexane (0.295 mL, 0.589 mmol), and TEA (0.164 mL, 1.178 mmol) were dissolved in ethanol (2 mL) and placed under N₂. The reaction was stirred at rt for 15 hr. Solvent was removed under vacuum. The residue was dissolved in EtOAc (30 mL), washed with 1N HCl (3 mL×3), brine, dried over Na₂SO₄ and concentrated. The residue was purification by FCC (0-30% EtOAc/heptane) gave title compound (58 mg, 32% yield).

LCMS (m/z): 308.1, 310.0, RT=0.88 min (ii) tert-butyl ((S)-1-((R)-1-(1-cyclopropyl-3-methoxy-8-methyl-2-oxo-1,2-dihydroquinolin-7-yl)pyrrolidin-3-yl)ethyl)carbamate To a suspension of i (56 mg, 0.182 mmol) in dioxane (2672 µL) was added tert-butyl ((S)-1-((R)-pyrrolidin-3-yl)ethyl)carbamate (56 mg, 0.182 mmol), Cs₂CO₃ (89 mg, 0.273 mmol)), xantphos (63.1 mg, 0.109 mmol)) and Pd₂(dba)₃ (38.3 mg, 0.042 mmol) at ambient temperature. The resulting mixture was purged with nitrogen for 5 min and heated at 110° C. for 2 h in an oil bath. The mixture was diluted with ethyl acetate, washed with water, dried and concentrated. The residue was purification by Fcc (0-50% EtOAc/heptane) gave title compound ii (76 mg, 90% yield).

LCMS (m/z): 442.4, RT=0.82 min (iii) 7-((R)-3-((S)-1-aminoethyl)pyrrolidin-1-yl)-1-cyclopropyl-3-methoxy-8-methylquinolin-2(1H)-one TFA salt Compound ii was dissolved in DCM (1 mL) and followed by addition of TFA (1 mL). After 10 mins, solvent was removed under vacuum. The residue was purified by HPLC to give title compound (47 mg, 58.8% yield).

¹H NMR (500 MHz, CD₃OD) δ ppm 7.32 (d, J=8.51 Hz, 1H), 7.05 (s, 1H), 6.95 (d, J=8.51 Hz, 1H), 3.87 (s, 3H), 3.50-3.61 (m, 2H), 3.35-3.46 (m, 3H), 3.31 (br. s., 1H), 2.52 (s, 3H), 2.50 (br. s., 1H), 2.21-2.30 (m, 1H), 1.80-1.90 (m, 1H), 1.44 (d, J=6.62 Hz, 3H), 1.18-1.33 (m, 2H), 0.46-0.63 (m, 2H)

LCMS (m/z): 342.3, RT=0.50 min

UPLC_10 min_Acidic RT=1.586 min

Example 81: (S)-4-(aminomethyl)-7-(3-aminopyrrolidin-1-yl)-1-cyclopropyl-6-fluoro-8-methylquinolin-2(1H)-one TFA salt The title compound was prepared in accordance with the following scheme:

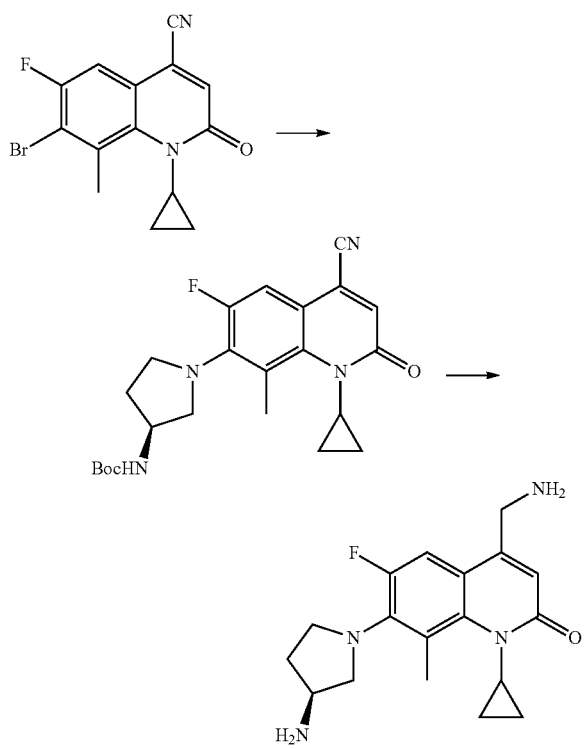

(i) (S)-tert-butyl (1-(4-cyano-1-cyclopropyl-6-fluoro-8-methyl-2-oxo-1,2-dihydroquinolin-7-yl)pyrrolidin-3-yl)carbamate Using a procedure similar to Example 31, but substituting (S)-tert-butyl pyrrolidin-3-ylcarbamate for (R)-tert-butyl (pyrrolidin-3-ylmethyl)carbamate, the title compound was made. 1H NMR (400 MHz, Chloroform-d) δ 7.34 (d, J=12.5 Hz, 1H), 6.87 (s, 1H), 4.75 (s, 1H), 4.35 (s, 1H), 3.81-3.73 (m, 1H), 3.61 (m, 1H), 3.49 (m, 2H), 3.30 (m, 1H), 2.48 (s, 3H), 2.33 (m, 1H), 1.92 (m, 1H), 1.47 (s, 9H), 0.88 (m, 2H), 0.56 (m, 2H); LC/MS calc'd for $C_{23}H_{28}FN_4O_3$ $[M+H]^+$ 427.5, found 427.1.

Alternative conditions for the amination reaction can be employed which may give improved yields for certain amines, e.g.:
1) BINAP, $Cs_2CO_3$, toluene, 100° C.
2) RuPhos Pd G1, DavePhos, $K_3PO_4$, 90° C.
3) RuPhos Pd G3, Ruphos, $Cs_2CO_3$, toluene or dioxane, 85-90° C.

(ii) (S)-4-(aminomethyl)-7-(3-aminopyrrolidin-1-yl)-1-cyclopropyl-6-fluoro-8-methylquinolin-2(1H)-one TFA salt A mixture of (S)-tert-butyl (1-(4-cyano-1-cyclopropyl-6-fluoro-8-methyl-2-oxo-1,2-dihydroquinolin-7-yl)pyrrolidin-3-yl)carbamate (54.7 mg, 0.128 mmol) in 2M NH3 in EtOH (Volume: 3 mL) was treated with Pd/C (10% dry wt, 50% water) (41.2 mg, 0.038 mmol) and sparged with hydrogen for 5 minutes. The reaction was left under an atmosphere of $H_2$ (g) for 1.5 hours. The reaction was filtered over Celite, concentrated under reduced pressure, diluted with dichloromethane (1 mL) and treated with TFA (1 mL). After 1 hour, the reaction was concentrated under reduced pressure and purified by reverse phase HPLC (13% yield). 1H NMR (400 MHz, DMSO-d6) δ 8.36 (bs, 2H), 8.11 (bs, 2H), 7.41 (d, J=14.0 Hz, 1H), 6.46 (s, 1H), 4.23 (m, 2H), 3.91 (m, 1H), 3.68 (m, 1H), 3.55 (m, 2H), 3.47 (m, 2H), 2.49 (s, 3H), 2.33 (m, 1H), 2.04-1.92 (m, 1H), 1.14 (m, 2H), 0.33 (m, 2H); LC/MS calc'd for $C_{18}H_{24}FN_4O$ $[M+H]^+$ 331.4, found 331.1.

Using the procedures described for Example 81 the following compounds were prepared as TFA salts (unless indicated otherwise):

| Ex# | Structure | Chemical Name | LCMS $t_R$ (min) | LCMS $[M + H]^+$ |
|---|---|---|---|---|
| 81.2 | 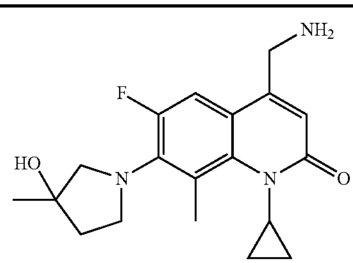 | 4-(aminomethyl)-1-cyclopropyl-6-fluoro-7-(3-hydroxy-3-methylpyrrolidin-1-yl)-8-methylquinolin-2(1H)-one | 1.78 | 346.2 |
| 81.3 | 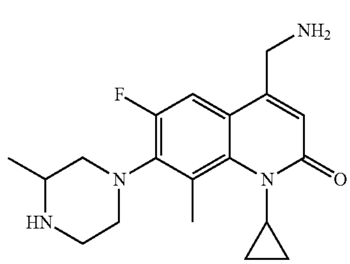 [SMILES: Cc1c(N2CCNC(C)C2)c(F)cc2c(CN)cc(=O)n(C3CC3)c12] | 4-(aminomethyl)-1-cyclopropyl-6-fluoro-8-methyl-7-(3-methylpiperazin-1-yl)quinolin-2(1H)-one | 0.81 | 345.2 |

-continued

| Ex# | Structure | Chemical Name | LCMS $t_R$ (min) | LCMS [M + H]+ |
|---|---|---|---|---|
| 81.4 | 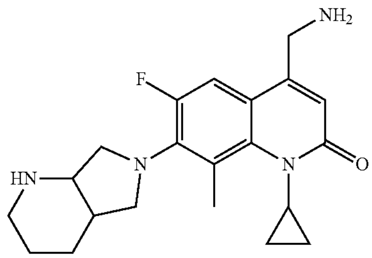 [SMILES: Cc1c(N2CC3CCCNC3C2)c(F)cc2c(CN)cc(=O)n(C3CC3)c12] | 4-(aminomethyl)-1-cyclopropyl-6-fluoro-7-(hexahydro-1H-pyrrolo[3,4-b]pyridin-6(2H)-yl)-8-methylquinolin-2(1H)-one | 1.24 | 371.2 |
| 81.5 | 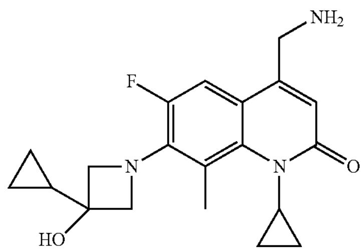 [SMILES: Cc1c(N2CC(O)(C3CC3)C2)c(F)cc2c(CN)cc(=O)n(C3CC3)c12] | 4-(aminomethyl)-1-cyclopropyl-7-(3-cyclopropyl-3-hydroxyazetidin-1-yl)-6-fluoro-8-methylquinolin-2(1H)-one (prepared as the free base) | 1.87 | 358.2 |
| 81.6 | 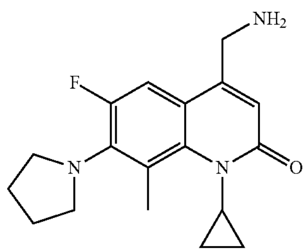 [SMILES: Cc1c(N2CCCC2)c(F)cc2c(CN)cc(=O)n(C3CC3)c12] | 4-(aminomethyl)-1-cyclopropyl-6-fluoro-8-methyl-7-(pyrrolidin-1-yl)quinolin-2(1H)-one | 2.25 | 316.2 |
| 81.7 | 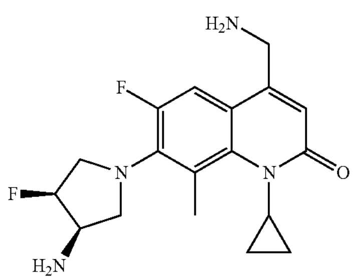 [SMILES: Cc1c(N2C[C@@H](N)[C@@H](F)C2)c(F)cc2c(CN)cc(=O)n(C3CC3)c12] | 7-((3R,4S)-3-amino-4-fluoropyrrolidin-1-yl)-4-(aminomethyl)-1-cyclopropyl-6-fluoro-8-methylquinolin-2(1H)-one | 0.73 | 349.1 |
| 81.8 | 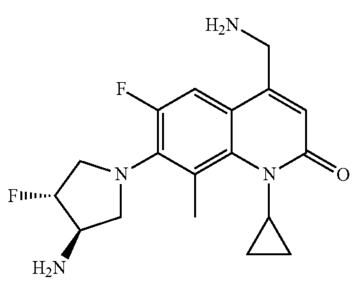 [SMILES: Cc1c(N2C[C@@H](N)[C@H](F)C2)c(F)cc2c(CN)cc(=O)n(C3CC3)c12] | 7-((3R,4R)-3-amino-4-fluoropyrrolidin-1-yl)-4-(aminomethyl)-1-cyclopropyl-6-fluoro-8-methylquinolin-2(1H)-one | 0.89 | 349.1 |
| 81.9 | 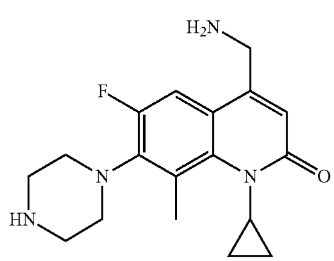 [SMILES: Cc1c(N2CCNCC2)c(F)cc2c(CN)cc(=O)n(C3CC3)c12] | 4-(aminomethyl)-1-cyclopropyl-6-fluoro-8-methyl-7-(piperazin-1-yl)quinolin-2(1H)-one | 0.31 (2 min LC/MS) | 331.1 |

| Ex# | Structure | Chemical Name | LCMS $t_R$ (min) | LCMS [M + H]$^+$ |
|---|---|---|---|---|
| 81.10 | 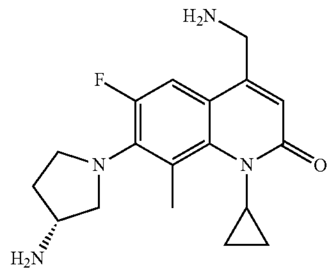 [SMILES: Cc1c(N2CC[C@@H](N)C2)c(F)cc2c(CN)cc(=O)n(C3CC3)c12] | (R)-4-(aminomethyl)-7-(3-aminopyrrolidin-1-yl)-1-cyclopropyl-6-fluoro-8-methylquinolin-2(1H)-one | 1.18 | 331.2 |
| 81.11 | 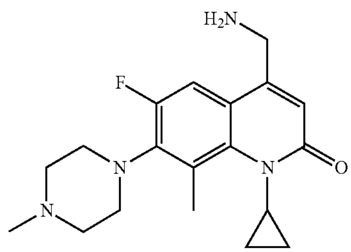 [SMILES: Cc1c(N2CCN(C)CC2)c(F)cc2c(CN)cc(=O)n(C3CC3)c12] | 4-(aminomethyl)-1-cyclopropyl-6-fluoro-8-methyl-7-(4-methylpiperazin-1-yl)quinolin-2(1H)-one | 0.82 | 345.3 |
| 81.12 | 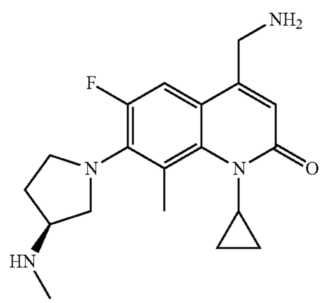 [SMILES: CN[C@H]1CCN(c2c(F)cc3c(CN)cc(=O)n(C4CC4)c3c2C)C1] | (S)-4-(aminomethyl)-1-cyclopropyl-6-fluoro-8-methyl-7-(3-(methylamino)pyrrolidin-1-yl)quinolin-2(1H)-one | 1.42 | 345.1 |
| 81.13 | 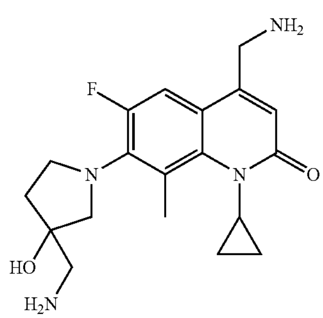 [SMILES: Cc1c(N2CCC(O)(CN)C2)c(F)cc2c(CN)cc(=O)n(C3CC3)c12] | 4-(aminomethyl)-7-(3-(aminomethyl)-3-hydroxypyrrolidin-1-yl)-1-cyclopropyl-6-fluoro-8-methylquinolin-2(1H)-one | 0.74 | 360.9 |
| 81.14 | 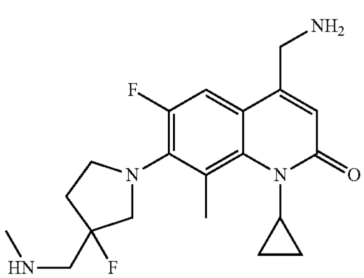 [SMILES: CNCC1(F)CCN(c2c(F)cc3c(CN)cc(=O)n(C4CC4)c3c2C)C1] | 4-(aminomethyl)-1-cyclopropyl-6-fluoro-7-(3-fluoro-3-((methylamino)methyl)pyrrolidin-1-yl)-8-methylquinolin-2(1H)-one | 1.00 | 377.0 |

-continued

| Ex# | Structure | Chemical Name | LCMS $t_R$ (min) | LCMS [M + H]⁺ |
|---|---|---|---|---|
| 81.15 | 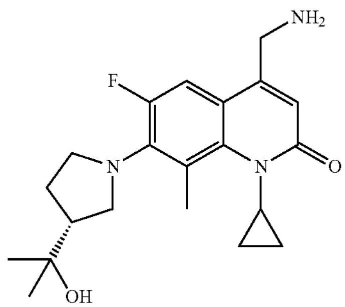 [SMILES: Cc1c(N2CC[C@@H](C(C)(C)O)C2)c(F)cc2c(CN)cc(=O)n(C3CC3)c12] | (R)-4-(aminomethyl)-1-cyclopropyl-6-fluoro-7-(3-(2-hydroxypropan-2-yl)pyrrolidin-1-yl)-8-methylquinolin-2(1H)-one | 2.13 | 374.0 |
| 81.16 | 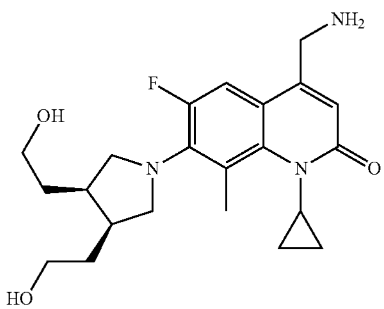 [SMILES: Cc1c(N2C[C@@H](CCO)[C@@H](CCO)C2)c(F)cc2c(CN)cc(=O)n(C3CC3)c12] | 4-(aminomethyl)-7-((3R,4S)-3,4-bis(2-hydroxyethyl)pyrrolidin-1-yl)-1-cyclopropyl-6-fluoro-8-methylquinolin-2(1H)-one | 1.56 | 404.2 |
| 81.17 | 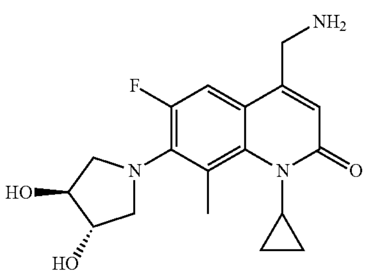 [SMILES: Cc1c(N2C[C@H](O)[C@@H](O)C2)c(F)cc2c(CN)cc(=O)n(C3CC3)c12] | 4-(aminomethyl)-1-cyclopropyl-7-((3S,4S)-3,4-dihydroxypyrrolidin-1-yl)-6-fluoro-8-methylquinolin-2(1H)-one | 0.84 | 348.1 |
| 81.18 | 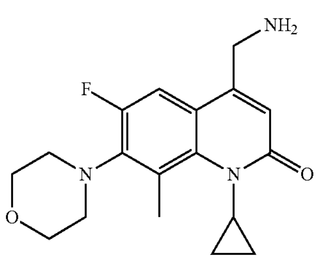 [SMILES: Cc1c(N2CCOCC2)c(F)cc2c(CN)cc(=O)n(C3CC3)c12] | 4-(aminomethyl)-1-cyclopropyl-6-fluoro-8-methyl-7-morpholinoquinolin-2(1H)-one | 1.80 | 332.1 |
| 81.19 | 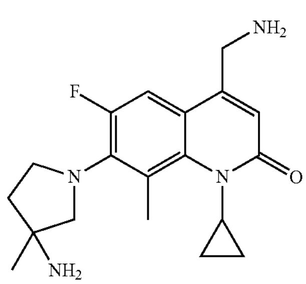 [SMILES: Cc1c(N2CCC(C)(N)C2)c(F)cc2c(CN)cc(=O)n(C3CC3)c12] | 7-(3-amino-3-methylpyrrolidin-1-yl)-4-(aminomethyl)-1-cyclopropyl-6-fluoro-8-methylquinolin-2(1H)-one | 1.09 | 345.1 |

| Ex# | Structure | Chemical Name | LCMS $t_R$ (min) | LCMS $[M + H]^+$ |
|---|---|---|---|---|
| 81.20 | 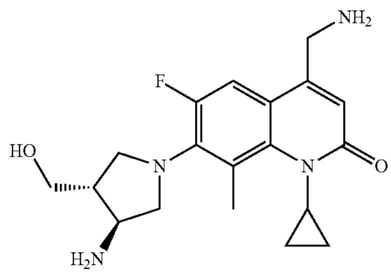 [SMILES: Cc1c(N2C[C@@H](CO)[C@H](N)C2)c(F)cc2c(CN)cc(=O)n(C3CC3)c12] | 7-((3S,4R)-3-amino-4-(hydroxymethyl)pyrrolidin-1-yl)-4-(aminomethyl)-1-cyclopropyl-6-fluoro-8-methylquinolin-2(1H)-one | 0.71 | 361.1 |
| 81.21 | 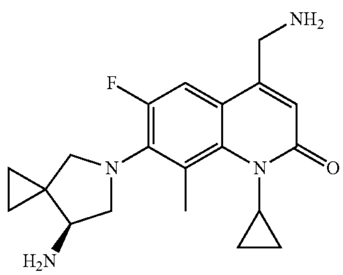 [SMILES: Cc1c(N2C[C@@H](N)C3(CC3)C2)c(F)cc2c(CN)cc(=O)n(C3CC3)c12] | (S)-7-(7-amino-5-azaspiro[2.4]heptan-5-yl)-4-(aminomethyl)-1-cyclopropyl-6-fluoro-8-methylquinolin-2(1H)-one | 1.24 | 357.2 |
| 81.22 | 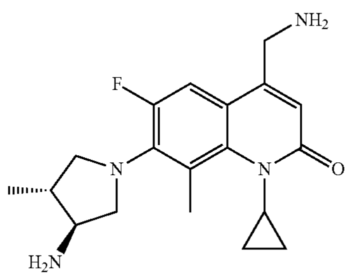 [SMILES: Cc1c(N2C[C@@H](C)[C@H](N)C2)c(F)cc2c(CN)cc(=O)n(C3CC3)c12] | 7-((3S,4R)-3-amino-4-methylpyrrolidin-1-yl)-4-(aminomethyl)-1-cyclopropyl-6-fluoro-8-methylquinolin-2(1H)-one | 1.16 | 345.2 |
| 81.23 | 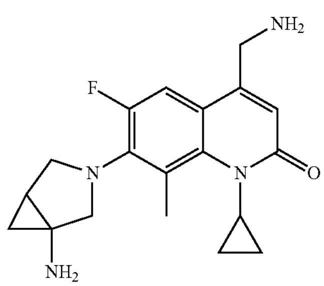 [SMILES: Cc1c(N2CC3CC3(N)C2)c(F)cc2c(CN)cc(=O)n(C3CC3)c12] | 7-(1-amino-3-azabicyclo[3.1.0]hexan-3-yl)-4-(aminomethyl)-1-cyclopropyl-6-fluoro-8-methylquinolin-2(1H)-one | 1.02 | 343.1 |
| 81.24 | 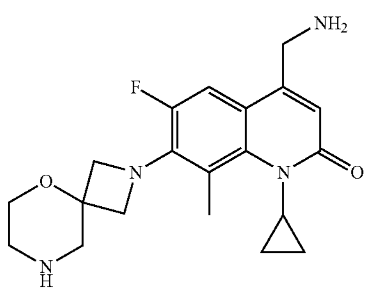 [SMILES: Cc1c(N2CC3(CNCCO3)C2)c(F)cc2c(CN)cc(=O)n(C3CC3)c12] | 4-(aminomethyl)-1-cyclopropyl-6-fluoro-8-methyl-7-(5-oxa-2,8-diazaspiro[3.5]nonan-2-yl)quinolin-2(1H)-one | 1.01 | 373.2 |

-continued

| Ex# | Structure | Chemical Name | LCMS $t_R$ (min) | LCMS [M + H]$^+$ |
|---|---|---|---|---|
| 81.25 | 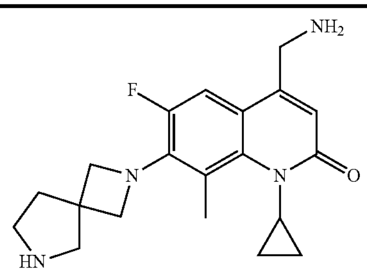 | 4-(aminomethyl)-1-cyclopropyl-6-fluoro-8-methyl-7-(2,6-diazaspiro[3.4]octan-2-yl)quinolin-2(1H)-one | 1.11 | 357.2 |
| 81.26 | 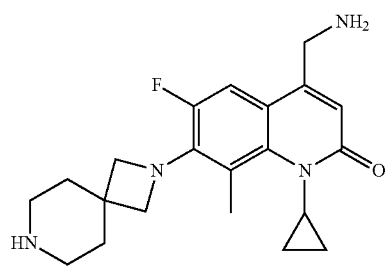 [SMILES: Cc1c(N2CC3(CCNCC3)C2)c(F)cc2c(CN)cc(=O)n(C3CC3)c12] | 4-(aminomethyl)-1-cyclopropyl-6-fluoro-8-methyl-7-(2,7-diazaspiro[3.5]nonan-2-yl)quinolin-2(1H)-one | 1.00 | 371.2 |
| 81.27 | 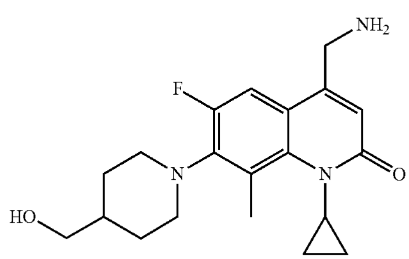 [SMILES: Cc1c(N2CCC(CO)CC2)c(F)cc2c(CN)cc(=O)n(C3CC3)c12] | 4-(aminomethyl)-1-cyclopropyl-6-fluoro-7-(4-(hydroxymethyl)piperidin-1-yl)-8-methylquinolin-2(1H)-one | 1.94 | 360.2 |
| 81.28 | 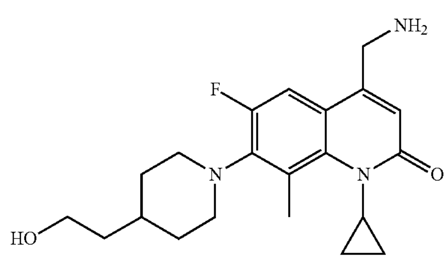 [SMILES: Cc1c(N2CCC(CCO)CC2)c(F)cc2c(CN)cc(=O)n(C3CC3)c12] | 4-(aminomethyl)-1-cyclopropyl-6-fluoro-7-(4-(2-hydroxyethyl)piperidin-1-yl)-8-methylquinolin-2(1H)-one | 2.22 | 374.2 |
| 81.29 | 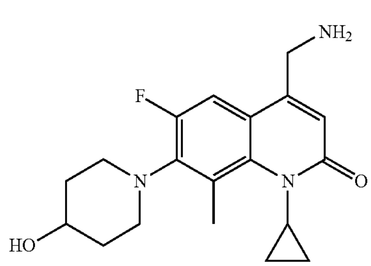 [SMILES: Cc1c(N2CCC(O)CC2)c(F)cc2c(CN)cc(=O)n(C3CC3)c12] | 4-(aminomethyl)-1-cyclopropyl-6-fluoro-7-(4-hydroxypiperidin-1-yl)-8-methylquinolin-2(1H)-one | 1.57 | 346.2 |
| 81.32 | 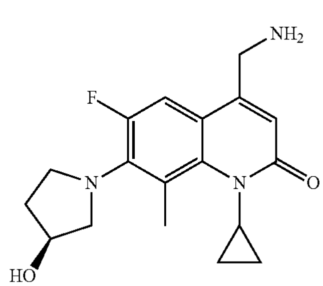 [SMILES: Cc1c(N2CC[C@H](O)C2)c(F)cc2c(CN)cc(=O)n(C3CC3)c12] | (S)-4-(aminomethyl)-1-cyclopropyl-6-fluoro-7-(3-hydroxypyrrolidin-1-yl)-8-methylquinolin-2(1H)-one | 0.95 | 332.1 |

| Ex# | Structure | Chemical Name | LCMS $t_R$ (min) | LCMS $[M + H]^+$ |
|---|---|---|---|---|
| 81.33 | 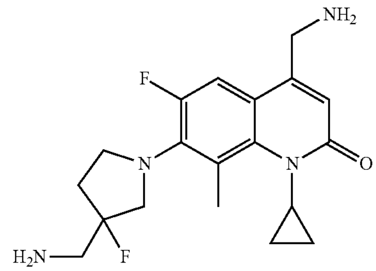 [SMILES: Cc1c(N2CCC(F)(CN)C2)c(F)cc2c(CN)cc(=O)n(C3CC3)c12] | 4-(aminomethyl)-7-(3-(aminomethyl)-3-fluoropyrrolidin-1-yl)-1-cyclopropyl-6-fluoro-8-methylquinolin-2(1H)-one | 0.64 | 363.1 |

The compounds in the preceding table were characterized by high performance liquid chromatography (HPLC) on a Waters ACQUITY UPLC system with 1.2 mL/min flow rate; column Kinetex-C18, 2.6 um, 2.1×50 mm from Phenomenex, column temperature: 50° C.; gradient: 2-88% MeCN in water with 0.1% TFA over a 9.29 min period (unless indicated otherwise); Compounds were detected by ultraviolet light (UV) absorption at 220 nm.

Intermediate 82: 7-bromo-1-cyclopropyl-5,6-difluoro-8-methyl-2-oxo-1,2-dihydroquinoline-4-carbonitrile The title compound was prepared in accordance with the following scheme:

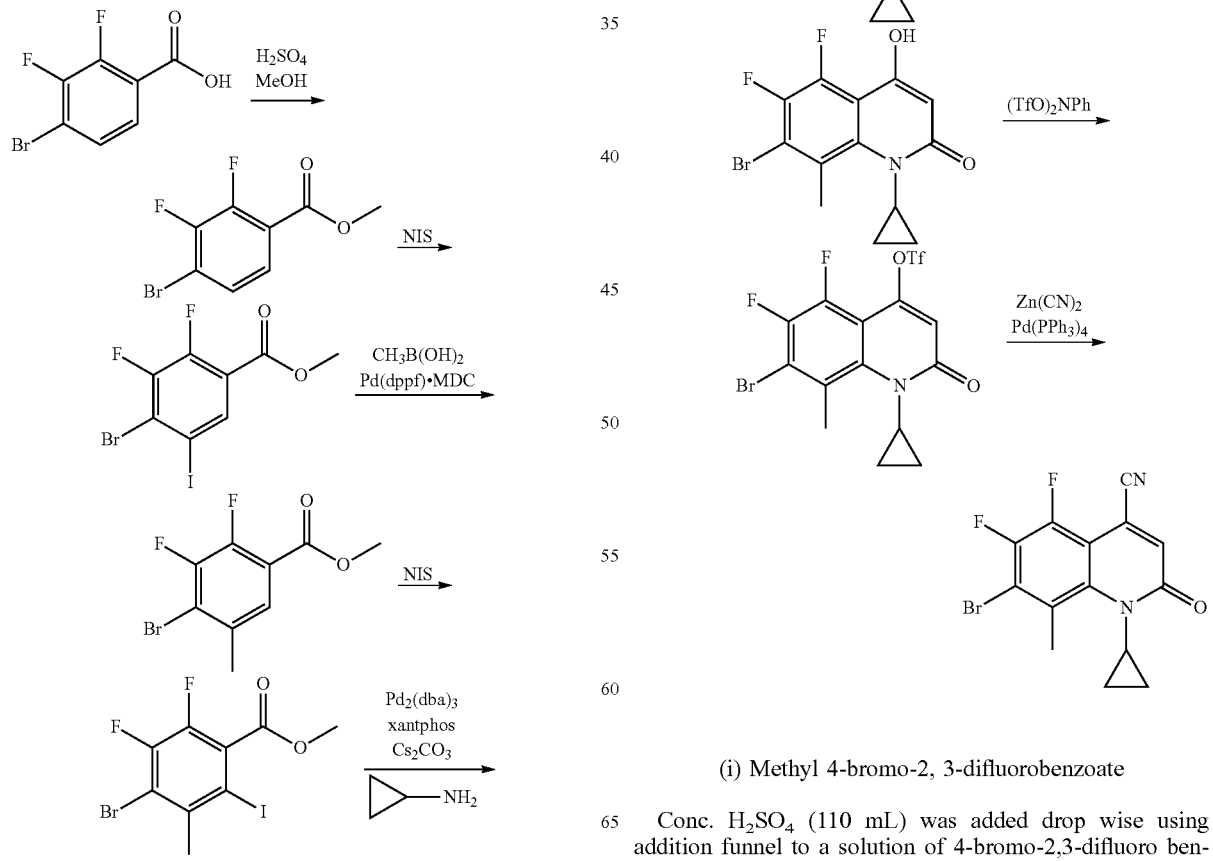

(i) Methyl 4-bromo-2, 3-difluorobenzoate

Conc. $H_2SO_4$ (110 mL) was added drop wise using addition funnel to a solution of 4-bromo-2,3-difluoro benzoic acid (110 g) in (550 mL) of methanol at 0° C. under nitrogen. The reaction mixture was stirred at reflux temperature for overnight. The reaction mixture was quenched with cold water and extracted with EtOAc. The organic layer was washed with saturated NaHCO$_3$ solution, dried over sodium sulfate and concentrated to afford white solid as the desired product (115 g, 98% yield). The product was used in the next step without further purification.

$^1$H NMR (400 MHz, DMSO) δ 7.74-7.63 (m, 2H), 3.89 (s, 3H).

(ii) Methyl 4-bromo-2,3-difluoro-5-iodobenzoate

Methyl 4-bromo-2,3-difluorobenzoate (115 g, 458.16 mmol, 1.0 equiv) was dissolved in dichloromethane (460 mL) under nitrogen. The reaction mixture was cooled to 0° C. and conc. H$_2$SO$_4$ (460 mL) was added drop wise at 0° C. NIS (155 g, 687.25 mmol, 1.5 equiv) was added portion wise at 0° C. and the reaction mixture was stirred at RT for 2-3 hours. The reaction mixture was quenched with cold water and extracted with EtOAc. The organic layer was washed with saturated NaHCO$_3$ solution, saturated Na$_2$S$_2$O$_3$ solution, dried over sodium sulfate and concentrated to afford the desired product (167 g, 97% yield) as a white solid. The product was used in next step without further purification.

$^1$H NMR (400 MHz, DMSO) δ 8.18 (dd, J=6.7, 2.1 Hz, 1H), 3.89 (d, J=4.3 Hz, 3H).

(iii) Methyl 4-bromo-2,3-difluoro-5-methylbenzoate

Methyl 4-bromo-2,3-difluoro-5-iodobenzoate (60 g, 159.15 mmol, 1.0 equiv), methyl boronic acid (19.05 g, 318.3 mmol, 2.0 equiv), K$_3$PO$_4$ (67.47 g, 318.3 mmol, 2.0 equiv) were added in THF (600 mL) at RT in sealed tube and the reaction mixture was degassed for 5 minutes. PdCl$_2$(dppf).MDC complex (3.9 g, 4.775 mmol, 0.03 equiv) was added and the reaction mixture was stirred at 90-95° C. for overnight. The reaction mixture was quenched with cold water and extracted with EtOAc. The organic layer was washed with cold water, brine, dried over sodium sulfate and concentrated to afford a crude residue. The crude residue was purified by 100-200 mesh silica gel column chromatography (0% DCM/Hexane) to afford the desired product (22.0 g, 52% yield) as a white solid. $^1$H NMR (400 MHz, CDCl$_3$) δ 7.65 (d, J=6.8 Hz, 1H), 3.97 (s, 3H), 2.45 (s, 3H).

(iv) methyl 4-bromo-2,3-difluoro-6-iodo-5-methylbenzoate

Methyl 4-bromo-2,3-difluoro-5-methylbenzoate (44.0 g, 166.04 mmol, 1.0 equiv) was dissolved in dichloromethane (166 mL) under nitrogen. The reaction mixture was cooled to 0° C. and Conc H$_2$SO$_4$ (166 mL) was added drop wise at 0° C. NIS (149.4 g, 664.15 mmol, 4.0 equiv) was added portion wise at 0° C. and the reaction mixture was stirred at RT for 2-3 hours. The reaction mixture was quenched with cold water and extracted with EtOAc. The organic layer was washed with saturated NaHCO$_3$ solution, saturated Na$_2$S$_2$O$_3$ solution, dried over sodium sulfate and concentrated to afford a crude residue. The crude residue was purified by 60-120 mesh silica gel column chromatography (0-12% EtOAc/Hexane) to afford the desired product (52 g, 80% yield).

(v) Methyl 4-bromo-2-(cyclopropylamino)-5,6-difluoro-3-methylbenzoate

Methyl 4-bromo-2,3-difluoro-6-iodo-5-methylbenzoate (5.73 g, 14.66 mmol) was dissolved in 1,4-dioxane (Volume: 117 mL) and de-gassed by sparging with nitrogen for 10 minutes. Pd$_2$dba$_3$ (0.671 g, 0.733 mmol), xantphos (1.272 g, 2.199 mmol) and cesium carbonate (7.16 g, 21.99 mmol) were added. The flask was fitted with a reflux condenser and the top of the condenser was attached to a three-way PTFE stopcock featuring a vacuum line (house vacuum) and nitrogen balloon. The entire apparatus was evacuated and back-filled with nitrogen three times. Cyclopropylamine (2.1 mL, 29.3 mmol) was added and the mixture was heated to 80° C. for 15 hours under nitrogen. Upon cooling to rt the mixture was diluted with water (400 mL) and extracted with EtOAc (1×150 mL and 2×100 mL). The combined organic extracts were washed with brine (150 mL), dried over MgSO$_4$ and concentrated under reduced pressure. SiO$_2$ flash chromatography (ISCO combiflash, 0-15% EtOAc/heptane, 120 g cartridge) provided the title compound (3.51 g, 10.96 mmol, 74.8% yield) as a yellow oil.

$^1$H NMR (400 MHz, Chloroform-d) δ 3.92 (s, 3H), 2.67-2.61 (m, 1H), 2.39 (d, J=1.2 Hz, 3H), 0.68-0.61 (m, 2H), 0.47-0.41 (m, 2H)

LCMS: t$_R$=0.96 min, m/z=320/322 [M+H]$^+$ (vi) Methyl 4-bromo-2-(N-cyclopropylacetamido)-5,6-difluoro-3-methylbenzoate Methyl 4-bromo-2-(cyclopropylamino)-5,6-difluoro-3-methylbenzoate (32 g, 100.0 mmol, 1.0 equiv) was dissolved in toluene (180 mL). Acetyl chloride (11.77 g, 150.0 mmol, 1.5 equiv) was added and the reaction mixture was stirred at 100° C. for 1 hour. The reaction mixture was quenched with water, neutralized with NaHCO$_3$ solution and extracted with EtOAc. The organic layer was washed with brine solution, dried over sodium sulfate and concentrated to afford a crude residue. The crude residue was purified by 100-200 mesh silica gel column chromatography (40-45% EtOAc/Hexane) to afford the title compound (29 g, 80% yield).

$^1$H NMR (400 MHz, Chloroform-d) δ 3.91 (s, 1.3H, OCH$_3$ rotamer), 3.88 (s, 1.6H, OCH$_3$ rotamer), 3.02-2.92 (m, 1H), 2.36 (s, 1.7H, CH$_3$ rotamer), 2.28 (d, J=1.2 Hz, 1.4H, CH$_3$ rotamer), 2.23 (d, J=1.1 Hz, 1.6H, CH$_3$ rotamer), 1.82 (s, 1.4H, CH$_3$ rotamer), 0.92-0.64 (m, 3H), 0.53-0.44 (m, 0.5H, CH rotamer), 0.37-0.29 (m, 0.5H, CH rotamer)

LCMS: t$_R$=0.79 min, m/z=362/364 [M+H]$^+$ (vii) 7-bromo-1-cyclopropyl-5,6-difluoro-4-hydroxy-8-methylquinolin-2(1H)-one NaHMDS (1M in THF, 19.05 ml, 19.05 mmol) was added as a slow stream to a mixture of methyl 4-bromo-2-(N-cyclopropylacetamido)-5,6-difluoro-3-methylbenzoate (2.3 g, 6.35 mmol) in THF (Volume: 63.5 ml) at −78° C. The mixture rapidly turned dark yellow and was stirred 30 minutes at −78° C. Water (~60 mL) was added and the reaction flask was removed from the dry-ice/acetone bath. More water (200 mL) was added along with a small amount of saturated brine. The aqueous mixture was washed with EtOAc (50 mL). The aqueous layer (containing desired product) was acidified with 2M HCl (20 mL) and extracted with 7:3 CHCl$_3$/i-PrOH (3×100 mL). The latter organic extracts were combined and concentrated under reduced pressure. The crude solid material was suspended in Et$_2$O, diluted with heptane and filtered, washing with heptane to give the title compound (1.86 g, 5.63 mmol, 89% yield) as a cream-colored powder.

$^1$H NMR (400 MHz, DMSO-d6) δ 11.52 (d, J=2.2 Hz, 1H), 5.78 (s, 1H), 3.43-3.35 (m, 1H), 2.62 (s, 3H), 1.09—

(viii) 7-bromo-1-cyclopropyl-5,6-difluoro-8-methyl-2-oxo-1,2-dihydroquinolin-4-yl trifluoromethanesulfonate 1,1,1-trifluoro-N-phenyl-N-((trifluoromethyl)sulfonyl)methanesulfonamide (3.34 g, 9.34 mmol) was added dropwise as a solution in DMF (18 mL+3 mL rinse) to a mixture of 7-bromo-1-cyclopropyl-5,6-difluoro-4-hydroxy-8-methylquinolin-2(1H)-one (2.57 g, 7.78 mmol) and triethylamine (3.26 ml, 23.35 mmol) in DMF (60 mL) at 0° C. The resulting clear, pale yellow mixture was stirred for 3 hours by which time the temperature had increased to −5° C. and the color had become dark. LCMS indicated complete consumption of starting material. The mixture was diluted with water (300 mL) and brine and extracted three times with EtOAc (3×100 mL). The combined organic extracts were washed with brine, dried over MgSO$_4$ and concentrated under reduced pressure. SiO$_2$ flash chromatography (ISCO combiflash, 0-100% EtOAc/heptane, 120 g cartridge) provided the title compound (3.07 g, 6.64 mmol, 85% yield) as an orange solid.

$^1$H NMR (400 MHz, Chloroform-d) δ 6.64 (s, 1H), 3.56-3.46 (m, 1H), 2.74 (d, J=1.1 Hz, 3H), 1.31-1.21 (m, 2H), 0.63-0.49 (m, 2H)

LCMS: $t_R$=0.98 min, m/z=462/464 [M+H]$^+$ (ix) 7-bromo-1-cyclopropyl-5,6-difluoro-8-methyl-2-oxo-1,2-dihydroquinoline-4-carbonitrile A solution of 7-bromo-1-cyclopropyl-5,6-difluoro-8-methyl-2-oxo-1,2-dihydroquinolin-4-yl trifluoromethanesulfonate (3.07 g, 6.64 mmol) in DMF (Volume: 66.4 ml) in a 200 mL recovery flask was treated with tetrakis(triphenylphosphine)palladium(0) (0.768 g, 0.664 mmol), followed by zinc cyanide (0.406 g, 3.45 mmol). The flask was fitted with a reflux condensor and a balloon of nitrogen, then the mixture was heated to 80° C. for 16 hours, becoming dark green-brown in color. After cooling to rt, the reaction mixture was diluted with saturated aqueous NaHCO$_3$ (300 mL) and water (50 mL) and extracted three times with EtOAc (100 mL). The combined organic extracts were washed successively with saturated aqueous NaHCO$_3$, water and brine (100 mL each), then dried over Na$_2$SO$_4$ and concentrated under reduced pressure to give a greenish solid. SiO$_2$ flash chromatography (ISCO combiflash, 0-100% EtOAc/heptane, 80 g cartridge) gave the title compound (1.83 g, 5.40 mmol, 81% yield) as a pale yellow solid.

$^1$H NMR (400 MHz, Chloroform-d) δ 7.11 (s, 1H), 3.57-3.48 (m, 1H), 2.74 (d, J=1.1 Hz, 3H), 1.32-1.23 (m, 2H), 0.59-0.51 (m, 2H)

LCMS: $t_R$=0.81 min, m/z=339/341 [M+H]$^+$

Example 83: 4-(aminomethyl)-7-(3-(aminomethyl)-3-fluoropyrrolidin-1-yl)-1-cyclopropyl-5,6-difluoro-8-methylquinolin-2(1H)-one TFA salt

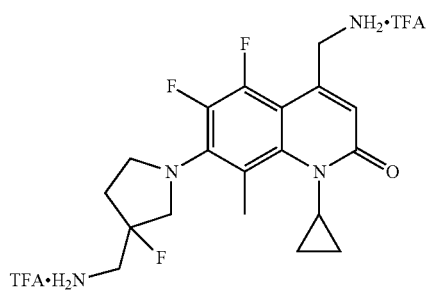

The title compound was prepared in accordance with the following scheme:

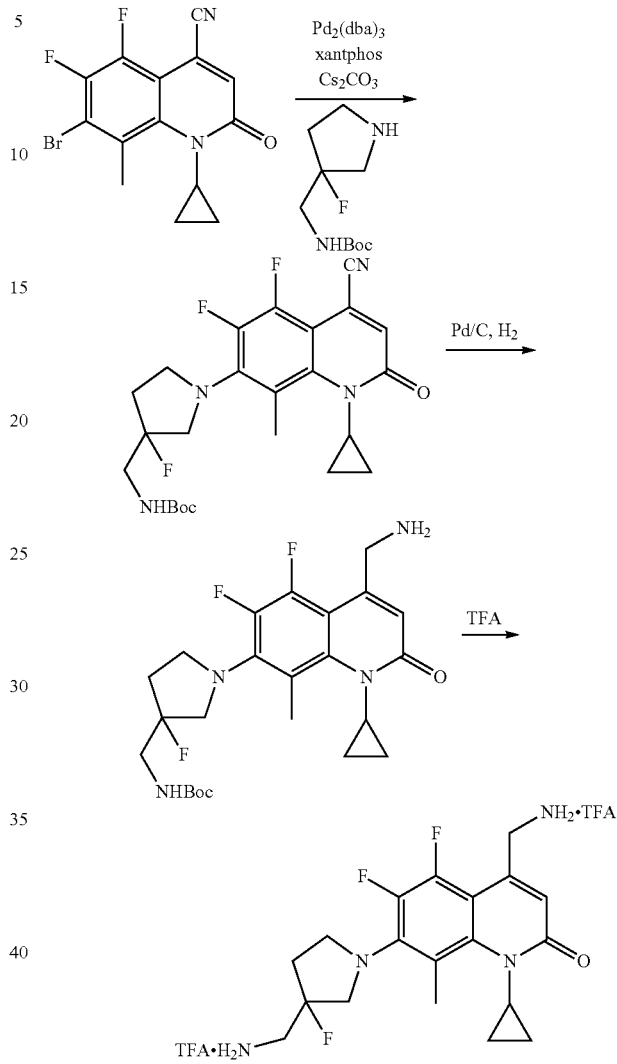

(i) Tert-butyl ((1-(4-cyano-1-cyclopropyl-5,6-difluoro-8-methyl-2-oxo-1,2-dihydroquinolin-7-yl)-3-fluoropyrrolidin-3-yl)methyl)carbamate A 5 mL microwave vial was charged with 7-bromo-1-cyclopropyl-5,6-difluoro-8-methyl-2-oxo-1,2-dihydroquinoline-4-carbonitrile (75 mg, 0.221 mmol), tert-butyl ((3-fluoropyrrolidin-3-yl)methyl)carbamate (113 mg, 0.442 mmol), xantphos (38.4 mg, 0.066 mmol), Pd$_2$(dba)$_3$ (20.25 mg, 0.022 mmol) and cesium carbonate (216 mg, 0.663 mmol). The vial was sealed, evacuated and back-filled with nitrogen. Toluene (Volume: 2.2 mL, previously degassed by sparging with nitrogen) was added and the mixture was heated to 100° C. for 15.5 hours. The crude reaction mixture was diluted with water then extracted with EtOAc (3 times). The combined organic extracts were washed with brine, dried over Na$_2$SO$_4$ and concentrated under reduced pressure to give a brown oil. SiO$_2$ flash chromatography (ISCO combiflash, 0-100% EtOAc/heptane, 4 g cartridge) provided the title compound (68 mg, 0.143 mmol, 64.5% yield) as a yellow-brown foam.

¹H NMR (400 MHz, Chloroform-d) δ 6.92 (s, 1H), 4.95 (s, 1H), 4.00-3.76 (m, 2H), 3.65-3.42 (m, 5H), 2.41 (s, 3H), 2.34-2.06 (m, 2H), 1.47 (s, 9H), 1.34-1.22 (m, 1H), 1.19-1.10 (m, 1H), 0.61-0.47 (m, 2H)

LCMS: $t_R$=1.04 min, m/z=477.3 [M+H]$^+$

Alternative conditions for the amination reaction can be employed which may give improved yields for certain amines, e.g.:

4) RuPhos Pd G3, Ruphos, Cs$_2$CO$_3$, toluene, 90° C.
5) Xphos Pd G3, Ruphos, Cs$_2$CO$_3$, dioxane, 85° C.

(ii) Tert-butyl ((1-(4-(aminomethyl)-1-cyclopropyl-5,6-difluoro-8-methyl-2-oxo-1,2-dihydroquinolin-7-yl)-3-fluoropyrrolidin-3-yl)methyl)carbamate A mixture of tert-butyl ((1-(4-cyano-1-cyclopropyl-5,6-difluoro-8-methyl-2-oxo-1,2-dihydroquinolin-7-yl)-3-fluoropyrrolidin-3-yl)methyl)carbamate (68 mg, 0.143 mmol) in 2M NH$_3$ in MeOH (Volume: 5.7 mL) was treated with Pd/C (10% dry wt, 50% water, 91 mg, 0.043 mmol) and sparged with hydrogen for 5 minutes, then stirred under a balloon of hydrogen for 30 minutes. The mixture was sparged with nitrogen for several minutes then passed through a 1 μm syringe filter and concentrated under reduced pressure to give the title compound (56 mg, 0.117 mmol, 82% yield) as a yellow film. The crude material was used immediately without further purification.

LCMS: $t_R$=0.74 min, m/z=481.3 [M+H]$^+$ (iii) 4-(aminomethyl)-7-(3-(aminomethyl)-3-fluoropyrrolidin-1-yl)-1-cyclopropyl-5,6-difluoro-8-methylquinolin-2(1H)-one TFA salt A mixture of tert-butyl ((1-(4-(aminomethyl)-1-cyclopropyl-5,6-difluoro-8-methyl-2-oxo-1,2-dihydroquinolin-7-yl)-3-fluoropyrrolidin-3-yl)methyl)carbamate (56 mg, 0.117 mmol) in DCM (Volume: 1.2 mL) and TFA (Volume: 1.2 mL) was stirred at rt for 30 minutes. The mixture was concentrated under reduced pressure. The residue was concentrated from DCM-toluene, then MeOH-toluene. Finally, the dark yellow oily residue was dissolved in DMSO (2.5 mL) and passed through a 0.45 μm syringe filter and purified by preparative RP-HPLC (MeCN—H$_2$O-TFA) to give the title compound (17.3 mg, 0.027 mmol, 23.42% yield) as a yellow solid.

¹H NMR (500 MHz, DMSO-d6) δ 8.39 (s, 3H), 8.27 (s, 3H), 6.43 (s, 1H), 4.29 (s, 2H), 3.94-3.79 (m, 2H), 3.60-3.40 (m, 5H, obscured by H$_2$O peak), 2.38 (s, 3H), 2.34-2.18 (m, 2H), 1.22-1.15 (m, 1H), 1.15-1.07 (m, 1H), 0.42-0.34 (m, 1H), 0.33-0.25 (m, 1H).

¹H NMR (500 MHz, Methanol-d4) δ 6.50 (s, 1H), 4.40 (s, 2H), 4.04-3.87 (m, 2H), 3.71 (dd, J=21.7, 11.5 Hz, 1H), 3.64-3.48 (m, 4H), 2.50 (s, 3H), 2.48-2.22 (m, 2H), 1.32-1.15 (m, 2H), 0.56-0.38 (m, 2H).

LCMS: $t_R$=1.05 min, m/z=381.2 [M+H]$^+$ (10 minute run)

Using the procedures described for Example 83 the following compounds were prepared as TFA salts:

| Ex# | Structure | Chemical Name | LCMS $t_R$ (min) | LCMS [M + H]$^+$ |
|---|---|---|---|---|
| 83.2 | 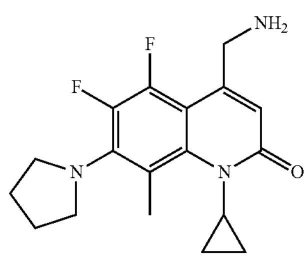 [SMILES: Cc1c(N2CCCC2)c(F)c(F)c2c(CN)cc(=O)n(C3CC3)c12] | 4-(aminomethyl)-1-cyclopropyl-5,6-difluoro-8-methyl-7-(pyrrolidin-1-yl)quinolin-2(1H)-one | 2.68 | 334.2 |
| 83.3 | 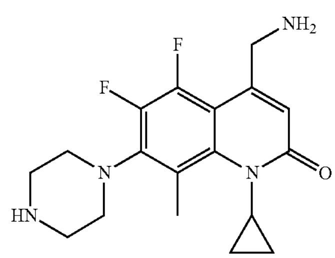 [SMILES: Cc1c(N2CCNCC2)c(F)c(F)c2c(CN)cc(=O)n(C3CC3)c12] | 4-(aminomethyl)-1-cyclopropyl-5,6-difluoro-8-methyl-7-(piperazin-1-yl)quinolin-2(1H)-one | 0.68 | 349.1 |
| 83.4 | 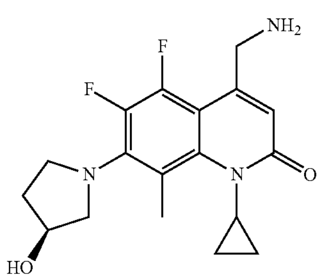 [SMILES: Cc1c(N2CC[C@H](O)C2)c(F)c(F)c2c(CN)cc(=O)n(C3CC3)c12] | (S)-4-(aminomethyl)-1-cyclopropyl-5,6-difluoro-7-(3-hydroxypyrrolidin-1-yl)-8-methylquinolin-2(1H)-one | 1.59 | 350.1 |

| Ex# | Structure | Chemical Name | LCMS $t_R$ (min) | LCMS $[M + H]^+$ |
|---|---|---|---|---|
| 83.5 | 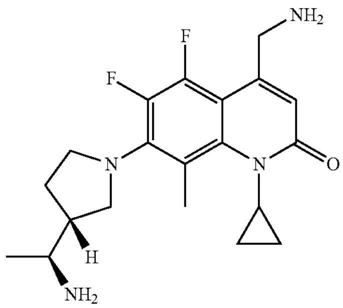 [SMILES: Cc1c(N2CC[C@@H]([C@H](C)N)C2)c(F)c(F)c2c(CN)cc(=O)n(C3CC3)c12] | 7-((R)-3-((S)-1-aminoethyl)pyrrolidin-1-yl)-4-(aminomethyl)-1-cyclopropyl-5,6-difluoro-8-methylquinolin-2(1H)-one | 1.34 | 377.2 |
| 83.6 | 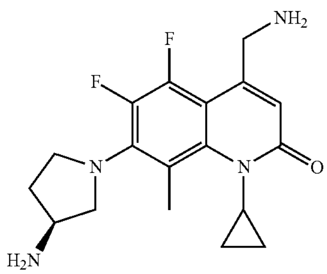 [SMILES: Cc1c(N2CC[C@H](N)C2)c(F)c(F)c2c(CN)cc(=O)n(C3CC3)c12] | (S)-4-(aminomethyl)-7-(3-aminopyrrolidin-1-yl)-1-cyclopropyl-5,6-difluoro-8-methylquinolin-2(1H)-one | 0.86 | 349.1 |

The compounds in the preceding table were characterized by high performance liquid chromatography (HPLC) on a Waters ACQUITY UPLC system with 1.2 mL/min flow rate; column Kinetex-C18, 2.6 um, 2.1×50 mm from Phenomenex, column temperature: 50° C.; gradient: 2-88% MeCN in water with 0.1% TFA over a 9.29 min period (unless indicated otherwise); Compounds were detected by ultraviolet light (UV) absorption at 220 nm.

Example 84: tert-butyl ((1-(4-cyano-1-cyclopropyl-5,6-difluoro-8-methyl-2-oxo-1,2-dihydroquinolin-7-yl)-3-fluoropyrrolidin-3-yl)methyl)carbamate The title compound was prepared in accordance with the following scheme:

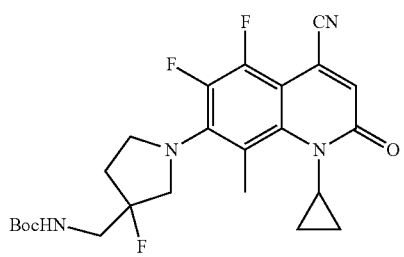 [SMILES: Cc1c(N2CCC(F)(CNC(=O)OC(C)(C)C)C2)c(F)c(F)c2c(C#N)cc(=O)n(C3CC3)c12]

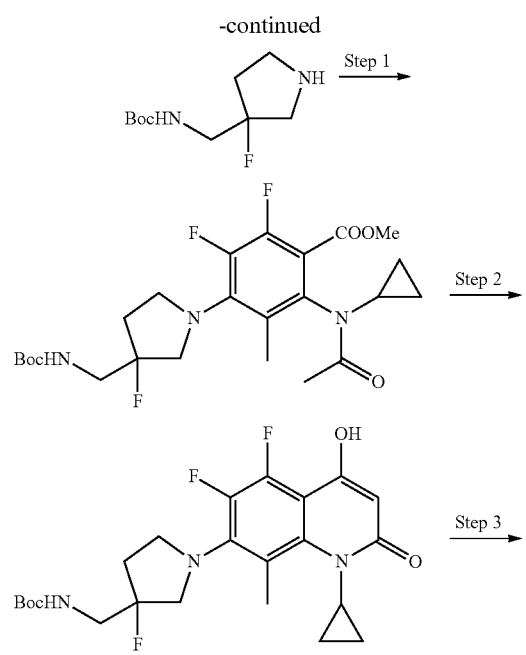

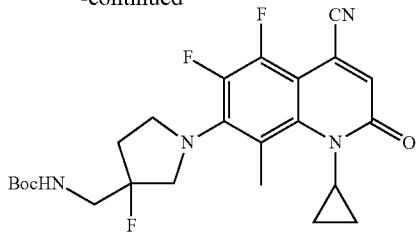

(i) methyl 4-(3-(((tert-butoxy carbonyl)amino) methyl)-3-fluoropyrrolidin-1-yl)-2-(N-cyclopropy-lacetamido)-5,6-difluoro-3-methylbenzoate methyl 4-bromo-2-(N-cyclopropylacetamido)-5,6-difluoro-3-methylbenzoate (0.7 g, 1.93 mmol, 1.0 equiv), Cs₂CO₃ (1.57 g, 4.83 mmol, 2.5 equiv), tert-butyl ((3-fluoropyrrolidin-3-yl) methyl) carbamate (0.84 g, 3.86 mmol, 2.0 equiv) were added in 1,4-dioxane (25 mL) and the reaction mixture was degassed for 5 minutes. Pd₂(dba)₃ (0.17 g, 0.19 mmol, 0.1 equiv), Xantphos (0.22 g, 0.39 mmol, 0.2 equiv) were added and the reaction mixture was stirred at 130° C. for 24 hours. The reaction mixture was quenched with cold water and extracted with EtOAc. The organic layer was washed with brine, dried over sodium sulfate and concentrated to afford a crude residue. The crude residue was purified by silica gel column chromatography (30-100% EtOAc/Hexane) to afford the desired product 84-i (0.34 g, 35.4% yield). LCMS (m/z): 500.4 [M+H].

(ii) tert-butyl ((1-(1-cyclopropyl-5, 6-difluoro-4-hydroxy-8-methyl-2-oxo-1,2-dihydro quinolin-7-yl)-3-fluoropyrrolidin-3-yl) methyl) carbamate 84-i (0.29 g, 0.58 mmol, 1.0 equiv) was dissolved in THF (5 mL) and cooled to −40° C. NaHMDS (1.0 M in THF) (1.16 mL, 1.16 mmol, 2.0 equiv) was added drop wise and the reaction mixture was stirred at 0° C. for 15 minutes. The reaction mixture was quenched with saturated aqueous ammonium chloride solution, diluted with water and extracted with EtOAc. The aqueous layer was acidified by 1.0 N HCl aqueous solution to the pH 3 to 4 and extracted with EtOAc. The organic layer was washed with brine, dried over sodium sulfate and concentrated to afford the desired product 84-ii (0.27 g, 85% yield, crude). The crude product was used in next step without further purification.

¹H NMR (400 MHz, DMSO) δ 5.76 (s, 1H), 3.87-3.70 (m, 3H), 3.41 (d, J=18.7 Hz, 4H), 2.50 (s, 3H), 2.09 (s, 2H), 1.39 (d, J=3.7 Hz, 9H), 0.77 (s, 2H), 0.35 (s, 2H)

LCMS (m/z): 468.4 [M+H]

(iii) 7-(3-(((tert-butoxycarbonyl) amino) methyl)-3-fluoropyrrolidin-1-yl)-1-cyclopropyl-5, 6-difluoro-8-methyl-2-oxo-1,2-dihydroquinolin-4-yl 84-ii (0.27 g, 0.6 mmol, 1.0 equiv) was dissolved in N,N-dimethylformamide (8 mL) and cooled to 0° C. TEA (0.24 mL, 1.73 mmol, 3.0 equiv), PhN(SO₂CF₃)₂ (0.24 g, 0.7 mmol, 1.2 equiv) were added drop wise and the reaction mixture was stirred at room temperature for 1 hour. The reaction mixture was quenched with water and extracted with EtOAc. The organic layer was washed with cold water, brine, dried over sodium sulfate and concentrated to afford a crude residue. The crude residue was purified by silica gel column chromatography (10-50% EtOAc/Hexane) to afford the desired product 84-iii (0.1 g, 30% yield).

¹H NMR (400 MHz, DMSO) δ 7.30 (s, 1H), 6.59 (s, 1H), 3.83 (d, J=11.4 Hz, 4H), 3.49 (s, 3H), 2.35 (s, 3H), 2.23 (d, J=4.3 Hz, 1H), 2.12 (s, 1H), 1.40 (d, J=4.6 Hz, 9H), 0.79-0.75 (m, 1H), 0.65-0.60 (m, 1H), 0.53-0.49 (m, 1H), 0.43-0.38 (m, 1H)

LCMS (m/z): 600.4 [M+H]

(iv) tert-butyl ((1-(4-cyano-1-cyclopropyl-5,6-difluoro-8-methyl-2-oxo-1,2-dihydro quinolin-7-yl)-3-fluoropyrrolidin-3-yl)methyl)carbamate 84-iii (0.09 g, 0.15 mmol, 1.0 equiv) was added in DMA (4 mL), Zn(CN)₂ (0.23 g, 1.95 mmol, 13 equiv), Zn (powder) (0.009 g, 0.15 mmol, 1.0 equiv) were added in sealed tube and the reaction mixture was degassed for 10 minutes. Pd(P(t-Bu)₃)₂ (0.015 g, 0.03 mmol, 0.2 equiv) was added and the reaction mixture was stirred at 55° C. for 24 hours. The reaction mixture was filtered through celite bed and extracted with EtOAc. The organic layer was washed with brine, dried over sodium sulfate and concentrated to afford a crude residue. The crude residue was purified by preparative TLC (60% EtOAc/Hexane) to afford the desired product 84-iv (0.06 g, 76% yield).

LCMS (06_4 min), [MH]⁺=477.4, RT=2.381 minutes
LCMS Method C_4 MIN
Column: HSS C18 (50*2.1 mm), 1.8 um; ESI source, Positive ion mode; Wavelength 237/396 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes

Example 85: 4-(aminomethyl)-7-(3-(aminomethyl)-3-fluoropyrrolidin-1-yl)-1-cyclopropyl-5,6-difluoro-8-methylquinolin-2(1H)-one TFA salt

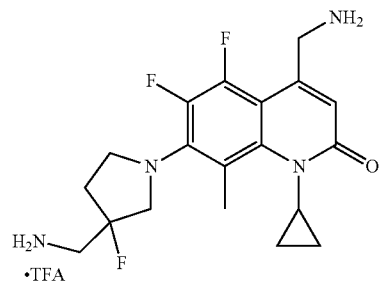 [SMILES: Cc1c(N2CCC(F)(CN)C2)c(F)c(F)c2c(CN)cc(=O)n(C3CC3)c12]

The title compound was prepared in accordance with the following scheme:

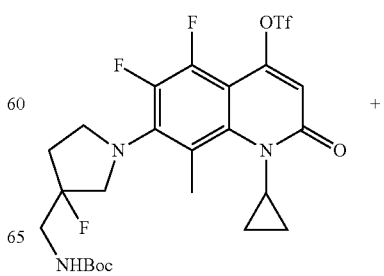

-continued

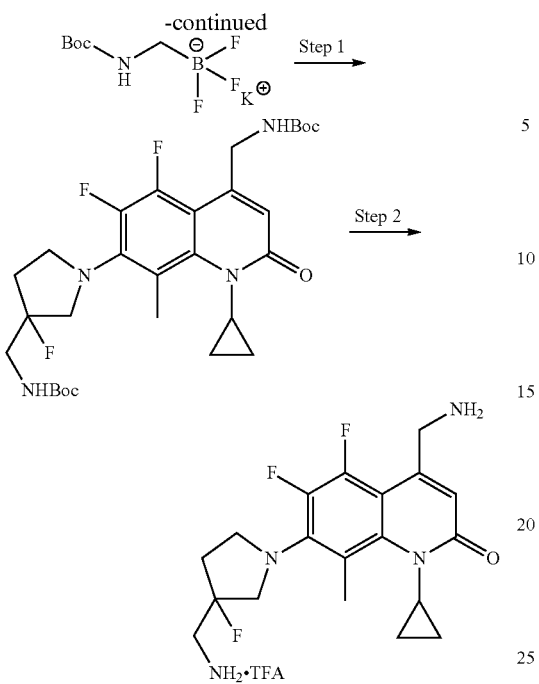

(i) tert-butyl ((1-(4-(((tert-butoxycarbonyl) amino) methyl)-1-cyclopropyl-5,6-difluoro-8-methyl-2-oxo-1,2-dihydroquinolin-7-yl)-3-fluoropyrrolidin-3-yl) methyl) carbamate 84-iii (0.27 g, 0.45 mmol, 1.0 equiv), potassium (((tert-butoxycarbonyl) amino) methyl) trifluoroborate (0.21 g, 0.89 mmol, 2.0 equiv) were added to toluene:water (5:0.5) and the reaction mixture was degassed for 5 minutes. Pd (II)OAc (0.005 g, 0.022 mmol, 0.05 equiv), RuPhos (0.02 g, 0.044 mmol, 0.1 equiv), $K_2CO_3$ (0.19 g, 1.34 mmol, 3.0 equiv) were added and the reaction mixture was stirred at 80° C. for 24 hours. The reaction mixture was quenched with cold water and extracted with EtOAc. The organic layer was washed with brine, dried over sodium sulfate and concentrated to afford a crude residue. The crude residue was purified by preparative HPLC purification to afford the desired product 85-i (0.038 g, 15% yield).
$^1$H NMR (400 MHz, MeOD) δ 7.27 (s, 1H), 7.09 (s, 1H), 6.43 (s, 1H), 4.49 (s, 2H), 3.96-3.80 (m, 2H), 3.53 (dd, J=18.0, 5.8 Hz, 5H), 2.47 (s, 3H), 2.23 (d, J=7.5 Hz, 1H), 2.18 (d, J=7.7 Hz, 1H), 1.48 (d, J=10.2 Hz, 18H), 1.15 (d, J=5.5 Hz, 1H), 0.90 (d, J=7.1 Hz, 1H), 0.53-0.43 (m, 2H)
LCMS (m/z): 581.5 [M+H]

(ii) 4-(aminomethyl)-7-(3-(aminomethyl)-3-fluoro-pyrrolidin-1-yl)-1-cyclopropyl-5,6-difluoro-8-methylquinolin-2(1H)-one TFA salt 85-i (0.038 g, 0.067 mmol, 1.0 equiv) was dissolved in dichloromethane (3 mL) and cooled to 0° C. TFA (0.4 mL) was added and the reaction mixture was stirred at room temperature for 30 minutes. The reaction mixture was concentrated, co-distilled with diethyl ether to afford a crude residue. The crude residue was triturated with diethyl ether, the solvent was decanted to afford the desired product 85-ii (0.03 g, 75.3% yield).
$^1$H NMR (400 MHz, MeOD) δ 6.50 (s, 1H), 4.42 (s, 2H), 4.02-3.91 (m, 2H), 3.76-3.48 (m, 5H), 2.52 (s, 3H), 2.46-2.26 (m, 2H), 1.28-1.21 (m, 2H), 0.53 (m, 2H)

LCMS (06_4 min), [MH]$^+$=381.3, RT=1.310 minutes
LCMS Method C_4 MIN
Column: HSS C18 (50*2.1 mm), 1.8 um; ESI source, Positive ion mode; Wavelength 235/359 nm;
Column temperature: Ambient;
Mobile Phase: A: 5 mM Ammonium acetate in 0.1% formic acid in water, B: 0.1% formic acid in ACN;
Flow rate: 0.55 mL/min;
Gradient: 5%-100% (solvent B) over 2.5 minutes and holding at 100% for 0.6 minutes Example 86: 4-(amino methyl)-7-(3-(amino methyl) pyrrolidin-1-yl)-1-cyclopropyl-6-fluoro-8-methylquinolin-2(1H)-one

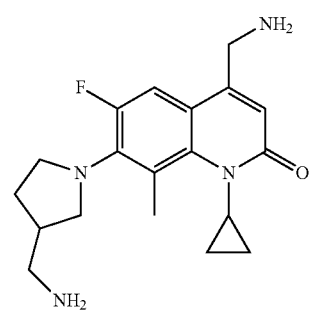 [SMILES: Cc1c(N2CCC(CN)C2)c(F)cc2c(CN)cc(=O)n(C3CC3)c12]

The title compound was prepared in accordance with the following scheme:

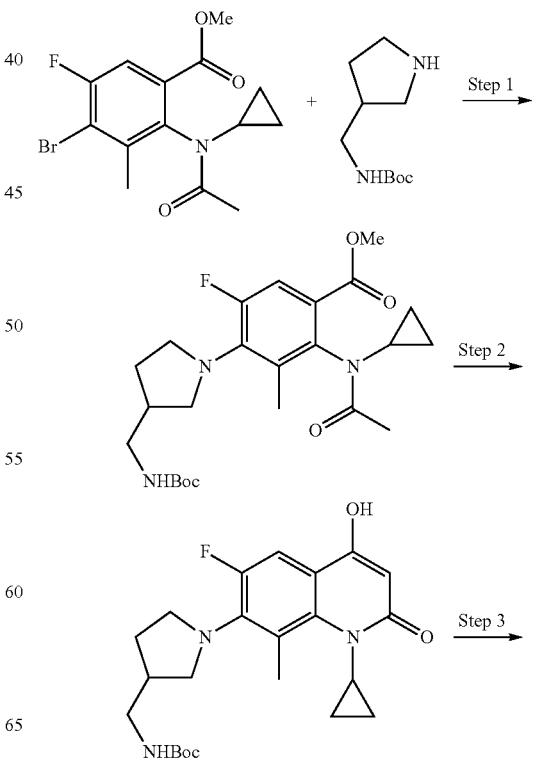

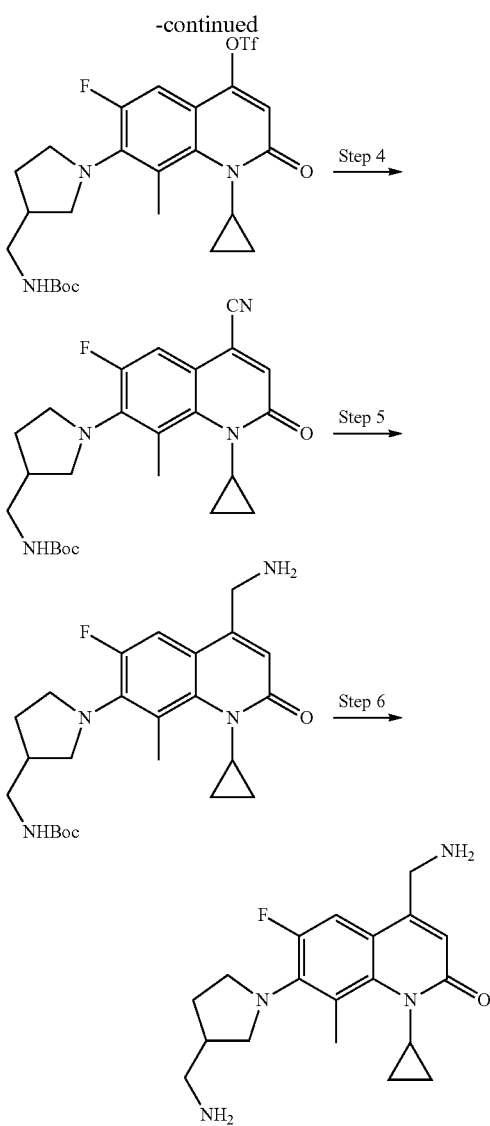

(i) methyl 4-(3-(((tert-butoxy carbonyl) amino) methyl) pyrrolidin-1-yl)-2-(N-cyclopropyl acetamido)-5-fluoro-3-methylbenzoate Methyl 4-bromo-2-(N-cyclopropylacetamido)-5-fluoro-3-methylbenzoate (2 g, 5.8 mmol, 1.0 equiv), tert-butyl (pyrrolidin-3-ylmethyl) carbamate (2.3 g, 11.6 mmol, 2.0 equiv), $Cs_2CO_3$ (5.7 g, 17.4 mmol, 3.0 equiv) were added in toluene (22 mL) in sealed tube and the reaction mixture was degassed for 10 minutes. $Pd_2(dba)_3$ (0.27 g, 0.3 mmol, 0.05 equiv), xantphos (0.5 g, 0.87 mmol, 0.15 equiv) were added and the reaction mixture was stirred at 110° C. for 24 hours. The reaction mixture was quenched with water and extracted with EtOAc. The organic layer was washed with brine, dried over sodium sulfate and concentrated to afford a crude residue. The crude residue was purified by silica gel column chromatography (60-65% EtOAc/Hexane) to afford the desired product 86-i (1.6 g, 59% yield).

$^1$H NMR (400 MHz, $CDCl_3$) δ 7.52 (t, J=13.1 Hz, 1H), 4.74 (s, 1H), 3.87 (t, J=13.5 Hz, 3H), 3.51-2.99 (m, 7H), 2.50 (m, 1H), 2.43 (s, 1.7H), 2.11 (d, J=29.4 Hz, 4H), 1.78 (d, J=3.6 Hz, 1.3H), 1.68 (m, 1H), 0.88 (d, J=17.1 Hz, 1H), 0.70 (m, 2H), 0.40 (m, 1H)

LCMS (m/z): 465.0 [M+H].

(ii) tert-butyl ((1-(1-cyclopropyl-6-fluoro-4-hydroxy-8-methyl-2-oxo-1,2-dihydroquinolin-7-yl) pyrrolidin-3-yl) methyl) carbamate 86-i (1.5 g, 3.2 mmol, 1.0 equiv) was dissolved in THF (30 mL) and cooled to 0° C. NaHMDS (1 M in THF) (16.2 mL, 16.2 mmol, 5.0 equiv) was added drop wise and the reaction mixture was stirred at 0° C. for 30 minutes. The reaction mixture was quenched with water, acidified by 1.0 N HCl aqueous solution to the pH 4 to 5 and extracted with EtOAc. The organic layer was washed with brine, dried over sodium sulfate and concentrated to afford a crude residue. The crude residue was triturated with n-pentane, the solvent was decanted to afford the desired product 86-ii (1.2 g, crude). The crude product was used in next step without further purification. LCMS (m/z): 432.8 [M+H].

(iii) 7-(3-(((tert-butoxycarbonyl) amino) methyl) pyrrolidin-1-yl)-1-cyclopropyl-6-fluoro-8-methyl-2-oxo-1,2-dihydroquinolin-4-yl trifluoro methane sulfonate 86-ii (1.2 g, 2.8 mmol, 1.0 equiv), TEA (1.16 g, 8.4 mmol, 3.0 equiv) were dissolved in N,N-dimethylformamide (15 mL) and cooled to 0° C. $PhN(SO_2CF_3)_2$ (1.2 g, 3.34 mmol, 1.2 equiv) in N,N-dimethylformamide (5 mL) was added drop wise and the reaction mixture was stirred at room temperature for 1 hour. The reaction mixture was quenched with water and extracted with EtOAc. The organic layer was washed with brine, dried over sodium sulfate and concentrated to afford a crude residue. The crude residue was purified by silica gel column chromatography (40% EtOAc/Hexane) to afford the desired product 86-iii (0.6 g, 40% yield).

$^1$H NMR (400 MHz, DMSO) δ 7.11 (d, J=13.3 Hz, 1H), 7.05 (s, 1H), 6.55 (s, 1H), 3.50 (s, 4H), 3.27 (s, 1H), 3.05 (d, J=6.0 Hz, 2H), 2.42 (s, 3H), 2.38 (d, J=7.0 Hz, 1H), 2.00 (d, J=6.3 Hz, 1H), 1.69 (s, 1H), 1.19-1.11 (m, 2H), 0.45 (m, 2H)
LCMS (m/z): 565.1 [M+H]

(iv) tert-butyl ((1-(4-cyano-1-cyclopropyl-6-fluoro-8-methyl-2-oxo-1,2-dihydro quinolin-7-yl) pyrrolidin-3-yl) methyl) carbamate 86-iii (0.54 g, 0.96 mmol, 1.0 equiv) was dissolved in N,N-dimethylformamide (16 mL) in sealed tube and the reaction mixture was degassed for 10 minutes. $Pd(PPh_3)_4$ (0.055 g, 0.048 mmol, 0.05 equiv), $Zn(CN)_2$ (0.12 g, 1.1 mmol, 1.1 equiv) were added and the reaction mixture was stirred at 70° C. for 24 hours. The reaction mixture was quenched with cold water and extracted with EtOAc. The organic layer was washed with brine, dried over sodium sulfate and concentrated to afford a crude residue. The crude residue was purified by silica gel column chromatography (35-40% EtOAc/Hexane) to afford the desired product 86-iv (0.27 g, 63% yield). LCMS (m/z): 441.7 [M+H].

(v) tert-butyl ((1-(4-(amino methyl)-1-cyclopropyl-6-fluoro-8-methyl-2-oxo-1,2-dihydroquinolin-7-yl) pyrrolidin-3-yl) methyl) carbamate 86-iv (0.2 g, 0.5 mmol, 1.0 equiv) was dissolved in methanol (4 mL), acetic acid (0.4 mL), 10% Pd/C (50% moisture) (0.04 g) were added and $H_2$ (gas) was purged into the solution for 5 minutes. The reaction mixture was stirred under H₂ (gas) atmosphere at room temperature for 5 hours. The reaction mixture was filtered through celite bed and the filtrate was concentrated to afford the desired product 86-v (0.1 g, 49.8% yield). The crude product was used in next step without further purification. LCMS (m/z): 446.0 [M+H].

(vi) 4-(amino methyl)-7-(3-(amino methyl) pyrrolidin-1-yl)-1-cyclopropyl-6-fluoro-8-methylquinolin-2(1H)-one 86-v (0.1 g, 0.23 mmol, 1.0 equiv) was dissolved in dichloromethane (2 mL) and cooled to 0° C. HCl (in 1,4-dioxane) (2 mL) was added and the reaction mixture was stirred at room temperature for 3 hours. The reaction mixture was concentrated and co-distilled with dichloromethane to afford a crude residue. The crude residue was purified by preparative HPLC purification to afford the desired product 86-vi (0.015 g, 21% yield).

¹H NMR (400 MHz, MeOD) δ 7.37 (d, J=13.7 Hz, 1H), 6.53 (s, 1H), 4.36 (s, 2H), 3.68 (dd, J=14.6, 6.7 Hz, 1H), 3.64-3.58 (m, 1H), 3.58-3.51 (m, 2H), 3.42-3.36 (m, 1H), 3.19-3.08 (m, 2H), 2.68 (dq, J=14.5, 7.3 Hz, 1H), 2.59 (s, 3H), 2.31 (ddd, J=14.3, 9.5, 5.8 Hz, 1H), 1.85 (dq, J=12.4, 7.8 Hz, 1H), 1.28-1.17 (m, 2H), 0.50 (dd, J=8.6, 4.2 Hz, 2H)

LCMS (02_4 min), [MH]⁺=345.0, RT=1.43 mins.

LCMS Method C_4 MIN

Column: HSS C18 (50*2.1 mm), 1.8 um; ESI source, Positive ion mode; Wavelength 232/372 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 87: 4-(((2-aminoethyl)amino)methyl)-7-(3-(aminomethyl)pyrrolidin-1-yl)-1-cyclopropyl-6-fluoro-8-methylquinolin-2(1H)-one TFA salt

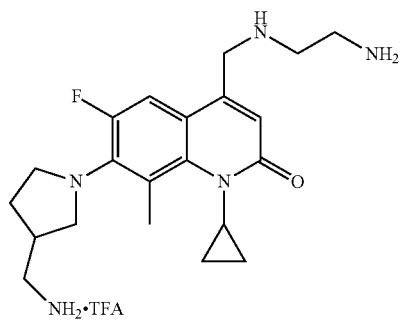

The title compound was prepared in accordance with the following scheme:

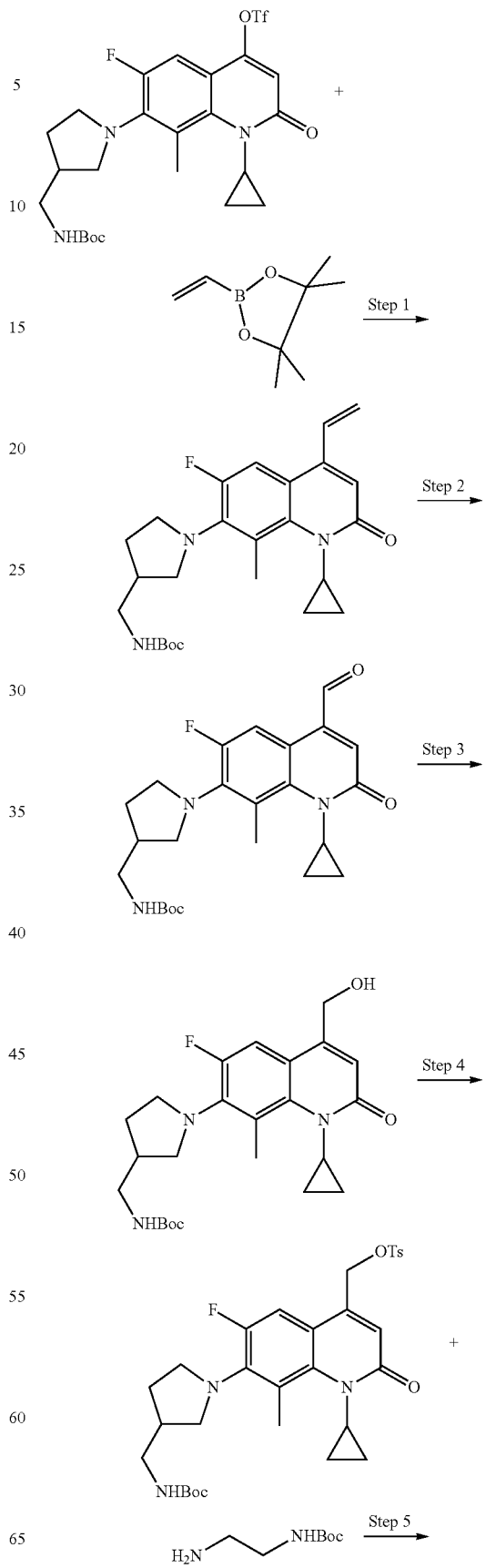

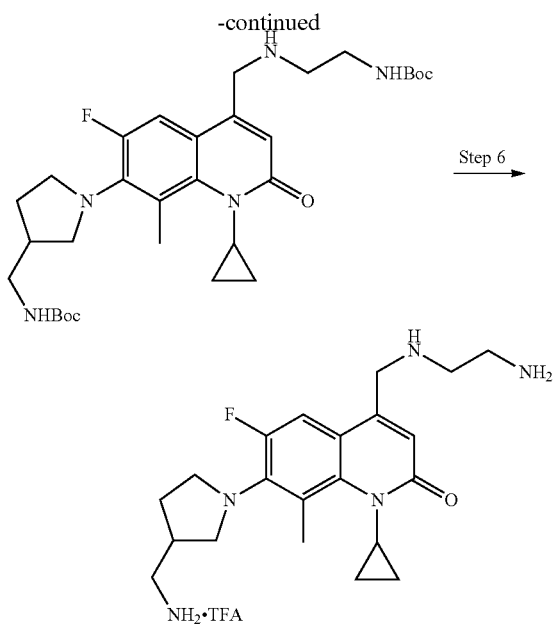

(i) tert-butyl ((1-(1-cyclopropyl-6-fluoro-8-methyl-2-oxo-4-vinyl-1,2-dihydroquinolin-7-yl) pyrrolidin-3-yl)methyl) carbamate 86-iii (1 g, 1.78 mmol, 1.0 equiv), Na₂CO₃ (0.57 g, 5.33 mmol, 3.0 equiv) were suspended in 1, 4-dioxane:water (22 mL) in sealed tube and the reaction mixture was degassed for 5 minutes. 4,4,5,5-tetramethyl-2-vinyl-1,3,2-dioxaborolane (0.33 g, 2.12 mmol, 1.2 equiv), PdCl₂(PPh₃)₂ (0.025 g, 0.04 mmol, 0.02 equiv) were added and the reaction mixture was stirred at 80° C. for 3 hours. The reaction mixture was quenched with cold water and extracted with EtOAc. The organic layer was washed with brine, dried over sodium sulfate and concentrated to afford a crude residue. The crude residue was purified by flash chromatography (reverse phase) (70% MeOH/water) to afford the desired product 87-i (0.47 g, 60% yield).

¹H NMR (400 MHz, DMSO) δ 7.40 (d, J=14.3 Hz, 1H), 7.13 (dd, J=17.1, 11.1 Hz, 1H), 7.04 (s, 1H), 5.92 (dd, J=17.1, 1.2 Hz, 1H), 5.60-5.54 (m, 1H), 3.42 (d, J=3.0 Hz, 4H), 3.21-3.14 (m, 1H), 3.07-3.03 (m, 2H), 2.43 (s, 3H), 2.35 (d, J=14.7 Hz, 1H), 2.03-1.98 (m, 1H), 1.66 (dd, J=11.9, 7.0 Hz, 1H), 1.39 (s, 9H), 1.10 (d, J=7.0 Hz, 2H), 0.37 (d, J=3.6 Hz, 2H)

LCMS (m/z): 442.8 [M+H]

(ii) tert-butyl ((1-(1-cyclopropyl-6-fluoro-4-formyl-8-methyl-2-oxo-1,2-dihydro quinolin-7-yl) pyrrolidin-3-yl) methyl) carbamate 87-i (0.47 g, 1.07 mmol, 1.0 equiv) was dissolved in 1,4-dioxane:water (3:1, 20 mL). 2,6-Lutidine (0.23 g, 2.13 mmol, 2.0 equiv), NaIO₄ (0.91 g, 4.3 mmol, 4.0 equiv) were added and the reaction mixture was stirred at room temperature for 5 minutes. OsO₄ (0.0054 g, 0.021 mmol, 0.02 equiv) was added and the reaction mixture was stirred at room temperature for 4 hours. The reaction mixture was quenched with cold water, acidified by 50% HCl aqueous solution to the pH 4 to 5 and extracted with EtOAc. The organic layer was washed with brine, dried over sodium sulfate and concentrated to afford the desired product 87-ii (0.42 g, 89.4% yield).

¹H NMR (400 MHz, DMSO) δ 10.06 (s, 1H), 8.12 (d, J=15.0 Hz, 1H), 7.04 (s, 1H), 7.01 (s, 1H), 3.44 (d, J=6.0 Hz, 3H), 3.22 (s, 1H), 3.04 (s, 3H), 2.43 (s, 3H), 2.02 (d, J=5.1 Hz, 1H), 1.67 (s, 1H), 1.38 (s, 9H), 1.14 (d, J=6.7 Hz, 2H), 0.40 (d, J=4.4 Hz, 2H)

LCMS (m/z): 442.7 [M+H]

(iii) tert-butyl ((1-(1-cyclopropyl-6-fluoro-4-(hydroxyl methyl)-8-methyl-2-oxo-1,2-dihydroquinolin-7-yl)pyrrolidin-3-yl) methyl) carbamate 87-ii (0.5 g, 1.13 mmol, 1.0 equiv) was dissolved in methanol (10 mL) and cooled to 0° C. Sodium borohydride (0.034 g, 0.09 mmol, 0.8 equiv) was added in portion wise and the reaction mixture was stirred at room temperature for 2 hours. The reaction mixture was quenched with water and extracted with EtOAc. The organic layer was washed with brine, dried over sodium sulfate and concentrated to afford the desired product 87-iii (0.46 g, 92% yield). The crude product was used in next step without further purification.

¹H NMR (400 MHz, DMSO) δ 7.22 (d, J=14.1 Hz, 1H), 7.04 (s, 1H), 6.40 (s, 1H), 5.42 (t, J=5.6 Hz, 1H), 4.59 (d, J=5.4 Hz, 2H), 3.69 (d, J=23.1 Hz, 1H), 3.40 (s, 3H), 3.16 (d, J=7.2 Hz, 1H), 3.03 (d, J=7.0 Hz, 2H), 2.44 (s, 3H), 2.33-2.24 (m, 1H), 2.01 (s, 1H), 1.66 (s, 1H), 1.38 (s, 9H), 1.11 (s, 2H), 0.34 (d, J=3.6 Hz, 2H)

LCMS (m/z): 445.7 [M+H]

(iv) (7-(3-(((tert-butoxycarbonyl) amino) methyl) pyrrolidin-1-yl)-1-cyclopropyl-6-fluoro-8-methyl-2-oxo-1,2-dihydroquinolin-4-yl)methyl 4-methyl benzenesulfonate 87-iii (0.25 g, 0.56 mmol, 1.0 equiv) was dissolved in dichloromethane (10 mL) and cooled to 0° C. TEA (0.4 mL, 2.8 mmol, 5.0 equiv), DMAP (0.014 g, 0.11 mmol, 0.2 equiv), 4-Methylbenzenesulfonyl chloride (0.16 g, 0.84 mmol, 1.5 equiv) were added and the reaction mixture was stirred at room temperature for 4 hours. The reaction mixture was quenched with water and extracted with EtOAc. The organic layer was washed with brine, dried over sodium sulfate and concentrated to afford the desired product 87-iv (0.24 g, 71% yield). The crude product was used in next step without further purification.

¹H NMR (400 MHz, DMSO) δ 7.79 (d, J=8.3 Hz, 1H), 7.45 (dd, J=15.0, 8.0 Hz, 2H), 7.09 (dd, J=18.2, 11.0 Hz, 2H), 6.32 (s, 1H), 5.30 (s, 2H), 3.40 (m, 4H), 3.21-3.10 (m, 1H), 3.05 (m, 2H), 2.39 (d, J=7.1 Hz, 6H), 2.33 (m, 1H), 1.99 (m, 1H), 1.66 (m, 1H), 1.39 (s, 9H), 1.09 (m, 2H), 0.28 (m, 2H)

LCMS (m/z): 600.9 [M+H]

(v) tert-butyl ((1-(4-(((2-((tert-butoxycarbonyl) amino) ethyl) amino) methyl)-1-cyclopropyl-6-fluoro-8-methyl-2-oxo-1,2-dihydroquinolin-7-yl) pyrrolidin-3-yl) methyl) carbamate 87-iv (0.1 g, 0.16 mmol, 1.0 equiv), tert-butyl (2-aminoethyl) carbamate (0.27 g, 1.66 mmol, 10.0 equiv) were dissolved in acetonitrile (5 mL) in sealed tube and the reaction mixture was stirred at 80° C. for 5 hours. The reaction mixture was quenched with water and extracted with EtOAc. The organic layer was washed with brine, dried over sodium sulfate and concentrated to afford the desired product 87-v (0.09 g, 91.8% yield). The crude product was used in next step without further purification. LCMS (m/z): 588.6 [M+H].

(vi) 4-(((2-aminoethyl)amino)methyl)-7-(3-(aminomethyl)pyrrolidin-1-yl)-1-cyclopropyl-6-fluoro-8-methylquinolin-2(1H)-one TFA Salt 87-iv (0.09 g, 0.15 mmol, 1.0 equiv) was dissolved in dichloromethane (2 mL) and cooled to 0° C. TFA (2 mL) was added and the reaction mixture was stirred at room temperature for 3 hours. The reaction mixture was concentrated and co-distilled with dichloromethane to afford a crude residue. The crude residue was purified by preparative HPLC purification to afford the desired product 87-vi (0.022 g, 19.8% yield).

$^1$H NMR (400 MHz, MeOD) δ 7.43 (d, J=13.7 Hz, 1H), 6.63 (s, 1H), 4.37 (s, 2H), 3.70-3.65 (m, 1H), 3.63-3.51 (m, 3H), 3.39 (d, J=6.3 Hz, 2H), 3.13 (d, J=3.6 Hz, 2H), 2.66 (dd, J=14.6, 7.2 Hz, 1H), 2.58 (s, 3H), 2.31 (dd, J=11.7, 5.1 Hz, 1H), 1.85 (dd, J=12.2, 7.7 Hz, 1H), 1.28-1.22 (m, 2H), 0.50 (s, 2H)

LCMS (02_4 min), [MH]$^+$=388.0, RT=1.389 mins

LCMS Method C_4 MIN

Column: HSS C18 (50*2.1 mm), 1.8 um; ESI source, Positive ion mode; Wavelength 202/232 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

Example 88: 7-(3-(aminomethyl)pyrrolidin-1-yl)-1-cyclopropyl-6-fluoro-8-methyl-4-((methylamino)methyl)quinolin-2(1H)-one TFA salt

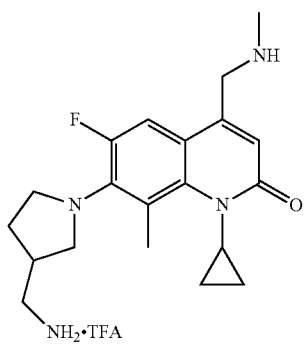

The title compound was prepared in accordance with the following scheme:

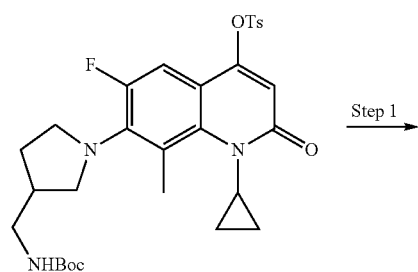

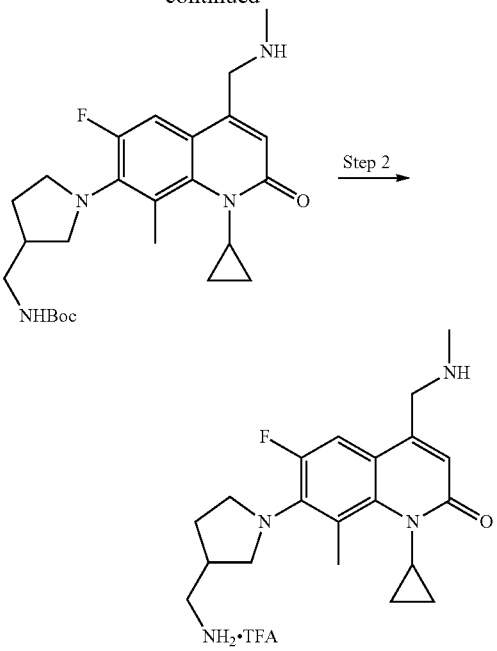

(i) tert-butyl ((1-(1-cyclopropyl-6-fluoro-8-methyl-4-((methyl amino) methyl)-2-oxo-1,2-dihydroquinolin-7-yl)pyrrolidin-3-yl)methyl) carbamate 87-iv (0.21 g, 0.35 mmol, 1.0 equiv), methanamine (1 M in THF) (10.5 mL, 10.5 mmol, 30.0 equiv) were dissolved in THF (6 mL) and the reaction mixture was stirred at 80° C. for 2 hours. The reaction mixture was quenched with water and extracted with EtOAc. The organic layer was washed with brine, dried over sodium sulfate and concentrated to afford the desired product 88-i (0.14 g, 87% yield).

$^1$H NMR (400 MHz, MeOD) δ 7.34 (d, J=13.9 Hz, 1H), 6.52 (s, 1H), 4.66 (s, 2H), 3.61-3.46 (m, 3H), 3.30-3.25 (m, 1H), 3.24-3.17 (m, 3H), 2.56 (s, 3H), 2.49 (s, 3H), 2.42-2.28 (m, 1H), 2.14 (dd, J=12.7, 6.2 Hz, 1H), 1.78 (d, J=6.8 Hz, 1H), 1.46 (s, 9H), 0.92 (t, J=6.9 Hz, 2H), 0.49 (d, J=3.6 Hz, 2H)

LCMS (m/z): 459.9 [M+H]

(ii) 7-(3-(aminomethyl)pyrrolidin-1-yl)-1-cyclopropyl-6-fluoro-8-methyl-4-((methyl amino)methyl)quinolin-2(1H)-one TFA salt 88-i (0.14 g, 0.31 mmol, 1.0 equiv) was dissolved in dichloromethane (5 mL) and cooled to 0° C. TFA (0.5 mL) was added and the reaction mixture was stirred at room temperature for 1 hour. The reaction mixture was concentrated to afford a crude residue. The crude residue was purified by preparative HPLC purification to afford the desired product 88-ii (0.021 g, 21% yield).

$^1$H NMR (400 MHz, MeOD) δ 7.43 (d, J=13.6 Hz, 1H), 6.56 (s, 1H), 4.43 (s, 2H), 3.71-3.63 (m, 2H), 3.56 (d, J=4.1 Hz, 2H), 3.40 (s, 1H), 3.13 (dd, J=7.1, 4.0 Hz, 2H), 2.88 (s, 3H), 2.71-2.64 (m, 1H), 2.58 (s, 3H), 2.32 (s, 1H), 1.86 (dd, J=12.3, 7.9 Hz, 1H), 1.27 (s, 2H), 0.51 (s, 2H)

LCMS (06_4 min), [MH]$^+$=359.7, RT=1.394 minutes

LCMS Method C_4 MIN

Column: HSS C18 (50*2.1 mm), 1.8 um; ESI source, Positive ion mode; Wavelength 374 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 89: 7-(3-(aminomethyl)pyrrolidin-1-yl)-1-cyclopropyl-4-((dimethylamino)methyl)-6-fluoro-8-methylquinolin-2(1H)-one TFA salt The title compound was prepared in accordance with the following scheme:

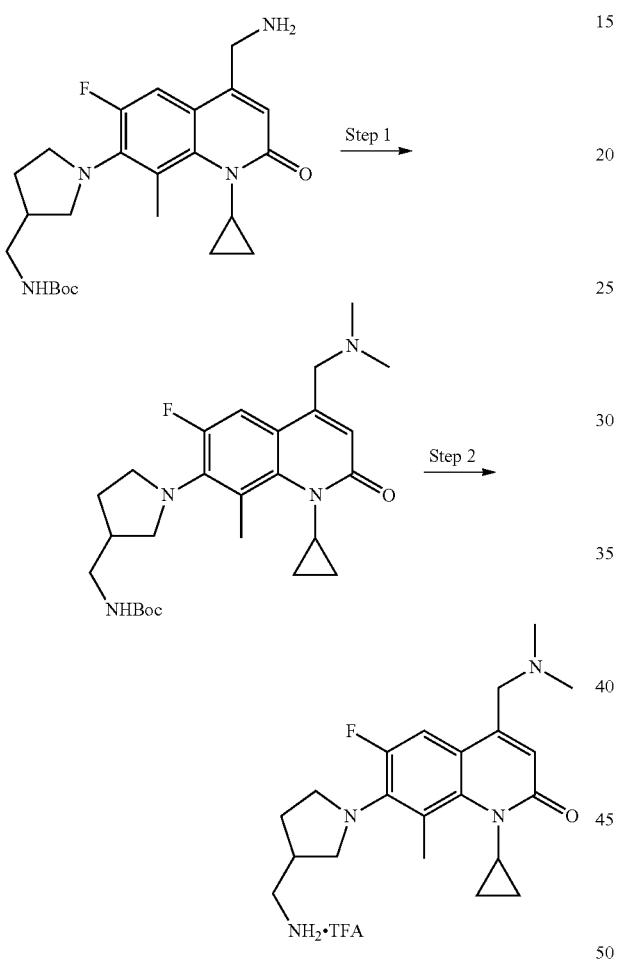

(i) tert-butyl ((1-(1-cyclopropyl-4-((dimethyl amino)methyl)-6-fluoro-8-methyl-2-oxo-1,2-dihydroquinolin-7-yl)pyrrolidin-3-yl)methyl) carbamate 86-v (0.1 g, 0.23 mmol, 1.0 equiv) and paraformaldehyde (0.01 g, 0.3 mmol, 1.5 equiv) were dissolved in methanol (4 mL). Acetic acid (0.14 g, 2.3 mmol, 10.0 equiv), NaCNBH$_3$ (0.044 g, 0.7 mmol, 3.1 equiv) were added and the reaction mixture was stirred at room temperature for 24 hours. The reaction mixture was quenched with cold water and basified with solid sodium bicarbonate to the pH 8 to 9 and extracted with EtOAc. The organic layer was washed with brine, dried over sodium sulfate and concentrated to afford the desired product 89-i (0.09 g, 85% yield). The product was used in the next step without further purification.

LCMS (m/z): 473.8 [M+H].

(ii) 7-(3-(aminomethyl)pyrrolidin-1-yl)-1-cyclopropyl-4-((dimethylamino)methyl)-6-fluoro-8-methylquinolin-2(1H)-one TFA salt 89-i (0.09 g, 0.2 mmol, 1.0 equiv) was dissolved in dichloromethane (2 mL) and cooled to 0° C. TFA (2 mL) was added and the reaction mixture was stirred at room temperature for 3 hours. The reaction mixture was concentrated and co-distilled with dichloromethane to afford a crude residue. The crude residue was purified by preparative HPLC purification to afford the desired product 89-ii (0.008 g, 11% yield).

$^1$H NMR (400 MHz, MeOD) δ 7.55 (d, J=14.1 Hz, 1H), 6.70 (s, 1H), 4.53 (s, 2H), 3.60 (t, J=35.9 Hz, 4H), 3.42 (s, 1H), 3.13 (s, 2H), 2.96 (s, 6H), 2.69 (d, J=17.7 Hz, 1H), 2.58 (s, 3H), 2.31 (s, 1H), 1.86 (s, 1H), 1.26 (s, 2H), 0.54 (s, 2H)

LCMS (06_4 min), [MH]$^+$=373.6, RT=1.40 mins

LCMS Method C_4 MIN

Column: HSS C18 (50*2.1 mm), 1.8 um; ESI source, Positive ion mode; Wavelength 202/380 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 90: (S)-1-cyclopropyl-5,6-difluoro-7-(3-hydroxypyrrolidin-1-yl)-8-methyl-4-((4-methylpiperazin-1-yl) methyl)quinolin-2(1H)-one trifluoro acetic acid

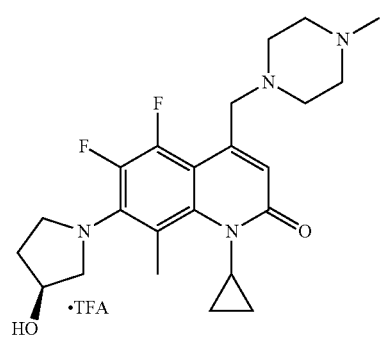 [SMILES: Cc1c(N2CC[C@H](O)C2)c(F)c(F)c2c(CN3CCN(C)CC3)cc(=O)n(C3CC3)c12]

The title compound was prepared in accordance with the following scheme:

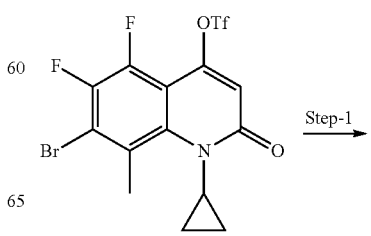

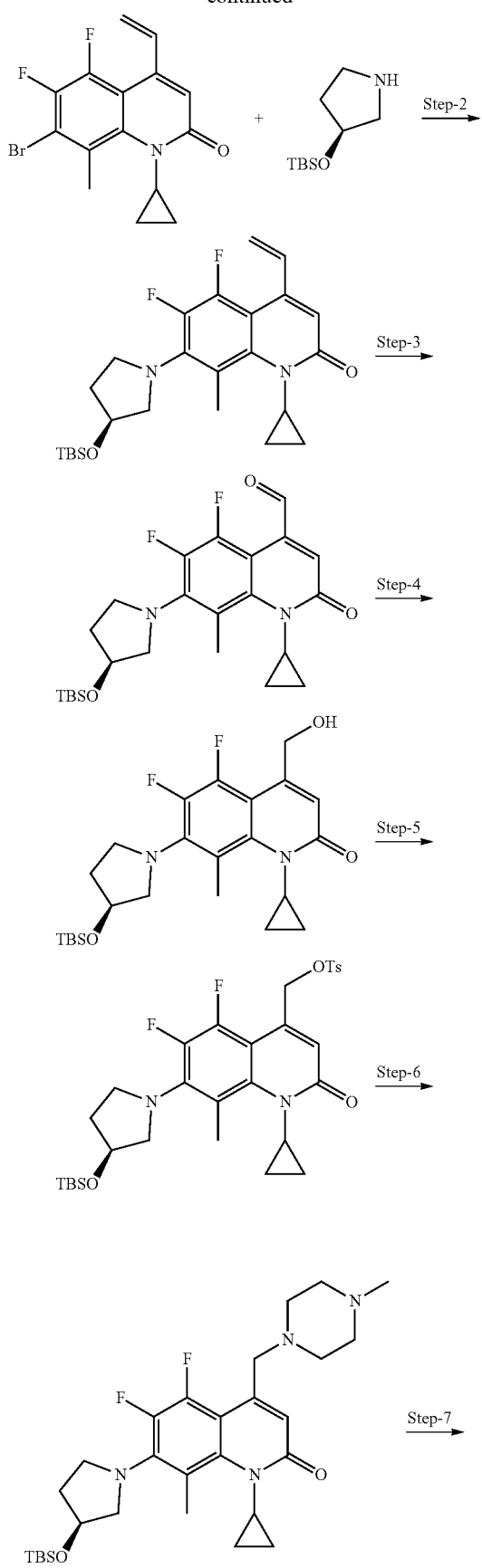

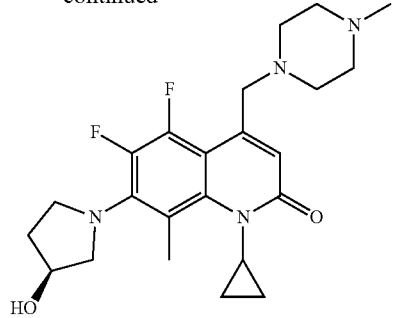

(i) 7-bromo-1-cyclopropyl-5,6-difluoro-8-methyl-4-vinylquinolin-2(1H)-one 7-bromo-1-cyclopropyl-5,6-difluoro-8-methyl-2-oxo-1,2-dihydroquinolin-4-yl trifluoro methane sulfonate (0.65 g, 1.41 mmol, 1.0 equiv), TEA (0.39 mL, 2.81 mmol, 2.0 equiv) were added in IPA:THF (3:1, 16 mL) at RT and the reaction mixture was degassed for 10 minutes. $PdCl_2dppf.MDC$ (0.11 g, 0.14 mmol, 0.1 equiv) was added and the reaction mixture was degassed for 10 minutes. Vinyl boronate pinacol ester (0.26 g, 1.7 mmol, 1.2 equiv) was added and the reaction mixture was stirred at 80° C. for 5 hours. The reaction mixture was diluted with cold water and extracted with EtOAc. The organic layer was washed with brine, dried over sodium sulfate and concentrated to afford crude residue. The crude residue was purified by 100-200 mesh silica gel column chromatography (0-30% EtOAc/Hexane) to afford the desired product 90-i (0.2 g, 43% yield).

$^1$H NMR (400 MHz, $CDCl_3$) δ 7.21-7.08 (m, 1H), 6.63 (s, 1H), 5.67 (d, J=17.0 Hz, 1H), 5.47 (d, J=11.1 Hz, 1H), 3.55-3.50 (m, 1H), 2.79-2.68 (m, 3H), 1.23 (d, J=6.9 Hz, 2H), 0.54 (d, J=3.0 Hz, 2H)

LCMS (m/z): 342.3 [M+H]

(ii) (S)-7-(3-((tert-butyl dimethyl silyl) oxy) pyrrolidin-1-yl)-1-cyclopropyl-5,6-difluoro-8-methyl-4-vinylquinolin-2(1H)-one 90-i (0.02 g, 0.53 mmol, 1.0 equiv), (S)-3-((tert-butyl dimethylsilyl) oxy) pyrrolidine (0.017 g, 0.088 mmol, 1.5 equiv), $Cs_2CO_3$ (0.028 g, 0.088 mmol, 1.5 equiv) were added in 1,4-dioxane (1 mL) and the reaction mixture was degassed for 10 minutes. $Pd_2dba_3$ (0.0026 g, 0.015 mmol, 0.05 equiv), Xantphos (0.0033 g, 0.0058 mmol, 0.1 equiv) were and the reaction mixture was degassed for 10 minutes. The reaction mixture was stirred at 110° C. for overnight. The reaction mixture was quenched with cold water and extracted with EtOAc. The organic layer was washed brine solution, dried over sodium sulfate and concentrated to afford crude residue. The crude residue was purified by 100-200 mesh silica gel column chromatography (10-100% EtOAc/Hexane) to afford the desired product 90-ii (0.016 g, 60% yield $^1$H NMR (400 MHz, MeOD) δ 7.20 (dd, J=18.9, 8.9 Hz, 1H), 6.44 (s, 1H), 5.75-5.68 (m, 1H), 5.46 (d, J=10.9 Hz, 1H), 4.63 (s, 1H), 3.90-3.80 (m, 2H), 3.54-3.45 (m, 2H), 3.28 (s, 1H), 2.47 (d, J=15.2 Hz, 3H), 2.17 (dd, J=7.8, 4.8 Hz, 1H), 1.98 (s, 1H), 1.23 (dd, J=10.9, 4.2 Hz, 2H), 0.94 (d, J=2.9 Hz, 9H), 0.55-0.49 (m, 2H), 0.14 (d, J=11.7 Hz, 6H)

LCMS (m/z): 461.4 [M+H].

(iii) (S)-7-(3-((tert-butyl dimethyl silyl) oxy) pyrrolidin-1-yl)-1-cyclopropyl-5,6-difluoro-8-methyl-2-oxo-1,2-dihydroquinoline-4-carbaldehyde 90-ii (0.34 g, 0.74 mmol, 1.0 equiv) was added in 1,4-dioxane:water (3:1, 4 mL), OsO₄ (1 g in 50 mL of t-BuOH) (0.94 mL) was added at 0° C. and the reaction mixture was stirred at RT for 5 minutes. Sodium periodate (0.63 g, 3.0 mmol, 4.0 equiv) was added in portion wise and the reaction mixture was stirred at 95° C. for 2 hours. The reaction mixture was diluted with water and extracted with EtOAc. The organic layer was washed brine solution, dried over sodium sulfate and concentrated to afford the desired product 90-iii (0.36 g, crude). The crude product was used in next step without further purification. LCMS (m/z): 463.4 [M+H].

(iv) (S)-7-(3-((tert-butyl dimethyl silyl) oxy) pyrrolidin-1-yl)-1-cyclopropyl-5,6-difluoro-4-(hydroxy methyl)-8-methylquinolin-2(1H)-one 90-iii (0.36 g, 0.78 mmol, 1.0 equiv) was added in methanol (6 mL) and cooled to 0° C. Sodium borohydride (0.029 g, 0.78 mmol, 1.0 equiv) was added and the reaction mixture was stirred at RT for 45 minutes. The reaction mixture was quenched with NH₄Cl and extracted with EtOAc. The organic layer was washed with brine solution, dried over sodium sulfate and concentrated to afford the desired product 90-iv (0.38 g, crude). The crude product was used in next step without further purification. LCMS (m/z): 465.4 [M+H].

(v) (S)-(7-(3-((tert-butyl dimethyl silyl) oxy) pyrrolidin-1-yl)-1-cyclopropyl-5,6-difluoro-8-methyl-2-oxo-1,2-dihydroquinolin-4-yl) methyl 4-methylbenzenesulfonate 90-iv (0.38 g, 0.82 mmol, 1.0 equiv) was added in dichloromethane (15 mL), DMAP (0.019 g, 0.16 mmol, 0.2 equiv), TEA (0.56 mL, 4.1 mmol, 5.0 equiv) and cooled to 0° C. TsCl (0.23 g, 1.23 mmol, 1.5 equiv) were added and the reaction mixture was stirred at RT for 1 hour. The reaction mixture was quenched with water and extracted with dichloromethane. The organic layer was washed dilute HCl, followed by washed with NaHCO₃, brine solution, dried over sodium sulfate and concentrated to afford a crude residue. The crude residue was purified by 60-120 mesh silica gel column chromatography (10-100% EtOAc/Hexane and then 10% MeOH/dichloromethane) to afford the desired product 90-v (0.31 g, 30-35% by LCMS). LCMS (m/z): 619.4 [M+H].

(vi) (S)-7-(3-((tert-butyl dimethyl silyl) oxy) pyrrolidin-1-yl)-1-cyclopropyl-5,6-difluoro-8-methyl-4-((4-methylpiperazin-1-yl) methyl) quinolin-2(1H)-one 90-v (0.31 g, 0.5 mmol, 1.0 equiv) was dissolved in dry THF (8 mL), N-methyl piperazine (0.17 g, 1.5 mmol, 3.0 equiv) was added and the reaction mixture was stirred at 80° C. for 1 hour. The reaction mixture was quenched with cold water and extracted with EtOAc. The organic layer was washed with brine, dried over sodium sulfate and concentrated to afford the desired product 90-vi (0.28 g, 30-35% by LCMS). The crude product was used in next step without further purification. LCMS (m/z): 547.5 [M+H].

(vii) (S)-1-cyclopropyl-5,6-difluoro-7-(3-hydroxypyrrolidin-1-yl)-8-methyl-4-((4-methyl piperazin-1-yl)methyl)quinolin-2(1H)-one TFA salt 90-vi (0.093 g, 0.17 mmol, 1.0 equiv) was dissolved in methanol (3 mL), HCl (in 1,4-dioxane) (0.1 mL) was added at 0° C. and the reaction mixture was stirred at RT for 1 hour. The reaction mixture was concentrated, co-distilled with dichloromethane, diethyl ether and n-pentane to afford a crude residue. The crude residue was purified by preparative HPLC purification to afford the desired product 90-vii as TFA salt (TFA used as additive in preparative HPLC purification) (0.017 g, 23% yield).

¹H NMR (400 MHz, MeOD) δ 6.61 (s, 1H), 4.55 (d, J=2.6 Hz, 1H), 3.96-3.82 (m, 4H), 3.50 (d, J=4.1 Hz, 5H), 3.22 (s, 2H), 3.15-3.06 (m, 2H), 2.92 (s, 3H), 2.57 (s, 2H), 2.46 (s, 3H), 2.20 (dd, J=12.8, 4.8 Hz, 1H), 2.03 (s, 1H), 1.27-1.18 (m, 2H), 0.55-0.45 (m, 2H)

LCMS (06_4 min), [MH]⁺=433.4, RT=1.557 minutes.
LCMS Method C_4 MIN
Column: HSS C18 (50*2.1 mm), 1.8 um; ESI source, Positive ion mode; Wavelength 361 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes

Example 91: 4-(2-aminoethyl)-7-(3-(aminomethyl) pyrrolidin-1-yl)-1-cyclopropyl-6-fluoro-8-methylquinolin-2(1H)-one TFA salt

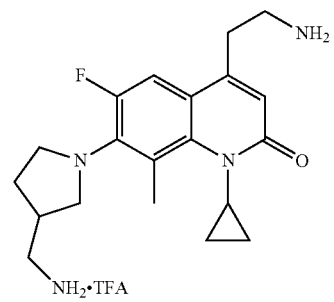

The title compound was prepared in accordance with the following scheme:

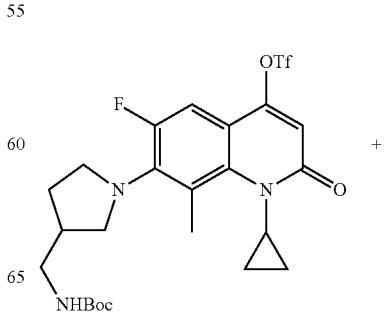

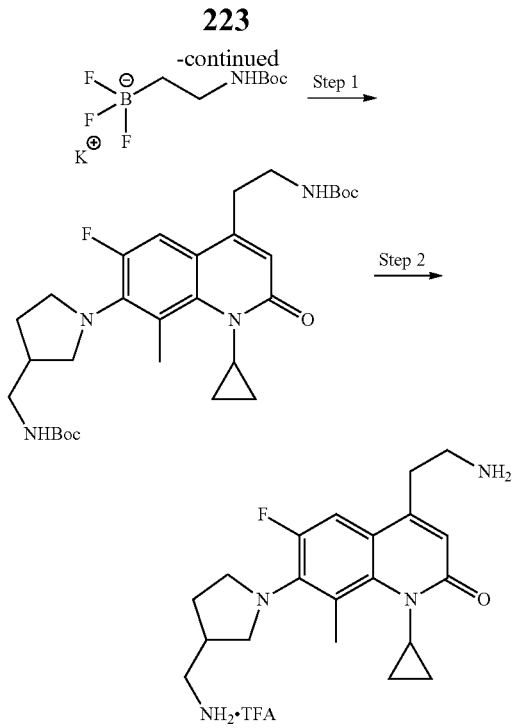

(i) tert-butyl ((1-(4-(2-((tert-butoxycarbonyl) amino) ethyl)-1-cyclopropyl-6-fluoro-8-methyl-2-oxo-1,2-dihydroquinolin-7-yl) pyrrolidin-3-yl) methyl) carbamate 86-iii (0.25 g, 0.44 mmol, 1.0 equiv) was dissolved in 1,4-dioxane:water (4:0.4 mL). Potassium (2-((tert-butoxycarbonyl) amino) ethyl) trifluoroborate (0.22 g, 0.88 mmol, 2.0 equiv), $Cs_2CO_3$ (0.14 g, 0.44 mmol, 1.0 equiv), $PdCl_2$ (dppf) (0.032 g, 0.044 mmol, 0.1 equiv) were added and the reaction mixture was degassed for 20 minutes. The reaction mixture was stirred at 100° C. for 2 hours. The reaction mixture was quenched with water and extracted with EtOAc. The organic layer was washed with brine, dried over sodium sulfate and concentrated to afford a crude residue. The crude residue was purified by preparative TLC (5% MeOH/dichloromethane) to afford the desired product 91-i (0.09 g, 36% yield).

$^1$H NMR (400 MHz, MeOD) δ 7.42 (d, J=13.8 Hz, 1H), 6.37 (s, 1H), 3.52 (d, J=7.1 Hz, 5H), 3.35 (d, J=10.8 Hz, 2H), 3.28 (s, 2H), 3.20 (dd, J=7.1, 2.7 Hz, 2H), 2.55 (s, 3H), 2.51 (d, J=7.0 Hz, 1H), 2.14 (dd, J=12.4, 6.0 Hz, 1H), 1.78 (s, 1H), 1.45 (s, 9H), 1.22 (s, 2H), 0.51 (d, J=3.5 Hz, 2H)

LCMS (m/z): 560.5 [M+H]

(ii) 4-(2-aminoethyl)-7-(3-(aminomethyl)pyrrolidin-1-yl)-1-cyclopropyl-6-fluoro-8-methylquinolin-2 (1H)-one TFA salt 91-ii (0.09 g, 0.16 mmol, 1.0 equiv) was dissolved in dichloromethane (5 mL) and cooled to 0° C. TFA (1 mL) was added and the reaction mixture was stirred at room temperature for 1 hour. The reaction mixture was concentrated to afford a crude residue. The crude residue was purified by preparative HPLC purification to afford the desired product 91-iii (0.018 g, 31% yield).

$^1$H NMR (400 MHz, MeOD) δ 7.40 (d, J=13.8 Hz, 1H), 6.44 (s, 1H), 3.70-3.64 (m, 1H), 3.63-3.50 (m, 3H), 3.37 (t, J=7.7 Hz, 1H), 3.26 (t, J=7.6 Hz, 2H), 3.12 (dd, J=13.1, 7.4 Hz, 4H), 2.67 (dt, J=19.1, 7.2 Hz, 1H), 2.58 (s, 3H), 2.31 (dt, J=11.9, 7.2 Hz, 1H), 1.85 (dq, J=15.5, 7.8 Hz, 1H), 1.24 (dd, J=9.8, 6.6 Hz, 2H), 0.56-0.47 (m, 2H)

LCMS (02_4 min), [MH]$^+$=359.1, RT=1.465 minutes.

LCMS Method C_4 MIN

Column: HSS C18 (50*2.1 mm), 1.8 um; ESI source, Positive ion mode; Wavelength 202/232 nm;

Column temperature: Ambient;

Mobile Phase: A: 5 mM Ammonium acetate in 0.1% formic acid in water, B: 0.1% formic acid in ACN;

Flow rate: 0.55 mL/min;

Gradient: 5%-100% (solvent B) over 2.5 minutes and holding at 100% for 0.6 minutes.

Example 92: 7-(3-(aminomethyl)-3-fluoropyrrolidin-1-yl)-1-cyclopropyl-6-fluoro-8-methyl-2-oxo-1,2-dihydroquinoline-3-carbonitrile HCl salt

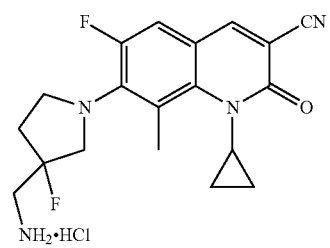

The title compound was prepared in accordance with the following scheme:

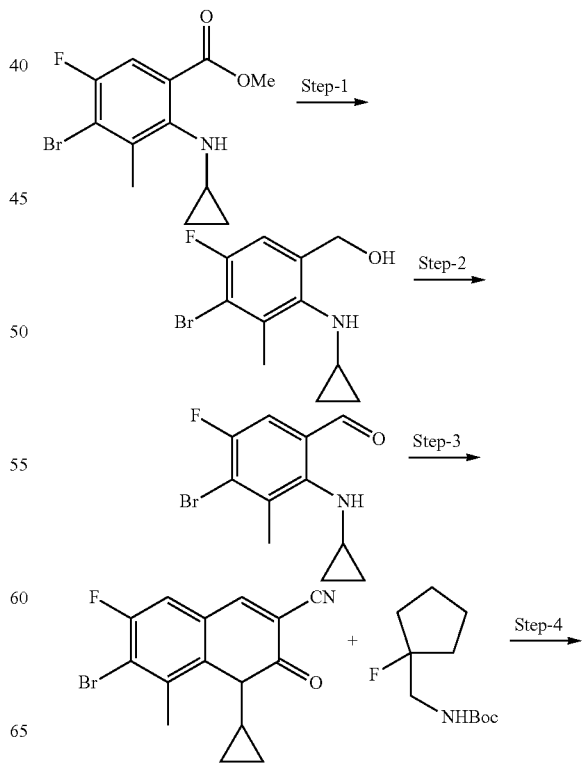

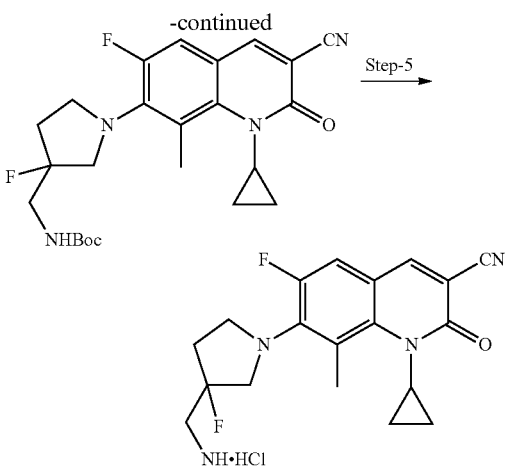

(i) (4-bromo-2-(cyclopropylamino)-5-fluoro-3-methylphenyl) methanol

Methyl 4-bromo-2-(cyclopropylamino)-5-fluoro-3-methylbenzoate (2.0 g, 6.6 mmol, 1.0 equiv) was dissolved in dry THF (20 mL) and cooled to 0° C. LiAlH$_4$ (1.0 M in THF) (13.2 mL, 13.2 mmol, 2.0 equiv) was added drop wise within 10 minutes at 0° C. The reaction mixture was stirred at 0° C. for 30 minutes. The reaction mixture was diluted with THF (20 mL) and treated with NH$_4$Cl at 0° C. The reaction mixture was filtered through celite bed, the filtrate was concentrated and extracted with EtOAc. The organic layer was washed with brine, dried over sodium sulfate and concentrated to afford the desired product 92-i (1.3 g, 71.8% yield).

$^1$H NMR (400 MHz, DMSO) δ 7.11 (d, J=9.6 Hz, 1H), 5.35 (t, J=5.5 Hz, 1H), 4.45 (d, J=5.3 Hz, 2H), 2.48 (dd, J=7.3, 3.9 Hz, 1H), 2.36 (d, J=11.7 Hz, 3H), 0.52 (dd, J=6.5, 1.7 Hz, 2H), 0.39-0.36 (m, 2H).

LCMS (m/z): 276.1 [M+H]

(ii) 4-bromo-2-(cyclopropyl amino)-5-fluoro-3-methyl benzaldehyde 92-i (0.9 g, 3.3 mmol, 1.0 equiv) was dissolved in dichloromethane (20 mL) at 0° C. Dess-Martin periodinane (2.8 g, 6.6 mmol, 2.0 equiv) was added in portions within 10 minutes and the reaction mixture was stirred at 0° C. for 30 minutes. The reaction mixture was quenched with NaHCO$_3$ and stirred for 15 minutes. The organic layer was washed sodium thiosulphate, brine solution, dried over sodium sulfate and concentrated to afford a crude residue. The crude residue was purified by 60-120 mesh silica gel column chromatography (1% EtOAc/Hexane) to afford the desired product 92-ii (0.3 g, 22% yield).

$^1$H NMR (400 MHz, DMSO) δ 10.02 (d, J=1.0 Hz, 1H), 7.49 (d, J=8.7 Hz, 1H), 7.31 (s, 1H), 2.89 (dt, J=6.7, 3.0 Hz, 1H), 2.49 (s, 3H), 0.73 (dt, J=6.7, 3.3 Hz, 2H), 0.50-0.42 (m, 2H)

LCMS (m/z): 274.2 [M+H]

(iii) 7-bromo-1-cyclopropyl-6-fluoro-8-methyl-2-oxo-1,2-dihydroquinoline-3-carbonitrile 92-ii (0.3 g, 1.1 mmol, 1.0 equiv), ethyl 2-cyano acetate (0.25 g, 2.2 mmol, 2.0 equiv) was added in EtOH (2 mL) at RT in sealed tube. Piperidine (0.37 g, 4.4 mmol, 4.0 equiv) was added and the reaction mixture was stirred at 100° C. for 6 hours. The reaction mixture was quenched with cold water and extracted with EtOAc. The organic layer was washed brine solution, dried over sodium sulfate and concentrated to afford a crude residue. The crude residue was purified by 60-120 mesh silica gel column chromatography (12% EtOAc/Hexane) to afford the desired product 92-iii (0.08 g, 22% yield).

$^1$H NMR (400 MHz, DMSO) δ 8.63 (s, 1H), 7.66 (d, J=7.9 Hz, 1H), 3.62-3.55 (m, 1H), 2.74 (d, J=7.3 Hz, 3H), 1.17 (q, J=7.0 Hz, 2H), 0.56-0.47 (m, 2H)

LCMS (m/z): 323.2 [M+H]

(iv) tert-butyl ((1-(3-cyano-1-cyclopropyl-6-fluoro-8-methyl-2-oxo-1,2-dihydro quinolin-7-yl)-3-fluoropyrrolidin-3-yl) methyl) carbamate 92-iii (0.08 g, 0.24 mmol, 1.0 equiv), Cs$_2$CO$_3$ (0.12 g, 0.37 mmol, 1.5 equiv), tert-butyl ((3-fluoropyrrolidin-3-yl) methyl) carbamate (0.08 g, 0.37 mmol, 1.5 equiv), Pd$_2$(dba)$_3$ (0.011 g, 0.0013 mmol, 0.05 equiv), xantphos (0.014 g, 0.025 mmol, 0.1 equiv) were added in 1,4-dioxane (2 mL) and the reaction mixture was degassed for 5 minutes. The reaction mixture was stirred at 110° C. for 18 hours. The reaction mixture was quenched with cold water and extracted with EtOAc. The organic layer was washed with brine, dried over sodium sulfate and concentrated to afford a crude residue. The crude residue was purified by preparative TLC (50% EtOAc/Hexane) to afford the desired product 92-iv (0.03 g, 26% yield).

$^1$H NMR (400 MHz, CDCl$_3$) δ 7.91 (s, 1H), 7.04 (d, J=12.1 Hz, 1H), 4.99 (s, 1H), 4.01-3.82 (m, 2H), 3.57 (ddd, J=14.5, 13.5, 4.6 Hz, 5H), 2.48 (s, 3H), 2.31-2.11 (m, 2H), 1.49 (s, 9H), 1.34 (s, 1H), 1.22-1.14 (m, 1H), 0.67-0.55 (m, 2H)

LCMS (m/z): 459.5 [M+H]

(v) 7-(3-(aminomethyl)-3-fluoropyrrolidin-1-yl)-1-cyclopropyl-6-fluoro-8-methyl-2-oxo-1,2-dihydroquinoline-3-carbonitrile HCl salt 92-iv (0.03 g, 0.066 mmol, 1.0 equiv) was dissolved in dichloromethane (2.5 mL), HCl (4 M in 1,4-dioxane) (1 mL) was added at 0° C. and the reaction mixture was stirred at RT for 2 hours. The reaction mixture was concentrated and co-distilled with dichloromethane to afford a crude residue. The crude residue was triturated with diethyl ether and dichloromethane to afford the desired product 92-v (0.02 g, 86% yield).

$^1$H NMR (400 MHz, MeOD) δ 8.32 (s, 1H), 7.33 (d, J=12.6 Hz, 1H), 4.08-3.93 (m, 2H), 3.72 (dd, J=21.3, 11.8 Hz, 1H), 3.63-3.50 (m, 4H), 2.59 (d, J=16.0 Hz, 3H), 2.46-2.24 (m, 2H), 1.33-1.23 (m, 2H), 0.68-0.53 (m, 2H)

LCMS (06_4 min), [MH]$^+$=359.4, RT=1.579 minutes

LCMS Method C_4 MIN

Column: HSS C18 (50*2.1 mm), 1.8 um; ESI source, Positive ion mode; Wavelength 239 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

Example 93: 3-(aminomethyl)-7-(3-(aminomethyl)-3-fluoropyrrolidin-1-yl)-1-cyclopropyl-6-fluoro-8-methylquinolin-2(1H)-one formic acid salt

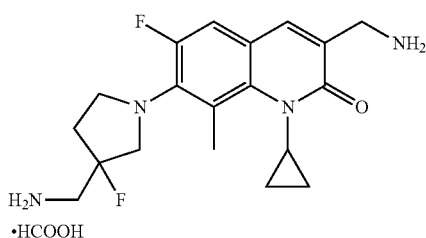 [SMILES: Cc1c(N2CCC(F)(CN)C2)c(F)cc2cc(CN)c(=O)n(C3CC3)c12 ; "·HCOOH"]

The title compound was prepared in accordance with the following scheme:

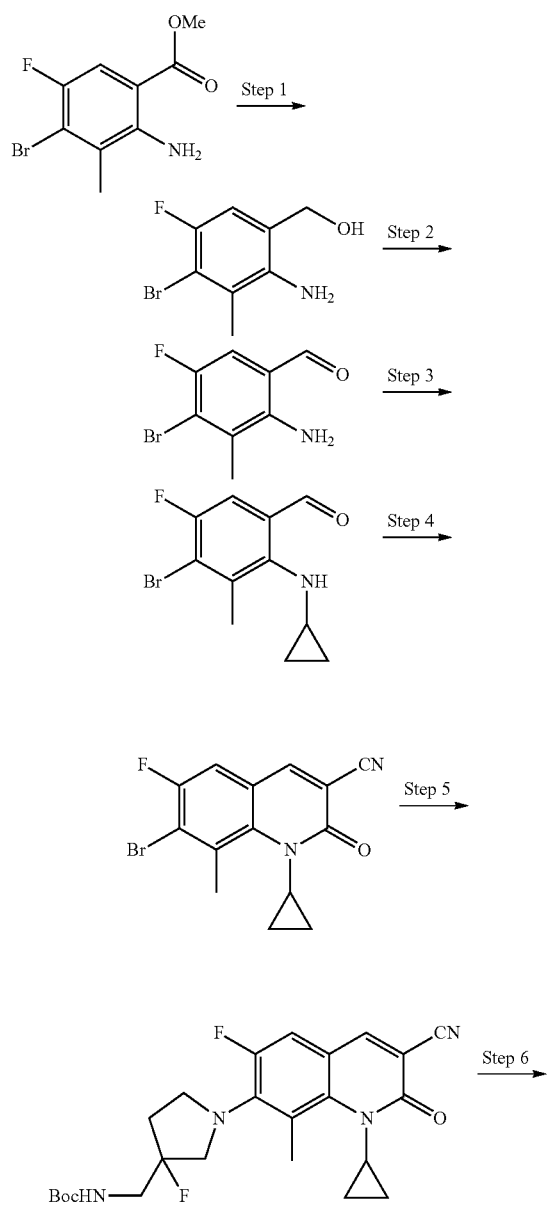

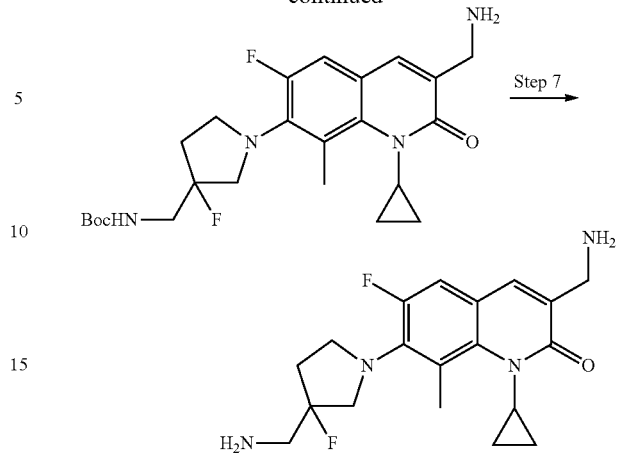

(i) (2-amino-4-bromo-5-fluoro-3-methylphenyl) methanol

Methyl 2-amino-4-bromo-5-fluoro-3-methylbenzoate (2.7 g, 10.3 mmol, 1.0 equiv) was dissolved in THF (30 mL) and cooled to −10° C. LAH (1M in THF) (15.4 mL, 15.4 mml, 1.5 equiv) was added drop wise and the reaction mixture was stirred at room temperature for 1 hour. The reaction mixture was quenched with EtOAc (2 mL) at −10° C., poured to moisten sodium sulfate and diluted with EtOAc. Organic layer was concentrated under vacuum to afford the desired product 93-i (2.5 g, crude). The crude product was used in next step without further purification.

$^1$H NMR (400 MHz, MeOD) δ 6.91 (d, J=9.1 Hz, 1H), 4.55 (s, 2H), 2.33 (s, 3H).

(ii) 2-amino-4-bromo-5-fluoro-3-methylbenzaldehyde 93-i (2.5 g, 10.8 mmol, 1.0 equiv) was dissolved in DCM (30 mL) and cooled to −10° C. MnO$_2$ (4.7 g, 54.3 mmol, 5 equiv) was added portion wise and the mixture was stirred at room temperature for 1 hour. The reaction mixture was filtered through celite pad. Filtrate was concentrated under vacuum to afford the desired product 93-ii (2.2 g, 88.7% yield). The crude product was used in next step without further purification.

$^1$H NMR (400 MHz, CDCl$_3$) δ 9.82 (d, J=10.6 Hz, 1H), 7.28 (s, 1H), 7.17 (d, J=8.1 Hz, 1H), 6.26 (s, 2H), 2.35 (s, 3H).

(iii) 4-bromo-2-(cyclopropylamino)-5-fluoro-3-methylbenzaldehyde 93-ii (2.2 g, 9.6 mmol, 1.0 equiv) was dissolved in EDC (30 mL). Cyclopropyl boronic acid (1.42 g, 19.2 mmol, 2 equiv), copper(II) acetate (1.73 g, 9.6 mmol, 1 equiv), Bipyridine (1.5 g, 9.6 mmol, 1 equiv) and sodium carbonate (2.0 g, 19.2 mmol, 2.0 equiv) were added and the mixture was heated to 70° C. for 4 hour under oxygen purging. The reaction mixture was then allowed to stir at room temperature for overnight. The reaction mixture was filtered through celite pad and washed with excess of DCM. Filtrate was washed with water, brine, dried over sodium sulfate and concentrated under vacuum to afford crude residue. The crude residue was purified by silica gel column chromatography (0-2% EtOAc/Hexane) to afford the desired product 93-iii (1.1 g, 42.3% yield).

$^1$H NMR (400 MHz, CDCl$_3$) δ 9.76 (s, 1H), 7.28 (s, 1H), 7.11 (d, J=7.9 Hz, 1H), 2.84 (td, J=6.9, 3.5 Hz, 1H), 0.76 (dt, J=6.4, 3.2 Hz, 2H), 0.60-0.56 (m, 2H)

(iv) 7-bromo-1-cyclopropyl-6-fluoro-8-methyl-2-oxo-1,2-dihydroquinoline-3-carbonitrile 93-iii (0.8 g, 2.95 mmol, 1.0 equiv) was dissolved in EtOH (7 mL). Ethylcyano acetate (0.667 g, 5.9 mmol, 2.0 equiv) and piperidine (1.0 g, 11.8 mmol, 4.0 equiv) were added and the reaction mixture was heated to 100° C. for 6 hours. The reaction mixture was cooled to 0° C. and solid was filtered through vacuum to afford the desired product 93-iv (0.44 g, 46.5% yield).

$^1$H NMR (400 MHz, DMSO) δ 8.62 (d, J=2.0 Hz, 1H), 7.66 (d, J=7.9 Hz, 1H), 3.62-3.55 (m, 1H), 2.74 (d, J=7.4 Hz, 3H), 1.20-1.12 (m, 2H), 0.54-0.47 (m, 2H)

LCMS (m/z): 321.2 [M+H]

(v) tert-butyl ((1-(3-cyano-1-cyclopropyl-6-fluoro-8-methyl-2-oxo-1,2-dihydro quinolin-7-yl)-3-fluoropyrrolidin-3-yl)methyl)carbamate 93-iv (0.22 g, 0.68 mmol, 1.0 equiv) was dissolved in 1,4-Dioxane. tert-butyl ((3-fluoropyrrolidin-3-yl)methyl) carbamate (0.224 g, 0.1 mmol, 1.5 equiv) and cesium carbonate (0.444 g, 1.3 mmol, 2.0 equiv) were added to the reaction mixture and degassed with nitrogen for 5 minutes. Pd2dba3 (0.031 g, 0.034 mmol, 0.05 equiv) and xantphos (0.039 g, 0.068 mmol, 0.1 equiv) were added and degassed again for 5 minutes. The reaction mixture was heated to 100 0° C. for 6 hours in sealed tube. The reaction mixture was quenched with water and extracted with EtOAc. Organic layer was washed with brine, dried over sodium sulfate and concentrated under vacuum to afford crude residue. The crude residue was purified by Prep TLC (40% EtOAc/Hexane) to afford the desired product 93-v (0.065 g, 20.7% yield).

$^1$H NMR (400 MHz, MeOD) δ 8.29 (s, 1H), 7.44 (d, J=22.2 Hz, 1H), 7.29 (d, J=12.9 Hz, 1H), 3.97 (dd, J=30.8, 11.1 Hz, 2H), 3.52 (dd, J=22.8, 17.2 Hz, 5H), 2.52 (s, 3H), 2.24 (d, J=7.9 Hz, 1H), 2.18 (s, 1H), 1.48 (s, 9H), 1.27-1.18 (m, 2H), 0.66-0.53 (m, 2H)

(vi) tert-butyl ((1-(3-(aminomethyl)-1-cyclopropyl-6-fluoro-8-methyl-2-oxo-1,2-dihydroquinolin-7-yl)-3-fluoropyrrolidin-3-yl)methyl)carbamate 93-v (0.07 g, 0.15 mmol, 1.0 equiv) was dissolved in methanolic ammonia (2M) (4 mL). Pd/C (10%) (0.105 g, 0,045 mmol, 0.3 equiv) was added and the reaction was stirred at room temperature for 45 minutes under H2 atmosphere (balloon pressure). The reaction mixture was filtered through celite pad and washed with excess of EtOAc. Filtrate was concentrated under vacuum to give desired product 93-vi (0.065 g, 92% crude). The crude was directly used in the next step without any further purification. LCMS (m/z): 463.8 [M+H]

(vii) 3-(aminomethyl)-7-(3-(aminomethyl)-3-fluoropyrrolidin-1-yl)-1-cyclopropyl-6-fluoro-8-methylquinolin-2(1H)-one formic acid salt 93-vi (0.065 g, 0.14 mmol, 1.0 equiv) was dissolved in DCM (2 mL) and cooled to 0° C. HCl-Dioxane (6M) (1 mL) was added and stirred at room temperature for 2 hours. The reaction mixture was concentrated and triturated with n-pentane to obtain crude residue. The crude was purified with Prep HPLC to afford the desired product 93-vii (0.01 g, 19.65% yield).

$^1$H NMR (400 MHz, MeOD) δ 8.54 (s, 2H), 7.82 (s, 1H), 7.26 (d, J=12.2 Hz, 1H), 4.03 (s, 2H), 3.84 (dd, J=28.7, 10.4 Hz, 2H), 3.69-3.48 (m, 3H), 3.39 (d, J=20.2 Hz, 2H), 2.63 (s, 3H), 2.39-2.22 (m, 2H), 1.28 (dd, J=13.8, 5.9 Hz, 2H), 0.58 (s, 2H)

LCMS (06_4 min), [MH]$^+$=363.5, RT=2.367 minutes
LCMS Method C_4 MIN
Column: HSS C18 (50*2.1 mm), 1.8 um; ESI source, Positive ion mode; Wavelength 230/362 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 94: (S)-7-(3-aminopyrrolidin-1-yl)-1-cyclopropyl-6-fluoro-8-methyl-2-oxo-1,2-dihydroquinoline-3-carbonitrile HCl salt The title compound was prepared in accordance with the following scheme:

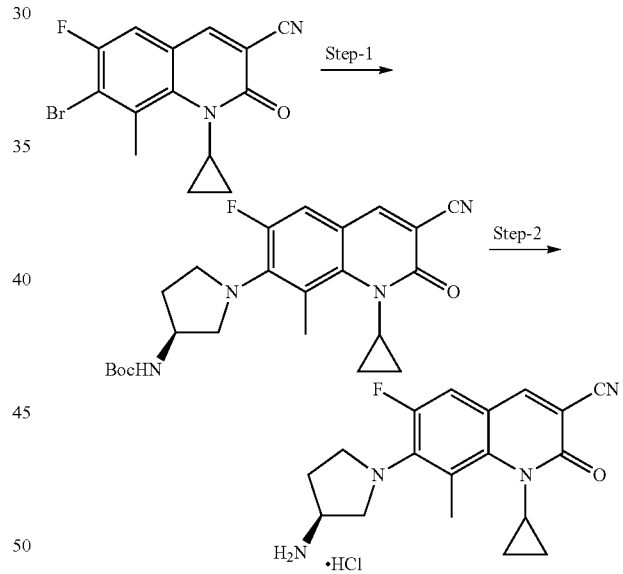

(i) tert-butyl (S)-(1-(3-cyano-1-cyclopropyl-6-fluoro-8-methyl-2-oxo-1,2-dihydro quinolin-7-yl) pyrrolidin-3-yl)carbamate 93-iv (0.2 g, 0.62 mmol, 1.0 equiv) was dissolved in 1,4-Dioxane. tert-butyl (S)-pyrrolidin-3-ylcarbamate (0.173 g, 0.93 mmol, 1.5 equiv), cesium carbonate (0.4 g, 1.2 mmol, 2.0 equiv) were added and degassed with nitrogen for 5 minutes. Pd$_2$dba$_3$ (0.028 g, 0.031 mmol, 0.05 equiv), xantphos (0.036 g, 0.062 mmol, 0.1 equiv) were added and the reaction mixture was heated to 100° C. for 6 hours in sealed tube. The reaction mixture was quenched with water and extracted with EtOAc. Organic layer was washed with brine, dried over sodium sulfate and concentrated to afford crude residue. The crude residue was purified by Prep TLC (50% EtOAc/Hexane) to afford the desired product 94-i (0.045 g, 16.98% yield).

$^1$H NMR (400 MHz, MeOD) δ 8.27 (s, 1H), 7.27 (d, J=13.1 Hz, 1H), 4.25-4.19 (m, 1H), 3.86-3.81 (m, 1H), 3.76-3.70 (m, 1H), 3.66-3.60 (m, 1H), 3.56 (s, 1H), 3.47-3.43 (m, 1H), 2.51 (s, 3H), 2.33-2.26 (m, 1H), 2.01-1.94 (m, 1H), 1.48 (s, 9H), 1.27 (d, J=7.2 Hz, 2H), 0.60 (s, 2H)

LCMS (m/z): 327.5 [M+H]

(ii) (S)-7-(3-aminopyrrolidin-1-yl)-1-cyclopropyl-6-fluoro-8-methyl-2-oxo-1,2-dihydroquinoline-3-carbonitrile HCl salt 94-i (0.045 g, 0.105 mmol, 1.0 equiv) was dissolved in Dichloromethane (2 mL) and cooled to 0° C. HCl-Dioxane (4M) (1 mL) was added and the reaction mixture was stirred at room temperature for 2 hours. The reaction mixture was concentrated, triturated with n-pentane and diethylether to afford the desired product 94-ii (0.02 g, 58.8% yield).

$^1$H NMR (400 MHz, MeOD) δ 8.33 (s, 1H), 7.35 (d, J=12.7 Hz, 1H), 4.03 (s, 1H), 3.97-3.90 (m, 1H), 3.74 (dd, J=15.1, 8.5 Hz, 1H), 3.66-3.55 (m, 3H), 2.61 (d, J=16.1 Hz, 3H), 2.57-2.47 (m, 1H), 2.13 (d, J=5.4 Hz, 1H), 1.28 (dd, J=13.6, 7.5 Hz, 2H), 0.65-0.55 (m, 2H)

LCMS (06_4 min), [MH]$^+$=327.3, RT=1.535 minutes.
LCMS Method C_4 MIN
Column: HSS C18 (50*2.1 mm), 1.8 um; ESI source, Positive ion mode; Wavelength 230/362 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 95: (S)-3-(aminomethyl)-7-(3-aminopyrrolidin-1-yl)-1-cyclopropyl-6-fluoro-8-methylquinolin-2(1H)-one HCl salt The title compound was prepared in accordance with the following scheme:

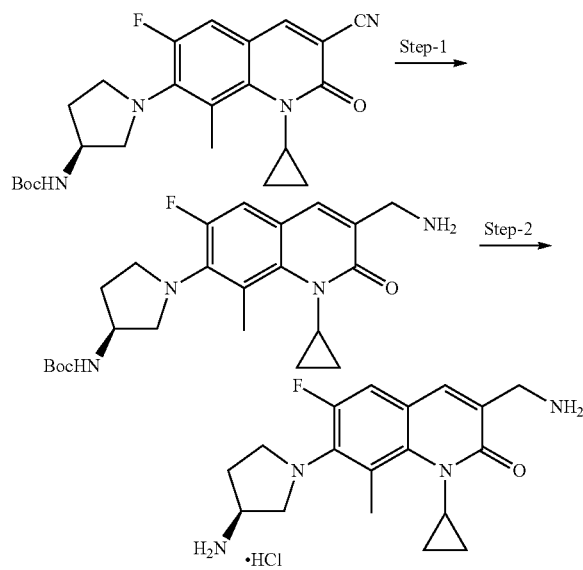

(i) tert-butyl (S)-(1-(3-cyano-1-cyclopropyl-6-fluoro-8-methyl-2-oxo-1,2-dihydroquinolin-7-yl)pyrrolidin-3-yl)carbamate 94-i (0.045 g, 0.105 mmol, 1.0 equiv) was dissolved in methanolic ammonia (2M) (2 mL). Pd/C (10%, 50% moistened with H$_2$O) (0.066 g, 0.031 mmol, 0.3 equiv) was added and the reaction mixture was stirred at room temperature for 1 hour under hydrogen atmosphere (balloon pressure). The reaction mixture was filtered through celite pad and washed with excess of EtOAc and the filtrate was concentrated to afford the desired product 95-i (0.030 g, 66% crude). The crude was directly used in the next step without any further purification.

LCMS (m/z): 431.7 [M+H].

(ii) (S)-3-(aminomethyl)-7-(3-aminopyrrolidin-1-yl)-1-cyclopropyl-6-fluoro-8-methylquinolin-2(1H)-one HCl salt 95-i (0.03 g, 0.069 mmol, 1.0 equiv) was dissolved in Dichloromethane (2 mL) and cooled to 0° C. HCl-Dioxane (4M) (1 mL) was added and the reaction mixture was stirred at room temperature for 2 hours. The reaction mixture was concentrated and triturated with n-pentane to afford the desired product 95-ii (0.01 g, 43.5% yield).

$^1$H NMR (400 MHz, MeOD) δ 7.85 (s, 1H), 7.30 (d, J=12.4 Hz, 1H), 4.04 (m, 3H), 3.88-3.82 (m, 1H), 3.63 (dd, J=16.3, 6.0 Hz, 4H), 2.67 (s, 3H), 2.53 (m, 1H), 2.11 (m, 1H), 1.28 (m, 2H), 0.58 (s, 2H)

LCMS (06_4 min), [MH]$^+$=331.5, RT=1.332 minutes
LCMS Method C_4 MIN
Column: HSS C18 (50*2.1 mm), 1.8 um; ESI source, Positive ion mode; Wavelength 360 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 96: 7-(3-(aminomethyl)-3-fluoropyrrolidin-1-yl)-1-cyclopropyl-6-fluoro-3-(hydroxymethyl)-8-methylquinolin-2(1H)-one

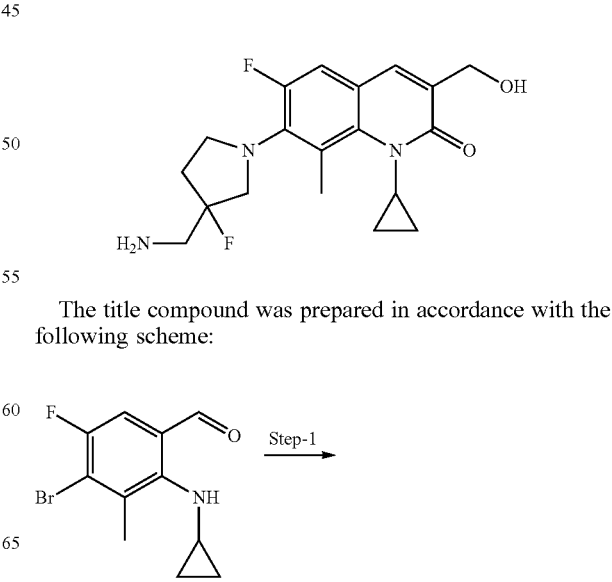

The title compound was prepared in accordance with the following scheme:

233

-continued

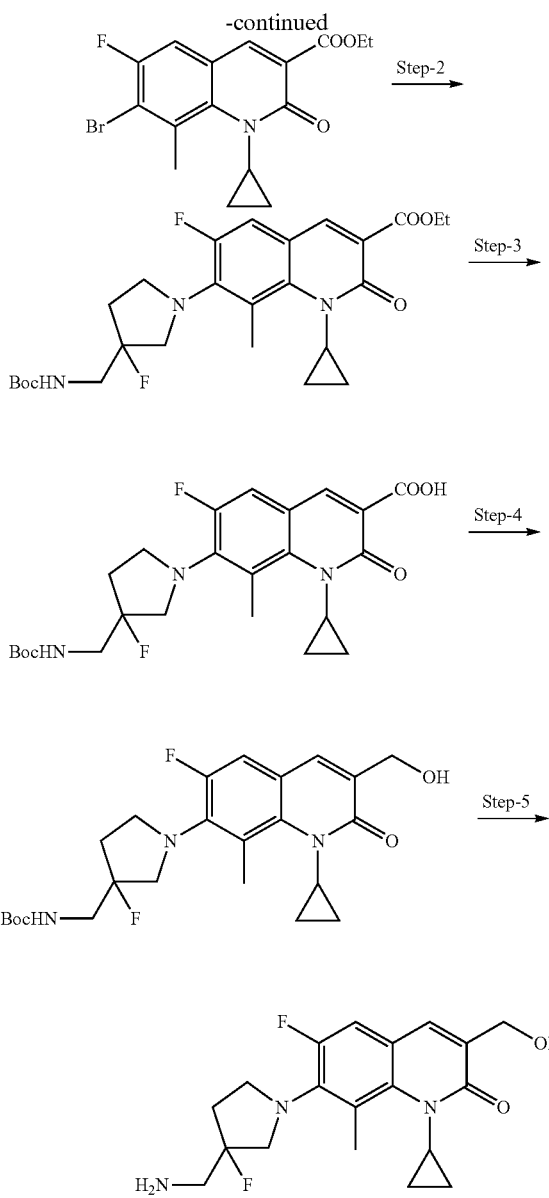

(i) ethyl 7-bromo-1-cyclopropyl-6-fluoro-8-methyl-2-oxo-1,2-dihydroquinoline-3-carboxylate 4-Bromo-2-(cyclopropylamino)-5-fluoro-3-methylbenzaldehyde (1.3 g, 4.7 mmol, 1.0 equiv) was dissolved in Ethanol (10 mL). Piperidine (1.63 g, 19.2 mmol, 4.0 equiv), diethylmalonate (1.53 g, 9.5 mmol, 2.0 equiv) were added and the reaction mixture was stirred at 90° C. for 5 hours. The reaction mixture was quenched with water and extracted with EtOAc. Organic layer was washed with brine, dried over sodium sulfate and concentrated to afford crude residue. The crude residue was purified by Prep TLC (40% EtOAc/Hexane) to afford the desired product 96-i (0.54 g, 32% yield).

$^1$H NMR (400 MHz, CDCl$_3$) δ 8.16 (d, J=6.4 Hz, 1H), 7.19 (d, J=7.3 Hz, 1H), 4.42 (q, J=7.1 Hz, 2H), 3.54 (td, J=6.8, 3.4 Hz, 1H), 2.78 (d, J=16.0 Hz, 3H), 1.43 (t, J=7.1 Hz, 3H), 1.27 (q, J=6.9 Hz, 2H), 0.59 (q, J=7.1 Hz, 2H)

LCMS (m/z): 368.2 [M+H]

234

(ii) ethyl 7-(3-(((tert-butoxycarbonyl)amino)methyl)-3-fluoropyrrolidin-1-yl)-1-cyclopropyl-6-fluoro-8-methyl-2-oxo-1,2-dihydroquinoline-3-carboxylate 96-i (0.35 g, 0.95 mmol, 1.0 equiv), tert-butyl ((3-fluoropyrrolidin-3-yl) methyl)carbamate (0.312 g, 1.43 mmol, 1.5 equiv), cesium carbonate (0.526 g, 1.6 mmol, 1.7 equiv) were suspended in 1,4-dioxane (7 mL) and the reaction mixture degassed for 5 minutes. Pd$_2$dba$_3$ (0.043 g, 0.047 mmol, 0.05 equiv), Xantphos (0.082 g, 0.142 mmol, 0.15 equiv) were added and the reaction mixture was stirred at 100° C. for 6 hours in sealed tube. The reaction mixture was quenched with water and extracted with EtOAc. Organic layer was washed with brine, dried over sodium sulfate and concentrated under vacuum to afford crude residue. The crude residue was purified by silica gel chromatography (30-40% EtOAc/Hexane) to afford the desired product 96-ii (0.15 g, 41% yield).

$^1$H NMR (400 MHz, CDCl$_3$) δ 8.17 (s, 1H), 7.07 (d, J=12.1 Hz, 1H), 4.98 (s, 1H), 4.40 (q, J=7.1 Hz, 2H), 3.93-3.85 (m, 1H), 3.78 (d, J=12.2 Hz, 1H), 3.70-3.55 (m, 3H), 3.51 (d, J=5.1 Hz, 2H), 2.49 (s, 2H), 2.31-2.13 (m, 2H), 1.48 (s, 9H), 1.42 (t, J=7.1 Hz, 3H), 1.16 (s, 2H), 0.58 (t, J=8.8 Hz, 2H)

LCMS (m/z): 506.6 [M+H]

(iii) 7-(3-(((tert-butoxycarbonyl)amino)methyl)-3-fluoropyrrolidin-1-yl)-1-cyclopropyl-6-fluoro-8-methyl-2-oxo-1,2-dihydroquinoline-3-carboxylic acid 96-ii (0.195 g, 0.37 mmol, 1.0 equiv) was dissolved in THF:MeOH:H$_2$O (2:1:1) (1.8 mL). LiOH.H$_2$O (0.031 g, 0.75 mmol, 2.0 equiv) was added and the mixture was stirred at room temperature for 30 minutes. The reaction mixture was diluted with cold water, acidified with dilute HCl to pH 4. Precipitates were filtered through vacuum and dried to afford the desired product 96-iii (0.15 g, 81% yield).

$^1$H NMR (400 MHz, CDCl$_3$) δ 8.62 (s, 1H), 7.20 (d, J=12.0 Hz, 1H), 4.99 (s, 1H), 3.94 (dd, J=31.4, 19.9 Hz, 3H), 3.60 (m, 4H), 2.53 (s, 3H), 2.30 (s, 2H), 1.49 (s, 9H), 1.24 (m, 2H), 0.71-0.62 (m, 2H)

LCMS (m/z): 478.6 [M+H]

(iv) tert-butyl ((1-(1-cyclopropyl-6-fluoro-3-(hydroxymethyl)-8-methyl-2-oxo-1,2-dihydroquinolin-7-yl)-3-fluoropyrrolidin-3-yl)methyl)carbamate 96-iii (0.15 g, 0.314 mmol, 1.0 equiv) was dissolved in THF (6 mL) and cooled to 0° C. Triethylamine (0.041 g, 0.408 mmol, 1.3 equiv), Isobutyl chloroformate (0.055 g, 0.408 mmol, 1.3 equiv) were added and the reaction mixture was stirred at 0° C. for 15 minutes. The reaction mixture was added slowly to the suspension of sodium borohydride (0.015 g, 0.408 mmol, 1.3 equiv) in H$_2$O (3 mL) at 0° C., stirred for 5-10 minutes. The reaction mixture was quenched with water and extracted with EtOAc. Organic layer was washed with brine, dried over sodium sulfate and concentrated under vacuum to afford crude residue. The crude residue was purified by Prep TLC (30% EtOAc/Hexane) to afford the desired product 96-iv (0.024 g, 17% yield). LCMS (m/z): 464.5 [M+H].

(v) 7-(3-(aminomethyl)-3-fluoropyrrolidin-1-yl)-1-cyclopropyl-6-fluoro-3-(hydroxymethyl)-8-methylquinolin-2(1H)-one 96-iv (0.024 g, 0.051 mmol, 1.0 equiv) was dissolved in DCM (2 mL) and cooled to 0° C. HCl-Dioxane (4M) (1.0 mL) was added and stirred at room temperature for 30 minutes. The reaction mixture was concentrated and triturated with n-pentane to afford a crude residue. The crude was purified with Prep HPLC to afford the desired product 96-v (0.002 g, 10.6% yield).

$^1$H NMR (400 MHz, CD$_3$CN) δ 7.53 (s, 1H), 7.15 (d, J=12.7 Hz, 1H), 5.38 (m, 1H), 4.46 (d, J=1.3 Hz, 2H), 3.77 (dd, J=18.5, 9.9 Hz, 2H), 3.52-3.42 (m, 3H), 3.06 (d, J=2.4 Hz, 1H), 3.01 (d, J=3.9 Hz, 1H), 2.56 (s, 3H), 1.19-1.13 (m, 2H), 0.52-0.42 (m, 2H)

LCMS (06_4 min), [MH]$^E$=364.5, RT=1.482 minutes

LCMS Method C_4 MIN

Column: HSS C18 (50*2.1 mm), 1.8 um; ESI source, Positive ion mode; Wavelength 229/354 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

Example 97: 5-(3-(aminomethyl)pyrrolidin-1-yl)-7-bromo-1-cyclopropyl-6-fluoro-8-methylquinolin-2(1H)-one trifluoro acetic acid salt (Isomer-A) and 7-(3-(aminomethyl)pyrrolidin-1-yl)-5-bromo-1-cyclopropyl-6-fluoro-8-methylquinolin-2(1H)-one trifluoro acetic acid salt (Isomer-B)

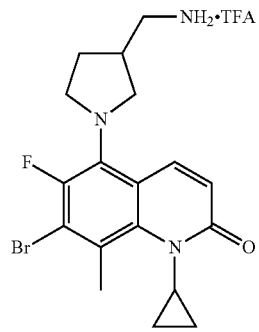

Isomer-A

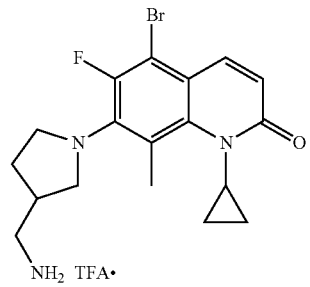

Isomer-B

The title compound was prepared in accordance with the following scheme:

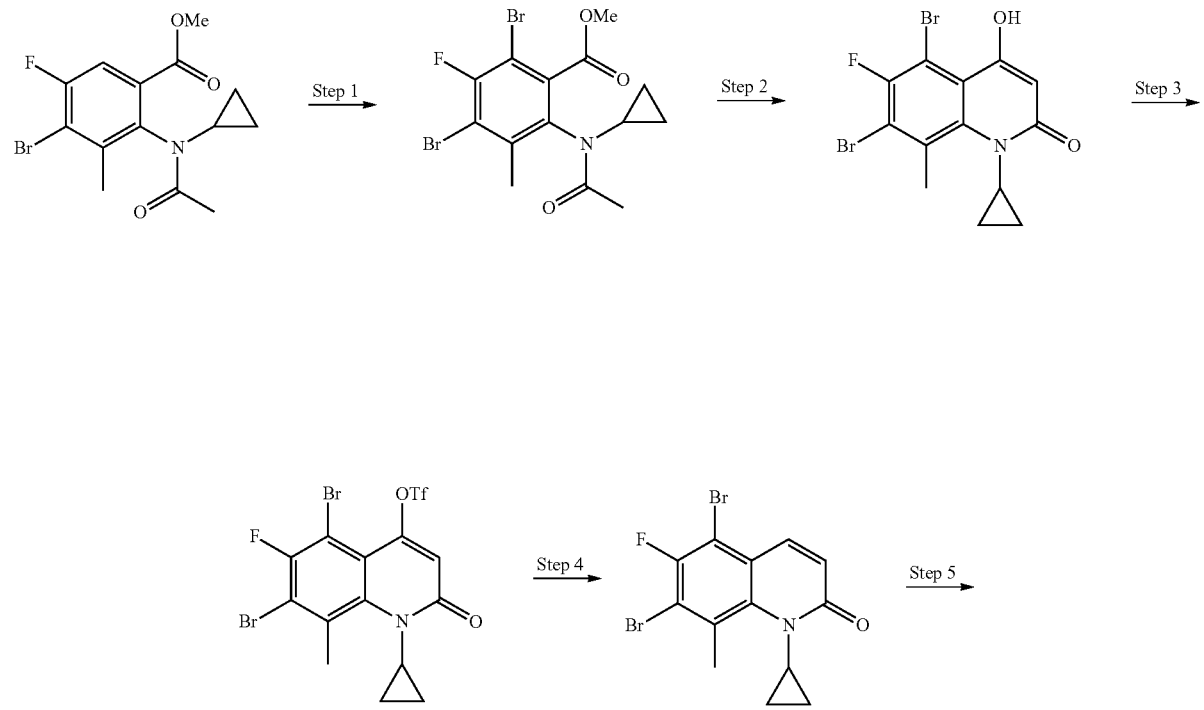

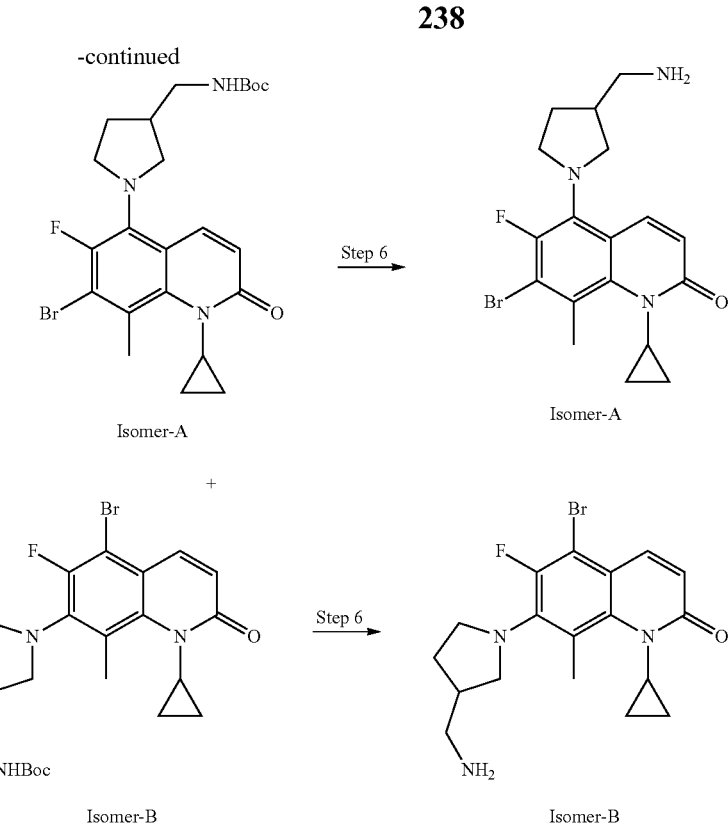

Isomer-A

Isomer-A

Isomer-B

Isomer-B (i) methyl 2,4-dibromo-6-(N-cyclopropyl acetamido)-3-fluoro-5-methyl benzoate Methyl 4-bromo-2-(N-cyclopropylacetamido)-5-fluoro-3-methylbenzoate (0.5 g, 1.45 mmol, 1.0 equiv) was dissolved in conc. $H_2SO_4$ (3 mL), NBS (0.37 g, 1.88 mmol, 1.3 equiv) was added and the reaction mixture was stirred at room temperature for 4 hours. NBS (0.37 g, 1.88 mmol, 1.3 equiv) was added and the reaction mixture was stirred at room temperature for 24 hours. The reaction mixture was quenched with cold water, neutralized with solid sodium bicarbonate and extracted with EtOAc. The organic layer was washed with brine, dried over sodium sulfate and concentrated to afford a crude residue. The crude residue was purified by silica gel column chromatography (0-70% EtOAc/Hexane) to afford the desired product 97-i (0.39 g, 64.6% yield).

$^1$H NMR (400 MHz, DMSO) δ 3.86 (d, J=4.8 Hz, 3H), 3.03-2.96 (m, 0.6H), 2.87 (ddd, J=11.3, 7.3, 3.9 Hz, 0.4H), 2.57 (s, 2H), 2.28 (s, 1.5H), 2.25 (s, 1H), 2.13 (s, 1.5H), 1.26-0.23 (m, 4H)

LCMS (m/z): 424.6 [M+H]

(ii) 5, 7-dibromo-1-cyclopropyl-6-fluoro-4-hydroxy-8-methylquinolin-2(1H)-one 97-i (0.39 g, 0.92 mmol, 1.0 equiv) was dissolved in THF (5 mL) and cooled to −45° C. KHMDS (0.91 M in THF) (2 mL, 1.84 mmol, 2.0 equiv) was added drop wise and the reaction mixture was stirred at −45° C. for 10 minutes (the reaction mixture was become dark in color). The reaction mixture was quenched with saturated aqueous ammonium chloride solution and extracted with EtOAc. The organic layer was washed with brine, dried over sodium sulfate and concentrated to afford the desired product 97-ii (0.33 g, crude). LCMS (m/z): 392.5 [M+1-1]. The crude product was used in next step without further purification.

(iii) 5,7-dibromo-1-cyclopropyl-6-fluoro-8-methyl-2-oxo-1,2-dihydroquinolin-4-yl trifluoromethane sulfonate 97-ii (0.33 g, 0.87 mmol, 1.0 equiv) was dissolved in N,N-dimethylformamide (5 mL), TEA (0.26 g, 2.6 mmol, 3.0 equiv) was added and cooled to 0° C. $PhN(SO_2CF_3)_2$ (0.37 g, 1.04 mmol, 1.2 equiv) was added drop wise and the reaction mixture was stirred at room temperature for 1 hour. The reaction mixture was quenched with water and extracted with EtOAc. The organic layer was washed with water, brine, dried over sodium sulfate and concentrated to afford a crude residue. The crude residue was purified by silica gel column chromatography (0-20% EtOAc/Hexane) to afford the desired product 97-iii (0.17 g, 37.9% yield).

$^1$H NMR (400 MHz, DMSO) δ 6.85 (s, 1H), 3.58-3.51 (m, 1H), 2.74-2.69 (m, 3H), 1.14 (m, 2H), 0.43 (m, 2H)

LCMS (m/z): 524.0 [M+H]

(iv) 5,7-dibromo-1-cyclopropyl-6-fluoro-8-methylquinolin-2(1H)-one 97-iii (0.13 g, 0.25 mmol, 1.0 equiv), Pd(II)OAc (0.0083 g, 0.04 mmol, 0.15 equiv) and dppp (0.03 g, 0.074 mmol, 0.3 equiv) were added in N,N-dimethylformamide (2 mL). $Et_3SiH$ (0.034 g, 0.3 mmol, 1.2 equiv) was added and the reaction mixture was stirred at 80° C. for 20 minutes under microwave irradiation. The reaction mixture was quenched with cold water and extracted with EtOAc. The organic layer was washed with brine, dried over sodium sulfate and concentrated to afford a crude residue. The crude residue was purified by silica gel column chromatography (0-20% EtOAc/Hexane) to afford the desired product 97-iv (0.04 g, 43% yield).

$^1$H NMR (400 MHz, DMSO) δ 7.95 (d, J=9.8 Hz, 1H), 6.69 (d, J=9.8 Hz, 1H), 3.58-3.51 (m, 1H), 2.74-2.69 (m, 3H), 1.14 (d, J=5.5 Hz, 2H), 0.43 (d, J=9.3 Hz, 2H)

LCMS (m/z): 376.7 [M+H]

(v) tert-butyl ((1-(7-bromo-1-cyclopropyl-6-fluoro-8-methyl-2-oxo-1,2-dihydro quinolin-5-yl)pyrrolidin-3-yl)methyl)carbamate (Isomer A) and tert-butyl ((1-(5-bromo-1-cyclopropyl-6-fluoro-8-methyl-2-oxo-1,2-dihydroquinolin-7-yl)pyrrolidin-3-yl)methyl) carbamate (Isomer B)

97-iv (0.1 g, 0.27 mmol, 1.0 equiv), $Cs_2CO_3$ (0.13 g, 0.39 mmol, 1.5 equiv), tert-butyl (pyrrolidin-3-ylmethyl)carbamate (0.064 g, 0.32 mmol, 1.2 equiv) were added in 1,4-dioxane (5 mL) and the reaction mixture was degassed for 5 minutes. $Pd_2(dba)_3$ (0.012 g, 0.013 mmol, 0.05 equiv), xantphos (0.023 g, 0.4 mmol, 0.15 equiv) were added and the reaction mixture was stirred at 110° C. for 10 hours. The reaction mixture was quenched with water and extracted with EtOAc. The organic layer was washed with brine, dried over sodium sulfate and concentrated to afford a crude residue. The crude residue was purified by preparative TLC (30% EtOAc/Hexane) to afford the isomer product 97-v-Isomer A (0.06 g, 45.6% yield) and isomer product 97-v-Isomer B (0.021 g, 16% yield).

97-v-Isomer A:
$^1$H NMR (400 MHz, DMSO) δ 8.00 (d, J=9.7 Hz, 1H), 7.01 (s, 1H), 6.51 (d, J=9.7 Hz, 1H), 3.48 (d, J=3.4 Hz, 1H), 3.31-3.20 (m, 3H), 3.04 (s, 2H), 2.99-2.93 (m, 1H), 2.67 (s, 3H), 2.45-2.38 (m, 1H), 2.07-1.99 (m, 1H), 1.67 (dd, J=12.1, 7.4 Hz, 1H), 1.31 (d, J=51.4 Hz, 9H), 1.15 (t, J=12.3 Hz, 2H), 0.39 (s, 2H)

LCMS (m/z): 495.1 [M+H]

97-v-Isomer B:
$^1$H NMR (400 MHz, DMSO) δ 7.84 (d, J=9.6 Hz, 1H), 6.46 (d, J=9.6 Hz, 1H), 3.44 (s, 3H), 3.30 (s, 1H), 3.19 (s, 1H), 3.07-3.01 (m, 2H), 2.40 (s, 4H), 2.03 (s, 2H), 1.69 (s, 1H), 1.4 (s, 9H), 1.12 (s, 2H), 0.39 (d, J=3.9 Hz, 2H)

LCMS (m/z): 495.3 [M+H]

(vi) 5-(3-(aminomethyl)pyrrolidin-1-yl)-7-bromo-1-cyclopropyl-6-fluoro-8-methyl quinolin-2(1H)-one TFA salt (Isomer A)

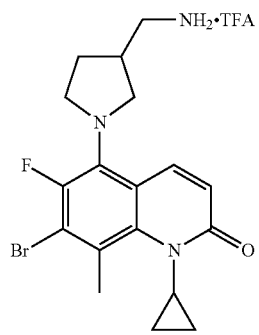

97-v-Isomer A (0.06 g, 0.12 mmol, 1.0 equiv) was added in dichloromethane (2 mL) and cooled to 0° C. TFA (0.6 mL) was added and the reaction mixture was stirred at room temperature for 30 minutes. The reaction mixture was concentrated and co-distilled with THF, diethyl ether and dichloromethane to afford a crude residue. The crude residue was triturated with diethyl ether, n-pentane and the solvent was decanted to afford the desired product 97-vi (0.04 g, 67% yield).

$^1$H NMR (400 MHz, DMSO) δ 8.02 (d, J=9.7 Hz, 1H), 7.83 (s, 3H), 6.53 (d, J=9.7 Hz, 1H), 3.40-3.33 (m, 2H), 3.31-3.22 (m, 2H), 3.10-3.03 (m, 1H), 3.01-2.92 (m, 2H), 2.68 (s, 3H), 2.58 (d, J=6.6 Hz, 1H), 2.20-2.11 (m, 1H), 1.75 (dd, J=12.0, 7.2 Hz, 1H), 1.18-1.11 (m, 2H), 0.38 (s, 2H)

LCMS (03_4 min), [MH]$^+$=394.8, RT=1.757 minutes

LCMS Method C_4 MIN

Column: HSS C18 (50*2.1 mm), 1.8 um; ESI source, Positive ion mode; Wavelength 226 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes (vii) 7-(3-(aminomethyl)pyrrolidin-1-yl)-5-bromo-1-cyclopropyl-6-fluoro-8-methyl quinolin-2(1H)-one TFA salt (Isomer B)

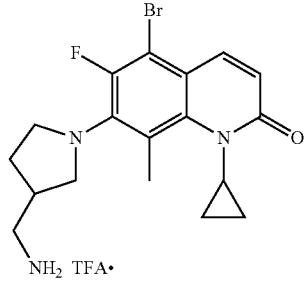

97-v-Isomer B (0.021 g, 0.042 mmol, 1.0 equiv) was added in dichloromethane (1 mL) and cooled to 0° C. TFA (0.2 mL) was added and the reaction mixture was stirred at room temperature for 1 hour. The reaction mixture was concentrated, co-distilled with diethyl ether and triturated with diethyl ether to afford a crude product. The crude product was further purified by preparative HPLC purification to afford the desired product 97-vii (0.01 g, 90% yield).

$^1$H NMR (400 MHz, DMSO) δ 7.85 (d, J=9.7 Hz, 1H), 7.7 (s, 3H), 6.49 (d, J=9.7 Hz, 1H), 3.53-2.50 (m, 8H), 2.14 (m, 1H), 1.76 (m, 1H), 1.18-1.11 (m, 2H), 0.38 (s, 2H)

LCMS (03_4 min), [MH]$^+$=394.8, RT=1.719 minutes

LCMS Method C_4 MIN

Column: HSS C18 (50*2.1 mm), 1.8 um; ESI source, Positive ion mode; Wavelength 235 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

Example 98: 7-(3-(aminomethyl)pyrrolidin-1-yl)-1-cyclopropyl-6-fluoro-8-methyl-5-(1H-pyrazol-4-yl)quinolin-2(1H)-one TFA salt

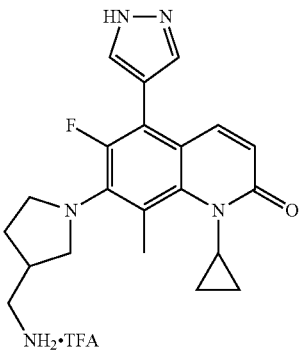

The title compound was prepared in accordance with the following scheme:

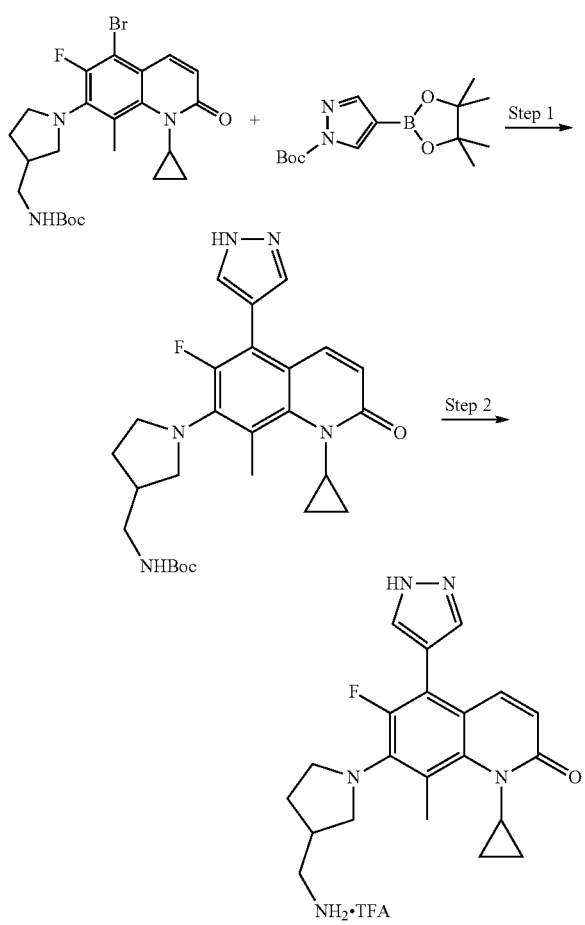

(i) tert-butyl ((1-(1-cyclopropyl-6-fluoro-8-methyl-2-oxo-5-(1H-pyrazol-4-yl)-1,2-dihydroquinolin-7-yl)pyrrolidin-3-yl)methyl) carbamate 97-v-Isomer B (0.025 g, 0.051 mmol, 1.0 equiv), tert-butyl 4-(4,4,5,5-tetramethyl-1,3,2-dioxaborolan-2-yl)-1H-pyrazole-1-carboxylate (0.029 g, 0.1 mmol, 2.0 equiv), $K_3PO_4$ (0.032 g, 0.15 mmol, 3.0 equiv) were added in DME:water (2:1, 1.5 mL) and the reaction mixture was degassed for 5 minutes. $Pd_2(dba)_3$ (0.0045 g, 0.005 mmol, 0.1 equiv), $t-Bu_3P$ (0.0014 g, 0.005 mmol, 0.1 equiv) were added and the reaction mixture was stirred at 110° C. for 1 hour under microwave irradiation. The reaction mixture was quenched with water and extracted with EtOAc. The organic layer was washed with brine, dried over sodium sulfate and concentrated to afford the desired product 98-i (0.03 g, crude). The product was used in the next step without further purification. LCMS (m/z): 482.4 [M+H].

(ii) 7-(3-(aminomethyl)pyrrolidin-1-yl)-1-cyclopropyl-6-fluoro-8-methyl-5-(1H-pyrazol-4-yl)quinolin-2(1H)-one TFA salt 98-i (0.03 g, 0.06 mmol, 1.0 equiv) was added in dichloromethane (2 mL) and cooled to 0° C. TFA (0.3 mL) was added and the reaction mixture was stirred at room temperature for 1 hour. The reaction mixture was concentrated to afford a crude residue. The crude residue was purified by preparative HPLC purification to afford the desired product 98-ii (0.004 g, 16.4% yield).

$^1$H NMR (400 MHz, MeOD) δ 7.79 (d, J=9.6 Hz, 3H), 6.45 (d, J=9.6 Hz, 1H), 3.70-3.65 (m, 1H), 3.57 (d, J=4.5 Hz, 3H), 3.35 (s, 1H), 3.06 (d, J=7.0 Hz, 2H), 2.65-2.58 (m, 4H), 2.32-2.25 (m, 1H), 1.84 (dd, J=12.2, 7.6 Hz, 1H), 1.26 (d, J=6.0 Hz, 2H), 0.55 (d, J=3.7 Hz, 2H)

LCMS (03_4 min), [MH]$^+$=382.3, RT=1.448 minutes

LCMS Method C_4 MIN

Column: HSS C18 (50*2.1 mm), 1.8 um; ESI source, Positive ion mode; Wavelength 226 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

Example 99: 7-(3-(aminomethyl)pyrrolidin-1-yl)-1-cyclopropyl-6-fluoro-8-methyl-2-oxo-1,2-dihydroquinoline-5-carbonitrile TFA salt

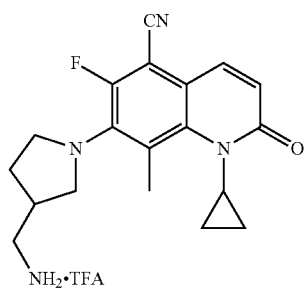

The title compound was prepared in accordance with the following scheme:

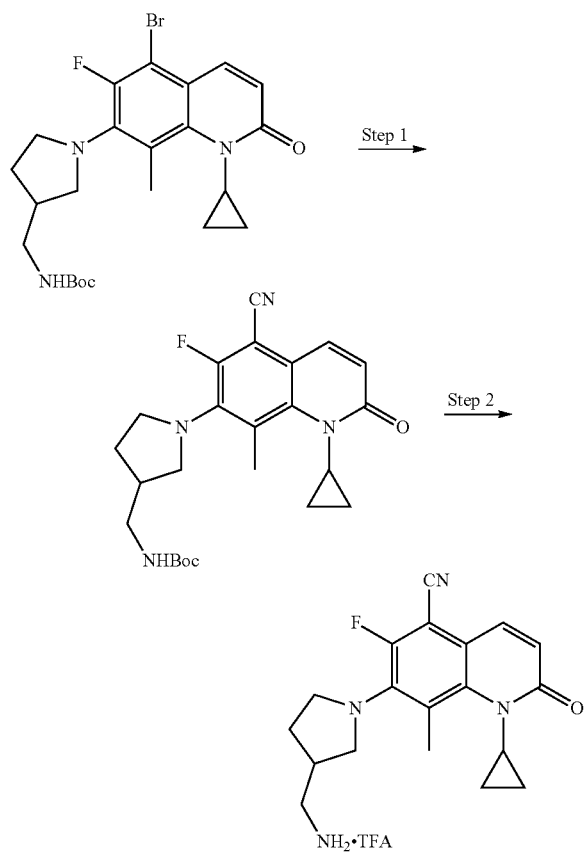

(i) tert-butyl ((1-(5-cyano-1-cyclopropyl-6-fluoro-8-methyl-2-oxo-1,2-dihydro quinolin-7-yl) pyrrolidin-3-yl) methyl) carbamate 97-v-Isomer B (0.05 g, 0.1 mmol, 1.0 equiv) was added in DMA (2 mL), $Zn(CN)_2$ (0.14 g, 1.2 mmol, 12.0 equiv) was added and the reaction mixture was degassed for 10 minutes. $Pd(t-Bu_3P)_2$ (0.005 g, 0.01 mmol, 0.1 equiv) was added and the reaction mixture was stirred at 120° C. for 5 hours. The reaction mixture was quenched with water and extracted with EtOAc. The organic layer was washed with brine, dried over sodium sulfate and concentrated to afford the desired product 99-i (0.05 g, crude). The product was used in the next step with no further purification. LCMS (m/z): 441.4 [M+H].

(ii) 7-(3-(aminomethyl)pyrrolidin-1-yl)-1-cyclopropyl-6-fluoro-8-methyl-2-oxo-1,2-dihydroquinoline-5-carbonitrile TFA salt 99-i (0.05 g, 0.11 mmol, 1.0 equiv) was added in dichloromethane (2 mL) and cooled to 0° C. TFA (0.5 mL) was added and the reaction mixture was stirred at room temperature for 1.5 hours. The reaction mixture was concentrated to afford a crude residue. The crude residue was purified by preparative HPLC purification to afford the desired product 99-ii (0.011 g, 32% yield).

$^1$H NMR (400 MHz, MeOD) δ 7.88 (d, J=9.5 Hz, 1H), 6.65 (d, J=9.5 Hz, 1H), 3.65 (d, J=8.0 Hz, 2H), 3.54 (t, J=11.4 Hz, 2H), 3.37 (s, 1H), 2.87 (d, J=6.5 Hz, 2H), 2.60 (s, 3H), 2.49 (d, J=7.5 Hz, 1H), 2.24 (s, 1H), 1.82 (s, 1H), 1.26 (s, 2H), 0.55 (s, 2H)

LCMS (03_4 min), [MH]$^+$=341.3, RT=1.544 minutes

LCMS Method C_4 MIN

Column: HSS C18 (50*2.1 mm), 1.8 um; ESI source, Positive ion mode; Wavelength 230 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 100: 5-(aminomethyl)-7-(3-(aminomethyl) pyrrolidin-1-yl)-1-cyclopropyl-6-fluoro-8-methylquinolin-2(1H)-one TFA salt

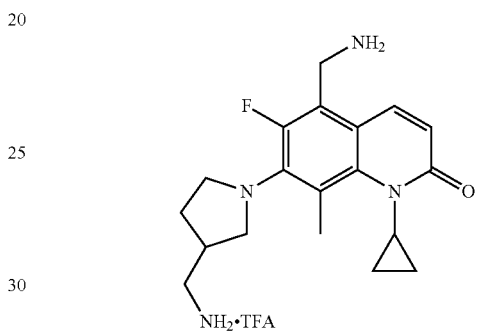

The title compound was prepared in accordance with the following scheme:

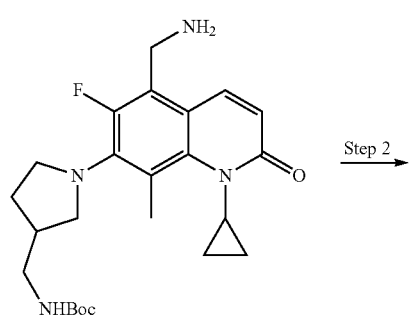

245

-continued

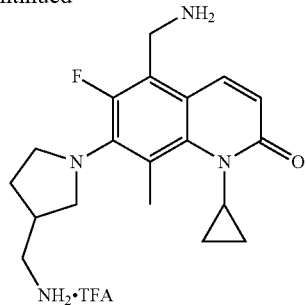

(i) tert-butyl ((1-(5-(amino methyl)-1-cyclopropyl-6-fluoro-8-methyl-2-oxo-1,2-dihydroquinolin-7-yl) pyrrolidin-3-yl) methyl) carbamate 99-i (0.04 g, 0.091 mmol, 1.0 equiv) was added in methanol (4 mL) and cooled to 0° C. NiCl$_2$.6H$_2$O (0.0021 g, 0.0091 mmol, 0.1 equiv) was added and the reaction mixture was stirred at 0° C. for 5 minutes. NaBH$_4$ (0.0034 g, 0.91 mmol, 1.0 equiv) was added and the reaction mixture was stirred at 0° C. for 30 minutes. The reaction mixture was quenched with cold water and extracted with EtOAc. The organic layer was washed with brine, dried over sodium sulfate and concentrated to afford the desired product 100-i (0.045 g, crude). The product was used in the next step without further purification. LCMS (m/z): 445.3 [M+H].

(ii) 5-(aminomethyl)-7-(3-(aminomethyl)pyrrolidin-1-yl)-1-cyclopropyl-6-fluoro-8-methylquinolin-2(1H)-one TFA salt 100-i (0.045 g, 0.1 mmol, 1.0 equiv) was added in dichloromethane (5 mL) and cooled to 0° C. TFA (0.5 mL) was added and the reaction mixture was stirred at room temperature for 1.5 hours. The reaction mixture was concentrated, co-distilled with dichloromethane, triturated with diethyl ether and the solvent was decanted to afford a crude product. The crude product was purified by preparative HPLC purification to afford the desired product 100-ii (0.009 g, 23% yield).

$^1$H NMR (400 MHz, MeOD) δ 8.02 (d, J=9.7 Hz, 1H), 6.60 (d, J=9.7 Hz, 1H), 4.48 (s, 2H), 3.67 (d, J=7.4 Hz, 2H), 3.56 (d, J=15.6 Hz, 2H), 3.37 (s, 1H), 3.14 (t, J=7.5 Hz, 2H), 2.72-2.65 (m, 1H), 2.60 (s, 3H), 2.32 (s, 1H), 1.87 (dd, J=12.3, 7.9 Hz, 1H), 1.31 (s, 2H), 1.19 (d, J=7.1 Hz, 1H), 0.48 (d, J=4.4 Hz, 2H)

LCMS (03_4 min), [MH]$^+$=345.3, RT=1.281 mins

LCMS Method C_4 MIN

Column: HSS C18 (50*2.1 mm), 1.8 um; ESI source, Positive ion mode; Wavelength 233/368 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

246

Example 101: 7-(3-(aminomethyl)pyrrolidin-1-yl)-1-cyclopropyl-6-fluoro-5,8-dimethylquinolin-2(1H)-one TFA salt

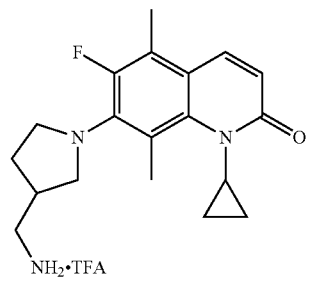

The title compound was prepared in accordance with the following scheme:

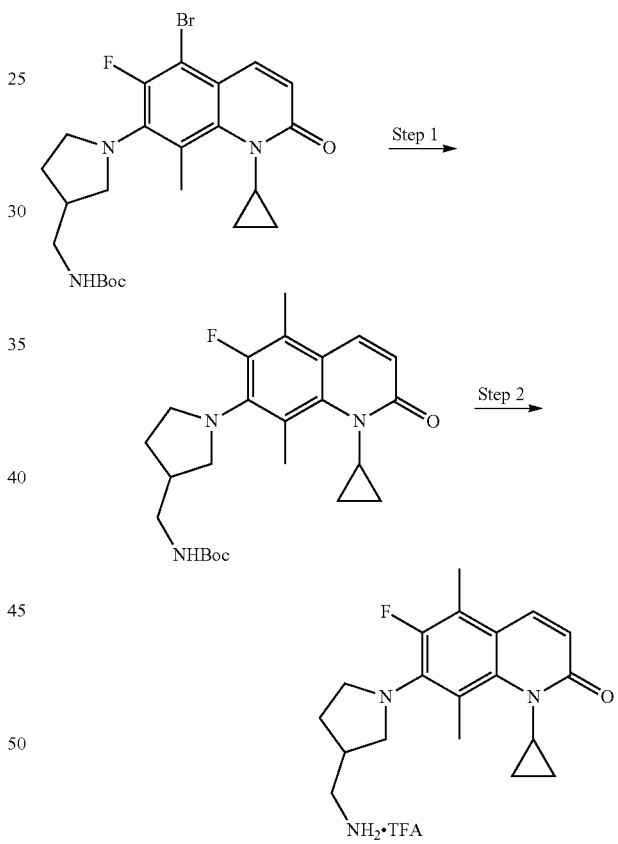

(i) tert-butyl ((1-(1-cyclopropyl-6-fluoro-5, 8-dimethyl-2-oxo-1,2-dihydroquinolin-7-yl) pyrrolidin-3-yl) methyl) carbamate 97-v-Isomer B (0.055 g, 0.11 mmol, 1.0 equiv), methyl boronic acid (0.013 g, 0.22 mmol, 2.0 equiv), K$_3$PO$_4$ (0.071 g, 0.33 mmol, 3.0 equiv) were added in THF: water (5:1, 2.4 mL) and the reaction mixture was degassed for 10 minutes. PdCl$_2$(dppf).DCM (0.0045 g, 0.006 mmol, 0.05 equiv) was added and the reaction mixture was degassed for 10 minutes. The reaction mixture was stirred at 80° C. for 24 hours. The reaction mixture was quenched with water and extracted with EtOAc. The organic layer was washed with brine, dried over sodium sulfate and concentrated to afford a crude residue. The crude residue was purified by preparative TLC (30% EtOAc/Hexane, three times run) to afford the desired product 101-i (0.03 g, 63.8% yield). LCMS (m/z): 430.5 [M+H].

(ii) 7-(3-(aminomethyl)pyrrolidin-1-yl)-1-cyclopropyl-6-fluoro-5,8-dimethylquinolin-2(1H)-one TFA salt 101-i (0.03 g, 0.069 mmol, 1.0 equiv) was added in dichloromethane (2 mL) and cooled to 0° C. TFA (0.3 mL) was added and the reaction mixture was stirred at room temperature for 1 hours. The reaction mixture was concentrated to afford a crude residue. The crude residue was purified by preparative HPLC purification to afford the desired product 101-ii (0.01 g, 33.7% yield).

$^1$H NMR (400 MHz, MeOD) δ 7.97 (d, J=9.6 Hz, 1H), 6.51 (d, J=9.6 Hz, 1H), 3.69-3.60 (m, 1H), 3.53 (dd, J=14.7, 7.9 Hz, 3H), 3.12 (d, J=6.0 Hz, 2H), 2.65 (dd, J=14.4, 7.3 Hz, 1H), 2.56 (s, 3H), 2.42 (d, J=2.4 Hz, 3H), 2.30 (dd, J=12.2, 4.9 Hz, 2H), 1.84 (dd, J=12.3, 7.5 Hz, 1H), 1.22 (dd, J=10.9, 4.3 Hz, 2H), 0.50 (d, J=2.8 Hz, 2H)

LCMS (03_4 min), [MH]$^+$=330.4, RT=1.565 minutes
LCMS Method C_4 MIN
Column: HSS C18 (50*2.1 mm), 1.8 um; ESI source, Positive ion mode; Wavelength 365/234 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 102: 7-(3-(aminomethyl)pyrrolidin-1-yl)-1-cyclopropyl-6-fluoro-5-methoxy-8-methyl quinolin-2(1H)-one TFA salt The title compound was prepared in accordance with the following scheme:

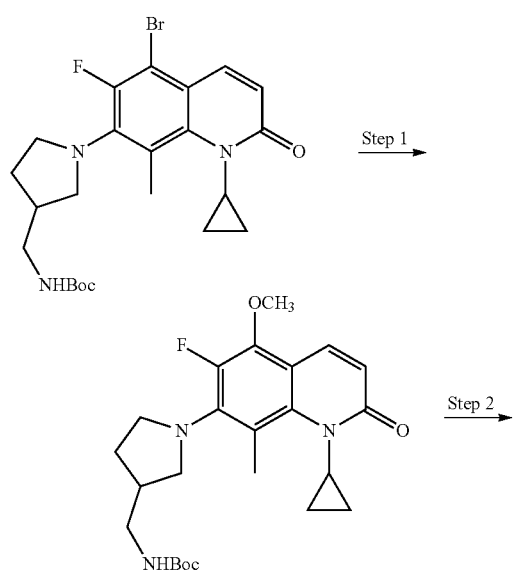

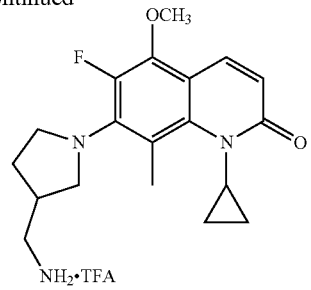

(i) tert-butyl ((1-(1-cyclopropyl-6-fluoro-5-methoxy-8-methyl-2-oxo-1,2-dihydro quinolin-7-yl) pyrrolidin-3-yl) methyl) carbamate Pd(II)OAc (0.056 g, 0.002 mmol, 0.05 equiv), t-Bu-Xphos (0.0032 g, 0.007 mmol, 0.15 equiv), Cs$_2$CO$_3$ (0.032 g, 0.1 mmol, 2.0 equiv) were added in toluene (1 mL) in sealed tube and the reaction mixture was degassed for 5 minutes. The reaction mixture was stirred at 45° C. for 5 minutes and 97-v-Isomer B (0.025 g, 0.05 mmol, 1.0 equiv) in methanol (1 mL) was added. The reaction mixture was degassed for 5 minutes and the reaction mixture was stirred at 80° C. for 24 hours. The reaction mixture was quenched with water and extracted with EtOAc. The organic layer was washed with brine, dried over sodium sulfate and concentrated to afford the desired product 102-i (0.03 g, crude). The product was used in the next step without further purification. LCMS (m/z): 446.5 [M+H].

(ii) 7-(3-(aminomethyl)pyrrolidin-1-yl)-1-cyclopropyl-6-fluoro-5-methoxy-8-methyl quinolin-2(1H)-one TFA salt 102-i (0.03 g, 0.067 mmol, 1.0 equiv) was dissolved in dichloromethane (1 mL) and cooled to 0° C. TFA (0.3 mL) was added and the reaction mixture was stirred at room temperature for 1.5 hours. The reaction mixture was concentrated to afford a crude residue. The crude residue was purified by preparative HPLC purification to afford the desired product 102-ii (0.005 g, 22.3% yield).

$^1$H NMR (400 MHz, MeOD) δ 7.99 (d, J=9.6 Hz, 1H), 6.44 (d, J=9.6 Hz, 1H), 4.00 (s, 3H), 3.69 (d, J=5.0 Hz, 1H), 3.58 (d, J=5.0 Hz, 3H), 3.51 (s, 2H), 2.89 (s, 2H), 2.50 (s, 3H), 2.26-2.20 (m, 1H), 2.06-2.01 (m, 1H), 1.24 (s, 2H), 0.52 (s, 2H)

LCMS (03_4 min), [MH]$^+$=346.4, RT=1.547 minutes
LCMS Method C_4 MIN
Column: HSS C18 (50*2.1 mm), 1.8 um; ESI source, Positive ion mode; Wavelength 202/236 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 103: 1-cyclopropyl-6-fluoro-8-methyl-7-(3-(((2,2,2-trifluoroacetyl)-14-azanyl)methyl)pyrrolidin-1-yl)-5-vinylquinolin-2(1H)-one TFA salt The title compound was prepared in accordance with the following scheme:

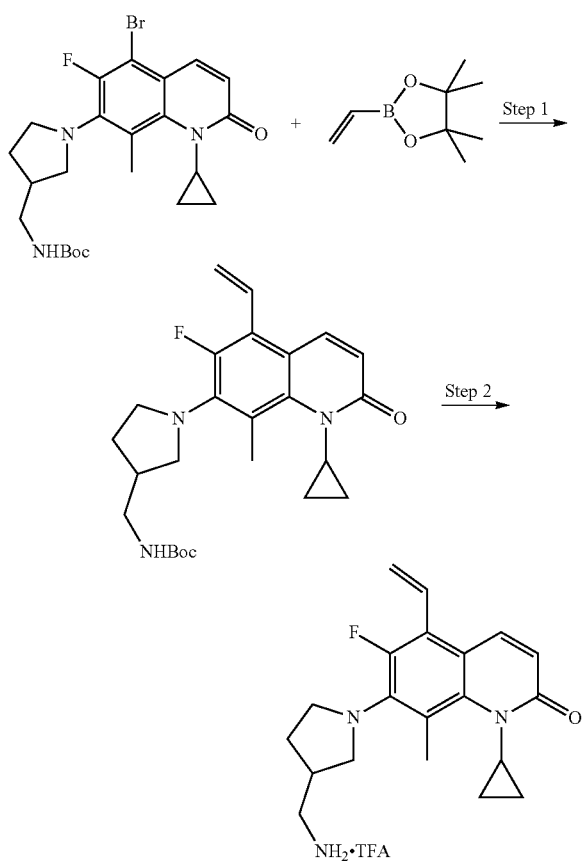

(i) tert-butyl ((1-(1-cyclopropyl-6-fluoro-8-methyl-2-oxo-5-vinyl-1,2-dihydro quinolin-7-yl) pyrrolidin-3-yl) methyl) carbamate 97-v-Isomer B (0.055 g, 0.13 mmol, 1.0 equiv), 4, 4, 5, 5-tetramethyl-2-vinyl-1, 3, 2-dioxaborolane (0.029 g, 0.19 mmol, 1.5 equiv), K₃PO₄ (0.081 g, 0.38 mmol, 3.0 equiv) were added in THF: Water (2:1, 2 mL) and the reaction mixture was degassed for 5 minutes. PdCl₂(dppf).DMC (0.005 g, 0.006 mmol, 0.05 equiv) was added and the reaction mixture was stirred at 80° C. for 24 hours. The reaction mixture was quenched with water and extracted with EtOAc. The organic layer was washed with brine, dried over sodium sulfate and concentrated to afford a crude residue. The crude residue was purified by preparative TLC purification (40% EtOAc/Hexane) to afford the desired product 103-i (0.04 g, 81.6% yield). LCMS (m/z): 442.3 [M+H].

(ii) 1-cyclopropyl-6-fluoro-8-methyl-7-(3-(((2,2,2-trifluoroacetyl)-14-azanyl)methyl) pyrrolidin-1-yl)-5-vinylquinolin-2(1H)-one TFA salt 103-i (0.04 g, 0.091 mmol, 1.0 equiv) was dissolved in dichloromethane (2 mL) and cooled to 0° C. TFA (0.4 mL) was added and the reaction mixture was stirred at room temperature for 1.5 hours. The reaction mixture was concentrated to afford a crude residue. The crude residue was purified by preparative HPLC purification to afford the desired product 103-ii (0.013 g, 33.3% yield).

¹H NMR (400 MHz, MeOD) δ 8.04 (d, J=9.7 Hz, 1H), 6.90 (dd, J=17.9, 11.4 Hz, 1H), 6.49 (d, J=9.6 Hz, 1H), 5.81-5.76 (m, 1H), 5.66 (d, J=17.7 Hz, 1H), 3.66 (d, J=7.7 Hz, 1H), 3.59-3.51 (m, 3H), 3.34 (s, 1H), 3.13 (d, J=7.7 Hz, 2H), 2.71-2.65 (m, 1H), 2.59 (s, 3H), 2.31 (d, J=6.8 Hz, 1H), 1.85 (dd, J=12.3, 7.5 Hz, 1H), 1.28-1.22 (m, 2H), 0.52 (d, J=2.7 Hz, 2H).

LCMS (03_4 min), [MH]⁺=342.4, RT=1.609 minutes.
LCMS Method C_4 MIN
Column: HSS C18 (50*2.1 mm), 1.8 um; ESI source, Positive ion mode; Wavelength 236 nm;
Column temperature: Ambient;
Mobile Phase: A: 5 mM Ammonium acetate in 0.1% formic acid in water, B: 0.1% formic acid in ACN;
Flow rate: 0.55 mL/min;
Gradient: 5%-100% (solvent B) over 2.5 minutes and holding at 100% for 0.6 minutes.

Example 104: 5-amino-7-(3-(aminomethyl)pyrrolidin-1-yl)-1-cyclopropyl-6-fluoro-8-methyl quinolin-2(1H)-one TFA salt The title compound was prepared in accordance with the following scheme:

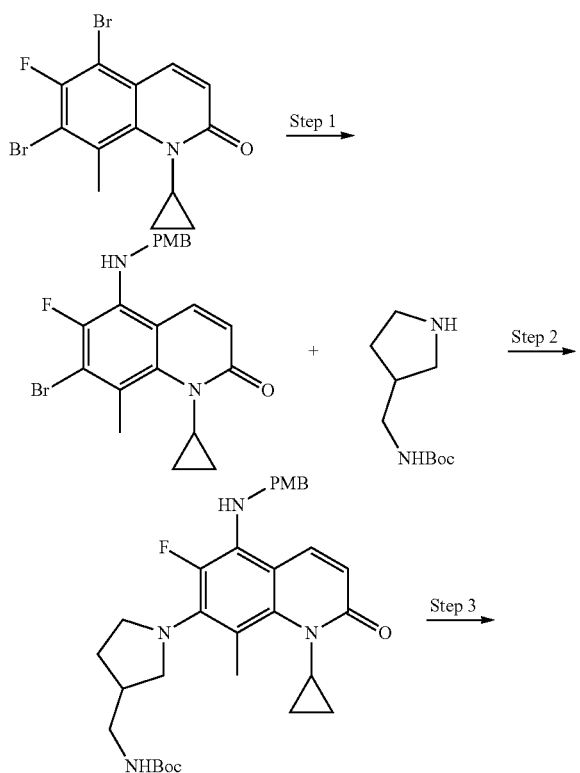

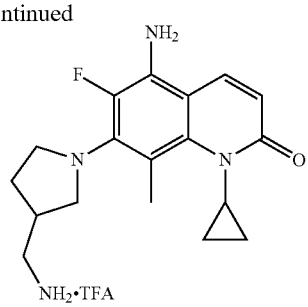

(i) 7-bromo-1-cyclopropyl-6-fluoro-5-((4-methoxybenzyl)amino)-8-methyl quinolin-2(1H)-one 97-iv (0.15 g, 0.39 mmol, 1.0 equiv), Cs$_2$CO$_3$ (0.19 g, 0.59 mmol, 1.5 equiv), PMB-amine (0.064 g, 0.47 mmol, 1.2 equiv), Pd$_2$(dba)$_3$ (0.017 g, 0.019 mmol, 0.05 equiv), xantphos (0.034 g, 0.059 mmol, 0.15 equiv) were added in 1,4-dioxane (6 mL) and the reaction mixture was degassed for 5 minutes. The reaction mixture was stirred at 100° C. for 9 hours. The reaction mixture was quenched with water and extracted with EtOAc. The organic layer was washed with brine, dried over sodium sulfate and concentrated to afford a crude residue. The crude residue was purified by preparative TLC (30% EtOAc/Hexane, 4-times run) to afford the desired product 104-i (0.12 g, 75.6% yield). LCMS (m/z): 431.2 [M+H].

$^1$H NMR (400 MHz, MeOD) δ 8.04 (d, J=9.7 Hz, 1H), 7.19 (d, J=8.6 Hz, 2H), 6.83 (dd, J=11.2, 8.7 Hz, 2H), 6.47 (d, J=9.2 Hz, 1H), 4.38 (s, 2H), 3.75 (d, J=1.6 Hz, 3H), 3.51 (s, 1H), 2.68 (s, 3H), 1.20 (d, J=5.7 Hz, 2H), 0.46 (s, 2H)

LCMS (m/z): 431.2 [M+H]

(ii) tert-butyl ((1-(1-cyclopropyl-6-fluoro-5-((4-methoxybenzyl)amino)-8-methyl-2-oxo-1,2-dihydroquinolin-7-yl) pyrrolidin-3-yl) methyl) carbamate 104-i (0.13 g, 0.3 mmol, 1.0 equiv), Cs$_2$CO$_3$ (0.19 g, 0.58 mmol, 2.0 equiv), tert-butyl (pyrrolidin-3-ylmethyl) carbamate (0.087 g, 0.44 mmol, 1.5 equiv) were added in 1,4-dioxane (5 mL) and the reaction mixture was degassed for 5 minutes. Pd$_2$(dba)$_3$ (0.013 g, 0.014 mmol, 0.05 equiv), xantphos (0.025 g, 0.043 mmol, 0.15 equiv) were added and the reaction mixture was stirred at 110° C. for 24 hours. The reaction mixture was quenched with water and extracted with EtOAc. The organic layer was washed with brine, dried over sodium sulfate and concentrated to afford a crude residue. The crude residue was purified by preparative TLC (40% EtOAc/Hexane, 4-times run) to afford the desired product 104-ii (0.07 g, 55% yield).

$^1$H NMR (400 MHz, MeOD) δ 7.96 (d, J=9.6 Hz, 1H), 7.19 (d, J=8.6 Hz, 2H), 6.81 (d, J=8.7 Hz, 2H), 6.33 (d, J=9.6 Hz, 1H), 4.32 (s, 2H), 3.75 (s, 3H), 3.52-3.42 (m, 4H), 3.25-3.14 (m, 3H), 2.49 (dd, J=13.8, 6.8 Hz, 1H), 2.39 (d, J=16.7 Hz, 3H), 2.12 (dd, J=12.6, 6.1 Hz, 1H), 1.74 (dd, J=12.0, 7.2 Hz, 1H), 1.19 (d, J=5.9 Hz, 2H), 0.47 (d, J=2.8 Hz, 2H)

LCMS (m/z): 551.5 [M+H]

(iii) 5-amino-7-(3-(aminomethyl)pyrrolidin-1-yl)-1-cyclopropyl-6-fluoro-8-methyl quinolin-2(1H)-one TFA salt 103-ii (0.045 g, 0.082 mmol, 1.0 equiv) was taken and TFA (0.45 mL) was added and the reaction mixture was stirred at 50° C. for 10 minutes under microwave irradiation. The reaction mixture was concentrated and co-distilled with THF to afford a crude residue. The crude residue was purified by preparative HPLC purification to afford the desired product 104-iii (0.005 g, 11.6% yield).

$^1$H NMR (400 MHz, MeOD) δ 8.09 (d, J=9.4 Hz, 1H), 6.29 (d, J=9.4 Hz, 1H), 3.53 (dd, J=10.4, 6.2 Hz, 2H), 3.41-3.34 (m, 2H), 3.11 (d, J=6.2 Hz, 3H), 2.73-2.65 (m, 1H), 2.48 (s, 3H), 2.33-2.26 (m, 1H), 1.82 (dd, J=12.5, 7.4 Hz, 1H), 1.22 (d, J=6.1 Hz, 2H), 0.49 (d, J=2.4 Hz, 2H)

LCMS (02_4 min), [MH]$^+$=331.0, RT=1.586 minutes

LCMS Method C_4 MIN

Column: HSS C18 (50*2.1 mm), 1.8 um; ESI source, Positive ion mode; Wavelength 223 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes

Example 105: 7-(3-(aminomethyl)pyrrolidin-1-yl)-5-chloro-1-cyclopropyl-6-fluoro-8-methyl quinolin-2(1H)-one TFA salt

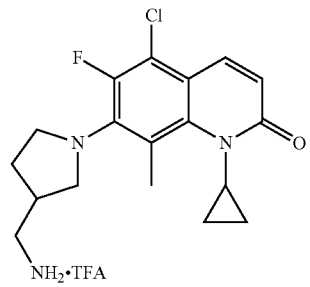

The title compound was prepared in accordance with the following scheme:

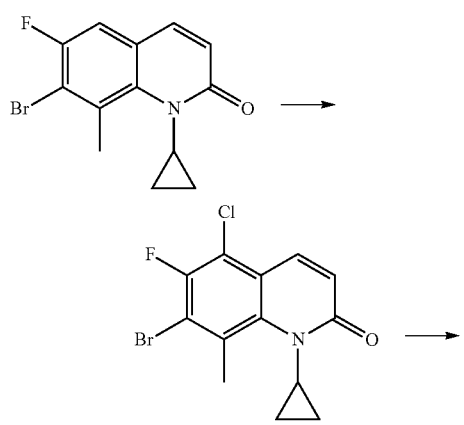

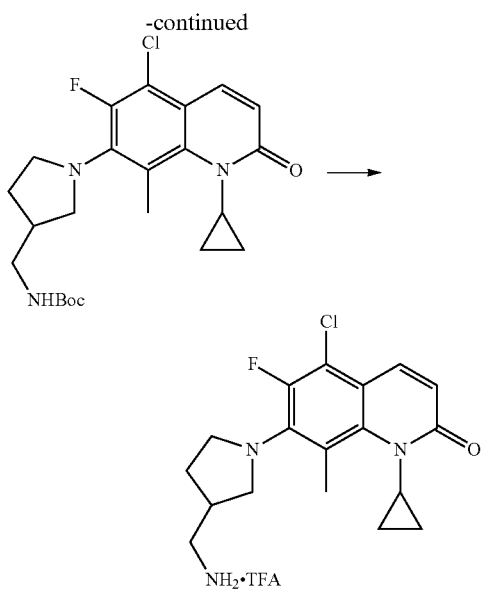

(i) 7-bromo-5-chloro-1-cyclopropyl-6-fluoro-8-methylquinolin-2(1H)-one 15-x (0.1 g, 0.33 mmol, 1.0 equiv) was added in H₂SO₄ (0.5 M) (0.15 mL), NCS (0.058 g, 0.43 mmol, 1.3 equiv) was added and the reaction mixture was stirred at room temperature for 4 hours. NCS (0.058 g, 0.43 mmol, 1.3 equiv) was added and the reaction mixture was stirred at room temperature for 24 hours. The reaction mixture was quenched with cold water and extracted with EtOAc. The organic layer was washed with brine, dried over sodium sulfate and concentrated to afford a crude residue. The crude residue was purified by silica gel flash column chromatography (10-12% EtOAc/Hexane) to afford the desired product 105-i (0.085 g, 75% yield).

$^1$H NMR (400 MHz, DMSO) δ 7.99 (d, J=9.8 Hz, 1H), 6.70 (d, J=9.4 Hz, 1H), 3.54 (dd, J=8.8, 4.8 Hz, 1H), 2.73 (s, 3H), 1.16-1.11 (m, 2H), 0.43 (s, 2H)

LCMS (m/z): 330.1 [M+H]

(ii) tert-butyl ((1-(5-chloro-1-cyclopropyl-6-fluoro-8-methyl-2-oxo-1,2-dihydroquinolin-7-yl) pyrrolidin-3-yl) methyl) carbamate 105-i (0.085 g, 0.2 mmol, 1.0 equiv), Cs₂CO₃ (0.13 g, 0.38 mmol, 1.5 equiv), tert-butyl (pyrrolidin-3-ylmethyl) carbamate (0.06 g, 0.3 mmol, 1.2 equiv) were added in 1,4-dioxane (10 mL) and the reaction mixture was degassed for 5 minutes. Pd₂(dba)₃ (0.011 g, 0.012 mmol, 0.05 equiv), xantphos (0.022 g, 0.038 mmol, 0.15 equiv) were added, the reaction mixture was degassed for 5 minutes and the reaction mixture was stirred at 120° C. for 24 hours. The reaction mixture was quenched with water and extracted with EtOAc. The organic layer was washed with brine, dried over sodium sulfate and concentrated to afford a crude residue. The crude residue was purified by silica gel column chromatography (40-50% EtOAc/Hexane) to afford the desired product 105-ii (0.085 g, 73% yield). LCMS (m/z): 450.3 [M+H].

(iii) 7-(3-(aminomethyl)pyrrolidin-1-yl)-5-chloro-1-cyclopropyl-6-fluoro-8-methyl quinolin-2(1H)-one TFA salt 105-ii (0.08 g, 0.17 mmol, 1.0 equiv) was added in dichloromethane (2 mL) and cooled to 0° C. TFA (0.4 mL) was added and the reaction mixture was stirred at room temperature for 3 hours. The reaction mixture was concentrated, co-distilled with dichloromethane and triturated with diethyl ether to afford a crude residue. The crude residue was purified by preparative HPLC purification to afford the desired product 105-iii (0.013 g, 16.5% yield).

$^1$H NMR (400 MHz, MeOD) δ 8.09 (d, J=9.6 Hz, 1H), 6.59 (d, J=9.5 Hz, 1H), 3.69 (s, 1H), 3.55 (t, J=19.0 Hz, 3H), 3.35 (s, 1H), 3.13 (d, J=7.9 Hz, 2H), 2.66 (d, J=7.2 Hz, 1H), 2.57 (s, 3H), 2.31 (s, 1H), 1.88 (d, J=7.7 Hz, 1H), 1.25 (d, J=3.3 Hz, 2H), 0.53 (d, J=4.3 Hz, 2H).

LCMS (02_4 min), [MH]⁺=349.9, RT=1.749 mins.

LCMS Method C_4 MIN

Column: HSS C18 (50*2.1 mm), 1.8 um; ESI source, Positive ion mode; Wavelength 238 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 106: 7-((R)-3-((S)-1-aminoethyl)pyrrolidin-1-yl)-1-cyclopropyl-5,6-difluoro-8-methyl quinolin-2(1H)-one TFA

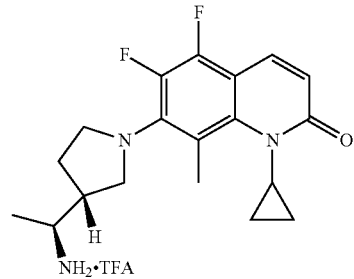

The title compound was prepared in accordance with the following scheme:

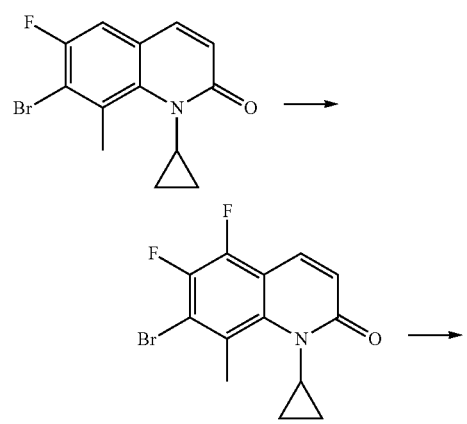

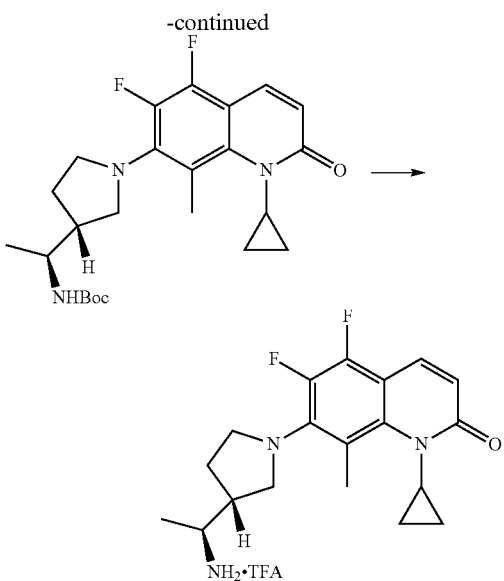

(i) 7-bromo-1-cyclopropyl-5,6-difluoro-8-methylquinolin-2(1H)-one 15-x (0.38 g, 1.2 mmol, 1.0 equiv) was dissolved in acetonitrile (10 mL), Selectfluor (0.9 g, 2.5 mmol, 2.0 equiv) was added and the reaction mixture was stirred at 75° C. for 3 hours under microwave irradiation. The reaction mixture was diluted with water and extracted with EtOAc. The organic layer was washed with brine, dried over sodium sulfate and concentrated to afford a crude residue. The crude residue was purified by silica gel column chromatography (20-25% EtOAc/Hexane) to afford the desired product 106-i (0.045 g, 11.3% yield). Starting material (0.18 g) was recovered.

$^1$H NMR (400 MHz, DMSO) δ 7.73 (d, J=9.8 Hz, 1H), 7.56 (d, J=8.2 Hz, 1H), 3.60 (s, 1H), 2.72 (d, J=28.1 Hz, 3H), 1.17 (d, J=5.6 Hz, 2H), 0.47 (s, 2H)

LCMS (m/z): 314.3 [M+H]

(ii) tert-butyl ((S)-1-((R)-1-(1-cyclopropyl-5,6-difluoro-8-methyl-2-oxo-1,2-dihydro quinolin-7-yl) pyrrolidin-3-yl) ethyl) carbamate 106-i (0.089 g, 0.25 mmol, 1.0 equiv), Cs$_2$CO$_3$ (0.12 g, 0.38 mmol, 1.5 equiv), (S)-2-((tert-butoxycarbonyl)amino)-2-((R)-pyrrolidin-3-yl)ethan-1-ylium (0.06 g, 0.3 mmol, 1.2 equiv) were added in 1,4-dioxane (8 mL) and the reaction mixture was degassed for 5 minutes. Pd$_2$(dba)$_3$ (0.012 g, 0.012 mmol, 0.05 equiv), xantphos (0.022 g, 0.038 mmol, 0.15 equiv) were added and the reaction mixture was stirred at 130° C. for 10 hours. The reaction mixture was quenched with cold water and extracted with EtOAc. The organic layer was washed with brine, dried over sodium sulfate and concentrated to afford a crude residue. The crude residue was purified by flash chromatography (30-35% EtOAc/Hexane) to afford the desired product 106-ii (0.09 g, 82% yield). LCMS (m/z): 449.1 [M+H].

(iii) 7-((R)-3-((S)-1-aminoethyl)pyrrolidin-1-yl)-1-cyclopropyl-5,6-difluoro-8-methyl quinolin-2(1H)-one TFA salt 106-ii (0.092 g, 0.2 mmol, 1.0 equiv) was added in dichloromethane (10 mL) and cooled to 0° C. TFA (0.7 mL) was added and the reaction mixture was stirred at room temperature for 2 hours. The reaction mixture was concentrated to afford a crude residue. The crude residue was purified by preparative HPLC purification to afford the desired product 106-iii (0.023 g, 32% yield).

$^1$H NMR (400 MHz, MeOD) δ 7.51 (d, J=9.4 Hz, 1H), 7.21 (d, J=12.4 Hz, 1H), 3.63-3.48 (m, 3H), 3.41 (ddd, J=12.9, 7.5, 4.7 Hz, 3H), 2.63 (s, 3H), 2.52 (dd, J=16.5, 8.4 Hz, 1H), 2.25 (dd, J=8.4, 3.6 Hz, 1H), 1.90-1.81 (m, 1H), 1.43 (d, J=6.6 Hz, 3H), 1.27 (t, J=6.7 Hz, 2H), 0.58 (dd, J=9.3, 4.1 Hz, 2H)

LCMS (03_4 min), [MH]$^+$=347.41, RT=1.626 mins
LCMS Method C_4 MIN
Column: HSS C18 (50*2.1 mm), 1.8 um; ESI source, Positive ion mode; Wavelength 228/298 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Intermediate 107: Methyl 4-bromo-5-fluoro-3-(hydroxymethyl)-2-iodobenzoate The title compound was prepared in accordance with the following scheme:

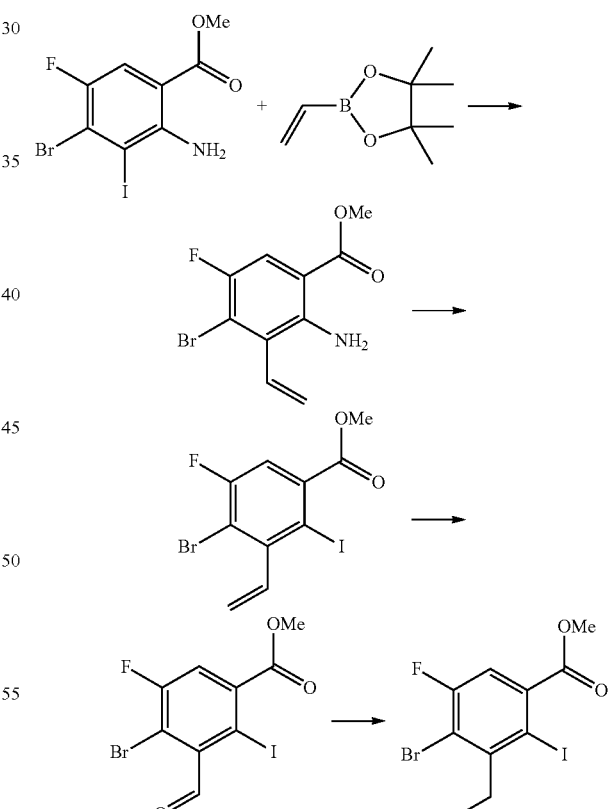

(i) methyl 2-amino-4-bromo-5-fluoro-3-vinylbenzoate

Methyl 2-amino-4-bromo-5-fluoro-3-iodobenzoate (12.5 g, 33.4 mmol, 1.0 equiv), 4,4,5,5-tetramethyl-2-vinyl-1,3,2- dioxaborolane (10.25 g, 66.8 mmol, 2.0 equiv), K₂CO₃ (13.82 g, 100 mmol, 3.0 equiv) were added in N,N-dimethylformamide (50 mL) and the reaction mixture was degassed for 5 minutes. PdCl₂ (dppf).MDC (1.36 g, 1.60 mmol, 0.05 equiv) was added and the reaction mixture was stirred at 60° C. for 48 hours. The reaction mixture was quenched with water and extracted with EtOAc. The organic layer was washed with cold water, brine, dried over sodium sulfate and concentrated to afford a crude residue. The crude residue was purified by silica gel column chromatography (0-2% EtOAc/Hexane) to afford the desired product 107-i (13.0 g, 82%).

H NMR (400 MHz, DMSO) δ 7.57 (d, J=9.6 Hz, 1H), 6.70-6.44 (m, 3H), 5.79 (dd, J=11.5, 0.9 Hz, 1H), 5.69-5.55 (m, 1H), 3.83 (d, J=6.6 Hz, 3H)

LCMS (m/z): 274.1 [M+H]

(ii) methyl 4-bromo-5-fluoro-2-iodo-3-vinylbenzoate 107-i (7.5 g, 28.3 mmol, 1.0 equiv) was dissolved in acetonitrile (45 mL), 6M HCl (90 mL) was added and the reaction mixture was stirred at 0° C. for 10 minutes. Solution of NaNO₂ (2.04 g, 29.7 mmol, 1.05 equiv) in water (40 mL) was added drop wise at 0° C. and to the reaction mixture was stirred for 60 minutes. The reaction mixture turned into clear pale yellow solution. Solution of KI (9.39 g, 56.7 mmol, 2.0 equiv) in water (60 mL) was added drop wise to the reaction mixture at 0° C. and stirred for 20 minutes. The reaction mixture was quenched with cold water and extracted with EtOAc. The organic layer was washed with 10% aqueous sodium thiosulphate solution, dried over sodium sulfate and concentrated to afford crude residue. The crude residue was purified by silica gel column chromatography (0-3% EtOAc/Hexane) to afford the desired product 107-ii (15.0 g, 71.0% yield).

¹H NMR (400 MHz, DMSO) δ 7.59 (t, J=8.9 Hz, 1H), 6.58 (dd, J=17.7, 11.4 Hz, 1H), 5.71 (dd, J=11.4, 1.0 Hz, 1H), 5.42 (dd, J=17.7, 1.0 Hz, 1H), 3.86 (d, J=7.8 Hz, 3H).

(iii) methyl 4-bromo-5-fluoro-3-formyl-2-iodobenzoate 107-ii (15.0 g, 39.06 mmol, 1.0 equiv) was dissolved in 1,4-Dioxane:Water (3:1) (120 mL) and cooled to 0° C. Osmium tetroxide (0.99 g, 3.9 mmol, 0.1 equiv) in tert-butanol (49 mL) was added in 10 minutes. The reaction mixture was stirred at room temperature for another 10 minutes. Sodium periodate (33.3 g, 156.2 mmol, 4.0 equiv) was added portion wise at room temperature and the mixture was stirred at the same temperature for overnight. The reaction mixture was quenched with water and extracted with EtOAc. The organic layer was washed with brine, dried over sodium sulfate and concentrated to afford crude residue. The crude residue was purified by silica gel column chromatography (0-5% EtOAc/Hexane) to afford the desired product 107-iii (9.3 g, 61.0% yield).

¹H NMR (400 MHz, DMSO) δ 9.85 (s, 1H), 7.89 (d, J=8.7 Hz, 1H), 3.89 (s, 3H)

(iv) methyl 4-bromo-5-fluoro-3-(hydroxymethyl)-2-iodobenzoate 107-iii (4.5 g, 11.62 mmol, 1.0 equiv) was dissolved in EtOH (90 mL) and cooled to −5° C. Sodium borohydride (0.132 g, 3.40 mmol, 0.3 equiv) was portion wise in 10 minutes and the reaction mixture was stirred at −5° C. for 30 minutes. The reaction mixture was quenched with saturated aqueous ammonium chloride solution and extracted with EtOAc. The organic layer was washed with brine, dried over sodium sulfate and concentrated to afford crude residue. The crude residue was purified by silica gel column chromatography (0-1% EtOAc/Hexane) to afford the desired product 107-iv (7.2 g, 89.0% yield).

¹H NMR (400 MHz, DMSO) δ 7.60 (d, J=8.5 Hz, 1H), 5.35 (t, J=5.1 Hz, 1H), 4.88 (d, J=5.0 Hz, 2H), 3.87 (s, 3H)

LCMS (06_4 min), [MH]⁺=389.1, RT=2.017 minutes

LCMS Method C_4 MIN

Column: HSS C18 (50*2.1 mm), 1.8 um; ESI source, Positive ion mode; Wavelength 232 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 108: 7-(3-(aminomethyl)-3-fluoropyrrolidin-1-yl)-1-cyclopropyl-6-fluoro-8-(hydroxy methyl) quinolin-2(1H)-one formic acid salt The title compound was prepared in accordance with the following scheme:

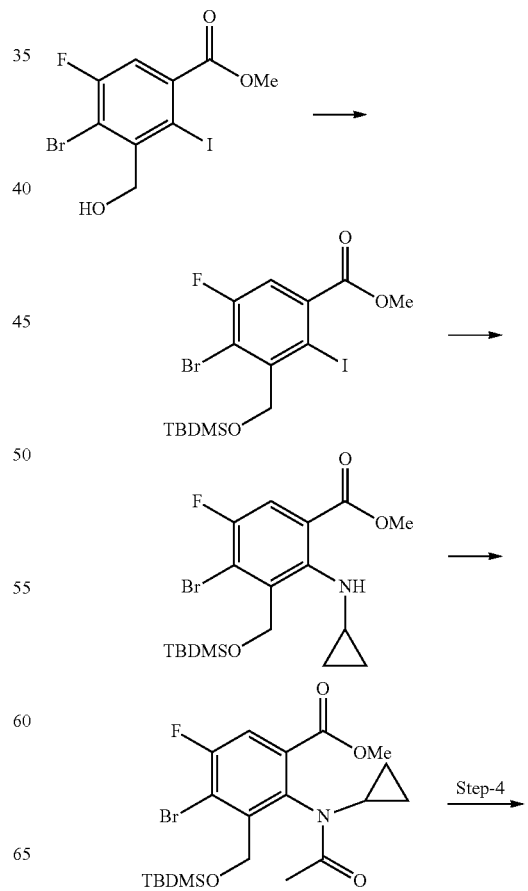

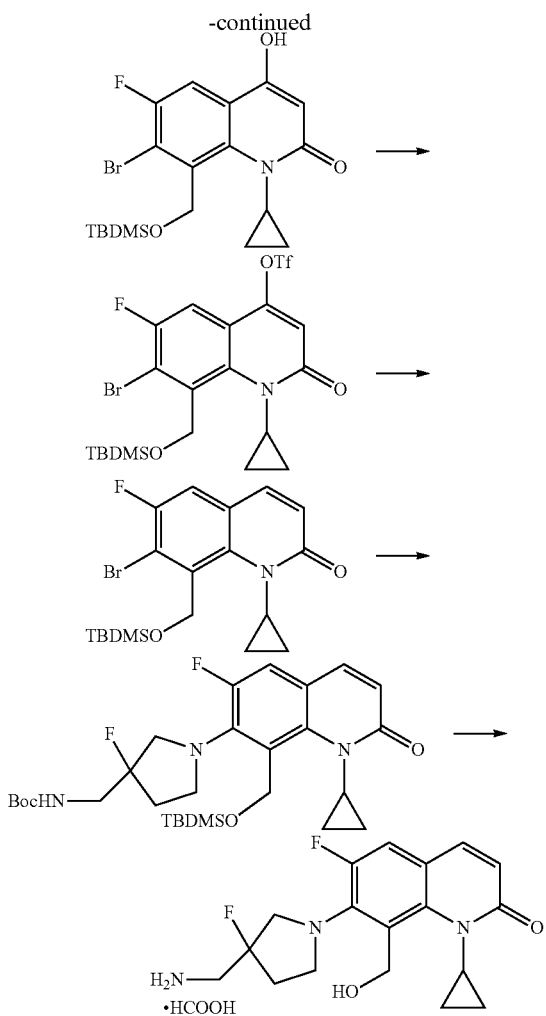

(i) methyl 4-bromo-3-(((tert-butyldimethylsilyl)oxy)methyl)-5-fluoro-2-iodobenzoate 107-iv (2.5 g, 6.42 mmol, 1.0 equiv), Imidazole (0.874 g, 12.8 mmol, 2.0 equiv) were dissolved in DCM (25 mL) and cooled to 0° C. TBDMS-Cl (1.93 g, 12.8 mmol, 2.0 equiv) in DCM (5 mL), DMAP (0.078 g, 0.64 mmol, 0.1 equiv) were added to the reaction mixture at 0° C. and the reaction mixture was stirred at room temperature for 4 hours. The reaction mixture was quenched with ammonium chloride solution and extracted with DCM. Organic layer was washed with water, brine, dried over sodium sulfate and concentrated under vacuum to afford crude residue. The crude residue was purified by silica gel column chromatography (1.5% EtOAc/Hexane) to afford the desired product 108-i (3.0 g, 90% yield).

$^1$H NMR (400 MHz, DMSO) δ 7.63 (d, J=8.5 Hz, 1H), 5.04 (s, 2H), 3.87 (s, 3H), 0.93 (d, J=12.6 Hz, 9H), 0.15 (d, J=11.6 Hz, 6H)

LCMS (m/z): 503.4 [M+H]

(ii) methyl 4-bromo-3-(((tert-butyldimethylsilyl)oxy)methyl)-2-(cyclopropyl amino)-5-fluorobenzoate 108-i (1.5 g, 2.99 mmol, 1.0 equiv), cesium carbonate (1.46 g, 4.4 mmol, 1.5 equiv), Xantphos (0.259 g, 0.44 mmol, 0.15 equiv) were suspended in 1,4-dioxane (15 mL) and the reaction mixture was degassed for 5 minutes. Cyclopropyl amine (0.24 g, 5.9 mmol, 2.0 equiv), Pd$_2$dba$_3$ (0.15 g, 0.16 mmol, 0.05 equiv) were added and the reaction mixture was stirred at 90° C. for 6 hours. The reaction mixture was quenched with water and extracted with EtOAc. The organic layer was washed with brine, dried over sodium sulfate and concentrated to afford a crude residue. The crude residue was purified by silica gel column chromatography (27-30% EtOAc/Hexane) to afford the desired product 108-ii (1.67 g, 63% yield).

$^1$H NMR (400 MHz, CDCl$_3$) δ 7.53 (d, J=9.0 Hz, 1H), 6.97 (s, 1H), 5.05 (s, 2H), 3.88 (s, 3H), 2.97 (dt, J=10.3, 3.3 Hz, 1H), 0.92 (s, 9H), 0.69 (q, J=6.5 Hz, 2H), 0.54-0.46 (m, 2H), 0.14 (s, 6H)

LCMS (m/z): 434.4 [M+H]

(iii) methyl 4-bromo-3-(((tert-butyldimethylsilyloxy)methyl)-2-(N-cyclopropyl acetamido)-5-fluorobenzoate 108-ii (2.67 g, 6.2 mmol, 1.0 equiv) was dissolved in toluene (30 mL). Acetyl chloride (0.708 g, 10.4 mmol, 1.5 equiv) was added at room temperature and the reaction mixture was stirred at 60° C. for 2 hours. The reaction mixture was quenched with water and extracted with EtOAc. The organic layer was washed with saturated NaHCO$_3$ solution, brine, dried over sodium sulfate and concentrated to afford a crude residue. The crude residue was purified by silica gel column chromatography (15% EtOAc/Hexane) to afford the desired product 108-iii (2.92 g, 59% yield).

$^1$H NMR (400 MHz, CDCl$_3$) δ 7.77 (d, J=8.6 Hz, 0.7H), 7.69 (d, J=8.2 Hz, 0.3H), 4.67 (dd, J=22.1, 10.4 Hz, 1.3H), 4.43 (dd, J=10.7, 2.0 Hz, 0.7H), 3.91 (d, J=11.6 Hz, 3H), 3.16-3.09 (m, 0.7H), 3.08-3.02 (m, 0.3H), 2.44 (s, 2H), 1.82 (s, 1H), 0.93 (d, J=3.4 Hz, 9H), 0.91-0.87 (m, 1H), 0.82-0.72 (m, 1H), 0.66-0.59 (m, 1H), 0.52-0.44 (m, 0.5H), 0.42-0.33 (m, 0.5H), 0.18 (dd, J=10.9, 7.5 Hz, 6H)

LCMS (m/z): 474.5 [M+H]

(iv) 7-bromo-8-(((tert-butyldimethylsilyl)oxy)methyl)-1-cyclopropyl-6-fluoro-4-hydroxyquinolin-2(1H)-one 108-iii (1.5 g, 3.1 mmol, 1.0 equiv) was dissolved in THF (20 mL) and cooled to 0° C. NaHMDS (1.0 M in THF) (15.8 mL, 15.8 mmol, 5.0 equiv) was added drop wise and the reaction mixture was stirred at room temperature for 6 hours. The reaction mixture was quenched with ice-water, acidified with dilute HCl and extracted with EtOAc. The organic layer was washed with brine, dried over sodium sulfate and concentrated to afford a crude residue. The crude residue was triturated with n-pentane to afford the desired product 108-iv (0.9 g, 45% yield).

$^1$H NMR (400 MHz, DMSO) δ 11.65 (s, 1H), 7.61 (d, J=8.6 Hz, 1H), 5.35 (s, 2H), 3.47-3.41 (m, 1H), 1.10 (q, J=6.9 Hz, 2H), 0.72 (s, 9H), 0.38 (t, J=8.2 Hz, 2H), −0.21 (d, J=7.7 Hz, 6H)

LCMS (m/z): 442.4 [M+H]

(v) 7-bromo-8-(((tert-butyldimethylsilyl)oxy)methyl)-1-cyclopropyl-6-fluoro-2-oxo-1,2-dihydroquinolin-4-yl trifluoromethanesulfonate 108-iv (0.9 g, 1.9 mmol, 1.0 equiv) was dissolved in DMF (6 mL) and cooled to 0° C. Triethylamine (0.59 g, 5.8 mmol, 3.0 equiv), PhNTF (1.38 g, 3.8 mmol, 2.0 equiv) in DMF (1 mL) were added and the reaction mixture was stirred at room temperature for 5 hours. The reaction mixture was quenched with ice-water and extracted with EtOAc. The organic layer was washed with cold water, brine, dried over sodium sulfate and concentrated to afford a crude residue. The crude residue was purified by silica gel column chromatography (5% EtOAc/Hexane) to afford the desired product 108-v (0.8 g, 71% yield).

$^1$H NMR (400 MHz, CDCl$_3$) δ 7.44 (d, J=8.6 Hz, 1H), 6.73 (s, 1H), 5.41 (s, 2H), 3.78 (ddd, J=11.0, 7.0, 4.1 Hz, 1H), 1.29-1.24 (m, 2H), 0.78 (s, 9H), 0.62 (q, J=6.9 Hz, 2H), −0.14 (s, 6H)

LCMS (m/z): 574.5 [M+H]

(vi) 7-bromo-8-(((tert-butyldimethylsilyloxy) methyl)-1-cyclopropyl-6-fluoro quinolin-2(1H)-one 108-v (0.8 g, 1.04 mmol, 1.0 equiv) was dissolved in DMF (10 mL). Pd(II)OAc (0.04 g, 0.156 mmol, 0.15 equiv), 1,3-Bis(diphenylphosphino)propane (0.2 g, 0.31 mmol, 0.3 equiv) were added and the reaction mixture was cooled to 0° C. Triethylsilane (0.3 g, 1.25 mmol, 1.2 equiv) was added and the reaction mixture was stirred at room temperature for 5 hours. The reaction mixture was quenched with water and extracted with EtOAc. The organic layer was washed with cold water, brine, dried over sodium sulfate and concentrated to afford a crude residue. The crude residue was purified by silica gel column chromatography (20% EtOAc/Hexane) to afford the desired product 108-vi (0.15 g, 25% yield).

$^1$H NMR (400 MHz, CDCl$_3$) δ 7.46 (d, J=9.4 Hz, 1H), 7.18 (d, J=7.5 Hz, 1H), 6.65 (d, J=9.6 Hz, 1H), 5.41 (s, 2H), 3.78-3.73 (m, 1H), 1.24 (d, J=6.0 Hz, 2H), 0.80 (s, 9H), 0.59 (d, J=2.8 Hz, 2H), −0.11-0.21 (s, 6H)

LCMS (m/z): 426.4 [M+H]

(vii) 7-bromo-8-(((tert-butyldimethylsilyl)oxy) methyl)-1-cyclopropyl-6-fluoro quinolin-2(1H)-one 108-vi (0.05 g, 0.117 mmol, 1.0 equiv), tert-butyl ((3-fluoropyrrolidin-3-yl)methyl)carbamate (0.045 g, 0.234 mmol, 2.0 equiv), cesium carbonate (0.057 g, 0.175 mmol, 1.5 equiv) were suspended in 1,4-dioxane (1 mL) and the reaction mixture was degassed for 5 minutes. Pd$_2$dba$_3$ (0.005 g, 0.006 mmol, 0.05 equiv), Xantphos (0.01 g, 0.017 mmol, 0.15 equiv) were added and the reaction mixture was stirred at 120° C. for 48 hours in seal tube. The reaction mixture was quenched with water and extracted with EtOAc. The organic layer was washed with brine, dried over sodium sulfate and concentrated to afford a crude residue. The crude residue was purified by Prep TLC (30% EtOAc/Hexane) to afford the desired product 108-vii (0.026 g, 43% yield).

$^1$H NMR (400 MHz, CDCl$_3$) δ 7.42 (d, J=9.4 Hz, 1H), 7.05 (d, J=11.9 Hz, 1H), 6.52 (d, J=9.4 Hz, 1H), 5.24 (dd, J=37.6, 21.0 Hz, 2H), 4.97 (s, 1H), 3.79-3.40 (m, 7H), 2.24 (s, 2H), 1.49 (s, 9H), 1.25-1.21 (m, 2H), 0.72 (s, 9H), 0.58 (s, 2H), −0.32 (d, J=34.9 Hz, 6H)

(viii) 7-(3-(aminomethyl)-3-fluoropyrrolidin-1-yl)-1-cyclopropyl-6-fluoro-8-(hydroxy methyl)quinolin-2(1H)-one formic acid salt 108-vii (0.026 g, 0.046 mmol, 1.0 equiv) was dissolved in dichloromethane (1 mL) at 0° C. HCl-Dioxane (4 M) (1.0 mL) was added and the reaction mixture was stirred at room temperature for 2 hours. The reaction mixture was concentrated and co-distilled with DCM to afford crude residue. The crude residue was purified by Prep HPLC to afford 108-viii (0.003 g, 16.5% yield).

$^1$H NMR (400 MHz, CD$_3$CN) δ 8.27 (s, 1H), 7.61 (d, J=9.4 Hz, 1H), 7.23 (d, J=12.5 Hz, 1H), 6.44 (d, J=9.3 Hz, 1H), 5.04 (q, J=13.5 Hz, 2H), 3.73 (dd, J=14.7, 8.3 Hz, 2H), 3.58-3.51 (m, 2H), 3.41 (td, J=8.5, 3.6 Hz, 1H), 3.16 (d, J=20.2 Hz, 2H), 2.31-2.18 (m, 2H), 1.18-1.11 (m, 2H), 0.52-0.42 (m, 2H)

LCMS (06_4 min), [MH]$^+$=350.3, RT=1.535 minutes

LCMS Method C_4 MIN

Column: HSS C18 (50*2.1 mm), 1.8 um; ESI source, Positive ion mode; Wavelength 230/362 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 109: 7-(3-(aminomethyl)pyrrolidin-1-yl)-1-cyclopropyl-6-fluoro-8-vinylquinolin-2(1H)-one TFA salt

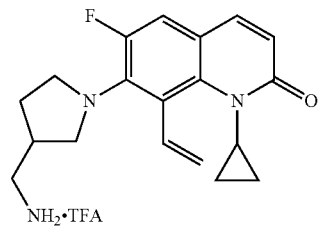

The title compound was prepared in accordance with the following scheme:

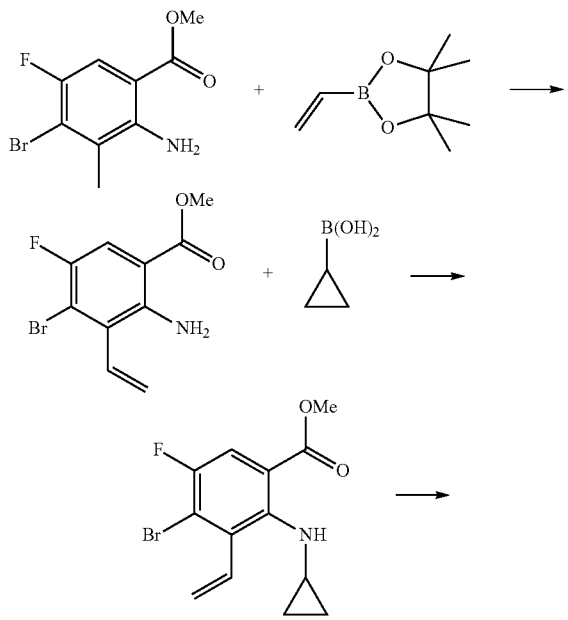

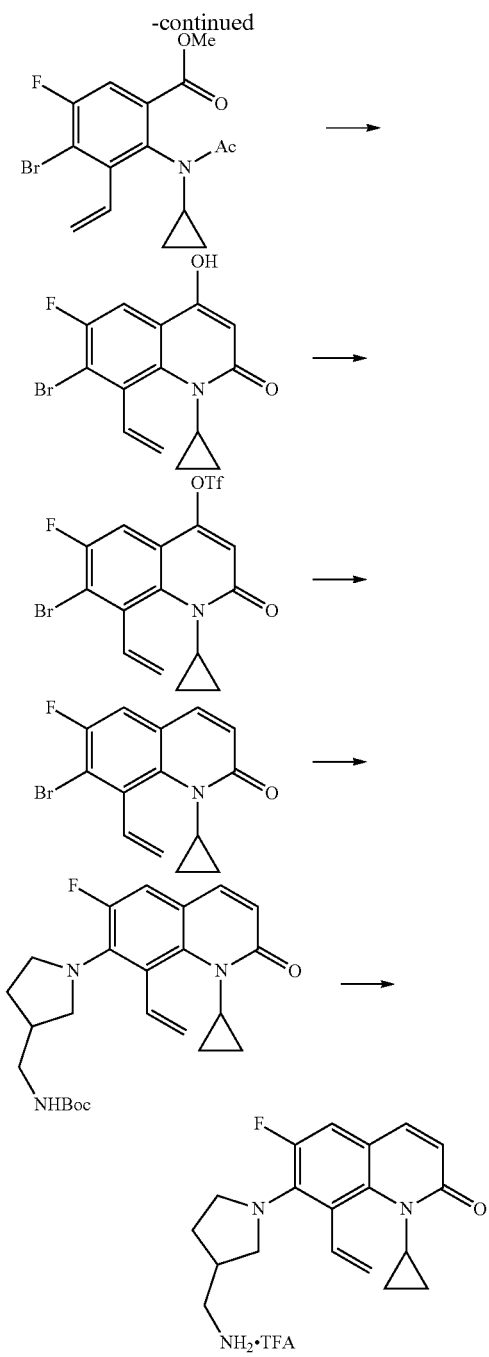

chromatography (0-20% dichloromethane/Hexane) to afford the desired product 109-i (0.42 g, 39.7% yield).

$^1$H NMR (400 MHz, DMSO) δ 7.56 (d, J=9.6 Hz, 1H), 6.67-6.45 (m, 3H), 5.82-5.75 (m, 1H), 5.61 (dd, J=18.0, 1.3 Hz, 1H), 3.82 (s, 3H)

LCMS (m/z): 274.1 [M+H]

(ii) methyl 4-bromo-2-(cyclopropyl amino)-5-fluoro-3-vinylbenzoate 109-i (0.52 g, 1.89 mmol, 1.0 equiv), cyclopropyl boronic acid (0.32 g, 3.79 mmol, 2.0 equiv), 2, 2'-bipyridine (0.58 g, 3.73 mmol, 2.0 equiv), Cu(II)(OAc)$_2$ (0.68 g, 3.74 mmol, 2.0 equiv) and Na$_2$CO$_3$ (1.1 g, 10.2 mmol, 5.4 equiv) were added in dichloromethane (29 mL). Molecular sieves (4°A) (2 g) was added, Oxygen (gas) was purged continuously and the reaction mixture was stirred at room temperature for 4 days. The reaction mixture was filtered through celite bed, the filtrate was quenched with water and extracted with dichloromethane. The organic layer was washed with brine, dried over sodium sulfate and concentrated to afford a crude residue. The crude residue was purified by flash chromatography (0-30% dichloromethane/Hexane) to afford the desired product 109-ii (0.25 g, 41.8% yield).

$^1$H NMR (400 MHz, DMSO) δ 7.57 (d, J=9.3 Hz, 1H), 7.14 (d, J=2.6 Hz, 1H), 6.74 (dd, J=17.9, 11.4 Hz, 1H), 5.65 (dt, J=4.2, 2.1 Hz, 1H), 5.39 (dd, J=17.9, 1.5 Hz, 1H), 3.84-3.79 (m, 3H), 2.67 (dt, J=10.0, 3.2 Hz, 1H), 0.67-0.58 (m, 2H), 0.39-0.30 (m, 2H)

LCMS (m/z): 314.6 [M+H]

(iii) methyl 4-bromo-2-(N-cyclopropyl acetamido)-5-fluoro-3-vinylbenzoate 109-ii (0.21 g, 0.66 mmol, 1.0 equiv) was dissolved in dichloromethane (25 mL) and cooled to 0° C. DIPEA (0.42 mL, 3.3 mmol, 5.0 equiv), acetyl chloride (0.52 g, 6.58 mmol, 10.0 equiv) were added and the reaction mixture was stirred at room temperature for 1 hour. The reaction mixture was quenched with water and extracted with dichloromethane. The organic layer was washed with brine, dried over sodium sulfate and concentrated to afford the desired product 109-iii (0.29 g, crude). The product was used in the next step without further purification.

$^1$H NMR (400 MHz, DMSO) δ 7.72 (d, J=8.8 Hz, 1H), 6.52 (dd, J=17.8, 11.6 Hz, 1H), 5.63 (d, J=11.6 Hz, 1H), 5.40 (d, J=17.9 Hz, 1H), 3.79 (s, 3H), 3.02 (d, J=3.8 Hz, 1H), 2.22 (s, 3H), 0.78-0.67 (m, 3H), 0.50-0.43 (m, 1H)

LCMS (m/z): 356.7 [M+H]

(iv) 7-bromo-1-cyclopropyl-6-fluoro-4-hydroxy-8-vinylquinolin-2(1H)-one 109-iii (0.29 g, 0.81 mmol, 1.0 equiv) was dissolved in THF (25 mL) and cooled to −40° C. NaHMDS (1.0 M in THF) (2.44 mL, 2.44 mmol, 3.0 equiv) was added drop wise and the reaction mixture was stirred at 0° C. for 30 minutes. The reaction mixture was quenched with saturated aqueous ammonium chloride solution and extracted with EtOAc. The organic layer was washed with brine, dried over sodium sulfate and concentrated to afford the desired product 109-iv (0.26 g, crude). The product was used in the next step without further purification.

$^1$H NMR (400 MHz, DMSO) δ 11.69 (s, 1H), 7.61 (d, J=8.7 Hz, 1H), 7.10 (dd, J=17.6, 11.3 Hz, 1H), 5.82 (s, 1H), 5.52 (d, J=11.2 Hz, 1H), 5.04 (d, J=17.7 Hz, 1H), 2.91 (s, 1H), 1.05 (d, J=5.9 Hz, 2H), 0.36 (s, 2H).

LCMS (m/z): 323.9 [M+H]

(i) methyl 2-amino-4-bromo-5-fluoro-3-vinylbenzoate

Methyl 2-amino-4-bromo-5-fluoro-3-iodobenzoate (2 g, 5.34 mmol, 1.0 equiv), 4,4,5,5-tetramethyl-2-vinyl-1,3,2-dioxaborolane (0.99 g, 6.4 mmol, 1.2 equiv), K$_2$CO$_3$ (2.2 g, 16.0 mmol, 3.0 equiv) were added in N,N-dimethylformamide (30 mL) and the reaction mixture was degassed for 5 minutes. PdCl$_2$ (dppf).MDC (0.22 g, 0.26 mmol, 0.05 equiv) was added and the reaction mixture was stirred at 60° C. for 24 hours. The reaction mixture was quenched with water and extracted with EtOAc. The organic layer was washed with brine, dried over sodium sulfate and concentrated to afford a crude residue. The crude residue was purified by flash

(v) 7-bromo-1-cyclopropyl-6-fluoro-2-oxo-8-vinyl-1,2-dihydroquinolin-4-yl trifluoro methane sulfonate 109-iv (0.26 g, 0.8 mmol, 1.0 equiv) was dissolved in N,N-dimethylformamide (22 mL) and cooled to 0° C. TEA (0.24 mL, 2.41 mmol, 3.0 equiv), PhN(SO$_2$CF$_3$)$_2$ (0.35 g, 0.96 mmol, 1.2 equiv) was added and the reaction mixture was stirred at room temperature for 1 hour. The reaction mixture was quenched with cold water and extracted with EtOAc. The organic layer was washed with brine, dried over sodium sulfate and concentrated to afford a crude residue. The crude residue was purified by silica gel column chromatography (0-25% EtOAc/Hexane) to afford the desired product 109-v (0.25 g, crude).

$^1$H NMR (400 MHz, DMSO) δ 7.54 (d, J=8.2 Hz, 1H), 7.13 (dd, J=17.6, 11.3 Hz, 1H), 6.91 (s, 1H), 5.57 (d, J=12.0 Hz, 1H), 5.17 (d, J=17.7 Hz, 1H), 3.04 (s, 1H), 1.14 (d, J=6.4 Hz, 2H), 0.47 (s, 2H)

LCMS (m/z): 456.9 [M+H]

(vi) 7-bromo-1-cyclopropyl-6-fluoro-8-vinylquinolin-2(1H)-one 109-v (0.2 g, 0.44 mmol, 1.0 equiv), Pd(II)OAc (0.015 g, 0.065 mmol, 0.15 equiv) and dppp (0.053 g, 0.12 mmol, 0.3 equiv) were added in N,N-dimethylformamide (16 mL). Et$_3$SiH (0.06 g, 0.52 mmol, 1.2 equiv) was added and the reaction mixture was stirred at 75° C. for 15 minutes under microwave irradiation. The reaction mixture was quenched with cold water and extracted with EtOAc. The organic layer was washed with cold water, brine, dried over sodium sulfate and concentrated to afford a crude residue. The crude residue was purified by silica gel column chromatography (0-30% EtOAc/Hexane) to afford the desired product 109-vi (0.08 g, 59.2% yield).

$^1$H NMR (400 MHz, DMSO) δ 7.80 (d, J=9.5 Hz, 1H), 7.70 (d, J=8.3 Hz, 1H), 7.12 (dd, J=17.6, 11.2 Hz, 1H), 6.61 (d, J=9.4 Hz, 1H), 5.53 (d, J=12.3 Hz, 1H), 5.06 (d, J=18.1 Hz, 1H), 3.00 (s, 1H), 1.14-1.08 (m, 2H), 0.40 (s, 2H)

LCMS (m/z): 308.6 [M+H]

(vii) tert-butyl ((1-(1-cyclopropyl-6-fluoro-2-oxo-8-vinyl-1,2-dihydroquinolin-7-yl) pyrrolidin-3-yl) methyl) carbamate 109-vi (0.06 g, 0.19 mmol, 1.0 equiv) was dissolved in toluene (8 mL), tert-butyl (pyrrolidin-3-ylmethyl) carbamate (0.058 g, 0.29 mmol, 1.5 equiv), NaOtBu (0.055 g, 0.58 mmol, 3.0 equiv) were added and the reaction mixture was degassed for 10 minutes. Pd$_2$(dba)$_3$ (0.009 g, 0.0097 mmol, 0.05 equiv), BINAP (0.018 g, 0.029 mmol, 0.15 equiv) were added and the reaction mixture was stirred at 110° C. for 24 hours. The reaction mixture was quenched with cold water and extracted with EtOAc. The organic layer was washed with brine, dried over sodium sulfate and concentrated to afford a crude residue. The crude residue was purified by preparative TLC purification (60% EtOAc/Hexane) to afford the desired product 109-vii (0.035 g, 42% yield).

$^1$H NMR (400 MHz, MeOD) δ 7.71 (d, J=9.3 Hz, 1H), 7.36 (dd, J=17.7, 11.0 Hz, 1H), 7.27 (d, J=12.6 Hz, 1H), 6.85 (s, 1H), 6.46 (d, J=9.3 Hz, 1H), 5.36 (dd, J=11.0, 1.9 Hz, 1H), 4.81 (dd, J=17.7, 1.8 Hz, 1H), 3.47 (d, J=7.1 Hz, 2H), 3.31-3.20 (m, 3H), 3.16 (t, J=7.4 Hz, 2H), 2.50-2.43 (m, 1H), 2.09 (d, J=6.6 Hz, 1H), 1.74 (d, J=6.7 Hz, 1H), 1.47 (s, 8H), 1.21 (s, 2H), 0.54 (s, 2H).

LCMS (m/z): 428.3 [M+H]

(viii) 7-(3-(aminomethyl)pyrrolidin-1-yl)-1-cyclopropyl-6-fluoro-8-vinylquinolin-2(1H)-one TFA salt 109-vii (0.03 g, 0.7 mmol, 1.0 equiv) was dissolved in dichloromethane (4 mL) and cooled to 0° C. TFA (0.3 mL) was added and the reaction mixture was stirred at room temperature for 30 minutes. The reaction mixture was concentrated, co-distilled with dichloromethane and diethyl ether to afford a crude residue. The crude residue was triturated with n-pentane and diethyl ether, the solvents were decanted to afford the desired product 109-viii (0.013 g, 48% yield).

$^1$H NMR (400 MHz, MeOD) δ 7.73 (d, J=9.3 Hz, 1H), 7.42-7.25 (m, 2H), 6.51 (d, J=9.4 Hz, 1H), 5.39 (dd, J=11.1, 1.8 Hz, 1H), 4.86 (d, J=1.8 Hz, 1H), 3.64-3.56 (m, 1H), 3.54-3.44 (m, 2H), 3.25 (dt, J=9.7, 5.7 Hz, 2H), 3.08 (d, J=6.4 Hz, 2H), 2.61 (dt, J=13.9, 7.0 Hz, 1H), 2.30-2.22 (m, 1H), 1.84-1.75 (m, 1H), 1.28-1.20 (m, 2H), 0.54 (d, J=1.3 Hz, 2H)

LCMS (03_4 min), [MH]$^+$=328.2, RT=1.651 minutes
LCMS Method C_4 MIN
Column: HSS C18 (50*2.1 mm), 1.8 um; ESI source, Positive ion mode; Wavelength 328/364 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes

Example 110: 7-(3-(aminomethyl)pyrrolidin-1-yl)-1-cyclopropyl-6-fluoro-8-methoxyquinolin-2(1H)-one TFA salt

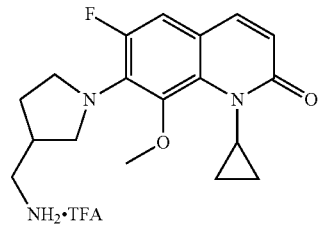

The title compound was prepared in accordance with the following scheme:

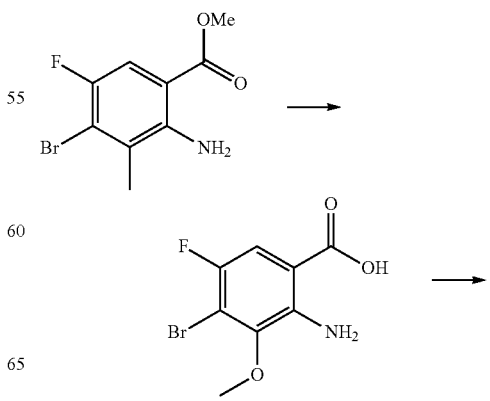

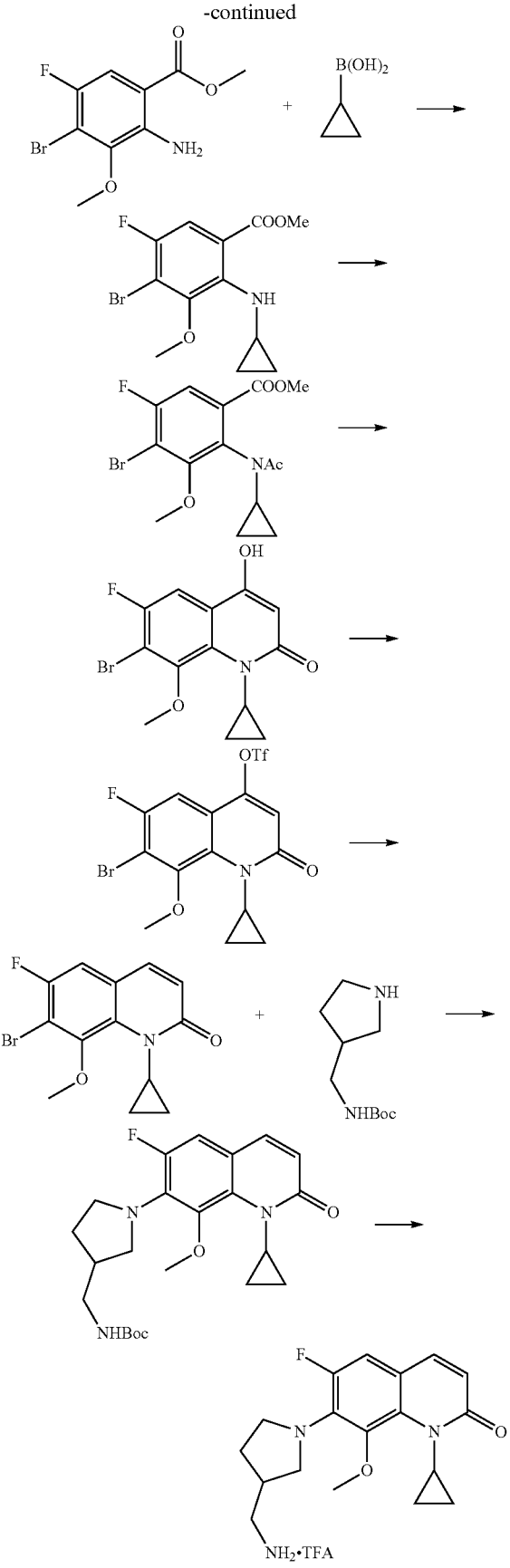

(i) 2-amino-4-bromo-5-fluoro-3-methoxybenzoic acid

Methyl 2-amino-4-bromo-5-fluoro-3-iodobenzoate (1 g, 2.67 mmol, 1.0 equiv), CuI (0.1 g, 0.5 mmol, 0.2 equiv) were added in pyridine: MeOH (1:1, 28 mL). NaOMe (1.44 g, 26.7 mmol, 10 equiv) was added and the reaction mixture was stirred at 110° C. for 1 hour under microwave irradiation. The reaction mixture was quenched with cold water, acidified by 1.0 N HCl aqueous solution to the pH 3-4 and extracted with EtOAc. The organic layer was washed with brine, dried over sodium sulfate and concentrated to afford a crude residue. The crude residue was triturated with n-pentane: diethyl ether (1:1) and the solvents were decanted to afford the desired product 110-i (2 g, crude). LCMS (m/z): 264.1 [M+H].

(ii) methyl 2-amino-4-bromo-5-fluoro-3-methoxybenzoate 110-i (2 g, 7.57 mmol, 1.0 equiv) was added in methanol (20 mL), Conc. $H_2SO_4$ (2 g) was added and the reaction mixture was stirred at 80° C. for 24 hours. The reaction mixture was quenched with water and extracted with EtOAc. The organic layer was washed with brine, dried over sodium sulfate and concentrated to afford a crude residue. The crude residue was purified by flash chromatography (0-50% dichloromethane/Hexane) to afford the desired product 110-ii (1.1 g, 67% yield).
$^1$H NMR (400 MHz, DMSO) δ 7.41 (d, J=9.6 Hz, 1H), 6.56 (s, 2H), 3.90 (s, 3H)
LCMS (m/z): 277.9 [M+H]

(iii) methyl 4-bromo-2-(cyclopropyl amino)-5-fluoro-3-methoxybenzoate 110-ii (1.1 g, 3.96 mmol, 1.0 equiv), cyclopropyl boronic acid (0.67 g, 7.91 mmol, 2.0 equiv), 2, 2'-bipyridine (1.24 g, 7.9 mmol, 2.0 equiv), Cu(II)(OAc) (1.44 g, 7.91 mmol, 2.0 equiv) and $Na_2CO_3$ (1.26 g, 11.9 mmol, 3.0 equiv) were added in dichloromethane (30 mL). The reaction mixture was stirred at room temperature for 24 hours under oxygen atmosphere. The reaction mixture was filtered through celite bed, the filtrate was quenched with water and extracted with dichloromethane. The organic layer was washed with brine, dried over sodium sulfate and concentrated to afford a crude residue. The crude residue was purified by silica gel column chromatography (0-15% dichloromethane/Hexane) to afford the desired product 110-iii (0.65 g, 51.6% yield).
$^1$H NMR (400 MHz, $CDCl_3$) δ 7.46 (d, J=9.4 Hz, 1H), 3.90 (s, 3H), 3.88 (s, 3H)
LCMS (m/z): 318.1 [M+H]

(iv) methyl 4-bromo-2-(N-cyclopropyl acetamido)-5-fluoro-3-methoxy benzoate 110-iii (0.65 g, 2.04 mmol, 1.0 equiv) was dissolved in dichloromethane (25 mL) and cooled to 0° C. DIPEA (1.32 g, 10.2 mmol, 5.0 equiv), acetyl chloride (1.6 g, 20.4 mmol, 10.0 equiv) were added and the reaction mixture was stirred at room temperature for 1 hour. The reaction mixture was quenched with water and extracted with dichloromethane. The organic layer was washed with brine, dried over sodium sulfate and concentrated to afford the desired product 110-iv (0.7 g, crude). The product was used in the next step without further purification.

¹H NMR (400 MHz, CDCl₃) δ 7.50 (d, J=9.0 Hz, 1H), 3.91 (s, 3H), 3.89 (s, 3H), 3.11-3.05 (m, 1H), 0.75 (q, J=6.7 Hz, 2H), 0.61 (d, J=6.9 Hz, 2H)
LCMS (m/z): 360.7 [M+H]

(v) 7-bromo-1-cyclopropyl-6-fluoro-4-hydroxy-8-methoxyquinolin-2(1H)-one 110-iv (0.7 g, 1.94 mmol, 1.0 equiv) was dissolved in THF (10 mL) and cooled to −30° C. NaHMDS (1.0 M in THF) (5.83 mL, 5.83 mmol, 3.0 equiv) was added drop wise and the reaction mixture was stirred at 0° C. for 15 minutes. The reaction mixture was quenched with saturated aqueous ammonium chloride solution, acidified by 1.0 N HCl aqueous solution to the pH 2 to 3 and extracted with EtOAc. The organic layer was washed with brine, dried over sodium sulfate and concentrated to afford the desired product 110-v (0.5 g, crude). The product was used in the next step without further purification.
¹H NMR (400 MHz, CDCl₃) δ 7.54 (d, J=9.0 Hz, 1H), 3.91 (s, 3H), 3.89 (s, 3H), 3.11-3.05 (m, 1H), 2.43 (s, 3H), 0.64-1.0 (m, 4H)
LCMS (m/z): 328.6 [M+H]

(vi) 7-bromo-1-cyclopropyl-6-fluoro-8-methoxy-2-oxo-1,2-dihydroquinolin-4-yl trifluoro methane sulfonate 110-v (0.5 g, 1.52 mmol, 1.0 equiv) was dissolved in N,N-dimethylformamide (15 mL) and cooled to 0° C. TEA (0.46 mL, 4.57 mmol, 3.0 equiv), PhN(SO₂CF₃)₂ (0.65 g, 1.83 mmol, 1.2 equiv) were added and the reaction mixture was stirred at room temperature for 1.5 hours. The reaction mixture was quenched with cold water and extracted with EtOAc. The organic layer was washed with cold water, brine, dried over sodium sulfate and concentrated to afford a crude residue. The crude residue was purified by silica gel column chromatography (0-20% EtOAc/Hexane) to afford the desired product 110-vi (0.26 g, 37.1%).
¹H NMR (400 MHz, DMSO) δ 11.70 (s, 1H), 7.48 (d, J=8.7 Hz, 1H), 5.81 (s, 1H), 3.69 (s, 3H), 3.24 (s, 1H), 1.02 (d, J=6.1 Hz, 2H), 0.44 (s, 2H)
LCMS (m/z): 460.1 [M+H]

(vii) 7-bromo-1-cyclopropyl-6-fluoro-8-methoxyquinolin-2(1H)-one 110-vi (0.26 g, 0.55 mmol, 1.0 equiv), Pd(II)OAc (0.018 g, 0.083 mmol, 0.15 equiv) and dppp (0.069 g, 0.17 mmol, 0.3 equiv) were added in N,N-dimethylformamide (5 mL). Et₃SiH (0.07 g, 0.67 mmol, 1.2 equiv) was added and the reaction mixture was stirred at 100° C. for 20 minutes. The reaction mixture was quenched with cold water and extracted with EtOAc. The organic layer was washed with brine, dried over sodium sulfate and concentrated to afford a crude residue. The crude residue was purified by flash chromatography (20-100% EtOAc/Hexane) to afford the desired product 110-vii (0.12 g, 67% yield).
¹H NMR (400 MHz, CDCl₃) δ 7.31 (d, J=7.7 Hz, 1H), 6.73 (s, 1H), 3.40 (td, J=7.0, 3.6 Hz, 1H), 1.32-1.27 (m, 2H), 0.67-0.63 (m, 2H)
LCMS (m/z): 313.9 [M+H]

(viii) tert-butyl ((1-(1-cyclopropyl-6-fluoro-8-methoxy-2-oxo-1,2-dihydroquinolin-7-yl) pyrrolidin-3-yl) methyl) carbamate 110-vii (0.08 g, 0.26 mmol, 1.0 equiv), tert-butyl (pyrrolidin-3-ylmethyl) carbamate (0.1 g, 0.51 mmol, 2.0 equiv), Cs₂CO₃ (0.17 g, 0.52 mmol, 2.0 equiv) were added in sealed tube and the reaction mixture was degassed for 10 minutes. Pd₂(dba)₃ (0.011 g, 0.012 mmol, 0.05 equiv), xantphos (0.022 g, 0.038 mmol, 0.15 equiv) were added and the reaction mixture was stirred at 110° C. for 24 hours. The reaction mixture was quenched with cold water and extracted with EtOAc. The organic layer was washed with brine, dried over sodium sulfate and concentrated to afford a crude residue. The crude residue was purified by preparative TLC purification (60% EtOAc/Hexane, two times run) to afford the desired product 110-viii (0.04 g, 36.2% yield).
¹H NMR (400 MHz, MeOD) δ 7.65 (d, J=9.3 Hz, 1H), 7.09 (d, J=13.2 Hz, 1H), 6.38 (d, J=9.1 Hz, 1H), 3.68 (s, 3H), 3.53 (s, 3H), 3.42 (s, 2H), 3.19 (d, J=6.1 Hz, 2H), 2.46 (d, J=6.7 Hz, 1H), 2.11 (d, J=6.3 Hz, 1H), 1.75 (s, 1H), 1.16 (d, J=13.8 Hz, 2H), 0.56 (d, J=3.4 Hz, 2H)

(ix) 7-(3-(aminomethyl)pyrrolidin-1-yl)-1-cyclopropyl-6-fluoro-8-methoxyquinolin-2(1H)-one TFA salt 110-viii (0.04 g, 0.093 mmol, 1.0 equiv) was dissolved in dichloromethane (2 mL) and cooled to 0° C. TFA (0.4 mL) was added and the reaction mixture was stirred at room temperature for 1 hour. The reaction mixture was concentrated, co-distilled with diethyl ether to afford a crude residue. The crude residue was triturated with diethyl ether, the solvents were decanted to afford the desired product 110-ix (0.013 g, 32.7% yield).
¹H NMR (400 MHz, MeOD) δ 7.67 (d, J=9.3 Hz, 1H), 7.13 (d, J=13.1 Hz, 1H), 6.42 (d, J=9.3 Hz, 1H), 3.79 (dd, J=16.6, 8.3 Hz, 2H), 3.68 (dd, J=7.2, 3.1 Hz, 1H), 3.56 (s, 3H), 3.54-3.50 (m, 1H), 3.43 (ddd, J=11.1, 7.0, 4.1 Hz, 1H), 3.13 (dd, J=7.2, 3.2 Hz, 2H), 2.61 (dt, J=14.6, 7.3 Hz, 1H), 2.31-2.23 (m, 1H), 1.87-1.77 (m, 1H), 1.24-1.10 (m, 2H), 0.62-0.53 (m, 2H)
LCMS (02_4 min), [MH]⁺=332.2, RT=1.627 minutes
LCMS Method C_4 MIN
Column: HSS C18 (50*2.1 mm), 1.8 um; ESI source, Positive ion mode; Wavelength 230/366 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 111: 8-(aminomethyl)-7-(3-(aminomethyl)-3-fluoropyrrolidin-1-yl)-1-cyclopropyl-6-fluoroquinolin-2(1H)-one HCl salt

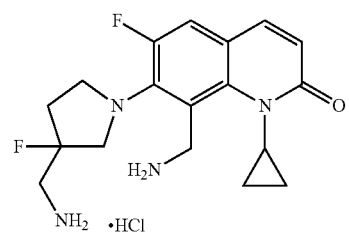 [SMILES: NCc1c(N2CCC(F)(CN)C2)c(F)cc2ccc(=O)n(C3CC3)c12 ; Cl]

The title compound was prepared in accordance with the following scheme:

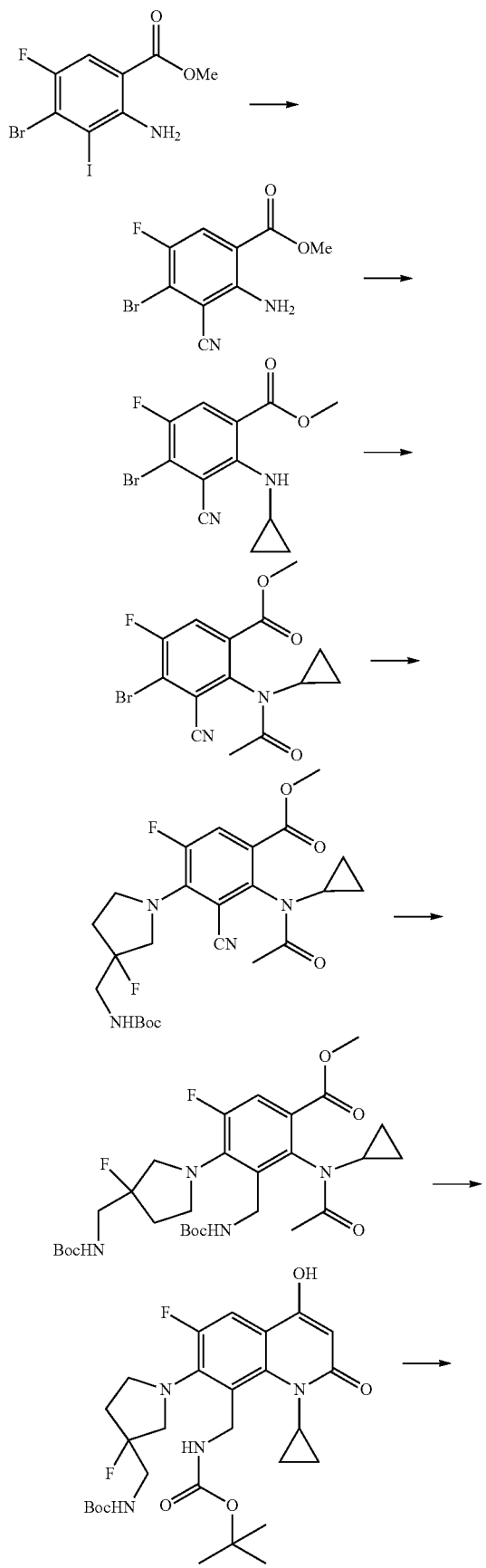

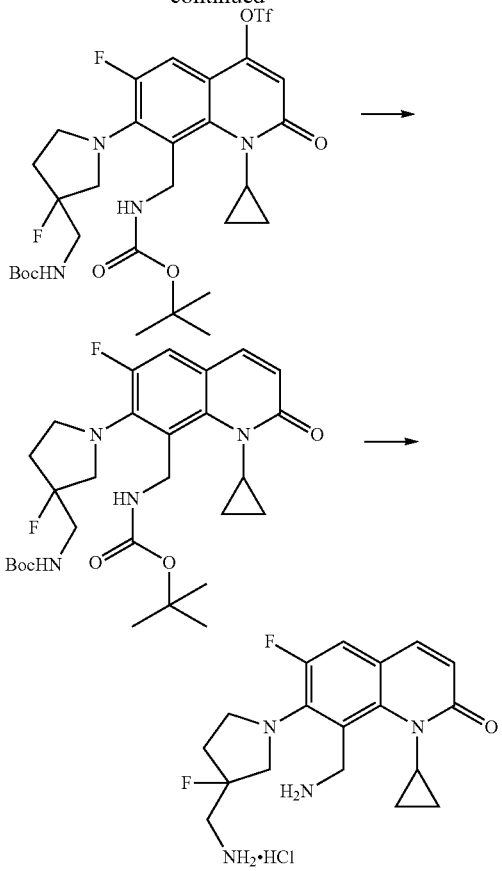

(i) methyl 2-amino-4-bromo-3-cyano-5-fluorobenzoate

Methyl 2-amino-4-bromo-5-fluoro-3-iodobenzoate (5 g, 13.4 mmol, 1.0 equiv) was dissolved in DMSO (50 mL) in sealed tube, Cu(II)CN (2.4 g, 26.7 mmol, 2.0 equiv) was added and the reaction mixture was stirred at 90° C. for overnight. The reaction mixture was diluted with cold water, filtered through celite bed and extracted with EtOAc. The organic layer was washed with brine, dried over sodium sulfate and concentrated to afford a crude residue. The crude residue was purified by 60-120 mesh silica gel column chromatography (2.5% EtOAc/Hexane) to afford the desired product 111-i (2.8 g, 77% yield).

$^1$H NMR (400 MHz, DMSO) δ 7.92 (d, J=9.3 Hz, 1H), 7.25 (s, 2H), 3.85 (d, J=3.0 Hz, 3H), 1.23 (s, 2H), 0.84 (ddd, J=11.2, 6.1, 4.2 Hz, 2H)

LCMS (m/z): 273.1 [M+H]

(ii) methyl 4-bromo-3-cyano-2-(cyclopropyl amino)-5-fluorobenzoate 111-i (2.8 g, 10.2 mmol, 1.0 equiv), cyclopropyl boronic acid (1.8 g, 20.4 mmol, 2.0 equiv), 2, 2'-bipyridine (3.2 g, 20.4 mmol, 2.0 equiv), Cu(II)(OAc) (3.7 g, 20.4 mmol, 2.0 equiv) and Na$_2$CO$_3$ (3.2 g, 30.7 mmol, 3.0 equiv) were added in dichloromethane (60 mL). Oxygen (gas) was purged continuously and the reaction mixture was stirred at room temperature for 3 days. The reaction mixture was filtered through celite bed, washed the bed with dichloromethane and the filtrate was concentrated to afford a crude residue. The crude residue was purified by 100-200 mesh silica gel column chromatography (1-3% EtOAc/Hexane) to afford the desired product 111-ii (0.5 g, 15.6% yield). 1.5 g of starting material was recovered.

$^1$H NMR (400 MHz, DMSO) δ 8.36 (s, 1H), 7.98 (d, J=9.1 Hz, 1H), 3.83 (d, J=3.9 Hz, 3H), 3.06 (dd, J=6.4, 3.5 Hz, 1H), 0.92-0.86 (m, 2H), 0.71-0.66 (m, 2H)

LCMS (m/z): 313.1 [M+H]

(iii) methyl 4-bromo-3-cyano-2-(N-cyclopropyl acetamido)-5-fluorobenzoate 111-ii (0.9 g, 2.9 mmol, 1.0 equiv) was dissolved in toluene (15 mL), acetyl chloride (0.34 g, 4.3 mmol, 1.5 equiv) was added and the reaction mixture was stirred at 110° C. for 5 hours. The reaction mixture was quenched with water and extracted with EtOAc. The organic layer was washed with NaHCO$_3$, dried over sodium sulfate and concentrated to afford the desired product 111-iii (0.9 g, 87.5% yield).

$^1$H NMR (400 MHz, DMSO) δ 8.15 (d, J=8.7 Hz, 1H), 3.85 (d, J=4.1 Hz, 3H), 3.22 (dt, J=10.7, 3.6 Hz, 1H), 2.34 (d, J=4.0 Hz, 3H), 0.98-0.64 (m, 4H)

LCMS (m/z): 355.2 [M+H]

(iv) methyl 4-(3-(((tert-butoxycarbonyl) amino) methyl)-3-fluoro pyrrolidin-1-yl)-3-cyano-2-(N-cyclopropyl acetamido)-5-fluorobenzoate 111-iii (0.45 g, 1.3 mmol, 1.0 equiv) was added in toluene (6 mL) in sealed tube, Cs$_2$CO$_3$ (0.61 g, 1.9 mmol, 1.5 equiv), tert-butyl ((3-fluoropyrrolidin-3-yl) methyl) carbamate (0.41 g, 1.9 mmol, 1.5 equiv) and the reaction mixture was degassed for 15 minutes. Pd$_2$(dba)$_3$ (0.06 g, 0.06 mmol, 0.05 equiv), xantphos (0.072 g, 0.13 mmol, 0.1 equiv) were added and the reaction mixture was stirred at 110° C. for 6 hours. The reaction mixture was quenched with cold water and extracted with EtOAc. The organic layer was washed with brine, dried over sodium sulfate and concentrated to afford a crude residue. The crude residue was purified by flash chromatography (50-60% EtOAc/Hexane) to afford the desired product 111-iv (0.2 g, 32.5% yield). LCMS (m/z): 493.5 [M+H].

(v) methyl 3-(((tert-butoxy carbonyl)amino)methyl)-4-(3-(((tert-butoxy carbonyl) amino) methyl)-3-fluoropyrrolidin-1-yl)-2-(N-cyclopropyl acetamido)-5-fluorobenzoate 111-iv (0.18 g, 0.37 mmol, 1.0 equiv) was added in methanol (5 mL) and cooled to 0° C. NiCl$_2$.6H$_2$O (0.17 g, 0.73 mmol, 2.0 equiv), (Boc)$_2$O (0.16 g, 0.73 mmol, 2.0 equiv) were added. NaBH$_4$ (0.07 g, 1.8 mmol, 5.0 equiv) was added portion wise at 0-5° C. and the reaction mixture was stirred at RT for 2 days. The reaction mixture was filtered through celite bed, the filtrate was concentrated, quenched with cold water and extracted with EtOAc. The organic layer was washed with brine, dried over sodium sulfate and concentrated to afford the desired product 111-v (0.19 g, 87.2% yield).

$^1$H NMR (400 MHz, DMSO) δ 7.58 (d, J=12.6 Hz, 1H), 7.20 (s, 1H), 6.36 (s, 1H), 4.35-4.14 (m, 2H), 4.00 (d, J=7.7 Hz, 1H), 3.78 (d, J=2.3 Hz, 3H), 3.53-3.37 (m, 4H), 3.25 (s, 1H), 3.12 (s, 1H), 2.28 (d, J=20.8 Hz, 3H), 1.38 (d, J=10.1 Hz, 17H), 0.83-0.56 (m, 4H)

LCMS (m/z): 597.6 [M+H]

(vi) tert-butyl ((1-(8-(((tert-butoxycarbonyl) amino) methyl)-1-cyclopropyl-6-fluoro-4-hydroxy-2-oxo-1, 2-dihydroquinolin-7-yl)-3-fluoropyrrolidin-3-yl) methyl) carbamate 111-v (0.05 g, 0.083 mmol, 1.0 equiv) was dissolved in dry THF (1.0 mL) and the reaction mixture was cooled at −40° C. NaHMDS (1.0 M in THF) (0.17 mL, 0.17 mmol, 2.0 equiv) was added at −40° C. and the reaction mixture was allowed to stir at 0 to 5° C. for 1 hour. The reaction mixture was acidified using 1N HCl to the pH 4 to 5 and extracted with EtOAc. The organic layer was washed with brine, dried over sodium sulfate and concentrated to afford a crude residue. The crude residue was triturated with n-pentane and the solvent were decanted to afford the desired product 111-vi (0.03 g, 63.8% yield). The crude product was used in next step without further purification.

$^1$H NMR (400 MHz, DMSO) δ 11.26 (s, 1H), 7.34 (d, J=12.9 Hz, 1H), 7.23 (s, 1H), 6.70 (s, 1H), 4.66 (d, J=43.5 Hz, 2H), 3.62 (d, J=18.8 Hz, 2H), 3.49-3.36 (m, 4H), 3.31-3.26 (m, 1H), 2.26-2.08 (m, 2H), 1.46-1.23 (m, 17H), 1.03 (d, J=20.4 Hz, 2H), 0.33 (d, J=4.3 Hz, 2H)

LCMS (m/z): 565.5 [M+H]

(vii) 8-(((tert-butoxycarbonyl)amino) methyl)-7-(3-(((tert-butoxycarbonyl)amino) methyl)-3-fluoropyrrolidin-1-yl)-1-cyclopropyl-6-fluoro-2-oxo-1,2-dihydroquinolin-4-yltrifluoromethanesulfonate 111-vi (0.03 g, 0.05 mmol, 1.0 equiv) was dissolved in dry N,N-dimethylformamide (0.5 mL), TEA (0.016 g, 0.16 mmol, 3.0 equiv) was added and cooled to 0-5° C. PhN(SO$_2$CF$_3$)$_2$(0.021 g, 0.06 mmol, 1.1 equiv) added and the reaction mixture was stirred at room temperature for 1 hour. The reaction mixture was quenched with water and extracted with EtOAc. The organic layer was washed with brine, dried over sodium sulfate and concentrated to afford the desired product 111-vii (0.04 g, quantitative). The crude product was used in next step without further purification. LCMS (m/z): 697.6 [M+H].

(viii) tert-butyl ((1-(8-(((tert-butoxy carbonyl) amino) methyl)-1-cyclopropyl-6-fluoro-2-oxo-1,2-dihydroquinolin-7-yl)-3-fluoropyrrolidin-3-yl) methyl) carbamate 111-vii (0.04 g, 0.06 mmol, 1.0 equiv) was dissolved in dry N,N-dimethylformamide (0.5 mL) and the reaction mixture was cooled at 0 to 5° C. 1, 3 DPPP (0.007 g, 0.02 mmol, 0.3 equiv), Pd(II)OAc (0.002 g, 0.0009 mmol, 0.15 equiv), TES (0.01 g, 0.07 mmol, 1.2 equiv) was added at 0 to 5° C. and the reaction mixture was allowed to stir at 0 to 5° C. for 2 hours. The reaction mixture was quenched with cold water and extracted with EtOAc. The organic layer was washed with brine, dried over sodium sulfate and concentrated to afford a crude residue. The crude residue was purified by preparative HPLC purification to afford the desired product 111-viii (0.015 g, 52% yield). LCMS (m/z): 549.6 [M+H].

(ix) 8-(aminomethyl)-7-(3-(aminomethyl)-3-fluoropyrrolidin-1-yl)-1-cyclopropyl-6-fluoroquinolin-2 (1H)-one HCl salt 111-viii (0.015 g, 0.027 mmol, 1.0 equiv) was dissolved in dichloromethane (1 mL) and cooled to 0-5° C. HCl (in 1,4-dioxane) (0.5 mL) was added and the reaction mixture was stirred at RT for 1 hour. The reaction mixture was concentrated and co-distilled with dichloromethane to afford a crude residue. The crude residue was triturated with diethyl ether, n-pentane and the solvent was decanted to afford the desired product 111-ix (0.08 g, 84.2% yield).

$^1$H NMR (400 MHz, MeOD) δ 7.78 (d, J=9.4 Hz, 1H), 7.54 (d, J=12.1 Hz, 1H), 6.61 (d, J=9.4 Hz, 1H), 4.93 (q, J=14.8 Hz, 2H), 3.79 (ddd, J=30.5, 18.7, 7.7 Hz, 3H), 3.64-3.52 (m, 4H), 2.52-2.38 (m, 2H), 1.35-1.30 (m, 2H), 0.57 (s, 2H)

LCMS (06_4 min), [MH]$^+$=349.3, RT=1.355 minutes
LCMS Method C_4 MIN
Column: HSS C18 (50*2.1 mm), 1.8 um; ESI source, Positive ion mode; Wavelength 348 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 112: 7-(3-(aminomethyl)-3-fluoropyrrolidin-1-yl)-1-cyclopropyl-8-ethoxy-6-fluoroquinolin-2(1H)-one TFA salt

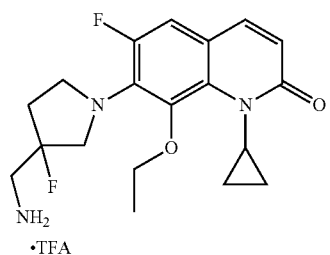 [SMILES: CCOc1c(N2CCC(F)(CN)C2)c(F)cc2ccc(=O)n(C3CC3)c12]

The title compound was prepared in accordance with the following scheme:

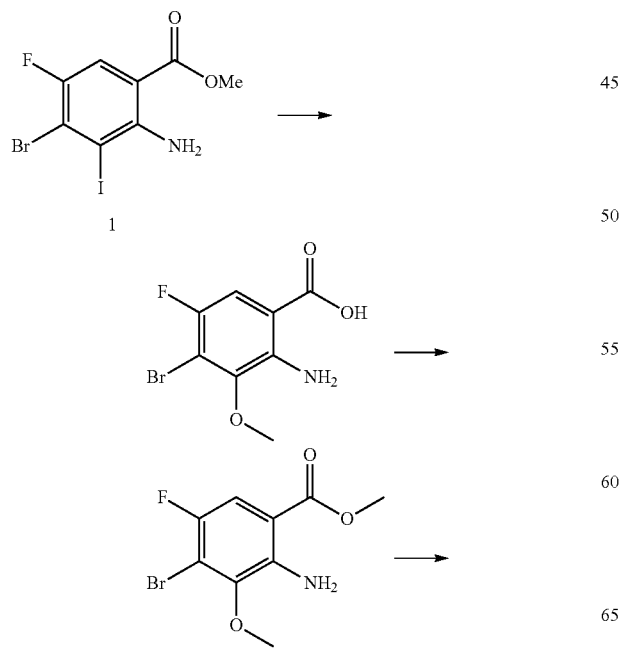

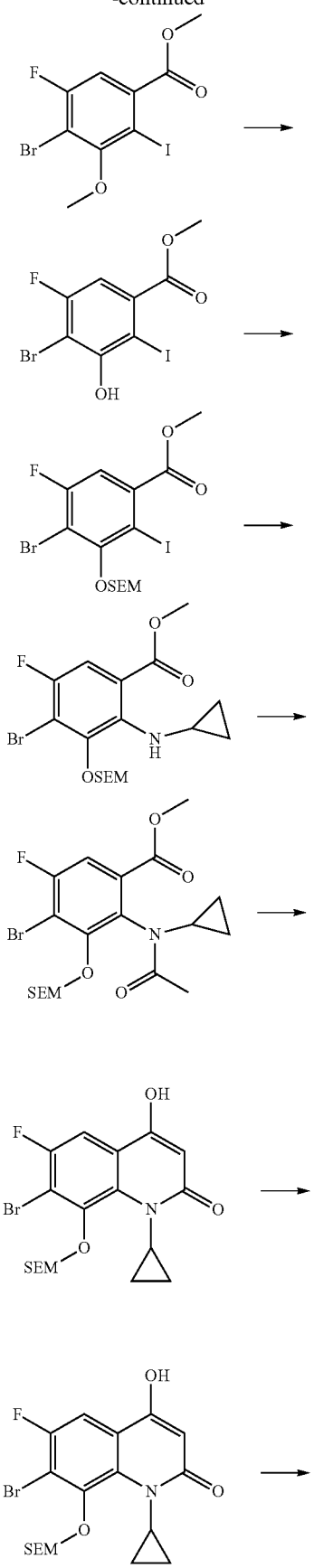

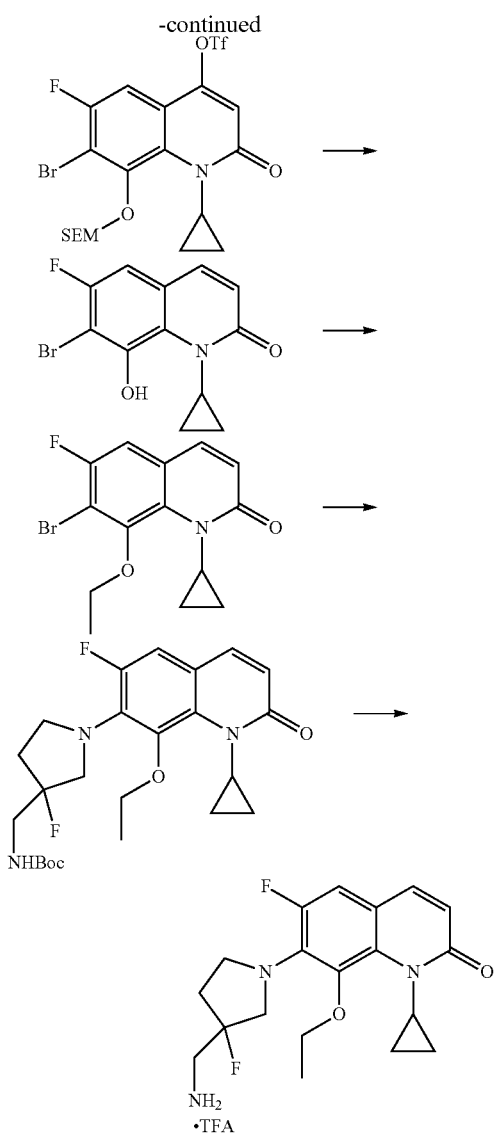

(i) 2-amino-4-bromo-5-fluoro-3-methoxybenzoic acid

Methyl 2-amino-4-bromo-5-fluoro-3-iodobenzoate (1 g, 2.652 mmol, 1.0 equiv) was dissolved in dry Methanol (15 mL) in 30 (mL) microwave vial. CuI (0.1 g, 0.53 mmol, 0.2 equiv) were added and the reaction mixture was stirred at RT for 5 minutes. NaOMe (1.432 g, 26.52 mmol, 10 equiv) was added and the reaction mixture was became light yellow-green. Dry pyridine (2 mL) was added and the reaction mixture was stirred at 110° C. for 1 hour under microwave irradiation. The reaction mixture was quenched with cold water, acidified by 1.0 N HCl aqueous solution to the pH 2 to 3 and extracted with EtOAc. The organic layer was washed with brine, dried over sodium sulfate and concentrated to afford a crude residue. The crude residue was triturated with n-pentane: diethyl ether (1:1) and the solvents were decanted to afford the desired product 112-i (6 g, without purification). The crude product was used in next step without further purification. LCMS (m/z): 264.2 [M−H].

(ii) methyl 2-amino-4-bromo-5-fluoro-3-methoxybenzoate 112-i (6 g, 22.72 mmol, 1.0 equiv) was added in methanol (120 mL), Conc. $H_2SO_4$ (12 mL) was added and the reaction mixture was stirred at 80-85° C. for 24 hours. The reaction mixture was quenched with ice-water and extracted with dichloromethane. The organic layer was washed with brine, dried over sodium sulfate and concentrated to afford a crude residue. The crude residue was purified by column chromatography (0-20% EtOAc/Hexane) to afford the desired product 112-ii (4.5 g, 71.2% yield).
$^1$H NMR (400 MHz, DMSO) δ 7.41 (d, J=9.7 Hz, 1H), 6.69 (s, 2H), 3.82 (s, 3H), 3.75 (s, 3H)
LCMS (m/z): 279.9 [M+H]

(iii) methyl 4-bromo-5-fluoro-2-iodo-3-methoxybenzoate 112-ii (4.5 g, 16.18 mmol, 1.0 equiv) was dissolved in acetonitrile (27 mL), 6M HCl (58.5 mL) was added and the reaction mixture was stirred at room temperature for 10 minutes. The reaction mixture was cooled to 0° C. and $NaNO_2$ (1.17 g, 16.99 mmol, 1.05 equiv) in water (18 mL) was added and the reaction mixture was stirred at 0° C. for 1 hour. KI (5.37 g, 32.37 mmol, 2.0 equiv) in water (36 mL) was added drop wise and the reaction mixture was stirred at 0° C. for 20-30 minutes. The reaction mixture was quenched with cold water and extracted with EtOAc. The organic layer was washed with saturated aqueous sodium thiosulfate solution, dried over sodium sulfate and concentrated to afford a crude residue. The crude residue was purified by silica gel column chromatography (10% EtOAc/Hexane) to afford the desired product 112-iii (1.8 g, 28.6% yield).
$^1$H NMR (400 MHz, DMSO) δ 7.55 (d, J=8.5 Hz, 1H), 3.87 (s, 3H), 3.83 (s, 3H)

(iv) methyl 4-bromo-5-fluoro-3-hydroxy-2-iodobenzoate 112-iii (1.8 g, 4.6 mmol, 1.0 equiv) was dissolved in dichloromethane (20 mL) and cooled to −78° C. $BBr_3$ (1M) (37 mL, 36.8 mmol, 8.0 equiv) was added and the reaction mixture was stirred at room temperature for 18 hours. The reaction mixture was quenched with ice-water and extracted with EtOAc. The organic layer was washed with brine, dried over sodium sulfate and concentrated to afford the crude residue. The crude residue was purified by silica gel column chromatography (0-10% EtOAc/Hexane) to afford the desired product 112-iv (0.851 g, 49% yield).
1H NMR (400 MHz, DMSO) δ 10.91-10.54 (m, 1H), 7.19 (d, J=8.6 Hz, 1H), 3.84 (s, 3H)
LCMS (m/z): 375.1 [M−H]

(v) methyl 4-bromo-5-fluoro-2-iodo-3-((2-(trimethylsilyl)ethoxy)methoxy) benzoate 112-iv (0.8 g, 2.1 mmol, 1.0 equiv) was dissolved in Acetonitrile (6 mL). $K_2CO_3$ (0.73 g, 5.3 mmol, 2.5 equiv) and SEM-Cl (0.42 g, 2.5 mmol, 1.2 equiv) were added and the reaction mixture was stirred at 100° C. for 1 hour. The reaction mixture was filtered, washed with EtOAc, and concentrated to afford the crude desired product 112-v (0.9 g, without purification). The crude product was used in the next step without further purification.

¹H NMR (400 MHz, CDCl₃) δ 7.37 (d, J=8.6 Hz, 1H), 5.30 (s, 2H), 4.11-4.01 (m, 2H), 3.96 (s, 3H), 1.11-1.00 (m, 2H), 0.08-0.04 (s, 9H)

(vi) methyl 4-bromo-2-(cyclopropylamino)-5-fluoro-3-((2-(trimethylsilyl)ethoxy)methoxy)benzoate 112-v (0.9 g, 1.7 mmol, 1.0 equiv), Cs₂CO₃ (0.86 g, 2.65 mmol, 1.5 equiv), xantphos (0.15 g, 0.265 mmol, 0.15 equiv) were added in 1,4-Dioxane (28 mL) at RT. Pd₂dba₃ (0.08 g, 0.085 mmol, 0.05 equiv), cyclopropyl amine (0.203 g, 3.5 mmol, 2.0 equiv) were added and the reaction mixture was stirred at 110° C. for 7-8 hours in seal tube. The reaction mixture was quenched with water and extracted with EtOAc. The organic layer was washed with brine, dried over sodium sulfate and concentrated to afford the crude residue. The crude residue was purified by silica gel column chromatography (0-1% EtOAc/Hexane) to afford the desired product 112-vi (0.303 g, 45% yield).

¹H NMR (400 MHz, DMSO) δ 7.43 (d, J=9.2 Hz, 1H), 6.68 (d, J=4.0 Hz, 1H), 5.13 (s, 2H), 3.87 (dd, J=10.7, 6.2 Hz, 2H), 3.81 (s, 3H), 2.89-2.83 (m, 1H), 0.96-0.84 (m, 2H), 0.62 (td, J=6.7, 4.9 Hz, 2H), 0.40-0.33 (m, 2H), 0.02-0.01 (s, 9H)

LCMS (m/z): 436.4 [M+H]

(vii) methyl 4-bromo-2-(N-cyclopropylacetamido)-5-fluoro-3-((2-(trimethylsilyl) ethoxy)methoxy)benzoate 112-vi (0.3 g, 0.6912 mmol, 1.0 equiv) was dissolved in dichloromethane (10 mL) and cooled to 0° C. DIPEA (0.44 g, 3.456 mmol, 5.0 equiv), acetyl chloride (0.27 g, 3.456 mmol, 5.0 equiv) were added and the reaction mixture was stirred at room temperature for 3-4 hours. The reaction mixture was quenched with water and extracted with dichloromethane. The organic layer was washed with brine, dried over sodium sulfate and concentrated to afford the crude residue. The crude residue was purified by silica gel column chromatography (20-30% EtOAc/Hexane) to afford the desired product 112-vii (0.301 g, 91% yield).

¹H NMR (400 MHz, CDCl₃) δ 7.55 (d, J=8.6 Hz, 1H), 5.10 (d, J=5.0 Hz, 1H), 5.02 (d, J=5.0 Hz, 1H), 3.90 (d, J=1.9 Hz, 2H), 3.85 (s, 3H), 3.22-3.19 (m, 1H), 2.41 (s, 3H), 1.28 (d, J=2.8 Hz, 2H), 1.03 (d, J=3.3 Hz, 2H), 0.84-0.81 (m, 1H), 0.68-0.64 (m, 1H), 0.06 (s, 9H)

LCMS (m/z): 346.2 [M-SEM]

(viii) 7-bromo-1-cyclopropyl-6-fluoro-4-hydroxy-8-((2-(trimethylsilyl)ethoxy) methoxy)quinolin-2(1H)-one 112-vii (0.3 g, 0.6302 mmol, 1.0 equiv) was dissolved in THF (10 mL) and cooled to −78° C. NaHMDS (1.0 M in THF) (1.9 mL, 1.9 mmol, 3.0 equiv) was added drop wise and the reaction mixture was stirred at −78° C. for 1 hours. The reaction mixture was quenched with ice-water, acidified by 1.0 N HCl aqueous solution to the pH 2 to 3 and extracted with EtOAc. The organic layer was washed with brine, dried over sodium sulfate and concentrated to afford the desired product 112-viii (0.161 g, crude). The crude product was used in the next step without further purification.

¹H NMR (400 MHz, DMSO) δ 11.69 (s, 1H), 7.48 (d, J=8.6 Hz, 1H), 5.80 (s, 1H), 5.08 (s, 2H), 3.74-3.66 (m, 2H), 3.24 (s, 1H), 1.01 (d, J=6.6 Hz, 2H), 0.85-0.79 (m, 2H), 0.42 (s, 2H), 0.00−−0.12 (s, 9H)

LCMS (m/z): 446.4 [M+H]

(ix) 7-bromo-1-cyclopropyl-6-fluoro-2-oxo-8-((2-(trimethylsilyl)ethoxy)methoxy)-1,2-dihydroquinolin-4-yl trifluoromethanesulfonate 112-viii (0.161 g, 0.30 mmol, 1.0 equiv) was dissolved in N,N-dimethylformamide (5 mL) and cooled to 0° C. TEA (0.1 g, 1.0 mmol, 3.0 equiv), PhN(SO₂CF₃)₂ (0.19 g, 0.5 mmol, 1.5 equiv) were added and the reaction mixture was stirred at room temperature for 1.5 hours. The reaction mixture was quenched with cold water and extracted with EtOAc. The organic layer was washed with cold water, brine, dried over sodium sulfate and concentrated to afford a crude residue. The crude residue was purified by silica gel column chromatography (0-20% EtOAc/Hexane) to afford the desired product 112-ix (0.19 g, 94%, contaminated with PhNTf &DMF).

¹H NMR (400 MHz, CDCl₃) δ 7.40 (d, J=8.6 Hz, 1H), 6.72 (s, 1H), 5.12 (s, 2H), 3.87-3.82 (m, 2H), 3.45 (s, 1H), 1.27 (m, 2H), 0.97-0.91 (m, 2H), 0.64 (s, 2H), 0.02 (s, 9H)

LCMS (m/z): 578.4 [M+H]

(x) 7-bromo-1-cyclopropyl-6-fluoro-8-hydroxyquinolin-2(1H)-one 112-ix (0.19 g, 0.3298 mmol, 1.0 equiv), Pd(II)OAc (0.08 g, 0.3958 mmol, 1.2 equiv) and dppp (0.04 g, 0.099 mmol, 0.3 equiv) were added in N,N-dimethylformamide (5 mL). Et₃SiH (0.065 g, 0.3958 mmol, 1.2 equiv) was added and the reaction mixture was stirred at 40-45° C. for 1-2 hours. The reaction mixture was quenched with cold water and extracted with EtOAc. The organic layer was washed with brine, dried over sodium sulfate and concentrated to afford a crude residue. The crude residue was purified by flash chromatography (20-100% EtOAc/Hexane) to afford the desired product 112-x (0.07 g, 73% yield, 60% pure).

¹H NMR (400 MHz, DMSO) δ 10.03 (s, 1H), 7.71 (d, J=9.4 Hz, 1H), 7.27 (d, J=8.4 Hz, 1H), 6.53 (d, J=9.2 Hz, 1H), 3.41 (m, 1H), 1.07 (d, J=6.7 Hz, 2H), 0.44 (s, 2H)

LCMS (m/z): 300.2 [M+H]

(xi) 7-bromo-1-cyclopropyl-8-ethoxy-6-fluoroquinolin-2(1H)-one 112-x (0.07 g, 0.23 mmol, 1.0 equiv), K₂CO₃ (0.081 g, 0.59 mmol, 2.5 equiv) were added in N,N-dimethylformamide (2 mL). Ethyl iodide (0.055 g, 0.35 mmol, 1.5 equiv) was added and the reaction mixture was stirred at 100° C. for 1-2 hours in sealed tube. The reaction mixture was quenched with cold water and extracted with EtOAc. The organic layer was washed with brine, dried over sodium sulfate and concentrated to afford a crude residue. The crude residue was purified by preparative TLC purification (50% EtOAc/Hexane) to afford the desired product R8-112-xi (0.04 g, 52.6% yield). LCMS (m/z): 328.3 [M+H].

(xii) tert-butyl ((1-(1-cyclopropyl-8-ethoxy-6-fluoro-2-oxo-1,2-dihydroquinolin-7-yl)-3-fluoropyrrolidin-3-yl)methyl)carbamate 112-xi (0.025 g, 0.076 mmol, 1.0 equiv) was dissolved in Dioxane (2 mL). tert-butyl ((3-fluoropyrrolidin-3-yl)methyl)carbamate (0.025 g, 0.11 mmol, 1.5 equiv), Cs₂CO₃ (0.037 g, 0.11 mmol, 1.5 equiv) were added and the reaction mixture was degassed for 5 minutes. Pd₂(dba)₃ (0.003 g, 0.0038 mmol, 0.05 equiv), Xantphos (0.006 g, 0.00115 mmol, 0.15 equiv) were added and the reaction mixture was stirred at 110° C. for 8-9 hours in seal tube. The reaction mixture was quenched with cold water and extracted with EtOAc. The organic layer was washed with brine, dried over sodium sulfate and concentrated to afford a crude product 112-xii (0.072 g, without purification). The crude product was used in next step without further purification. LCMS (m/z): 465.8 [M+H].

(xiii) 7-(3-(aminomethyl)-3-fluoropyrrolidin-1-yl)-1-cyclopropyl-8-ethoxy-6-fluoroquinolin-2(1H)-one TFA salt 112-xii (0.06 g, 0.18 mmol, 1.0 equiv) was dissolved in dichloromethane (3 mL) and cooled to 0° C. HCl in Dioxane (2 mL) was added and the reaction mixture was stirred at room temperature for 1 hour. The reaction mixture was concentrated, co-distilled with diethyl ether to afford a crude residue. The crude residue was triturated with diethyl ether, the solvents were decanted and purified by preparative HPLC purification (with TFA as modifier) to afford the desired product 112-xiii as TFA salt (0.004 g, 7% yield).

$^1$H NMR (400 MHz, CD$_3$CN) δ 7.54 (d, J=9.3 Hz, 1H), 7.06 (d, J=13.0 Hz, 1H), 6.35 (d, J=9.3 Hz, 1H), 4.02 (dd, J=11.4, 7.1 Hz, 2H), 3.78-3.66 (m, 3H), 3.60 (t, J=8.6 Hz, 1H), 3.45 (dd, J=19.7, 5.5 Hz, 2H), 3.39-3.33 (m, 1H), 2.37-2.07 (m, 2H), 1.27 (t, J=7.0 Hz, 3H), 1.16 (d, J=5.2 Hz, 1H), 1.07-1.00 (m, 1H), 0.53 (td, J=11.1, 5.5 Hz, 2H)

LCMS (06_4 min), [MH]$^+$=364.5, RT=1.549 minutes
LCMS Method C_4 MIN
Column: HSS C18 (50*2.1 mm), 1.8 um; ESI source, Positive ion mode; Wavelength 229 nm
Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 113: (S)-7-(3-aminopyrrolidin-1-yl)-1-cyclopropyl-6-fluoro-2-oxo-1,2-dihydroquinoline-8-carbonitrile HCl salt

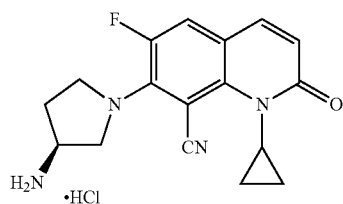 [SMILES: N#Cc1c(N2CC[C@H](N)C2)c(F)cc2ccc(=O)n(C3CC3)c12 ; Cl]

The title compound was prepared in accordance with the following scheme:

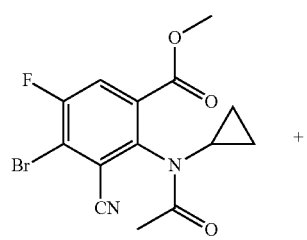

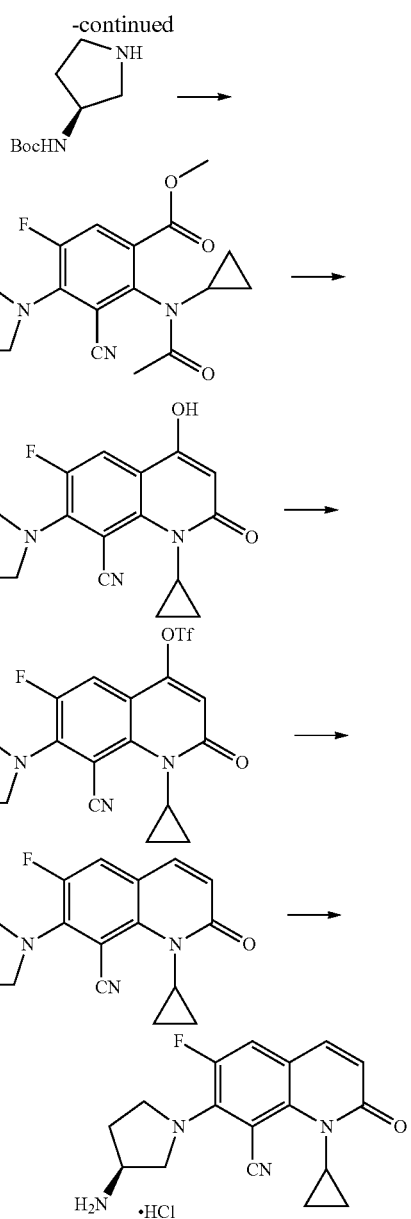

(i) methyl (S)-4-(3-((tert-butoxy carbonyl)amino) pyrrolidin-1-yl)-3-cyano-2-(N-cyclopropylacetamido)-5-fluorobenzoate 111-iii (0.5 g, 1.41 mmol, 1.0 equiv) was added in toluene (10 mL) in sealed tube, Cs$_2$CO$_3$ (0.69 g, 2.1 mmol, 1.5 equiv), tert-butyl (S)-pyrrolidin-3-ylcarbamate (0.4 g, 2.1 mmol, 1.5 equiv) were added and the reaction mixture was degassed for 15 minutes. Pd$_2$(dba)$_3$ (0.065 g, 0.07 mmol, 0.05 equiv), xantphos (0.081 g, 0.14 mmol, 0.1 equiv) were added and the reaction mixture was stirred at 110° C. for 6 hours. The reaction mixture was quenched with cold water and extracted with EtOAc. The organic layer was washed with brine, dried over sodium sulfate and concentrated to afford a crude residue. The crude residue was purified by 100-200 mesh silica gel column chromatography (45% EtOAc/Hexane) to afford the desired product 113-i (0.11 g, 17% yield).

¹H NMR (400 MHz, DMSO) δ 7.75-7.68 (m, 1H), 7.30 (s, 1H), 4.10 (s, 1H), 3.99 (s, 2H), 3.78 (s, 1H), 3.78-3.73 (m, 3H), 3.59 (s, 1H), 3.17 (d, J=5.3 Hz, 1H), 2.30 (d, J=21.8 Hz, 3H), 2.04 (s, 1H), 1.88 (s, 1H), 1.40 (s, 8H), 1.25 (d, J=10.4 Hz, 2H), 0.73 (d, J=4.1 Hz, 2H)

LCMS (m/z): 461.5 [M+H]

(ii) tert-butyl (S)-(1-(8-cyano-1-cyclopropyl-6-fluoro-4-hydroxy-2-oxo-1,2-dihydroquinolin-7-yl) pyrrolidin-3-yl) carbamate 113-i (0.14 g, 0.3 mmol, 1.0 equiv) was dissolved in dry THF (8 mL) and the reaction mixture was cooled at −40° C. NaHMDS (1.0 M in THF) (0.67 mL, 0.61 mmol, 2.0 equiv) was added at −40° C. and the reaction mixture was allowed to stir at 0 to 5° C. for 1 hour. The reaction mixture was acidified using 1N HCl to the pH 2 to 3 and extracted with EtOAc. The organic layer showed two spots on TLC, so the organic layer was washed with NaHCO₃. The organic layer was washed with brine, dried over sodium sulfate and concentrated to afford the desired product 113-ii (0.11 g, 74% yield).

¹H NMR (400 MHz, DMSO) δ 7.54 (d, J=15.2 Hz, 1H), 7.32 (s, 1H), 5.59 (s, 1H), 4.12 (s, 1H), 3.93 (s, 2H), 3.82 (s, 1H), 3.60-3.56 (m, 1H), 3.16 (s, 1H), 2.11 (s, 1H), 1.98-1.90 (m, 1H), 1.40 (s, 9H), 1.24 (s, 2H), 0.62 (s, 2H).

(iii) (S)-7-(3-((tert-butoxy carbonyl) amino) pyrrolidin-1-yl)-8-cyano-1-cyclopropyl-6-fluoro-2-oxo-1,2-dihydroquinolin-4-yl trifluoro methane sulfonate 113-ii (0.09 g, 0.21 mmol, 1.0 equiv) was dissolved in dry N,N-dimethylformamide (4 mL), TEA (0.083 g, 0.63 mmol, 3.0 equiv) was added and cooled to 0° C. PhN(SO₂CF₃)₂ (0.083 g, 0.23 mmol, 1.1 equiv) was added and the reaction mixture was stirred at RT for 2 hours. The reaction mixture was quenched with water and extracted with EtOAc. The organic layer was washed with brine, dried over sodium sulfate and concentrated to afford a crude residue. The crude residue was purified by 100-200 mesh silica gel column chromatography (25% EtOAc/Hexane) to afford the desired product 113-iii (0.075 g, 52% yield).

¹H NMR (400 MHz, DMSO) δ 7.43 (d, J=14.7 Hz, 1H), 7.34 (d, J=6.3 Hz, 1H), 6.62 (s, 1H), 4.16 (s, 1H), 4.06-3.97 (m, 2H), 3.88 (s, 1H), 3.62 (d, J=11.3 Hz, 1H), 3.30 (d, J=4.2 Hz, 1H), 2.18-2.09 (m, 1H), 1.96 (d, J=5.8 Hz, 1H), 1.41 (s, 8H), 1.34 (d, J=6.4 Hz, 2H), 0.75 (s, 2H).

(iv) tert-butyl (S)-(1-(8-cyano-1-cyclopropyl-6-fluoro-2-oxo-1,2-dihydroquinolin-7-yl) pyrrolidin-3-yl) carbamate 113-iii (0.065 g, 0.12 mmol, 1.0 equiv) was dissolved in dry N,N-dimethylformamide (3 mL) and the reaction mixture was cooled at −10° C. 1, 3 DPPP (0.014 g, 0.023 mmol, 0.3 equiv), Pd(II)OAc (0.004 g, 0.017 mmol, 0.15 equiv), TES (0.016 g, 0.14 mmol, 1.2 equiv) was added at 0 to 5° C. and the reaction mixture was allowed to stir at 0 to 5° C. for 2 hours. The reaction mixture was quenched with cold water and extracted with EtOAc. The organic layer was washed with cold water, dried over sodium sulfate and concentrated to afford a crude residue. The crude residue was purified by preparative HPLC purification to afford the desired product 113-iv (0.03 g, 54% yield).

¹H NMR (400 MHz, MeOD) δ 7.70 (d, J=9.4 Hz, 1H), 7.49 (d, J=14.4 Hz, 1H), 6.47 (d, J=9.3 Hz, 1H), 4.25 (s, 1H), 4.14-4.09 (m, 1H), 4.05 (s, 1H), 3.96 (s, 1H), 3.73 (s, 1H), 3.52-3.46 (m, 1H), 2.30-2.22 (m, 1H), 2.09-2.04 (m, 1H), 1.46 (d, J=12.8 Hz, 9H), 1.31 (s, 2H), 0.78 (d, J=9.2 Hz, 2H)

(v) (S)-7-(3-aminopyrrolidin-1-yl)-1-cyclopropyl-6-fluoro-2-oxo-1,2-dihydro quinoline-8-carbonitrile HCl salt 113-iv (0.03 g, 0.073 mmol, 1.0 equiv) was dissolved in dichloromethane (2 mL) and cooled to 0-5° C. HCl (in 1,4-dioxane) (0.3 mL) was added and the reaction mixture was stirred at RT for 2 hours. The reaction mixture was concentrated and co-distilled with dichloromethane to afford a crude residue. The crude residue was triturated with diethyl ether, n-pentane and the solvent was decanted to afford the desired product 113-v (0.016 g, 77% yield).

¹H NMR (400 MHz, MeOD) δ 7.74 (d, J=9.4 Hz, 1H), 7.59 (d, J=14.0 Hz, 1H), 6.51 (t, J=12.2 Hz, 1H), 4.19 (dd, J=9.6, 6.2 Hz, 1H), 4.06 (d, J=5.9 Hz, 3H), 3.97 (d, J=11.2 Hz, 1H), 3.50 (dt, J=7.0, 3.7 Hz, 1H), 2.54 (dd, J=13.4, 6.8 Hz, 1H), 2.20 (dt, J=13.1, 6.8 Hz, 1H), 1.50-1.41 (m, 2H), 0.83-0.75 (m, 2H)

LCMS (06_4 min), [MH]⁺=313.3, RT=1.437 minutes

LCMS Method C_4 MIN

Column: HSS C18 (50*2.1 mm), 1.8 um; ESI source, Positive ion mode; Wavelength 387 nm Column temperature: Ambient Mobile Phase: A: 5 mM Ammonium acetate in 0.1% formic acid in water, B: 0.1% formic acid in ACN Flow rate: 0.55 mL/min Gradient: 5%-100% (solvent B) over 2.5 minutes and holding at 100% for 0.6 minutes Example 114: (S)-4-(aminomethyl)-7-(3-aminopyrrolidin-1-yl)-1-cyclopropyl-6-fluoro-2-oxo-1,2-dihydroquinoline-8-carbonitrile

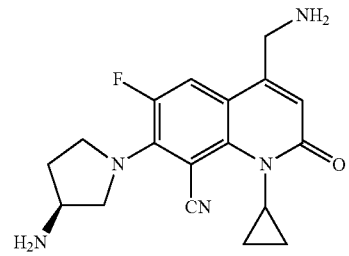 [SMILES: N#Cc1c(N2CC[C@H](N)C2)c(F)cc2c(CN)cc(=O)n(C3CC3)c12]

The title compound was prepared in accordance with the following scheme:

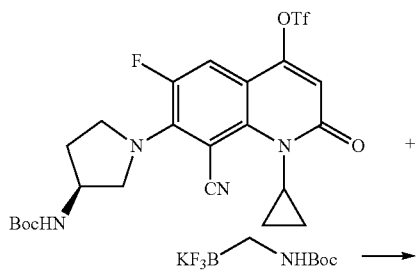

285

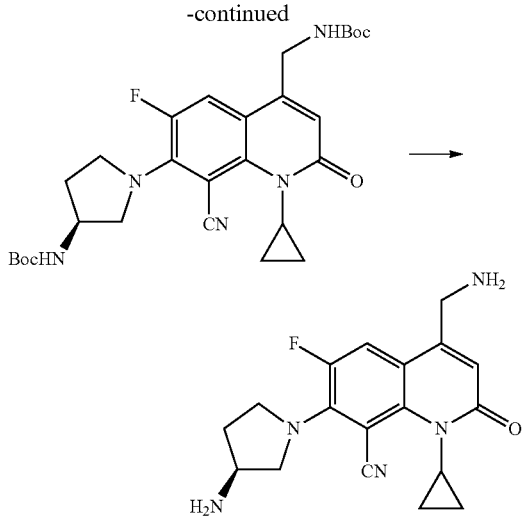

(i) tert-butyl (S)-(1-(4-(((tert-butoxycarbonyl)amino)methyl)-8-cyano-1-cyclopropyl-6-fluoro-2-oxo-1,2-dihydroquinolin-7-yl)pyrrolidin-3-yl)carbamate 113-ii (0.085 g, 0.15 mmol, 1.0 equiv) was dissolved in 1,4-Dioxane (1 mL). Potassium [[(tert-Butoxycarbonyl)amino]methyl]trifluoroborate (0.071 g, 0.30 mmol, 2.0 equiv), Sodium carbonate (0.032 g, 0.30 mmol, 2.0 equiv) in water (0.1 mL) were added and degassed for 5 min. PdCl$_2$dppf (0.011 g, 0.015 mmol, 0.1 equiv) was added and degassed again for 5 min. The reaction mixture was heated to 85° C. for 2 hours in sealed tube. The reaction mixture was quenched with water and extracted with EtOAc. The organic layer was washed with brine, dried over sodium sulfate and concentrated to afford crude residue. The crude was purified by Prep. TLC (70% EtOAc:Hexane) to afford the desired product 114-i (0.016 g, 19.5% yield).

$^1$H NMR (400 MHz, MeOD) δ 7.67 (d, J=15.6 Hz, 1H), 6.42 (s, 1H), 4.57 (s, 2H), 4.25 (s, 1H), 4.08 (d, J=23.3 Hz, 2H), 3.94 (d, J=6.2 Hz, 1H), 3.74 (s, 1H), 3.52 (d, J=13.1 Hz, 1H), 2.26 (d, J=6.9 Hz, 1H), 2.05 (dd, J=10.5, 5.9 Hz, 1H), 1.48 (d, J=6.4 Hz, 18H), 1.44 (s, 2H), 0.74 (s, 2H)

LCMS (m/z): 452.8 [M+H]

(ii) (S)-4-(aminomethyl)-7-(3-aminopyrrolidin-1-yl)-1-cyclopropyl-6-fluoro-2-oxo-1,2-dihydroquinoline-8-carbonitrile 114-i (0.9 g, 3.3 mmol, 1.0 equiv) was dissolved in dichloromethane (20 mL) at 0° C. HCl-Dioxane (4 M) (0.5 mL) was added and the reaction mixture was stirred at room temperature for 2 hours. The reaction mixture was concentrated and co-distilled with DCM to to afford crude residue. The crude residue was purified by Prep HPLC to afford 114-ii (0.002 g, 19.8% yield).

$^1$H NMR (400 MHz, MeOD) δ 7.61 (d, J=15.6 Hz, 1H), 6.57 (s, 1H), 4.04 (s, 3H), 3.95 (s, 2H), 3.68 (d, J=9.6 Hz, 2H), 3.50 (s, 1H), 2.32-2.23 (m, 1H), 1.97-1.89 (m, 1H), 1.47-1.39 (m, 2H), 0.74 (d, J=3.6 Hz, 2H)

LCMS (01_4 min), [MH]$^+$=341.9, RT=3.016 minutes
LCMS Method C_4 MIN
Column: HSS C18 (50*2.1 mm), 1.8 um; ESI source, Positive ion mode; Wavelength 254 nm

286

Column temperature: Ambient
Mobile Phase: A: 5 mM Ammonium acetate in 0.1% formic acid in water, B: 0.1% formic acid in ACN
Flow rate: 0.55 mL/min
Gradient: 5%-100% (solvent B) over 2.5 minutes and holding at 100% for 0.6 minutes Example 115: 4-(aminomethyl)-7-(3-(aminomethyl)-3-fluoropyrrolidin-1-yl)-1-cyclobutyl-5,6-difluoro-8-methylquinolin-2(1H)-one TFA salt

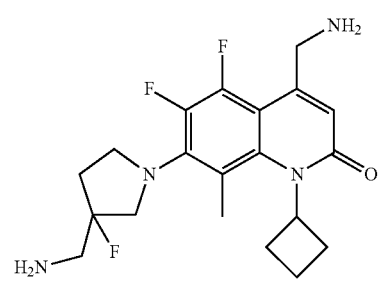 [SMILES: Cc1c(N2CCC(F)(CN)C2)c(F)c(F)c2c(CN)cc(=O)n(C3CCC3)c12]

The title compound was prepared according to the following scheme:

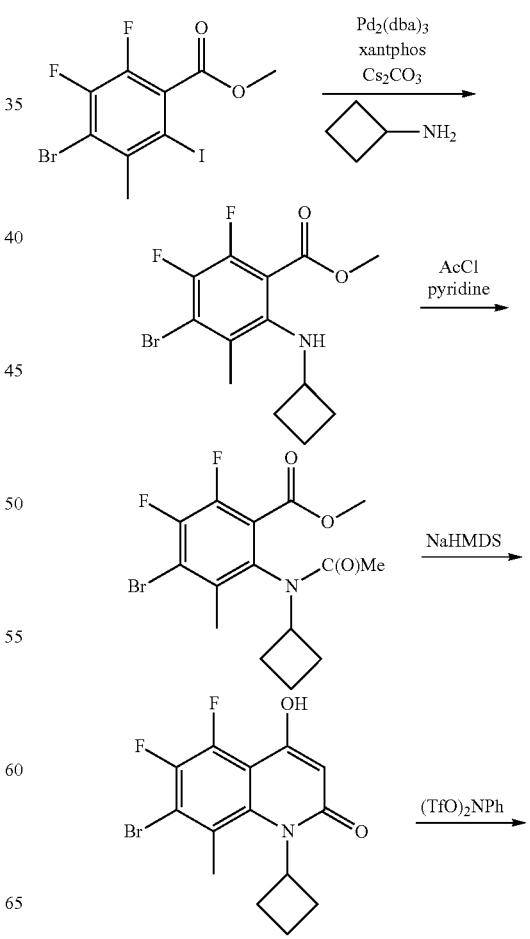

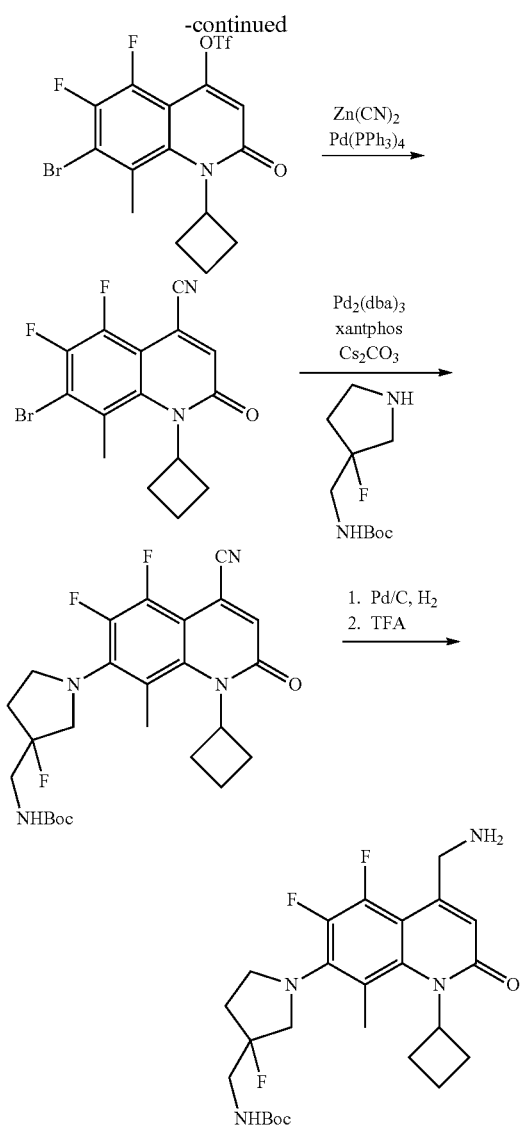

(i) Methyl 4-bromo-2-(cyclobutylamino)-5,6-difluoro-3-methylbenzoate

Methyl 4-bromo-2,3-difluoro-6-iodo-5-methylbenzoate (1.5 g, 3.84 mmol) was dissolved in 1,4-dioxane (Volume: 30.7 ml) and de-gassed by bubbling nitrogen for 10 minutes. $Pd_2dba_3$ (0.176 g, 0.192 mmol), xantphos (0.333 g, 0.576 mmol), cesium carbonate (1.875 g, 5.76 mmol) and cyclobutylamine (0.491 ml, 5.76 mmol) were added. The flask was fitted with a reflux condensor and the entire apparatus was evacuated and back-filled with nitrogen three times from a balloon using a 3-way stopcock. The mixture was heated to 80° C. for 15 hours under nitrogen. Upon cooling to rt the mixture was diluted with water (100 mL) and extracted with EtOAc (3×50 mL). The combined organic extracts were washed with brine, dried over $MgSO_4$ and concentrated under reduced pressure. $SiO_2$ flash chromatography (ISCO combiflash, 0-15% EtOAc/heptane, 40 g cartridge) provided methyl 4-bromo-2-(cyclobutylamino)-5,6-difluoro-3-methylbenzoate (1.07 g, 3.20 mmol, 83% yield) as a yellow oil.

$^1$H NMR (400 MHz, Chloroform-d) δ 3.95 (s, 3H), 3.55 (p, J=7.9 Hz, 1H), 2.34 (d, J=1.0 Hz, 3H), 2.30-2.19 (m, 2H), 1.90-1.75 (m, 2H), 1.72-1.60 (m, 1H), 1.58-1.46 (m, 1H)

LCMS: $t_R$=1.07 min, m/z=334/336 [M+H]$^+$ (ii) Methyl 4-bromo-2-(N-cyclobutylacetamido)-5,6-difluoro-3-methylbenzoate Acetyl chloride (0.532 mL, 7.48 mmol) was added to a mixture of methyl 4-bromo-2-(cyclobutylamino)-5,6-difluoro-3-methylbenzoate (500 mg, 1.496 mmol) and pyridine (0.605 mL, 7.48 mmol) in DCM (Volume: 15.000 mL) at 0° C. The mixture immediately turned cloudy, off-white. LCMS after 5 minutes showed only starting material, so the mixture was warmed rt. After 1 hour LCMS indicated consumption of starting material. The mixture was diluted with DCM (25 mL) and washed with saturated aqueous $NH_4Cl$ (50 mL), saturated aqueous $NaHCO_3$ (50 mL) and brine, then dried over $MgSO_4$ and concentrated under reduced pressure. $SiO_2$ flash chromatography (ISCO combiflash, 0-100% EtOAc/heptane, g cartridge) provided methyl 4-bromo-2-(N-cyclobutylacetamido)-5,6-difluoro-3-methylbenzoate (446 mg, 1.186 mmol, 79% yield) as a colorless solid.

$^1$H NMR (400 MHz, Chloroform-d) δ 4.78-4.61 (m, 1H), 3.91 (s, 3H), 2.30 (s, 3H), 2.14-2.04 (m, 2H), 1.78 (s, 3H), 1.77-1.54 (m, 4H)

LCMS: $t_R$=0.90 min, m/z=376/378 [M+H]$^+$ (iii) 7-bromo-1-cyclobutyl-5,6-difluoro-4-hydroxy-8-methylquinolin-2(1H)-one NaHMDS (1M in THF, 6.49 mL, 6.49 mmol) was added dropwise to a mixture of methyl 4-bromo-2-(N-cyclobutylacetamido)-5,6-difluoro-3-methylbenzoate (814 mg, 2.164 mmol) in THF (Volume: 21.6 mL) at −78° C. The mixture rapidly turned dark brown-black. After 20 minutes at this temperature LCMS indicated complete and clean conversion to desired product. Stirred 30 minutes total. Water (~5 mL) was added drop-wise and the reaction flask was removed from the dy-ice/acetone bath. More water (~7 mL) was added as the mixture warmed to rt, then it was diluted with water (100 mL) and brine and washed with EtOAc (50 mL). The aqueous layer (containing desired product) was acidified with 1M HCl (20 mL) and extracted with EtOAc (3×50 mL). The latter organic extracts were combined and washed with brine, dried over $MgSO_4$, filtered and concentrated under reduced pressure. The crude material was combined with that from an earlier test reaction and concentrated to give a yellow solid. The solid was suspended in $Et_2O$ and filtered, washing with $Et_2O$ to give a pale yellow powder. The filtrate was concentrated and the residue was triturated once more to give 450 mg of a pale yellow solid. Finally, the filtrate was concentrated to give an additional 130 mg of crude product (580 mg total, 69% yield).

$^1$H NMR (400 MHz, DMSO-d6) δ 11.56 (d, J=1.1 Hz, 1H), 5.77 (s, 1H), 4.46 (p, J=8.2 Hz, 1H), 2.46-2.36 (m, 5H), 2.31-2.20 (m, 2H), 1.74-1.54 (m, 2H)

LCMS: $t_R$=0.85 min, m/z=344/346 [M+H]$^+$ (iv) 7-bromo-1-cyclobutyl-5,6-difluoro-8-methyl-2-oxo-1,2-dihydroquinolin-4-yl trifluoromethanesulfonate, 1,1,1-trifluoro-N-phenylmethanesulfonamide 1,1,1-trifluoro-N-phenyl-N-((trifluoromethyl)sulfonyl)methanesulfonamide (561 mg, 1.569 mmol) was added dropwise as a solution in DMF to a mixture of 7-bromo-1-cyclobutyl-5,6-difluoro-4-hydroxy-8-methylquinolin-2 (1H)-one (450 mg, 1.308 mmol) and triethylamine (0.547 mL, 3.92 mmol) in DMF (Volume: 13.1 mL) at 0° C. After 5 minutes the reaction flask was removed from the ice bath, and after 30 minutes at rt LCMS indicated complete consumption of starting material. The mixture was diluted with water (50 mL) and brine and extracted three times with EtOAc (25 mL). The combined organic extracts were washed with brine, dried over MgSO$_4$ and concentrated under reduced pressure. Crude material was combined with that from an earlier test reaction. The combined crude residue was subjected to SiO$_2$ flash chromatography (ISCO combiflash, 0-20% EtOAc/heptane, 12 g cartridge) to provide 7-bromo-1-cyclobutyl-5,6-difluoro-8-methyl-2-oxo-1,2-dihydroquinolin-4-yl trifluoromethanesulfonate (550 mg, 76%) as a pale yellow solid contaminated with N-phenyl trifluoromethanesulfonamide (~10-20%).

$^1$H NMR (400 MHz, Chloroform-d) δ 6.61 (s, 1H), 4.59 (p, J=8.1 Hz, 1H), 2.51 (d, J=1.0 Hz, 3H), 2.48-2.38 (m, 4H), 1.89-1.78 (m, 1H), 1.77-1.64 (m, 1H)

LCMS: t$_R$=1.11 min, m/z=476/478 [M+H]$^+$ (v) 7-bromo-1-cyclobutyl-5,6-difluoro-8-methyl-2-oxo-1,2-dihydroquinoline-4-carbonitrile A mixture of 7-bromo-1-cyclobutyl-5,6-difluoro-8-methyl-2-oxo-1,2-dihydroquinolin-4-yl trifluoromethanesulfonate (300 mg, 0.630 mmol) in DMF (Volume: 6.3 mL) in a 25 mL round bottom flask was treated with tetrakis(triphenylphosphine)palladium(0) (72.8 mg, 0.063 mmol), followed by zinc cyanide (38.5 mg, 0.328 mmol). The flask was fitted with reflux condensor and a balloon of nitrogen, then the mixture was heated to 80° C. for 16 hours, becoming dark green in color. The reaction mixture was diluted with saturated aqueous NaHCO$_3$ (50 mL) and water (25 mL) and extracted three times with EtOAc (25 mL). The combined organic extracts were washed with saturated aqueous NaHCO$_3$ and brine, then dried over Na$_2$SO$_4$ and concentrated under reduced pressure. The resulting crude residue was combined with that from an earlier test reaction and subjected to SiO$_2$ flash chromatography (ISCO combiflash, 0-30% EtOAc/heptane, 12 g cartridge) gave 7-bromo-1-cyclobutyl-5,6-difluoro-8-methyl-2-oxo-1,2-dihydroquinoline-4-carbonitrile (180 mg, 0.510 mmol, 69% yield) as a yellow solid.

$^1$H NMR (500 MHz, Chloroform-d) δ 7.09 (s, 1H), 4.61 (p, J=8.7, 8.3 Hz, 1H), 2.50 (d, J=1.0 Hz, 3H), 2.47-2.34 (m, 4H), 1.87-1.78 (m, 1H), 1.77-1.66 (m, 1H)

LCMS: t$_R$=0.92 min, m/z=353/355 [M+H]$^+$ (vi) Tert-butyl ((1-(4-cyano-1-cyclobutyl-5,6-difluoro-8-methyl-2-oxo-1,2-dihydroquinolin-7-yl)-3-fluoropyrrolidin-3-yl)methyl)carbamate A 5 mL microwave vial was charged with 7-bromo-1-cyclobutyl-5,6-difluoro-8-methyl-2-oxo-1,2-dihydroquinoline-4-carbonitrile (90 mg, 0.255 mmol), tert-butyl ((3-fluoropyrrolidin-3-yl)methyl)carbamate (111 mg, 0.510 mmol), xantphos (44.2 mg, 0.076 mmol), Pd$_2$(dba)$_3$ (23.34 mg, 0.025 mmol) and cesium carbonate (166 mg, 0.510 mmol). The vial was sealed, evacuated and back-filled with nitrogen. Toluene (Volume: 2.55 mL, previously degassed by sparging with nitrogen) was added and the mixture was heated to 110° C. for 7 hours. The mixture was diluted with water and extracted three times with EtOAc. The combined organic extracts were washed with brine, dried over Na$_2$SO$_4$ and concentrated under reduced pressure. SiO$_2$ flash chromatography (ISCO combiflash, 0-100% EtOAc/heptane, 4 g cartridge) gave tert-butyl ((1-(4-cyano-1-cyclobutyl-5,6-difluoro-8-methyl-2-oxo-1,2-dihydroquinolin-7-yl)-3-fluoropyrrolidin-3-yl)methyl)carbamate (72 mg, 0.147 mmol, 57.6% yield) as a yellow solid.

$^1$H NMR (400 MHz, Chloroform-d) δ 6.88 (s, 1H), 5.00-4.89 (m, 1H), 4.58 (p, J=8.0 Hz, 1H), 4.00-3.76 (m, 2H), 3.67-3.43 (m, 4H), 2.61-2.50 (m, 1H), 2.41-2.02 (m, 8H), 1.82-1.60 (m, 2H), 1.47 (s, 9H)

LCMS: t$_R$=1.00 min, m/z=491.3 [M+H]$^+$ (vii) Tert-butyl ((1-(4-(aminomethyl)-1-cyclobutyl-5,6-difluoro-8-methyl-2-oxo-1,2-dihydroquinolin-7-yl)-3-fluoropyrrolidin-3-yl)methyl)carbamate A mixture of tert-butyl ((1-(4-cyano-1-cyclobutyl-5,6-difluoro-8-methyl-2-oxo-1,2-dihydroquinolin-7-yl)-3-fluoropyrrolidin-3-yl)methyl)carbamate (35 mg, 0.071 mmol) in 2M NH$_3$/MeOH (Volume: 3 mL) was treated with Pd/C (10% dry wt, 50% water, 45.6 mg, 0.021 mmol) and sparged with hydrogen for 5 minutes, then stirred under a balloon of hydrogen for 30 minutes. LCMS indicated complete consumption of starting material and conversion to a new product (t$_R$=0.76 min, m/z=495.3). The mixture was sparged with nitrogen for several minutes then passed through a 1 μm syringe filter and concentrated under reduced pressure to give a yellow oil. The reaction was repeated once more on the same scale with identical results. Crude material from both reactions was combined and used without further purification. tert-butyl ((1-(4-(aminomethyl)-1-cyclobutyl-5,6-difluoro-8-methyl-2-oxo-1,2-dihydroquinolin-7-yl)-3-fluoropyrrolidin-3-yl)methyl)carbamate (61 mg, 0.123 mmol, 85% yield) was obtained as a yellow foam.

LCMS: t$_R$=0.76 min, m/z=495.3 [M+H]$^+$ (viii) 4-(aminomethyl)-7-(3-(aminomethyl)-3-fluoropyrrolidin-1-yl)-1-cyclobutyl-5,6-difluoro-8-methylquinolin-2(1H)-one TFA salt A mixture of tert-butyl ((1-(4-(aminomethyl)-1-cyclobutyl-5,6-difluoro-8-methyl-2-oxo-1,2-dihydroquinolin-7-yl)-3-fluoropyrrolidin-3-yl)methyl)carbamate (61 mg, 0.123 mmol) in DCM (Volume: 1.2 mL, Ratio: 1.000) and TFA (Volume: 1.2 mL, Ratio: 1.000) was stirred at rt. After 15 minutes LCMS indicated complete consumption of starting material. The mixture was concentrated under reduced pressure. The residue was concentrated from DCM-toluene, then MeOH-toluene. Finally, the dark yellow oily residue was dissolved in DMSO (2 mL) and passed through a 0.45 μm syringe filter and submitted to preparative RP-HPLC (MeCN—H$_2$O-TFA). The pooled fractions containing the desired product were lyophilized to give the title compound (8.6 mg, 10% yield) as a sticky gum.

$^1$H NMR (500 MHz, Methanol-d4) δ 6.47 (s, 1H), 4.71 (p, J=8.3 Hz, 1H), 4.48-4.35 (m, 2H), 4.04-3.86 (m, 2H), 3.69 (dd, J=21.3, 11.7 Hz, 1H), 3.62-3.56 (m, 1H), 3.52 (dd, J=19.7, 5.7 Hz, 2H), 2.63-2.54 (m, 1H), 2.49-2.18 (m, 8H), 1.78-1.69 (m, 2H)

LCMS: t$_R$=1.29 min, m/z=395.3 [M+H]$^+$ (10 minute run)

Using the procedures described for Example 115 the following compounds were prepared as TFA salts:

| Ex# | Structure | Chemical Name | LCMS $t_R$ (min) | LCMS $[M + H]^+$ |
|---|---|---|---|---|
| 115.2 | 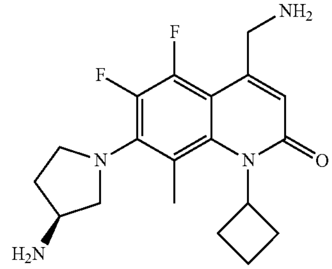 [SMILES: Cc1c(N2CC[C@H](N)C2)c(F)c(F)c2c(CN)cc(=O)n(C3CCC3)c12] | (S)-4-(aminomethyl)-7-(3-aminopyrrolidin-1-yl)-1-cyclobutyl-5,6-difluoro-8-methylquinolin-2(1H)-one trifluoroacetate | 1.18 | 363.3 |
| 115.3 | 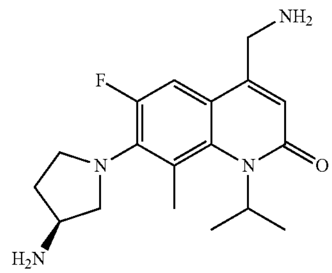 [SMILES: Cc1c(N2CC[C@H](N)C2)c(F)cc2c(CN)cc(=O)n(C(C)C)c12] | (S)-4-(aminomethyl)-7-(3-aminopyrrolidin-1-yl)-6-fluoro-1-isopropyl-8-methylquinolin-2(1H)-one trifluoroacetate | 1.05 | 333.1 |
| 115.4 | 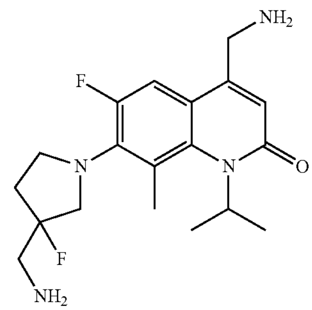 [SMILES: Cc1c(N2CCC(F)(CN)C2)c(F)cc2c(CN)cc(=O)n(C(C)C)c12] | 4-(aminomethyl)-7-(3-(aminomethyl)-3-fluoropyrrolidin-1-yl)-6-fluoro-1-isopropyl-8-methylquinolin-2(1H)-one trifluoroacetate | 1.2 | 365.2 |

The compounds in the preceding table were characterized by high performance liquid chromatography (HPLC) on a Waters ACQUITY UPLC system with 1.2 mL/min flow rate; column Kinetex-C18, 2.6 um, 2.1×50 mm from Phenomenex, column temperature: 50° C.; gradient: 2-88% MeCN in water with 0.1% TFA over a9.29 min period (unless indicated otherwise); compounds were detected by ultraviolet light (UV) absorption at 220 nm.

Example 116: 7-(1-amino-3-azabicyclo[3.1.0]hexan-3-yl)-4-(aminomethyl)-3-chloro-1-cyclopropyl-6-fluoro-8-methylquinolin-2(1H)-one TFA salt The title compound was prepared in accordance with the following scheme:

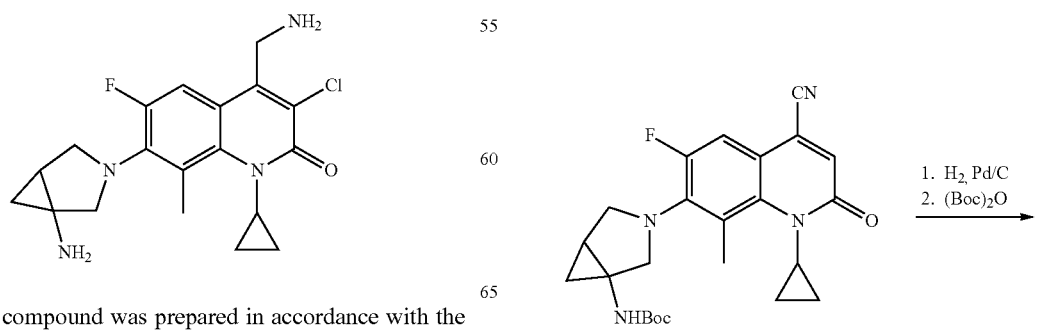

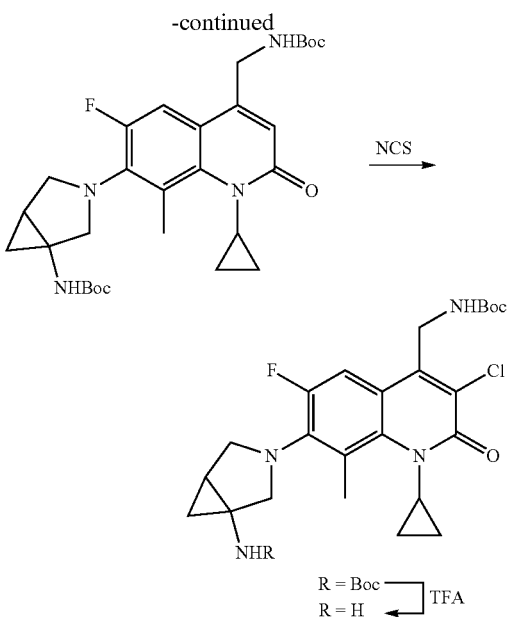

(i) Tert-butyl (3-(4-cyano-1-cyclopropyl-6-fluoro-8-methyl-2-oxo-1,2-dihydroquinolin-7-yl)-3-azabicyclo[3.1.0]hexan-1-yl)carbamate A 5 mL microwave vial was charged with 7-bromo-1-cyclopropyl-6-fluoro-8-methyl-2-oxo-1,2-dihydroquinoline-4-carbonitrile (250 mg, 0.778 mmol), tert-butyl 3-azabicyclo[3.1.0]hexan-1-ylcarbamate (309 mg, 1.557 mmol), BINAP (194 mg, 0.311 mmol), tris(dibenzylideneacetone)dipalladium(0) (143 mg, 0.156 mmol) and cesium carbonate (761 mg, 2.335 mmol). The vial was sealed, evacuated and back-filled with $N_2$. Toluene (Volume: 7.8 mL, previously degassed by sparging with nitrogen) was added and the mixture was heated to 100° C. for 5.5 hours. Upon cooling to room temperature the mixture was filtered through a disposable fritted funnel and volatiles were evaporated under reduced pressure. Crude material was combined with that from a second identical reaction and submitted to $SiO_2$ flash chromatography (ISCO combiflash, 0-100% EtOAc/heptane, 24 g cartridge) to give tert-butyl (3-(4-cyano-1-cyclopropyl-6-fluoro-8-methyl-2-oxo-1,2-dihydroquinolin-7-yl)-3-azabicyclo[3.1.0]hexan-1-yl)carbamate (650 mg, 1.482 mmol, 85% yield) as a dark yellow oil that became glassy under vacuum.

$^1$H NMR (400 MHz, Chloroform-d) δ 7.32 (d, J=12.1 Hz, 1H), 6.87 (s, 1H), 3.94-3.82 (m, 1H), 3.75-3.67 (m, 1H), 3.59-3.52 (m, 1H), 3.52-3.44 (m, 1H), 3.40-3.30 (m, 1H), 2.45 (s, 3H), 1.73 (s, 1H), 1.54 (s, 9H), 1.27-1.20 (m, 2H), 1.17-1.10 (m, 1H), 1.06-0.97 (m, 1H), 0.60-0.47 (m, 2H).

LCMS: $t_R$=0.93 min, m/z=439.4 [M+H]$^+$ (ii) tert-butyl (3-(4-(((tert-butoxycarbonyl)amino)methyl)-1-cyclopropyl-6-fluoro-8-methyl-2-oxo-1,2-dihydroquinolin-7-yl)-3-azabicyclo[3.1.0]hexan-1-yl)carbamate A mixture of tert-butyl (3-(4-cyano-1-cyclopropyl-6-fluoro-8-methyl-2-oxo-1,2-dihydroquinolin-7-yl)-3-azabicyclo[3.1.0]hexan-1-yl)carbamate (650 mg, 1.482 mmol) in 2M $NH_3$ in MeOH (Volume: 59.3 mL) in a 200 mL round bottom flask was treated with Pd/C (10% dry wt, 50% water, 947 mg, 0.445 mmol). The flask was partially evacuated and back-filled with $H_2$ 5 times, then stirred under a balloon of $H_2$ for 1 hour. The flask was partially evacuated and back-filled with $N_2$ 5 times, then the reaction mixture was filtered through a plug of celite and concentrated under reduced pressure to give the desired primary amine as a yellow-brown oil. The amine material was dissolved in THF (Volume: 7.4 mL) and treated with Huenig's Base (777 µl, 4.45 mmol) and Boc-anhydride (447 µl, 1.927 mmol) and stirred at room temperature for 1 hr. The mixture was diluted with saturated aqueous $NH_4Cl$ (50 mL) and water (10 mL) and extracted with EtOAc (3×25 mL). The combined organic extracts were washed with saturated brine, dried over $MgSO_4$, filtered and concentrated under reduced pressure. $SiO_2$ flash chromatography (ISCO combiflash, 0-100% EtOAc/heptane, 24 g cartridge) provided the title compound (448 mg, 0.743 mmol, 50.1% yield) as a yellow foam.

$^1$H NMR (400 MHz, Chloroform-d) δ 7.10 (d, J=13.2 Hz, 1H), 6.47 (s, 1H), 5.04 (s, 1H), 4.86-4.74 (m, 1H), 4.44-4.31 (m, 2H), 3.88-3.75 (m, 1H), 3.67 (d, J=8.6 Hz, 1H), 3.56-3.39 (m, 2H), 3.28 (d, J=9.3 Hz, 1H), 2.45 (s, 3H), 1.69 (s, 1H), 1.47 (s, 18H), 1.21-1.12 (m, 3H), 1.03-0.96 (m, 1H), 0.54-0.47 (m, 2H)

LCMS: $t_R$=0.96 min, m/z=543.4 [M+H]$^+$ (iii) tert-butyl (3-(4-(((tert-butoxycarbonyl)amino)methyl)-3-chloro-1-cyclopropyl-6-fluoro-8-methyl-2-oxo-1,2-dihydroquinolin-7-yl)-3-azabicyclo[3.1.0]hexan-1-yl)carbamate A mixture of tert-butyl (3-(4-(((tert-butoxycarbonyl)amino)methyl)-1-cyclopropyl-6-fluoro-8-methyl-2-oxo-1,2-dihydroquinolin-7-yl)-3-azabicyclo[3.1.0]hexan-1-yl)carbamate (176 mg, 0.324 mmol) in MeCN (Volume: 1.6 mL) was treated with N-chlorosuccinimide (130 mg, 0.973 mmol) and stirred 4 hours at room temperature. Volatiles were evaporated under reduced pressure. The residue was dissolved in EtOAc and washed with 10% aqueous citric acid, saturated aqueous $NaHCO_3$ and brine, then dried over $Na_2SO_4$, filtered and concentrated under reduced pressure. $SiO_2$ flash chromatography (ISCO combiflash, 0-100% EtOAc/heptane, 4 g cartridge) provided the title compound (127 mg, 0.198 mmol, 61.1% yield) as a pale yellow foam.

$^1$H NMR (400 MHz, Chloroform-d) δ 7.55-7.44 (m, 1H), 5.04 (br s, 1H), 4.83 (br s, 1H), 4.62 (d, J=5.7 Hz, 2H), 3.83 (br s, 1H), 3.68 (d, J=8.7 Hz, 1H), 3.61-3.45 (m, 2H), 3.31 (d, J=9.3 Hz, 1H), 2.44 (s, 3H), 1.70 (br s, 1H), 1.55-1.38 (m, 18H), 1.22-1.14 (m, 3H), 1.04-0.96 (m, 1H), 0.56-0.48 (m, 2H)

LCMS: $t_R$=1.01 min, m/z=577.3 [M+H]$^+$ (iv) 7-(1-amino-3-azabicyclo[3.1.0]hexan-3-yl)-4-(aminomethyl)-3-chloro-1-cyclopropyl-6-fluoro-8-methylquinolin-2(1H)-one A mixture of tert-butyl (3-(4-(((tert-butoxycarbonyl)amino)methyl)-3-chloro-1-cyclopropyl-6-fluoro-8-methyl-2-oxo-1,2-dihydroquinolin-7-yl)-3-azabicyclo[3.1.0]hexan-1-yl)carbamate (67 mg, 0.116 mmol) in DCM (Volume: 581 µl, Ratio: 1.000) and TFA (Volume: 581 µl, Ratio: 1.000) was stirred for 20 minutes at room temperature. Volatiles were evaporated under reduced pressure and the oily residue was concentrated twice from MeOH-toluene then subjected to preparative RP-HPLC (1-40% MeCN/$H_2O$+0.1% TFA). Fractions containing product were collected and lyophilized directly to give 7-(1-amino-3-azabicyclo[3.1.0]hexan-3-yl)-4-(aminomethyl)-3-chloro-1-cyclopropyl-6-fluoro-8-methylquinolin-2(1H)-one TFA salt (22.8 mg, 0.037 mmol, 31.8% yield) as a pale yellow, fluffy solid.

$^1$H NMR (500 MHz, Methanol-d4) δ 7.55 (d, J=13.5 Hz, 1H), 4.52 (s, 2H), 3.87-3.82 (m, 1H), 3.82-3.76 (m, 1H), 3.74-3.69 (m, 1H), 3.69-3.63 (m, 1H), 3.44-3.40 (m, 1H), 2.56 (s, 3H), 2.03-1.97 (m, 1H), 1.36-1.22 (m, 4H), 0.52-0.42 (m, 2H).

LCMS: $t_R$=0.38 min, m/z=377.2 [M+H]$^+$

Methods of Use

The compounds according to the any of Formulae I to V in free form or in pharmaceutically acceptable salt forms, exhibit valuable pharmacological properties including inhibiting DNA gyrase activity in bacteria as well as acting as antibacterials.

According to one embodiment, the present invention provides a method of inhibiting bacterial DNA gyrase activity in a subject, administering to said subject a compound of formulae I-VI or a composition comprising a compound of formula I-VI and a pharmaceutically acceptable carrier, adjuvant, or vehicle.

According to another embodiment, the present invention provides a method of decreasing bacterial quantity in a subject, comprising administering to said subject a compound of formula I-VI or a composition comprising a compound of formula I-VI and a pharmaceutically acceptable carrier, adjuvant, or vehicle.

According to another embodiment, the present invention provides a method of preventing, treating, or lessening the severity of a bacterial infection in a subject, comprising administering to said subject a compound of formula I-VI or a composition comprising a compound of formula I-VI and a pharmaceutically acceptable carrier, adjuvant, or vehicle.

According to another embodiment, the methods of the present invention are useful to treat patients in the veterinary field including, but not limited to, zoo, laboratory, and farm animals, including primates, rodents, and birds. Examples of said animals include, but are not limited to guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

In another embodiment, the present invention provides a method wherein the bacterial infection to be treated or prevented is characterized by the presence of one or more fermentative or non-fermentative bacterial species.

In another embodiment, the present invention provides a method wherein the bacterial infection to be treated or prevented is characterized by the presence of one or more fermentative or non-fermentative Gram-negative bacteria selected from the group consisting of *Pseudomonas aeruginosa* and other *Pseudomonas* species, *Stenotrophomonas maltophilia*, *Burkholderia cepacia* and other *Burkholderia* species, *Acinetobacter baumannii* and other *Acinetobacter* species, *Achromobacter xylosoxidans*, *Alcaligenes denitrificans* and other Achromobacteraceae, *Citrobacter freundii* and other *Citrobacter* species, *Campylobacter jejuni*, *Klebsiella pneumoniae*, *Klebsiella oxytoca* and other *Klebsiella* species, *Enterobacter cloacae*, *Enterobacter aerogenes* and other *Enterobacter* species, *Escherichia coli*, *Salmonella enterica* and other *Salmonella* species, *Yersinia pestis*, *Proteus vulgaris* and other *Proteus* species, *Serratia marscens* and other *Serratia* species, *Morganella morganii* and other members of the Enterobacteriaceae family, *Neisseria meningitidis*, *Haemophilus influenzae*, *Moraxella cattharallis*, *Bacteroides fragilis*, *Bacteroides thetaiotaomicron* and other *Bacteroides* species, *Pasteurella* multicoda and other *Pasteurella* species, *Fransicella tularensis*, *Shigella dysenteriae* and other *Shigella* species, *Vibrio cholera* and other *Vibrio* species, *Bordetella pertussis* and other *Bordetella* species, *Helicobactor pylori* and other *Helicobacter* species, *Legionella pneumophila* and *Campylobactor jejuni*.

In another embodiment, the present invention provides a method wherein the bacterial infection to be treated or prevented is characterized by the presence of one or more fermentative or non-fermentative Gram-positive bacteria selected from the group consisting of *Staphylococcus aureus*, *Staphylococcus epidermidis* and other *Staphylococcus* species, *Enterococcus faecalis*, *Enterococcus faecium* and other *Enterococcus* species, *Streptococcus pneumoniae*, *Streptococcus pyogenes*, *Streptococcus agalactiae* and other *Streptococcus* species, *Bacillus anthracis* and other *Bacillus* species, *Peptostreptococcus magnus* and other *Peptostreptococcus* species, *Clostridium difficile* and other *Clostridium* species, *Listeria monocytogenes* and other *Listeria* species, *Corynebacterium diptheriae* and other *Corynebacterium* species.

According to another embodiment, the present invention comprises administering to the subject one or more additional therapeutic antibacterial agents other than a compound of the present invention.

According to another embodiment, the invention comprises administering to said subject one or more additional therapeutic agents either as part of a multiple dosage form together with said compound or as a separate dosage form, wherein said one or more additional therapeutic agents include an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidinone, a rifamycin, or other antibiotics.

According to another embodiment, the invention comprises administering to a human one or more additional therapeutic agents either as part of a multiple dosage form together with said compound or as a separate dosage form wherein said one or more additional therapeutic agents include an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidone, a rifamycin, or other antibiotics.

According to another embodiment, the invention comprises administering to said subject one or more additional therapeutic agents either as part of a multiple dosage form together with said compound or as a separate dosage form wherein said one or more additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Piperacillin, Piperacillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, Ceftaroline and Ceftolozane, from a Cephamycin including Cefotetan and Cefoxitin, from a carbapenem including Imipenem, Doripenem and Meropenem, from a monobactam including Aztreonam and Carumonam, from a quinolone including Cinoxacin, Nalidixic acid, Oxolinincacid and Pipemidic acid, from a fluoroquinolone including Cirpofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin, Plazomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline, Tigecycline and Tetracycline, from a glycopeptide including Oritavancin, Teicoplanin, Dalbavancin, Telavancin and Vancomycin, from a streptogramin including Dalfopristin/quinupristin, from an oxazolidone including Linezolid, from a Rifamycin including Rifabutin and Rifampin and from other antibiotics including bactitracin, chloramphenicol, clindamycin, isoniazid, metronidazole, polymyxin B, pyrazinamide, and trimethoprim/sulfamethoxazole.

According to another embodiment, the invention comprises administering to a human one or more additional therapeutic agents either as part of a multiple dosage form together with said compound or as a separate dosage form wherein said one or more additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, from a Cephamycin including Cefotetan and Cefoxitin, from a carbapenem including Imipenem and Meropenem, from a monobactam including Aztreonam, from a quinolone including Cinoxacin, Nalidixic acid, Oxolinincacid and Pipemidic acid, from a fluoroquinolone including Cirpofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, chloramphenicol, clindamycin, isoniazid, metronidazole, polymyxin B, pyrazinamide, and trimethoprim/sulfamethoxazole.

According to another embodiment, the present invention provides a method of preventing, treating, or lessening the severity of a bacterial infection in a subject wherein the bacterial infection to be treated or prevented is selected from one or more of the following: upper respiratory infections, lower respiratory infections, ear infections, pleuropulmonary and bronchial infections, urinary tract infections, intraabdominal infections, cardiovascular infections, a blood stream infection, sepsis, CNS infections, skin and soft tissue infections, GI infections, bone and joint infections, genital infections, eye infections, or granulomatous infections.

In another embodiment, the bacterial infection to be treated is selected from one or more of the following: pharyngitis, sinusitis, otitis externa, otitis media, bronchitis, empyema, pneumonia, cystitis and pyelonephritis, renal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, or an infection of febrile neutropenic subjects.

According to another embodiment, the invention provides a method for treating or preventing a susceptible bacterial organism in a subject wherein said method further comprises the step of administering to said patient an additional therapeutic agent either as part of a multiple dosage form together with said compound or as a separate dosage form.

According to another embodiment, the invention provides a method for treating or preventing a susceptible bacterial organism in a subject wherein said method further comprises the step of administering to said subject an agent that increases the susceptibility of bacterial organisms to antibiotics.

According to another embodiment of the present invention, the methods further comprise the step of administering to a subject one or more additional therapeutic agents that increase the susceptibility of the bacterial organisms to antibiotics. For example, where a compound of the invention is administered with a beta-lactam such as a monobactam, penicillin, carbapenem, cephamycin or cephalosporin.

According to another embodiment of the present invention, the methods further comprise the step of administering to a subject one or more additional therapeutic agents that increase the susceptibility of bacterial organisms to antibiotics including a biofilm inhibitor.

In another embodiment, the pharmaceutical compositions and methods of this invention will be useful generally for controlling bacterial infections in vivo caused by the following organisms: *Pseudomonas aeruginosa* and other *Pseudomonas* species, *Stenotrophomonas maltophilia*, *Burkholderia cepacia* and other *Burkholderia* species, *Acinetobacter baumannii* and other *Acinetobacter* species, *Achromobacter xylosoxidans, Alcaligenes denitrificans* and other Achromobacteraceae, *Citrobacter freundii* and other *Citrobacter* species, *Campylobacter jejuni, Klebsiella pneumoniae, Klebsiella oxytoca* and other *Klebsiella* species, *Enterobacter cloacae, Enterobacter aerogenes* and other *Enterobacter* species, *Escherichia coli, Salmonella enterica* and other *Salmonella* species, *Yersinia pestis, Proteus vulgaris* and other *Proteus* species, *Serratia marscens* and other *Serratia* species, *Morganella morganii* and other members of the Enterobacteriaceae family, *Neisseria meningitidis, Haemophilus influenzae, Moraxella cattharallis, Bacte-*

*roides fragilis, Bacteroides thetaiotaomicron* and other *Bacteroides* species, *Pasteurella multicoda* and other *Pasteurella* species, *Fransicella tularensis, Shigella dysenteriae* and other *Shigella* species, *Vibrio cholera* and other *Vibrio* species, *Bordetella pertussis* and other *Bordetella* species, *Helicobactor pylori* and other *Helicobacter* species, *Legionella pneumophila, Campylobactor jejuni, Staphylococcus aureus, Staphylococcus epidermidis* and other *Staphylococcus* species, *Enterococcus faecalis, Enterococcus faecium* and other *Enterococcus* species, *Streptococcus pneumoniae, Streptococcus pyogenes, Streptococcus agalactiae* and other *Streptococcus* species, *Bacillus anthracis* and other *Bacillus* species, *Peptostreptococcus magnus* and other *Peptostreptococcus* species, *Clostridium difficile* and other *Clostridium* species, *Listeria monocytogenes* and other *Listeria* species, *Corynebacterium diptheriae* and other *Corynebacterium* species.

In another embodiment, the pharmaceutical compositions and methods of this invention will be useful generally for controlling bacterial infections in vivo caused by the following organisms: *Streptococcus pneumoniae, Streptococcus pyogenes, Enterococcus faecalis, Enterococcus faecium, Staphylococcus aureus*, Coag. Neg. Staph, *Bacillus anthracis, Staphylococcus epidermidis, Staphylococcus saprophyticus,* or *Mycobacterium tuberculosis.*

The compositions and methods will therefore be useful for controlling, treating or reducing the advancement, severity or effects of nosocomial or non-nosocomial infections.

Examples of nosocomial and non-nosocomial infections include but are not limited to upper respiratory infections, lower respiratory infections, ear infections, pleuropulmonary and bronchial infections, urinary tract infections, intra-abdominal infections, cardiovascular infections, cardiovascular infections, blood stream infection, sepsis, CNS infections, skin and soft tissue infections, GI infections, bone and joint infections, genital infections, or granulomatous infections. Examples of specific bacterial infections include but are not limited to pharyngitis, sinusitis, otitis externa, otitis media, bronchitis, empyema, pneumonia, cystitis and pyelonephritis, renal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, or an infection of febrile neutropenic subjects.

Most preferably, the pharmaceutically acceptable compositions of this invention are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium, Klebsiella pneumoniae, Enterobacter* sps., *Proteus* sps., *Pseudomonas aeruginosa, E. coli, Serratia marcesens, Staphylococcus aureus*, Coag. Neg. Staph, *Haemophilus influenzae, Bacillus anthracis, Mycoplasma pneumoniae, Moraxella catarrahs, Chlamydia pneumoniae, Legionella pneumophila, Mycobacterium tuberculosis, Staphylococcus epidermidis,* or *Helicobacter pylori.*

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of resistant bacterial infections caused by bacteria such as Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant Streptococcuspneumoniae, Vancomycin resistant *Enterococcus faecalis*, Linezolid resistant *Enterococcus faecalis*, Fluoroquinolone resistant *Enterococcus faecalis*, Vancomycin-resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistent Coagulase negative staphylcocci, Fluoroquinolone resistant Coagulase negative staphylcocci, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *staphylococcus epidermidis*.

The pharmaceutical compositions of this invention will be administered from about 1 to 5 times per day or alternatively, as a continuous infusion. Or, alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In an embodiment that comprises a combination of a compound of formula I-VI and one or more additional therapeutic or prophylactic agents, both the compound and the additional agent should be present at dosage levels of between about 10% to 80% of the dosage normally administered in a monotherapy regime.

The skilled artisan will appreciate, lower or higher doses than those recited above may be required. Specific dosage and treatment regimens for any particular subject will depend upon the judgment of the treating physician.

Pharmaceutical Activity

The activity of a compound according to the present invention can be assessed by the in vitro and in vivo methods.

Method 1: Supercoiling Assay of *E. Coli* Gyrase

Enzymatic activity of *E. coli* DNA gyrase reconstituted from its purified subunits was assessed by monitoring the introduction of supercoils into the relaxed plasmid pHOT-1

(TopoGEN, TG2035-3). To form the functional gyrase A2B2 heterotetrameric enzyme, equal molar concentrations of the GyrA and GyrB subunits were combined at high protein concentration (500 nM) and incubated on ice for 1 hour prior to assay start in reaction buffer without ATP or the pHOT-1 plasmid. The reaction mixture (25 µl) contained 10 nM enzyme, 10 ng/µl pHOT-1, 1 mM ATP, 35 mM Tris-HCl pH 7.5, 24 mM KCl, 4 mM MgCl2, 2 mM DTT, 1.8 mM spermidine, 6.5% glycerol, and 100 µg/ml bovine serum albumin. The reaction was carried out at 37° C. for 90 minutes and terminated by the addition of 2.5 µl of 10× stop solution (0.9% SDS, 50% glycerol, 0.05% bromophenol blue). Five microliters of each reaction mixture was loaded onto a 1% agarose gel in 0.5×TBE buffer (Tris 44.5 mM, boric acid 44.5 mM, EDTA 1.25 mM pH 8.3) and run for 40 minutes (120 V/80 mA). Gels were stained with ethidium bromide (0.5 µg/ml) for 30 minutes and destained in water for 20 minutes. All gels were analyzed using the BIO-RAD ChemiDocTm XRS+ with Image Lab 3.0 software. The 50% inhibition concentration ($IC_{50}$) was determined as being the compound concentration at which the supercoiled band was reduced by 50% from the DMSO drug free control (Microsoft Excel 2010 IDBS XLfit, GraftPad Prism 6).

Method 2: Decatenation Assay of E. Coli Topo IV

Enzymatic activity of the E. coli DNA topoisomerase IV (Topo IV) reconstituted from its purified subunits was monitored by the decatenation of kinetoplast DNA into minicircles (kDNA, TopoGEN, TG2013-3). To form the functional Topo IV $C_2E_2$ heterotetrameric enzyme, equal molar concentrations of the ParC and ParE subunits were combined at high protein concentration (500 nM) and incubated on ice for 1 hour prior to assay start in reaction buffer without ATP or the kDNA. The reaction mixture (25 µl) contained 12.5 nM enzyme, 5 ng/µl kDNA (at Km), 1 mM ATP (in excess of Km), 35 mM Tris-HCl pH 7.5, 24 mM KCl, 4 mM $MgCl_2$, 2 mM DTT, 1.8 mM spermidine, 6.5% glycerol, and 100 µg/ml bovine serum albumin. The reaction was carried out at 37° C. for 2 hours and terminated by the addition of 2.5 µl of 10× stop solution (0.9% SDS, 50% glycerol, 0.05% bromophenol blue). Five microliters of each reaction mixture was loaded onto a 1% agarose gel in 0.5×TBE (Tris 44.5 mM, boric acid 44.5 mM, EDTA 1.25 mM pH 8.3) and run for 40 minutes (120 V/80 mA). Gels were stained with ethidium bromide (0.5 µg/ml) for 30 minutes and destained in water for 20 minutes. All gels were analyzed using the BIO-RAD ChemiDoc™ XRS+ with Image Lab 3.0 software. The 50% inhibitor concentration ($IC_{50}$) was determined as being the compound concentration at which the presence of the kDNA minicircles in the gel was reduced by 50% from the DMSO drug free control (Microsoft Excel 2010 IDBS XLfit, Graph Pad Prism 6).

The compounds of present invention were found to inhibit the supercoiling/decatenation activity of the E. coli gyrase/Topoisomerase IV with exemplary $IC_{50}$ values listed in Table 1.

TABLE 1

$IC_{50}$ (µM) of compounds of the invention as inhibitors of the supercoiling/decatenation activity of the E. coli gyrase(GyrA-B) and topoIV(ParC-E)

| Example # | GyrA-B IC50 (Enzyme) | ParC-E IC50 (Enzyme) |
|---|---|---|
| 1.1 | 0.68 | NA |
| 8 | 1.68 | NA |
| 9.1 | 1.3 | 9.91 |
| 9.2 | 1.19 | NA |
| 9.3 | 11.9 | >100 |
| 10 | 1.2 | 1.93 |
| 11.2 | 8.07 | NA |
| 12 | 4.64 | NA |
| 25 | 1.03 | 6.46 |
| 27 | 0.13 | 0.59 |
| 30 | 0.98 | 14.56 |
| 33 | 16.3 | NA |
| 34 | 0.44 | 5.14 |
| 39 | 9.8 | NA |
| 42 | 0.83 | 1.86 |
| 43 | 0.56 | 3.35 |
| 45 | <0.10 | 0.24 |
| 64 | 3.2 | NA |
| 73 | 3.01 | 4.97 |
| 74 | 0.31 | 0.24 |
| 76 | 6.8 | 38.52 |
| 79 | 2.44 | 1.84 |

Method 3: Assessment of Antibacterial Activity In Vitro

Bacterial isolates were cultivated from −70° C. frozen stocks by two consecutive overnight passages at 35° C. in ambient air on 5% blood agar (Remel, Lenexa, Kans.). The following quality control and wild type strains were obtained from the American Type Culture Collection (ATCC; Rockville, Md.) and are coded in the Novartis strain collection as indicated: E. coli ATCC 25922 (NB27001) and S. aureus ATCC 29213 (NB01001). E. coli NB27177, obtained from the Coli Genetic Stock Center at Yale University (New Haven, Conn.), is the efflux deficient CGSC 11430 strain carrying the ΔtolC732::kan mutation. P. aeruginosa NB52019, obtained from Queen's University (Kingston, Ontario, Canada), is the wild-type PAO1 strain. P. aeruginosa NB52023, obtained from Queen's University, is the efflux deficient K1542 strain carrying ΔmexX ΔmexB mutations. P. aeruginosa NB52023-CDK0006, derived from P. aeruginosa NB52023 by site-directed mutagenesis, carries mutations resulting in amino acid substitutions in gyrA (T83I) and parC (S87L). S. aureus NB01006-AVR005, derived from S. aureus ATCC 49951 by selection on ciprofloxacin-containing Mueller Hinton agar, carries mutations resulting in amino acid substitutions in gyrA (S84L), grlA (S80F) and grlB (E471K).

Minimal Inhibitory Concentrations (MIC) were determined by the broth microdilution method in accordance with Clinical and Laboratories Institute (CLSI) guidelines. In brief, fresh bacterial overnight cultures were re-suspended in sterile saline, adjusted to a 0.5 McFarland turbidity standard and then diluted 200-fold in cation adjusted Mueller-Hinton Broth II (MHB; Remel BBL) to yield a final inoculum of approximately $5 \times 10^5$ colony-forming units (CFU)/mL. Two-fold serial dilutions of compounds were prepared in 100% dimethyl sulfoxide (DMSO) at 100-fold the highest final assay concentration; the resulting dilution series of compounds were diluted 1:10 with sterile water. Ten µl of the drug dilution series in 10% DMSO was transferred to microtiter wells and 90 µl of bacterial suspension was inoculated into the wells. All inoculated microdilution trays were incubated in ambient air at 35° C. for 20 hours. Following incubation, assay plates were read in a microtiter plate reader at 600 nm and visually inspected to confirm the MIC endpoint well with the OD value. The lowest concentration of the compound that prevented visible growth was recorded as the MIC (in μg/mL). Performance of the assay was monitored by testing ciprofloxacin against laboratory quality control strains in accordance with guidelines of the CLSI.

TABLE 2

Antibacterial activity (μg/mL) of compounds of the invention.

| Example # | NB27001 | NB27177 | NB52019 | NB52023 | NB52023-CDK0006 | NB01001 | NB01006-AVR005 |
|---|---|---|---|---|---|---|---|
| 1.1 | 8 | 0.25 | 32 | 8 | >32 | 0.125 | 2 |
| 6 | 2 | 0.125 | 32 | 8 | 32 | 0.125 | 0.5 |
| 7 | 32 | 0.25 | >32 | >32 | >32 | 2 | 4 |
| 9.1 | 1 | <0.03 | 16 | 4 | 8 | 0.06 | 0.06 |
| 9.2 | 4 | 0.06 | >32 | 16 | 32 | 0.125 | 0.125 |
| 9.3 | 4 | 0.25 | 32 | 16 | 16 | 16 | 16 |
| 10 | 4 | <0.03 | >32 | 4 | 8 | 0.25 | 0.25 |
| 11.1 | 8 | 0.25 | >32 | 32 | >32 | 0.25 | 0.25 |
| 11.2 | 8 | 0.125 | >32 | 16 | >32 | 1 | 2 |
| 18 | 32 | 0.125 | 32 | 8 | 16 | 0.5 | 0.25 |
| 19 | 32 | 0.5 | >32 | >32 | >32 | 0.5 | 0.5 |
| 20 | 32 | 0.125 | >32 | 32 | 16 | 0.5 | 0.25 |
| 21 | 16 | 0.125 | >32 | 32 | 32 | 0.125 | 0.125 |
| 22 | 32 | 8 | >32 | >32 | >32 | 8 | 8 |
| 24 | 8 | 0.06 | >32 | >32 | >32 | 0.06 | 0.06 |
| 25 | 4 | 0.06 | 8 | 2 | 4 | 0.06 | <0.03 |
| 26 | 32 | 1 | >32 | 16 | 32 | 1 | 0.25 |
| 27 | 1 | <0.03 | 4 | 1 | 2 | <0.03 | <0.03 |
| 28 | 2 | <0.03 | 16 | 2 | 0.5 | <0.03 | <0.03 |
| 29 | 1 | 0.03 | 8 | 2 | 4 | 0.125 | 0.125 |
| 30 | 1 | <0.03 | 8 | 1 | 4 | 0.5 | 0.5 |
| 31 | 2 | <0.03 | 8 | 2 | 4 | 0.06 | 0.06 |
| 32 | 4 | 0.125 | 32 | 16 | 32 | 4 | 2 |
| 33 | 32 | 16 | 32 | >32 | >32 | 32 | >32 |
| 34 | 32 | 2 | >32 | 16 | 16 | 4 | 4 |
| 35 | 4 | <0.03 | 8 | 8 | 8 | 0.06 | 0.06 |
| 36 | 16 | 1 | >16 | 16 | >16 | 2 | 1 |
| 37 | 32 | 4 | 32 | >32 | >32 | 8 | 16 |
| 38 | 32 | 2 | >32 | 32 | >32 | 4 | 4 |
| 39 | 32 | 32 | 32 | >32 | >32 | 32 | >32 |
| 40 | 4 | 0.5 | 16 | 4 | 8 | 4 | 4 |
| 41 | 4 | 0.125 | 16 | 4 | 8 | 0.5 | 0.5 |
| 42 | 8 | 0.25 | >32 | 8 | 32 | 0.5 | 0.5 |
| 43 | 32 | 4 | >32 | >32 | >32 | 8 | 16 |
| 44 | 2 | 0.03 | 8 | 4 | 8 | 0.06 | 0.03 |
| 45 | 1 | 0.06 | 2 | 0.5 | 2 | 0.25 | 0.5 |
| 46 | 32 | 2 | 32 | >32 | >32 | 8 | 2 |
| 47 | 16 | 0.25 | 16 | 4 | 8 | 0.25 | 0.25 |
| 48 | 8 | 0.06 | 32 | 16 | 16 | 0.125 | 0.125 |
| 49 | 1 | 0.06 | 8 | 4 | 8 | 0.125 | 0.25 |
| 50 | 32 | 0.125 | >32 | >32 | >32 | 1 | 2 |
| 51 | 2 | 0.06 | 4 | 2 | 2 | 0.5 | 0.5 |
| 53 | 4 | 0.125 | 16 | 4 | 4 | 0.5 | 0.5 |
| 54 | 32 | 4 | 32 | >32 | >32 | 8 | 4 |
| 55 | 8 | 0.125 | >32 | 32 | 32 | 0.5 | 0.5 |
| 56 | 32 | 2 | >32 | 16 | >32 | 4 | 4 |
| 57 | 32 | 0.25 | >32 | 16 | >32 | 0.25 | 0.25 |
| 58 | 32 | 1 | >32 | 32 | 32 | 4 | 2 |
| 60 | 32 | 1 | >32 | >32 | >32 | 8 | 4 |
| 61 | 32 | >32 | 32 | >32 | >32 | >32 | >32 |
| 64 | 32 | 4 | >32 | >32 | >32 | 8 | 4 |
| 65 | 32 | 4 | >32 | >32 | >32 | 4 | 2 |
| 66 | 32 | 2 | >32 | >32 | >32 | 4 | 4 |
| 67 | 8 | 0.06 | 32 | 8 | 16 | 0.06 | 0.06 |
| 68 | 32 | 0.25 | >32 | >32 | >32 | 0.5 | 1 |
| 69 | 32 | 0.5 | >32 | >32 | >32 | 2 | 2 |
| 70 | 32 | 2 | 32 | >32 | >32 | 16 | 4 |
| 71 | 32 | 6 | >32 | >32 | >32 | 2 | 6 |
| 72 | 32 | 16 | 32 | >32 | >32 | 16 | 8 |
| 73 | 32 | 2 | >32 | >32 | >32 | 1 | 4 |
| 74 | 8 | 0.25 | 32 | 8 | 16 | 1 | 2 |
| 75 | 32 | 0.5 | >32 | 32 | >32 | 8 | 8 |
| 76 | 4 | 0.125 | 32 | 8 | 16 | 0.25 | 0.5 |
| 77 | 32 | 0.5 | >32 | >32 | >32 | 4 | 32 |
| 78 | 32 | 1 | >32 | >32 | >32 | 8 | 16 |
| 79 | 8 | 1 | >32 | >32 | >32 | 2 | 8 |
| 80 | 32 | 2 | >32 | >32 | >32 | 1 | 2 |
| 81.09 | 2 | 0.5 | 4 | 0.5 | 2 | 16 | 16 |
| 81.23 | 0.25 | 0.06 | 4 | 0.5 | 1 | 0.5 | 0.5 |
| 81.32 | 0.5 | <0.03 | 4 | 0.25 | 1 | 0.5 | 1 |

TABLE 2-continued

Antibacterial activity (μg/mL) of compounds of the invention.

| Example # | NB27001 | NB27177 | NB52019 | NB52023 | NB52023-CDK0006 | NB01001 | NB01006-AVR005 |
|---|---|---|---|---|---|---|---|
| 81.33 | 0.5 | 0.06 | 2 | 0.5 | 1 | 0.5 | 1 |
| 83 | 0.125 | <0.03 | 2 | 0.25 | 0.5 | 0.125 | 0.125 |
| 83.6 | 0.5 | 0.06 | 4 | 0.25 | 0.5 | 1 | 2 |
| 87 | 8 | 0.5 | 16 | 4 | 8 | 0.5 | 0.25 |
| 88 | 4 | 0.25 | 16 | 2 | 4 | 1 | 2 |
| 89 | 4 | 0.5 | >32 | 16 | 32 | 1 | 4 |
| 90 | 16 | NA | >32 | 32 | 32 | 0.125 | 0.125 |
| 91 | 8 | 1 | 16 | 8 | 16 | 1 | 1 |
| 93 | 8 | 1 | 8 | 4 | 8 | 2 | 16 |
| 96 | 2 | NA | 32 | 8 | 8 | 0.5 | 1 |
| 99 | 4 | 0.125 | >32 | 2 | 4 | 0.125 | 0.06 |
| 100 | 32 | 2 | >32 | 8 | 16 | 8 | 4 |
| 101 | 8 | 0.125 | >32 | 8 | 16 | 0.5 | 0.125 |
| 106 | 0.125 | <0.03 | 2 | 0.5 | 1 | 0.015 | 0.015 |
| 110 | 4 | NA | >32 | 16 | 32 | 0.25 | 0.125 |
| 111 | 8 | 2 | >32 | 8 | 16 | 8 | 8 |
| 113 | 0.5 | 0.125 | 16 | 2 | 4 | 8 | 16 |
| 114 | 2 | 0.5 | 16 | 2 | 4 | 16 | 32 |
| 115 | 1 | 0.5 | >32 | 8 | 16 | 2 | 4 |
| Cipro | 0.008 | 0.002 | 0.12 | 0.03 | 4 | 0.25 | 64 |

Note:
Cipro = ciprofloxacin, included as a standard. The MICs for Cipro are mode values from about 100 assays.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound of formula (I):

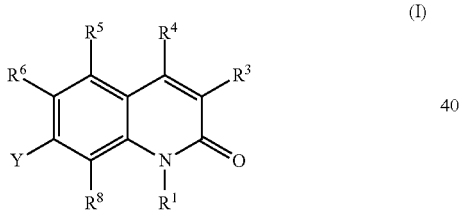

wherein:
R$^1$ is selected from the group consisting of C$_1$-C$_6$ alkyl, C$_2$-C$_6$ alkynyl, and C$_3$-C$_7$ cycloalkyl, each of which is optionally substituted with up to three groups selected from halogen, —OR$^2$, CN, —N(R$^2$)$_2$, and oxo;

R$^3$ is selected from the group consisting of -L$^1$-OR$^2$, C$_1$-C$_6$ alkyl, C$_2$-C$_6$ alkenyl, C$_2$-C$_6$ alkynyl, C$_3$-C$_7$ cycloalkyl, -L$^1$-CN, -L$^1$-N(R$^2$)$_2$, -L$^1$-COOR$^2$; -L$^1$-CON(R$^2$)$_2$, -L$^1$-N(R$^2$)C(O)R$^2$, -L$^1$-N(R$^2$)C(O)OR, -L$^1$-SO$_2$R, -L$^1$-N(R$^2$)—SO$_2$—R, and -L$^1$-SO$_2$—N(R$^2$)$_2$;

L$^1$ is a bond or a C$_1$-C$_4$ straight or branched chain alkylene linker;

each R is independently C$_1$-C$_4$ alkyl optionally substituted with one to three groups selected from halogen, —OH, C$_1$-C$_4$ alkoxy, CN, —NH$_2$, —NH(C$_1$-C$_4$ alkyl), —N(C$_1$-C$_4$ alkyl)$_2$, —SO$_2$(C$_1$-C$_4$ alkyl), and oxo;

each R$^2$ is independently H or C$_1$-C$_4$ alkyl optionally substituted with up to three groups selected from halogen, —OH, C$_1$-C$_4$ alkoxy, CN, —NR$^{12}$R$^{13}$, —SO$_2$R and oxo;

or two R$^2$ on the same nitrogen can be taken together to form a 4-6 membered heterocyclic ring optionally containing an additional heteroatom selected from N, O and S as a ring member and optionally substituted with up to three groups selected from halogen, —OH, C$_1$-C$_4$ alkyl, C$_1$-C$_4$ alkoxy, CN, —NR$^{12}$R$^{13}$, and oxo;

R$^4$ is selected from the group consisting of H, halo, C$_1$-C$_4$ haloalkyl, —NH$_2$, —CN, C$_1$-C$_6$ alkyl, C$_2$-C$_6$ alkenyl, C$_2$-C$_6$ alkynyl, C$_1$-C$_6$ alkoxy, -L$^2$-C$_3$-C$_7$ cycloalkyl, -L$^2$-CN, -L$^2$-N(R$^2$)$_2$, -L$^2$-NR$^2$C(O)—R$^2$, -L$^2$-NR$^2$C(O)—OR$^2$, -L$^2$-NR$^2$C(O)—N(R$^2$)$_2$, -L$^2$-NR$^2$C(=NR$^2$)—N(R$^2$)$_2$, -L$^2$-C(O)—NR$^2$—OR$^2$, -L$^2$-COOR$^2$, -L$^2$-CON(R$^2$)$_2$, -L$^2$-C(=NR$^2$)—N(R$^2$)$_2$, -L$^2$-C(=NR$^2$)—NR$^2$—OR$^2$, -L$^2$-SO$_2$R, -L$^2$-SO$_2$—N(R$^2$)$_2$, -L$^2$-Q, and -L$^2$-O—(C$_1$-C$_4$ alkyl), wherein the C$_1$-C$_4$ alkyl is optionally substituted with one or two groups selected from —OR$^2$, —CN, oxo, =N—OR$^2$, —N(R$^2$)$_2$, —COOR$^2$, —C(=X)—NR$^2$—OR$^2$, —C(=X)—N(R$^2$)$_2$, —NR$^2$C(=X)R$^2$, —NR$^2$C(=X)OR, —NR$^2$C(=X)N(R$^2$)$_2$, —NR$^2$C(O)—O-L$^2$-Q, —CON(R$^2$)$_2$, —SO$_2$R, —SO$_2$—N(R$^2$)$_2$, —NR$^2$—SO$_2$R, and Q;

wherein each Q is an optionally substituted ring selected from phenyl and a 5-6 membered heteroaryl or heterocyclyl ring containing up to four heteroatoms selected from N, O and S as ring members, wherein the optional substituents for the optionally substituted ring are up to three groups selected from C$_1$-C$_4$ alkyl, C$_1$-C$_4$ alkoxy, halo, oxo, =N—OR$^2$, —COOR$^2$, —CON(R$^2$)$_2$, —NR$^2$C(O)R$^2$, —NR$^2$C(O)OR, —C(O)NR$^2$—OR$^2$, —SO$_2$R, and —SO$_2$—N(R$^2$)$_2$, and each L$^2$ is independently selected from a bond and a divalent straight chain or branched C$_1$-C$_6$ alkyl, C$_2$-C$_6$ alkenyl, or C$_2$-C$_6$ alkynyl linking group;

and each X is independently O or =NR$^{11}$;

R$^5$ is selected from the group consisting of H, halo, amino, CN, C$_1$-C$_4$ alkyl, C$_{2-4}$ alkenyl, C$_{2-4}$ alkynyl, 5-6 membered heteroaryl containing 1-3 heteroatoms selected from N, O and S, C$_1$-C$_4$ alkoxy, and C$_1$-C$_4$ haloalkyl;

$R^6$ is selected from the group consisting of H, halo, CN, $C_1$-$C_4$ alkyl, $C_1$-$C_4$ alkoxy, and $C_1$-$C_4$ haloalkyl;

Y is pyridinyl optionally substituted with one to three groups selected from halo, CN, amino, hydroxy, $C_1$-$C_4$ alkyl, $C_1$-$C_4$ alkoxy, $C_1$-$C_4$ haloalkyl, and —(CH$_2$)$_{1-4}$—X, where X is selected from —OH, —CN, —N(R$^2$)$_2$, —COOR$^2$, —C(O)N(R$^2$)$_2$, —NR$^2$C(O)R$^2$, —NR$^2$C(O)OR, —SO$_2$R, and —SO$_2$N(R$^2$)$_2$;

or Y is a group of the formula —NR$^{7A}$R$^{7B}$, wherein R$^{7A}$ is selected from the group consisting of H, —C(O)R$^2$, —C(O)OR$^2$, and $C_1$-$C_6$ alkyl optionally substituted with up to two groups independently selected from halogen, —OH, $C_1$-$C_4$ haloalkyl, $C_1$-$C_4$ alkoxy, oxo, =N—OR$^2$, —N(R$^2$)$_2$, $C_3$-$C_7$ cycloalkyl, —COOR$^2$, —C(O)N(R$^2$)$_2$, —NR$^2$C(O)R$^2$, —NR$^2$C(O)OR, and a 4-6 membered heteroaryl or heterocyclyl group that contains up to two heteroatoms selected from N, O and S as ring members and is optionally substituted with up to two groups selected from hydroxy, amino, halogen, $C_1$-$C_4$ alkyl, $C_1$-$C_4$ haloalkyl, and $C_1$-$C_4$ alkoxy;

R$^{7B}$ is -L$^3$-Q$^3$;

wherein L$^3$ is a bond or a straight or branched chain $C_1$-$C_6$ alkyl linker, and Q$^3$ is selected from pyridinyl and a 4-7 membered heterocyclyl containing one or two heteroatoms selected from N, O and S as ring members, and wherein Q$^3$ is optionally substituted with up to three groups selected from halogen, CN, —OH, $C_1$-$C_4$ alkyl, $C_1$-$C_4$ haloalkyl, $C_1$-$C_4$ alkoxy, oxo, =N—OR$^2$, —N(R$^2$)$_2$, —COOR$^2$, —C(O)N(R$^2$)$_2$, —NR$^2$C(O)R$^2$, —NR$^2$C(O)OR;

or R$^{7A}$ and R$^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by R$^{7A}$ and R$^{7B}$ together with the nitrogen atom to which they are attached is optionally substituted by up to four groups selected from halogen, —CN, hydroxy, phenyl, oxo, —OR$^9$, —N(R$^9$)$_2$, —COOR$^9$, —C(O)N(R$^9$)$_2$, $C_1$-$C_4$ alkyl, $C_1$-$C_4$ haloalkyl, $C_1$-$C_4$ alkoxy, oxo, $C_3$-$C_6$ cycloalkyl, and a 4-6 membered heteroaryl or heterocyclyl group that contains up to two heteroatoms selected from N, O and S as ring members, wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —OR$^{10}$, =N—OR$^{10}$, —N(R$^{10}$)$_2$, —COOR$_{10}$, —N(R$^{10}$)—C(O)—O—(C$_1$-$C_4$ alkyl), —C(O)N(R$^{10}$)$_2$, $C_1$-$C_4$ alkyl, $C_1$-$C_4$ haloalkyl, and $C_1$-$C_4$ alkoxy;

R$^8$ is selected from the group consisting of H, halo, CN, $C_1$-$C_4$ alkyl optionally substituted with hydroxy or amino, $C_{2-4}$ alkenyl, $C_1$-$C_4$ alkoxy, and $C_1$-$C_4$ haloalkyl;

R$^9$ and R$^{10}$ are each independently selected from H and $C_1$-$C_4$ alkyl optionally substituted with up to three groups selected from halogen, —OH, $C_1$-$C_4$ alkoxy, CN, —NR$^{12}$R$^{13}$, —SO$_2$R and oxo;

or two R$^9$ or two R$^{10}$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —NR$^{12}$R$^{13}$, and oxo;

each R$^{11}$ is independently hydrogen or $C_1$-$C_4$ alkyl optionally substituted with one or two groups selected from halogen, —OH, $C_1$-$C_4$ alkoxy, CN, —NH$_2$, —NH(C$_1$-$C_4$ alkyl), —N(C$_1$-$C_4$ alkyl)$_2$, —SO$_2$(C$_1$-$C_4$ alkyl), and oxo;

each R$^{12}$ and R$^{13}$ is independently hydrogen or $C_1$-$C_4$ alkyl optionally substituted with one or two groups selected from halogen, —OH, $C_1$-$C_4$ alkoxy, CN, —NH$_2$, —NH(C$_1$-$C_4$ alkyl), —N(C$_1$-$C_4$ alkyl)$_2$, —SO$_2$(C$_1$-$C_4$ alkyl), and oxo;

or R$^{12}$ and R$^{13}$ together with the nitrogen atom to which they are attached form a 4- to 6-membered heterocyclyl optionally including an additional heteroatom selected from N, O and S as a ring member and optionally substituted by one to three substituents selected from OH, halogen, oxo, =N—OR$^{11}$, $C_1$-$C_6$ alkyl optionally substituted by one to three halogen atoms or NH$_2$, $C_1$-$C_6$ alkoxy optionally substituted by one or more OH groups or $C_1$-$C_6$ alkoxy; and —C(O)OC$_1$-$C_6$ alkyl;

or a pharmaceutically acceptable salt thereof.

2. The compound according to claim 1, wherein R$^1$ is $C_3$-$C_6$ cycloalkyl or $C_2$-$C_4$ alkyl.

3. The compound according to claim 1, wherein R$^5$ is H or halogen.

4. The compound of claim 1, wherein R$^6$ is H or F.

5. The compound of claim 1, wherein R$^8$ is methyl or methoxy.

6. The compound of claim 1, wherein R$^3$ is halo, $C_{1-2}$ alkyl, or $C_{1-2}$ haloalkyl.

7. The compound of claim 1, wherein R$^4$ is H.

8. The compound of claim 1, wherein R$^4$ is —CH$_2$NH$_2$.

9. The compound of claim 1, which is of the formula (II):

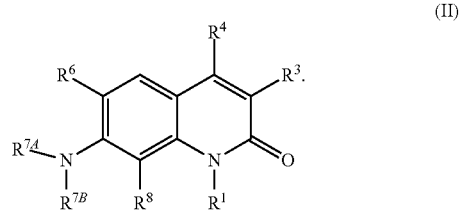

(II)

10. The compound according to claim 9, wherein R$^{7A}$ is H.

11. The compound according to claim 9, wherein R$^{7A}$ and R$^{7B}$ together with the nitrogen atom to which they are attached form a 4- to 7-membered monocyclic heterocyclic group optionally including one additional heteroatom selected from N, O and S as a ring member, or a 6-10 membered bicyclic heterocyclic group optionally including one or two additional heteroatoms selected from N, O and S as ring members, wherein the monocyclic or bicyclic heterocyclic group formed by R$^{7A}$ and R$^{7B}$ together with the nitrogen atom to which they are attached is optionally substituted by up to three groups selected from halogen, —CN, hydroxy, phenyl, oxo, —OR$^9$, —N(R$^9$)$_2$, —COOR$^9$, —C(O)N(R$^9$)$_2$, $C_1$-$C_4$ alkyl, $C_1$-$C_4$ haloalkyl, $C_1$-$C_4$ alkoxy, oxo, $C_3$-$C_6$ cycloalkyl, and a 4-6 membered heteroaryl or heterocyclyl group that contains up to two heteroatoms selected from N, O and S as ring members, wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —$OR^{10}$, =N—$OR^{10}$, —N($R^{10}$)$_2$, —COO$R^{10}$, —C(O)N($R^{10}$)$_2$, $C_1$-$C_4$ alkyl, $C_1$-$C_4$ haloalkyl, and $C_1$-$C_4$ alkoxy.

12. The compound of claim 1, wherein the compound is represented by formula (III):

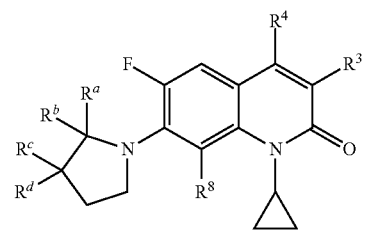

(III)

wherein, $R^3$ is —C(O)O$R^2$, halo, $C_{1-2}$ alkyl, or $C_{1-2}$ haloalkyl;

$R^4$ is H or CN or —CH$_2$NH$_2$;

$R^8$ is hydrogen, methyl, OMe, or CN;

$R^a$, $R^b$, $R^c$, and $R^d$ are independently selected from the group consisting of hydrogen, OH, $C_1$-$C_4$ alkyl, $C_3$-$C_5$ cycloalkyl, —NH($C_1$-$C_4$ alkyl), and —N($C_1$-$C_4$ alkyl)$_2$, wherein each $C_1$-$C_4$ alkyl and each $C_3$-$C_5$ cycloalkyl is optionally substituted by OH, $C_1$-$C_4$ alkyl, $C_1$-$C_4$ alkoxy, or —N$R^9{}_2$; or $R^a$ and $R^b$ taken together, or $R^c$ and $R^d$ taken together, may form oxo or a 3-6 membered spirocyclic ring that may contain N, O or S as a ring member;

$R^9$ is independently at each occurrence selected from H, —C(O)—($C_1$-$C_4$ alkyl), —C(O)—O—($C_1$-$C_4$ alkyl), and $C_1$-$C_4$ alkyl, where each $C_1$-$C_4$ alkyl is optionally substituted with up to three groups selected from halogen, —OH, $C_1$-$C_4$ alkoxy, CN, —N$R^{12}R^{13}$, —SO$_2$R and oxo;

and two $R^9$ on the same nitrogen can be taken together to form a 4-6 membered heterocyclic ring optionally containing an additional heteroatom selected from N, O and S as a ring member and optionally substituted with up to three groups selected from halogen, —OH, $C_1$-$C_4$ alkyl, $C_1$-$C_4$ alkoxy, CN, —N$R^{12}R^{13}$, and oxo; and each $R^{12}$ and $R^{13}$ is independently hydrogen or $C_1$-$C_4$ alkyl optionally substituted with one or two groups selected from halogen, —OH, $C_1$-$C_4$ alkoxy, CN, —NH$_2$, —NH($C_1$-$C_4$ alkyl), —NH—C(O)($C_1$-$C_4$ alkyl), NH—C(O)—O—($C_1$-$C_4$ alkyl), —N($C_1$-$C_4$ alkyl)$_2$, —SO$_2$($C_1$-$C_4$ alkyl), and oxo.

13. The compound according to claim 1, represented by formula (V):

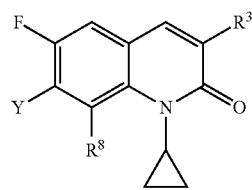

(V)

wherein, $R^3$ is $C_{1-2}$ alkyl, $C_{1-2}$ haloalkyl —C(O)OH, C(O)—O—($C_1$-$C_4$ alkyl) or —S(O)$_2$—($C_1$-$C_4$ alkyl);

$R^8$ is hydrogen, $C_1$-$C_4$ alkyl, $C_1$-$C_4$ alkoxy, or $C_1$-$C_4$ haloalkyl;

Y is selected from the group consisting of

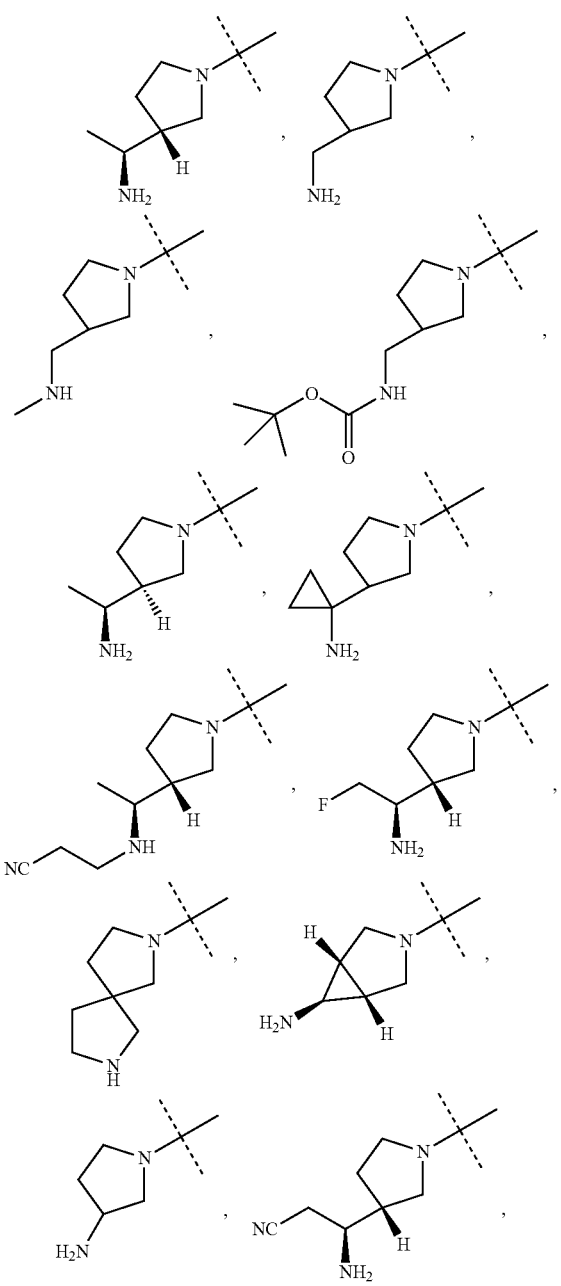

-continued

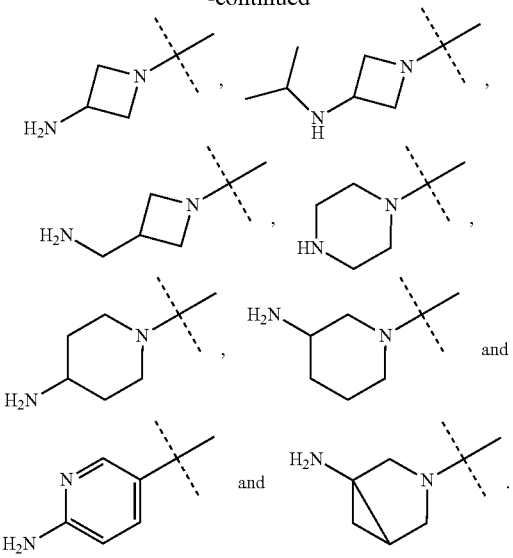

14. A compound of formula (VI):

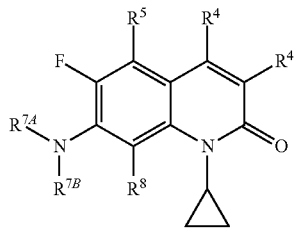

(VI)

wherein, $R^3$ is $C_{1-2}$ alkyl, $C_{1-2}$ haloalkyl or halo;
$R^4$ is hydrogen or —$CH_2NH_2$;
$R^5$ is hydrogen, Me or halo;
$R^8$ is hydrogen, $C_1$-$C_4$ alkyl, $C_1$-$C_4$ alkoxy, $C_1$-$C_4$ haloalkyl, or CN;
and $R^{7A}$ and $R^{7B}$ together with the nitrogen atom to which they are attached form a 5- to 6-membered monocyclic heterocyclic group optionally including one additional heteroatom selected from N, O and S as a ring member, or a 6-7 membered bicyclic heterocyclic group optionally including one additional heteroatom selected from N, O and S as ring members,
wherein the monocyclic or bicyclic heterocyclic group formed by $R^{7A}$ and $R^{7B}$ together with the nitrogen atom to which they are attached is optionally substituted by up to four groups selected from halogen, —CN, hydroxy, phenyl, oxo, —$OR^9$, —$N(R^9)_2$, —$COOR^9$, —$C(O)N(R^9)_2$, $C_1$-$C_4$ alkyl, $C_1$-$C_4$ haloalkyl, $C_3$-$C_6$ cycloalkyl, and a 4-6 membered heteroaryl or heterocyclyl group that contains up to two heteroatoms selected from N, O and S as ring members,
wherein the $C_1$-$C_4$ alkyl, $C_3$-$C_6$ cycloalkyl, phenyl, and 4-6 membered heteroaryl or heterocyclyl are each optionally substituted by up to three groups independently selected from halogen, —CN, hydroxy, oxo, —$OR^{10}$, =N—$OR^{10}$, —$N(R^{10})_2$, —$COOR^{10}$, —$N(R^{10})$—C(O)—O—($C_1$-$C_4$ alkyl), —C(O)N($R^{10})_2$, $C_1$-$C_4$ alkyl, $C_1$-$C_4$ haloalkyl, and $C_1$-$C_4$ alkoxy.

15. A pharmaceutical composition, comprising:
the compound of claim 1, and a
pharmaceutically acceptable carrier, adjuvant or vehicle.

16. The pharmaceutical composition according to claim 15, further comprising an additional therapeutic agent with antibacterial activity.

17. A method of inhibiting bacterial gyrase activity, comprising: contacting bacteria with a compound of claim 1.

18. A method for treating a subject having a bacterial infection, comprising: administering to the subject in need thereof an antibacterially effective amount of the compound of claim 1.

19. The method of claim 18, wherein the bacterial infection is an infection comprising at least one bacterium selected from the group consisting of *Pseudomonas aeruginosa* and other *Pseudomonas* species, *Stenotrophomonas maltophilia*, *Burkholderia cepacia* and other *Burkholderia* species, *Acinetobacter baumannii* and other *Acinetobacter* species, *Achromobacter xylosoxidans*, *Alcaligenes denitrificans* and other Achromobacteraceae, *Citrobacter freundii* and other *Citrobacter* species, *Campylobacter jejuni*, *Klebsiella pneumoniae*, *Klebsiella oxytoca* and other *Klebsiella* species, *Enterobacter cloacae*, *Enterobacter aerogenes* and other *Enterobacter* species, *Escherichia coli*, *Salmonella enterica* and other *Salmonella* species, *Yersinia pestis*, *Proteus vulgaris* and other *Proteus* species, *Serratia* marscens and other *Serratia* species, *Morganella morganii* and other members of the Enterobacteriaceae family, *Neisseria meningitidis*, *Haemophilus influenzae*, *Moraxella cattharallis*, *Bacteroides fragilis*, *Bacteroides thetaiotaomicron* and other *Bacteroides* species, *Pasteurella* multicoda and other *Pasteurella* species, *Fransicella tularensis*, *Shigella dysenteriae* and other *Shigella* species, *Vibrio cholera* and other *Vibrio* species, *Bordetella pertussis* and other *Bordetella* species, *Helicobactor pylori* and other *Helicobacter* species, *Legionella pneumophila* and *Campylobactor jejuni*, *Staphylococcus aureus*, *Staphylococcus epidermidis* and other *Staphylococcus* species, *Enterococcus faecalis*, *Enterococcus faecium* and other *Enterococcus* species, *Streptococcus pneumoniae*, *Streptococcus pyogenes*, *Streptococcus agalactiae* and other *Streptococcus* species, *Bacillus anthracis* and other *Bacillus* species, *Peptostreptococcus* magnus and other *Peptostreptococcus* species, *Clostridium difficile* and other *Clostridium* species, *Listeria monocytogenes* and other *Listeria* species, and *Corynebacterium diptheriae* and other *Corynebacterium* species.

20. A pharmaceutical composition comprising: a compound of claim 14, and a pharmaceutically acceptable carrier, adjuvant or vehicle.

21. A method for treating a subject having a bacterial infection, comprising: administering to the subject in need thereof an antibacterially effective amount of the compound of claim 14.

22. The compound of claim 1 selected from: 7-((R)-3-((S)-1-aminoethyl)pyrrolidin-1-yl)-1-cyclopropyl-6-fluoro-8-methyl-2-oxo-1,2-dihydroquinoline-3-carboxylic acid; 7-((S)-3-((S)-1-aminoethyl)pyrrolidin-1-yl)-1-cyclopropyl-6-fluoro-8-methyl-2-oxo-1,2-dihydroquinoline-3-carboxylic acid; 7-(3-aminopyrrolidin-1-yl)-1-cyclopropyl-6-fluoro-8-methyl-2-oxo-1,2-dihydroquinoline-3-carboxylic acid; 7-(3-(aminomethyl)pyrrolidin-1-yl)-1-cyclopropyl-6-fluoro-8-methyl-2-oxo-1,2-dihydroquinoline-3-carboxylic acid; 1-cyclopropyl-6-fluoro-8-methyl-7-(3-((methylamino)methyl)pyrrolidin-1-yl)-2-oxo-1,2-dihydroquinoline-3-carboxylic acid; 7-(3-aminopiperidin-1-yl)-1-cyclopropyl-6-fluoro-8-methyl-2-oxo-1,2-dihydroquinoline-3-carboxylic acid; 7-(3-aminoazetidin-1-yl)-1-cyclopropyl-6-fluoro-8-methyl-2-oxo-1,2-dihydroquinoline-3-carboxylic acid; 7-(3-(1-aminocyclopropyl)pyrrolidin-1-yl)-1-cyclopropyl-6-fluoro-8-methyl-2-oxo-1,2-dihydroquinoline-3-carboxylic acid; 7-((R)-3-((S)-1-((2-cyanoethyl)amino)ethyl)pyrrolidin-1-yl)-1-cyclopropyl-6-fluoro-8-methyl-2-oxo-1,2-dihydroquinoline-3-carboxylic acid; 7-(6-aminopyridin-3-yl)-1-cyclopropyl-6-fluoro-8-methyl-2-oxo-1,2-dihydroquinoline-3-carboxylic acid; 7-((R)-3-((S)-1-aminoethyl)pyrrolidin-1-yl)-1-cyclopropyl-6-fluoro-8-methyl-3-(methylsulfonyl)quinolin-2(1H)-one; 7-(3-(aminomethyl)pyrrolidin-1-yl)-1-cyclopropyl-6-fluoro-8-methyl-3-(methylsulfonyl)quinolin-2(1H)-one; 7-((R)-3-((S)-1-aminoethyl)pyrrolidin-1-yl)-1-cyclopropyl-6-fluoro-N,N,8-trimethyl-2-oxo-1,2-dihydroquinoline-3-sulfonamide; 7-((R)-3-((S)-1-aminoethyl)pyrrolidin-1-yl)-1-cyclopropyl-6-fluoro-3-methoxy-8-methylquinolin-2(1H)-one; 7-(6-aminopyridin-3-yl)-1-cyclopropyl-6-fluoro-3-methoxy-8-methylquinolin-2(1H)-one; 3-amino-7-((R)-3-((S)-1-aminoethyl)pyrrolidin-1-yl)-1-cyclopropyl-6-fluoro-8-methylquinolin-2(1H)-one; 7-((R)-3-((S)-1-aminoethyl)pyrrolidin-1-yl)-1-cyclopropyl-6-fluoro-8-methylquinolin-2(1H)-one; 7-(3-(1-Aminocyclopropyl)pyrrolidin-1-yl)-1-cyclopropyl-6-fluoro-8-methylquinolin-2(1H)-one; 1-Cyclopropyl-6-fluoro-8-methyl-7-(piperazin-1-yl)quinolin-2(1H)-one; 7-(6-Aminopyridin-3-yl)-1-cyclopropyl-6-fluoro-8-methylquinolin-2(1H)-one; 7-((R)-3-((S)-1-aminoethyl)pyrrolidin-1-yl)-1-cyclopropyl-6-fluoro-3-hydroxy-8-methylquinolin-2(1H)-one; 7-(6-aminopyridin-3-yl)-1-cyclopropyl-6-fluoro-3-hydroxy-8-methylquinolin-2(1H)-one; 7-((R)-3-((S)-1-aminoethyl)pyrrolidin-1-yl)-1-cyclopropyl-6-fluoro-8-methoxy-2-oxo-1,2-dihydroquinoline-3-carboxylic acid; 7-((R)-3-((S)-1-aminoethyl)pyrrolidin-1l-yl)-1-cyclopropyl-8-ethyl-6-fluoro-2-oxo-1,2-dihydroquinoline-3-carboxylic acid; 7-((R)-3-((S)-1-aminoethyl)pyrrolidin-1-yl)-1-cyclopropyl-6-fluoro-2-oxo-1,2-dihydroquinoline-3-carboxylic acid; tert-butyl ((S)-1-((R)-1-(1-cyclopropyl-6-fluoro-4-hydroxy-8-methyl-2-oxo-1,2-dihydroquinolin-7-yl)pyrrolidin-3-yl)ethyl)carbamate; 7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl trifluoromethanesulfonate; 7-((R)-3-((S)-1-aminoethyl)pyrrolidin-1-yl)-1-cyclopropyl-6-fluoro-8-methyl-4-(1H-pyrazol-4-yl)quinolin-2(1H)-one; 7-((R)-3-((S)-1-aminoethyl)pyrrolidin-1-yl)-1-cyclopropyl-6-fluoro-8-methyl-4-phenylquinolin-2(1H)-one; 7-((R)-3-((S)-1-aminoethyl)pyrrolidin-1-yl)-1-cyclopropyl-4-(3,5-difluoro-4-hydroxyphenyl)-6-fluoro-8-methylquinolin-2(1H)-one; (E)-ethyl 3-(7-((R)-3-((S)-1-aminoethyl)pyrrolidin-1-yl)-1-cyclopropyl-6-fluoro-8-methyl-2-oxo-1,2-dihydroquinolin-4-yl)acrylate; (E)-3-(7-((R)-3-((S)-1-aminoethyl)pyrrolidin-1-yl)-1-cyclopropyl-6-fluoro-8-methyl-2-oxo-1,2-dihydroquinolin-4-yl)acrylic acid; tert-butyl ((S)-1-((R)-1-(1-cyclopropyl-6-fluoro-8-methyl-2-oxo-4-vinyl-1,2-dihydroquinolin-7-yl)pyrrolidin-3-yl)ethyl)carbamate; 7-((R)-3-((S)-1-aminoethyl)pyrrolidin-1-yl)-1-cyclopropyl-4-ethyl-6-fluoro-8-methylquinolin-2(1H)-one; 7-((R)-3-((S)-1-aminoethyl)pyrrolidin-1-yl)-1-cyclopropyl-4-ethynyl-6-fluoro-8-methylquinolin-2(1H)-one; Methyl 3-(7-((R)-3-((S)-1-aminoethyl)pyrrolidin-1-yl)-1-cyclopropyl-6-fluoro-8-methyl-2-oxo-1,2-dihydroquinolin-4-yl)propiolate; 7-((R)-3-((S)-1-aminoethyl)pyrrolidin-1-yl)-1-cyclopropyl-6-fluoro-8-methyl-2-oxo-1,2-dihydroquinoline-4-carbonitrile; 7-((R)-3-((S)-1-aminoethyl)pyrrolidin-1-yl)-1-cyclopropyl-6-fluoro-3,8-dimethyl-2-oxo-1,2-dihydroquinoline-4-carbonitrile; (R)-7-(3-(aminomethyl)pyrrolidin-1-yl)-1-cyclopropyl-6-fluoro-8-methyl-2-oxo-1,2-dihydroquinoline-4-carbonitrile; (R)-7-(3-(((tert-butoxycarbonyl)amino)methyl)pyrrolidin-1-yl)-1-cyclopropyl-6-fluoro-8-methyl-2-oxo-1,2-dihydroquinolin-4-yl trifluoromethanesulfonate; (S)-7-(3-aminopyrrolidin-1-yl)-1-cyclopropyl-6-fluoro-8-methyl-2-oxo-1,2-dihydroquinoline-4-carbonitrile; (S)-7-(3-(aminomethyl)pyrrolidin-1-yl)-1-cyclopropyl-6-fluoro-8-methyl-2-oxo-1,2-dihydroquinoline-4-carbonitrile; 1-cyclopropyl-6-fluoro-8-methyl-2-oxo-7-(piperazin-1-yl)-1,2-dihydroquinoline-4-carbonitrile; 7-((R)-3-((S)-1-aminoethyl)pyrrolidin-1-yl)-1-cyclopropyl-6-fluoro-8-methyl-2-oxo-1,2-dihydroquinoline-4-carboxylic acid; 7-((R)-3-((S)-1-aminoethyl)pyrrolidin-1-yl)-1-cyclopropyl-6-fluoro-8-methyl-2-oxo-1,2-dihydroquinoline-4-carboxamide; ethyl 7-((R)-3-((S)-1-aminoethyl)pyrrolidin-1-yl)-1-cyclopropyl-6-fluoro-8-methyl-2-oxo-1,2-dihydroquinoline-4-carboxylate; 4-amino-7-((R)-3-((S)-1-aminoethyl)pyrrolidin-1-yl)l 1-cyclopropyl-6-fluoro-8-methylquinolin-2(1H)-one; N-(7-((R)-3-((S)-1-aminoethyl)pyrrolidin-1-yl)-1-cyclopropyl-6-fluoro-8-methyl-2-oxo-1,2-dihydroquinolin-4-yl)methanesulfonamide; 3-(7-((R)-3-((S)-1-aminoethyl)pyrrolidin-1-yl)-1-cyclopropyl-6-fluoro-8-methyl-2-oxo-1,2-dihydroquinolin-4-yl)-1,2,4-oxadiazol-5(4H)-one; 7-((R)-3-((S)-1-aminoethyl)pyrrolidin-1-yl)-1-cyclopropyl-6-fluoro-8-methyl-4-(1H-tetrazol-5-yl)quinolin-2(1H)-one; 7-((R)-3-((S)-1-aminoethyl)pyrrolidin-1-yl)-1-cyclopropyl-6-fluoro-N-hydroxy-8-methyl-2-oxo-1,2-dihydroquinoline-4-carboximidamide; 7-((R)-3-((S)-1-aminoethyl)pyrrolidin-1-yl)-1-cyclopropyl-6-fluoro-8-methyl-4-(2-oxido-3H-1,2,3,5-oxathiadiazol-4-yl)quinolin-2(1H)-one; 5-(7-((R)-3-((S)-1-aminoethyl)pyrrolidin-1-yl)-1-cyclopropyl-6-fluoro-8-methyl-2-oxo-1,2-dihydroquinolin-4-yl)-1,3,4-oxadiazol-2(3H)-one; 7-((R)-3-((S)-1-aminoethyl)pyrrolidin-1-yl)-1-cyclopropyl-6-fluoro-N-hydroxy-8-methyl-2-oxo-1,2-dihydroquinoline-4-carboxamide; 7-((R)-3-((S)-1-aminoethyl)pyrrolidin-1-yl)-4-chloro-1-cyclopropyl-6-fluoro-8-methylquinolin-2(1H)-one; 7-((R)-3-((S)-1-aminoethyl)pyrrolidin-1-yl)-4-(aminomethyl)-1-cyclopropyl-6-fluoro-8-methylquinolin-2(1H)-one; N-((7-((R)-3-((S)-1-aminoethyl)pyrrolidin-1-yl)-1-cyclopropyl-6-fluoro-8-methyl-2-oxo-1,2-dihydroquinolin-4-yl)methyl)acetamide; 7-((R)-3-((S)-1-aminoethyl)pyrrolidin-1-yl)-1-cyclopropyl-6-fluoro-4-(hydroxymethyl)-8-methylquinolin-2(1H)-one; 7-((R)-3-((S)-1-aminoethyl)pyrrolidin-1-yl)-1-cyclopropyl-6-fluoro-4-(methoxymethyl)-8-methylquinolin-2(1H)-one; 7-((R)-3-((S)-1-aminoethyl)pyrrolidin-1-yl)-1-cyclopropyl-4-(2-(dimethylamino)ethoxy)-6-fluoro-8-methylquinolin-2(1H)-one; N—((S)-1-((R)-1-(1-cyclopropyl-4-(2-(dimethylamino)ethoxy)-6-fluoro-8-methyl-2-oxo-1,2-dihydroquinolin-7-yl)pyrrolidin-3-yl)ethyl)acetamide; 4-(2-aminoethoxy)-7-((R)-3-((S)-1-aminoethyl)pyrrolidin-1-yl)-1-cyclopropyl-6-fluoro-8-methylquinolin-2(1H)-one; N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)-2-hydroxyacetamide; 1-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)guanidine; N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)acetamide; (S)-1-cyclopropyl-4-(2-(dimethylamino)ethoxy)-6-fluoro-7-(3-hydroxypyrrolidin-1-yl)-8-methylquinolin-2(1H)-one; 2-((7-((R)-3-((S)-1-aminoethyl)pyrrolidin-1-yl)-1-cyclopropyl-6-fluoro-8-methyl-2-oxo-1, 2-dihydroquinolin-4-yl)oxy)acetamide; 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)butanenitrile; 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)-N'-hydroxybutanimidamide; ethyl 4-((7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)oxy)butanoate; 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)-N-hydroxybutanamide; 4-((7-((R)-3-((S)-1-aminoethyl)pyrrolidin-1-yl)-1-cyclopropyl-6-fluoro-8-methyl-2-oxo-1,2-dihydroquinolin-4-yl)oxy)butanoic acid; Methyl 2-((7-((R)-3-((S)-1-((tert-butoxycarbonyl)amino)ethyl)pyrrolidin-1-yl)-1-cyclopropyl-6-fluoro-8-methyl-2-oxo-1,2-dihydroquinolin-4-yl)oxy)acetate; tert-butyl ((S)-1-((R)-1-(1-cyclopropyl-6-fluoro-4-(2-hydrazinyl-2-oxoethoxy)-8-methyl-2-oxo-1,2-dihydroquinolin-7-yl)pyrrolidin-3-yl)ethyl)carbamate; 5-(((7-((R)-3-((S)-1-aminoethyl)pyrrolidin-1-yl)-1-cyclopropyl-6-fluoro-8-methyl-2-oxo-1,2-dihydroquinolin-4-yl)oxy)methyl)-1,3,4-oxadiazol-2(3H)-one; 5-(3-((7-((R)-3-((S)-1-aminoethyl)pyrrolidin-1-yl)-1-cyclopropyl-6-fluoro-8-methyl-2-oxo-1,2-dihydroquinolin-4-yl)oxy)propyl)-1,3,4-oxadiazol-2(3H)-one; N-(2-((7-((R)-3-((S)-1-aminoethyl)pyrrolidin-1-yl)-1-cyclopropyl-6-fluoro-8-methyl-2-oxo-1,2-dihydroquinolin-4-yl)oxy)ethyl)methanesulfonamide; 7-((R)-3-((S)-1-aminoethyl)pyrrolidin-1-yl)-1-cyclopropyl-6-fluoro-4-methoxy-8-methylquinolin-2(1H)-one; 7-((R)-3-((S)-1-aminoethyl)pyrrolidin-1-yl)-1-cyclopropyl-4-methoxy-8-methylquinolin-2(1H)-one; 7-(6-aminopyridin-3-yl)-1-cyclopropyl-4-methoxy-8-methylquinolin-2(1H)-one; 7-(6-aminopyridin-3-yl)-1-cyclopropyl-4-methoxy-3,8-dimethylquinolin-2(1H)-one; 7-((R)-3-((S)-1-aminoethyl)pyrrolidin-1-yl)-4-(benzyloxy)-1-cyclopropyl-8-methylquinolin-2(1H)-one; 7-((R)-3-((S)-1-aminoethyl)pyrrolidin-1-yl)-1-cyclopropyl-4-hydroxy-8-methylquinolin-2(1H)-one; 7-((R)-3-((S)-1-aminoethyl)pyrrolidin-1-yl)-1-cyclopropyl-8-methyl-4-((tetrahydro-2H-pyran-4-yl)methoxy)quinolin-2(1H)-one; 7-((R)-3-((S)-1-aminoethyl)pyrrolidin-1-yl)-1-cyclopropyl-4-(2-(dimethylamino)ethoxy)-8-methylquinolin-2(1H)-one; 7-(6-aminopyridin-3-yl)-1-cyclopropyl-8-methylquinolin-2(1H)-one; 7-((R)-3-((S)-1-aminoethyl)pyrrolidin-1-yl)-1-cyclopropyl-8-methylquinolin-2(1H)-one trifluoroacetic; 7-(6-Aminopyridin-3-yl)-1 1-cyclopropyl-3-hydroxy-8-methylquinolin-2(1H)-one; 7-(6-Aminopyridin-3-yl)-1-cyclopropyl-3-methoxy-8-methylquinolin-2(1H)-one; 7-((R)-3-((S)-1-aminoethyl)pyrrolidin-1-yl)-1-cyclopropyl-3-hydroxy-8-methylquinolin-2(1H)-one; 7-((R)-3-((S)-1-aminoethyl)pyrrolidin-1-yl)-1-cyclopropyl-3-methoxy-8-methylquinolin-2(1H)-one; (S)-4-(aminomethyl)-7-(3-aminopyrrolidin-1-yl)-1-cyclopropyl-6-fluoro-8-methylquinolin-2(1H)-one; 4-(aminomethyl)-1-cyclopropyl-6-fluoro-7-(3-hydroxy-3-methylpyrrolidin-1-yl)-8-methylquinolin-2(1H)-one; 4-(aminomethyl)-1-cyclopropyl-6-fluoro-8-methyl-7-(3-methylpiperazin-1-yl)quinolin-2(1H)-one; 4-(aminomethyl)-1-cyclopropyl-6-fluoro-7-(hexahydro-1H-pyrrolo[3,4-b]pyridin-6(2H)-yl)-8-methylquinolin-2(1H)-one; 4-(aminomethyl)-1-cyclopropyl-7-(3-cyclopropyl-3-hydroxyazetidin-1-yl)-6-fluoro-8-methylquinolin-2(1H)-one; 4-(aminomethyl)-1-cyclopropyl-6-fluoro-8-methyl-7-(pyrrolidin-1-yl)quinolin-2(1H)-one; 7-((3R,4S)-3-amino-4-fluoropyrrolidin-1-yl)-4-(aminomethyl)-1-cyclopropyl-6-fluoro-8-methylquinolin-2(1H)-one; 7-((3R,4R)-3-amino-4-fluoropyrrolidin-1-yl)-4-(aminomethyl)-1-cyclopropyl-6-fluoro-8-methylquinolin-2(1H)-one; 4-(aminomethyl)-1-cyclopropyl-6-fluoro-8-methyl-7-(piperazin-1-yl)quinolin-2(1H)-one; (R)-4-(aminomethyl)-7-(3-aminopyrrolidin-1-yl)-1-cyclopropyl-6-fluoro-8-methylquinolin-2(1H)-one; 4-(aminomethyl)-1-cyclopropyl-6-fluoro-8-methyl-7-(4-methylpiperazin-1-yl)quinolin-2(1H)-one; (S)-4-(aminomethyl)-1-cyclopropyl-6-fluoro-8-methyl-7-(3-(methylamino)pyrrolidin-1-yl)quinolin-2(1H)-one; 4-(aminomethyl)-7-(3-(aminomethyl)-3-hydroxypyrrolidin-1-yl)-1-cyclopropyl-6-fluoro-8-methylquinolin-2(1H)-one; 4-(aminomethyl)-1-cyclopropyl-6-fluoro-7-(3-fluoro-3-((methylamino)methyl)pyrrolidin-1-yl)-8-methylquinolin-2(1H)-one; (R)-4-(aminomethyl)-1-cyclopropyl-6-fluoro-7-(3-(2-hydroxypropan-2-yl)pyrrolidin-1-yl)-8-methylquinolin-2(1H)-one; 4-(aminomethyl)-7-((3R,4S)-3,4-bis(2-hydroxyethyl)pyrrolidin-1-yl)-1-cyclopropyl-6-fluoro-8-methylquinolin-2(1H)-one; 4-(aminomethyl)-1-cyclopropyl-7-((3S,4S)-3,4-dihydroxypyrrolidin-1-yl)-6-fluoro-8-methylquinolin-2(1H)-one; 4-(aminomethyl)-1-cyclopropyl-6-fluoro-8-methyl-7-morpholinoquinolin-2(1H)-one; 7-(3-amino-3-methylpyrrolidin-1-yl)-4-(aminomethyl)-1-cyclopropyl-6-fluoro-8-methylquinolin-2(1H)-one; 7-((3S,4R)-3-amino-4-(hydroxymethyl)pyrrolidin-1-yl)-4-(aminomethyl)-1-cyclopropyl-6-fluoro-8-methylquinolin-2(1H)-one; (S)-7-(7-amino-5-azaspiro[2.4]heptan-5-yl)-4-(aminomethyl)-1-cyclopropyl-6-fluoro-8-methylquinolin-2(1H)-one; 7-((3S,4R)-3-amino-4-methylpyrrolidin-1-yl)-4-(aminomethyl)-1-cyclopropyl-6-fluoro-8-methylquinolin-2(1H)-one; 7-(1-amino-3-azabicyclo[3.1.0]hexan-3-yl)-4-(aminomethyl)-1-cyclopropyl-6-fluoro-8-methylquinolin-2(1H)-one; 4-(aminomethyl)-1-cyclopropyl-6-fluoro-8-methyl-7-(5-oxa-2,8-diazaspiro[3.5]nonan-2-yl)quinolin-2(1H)-one; 4-(aminomethyl)-1-cyclopropyl-6-fluoro-8-methyl-7-(2,6-diazaspiro [3.4]octan-2-yl)quinolin-2(1H)-one; 4-(aminomethyl)-1-cyclopropyl-6-fluoro-8-methyl-7-(2,7-diazaspiro[3.5]nonan-2-yl)quinolin-2(1H)-one; 4-(aminomethyl)-1-cyclopropyl-6-fluoro-7-(4-(hydroxymethyl)piperidin-1-yl)-8-methylquinolin-2(1H)-one; 4-(aminomethyl)-1-cyclopropyl-6-fluoro-7-(4-(2-hydroxyethyl)piperidin-1-yl)-8-methylquinolin-2(1H)-one; 4-(aminomethyl)-1-cyclopropyl-6-fluoro-7-(4-hydroxypiperidin-1-yl)-8-methylquinolin-2(1H)-one; (S)-4-(aminomethyl)-1-cyclopropyl-6-fluoro-7-(3-hydroxypyrrolidin-1-yl)-8-methylquinolin-2(1H)-one; 4-(aminomethyl)-7-(3-(aminomethyl)-3-fluoropyrrolidin-1-yl)-1-cyclopropyl-6-fluoro-8-methylquinolin-2(1H)-one; 4-(aminomethyl)-7-(3-(aminomethyl)-3-fluoropyrrolidin-1l-yl)-1-cyclopropyl-5,6-difluoro-8-methylquinolin-2(1H)-one; 4-(aminomethyl)-1-cyclopropyl-5,6-difluoro-8-methyl-7-(pyrrolidin-1-yl)quinolin-2(1H)-one; 4-(aminomethyl)-1-cyclopropyl-5,6-difluoro-8-methyl-7-(piperazin-1-yl)quinolin-2(1H)-one; (S)-4-(aminomethyl)-1-cyclopropyl-5,6-difluoro-7-(3-hydroxypyrrolidin-1-yl)-8-methylquinolin-2(1H)-one; 7-((R)-3-((S)-1-aminoethyl)pyrrolidin-1-yl)-4-(aminomethyl)-1-cyclopropyl-5,6-difluoro-8-methylquinolin-2(1H)-one; (S)-4-(aminomethyl)-7-(3-aminopyrrolidin-1-yl)-1-cyclopropyl-5,6-difluoro-8-methylquinolin-2(1H)-one; tert-butyl ((1-(4-cyano-1-cyclopropyl-5,6-difluoro-8-methyl-2-oxo-1,2-dihydroquinolin-7-yl)-3-fluoropyrrolidin-3-yl)methyl)carbamate; 4-(aminomethyl)-7-(3-(aminomethyl)-3-fluoropyrrolidin-1-yl)-1-cyclopropyl-5,6-difluoro-8-methylquinolin-2(1H)-one; 4-(amino methyl)-7-(3-(amino methyl) pyrrolidin-1-yl)-1-cyclopropyl-6-fluoro-8-methylquinolin-2(1H)-one; 4-(((2-aminoethyl)amino)methyl)-7-(3-(aminomethyl)pyrrolidin-1-yl)-1-cyclopropyl-6-fluoro-8-methylquinolin-2(1H)-one; 7-(3-(aminomethyl)

pyrrolidin-1-yl)-1-cyclopropyl-6-fluoro-8-methyl-4-((methylamino)methyl)quinolin-2(1H)-one; 7-(3-(aminomethyl)pyrrolidin-1-yl)-1-cyclopropyl-4-((dimethylamino)methyl)-6-fluoro-8-methylquinolin-2 (1H)-one; (S)-1-cyclopropyl-5,6-difluoro-7-(3-hydroxypyrrolidin-1-yl)-8-methyl-4-((4-methylpiperazin-1-yl) methyl)quinolin-2(1H)-one; 4-(2-aminoethyl)-7-(3-(aminomethyl)pyrrolidin-1-yl)-1-cyclopropyl-6-fluoro-8-methylquinolin-2(1H)-one; 7-(3-(aminomethyl)-3-fluoropyrrolidin-1-yl)-1-cyclopropyl-6-fluoro-8-methyl-2-oxo-1,2-dihydroquinoline-3-carbonitrile; 3-(aminomethyl)-7-(3-(aminomethyl)-3-fluoropyrrolidin-1-yl)-1-cyclopropyl-6-fluoro-8-methylquinolin-2(1H)-one; (S)-7-(3-aminopyrrolidin-1-yl)-1-cyclopropyl-6-fluoro-8-methyl-2-oxo-1,2-dihydroquinoline-3-carbonitrile; (S)-3-(aminomethyl)-7-(3-aminopyrrolidin-1-yl)-1-cyclopropyl-6-fluoro-8-methylquinolin-2(1H)-one; 7-(3-(aminomethyl)-3-fluoropyrrolidin-1-yl)-1-cyclopropyl-6-fluoro-3-(hydroxymethyl)-8-methylquinolin-2(1H)-one; 5-(3-(aminomethyl)pyrrolidin-1-yl)-7-bromo-1-cyclopropyl-6-fluoro-8-methylquinolin-2(1H)-one; 7-(3-(aminomethyl)pyrrolidin-1-yl)-5-bromo-1-cyclopropyl-6-fluoro-8-methylquinolin-2(1H)-one; 7-(3-(aminomethyl)pyrrolidin-1-yl)-1-cyclopropyl-6-fluoro-8-methyl-5-(1H-pyrazol-4-yl)quinolin-2(1H)-one; 7-(3-(aminomethyl)pyrrolidin-1-yl)-1-cyclopropyl-6-fluoro-8-methyl-2-oxo-1,2-dihydroquinoline-5-carbonitrile; 5-(aminomethyl)-7-(3-(aminomethyl)pyrrolidin-1-yl)-1-cyclopropyl-6-fluoro-8-methylquinolin-2(1H)-one; 7-(3-(aminomethyl)pyrrolidin-1-yl)-1-cyclopropyl-6-fluoro-5,8-dimethylquinolin-2(1H)-one; 7-(3-(aminomethyl)pyrrolidin-1-yl)-1-cyclopropyl-6-fluoro-5-methoxy-8-methyl quinolin-2(1H)-one; 1-cyclopropyl-6-fluoro-8-methyl-7-(3-(((2,2,2-trifluoroacetyl)-14-azanyl)methyl)pyrrolidin-1-yl)-5-vinylquinolin-2(1H)-one; 5-amino-7-(3-(aminomethyl)pyrrolidin-1-yl)-1-cyclopropyl-6-fluoro-8-methyl quinolin-2(1H)-one; 7-(3-(aminomethyl)pyrrolidin-1-yl)-5-chloro-1-cyclopropyl-6-fluoro-8-methyl quinolin-2(1H)-one; 7-((R)-3-((S)-1-aminoethyl)pyrrolidin-1-yl)-1-cyclopropyl-5,6-difluoro-8-methyl quinolin-2(1H)-one; 7-(3-(aminomethyl)-3-fluoropyrrolidin-1-yl)-1-cyclopropyl-6-fluoro-8-(hydroxy methyl)quinolin-2(1H)-one; 7-(3-(aminomethyl)pyrrolidin-1-yl)-1-cyclopropyl-6-fluoro-8-vinylquinolin-2(1H)-one; 7-(3-(aminomethyl)pyrrolidin-1-yl)-1-cyclopropyl-6-fluoro-8-methoxyquinolin-2(1H)-one; 8-(aminomethyl)-7-(3-(aminomethyl)-3-fluoropyrrolidin-1-yl)-1-cyclopropyl-6-fluoroquinolin-2(1H)-one; 7-(3-(aminomethyl)-3-fluoropyrrolidin-1-yl)-1-cyclopropyl-8-ethoxy-6-fluoroquinolin-2(1H)-one; (S)-7-(3-aminopyrrolidin-1-yl)-1-cyclopropyl-6-fluoro-2-oxo-1,2-dihydroquinoline-8-carbonitrile; (S)-4-(aminomethyl)-7-(3-aminopyrrolidin-1-yl)-1-cyclopropyl-6-fluoro-2-oxo-1,2-dihydroquinoline-8-carbonitrile; 4-(aminomethyl)-7-(3-(aminomethyl)-3-fluoropyrrolidin-1-yl)-1-cyclobutyl-5,6-difluoro-8-methylquinolin-2(1H)-one; (S)-4-(aminomethyl)-7-(3-aminopyrrolidin-1-yl)-1-cyclobutyl-5,6-difluoro-8-methylquinolin-2(1H)-one trifluoroacetate; (S)-4-(aminomethyl)-7-(3-aminopyrrolidin-1-yl)-6-fluoro-1-isopropyl-8-methylquinolin-2(1H)-one trifluoroacetate; 4-(aminomethyl)-7-(3-(aminomethyl)-3-fluoropyrrolidin-1-yl)-6-fluoro-1-isopropyl-8-methylquinolin-2(1H)-one trifluoroacetate; and 7-(1-amino-3-azabicyclo[3.1.0]hexan-3-yl)-4-(aminomethyl)-3-chloro-1-cyclopropyl-6-fluoro-8-methylquinolin-2(1H)-one.

\* \* \* \* \*